(12) United States Patent
Lemieux et al.

(10) Patent No.: US 10,087,172 B2
(45) Date of Patent: *Oct. 2, 2018

(54) COMPOUNDS AND THEIR METHODS OF USE

(71) Applicant: AGIOS PHARMACEUTICALS, INC, Cambridge, MA (US)

(72) Inventors: Rene M. Lemieux, Charlestown, MA (US); Janeta Popovici-Muller, Windham, NH (US); Francesco G. Salituro, Marlborough, MA (US); Jeffrey O. Saunders, Lincoln, MA (US); Jeremy Travins, Southborough, MA (US); Yongsheng Chen, Shanghai (CN)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/646,634

(22) PCT Filed: Nov. 21, 2013

(86) PCT No.: PCT/CN2013/001428
§ 371 (c)(1),
(2) Date: May 21, 2015

(87) PCT Pub. No.: WO2014/079150
PCT Pub. Date: May 30, 2014

(65) Prior Publication Data
US 2015/0291576 A1    Oct. 15, 2015

(30) Foreign Application Priority Data

Nov. 22, 2012  (WO) ................ PCT/CN2012/085023
Mar. 15, 2013  (WO) ................ PCT/CN2013/000294

(51) Int. Cl.
*C07D 417/08* (2006.01)
*C07D 417/14* (2006.01)
*C07D 285/135* (2006.01)

(52) U.S. Cl.
CPC ....... *C07D 417/14* (2013.01); *C07D 285/135* (2013.01)

(58) Field of Classification Search
CPC ............................ C07D 417/04; C07D 417/14
See application file for complete search history.

(56) References Cited

U.S. PATENT DOCUMENTS

| | | | |
|---|---|---|---|
| 4,070,400 A | 1/1978 | Dybas et al. | |
| 5,895,748 A | 4/1999 | Johnson et al. | |
| 5,997,866 A | 12/1999 | Johnson et al. | |
| 9,029,531 B2 | 5/2015 | Lemieux et al. | |
| 9,303,002 B2 | 4/2016 | Lemieux et al. | |
| 2002/0115698 A1 | 8/2002 | Newcomb et al. | |
| 2002/0142981 A1 | 10/2002 | Horne et al. | |
| 2003/0054985 A1 | 3/2003 | Aaronson et al. | |
| 2004/0023288 A1 | 2/2004 | Ridder et al. | |
| 2004/0038207 A1 | 2/2004 | Orntoft | |
| 2006/0211060 A1 | 9/2006 | Haley et al. | |
| 2009/0226396 A1 | 9/2009 | Haley et al. | |
| 2011/0182886 A1 | 7/2011 | Hongo et al. | |
| 2012/0141479 A1 | 6/2012 | Witta et al. | |
| 2012/0142028 A1 | 6/2012 | Richardson et al. | |
| 2012/0190565 A1 | 7/2012 | Lisanti et al. | |
| 2012/0220610 A1 | 8/2012 | Cerione et al. | |
| 2013/0331432 A1 | 12/2013 | Stephanopoulos et al. | |
| 2015/0299152 A1 | 10/2015 | Lemieux et al. | |
| 2016/0008380 A1 | 1/2016 | Raabe et al. | |
| 2017/0137414 A1 | 5/2017 | Cianchetta et al. | |

FOREIGN PATENT DOCUMENTS

| | | |
|---|---|---|
| DE | 2037257 A1 | 2/1972 |
| WO | 9422842 A1 | 10/1994 |
| WO | 1999065884 A1 | 12/1999 |
| WO | 2006040569 A1 | 4/2006 |
| WO | 2008048967 A1 | 4/2008 |
| WO | 2011143160 A2 | 11/2011 |
| WO | 2011163332 A2 | 12/2011 |
| WO | 2012006506 A1 | 1/2012 |
| WO | 2012120428 A1 | 9/2012 |
| WO | 2012171337 A1 | 12/2012 |

(Continued)

OTHER PUBLICATIONS

Delabarre et al. "Full-Length Human Glutaminase in Complex with an Allosteric Inhibitor" Biochemistry (2011) vol. 50, No. 50, pp. 10764-10770.
El-Asmar "Studies on the Mechanisms of Inhibition of Tumor Growth by the Enzyme Glutaminase" Cancer Research (1966) vol. 26, pp. 116-122.
Hands et al. "A Convenient Method for the Preparation of 5-, 6- and 7-Azaindoles and Their Derivatives" Synthesis (1996) pp. 877-882.
Hoffman et al. "Imidazol-4,5-dicarbonsäure-derivate; n-Alkyl-substituierte Amide oligomethylenverbrückter Bis-midazol-4,5-dicarbonsäuren" Zeitschrift Fur Chemie (1977) vol. 17, No. 4, pp. 138-139.
International Search Report and Written Opinion for International Application No. PCT/CN2013/000294 dated Sep. 5, 2013.
International Search Report and Written Opinion for International Application No. PCT/CN2013/001428 dated Mar. 6, 2014.

(Continued)

*Primary Examiner* — Matthew P Coughlin
*Assistant Examiner* — Karen Cheng
(74) *Attorney, Agent, or Firm* — Goodwin Procter LLP

(57) ABSTRACT

Provided are compounds of formula (I), which can inhibit glutaminase. Pharmaceutical compositions comprising these compounds and uses as glutaminase inhibitors for treating cancers thereof are also provided.

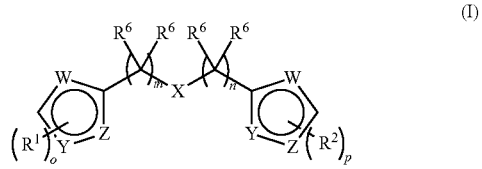

11 Claims, No Drawings

(56) References Cited

FOREIGN PATENT DOCUMENTS

| WO | 2013078123 A1 | 5/2013 |
|---|---|---|
| WO | 2013138790 A1 | 9/2013 |
| WO | 2014079150 A1 | 5/2014 |
| WO | 2015101958 A2 | 7/2015 |

OTHER PUBLICATIONS

International Search Report and Written Opinion for International Application No. PCT/CN2014/073812 dated Dec. 24, 2014.
International Search Report and Written Opinion for International Application No. PCT/US13/59967 dated Sep. 16, 2013.
International Search Report and Written Opinion for International Application No. PCT/US2013/071212 dated Apr. 9, 2014.
International Search Report for International Application No. PCT/CN2012/085023 dated Aug. 29, 2013.
International Search Report for International Application No. PCT/US2015/021781 dated Jun. 22, 2015.
Kafkewitz et al. "Enzyme-induced asparagine and glutamine depletion and immune system function 1-3" The American Journal of Clinical Nutrition (1983) vol. 37, pp. 1025-1030.
Kumar "Synthesis and Pharmacological Evaluation of Some Novel Imidazo[2,1-b][1,3,4]thiadiazole Derivatives" Chinese Journal of Chemistry (2010) vol. 28, No. 2, pp. 250-254.
Kung et al: 11 Glutamine Synthetase Is a Genetic Determinant of Cell Type-Specific Glutamine Independence in Breast Epithelia, PLOS Genetics~ vol. 7 No. 8, Aug. 11, 2011 (Aug. 11, 2011), p. e1002229.
Majee "Synthesis of thiosemicarbazides, triazoles, thiadiazoles and oxadiazoles" Current Science (1989) vol. 58, No. 21, pp. 1198-1201.
Mukhina et al. "di-(carbohydrazidomethyl)-sulfide,sulfoxide and sulfone and their derivatives that correspond to it" Izvestiya Vysshikh Uchebnykh Zavedeniy SSSR. Khimiya Ikhimicheskaya Tekhnologiya (1966) vol. 4, pp. 586-590.
Panwar et al. "Studies on Some Bioactive 1,1-Bis(2-benzylidene-5-aryliden-1,3-thiadiazolidin-4-one)cyclopropane" Journal of the Korean Chemical Society (2011) vol. 55, No. 6, pp. 994-999.
Partial Search Report from EP Application No. 13 83 7050 dated Mar. 8, 2016.
PubChem. CID 13735314. Feb. 9, 2007.
PubChem. CID 22812110. Dec. 5, 2007.
PubChem. CID 59841146. Aug. 20, 2012.
PubChem. CID 66760293. Nov. 30, 2012.
Ram et al. "Bis Heterocycles as Potential Chemotherapeutic Agents X. Synthesis of Bis(4-arylthiosemicarbazido)-, Bis(2-arylamino-1,3,4thiadiazol-5-yl) and Bis(4-aryl-1,2,4-triazolin-3- thione-5-yl)pentanes and Related Compounds" Journal of Heterocyclic Chemistry (1990) vol. 27, pp. 351-355.
Ram et al. "Bis-heterocycles. Part III*. Synthesis of tetramethylene-3,3di-1,2,4-triazoles and tetramethylene-2,2-di-1,3,4-thiadiazoles" Recueil des Travaux Chimiques des Pays-Bas, Journal of the Royal Netherlands Chemical Society (1977) vol. 96, No. 7-8, pp. 181-182.
Robinson et al. "Novel mechanism of inhibition of rat kidney-type glutaminase by bis-2-(5-phenylacetamido-1,2,4-thiadiazol-2-yl)ethyl sulfide (BPTES)" (2007) Biochemical Journal, vol. 406, No. 3, pp. 407-414.
Sharba et al. "Synthesis of Thiadiazoles and 1,2,4-Triazoles Derived from Cyclopropane Dicarboxylic Acid" Molecules (2005) vol. 10, No. 9, pp. 1153-1160.
Shukla et al. "Design, Synthesis, and Pharmacological Evaluation of Bis-2- (5-phenylacetamido-1,2,4-thiadiazol-2-yl) ethyl Sulfide 3 (BPTES) Analogs as Glutaminase Inhibitors" Journal of Medicinal Chemistry (2012) vol. 55, No. 2, pp. 10551-10563.
Singh et al: Selection of Metastatic Breast Cancer Cells Based on Adaptability of Their Metabolic State Plos One, vol. 7, No. 5, May 3, 2012 (May 3, 2012), p. E36510.
Srivasta et al. "Synthesis and Fungicidal Activity of some New Bis-heterocycles" Indian Chemical Society (1991) vol. 58, pp. 365-367.
Thangavelu et al: Structural basis for the allosteric inhibitory mechanism of human kidney-type glutaminase (KGA) and its regulation by Raf-Mek-Erk signaling in cancer cell metabolism Proceedings of the National Academy of Sciences,vol. 109, No. 20, Apr. 26, 2012 (Apr. 26, 2012), pp. 7705-7710.
Wise et al: 11 Glutamine addiction: a new therapeutic target in cancer, Trends in Biochemical Sciences, vol. 35, No. 8, Aug. 1, 2010 (Aug. 1, 2010), pp. 427-433.
Cao et al., "Tissue transglutaminase links TGF-b, epithelial to mesenchymal transition and a stem cell phenotype in ovarian cancer". Oncogene (2012) 31, 2521-2534.
Kumar et al., "Tissue Transglutaminase Promotes Drug Resistance and Invasion by Inducing Mesenchymal Transition in Mammary Epithelial Cells". PLoS One. Oct. 2010. vol. 5. Issue 10. e 13390.
Lin et al., "Role of tissue transglutaminase 2 in the acquisition of a mesenchymal-like phenotype in highly invasive A431 tumor cells". Molecular Cancer 2011 10:87. http://www.molecular-cancer.com/content/10/1/87.
Extended European Search Report for application PCT/US2013059967 dated Jul. 18, 2016.
Extended European Search Report for 15764391.7 dated Oct. 18, 2017.
Shaban et al. "Synthesis of 1,3,4-thiadiazole and 1,2,4-triazole acyclo C-nucleosides," Journal of Carbohydrate Chemistry, 1997, 14(7): 985-994.
Cancer Prevention Overview, retrieved from http://www.cancer.gov/cancertopics/pdq/prevention/overview/patient, on Nov. 14, 2012.
Golub et al. "Molecular classication of cancer: class discovery and class prediction by gene expression monitoring," Science, 1999, 286: 531-537.
Kocienski. Protecting Groups. Thieme, 2005, p. 52.
Targeted Cancer Therapies Fact Sheet, retreived from http://www.cancer.gov/about-cancer/treatment/types/targeted-therapies/targeted-therapies-fact-sheet, retrieved Dec. 8, 2015.
Yale et al. "Synthetic hypoglycemic agents," Journal of the American Chemical Society, 1953, 75:676.

COMPOUNDS AND THEIR METHODS OF USE

CLAIM OF PRIORITY

This application is a national stage application under 35 U.S.C. § 371 of International Application No. PCT/CN2013/001428, filed Nov. 21, 2013, published as International Publication No. WO2014/079150 on May 30, 2014, which claims priority from International Application No. PCT/CN2012/085023, filed Nov. 22, 2012, and International Application No. PCT/CN2013/000294, filed Mar. 15, 2013, each of which is incorporated herein by reference in its entirety.

BACKGROUND OF INVENTION

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells is termed the Warburg Effect. As a result of this difference, pyruvate generated via the glycolytic pathway is converted to lactic acid, rather than being used to generate acetyl-CoA and eventually, the citrate utilized in a normal citric acid cycle. To compensate for these energetic changes and to maintain a citric acid cycle, cancer cells rely on glutamine metabolism which is achieved through an elevation of glutaminase activity. Exploitation of this phenomenon can be achieved by inhibition of this elevated glutaminase activity.

SUMMARY OF INVENTION

Described herein are heterocyclic containing, pharmaceutically acceptable salts, solvates, and hydrates thereof. The compounds can be used to treat a disorder described herein, for example, by inhibiting glutaminase in a patient. Also provided are compositions (e.g., pharmaceutical compositions) comprising a compound provided herewith and the use of such compositions in methods of treating diseases and conditions, for example, that are associated with the aberrant function of glutaminase or elevated activity of glutaminase, including, e.g., cancer.

In one embodiment, provided is a compound of formula (I) or a pharmaceutically acceptable salt thereof:

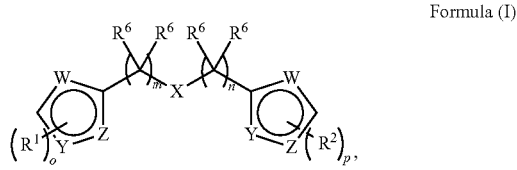

Formula (I)

wherein

X is an optionally substituted $C_3$-$C_7$ cycloalkylene;

each W, Y and Z is independently —S—, —CH=, —O—, —N=, or —NH—, provided that for each ring at least one of W, Y and Z is not —CH=;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, —O—$C_{1-6}$ alkylene$C_{1-6}$ alkoxy, —O-heterocyclyl, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —$OCHF_2$, —$SO_2$—$C_{1-6}$ alkyl, —$NO_2$, —$N(R^7)$—C(O)—$C_{1-6}$ alkyl, —C(O)$N(R^7)_2$, —$N(R^7)S(O)_{1-2}$—$C_{1-6}$ alkyl, —S(O)$_2N(R^7)_2$, —$N(R^7)_2$, —$C_{1-6}$ alkylene-$N(R^7)_2$, wherein said alkyl, $C_{1-6}$ alkoxy, —O—$C_{1-6}$ alkylene$C_{1-6}$ alkoxy, —O-heterocyclyl, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, —$SO_2$—$C_{1-6}$ alkyl, —$NO_2$, —$N(R^7)$—C(O)—$C_{1-6}$ alkyl, —C(O)$N(R^7)_2$, —$N(R^7)S(O)_{1-2}$—$C_{1-6}$ alkyl, —S(O)$_2N(R^7)_2$, —$N(R^7)_2$, or —$C_{1-6}$ alkylene-$N(R^7)_2$ is optionally substituted with 0-3 occurrences of $R^8$; or two adjacent $R^5$ moieties, taken together with the atoms to which they are attached form a cycloalkyl or heterocyclyl;

each $R^6$ is independently hydrogen, fluoro, $C_{1-6}$ alkyl, —OH, —$NH_2$, —$NH(CH_3)$, —$N(CH_3)_2$, or $C_{1-6}$ alkoxy;

each $R^7$ is independently hydrogen or $C_{1-6}$ alkyl;

each $R^8$ is independently halo, $C_{1-6}$ alkyl, $C_{1-6}$ haloalkyl, —OH, —$N(R^7)_2$, or $C_{1-6}$ alkoxy, —O—$C_{1-6}$ alkylene$C_{1-6}$ alkoxy, CN, $NO_2$, —$N(R^7)$—C(O)—$C_{1-6}$ alkyl, —C(O)N$(R^7)_2$, —$N(R^7)S(O)_{1-2}C_{1-6}$ alkyl, or —S(O)$_2N(R^7)_2$;

m is 0, 1, or 2;

n is 0, 1, or 2;

o is 1, 2 or 3; and p is 1, 2 or 3; provided that (1) when X is unsubstituted cyclopropyl, $R^1$ and $R^2$ are not both —$NH_2$ or —NH—C(O)-phenyl; (2) X is other than substituted cyclobutyl or substituted cyclopentyl; and (3) when X is unsubstituted cyclopropyl, and m and n are both 1, then $R^1$ and $R^2$ are not both —NH—C(O)-benzyl.

In another embodiment, provided is a composition comprising a compound of formula (I) or a pharmaceutically acceptable salt thereof. In some embodiments, the composition is a pharmaceutical composition.

In another embodiment, provided herein is a method for treating or preventing a disease, condition or disorder as described (e.g., treating) herein comprising administering a compound described herein, a pharmaceutically acceptable salt thereof or a pharmaceutical composition comprising a compound described herein or a pharmaceutically acceptable salt thereof.

In another embodiment, provided herein is a method of inhibiting glutaminase, e.g, in a patient in need thereof. In some embodiments, provided here is reducing the level of the product of glutaminase in a subject, e.g., a patient in need thereof. The methods include administering an effective amount of a compound described herein or a pharmaceutically acceptable salt thereof to a subject in need thereof, thereby inhibiting the level of glutaminase in the subject.

In another embodiment, provided herein is a method of treating a subject suffering from or susceptible to a disease or disorder associated with the aberrant function of glutaminase or elevated activity of glutaminase in a subject in need thereof. The method comprises the step of administering an effective amount of a compound described herein to the subject in need thereof, thereby treating, preventing or ameliorating the disease or disorder in the subject. In certain embodiments, the compound is provided in a pharmaceutical composition. In certain embodiments, the method includes identifying or selecting a subject who would benefit from inhibiting glutaminase or decreasing the level of glutaminase. E.g., the subject can be identified on the basis of the level of glutaminase activity in a cell or tissue sample of the subject for treatment of cancer associated with aberrant glutaminase function or activity. In another embodiment, the selected subject is a patient suffering from or susceptible to a disorder or disease identified herein, e.g., a disorder characterized by unwanted cell growth or proliferation, e.g., cancer or other neoplastic disorders.

In another embodiment, provided herein is a method for treating cancer in a subject, the method comprising: optionally, acquiring a subject sample; acquiring an evaluation of or evaluating the subject sample, wherein the subject sample is characterized by i) a low level of E-cadherin expression compared to a reference standard, ii) a high level of vimentin expression compared to a reference standard, or iii) a low or decreased level of pyruvate carboxylase expression; and administering to the subject in need thereof a therapeutically effective amount of a compound described here. In some embodiments, the subject sample is characterized by i) a low level of E-cadherin expression compared to a reference standard and ii) a high level of vimentin expression compared to a reference standard. In some embodiments, the subject sample is characterized or further characterized by low or decreased levels of pyruvate carboxylase expression compared to a reference standard.

In another embodiment, provided herein is a method for treating cancer in a subject characterized by i) a low level of E-cadherin expression compared to a reference standard, ii) a high level of vimentin expression compared to a reference standard, or iii) a low or decreased level of pyruvate carboxylase expression; comprising administering to the subject in need thereof a therapeutically effective amount of a compound described here. In some embodiments, the subject is characterized by i) a low level of E-cadherin expression compared to a reference standard and ii) a high level of vimentin expression compared to a reference standard. In some embodiments, the subject is characterized or further characterized by low or decreased levels of pyruvate carboxylase expression compared to a reference standard.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Compounds

Described herein are compounds and compositions that inhibit glutaminase. Compounds that inhibit glutaminase, can be used to treat disorders such as neoplastic disorders (e.g., cancer).

In one embodiment, provided is a compound of formula (I) or a pharmaceutically acceptable salt thereof, or a pharmaceutical composition comprising a compound of formula (I) or a pharmaceutically acceptable salt thereof:

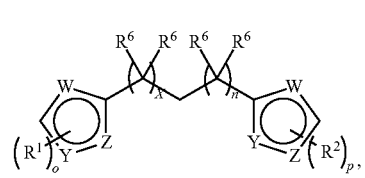

Formula (I)

wherein

X is an optionally substituted $C_3$-$C_7$ cycloalkylene;

each W, Y and Z is independently —S—, —CH=, —O—, —N=, or —NH—, provided that for each ring at least one of W, Y and Z is not —CH=;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, —O—$C_{1-6}$ alkylene$C_{1-6}$ alkoxy, —O-heterocyclyl, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —$OCHF_2$, —$SO_2$—$C_{1-6}$ alkyl, —$NO_2$, —$N(R^7)$—C(O)—$C_{1-6}$ alkyl, —$C(O)N(R^7)_2$, —$N(R^7)S(O)_{1-2}$—$C_{1-6}$ alkyl, —$S(O)_2N(R^7)_2$, —$N(R^7)_2$, —$C_{1-6}$ alkylene-$N(R^7)_2$, wherein said alkyl, $C_{1-6}$ alkoxy, alkylene$C_{1-6}$ alkoxy, —O-heterocyclyl, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, —$SO_2$—$C_{1-6}$ alkyl, —$NO_2$, —$N(R^7)$—C(O)—$C_{1-6}$ alkyl, —$C(O)N(R^7)_2$, —$N(R^7)S(O)_{1-2}$—$C_{1-6}$ alkyl, —$S(O)_2N(R^7)_2$, —$N(R^7)_2$, or —$C_{1-6}$ alkylene-$N(R^7)_2$ is optionally substituted with 0-3 occurrences of $R^8$; or two adjacent $R^5$ moieties, taken together with the atoms to which they are attached form a cycloalkyl or heterocyclyl;

each $R^6$ is independently hydrogen, fluoro, $C_{1-6}$ alkyl, —OH, —$NH_2$, —$NH(CH_3)$, —$N(CH_3)_2$, or $C_{1-6}$ alkoxy;

each $R^7$ is independently hydrogen or $C_{1-6}$ alkyl;

each $R^8$ is independently halo, $C_{1-6}$ alkyl, $C_{1-6}$ haloalkyl, —OH, —$N(R^7)_2$, or $C_{1-6}$ alkoxy, —O—$C_{1-6}$ alkylene$C_{1-6}$ alkoxy, CN, $NO_2$, —$N(R^7)$—C(O)—$C_{1-6}$ alkyl, —$C(O)N(R^7)_2$, —$N(R^7)S(O)_{1-2}C_{1-6}$ alkyl, or —$S(O)_2N(R^7)_2$;

m is 0, 1, or 2;

n is 0, 1, or 2;

o is 1, 2 or 3; and p is 1, 2 or 3; provided that (1) when X is unsubstituted cyclopropyl, $R^1$ and $R^2$ are not both —$NH_2$ or —NH—C(O)-phenyl; (2) X is other than substituted cyclobutyl or substituted cyclopentyl; and (3) when X is unsubstituted cyclopropyl, and m and n are both 1, then $R^1$ and $R^2$ are not both —NH—C(O)-benzyl.

In one embodiment, provided is a compound of formula (I) or a pharmaceutically acceptable salt thereof, or a pharmaceutical composition comprising a compound of formula (I) or a pharmaceutically acceptable salt thereof:

Formula (I)

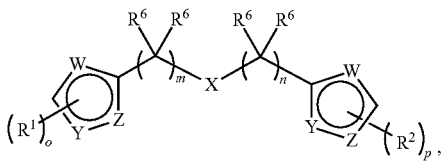

wherein

X is an optionally substituted $C_3$-$C_7$ cycloalkylene;

each W, Y and Z is independently —S—, —CH═, —O—, —N═, or —NH—, provided that for each ring at least one of W, Y and Z is not —CH═;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —$OCHF_2$, —$SO_2$—$C_{1-6}$ alkyl, —$NO_2$, —$N(R^7)$—C(O)—$C_{1-6}$ alkyl, —$N(R^7)_2$, or two adjacent $R^5$ moieties, taken together with the atoms to which they are attached form a heterocyclyl;

each $R^6$ is independently hydrogen, fluoro, $C_{1-6}$ alkyl, —OH, —$NH_2$, —$NH(CH_3)$, —$N(CH_3)_2$, or $C_{1-6}$ alkoxy;

each $R^7$ is independently hydrogen or $C_{1-6}$ alkyl;

m is 0, 1, or 2;

n is 0, 1, or 2;

o is 1, 2 or 3; and p is 1, 2 or 3; provided that (1) when X is unsubstituted cyclopropyl, $R^1$ and $R^2$ are not both —$NH_2$ or —NH—C(O)-phenyl; (2) X is other than substituted cyclobutyl or substituted cyclopentyl; and (3) when X is unsubstituted cyclopropyl, and m and n are both 1, then $R^1$ and $R^2$ are not both —NH—C(O)-benzyl.

In one embodiment, provided is a compound of formula (I) or a pharmaceutically acceptable salt thereof, or a pharmaceutical composition comprising a compound of formula (I) or a pharmaceutically acceptable salt thereof:

Formula (I)

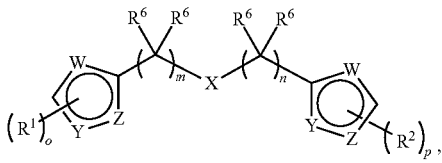

wherein

X is $C_3$-$C_7$ cycloalkylene;

each W, Y and Z is independently —S—, —CH═, —O—, —N═, or —NH—, provided that at least one of W, Y and Z is not —CH═;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, —O—$C_{1-6}$ alkylene$C_{1-6}$ alkoxy, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —$OCHF_2$, —$SO_2$—$C_{1-6}$ alkyl, —$NO_2$, —$N(R^7)$—C(O)—$C_{1-6}$ alkyl, —C(O)N$(R^7)_2$, —$N(R^7)S(O)_{1-2}$—$C_{1-6}$ alkyl, —$S(O)_2N(R^7)_2$, —$N(R^7)_2$, —$C_{1-6}$ alkylene-$N(R^7)_2$, wherein said alkyl, $C_{1-6}$ alkoxy, —O—$C_{1-6}$ alkylene$C_{1-6}$ alkoxy, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, —$SO_2$—$C_{1-6}$ alkyl, —$NO_2$, —$N(R^7)$—C(O)—$C_{1-6}$ alkyl, —C(O)N$(R^7)_2$, —$N(R^7)S(O)_{1-2}$—$C_{1-6}$ alkyl, —$S(O)_2N(R^7)_2$, —$N(R^7)_2$, or —$C_{1-6}$ alkylene-$N(R^7)_2$ is optionally substituted with 0-3 occurrences of $R^8$; or two adjacent $R^5$ moieties, taken together with the atoms to which they are attached form a cycloalkyl or heterocyclyl;

each $R^6$ is independently hydrogen, fluoro, $C_{1-6}$ alkyl, —OH, —$NH_2$, —$NH(CH_3)$, —$N(CH_3)_2$, or $C_{1-6}$ alkoxy;

each $R^7$ is independently hydrogen or $C_{1-6}$ alkyl;

each $R^8$ is independently halo, $C_{1-6}$ alkyl, $C_{1-6}$ haloalkyl, —OH, —$N(R^7)_2$, or $C_{1-6}$ alkoxy, —O—$C_{1-6}$ alkylene$C_{1-6}$ alkoxy, CN, $NO_2$, —$N(R^7)$—C(O)—$C_{1-6}$ alkyl, —C(O)N$(R^7)_2$, —$N(R^7)S(O)_{1-2}C_{1-6}$ alkyl, or —$S(O)_2N(R^7)_2$;

m is 0, 1, or 2;

n is 0, 1, or 2;

o is 1, 2 or 3; and p is 1, 2 or 3; provided that (1) when X is unsubstituted cyclopropyl, $R^1$ and $R^2$ are not both NH-phenyl; and (2) X is other than substituted cyclobutyl or substituted cyclopentyl.

In one embodiment, provided is a compound of formula (I) or a pharmaceutically acceptable salt thereof, or a pharmaceutical composition comprising a compound of formula (I) or a pharmaceutically acceptable salt thereof:

Formula (I)

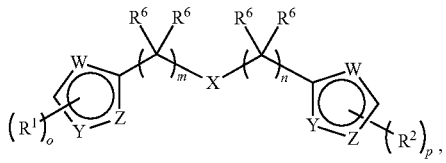

wherein

X is $C_3$-$C_7$ cycloalkylene;

each W, Y and Z is independently —S—, —CH═, —O—, —N═, or —NH—, provided that at least one of W, Y and Z is not —CH═;

each $R^1$ and $R^2$ is independently —$NH_2$, —$N(R^3)$—C(O)—$R^4$, —C(O)—$N(R^3)$—$R^4$, —$N(R^3)$—C(O)—O—$R^4$, —$N(R^3)$—C(O)—$N(R^3)$—$R^4$ or —$N(R^3)$—C(O)—$SR^4$;

each $R^3$ is independently hydrogen, $C_{1-6}$ alkyl or aryl;

each $R^4$ is independently $C_{1-6}$ alkyl, aryl, heteroaryl, aralkyl, heteroaralkyl, cycloalkyl, cycloalkylalkyl, heterocyclylalkyl, or heterocyclyl, each of which is substituted with 0-3 occurrences of $R^5$;

each $R^5$ is independently $C_{1-6}$ alkyl, $C_{1-6}$ alkoxy, $C_{1-6}$ thioalkoxy, $C_{1-6}$ haloalkyl, $C_{3-7}$ cycloalkyl, $C_{3-7}$ cycloalkylalkyl, aryl, heteroaryl, aralkyl, heteroaralkyl, heterocyclylalkyl, heterocyclyl, cyano, halo, oxo, —OH, —$OCF_3$, —OCHF$_2$, —SO$_2$—C$_{1-6}$ alkyl, —NO$_2$, —N(R$^7$)—C(O)—C$_{1-6}$ alkyl, —N(R$^7$)$_2$, or two adjacent R$^5$ moieties, taken together with the atoms to which they are attached form a heterocyclyl;

each R$^6$ is independently hydrogen, fluoro, C$_{1-6}$ alkyl, —OH, —NH$_2$, —NH(CH$_3$), —N(CH$_3$)$_2$, or C$_{1-6}$ alkoxy;

each R$^7$ is independently hydrogen or C$_{1-6}$ alkyl;

m is 0, 1, or 2;

n is 0, 1, or 2;

o is 1, 2 or 3; and p is 1, 2 or 3; provided that (1) when X is unsubstituted cyclopropyl, R$^1$ and R$^2$ are not both NH-phenyl; and (2) X is other than substituted cyclobutyl or substituted cyclopentyl.

In some embodiments, X is unsubstituted cyclopropyl. In some embodiments, X is unsubstituted cyclobutyl. In some embodiments, X is unsubstituted cyclopentyl. In some embodiments, X is cyclohexyl. In some embodiments, X is cycloheptyl. In some embodiments, X is substituted with 1-3 substituents. In some embodiments, X is substituted with 1 substituent. In some embodiments, X is substituted with 2 substituents.

In some embodiments, each Y is —N═. In some embodiments, each Z is —N═. In some embodiments, each W is —S—. In some aspects of these embodiments, each W is —S—, each Y is —N═ and each Z is —N═.

In some embodiments, o is 1. In some embodiments, p is 1. In some embodiments, o is 1 and p is 1.

In some embodiments, m is 0. In some embodiments, n is 0. In some embodiments, m is 0 and n is 0. In some embodiments, R$^1$ and R$^2$ are the same. In some embodiments, R$^1$ and R$^2$ are different.

In some embodiments, m is 1. In some embodiments, n is 1. In some embodiments, n is 1 and m is 1. In some aspects of these embodiments, each R$^6$ is hydrogen. In some embodiments, R$^1$ and R$^2$ are the same. In some embodiments, R$^1$ and R$^2$ are different.

In some embodiments, R$^1$ and R$^2$ are each —N(R$^3$)—C(O)—R$^4$ wherein each R$^3$ is hydrogen and each R$^4$ is aralkyl or heteroaralkyl, each of which is substituted with 0-3 occurrences of R$^5$. In some aspects of these embodiments, R$^1$ and R$^2$ are the same.

In some embodiments, R$^1$ and R$^2$ are each —N(R$^3$)—C(O)—R$^4$ wherein each R$^3$ is hydrogen. In some aspects of these embodiments, each R$^4$ is aralkyl substituted with 0-3 occurrences of R$^5$. In some aspects of these embodiments, R$^1$ and R$^2$ are the same.

In some aspects of these embodiments, each R$^4$ is aralkyl (e.g., benzyl) substituted with 0 occurrences of R$^5$. In some aspects of these embodiments, each R$^4$ is aralkyl (e.g., benzyl) substituted with one occurrence of R$^5$. In some further aspects of these embodiments, each R$^5$ is —N(CH$_3$)$_2$. In other further aspects of these embodiments, each R$^5$ is C$_{1-6}$ alkoxy (e.g., methoxy or isopropoxy). In other further aspects of these embodiments, each R$^5$ is —O-heterocyclyl (e.g., —O-oxetane). In other further aspects of these embodiments, each R$^5$ is halo (e.g., fluoro or chloro). In other further aspects of these embodiments, each R$^5$ is —NH$_2$. In other further aspects of these embodiments, each R$^5$ is —SO$_2$—CH$_3$. In other further aspects of these embodiments, each R$^5$ is —NHC(O)CH$_3$. In other further aspects of these embodiments, each R$^5$ is —NO$_2$. In other further aspects of these embodiments, each R$^5$ is cyano. In other further aspects of these embodiments, each R$^5$ is C$_{1-6}$ haloalkoxy (e.g., trifluoromethoxy). In other further aspects of these embodiments, each R$^5$ is C$_{1-6}$ haloalkyl (e.g., trifluoromethyl). In other further aspects of these embodiments, each R$^5$ is C$_{1-6}$ alkyl (e.g., methyl). In some aspects of these embodiments, each R$^4$ is aralkyl (e.g., benzyl) substituted with two occurrences of R$^5$. In some further aspects of these embodiments, two R$^5$ are halo (e.g., fluoro) and the other two R$^5$ are C$_{1-6}$ alkoxy (e.g., methoxy). In other further aspects of these embodiments, each R$^5$ is halo (e.g., fluoro). In other further aspects of these embodiments, each R$^5$ is C$_{1-6}$ alkoxy (e.g., methoxy). In other further aspects, of these embodiments, two adjacent R$^5$ moieties are taken together with the atoms to which they are attached to form a heterocyclyl ring resulting in a moiety of the following structure:

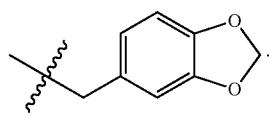 [SMILES: *Cc1ccc2c(c1)OCO2]

In some aspects of these embodiments, each R$^4$ is heteroaralkyl (e.g., 2-pyridinylmethyl, 2-pyridinylethyl, 3-pyridinylmethyl, 4-pyridinylmethyl, 2-pyrazinylmethyl, 2-thiophenylmethyl, 2-indolylmethyl, 4-indolylmethyl, 2-pyrimidinylmethyl or 2-thiazolylmethyl) substituted with 0-3 occurrences of R$^5$. In some aspects of these embodiments, each R$^4$ is heteroaralkyl (e.g., 2-pyridinylmethyl, 2-pyridinylethyl, 3-pyridinylmethyl, 4-pyridinylmethyl, 2-pyrazinylmethyl, 2-thiophenylmethyl, 2-indolylmethyl, 3-indolylmethyl, 4-indolylmethyl, 2-pyrimidinylmethyl or 2-thiazolylmethyl) substituted with 0 occurrences of R$^5$. In other aspects of these embodiments, each R$^4$ is heteroaralkyl (e.g., 5-isoxazolyl, 2-pyridinylmethyl or 3-indolylmethyl) substituted with one occurrence of R$^5$. In some further aspects of these embodiments, each R$^5$ is C$_{1-6}$ alkyl (e.g., methyl). In other further aspects of these embodiments, each R$^5$ is C$_{1-6}$ alkoxy (e.g., methoxy). In other further aspects of these embodiments, each R$^5$ is cyano. In other further aspects of these embodiments, each R$^5$ is —N(CH$_3$)$_2$. In other further aspects of these embodiments, each R$^5$ is —NHC(O)CH$_3$. In other further aspects of these embodiments, each R$^5$ is halo (e.g., bromo).

In some aspects of these embodiments, each R$^4$ is C$_{1-6}$ alkyl (e.g., methyl, ethyl, n-propyl or isopropyl) substituted with 0-3 occurrences of R$^5$. In some aspects of these embodiments, each R$^4$ is C$_{1-6}$ alkyl (e.g., methyl, ethyl, n-propyl or isopropyl) substituted with 0 occurrences of R$^5$. In other aspects of these embodiments, each R$^4$ is C$_{1-6}$ alkyl (e.g., methyl, ethyl or tert-butyl) substituted with one occurrence of R$^5$. In some further aspects of these embodiments, each R$^5$ is C$_{1-6}$ thioalkoxy (e.g., thiomethoxy). In other further aspects of these embodiments, each R$^5$ is C$_{1-6}$ haloalkyl (e.g., trifluoromethyl). In other further aspects of these embodiments, each R$^5$ is —OH.

In some aspects of these embodiments, each R$^4$ is aryl (e.g., phenyl) substituted with 0-3 occurrences of R$^5$. In some aspects of these embodiments, each R$^4$ is aryl (e.g., phenyl) substituted with 0 occurrences of R$^5$.

In some aspects of these embodiments, each R$^4$ is aryl (e.g., phenyl) substituted with one occurrence of R$^5$, wherein R$^5$ is heterocyclyl (e.g., azetidinyl), and R$^5$ is substituted with two occurrences of halo (e.g., fluoro).

In some aspects of these embodiments, each R$^4$ is heterocyclyl (e.g., 3-tetrahydrofuranyl) substituted with 0-3 occurrences of R$^5$. In some aspects of these embodiments, each R$^4$ is heterocyclyl (e.g., 3-tetrahydrofuranyl) substituted with 0 occurrences of R$^5$.

In some aspects of these embodiments, each R⁴ is heterocyclylalkyl (e.g., 2-tetrahydrofuranylmethyl) substituted with 0-3 occurrences of R⁵. In some aspects of these embodiments, each R⁴ is heterocyclylalkyl (e.g., 2-tetrahydrofuranylmethyl) substituted with 0 occurrences of R⁵. In some aspects of these embodiments, each R⁴ is heterocyclylalkyl substituted with 0 occurrences of R⁵ and is represented by the following structure:

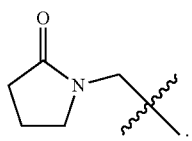 [SMILES: *CN1CCCC1=O]

In some aspects of these embodiments, each R⁴ is cycloalkyl (e.g., cyclopentyl) substituted with 0-3 occurrences of R⁵. In some aspects of these embodiments, each R⁴ is cycloalkyl (e.g., cyclopentyl) substituted with 0 occurrences of R⁵.

In some aspects of these embodiments, each R⁴ is cycloalkylalkyl (e.g., cyclopropylmethyl) substituted with 0-3 occurrences of R⁵. In some aspects of these embodiments, each R⁴ is cycloalkylalkyl (e.g., cyclopropylmethyl) substituted with 0 occurrences of R⁵.

In some aspects of these embodiments, each R⁴ is $C_{1-6}$ alkenyl (e.g., ethenyl) substituted with 0-3 occurrences of R⁵. In some aspects of these embodiments, each R⁴ is $C_{1-6}$ alkenyl (e.g., ethenyl) substituted with one occurrence of R⁵. In some further aspect of these embodiments, each R⁵ is heteroaryl (e.g., 2-pyridinyl).

In some aspects of these embodiments, one R⁴ is $C_{1-6}$ alkyl (e.g., methyl) substituted with 0 occurrences of R⁵ and the other R⁴ is heteroaralkyl (e.g., 3-indolylmethyl) substituted with one occurrence of R⁵, wherein R⁵ is $C_{1-6}$ alkyl (e.g., methyl).

In some aspects of these embodiments, one R⁴ is $C_{1-6}$ alkyl (e.g., methyl) substituted with 0 occurrences of R⁵ and the other R⁴ is heteroaralkyl (e.g., 2-pyridyl) substituted with one occurrence of R⁵, wherein R⁵ is heterocyclyl (e.g., azetidinyl), and R⁵ is substituted with two occurrences of halo (e.g., fluoro).

In some aspects of these embodiments, one R⁴ is $C_{1-6}$ alkyl (e.g., methyl) substituted with 0 occurrences of R⁵ and the other R⁴ is heteroaralkyl (e.g., 3-indolylmethyl) substituted with one occurrence of R⁵, wherein R⁵ is $C_{1-6}$ alkyl (e.g., methyl).

In some aspects of these embodiments, one R⁴ is $C_{1-6}$ alkyl (e.g., methyl) and the other R⁴ is heteroaralkyl (e.g., 2-pyridinylmethyl), each of which is substituted with 0 occurrences of R⁵.

In some aspects of these embodiments, one R⁴ is heteroaralkyl (e.g., 2-pyridinylmethyl) substituted with 0 occurrences of R⁵ and the other R⁴ is aralkyl (e.g., benzyl) substituted with one occurrence of R⁵, wherein R⁵ is $C_{1-6}$ alkoxy (e.g., methoxy).

In some aspects of these embodiments, one R⁴ is $C_{1-6}$ alkyl (e.g., methyl) substituted with 0 occurrences of R⁵ and the other R⁴ is aralkyl (e.g., benzyl) substituted with one occurrence of R⁵, wherein R⁵ is $C_{1-6}$ alkoxy (e.g., methoxy).

In some embodiments, R² is —NH₂ and R¹ is —N(R³)—C(O)—R⁴, wherein R³ is hydrogen and R⁴ is heteroaralkyl (e.g., 2-pyridinylmethyl) substituted with 0 occurrences of R⁵.

In some embodiments, each R⁶ is H.

In some embodiments, a compound of Formula (I) is represented by a compound of Formula (II):

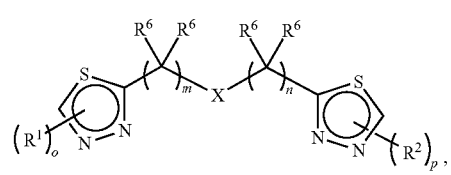

(II)

wherein R¹, R², R³, R⁴, R⁵, R⁶, o, p, m, n and X are as defined in Formula (I).

In some embodiments, a compound of Formula (I) or (II) is represented by a compound of Formula (IIa):

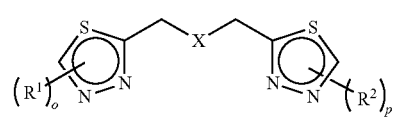

(IIa)

wherein R¹, R², R³, R⁴, R⁵, o, p and X are as defined in Formula (I).

In some embodiments, a compound of Formula (I), (II) or (IIa) is represented by a compound of Formula (III):

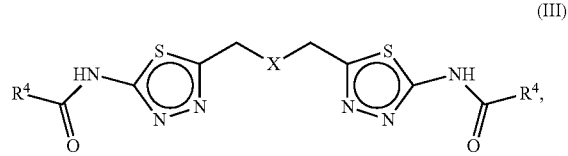

(III)

wherein R⁴, R⁵ and X are as defined in Formula (I).

In some embodiments, a compound of Formula (I) is represented by a compound of Formula (IV):

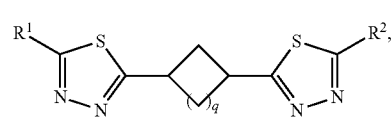

(IV)

wherein R¹, R², R³, R⁴ and R⁵ are as defined in Formula (I) and q is 0, 1, 2, 3 or 4.

In some embodiments, a compound of Formula (I) or (IV) is represented by a compound of Formula (IVa):

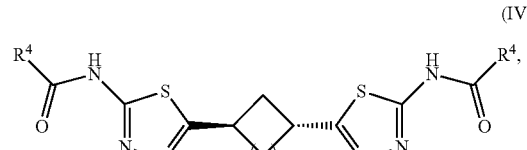

(IVa)

wherein R⁴, R⁵ and q are as defined in Formula (IV).

In some embodiments, a compound of Formula (I) or (IV) is represented by a compound of Formula (IVb):

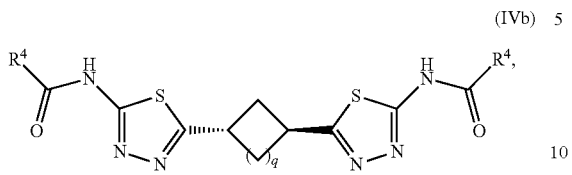

(IVb)

wherein $R^4$, $R^5$ and q are as defined in Formula (IV).

In some embodiments, a compound of Formula (I) or (IV) is represented by a compound of Formula (IVc):

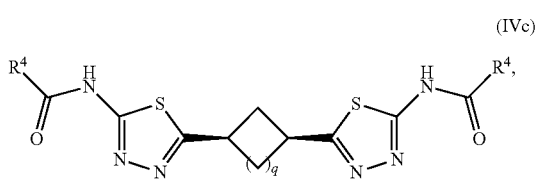

(IVc)

wherein $R^4$, $R^5$ and q are as defined in Formula (IV).

In some embodiments, a compound of Formula (I) is represented by a compound of Formula (V):

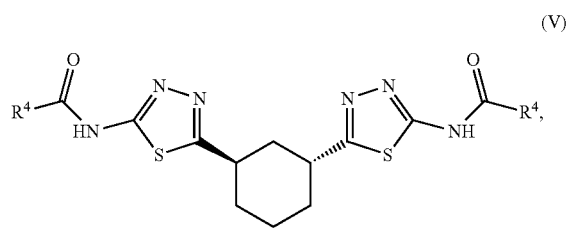

(V)

wherein $R^4$ is $C_{1-6}$ alkyl, aralkyl or heteroaralkyl substituted with 0, 1 or 2 occurrences of $R^5$, wherein $R^5$ is selected from methyl, methoxy, —$NH_2$, —$N(CH_3)_2$, —$SO_2$—$CH_3$, —$NHC(O)CH_3$, $NO_2$, CN, bromo or fluoro. In some embodiments of Formula (V), each $R^4$ is the same. In some embodiments of Formula (V), each $R^4$ is different.

In some embodiments, a compound of Formula (I) is represented by a compound of Formula (Va):

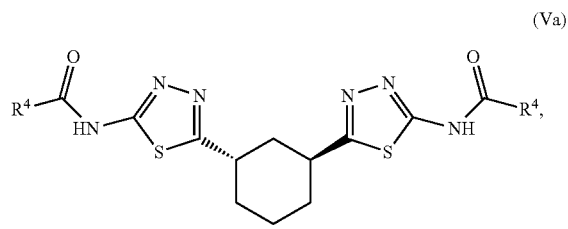

(Va)

wherein $R^4$ is $C_{1-6}$ alkyl, aralkyl or heteroaralkyl substituted with 0, 1 or 2 occurrences of $R^5$, wherein $R^5$ is selected from methyl, methoxy, —$NH_2$, —$N(CH_3)_2$, —$SO_2$—$CH_3$, —$NHC(O)CH_3$, $NO_2$, CN, bromo or fluoro. In some embodiments of Formula (Va), each $R^4$ is the same. In some embodiments of Formula (Va), each $R^4$ is different.

In some embodiments, a compound of Formula (I) is represented by a compound of Formula (Vb):

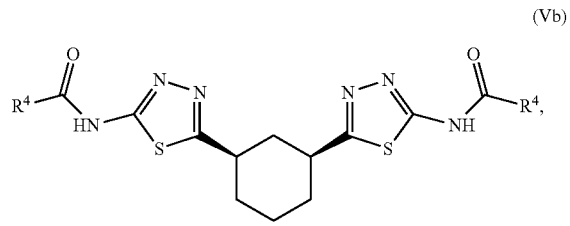

(Vb)

wherein $R^4$ is $C_{1-6}$ alkyl, aralkyl or heteroaralkyl substituted with 0, 1 or 2 occurrences of $R^5$, wherein $R^5$ is selected from methyl, methoxy, —$NH_2$, —$N(CH_3)_2$, —$SO_2$—$CH_3$, —$NHC(O)CH_3$, $NO_2$, CN, bromo or fluoro. In some embodiments of Formula (Vb), each $R^4$ is the same. In some embodiments of Formula (Vb), each $R^4$ is different.

In some embodiments, a compound of Formula (I) is represented by a compound of Formula (VI):

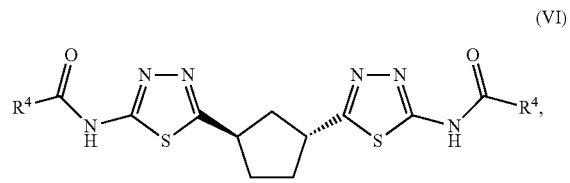

(VI)

wherein $R^4$ is aralkyl substituted with 1 occurrence of $R^5$, wherein $R^5$ is methoxy. In some aspects of these embodiments, each $R^4$ is the same.

In some embodiments, a compound of Formula (I) is represented by a compound of Formula (VIa):

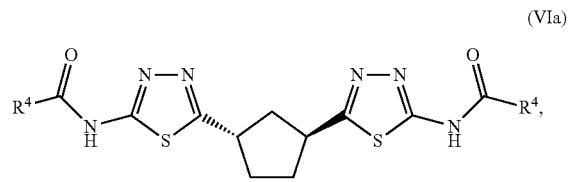

(VIa)

wherein $R^4$ is aralkyl substituted with 1 occurrence of $R^5$, wherein $R^5$ is methoxy. In some aspects of these embodiments, each $R^4$ is the same.

In some embodiments, a compound of Formula (I) is represented by a compound of Formula (VIb):

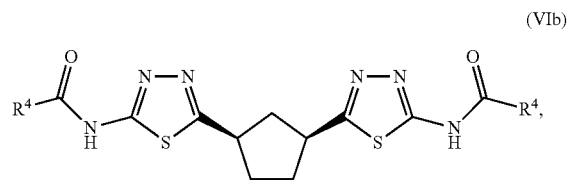

(VIb)

wherein $R^4$ is aralkyl substituted with 1 occurrence of $R^5$, wherein $R^5$ is methoxy. In some aspects of these embodiments, each $R^4$ is the same.

In certain embodiments, exemplary compounds of Formula I include the compounds described in Table 1 and in the Examples. A compound described herein may be tested for its ability to inhibit glutaminase, e.g., by an assay as described in the Examples. For simplicity, the inhibition activity of these compounds is represented as an IC$_{50}$ tested in an assay of Example A or Example B in Table 1. Exemplary compounds are shown in Table 1 below. As shown, "A" refers to an inhibitor of glutaminase with an IC$_{50}$<100 nM. "B" refers to inhibitor of glutaminase with an IC$_{50}$ between 100 nM and 500 nM. "C" refers to inhibitor of glutaminase with an IC$_{50}$ between 500 nM and 1000 nM. "D" refers to inhibitor of glutaminase with an IC$_{50}$ between 1 μM and 2 μM. "E" refers to inhibitor of glutaminase with an IC$_{50}$ between 2 μM and 10 μM. "N/A" refers to compounds wherein the IC$_{50}$ is unavailable.

TABLE 1

| Cmpd # | Structure | IC$_{50}$ |
|---|---|---|
| 1 | 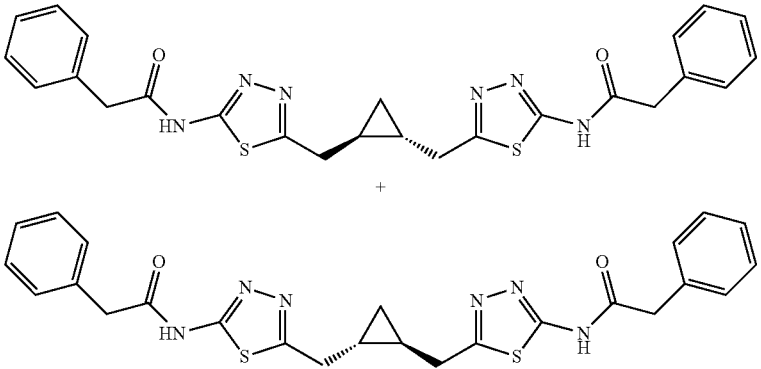 [SMILES: O=C(Cc1ccccc1)Nc1nnc(C[C@H]2C[C@@H]2Cc2nnc(NC(=O)Cc3ccccc3)s2)s1 ; O=C(Cc1ccccc1)Nc1nnc(C[C@@H]2C[C@H]2Cc2nnc(NC(=O)Cc3ccccc3)s2)s1] | B |
| 2 | 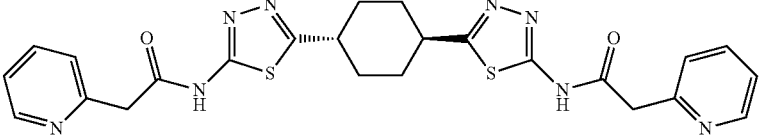 | C |
| 3 | 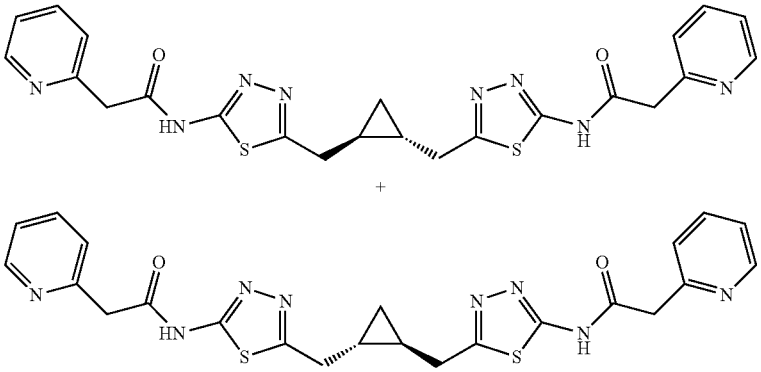 [SMILES: O=C(Cc1ccccn1)Nc1nnc(C[C@H]2C[C@@H]2Cc2nnc(NC(=O)Cc3ccccn3)s2)s1 ; O=C(Cc1ccccn1)Nc1nnc(C[C@@H]2C[C@H]2Cc2nnc(NC(=O)Cc3ccccn3)s2)s1] | C |
| 4 | 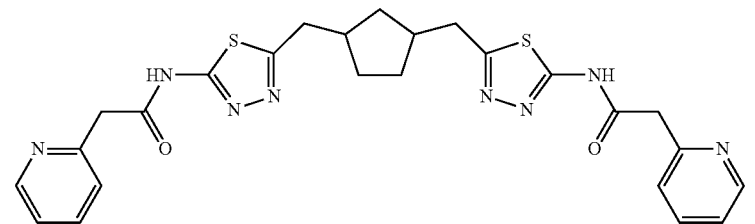 [SMILES: O=C(Cc1ccccn1)Nc1nnc(CC2CCC(Cc3nnc(NC(=O)Cc4ccccn4)s3)C2)s1] | E |

TABLE 1-continued

| Cmpd # | Structure | IC$_{50}$ |
|---|---|---|
| 5 | | B |
| 6 | | B |
| 7 | 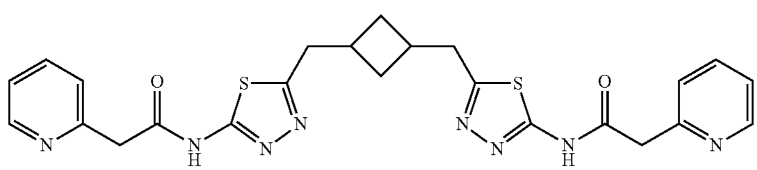 [SMILES: O=C(Cc1ccccn1)Nc1nnc(CC2CC(Cc3nnc(NC(=O)Cc4ccccn4)s3)C2)s1] | E |
| 8 | 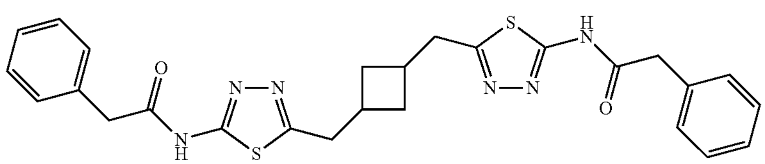 [SMILES: O=C(Cc1ccccc1)Nc1nnc(CC2CC(Cc3nnc(NC(=O)Cc4ccccc4)s3)C2)s1] | B |
| 9 | | A |

TABLE 1-continued

| Cmpd # | Structure | IC$_{50}$ |
|---|---|---|
| 10 | 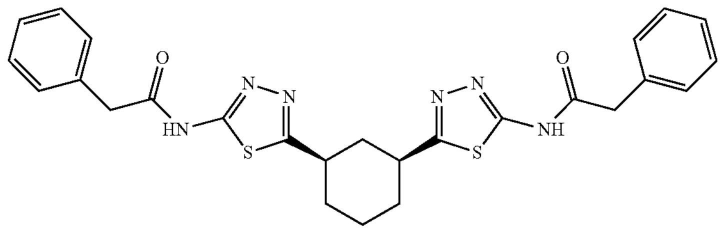 [SMILES: O=C(Cc1ccccc1)Nc1nnc([C@@H]2CCC[C@H](c3nnc(NC(=O)Cc4ccccc4)s3)C2)s1] | D |
| 11 | 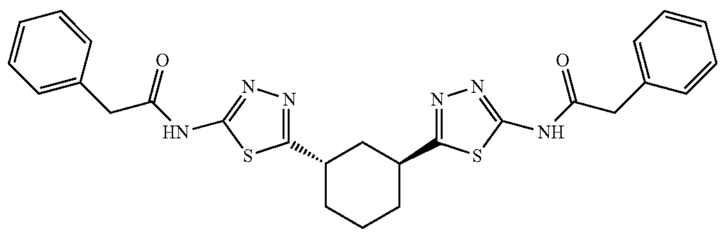 [SMILES: O=C(Cc1ccccc1)Nc1nnc([C@H]2CCC[C@H](c3nnc(NC(=O)Cc4ccccc4)s3)C2)s1] | A |
| 12 | | C |
| 13 | | B |

TABLE 1-continued
| Cmpd # | Structure | IC$_{50}$ |
|---|---|---|
| 14 | 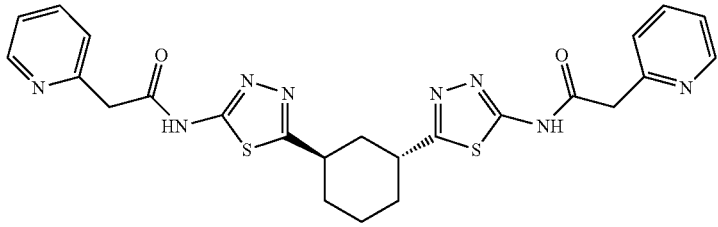 | A |
| 15 | 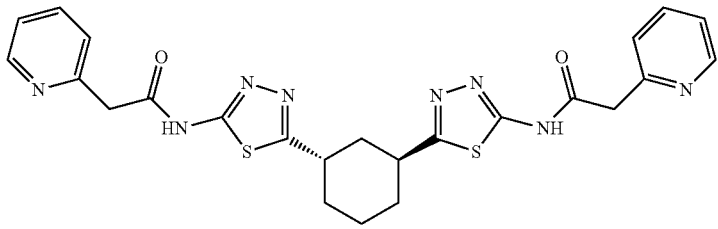 | C |
| 16 | 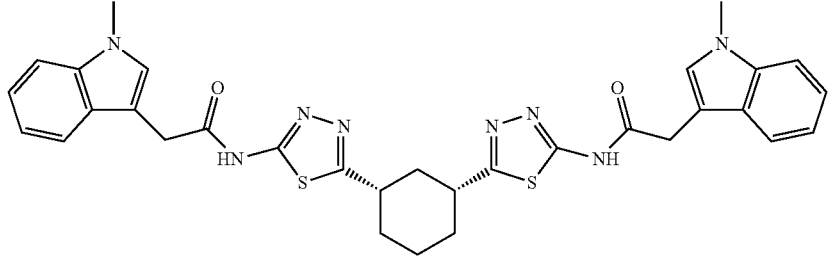 [SMILES: Cn1cc(CC(=O)Nc2nnc([C@@H]3CCC[C@H](c4nnc(NC(=O)Cc5cn(C)c6ccccc56)s4)C3)s2)c2ccccc21] | B |
| 17 | 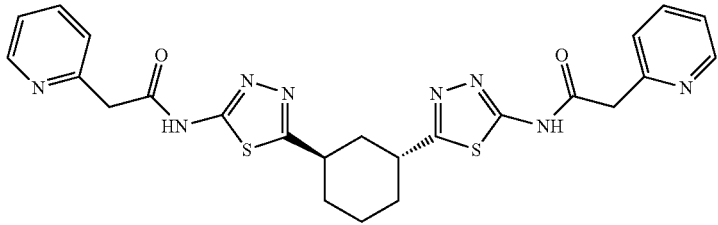 | D |

TABLE 1-continued

| Cmpd # | Structure | IC$_{50}$ |
|---|---|---|
| 18 | 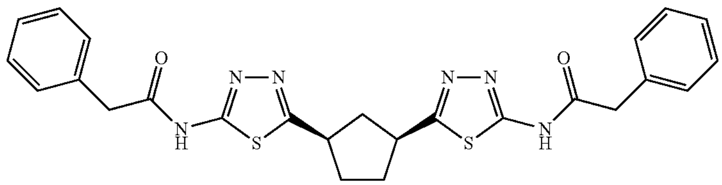 [SMILES: O=C(Cc1ccccc1)Nc1nnc([C@@H]2CC[C@H](c3nnc(NC(=O)Cc4ccccc4)s3)C2)s1] | D |
| 19 | 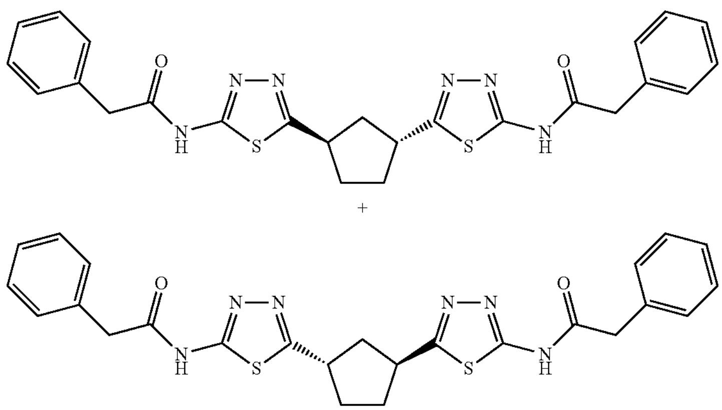 [SMILES: O=C(Cc1ccccc1)Nc1nnc([C@@H]2CC[C@@H](c3nnc(NC(=O)Cc4ccccc4)s3)C2)s1 ; O=C(Cc1ccccc1)Nc1nnc([C@H]2CC[C@H](c3nnc(NC(=O)Cc4ccccc4)s3)C2)s1] | B |
| 20 | 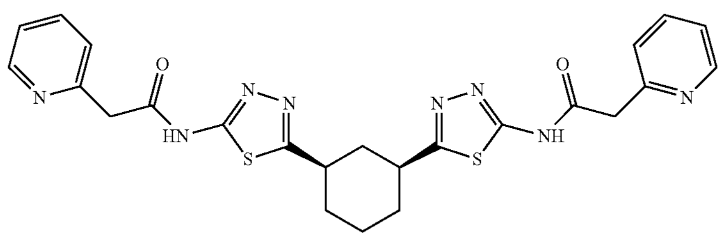 [SMILES: O=C(Cc1ccccn1)Nc1nnc([C@@H]2CCC[C@H](c3nnc(NC(=O)Cc4ccccn4)s3)C2)s1] | D |
| 21 | 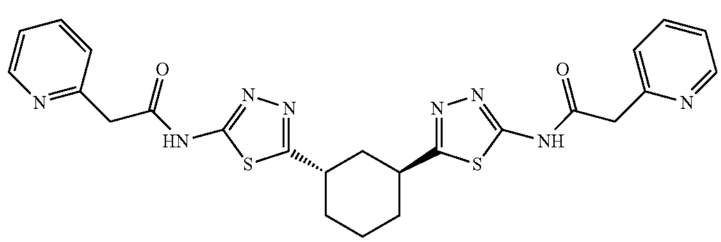 [SMILES: O=C(Cc1ccccn1)Nc1nnc([C@H]2CCC[C@H](c3nnc(NC(=O)Cc4ccccn4)s3)C2)s1] | A |

TABLE 1-continued
| Cmpd # | Structure | IC$_{50}$ |
|---|---|---|
| 22 | 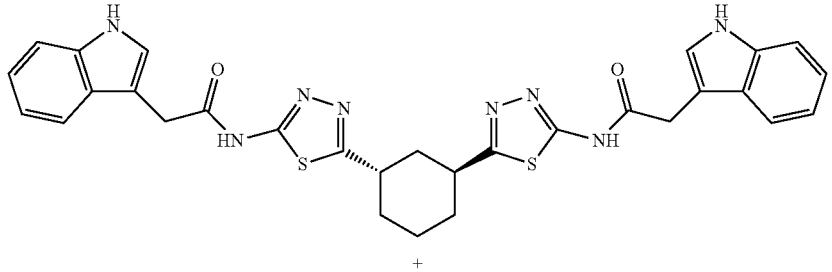 + 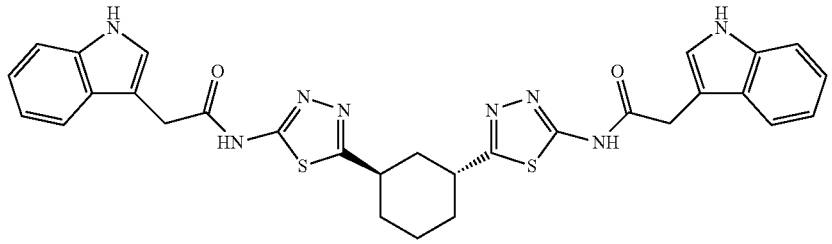 | A |
| 23 | 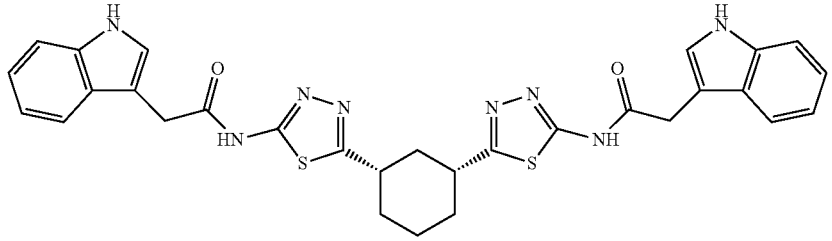 [SMILES: O=C(Cc1c[nH]c2ccccc12)Nc1nnc([C@@H]2CCC[C@H](c3nnc(NC(=O)Cc4c[nH]c5ccccc45)s3)C2)s1] | B |
| 24 | 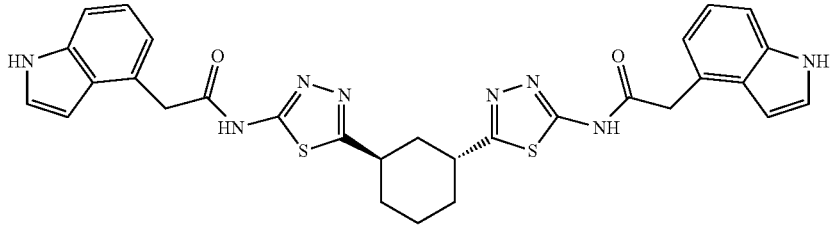 + 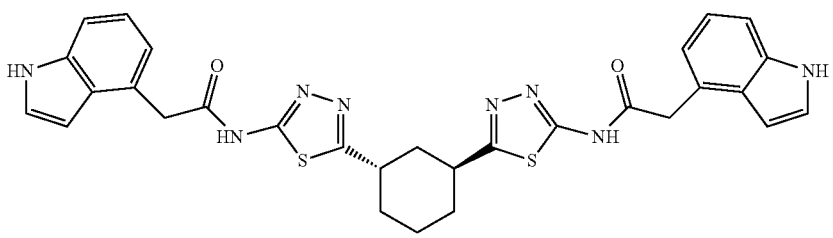 | A |
| 25 | 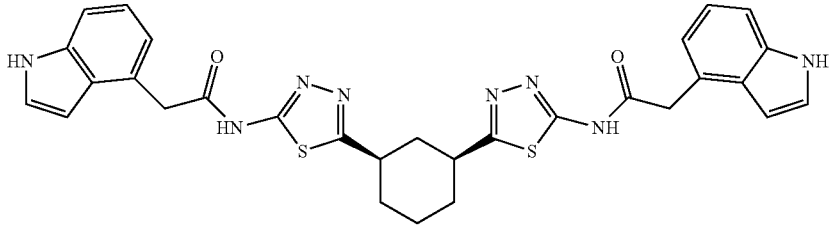 [SMILES: O=C(Cc1cccc2[nH]ccc12)Nc1nnc([C@@H]2CCC[C@H](c3nnc(NC(=O)Cc4cccc5[nH]ccc45)s3)C2)s1] | C |

TABLE 1-continued
| Cmpd # | Structure | IC$_{50}$ |
|---|---|---|
| 26 | 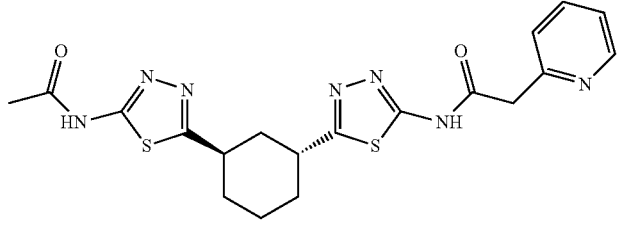 | B |
| 27 | 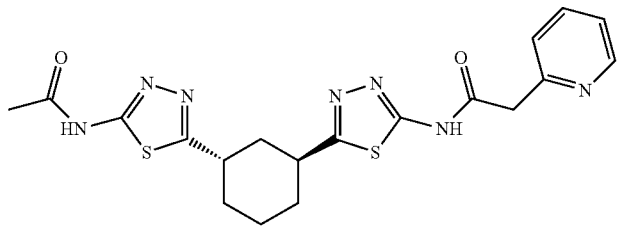 | A |
| 28 | 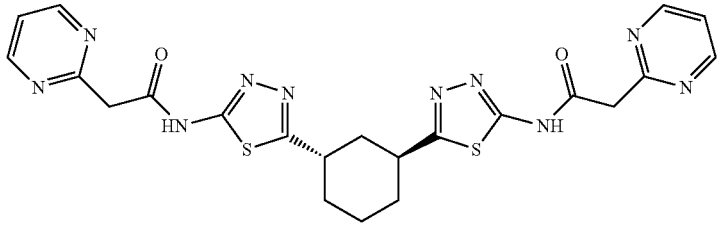 | A |
| 29 | 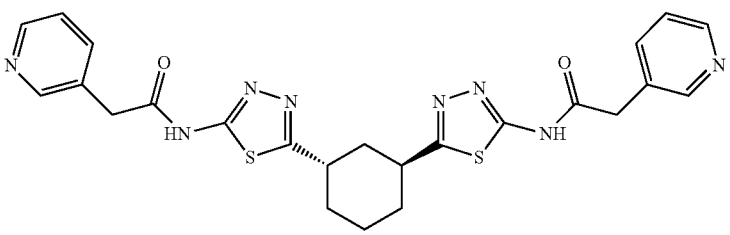 [SMILES: O=C(Cc1cccnc1)Nc1nnc([C@H]2CCC[C@H](c3nnc(NC(=O)Cc4cccnc4)s3)C2)s1] | A |
| 30 | 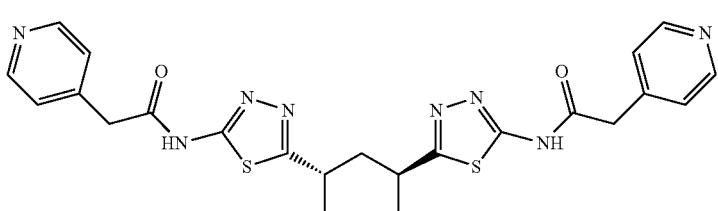 | A |

TABLE 1-continued
| Cmpd # | Structure | IC$_{50}$ |
|---|---|---|
| 31 | 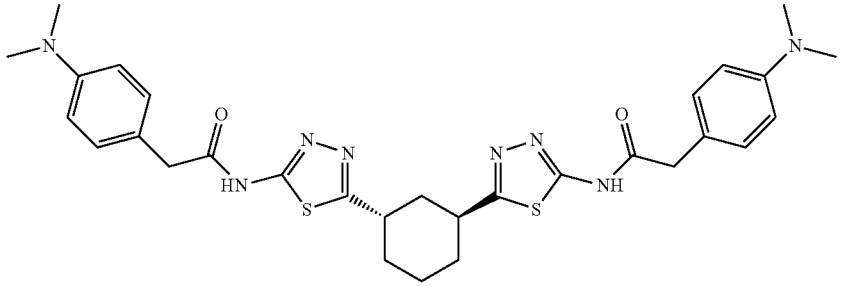 | A |
| 32 | 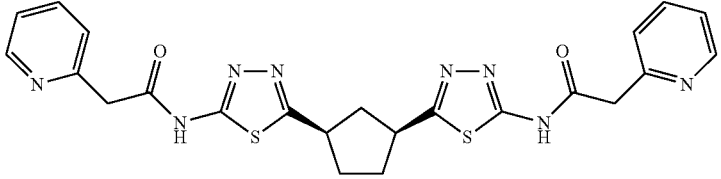 [SMILES: O=C(Cc1ccccn1)Nc1nnc([C@@H]2CC[C@H](c3nnc(NC(=O)Cc4ccccn4)s3)C2)s1] | C |
| 33 | 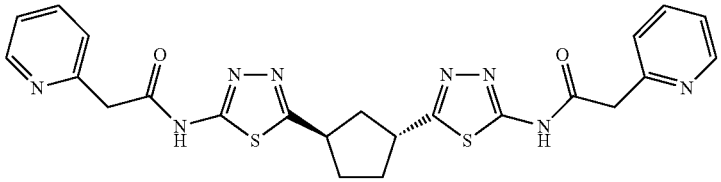 [SMILES: O=C(Cc1ccccn1)Nc1nnc([C@@H]2CC[C@@H](c3nnc(NC(=O)Cc4ccccn4)s3)C2)s1] | A |
| 34 | 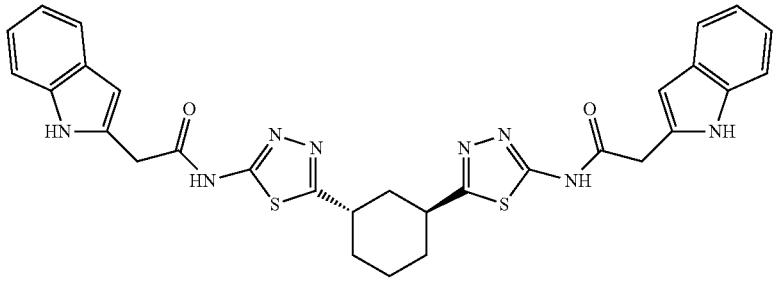 [SMILES: O=C(Cc1cc2ccccc2[nH]1)Nc1nnc([C@H]2CCC[C@H](c3nnc(NC(=O)Cc4cc5ccccc5[nH]4)s3)C2)s1] | B |
| 35 | 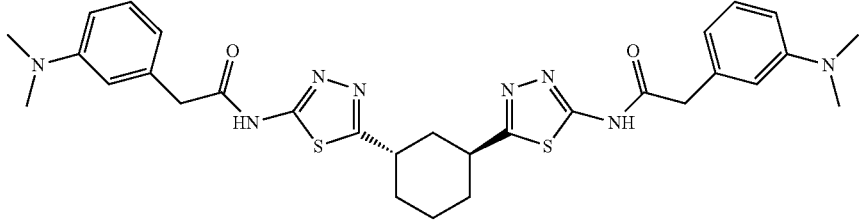 | A |
| 36 | 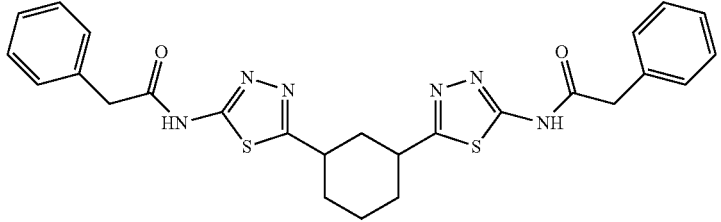 [SMILES: O=C(Cc1ccccc1)Nc1nnc(C2CCCC(c3nnc(NC(=O)Cc4ccccc4)s3)C2)s1] | D |

TABLE 1-continued

| Cmpd # | Structure | IC$_{50}$ |
|---|---|---|
| 37 | 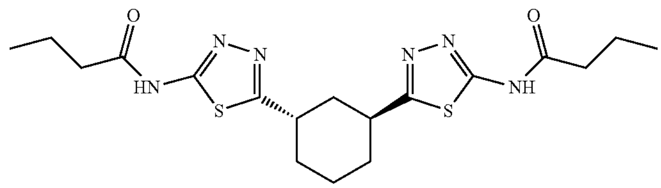 [SMILES: CCCC(=O)Nc1nnc([C@H]2CCC[C@H](c3nnc(NC(=O)CCC)s3)C2)s1] | B |
| 38 | 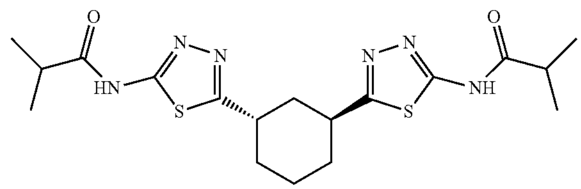 [SMILES: CC(C)C(=O)Nc1nnc([C@H]2CCC[C@H](c3nnc(NC(=O)C(C)C)s3)C2)s1] | B |
| 39 | 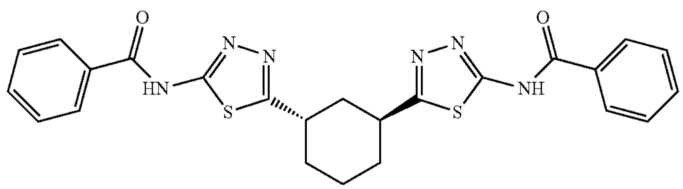 [SMILES: O=C(Nc1nnc([C@H]2CCC[C@H](c3nnc(NC(=O)c4ccccc4)s3)C2)s1)c1ccccc1] | D |
| 40 | 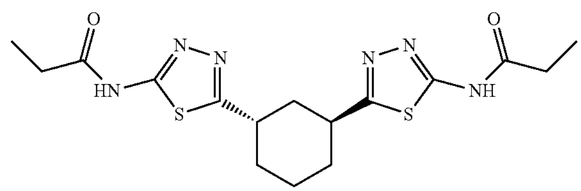 [SMILES: CCC(=O)Nc1nnc([C@H]2CCC[C@H](c3nnc(NC(=O)CC)s3)C2)s1] | B |
| 41 | 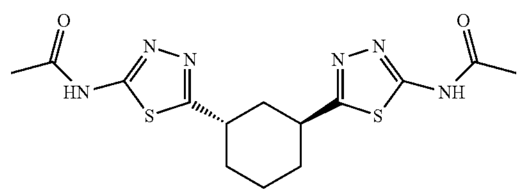 [SMILES: CC(=O)Nc1nnc([C@H]2CCC[C@H](c3nnc(NC(C)=O)s3)C2)s1] | B |
| 42 | 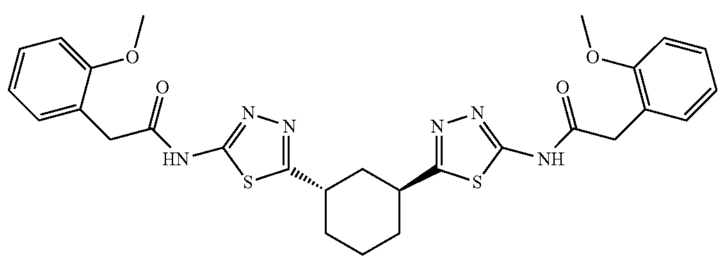 [SMILES: COc1ccccc1CC(=O)Nc1nnc([C@H]2CCC[C@H](c3nnc(NC(=O)Cc4ccccc4OC)s3)C2)s1] | A |
| 43 | 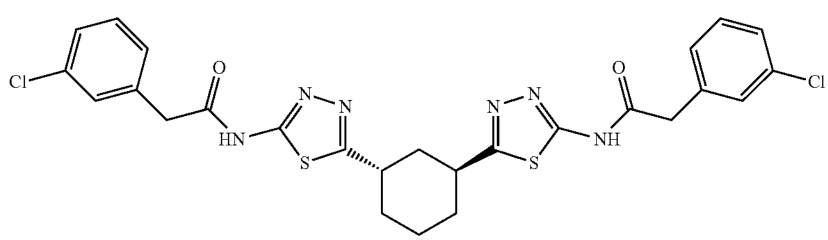 [SMILES: O=C(Cc1cccc(Cl)c1)Nc1nnc([C@H]2CCC[C@H](c3nnc(NC(=O)Cc4cccc(Cl)c4)s3)C2)s1] | B |

TABLE 1-continued
| Cmpd # | Structure | IC$_{50}$ |
|---|---|---|
| 44 | 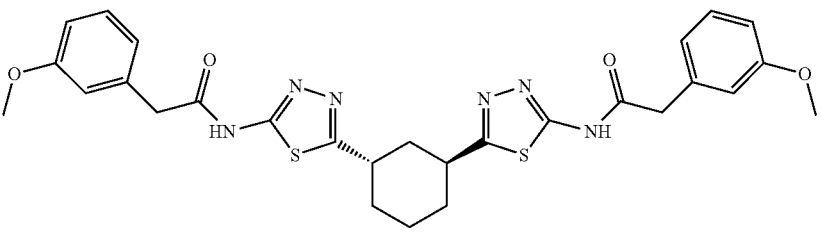 | A |
| 45 | 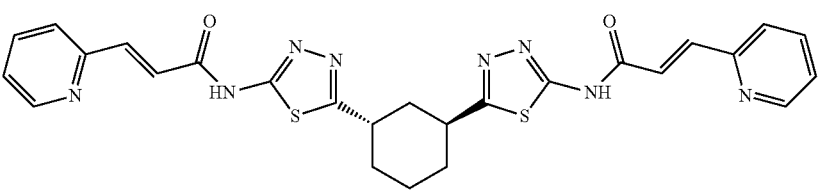 [SMILES: O=C(/C=C/c1ccccn1)Nc1nnc([C@H]2CCC[C@H](c3nnc(NC(=O)/C=C/c4ccccn4)s3)C2)s1] | B |
| 46 | 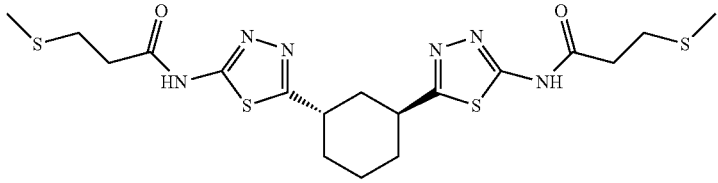 | B |
| 47 | 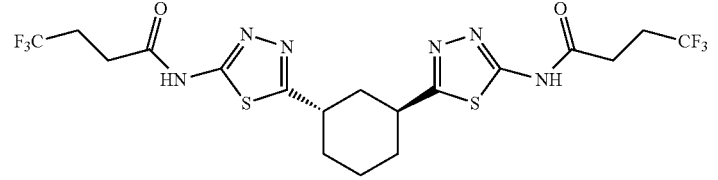 [SMILES: O=C(CCC(F)(F)F)Nc1nnc([C@H]2CCC[C@H](c3nnc(NC(=O)CCC(F)(F)F)s3)C2)s1] | D |
| 48 | 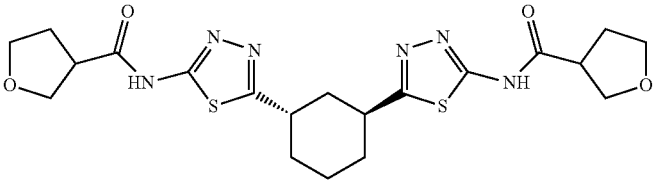 [SMILES: O=C(Nc1nnc([C@H]2CCC[C@H](c3nnc(NC(=O)C4CCOC4)s3)C2)s1)C1CCOC1] | C |
| 49 | 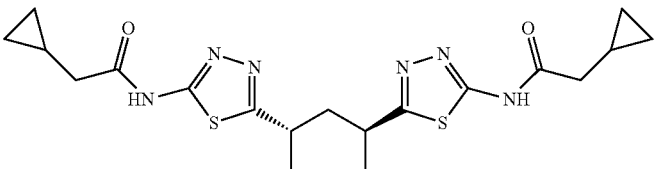 | B |
| 50 | 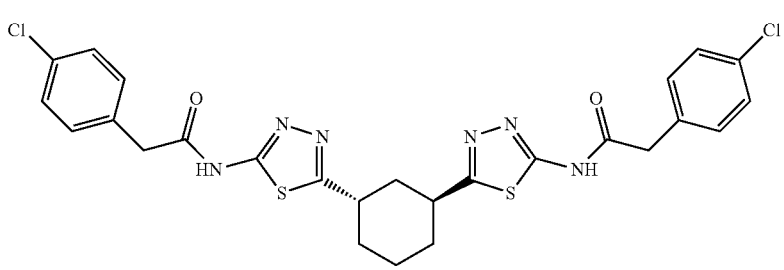 [SMILES: O=C(Cc1ccc(Cl)cc1)Nc1nnc([C@H]2CCC[C@H](c3nnc(NC(=O)Cc4ccc(Cl)cc4)s3)C2)s1] | B |

TABLE 1-continued

| Cmpd # | Structure | IC$_{50}$ |
|---|---|---|
| 51 | 2-chlorophenyl-CH$_2$-C(O)NH-[1,3,4-thiadiazol-2-yl]-(1,3-cyclohexyl)-[1,3,4-thiadiazol-2-yl]-NHC(O)-CH$_2$-2-chlorophenyl | B |
| 52 | 4-methoxyphenyl-CH$_2$-C(O)NH-[1,3,4-thiadiazol-2-yl]-(1,3-cyclohexyl)-[1,3,4-thiadiazol-2-yl]-NHC(O)-CH$_2$-4-methoxyphenyl | A |
| 53 | 3-aminophenyl-CH$_2$-C(O)NH-[1,3,4-thiadiazol-2-yl]-(1,3-cyclohexyl)-[1,3,4-thiadiazol-2-yl]-NHC(O)-CH$_2$-3-aminophenyl | A |
| 54 | 3-(methylsulfonyl)phenyl-CH$_2$-C(O)NH-[1,3,4-thiadiazol-2-yl]-(1,3-cyclohexyl)-[1,3,4-thiadiazol-2-yl]-NHC(O)-CH$_2$-3-(methylsulfonyl)phenyl | A |
| 55 | 2-acetamidophenyl-CH$_2$-C(O)NH-[1,3,4-thiadiazol-2-yl]-(1,3-cyclohexyl)-[1,3,4-thiadiazol-2-yl]-NHC(O)-CH$_2$-2-acetamidophenyl | B |

TABLE 1-continued
| Cmpd # | Structure | IC$_{50}$ |
|---|---|---|
| 56 | 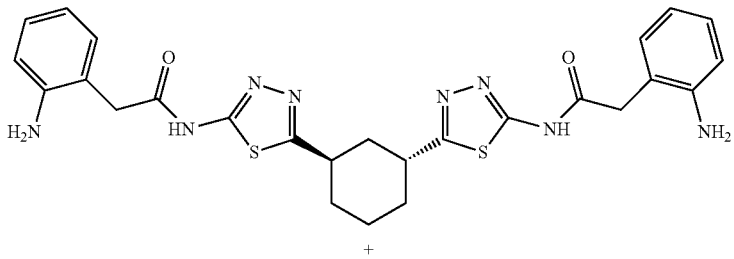 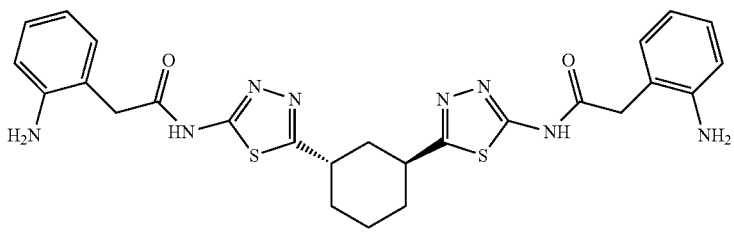 | A |
| 57 | 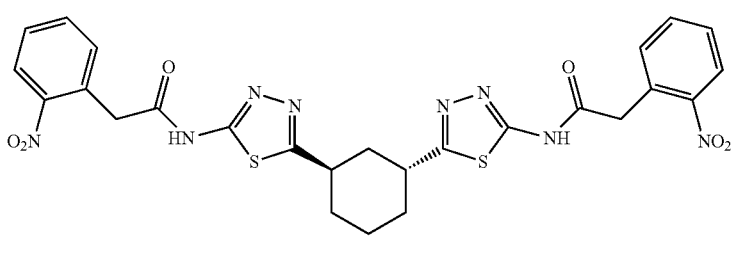 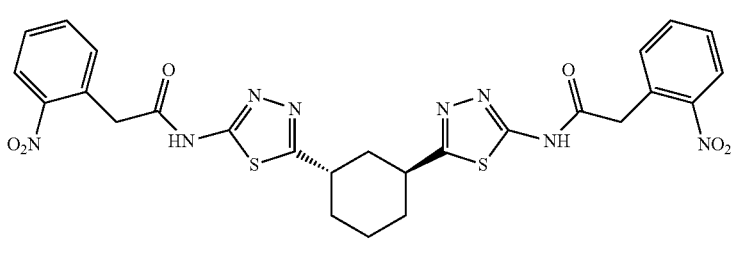 | B |
| 58 | 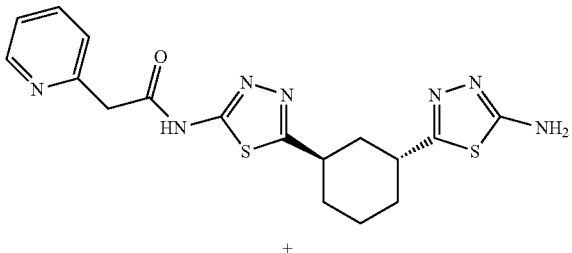 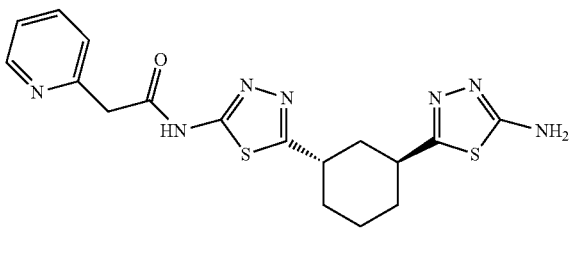 | D |

TABLE 1-continued

| Cmpd # | Structure | IC$_{50}$ |
|---|---|---|
| 59 | | A |
| 60 | | C |
| 61 | 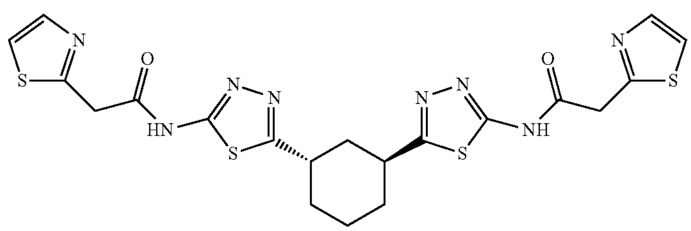 [SMILES: O=C(Cc1nccs1)Nc1nnc([C@H]2CCC[C@H](c3nnc(NC(=O)Cc4nccs4)s3)C2)s1] | B |
| 62 | 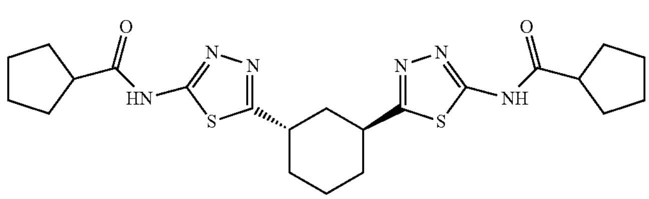 [SMILES: O=C(Nc1nnc([C@H]2CCC[C@H](c3nnc(NC(=O)C4CCCC4)s3)C2)s1)C1CCCC1] | D |
| 63 | 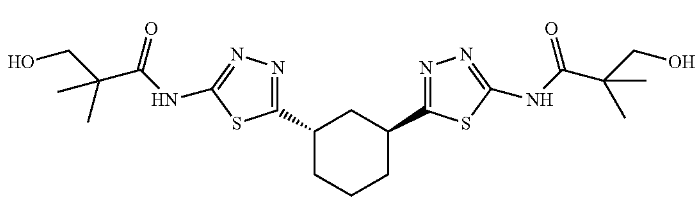 [SMILES: CC(C)(CO)C(=O)Nc1nnc([C@H]2CCC[C@H](c3nnc(NC(=O)C(C)(C)CO)s3)C2)s1] | C |

TABLE 1-continued
| Cmpd # | Structure | IC$_{50}$ |
|---|---|---|
| 64 | 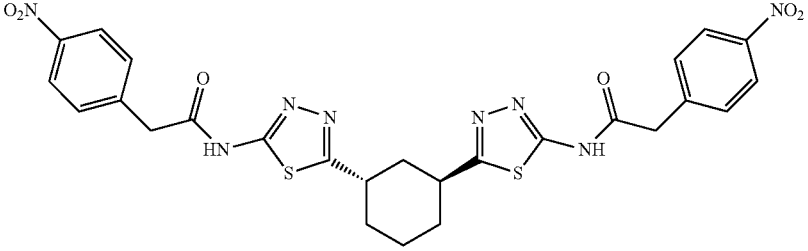 [SMILES: O=C(Cc1ccc([N+](=O)[O-])cc1)Nc1nnc([C@H]2CCC[C@H](c3nnc(NC(=O)Cc4ccc([N+](=O)[O-])cc4)s3)C2)s1] | D |
| 65 | 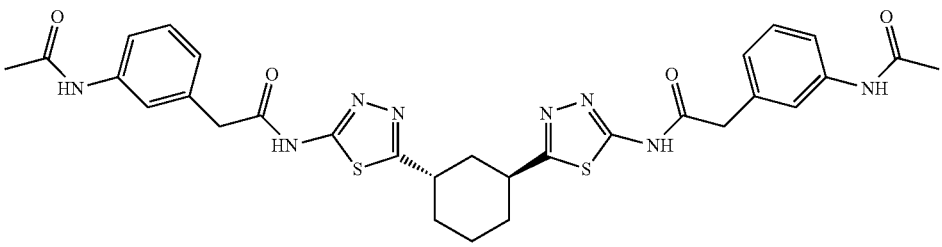 [SMILES: CC(=O)Nc1cccc(CC(=O)Nc2nnc([C@H]3CCC[C@H](c4nnc(NC(=O)Cc5cccc(NC(C)=O)c5)s4)C3)s2)c1] | A |
| 66 | 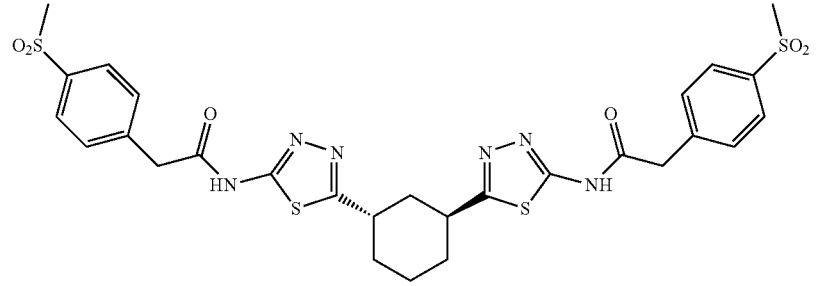 [SMILES: CS(=O)(=O)c1ccc(CC(=O)Nc2nnc([C@H]3CCC[C@H](c4nnc(NC(=O)Cc5ccc(S(C)(=O)=O)cc5)s4)C3)s2)cc1] | A |
| 67 | 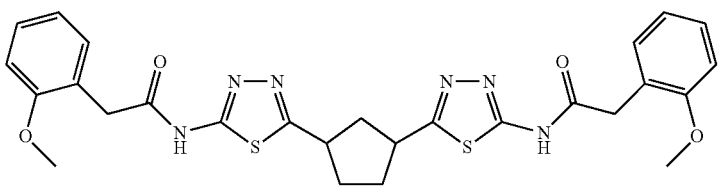 [SMILES: COc1ccccc1CC(=O)Nc1nnc(C2CCC(c3nnc(NC(=O)Cc4ccccc4OC)s3)C2)s1] | B |
| 68 | 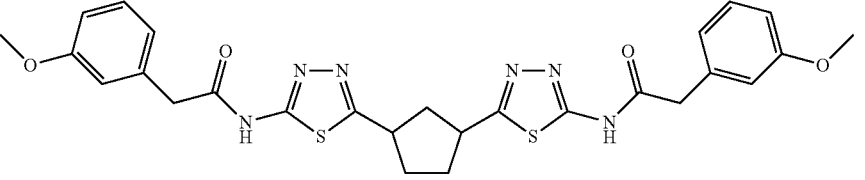 | B |
| 69 | 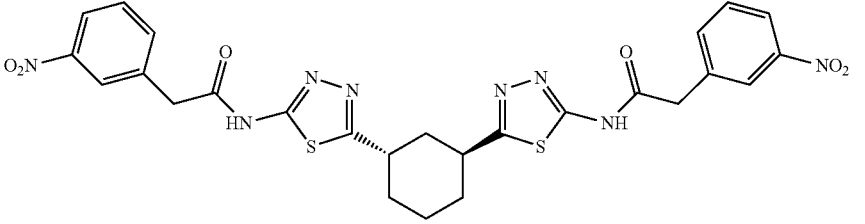 | A |

TABLE 1-continued

| Cmpd # | Structure | IC$_{50}$ |
|---|---|---|
| 70 | 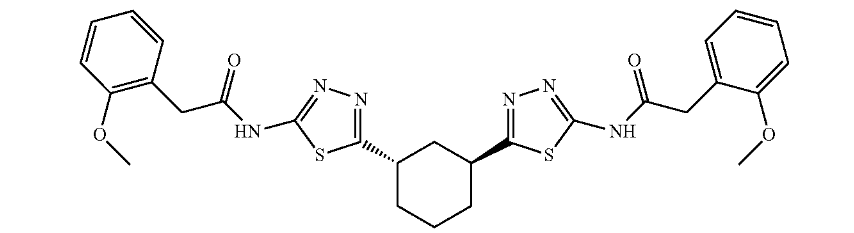 [SMILES: COc1ccccc1CC(=O)Nc1nnc([C@H]2CCC[C@H](c3nnc(NC(=O)Cc4ccccc4OC)s3)C2)s1] | A |
| 71 | 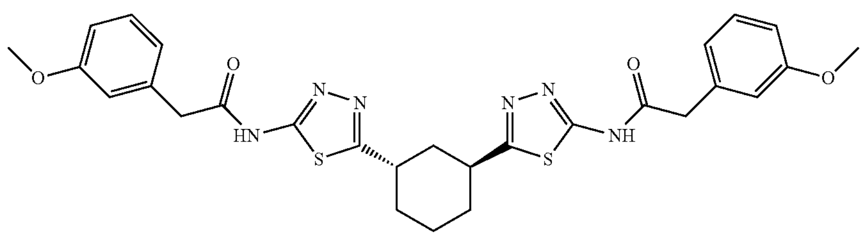 | A |
| 72 | 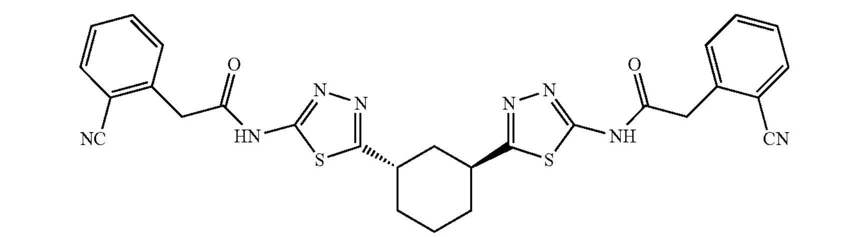 [SMILES: N#Cc1ccccc1CC(=O)Nc1nnc([C@H]2CCC[C@H](c3nnc(NC(=O)Cc4ccccc4C#N)s3)C2)s1] | A |
| 73 | 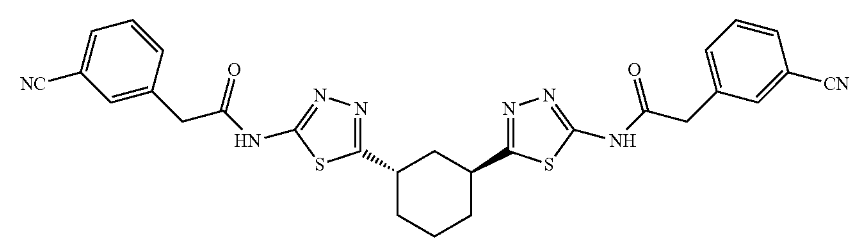 [SMILES: N#Cc1cccc(CC(=O)Nc2nnc([C@H]3CCC[C@H](c4nnc(NC(=O)Cc5cccc(C#N)c5)s4)C3)s2)c1] | A |
| 74 | 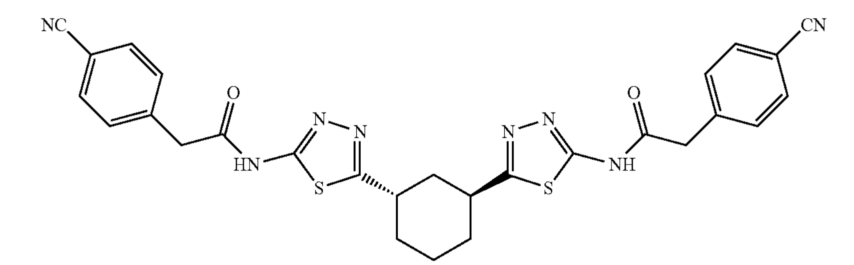 [SMILES: N#Cc1ccc(CC(=O)Nc2nnc([C@H]3CCC[C@H](c4nnc(NC(=O)Cc5ccc(C#N)cc5)s4)C3)s2)cc1] | B |
| 75 | 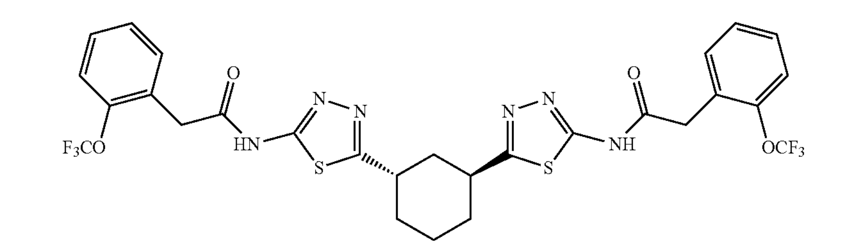 [SMILES: O=C(Cc1ccccc1OC(F)(F)F)Nc1nnc([C@H]2CCC[C@H](c3nnc(NC(=O)Cc4ccccc4OC(F)(F)F)s3)C2)s1] | B |

TABLE 1-continued
| Cmpd # | Structure | IC$_{50}$ |
|---|---|---|
| 76 | 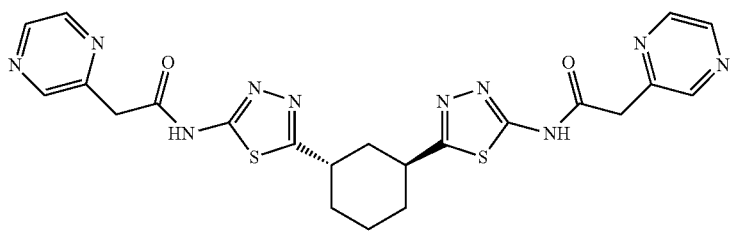 [SMILES: O=C(Cc1cnccn1)Nc1nnc([C@H]2CCC[C@H](c3nnc(NC(=O)Cc4cnccn4)s3)C2)s1] | A |
| 77 | 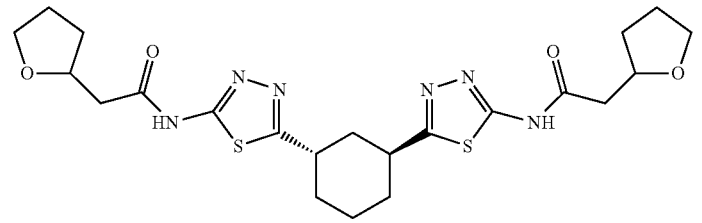 [SMILES: O=C(CC1CCCO1)Nc1nnc([C@H]2CCC[C@H](c3nnc(NC(=O)CC4CCCO4)s3)C2)s1] | D |
| 78 | 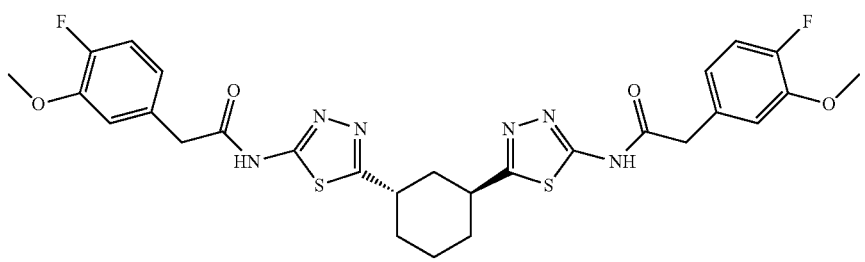 | B |
| 79 | 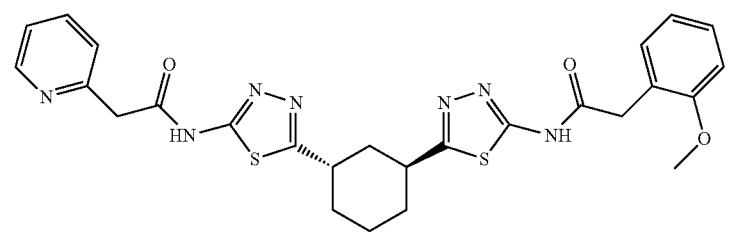 [SMILES: COc1ccccc1CC(=O)Nc1nnc([C@H]2CCC[C@H](c3nnc(NC(=O)Cc4ccccn4)s3)C2)s1] | A |
| 80 | 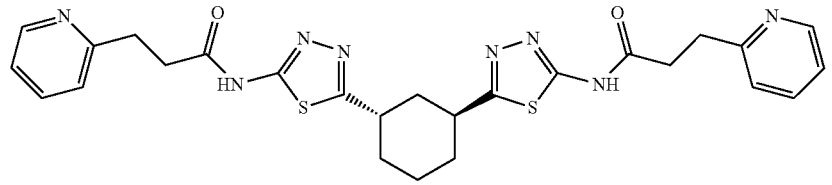 [SMILES: O=C(CCc1ccccn1)Nc1nnc([C@H]2CCC[C@H](c3nnc(NC(=O)CCc4ccccn4)s3)C2)s1] | B |
| 81 | 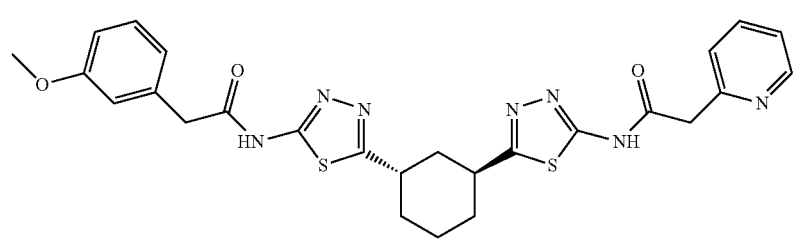 [SMILES: COc1cccc(CC(=O)Nc2nnc([C@H]3CCC[C@H](c4nnc(NC(=O)Cc5ccccn5)s4)C3)s2)c1] | A |

TABLE 1-continued
| Cmpd # | Structure | IC$_{50}$ |
|---|---|---|
| 82 | 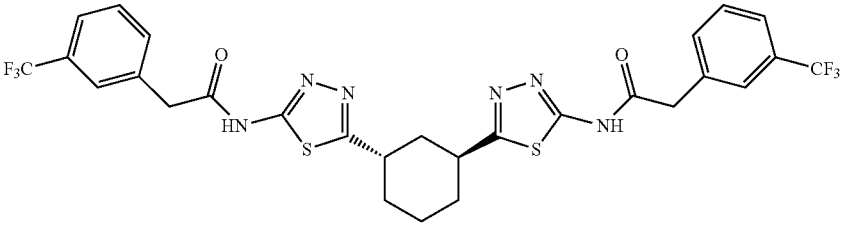 [SMILES: O=C(Cc1cccc(C(F)(F)F)c1)Nc1nnc([C@H]2CCC[C@H](c3nnc(NC(=O)Cc4cccc(C(F)(F)F)c4)s3)C2)s1] | C |
| 83 | 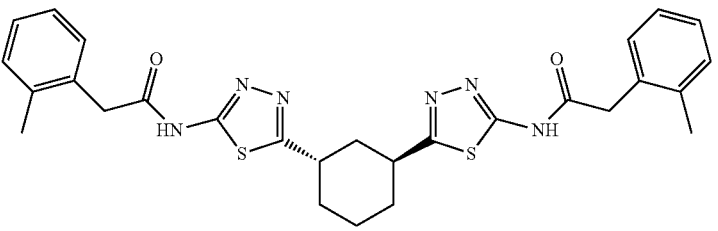 [SMILES: Cc1ccccc1CC(=O)Nc1nnc([C@H]2CCC[C@H](c3nnc(NC(=O)Cc4ccccc4C)s3)C2)s1] | B |
| 84 | 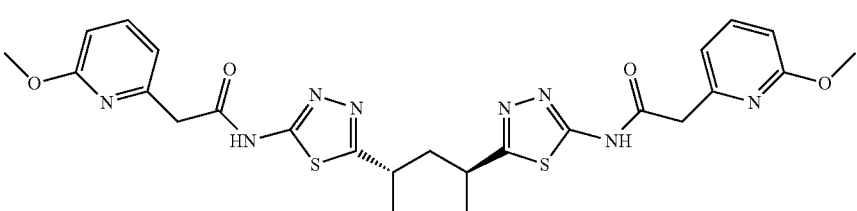 | A |
| 85 | 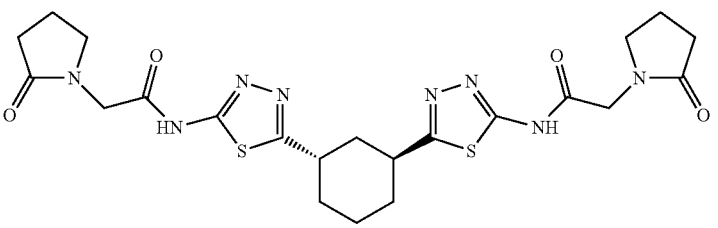 [SMILES: O=C(CN1CCCC1=O)Nc1nnc([C@H]2CCC[C@H](c3nnc(NC(=O)CN4CCCC4=O)s3)C2)s1] | C |
| 86 | 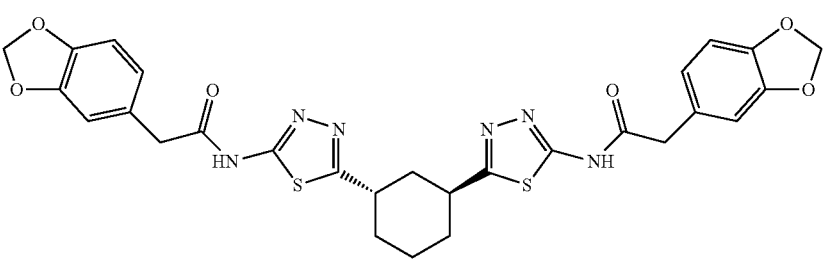 [SMILES: O=C(Cc1ccc2c(c1)OCO2)Nc1nnc([C@H]2CCC[C@H](c3nnc(NC(=O)Cc4ccc5c(c4)OCO5)s3)C2)s1] | A |
| 87 | 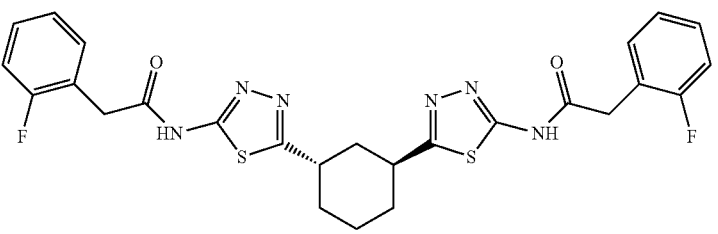 [SMILES: O=C(Cc1ccccc1F)Nc1nnc([C@H]2CCC[C@H](c3nnc(NC(=O)Cc4ccccc4F)s3)C2)s1] | A |

TABLE 1-continued
| Cmpd # | Structure | IC$_{50}$ |
|---|---|---|
| 88 | 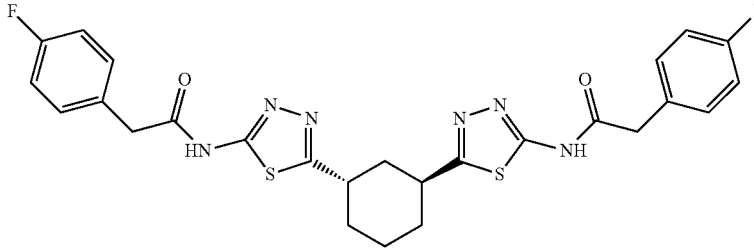 | B |
| 89 | 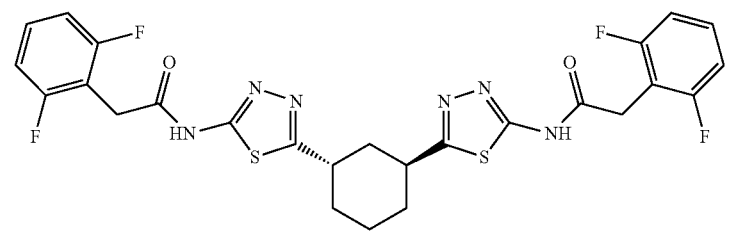 [SMILES: O=C(Cc1c(F)cccc1F)Nc1nnc([C@H]2CCC[C@H](c3nnc(NC(=O)Cc4c(F)cccc4F)s3)C2)s1] | B |
| 90 | 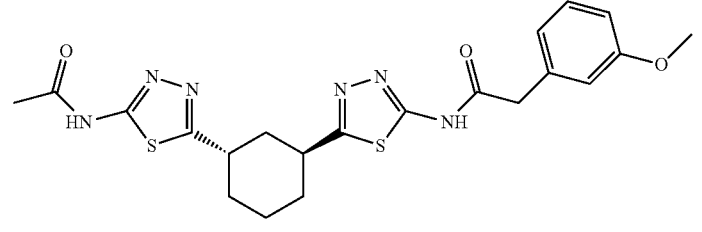 [SMILES: COc1cccc(CC(=O)Nc2nnc([C@H]3CCC[C@H](c4nnc(NC(C)=O)s4)C3)s2)c1] | B |
| 91 | 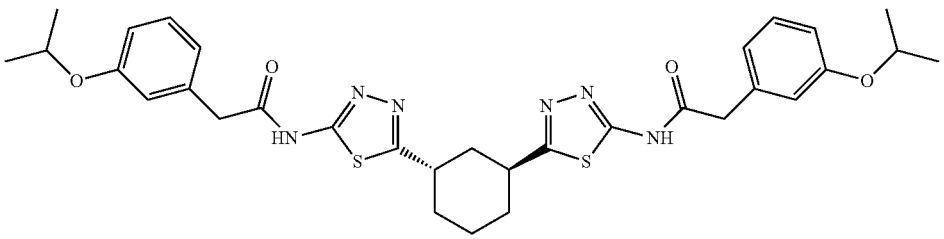 [SMILES: CC(C)Oc1cccc(CC(=O)Nc2nnc([C@H]3CCC[C@H](c4nnc(NC(=O)Cc5cccc(OC(C)C)c5)s4)C3)s2)c1] | B |
| 92 | 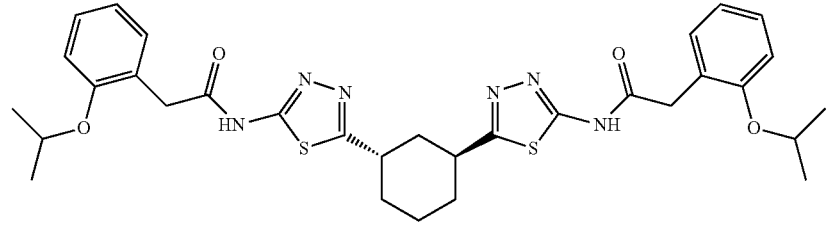 [SMILES: CC(C)Oc1ccccc1CC(=O)Nc1nnc([C@H]2CCC[C@H](c3nnc(NC(=O)Cc4ccccc4OC(C)C)s3)C2)s1] | B |
| 93 | 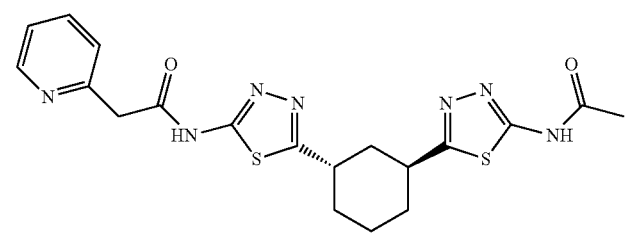 [SMILES: CC(=O)Nc1nnc([C@H]2CCC[C@H](c3nnc(NC(=O)Cc4ccccn4)s3)C2)s1] | A |

TABLE 1-continued

| Cmpd # | Structure | IC$_{50}$ |
|---|---|---|
| 94 | 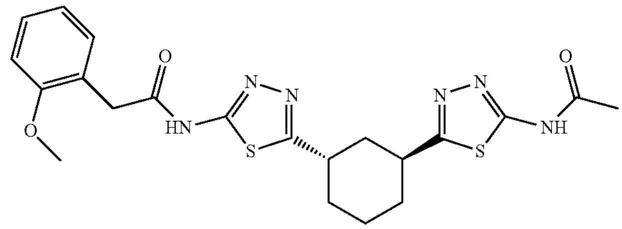 [SMILES: COc1ccccc1CC(=O)Nc1nnc([C@H]2CCC[C@H](c3nnc(NC(C)=O)s3)C2)s1] | A |
| 95 | 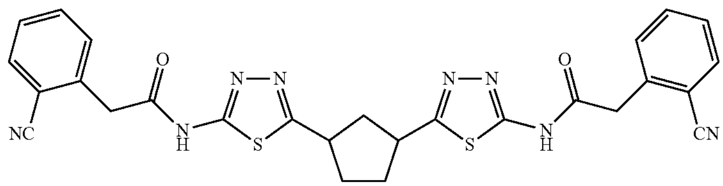 [SMILES: N#Cc1ccccc1CC(=O)Nc1nnc(C2CCC(c3nnc(NC(=O)Cc4ccccc4C#N)s3)C2)s1] | B |
| 96 | 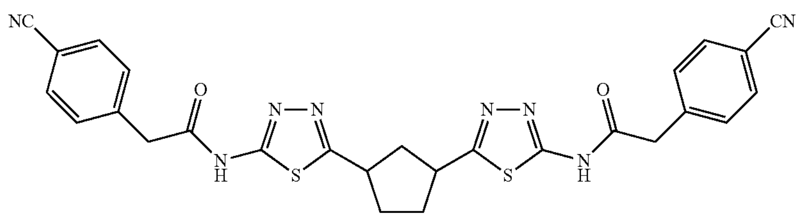 [SMILES: N#Cc1ccc(CC(=O)Nc2nnc(C3CCC(c4nnc(NC(=O)Cc5ccc(C#N)cc5)s4)C3)s2)cc1] | B |
| 97 | 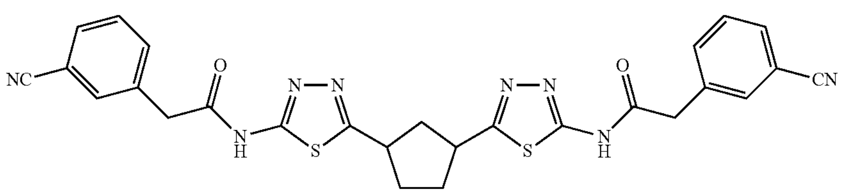 [SMILES: N#Cc1cccc(CC(=O)Nc2nnc(C3CCC(c4nnc(NC(=O)Cc5cccc(C#N)c5)s4)C3)s2)c1] | B |
| 98 | 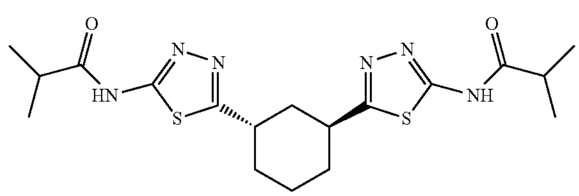 [SMILES: CC(C)C(=O)Nc1nnc([C@H]2CCC[C@H](c3nnc(NC(=O)C(C)C)s3)C2)s1] | B |
| 99 | 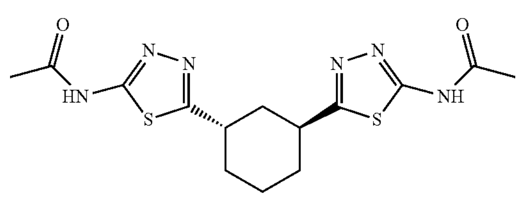 [SMILES: CC(=O)Nc1nnc([C@H]2CCC[C@H](c3nnc(NC(C)=O)s3)C2)s1] | B |
| 100 | 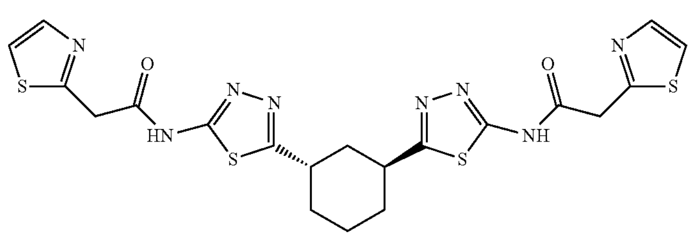 [SMILES: O=C(Cc1nccs1)Nc1nnc([C@H]2CCC[C@H](c3nnc(NC(=O)Cc4nccs4)s3)C2)s1] | A |

TABLE 1-continued

| Cmpd # | Structure | IC$_{50}$ |
|---|---|---|
| 101 | 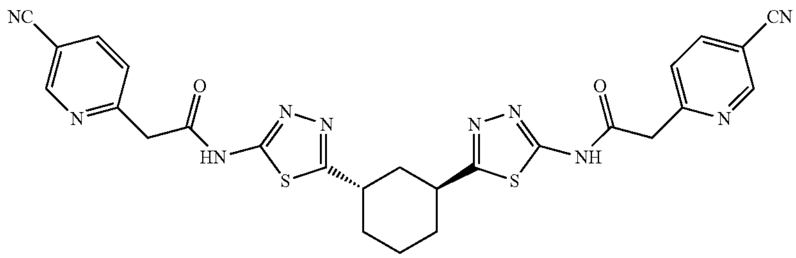 [SMILES: N#Cc1ccc(CC(=O)Nc2nnc([C@H]3CCC[C@H](c4nnc(NC(=O)Cc5ccc(C#N)cn5)s4)C3)s2)nc1] | A |
| 102 | 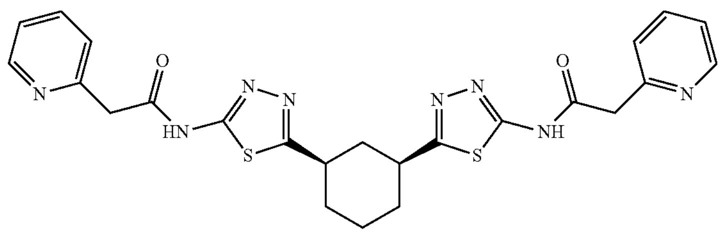 [SMILES: O=C(Cc1ccccn1)Nc1nnc([C@@H]2CCC[C@H](c3nnc(NC(=O)Cc4ccccn4)s3)C2)s1] | B |
| 103 | 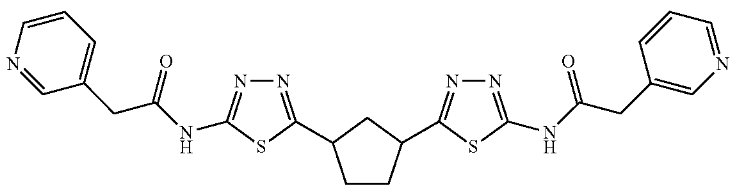 [SMILES: O=C(Cc1cccnc1)Nc1nnc(C2CCC(c3nnc(NC(=O)Cc4cccnc4)s3)C2)s1] | B |
| 104 | 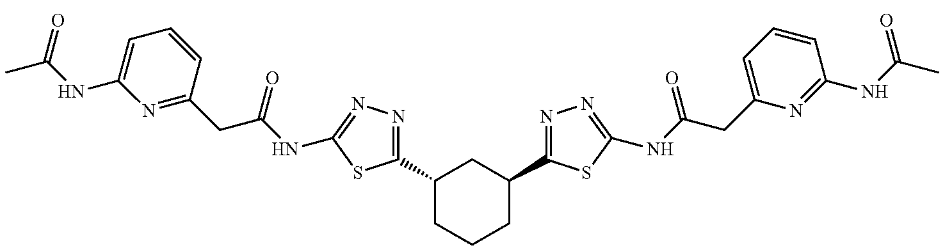 [SMILES: CC(=O)Nc1cccc(CC(=O)Nc2nnc([C@H]3CCC[C@H](c4nnc(NC(=O)Cc5cccc(NC(C)=O)n5)s4)C3)s2)n1] | A |
| 105 | 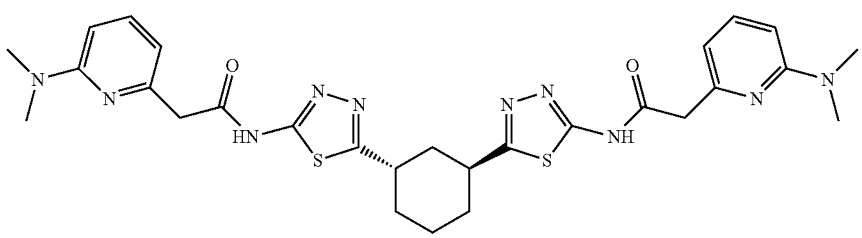 | A |
| 106 | 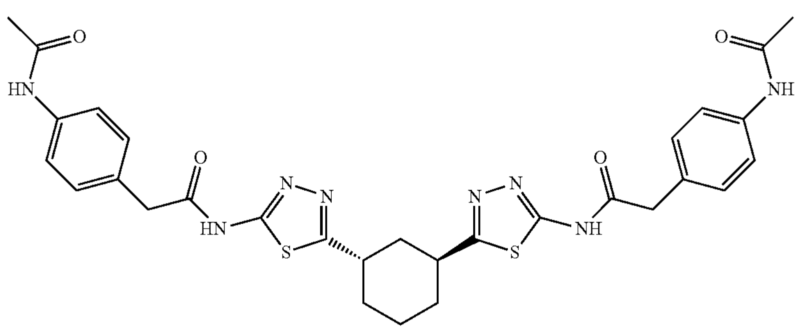 [SMILES: CC(=O)Nc1ccc(CC(=O)Nc2nnc([C@H]3CCC[C@H](c4nnc(NC(=O)Cc5ccc(NC(C)=O)cc5)s4)C3)s2)cc1] | A |

TABLE 1-continued

| Cmpd # | Structure | IC$_{50}$ |
|---|---|---|
| 107 | 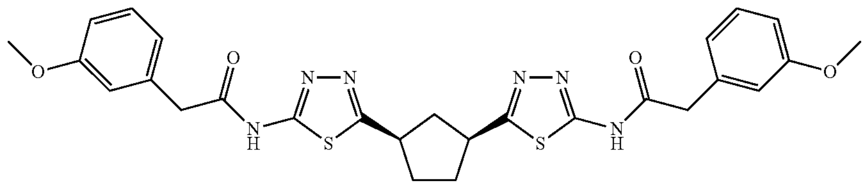 | B |
| 108 | 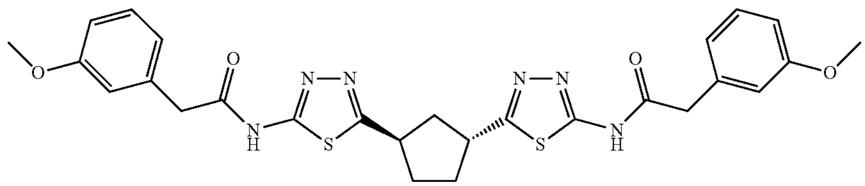 | A |
| 109 | 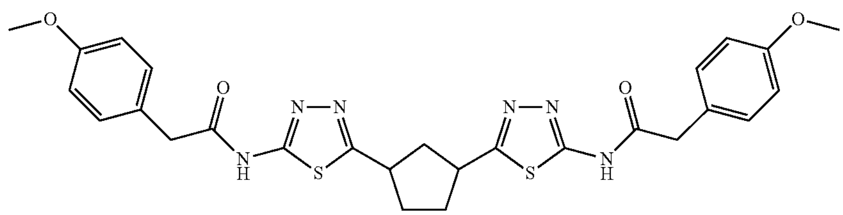 | B |
| 110 | 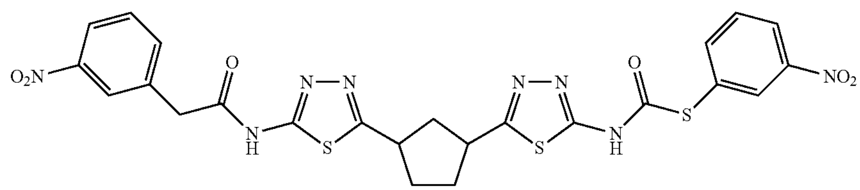 [SMILES: O=C(Cc1cccc([N+](=O)[O-])c1)Nc1nnc(C2CCC(c3nnc(NC(=O)Sc4cccc([N+](=O)[O-])c4)s3)C2)s1] | B |
| 111 | 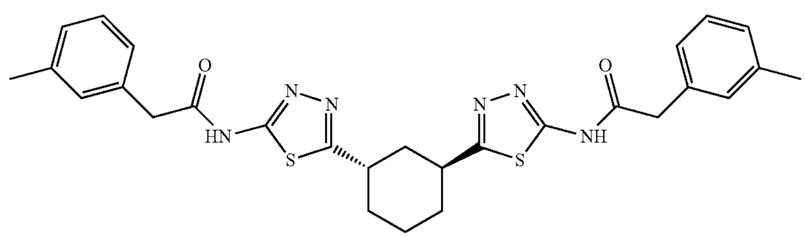 | B |
| 112 | 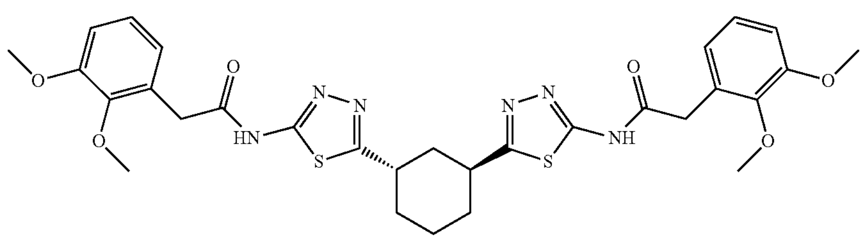 | A |
| 113 | 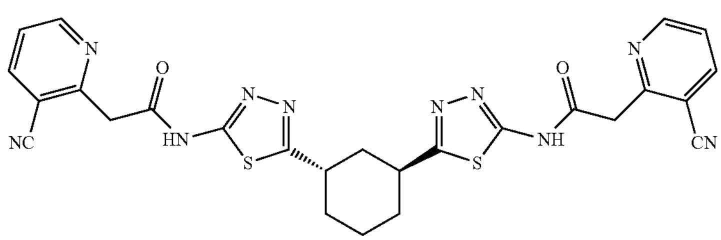 [SMILES: N#Cc1cccnc1CC(=O)Nc1nnc([C@H]2CCC[C@H](c3nnc(NC(=O)Cc4ncccc4C#N)s3)C2)s1] | A |

TABLE 1-continued

| Cmpd # | Structure | IC$_{50}$ |
|---|---|---|
| 115 | 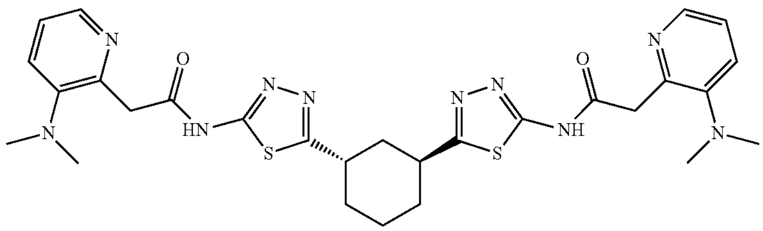 | C |
| 116 | | A |
| 117 | 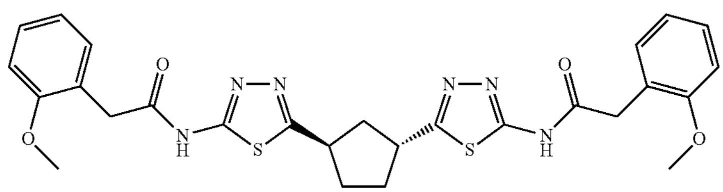 [SMILES: COc1ccccc1CC(=O)Nc1nnc([C@@H]2CC[C@@H](c3nnc(NC(=O)Cc4ccccc4OC)s3)C2)s1] | C |
| 118 | | A |

TABLE 1-continued
| Cmpd # | Structure | IC$_{50}$ |
|---|---|---|
| 119 | 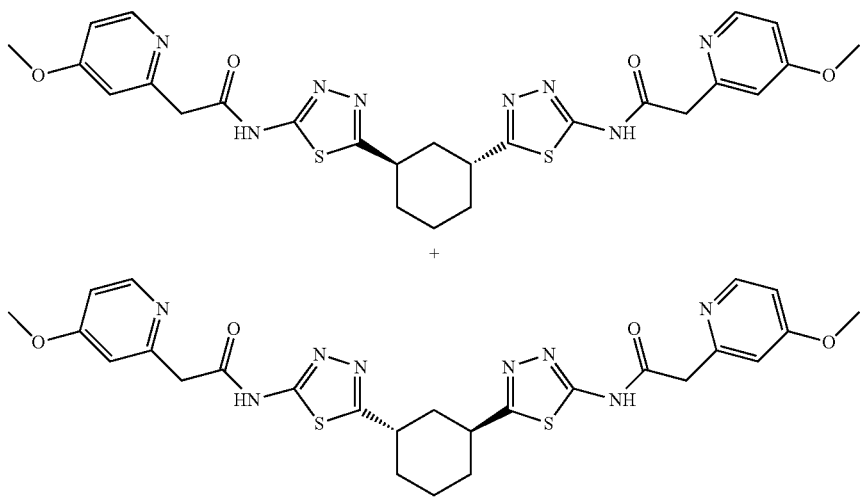 | A |
| 120 | 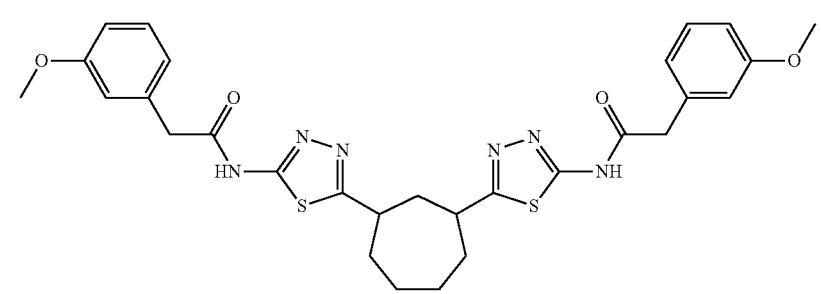 | C |
| 121 | 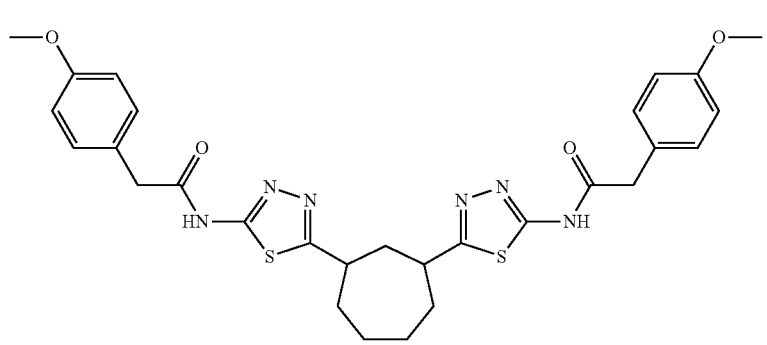 | D |
| 122 | 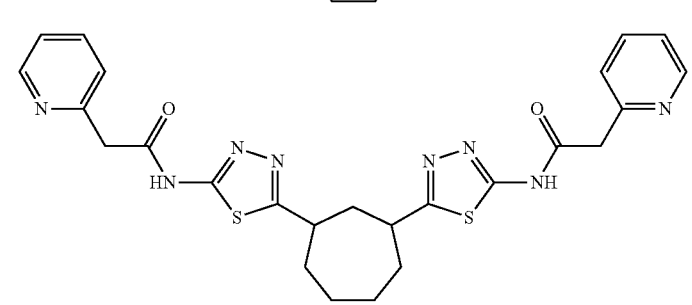 | D |

TABLE 1-continued

| Cmpd # | Structure | IC$_{50}$ |
|---|---|---|
| 123 | 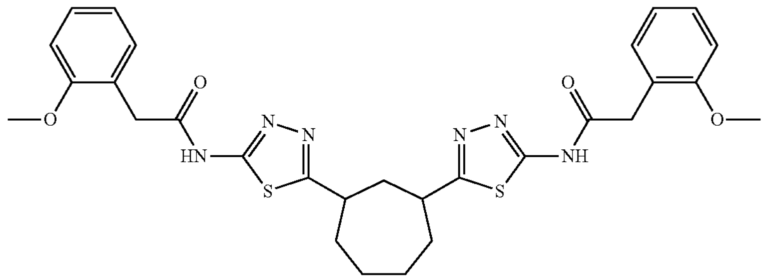 | D |
| 124 | 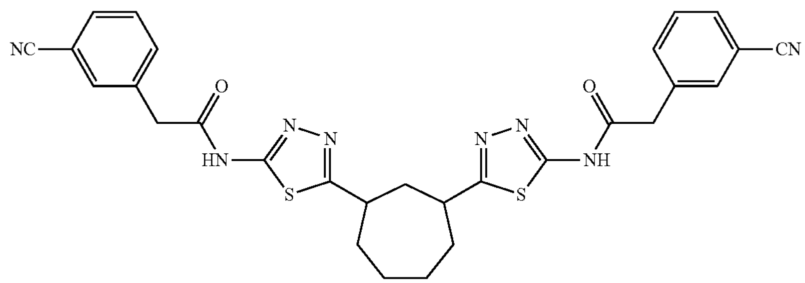 [SMILES: N#Cc1cccc(CC(=O)Nc2nnc(C3CCCCC(c4nnc(NC(=O)Cc5cccc(C#N)c5)s4)C3)s2)c1] | D |
| 125 | 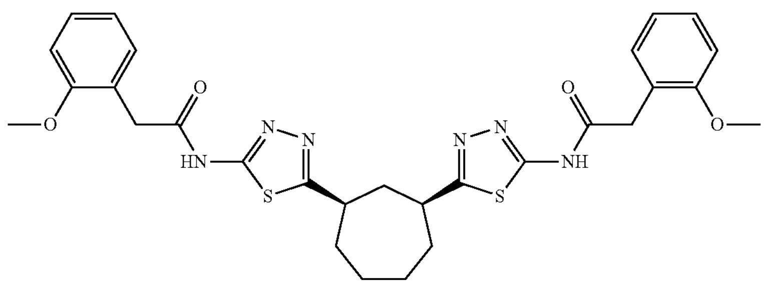 | D |
| 126 | 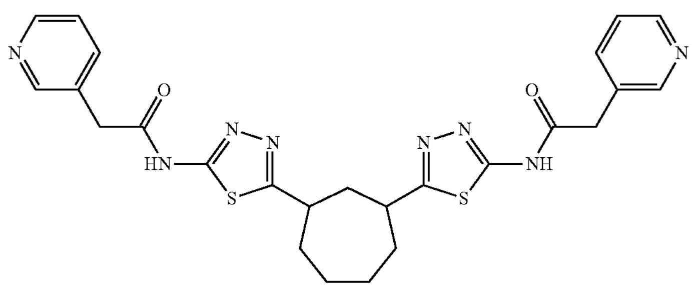 [SMILES: O=C(Cc1cccnc1)Nc1nnc(C2CCCCC(c3nnc(NC(=O)Cc4cccnc4)s3)C2)s1] | B |
| 127 | 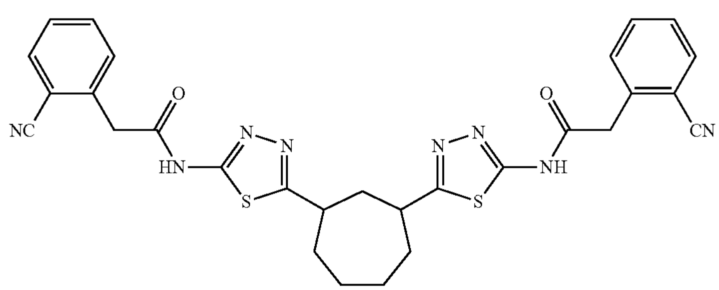 [SMILES: N#Cc1ccccc1CC(=O)Nc1nnc(C2CCCCC(c3nnc(NC(=O)Cc4ccccc4C#N)s3)C2)s1] | C |

TABLE 1-continued

| Cmpd # | Structure | IC$_{50}$ |
|---|---|---|
| 128 | 3-methoxybenzyl–C(O)NH–thiadiazole–cycloheptane–thiadiazole–NHC(O)–benzyl-3-methoxy | C |
| 129 | 3-methoxybenzyl–C(O)NH–thiadiazole–cycloheptane(cis)–thiadiazole–NHC(O)–benzyl-3-methoxy | C |
| 130 | 4-methoxybenzyl–C(O)NH–thiadiazole–cycloheptane–thiadiazole–NHC(O)–benzyl-4-methoxy | D |
| 131 | pyridin-2-yl-methyl–C(O)NH–thiadiazole–cyclohexane(trans)–thiadiazole–NHC(O)–methyl-pyridin-2-yl | N/A |
| 132 | benzyl–C(O)NH–thiadiazole–cyclohexane(cis)–thiadiazole–NHC(O)–benzyl | N/A |
| 133 | (1-methylindol-3-yl)methyl–C(O)NH–thiadiazole–cyclohexane(cis)–thiadiazole–NHC(O)–methyl-(1-methylindol-3-yl) | N/A |

TABLE 1-continued

| Cmpd # | Structure | IC$_{50}$ |
|---|---|---|
| 134 | 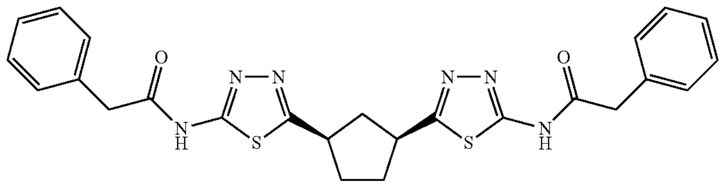 [SMILES: O=C(Cc1ccccc1)Nc1nnc([C@@H]2CC[C@H](c3nnc(NC(=O)Cc4ccccc4)s3)C2)s1] | N/A |
| 135 | 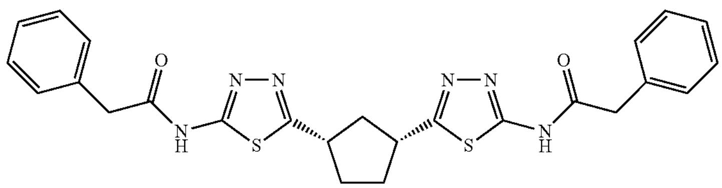 [SMILES: O=C(Cc1ccccc1)Nc1nnc([C@@H]2CC[C@H](c3nnc(NC(=O)Cc4ccccc4)s3)C2)s1] | N/A |
| 136 | 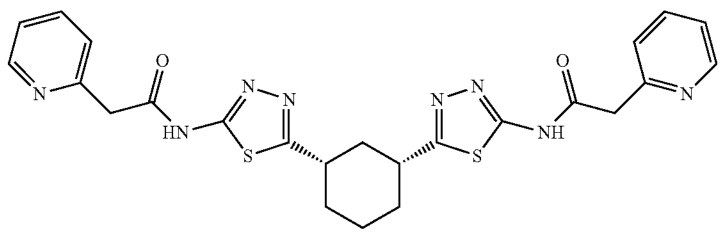 [SMILES: O=C(Cc1ccccn1)Nc1nnc([C@@H]2CCC[C@H](c3nnc(NC(=O)Cc4ccccn4)s3)C2)s1] | N/A |
| 137 | 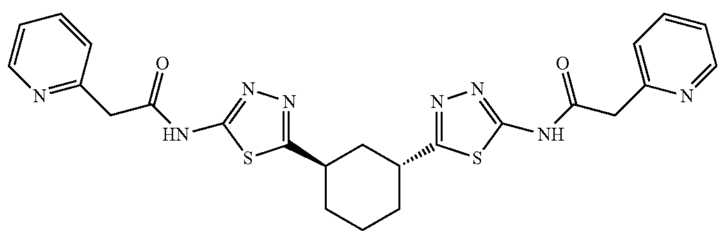 [SMILES: O=C(Cc1ccccn1)Nc1nnc([C@@H]2CCC[C@@H](c3nnc(NC(=O)Cc4ccccn4)s3)C2)s1] | N/A |
| 138 | 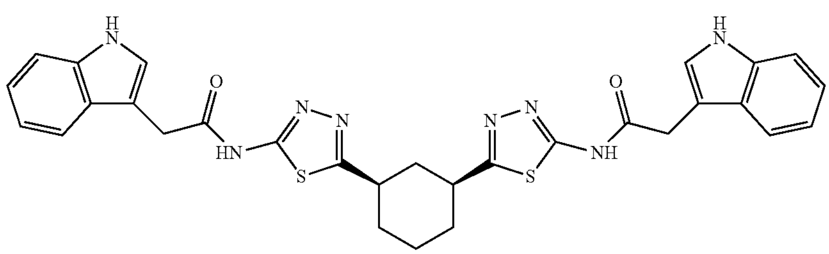 [SMILES: O=C(Cc1c[nH]c2ccccc12)Nc1nnc([C@@H]2CCC[C@H](c3nnc(NC(=O)Cc4c[nH]c5ccccc45)s3)C2)s1] | N/A |
| 139 | 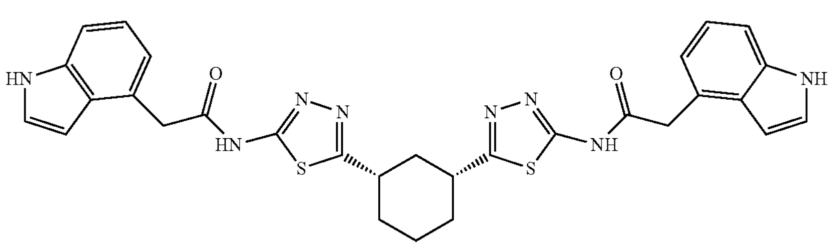 [SMILES: O=C(Cc1cccc2[nH]ccc12)Nc1nnc([C@@H]2CCC[C@H](c3nnc(NC(=O)Cc4cccc5[nH]ccc45)s3)C2)s1] | N/A |

TABLE 1-continued

| Cmpd # | Structure | IC$_{50}$ |
|---|---|---|
| 140 | 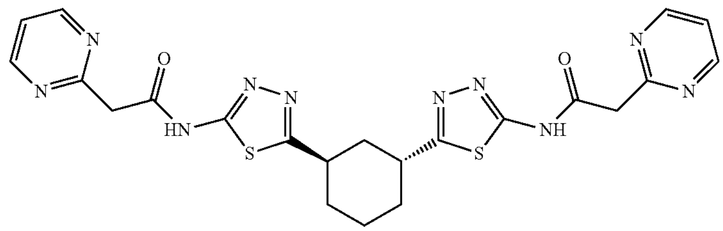 [SMILES: O=C(Cc1ncccn1)Nc1nnc([C@@H]2CCC[C@@H](c3nnc(NC(=O)Cc4ncccn4)s3)C2)s1] | N/A |
| 141 | 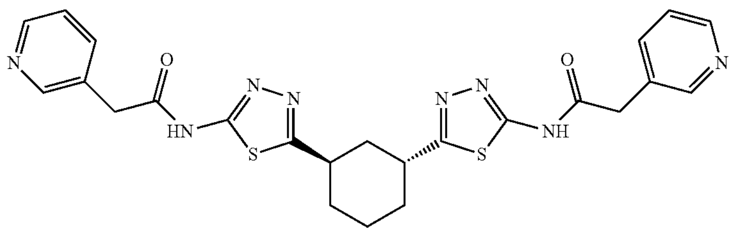 [SMILES: O=C(Cc1cccnc1)Nc1nnc([C@@H]2CCC[C@@H](c3nnc(NC(=O)Cc4cccnc4)s3)C2)s1] | N/A |
| 142 | 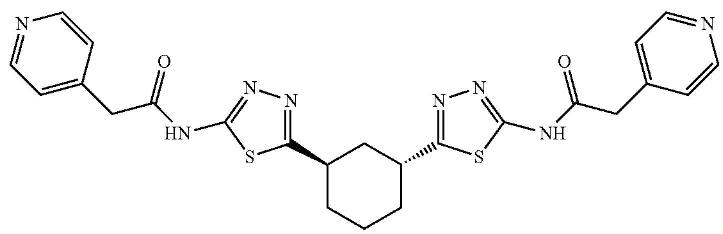 [SMILES: O=C(Cc1ccncc1)Nc1nnc([C@@H]2CCC[C@@H](c3nnc(NC(=O)Cc4ccncc4)s3)C2)s1] | N/A |
| 143 | 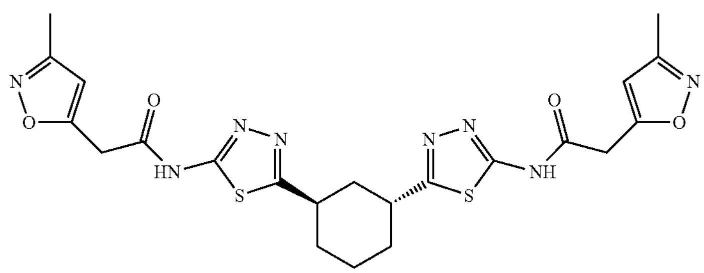 [SMILES: Cc1cc(CC(=O)Nc2nnc([C@@H]3CCC[C@@H](c4nnc(NC(=O)Cc5cc(C)no5)s4)C3)s2)on1] | N/A |
| 144 | 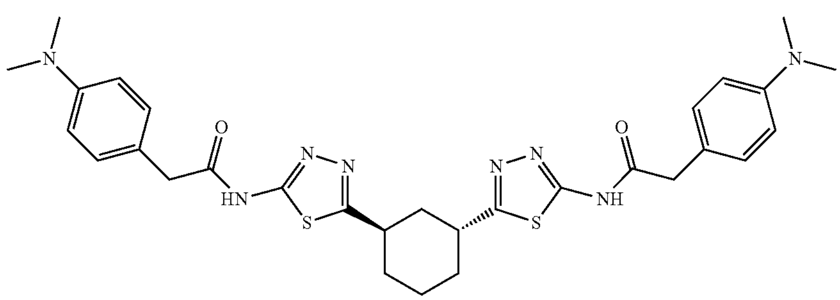 | N/A |
| 145 | 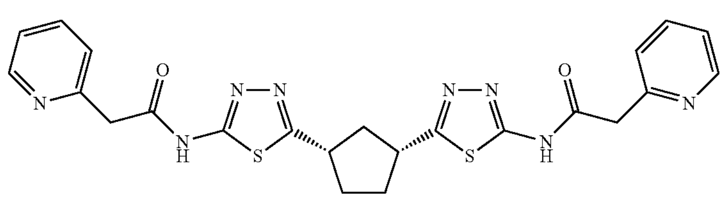 [SMILES: O=C(Cc1ccccn1)Nc1nnc([C@@H]2CC[C@H](c3nnc(NC(=O)Cc4ccccn4)s3)C2)s1] | N/A |

TABLE 1-continued
| Cmpd # | Structure | IC$_{50}$ |
|---|---|---|
| 146 | 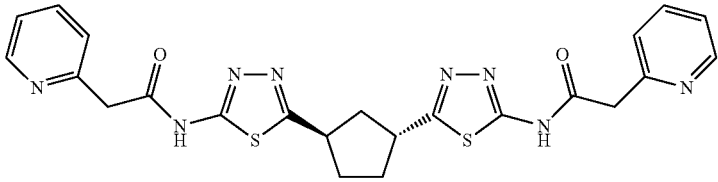 [SMILES: O=C(Cc1ccccn1)Nc1nnc([C@@H]2CC[C@@H](c3nnc(NC(=O)Cc4ccccn4)s3)C2)s1] | N/A |
| 147 | 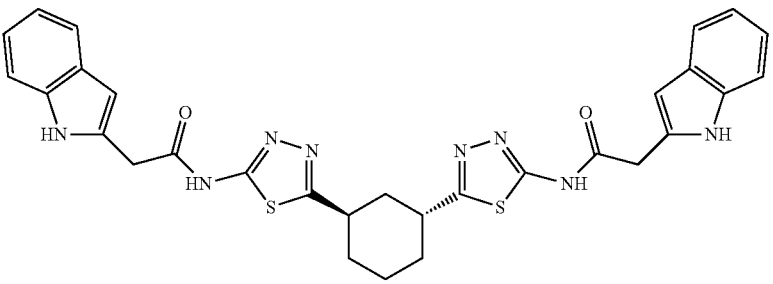 [SMILES: O=C(Cc1cc2ccccc2[nH]1)Nc1nnc([C@@H]2CCC[C@@H](c3nnc(NC(=O)Cc4cc5ccccc5[nH]4)s3)C2)s1] | N/A |
| 148 | 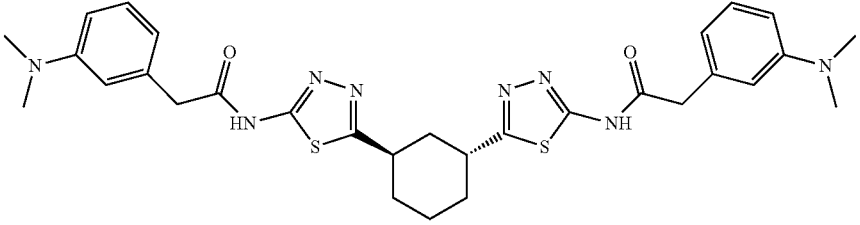 | N/A |
| 149 | 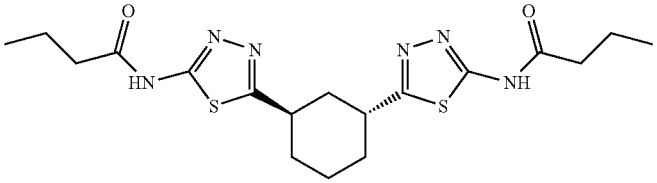 [SMILES: CCCC(=O)Nc1nnc([C@@H]2CCC[C@@H](c3nnc(NC(=O)CCC)s3)C2)s1] | N/A |
| 150 | 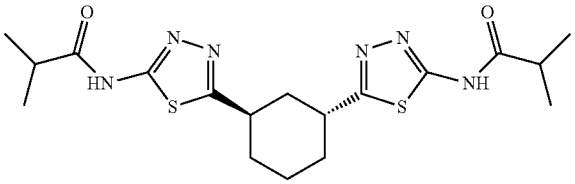 [SMILES: CC(C)C(=O)Nc1nnc([C@@H]2CCC[C@@H](c3nnc(NC(=O)C(C)C)s3)C2)s1] | N/A |
| 151 | 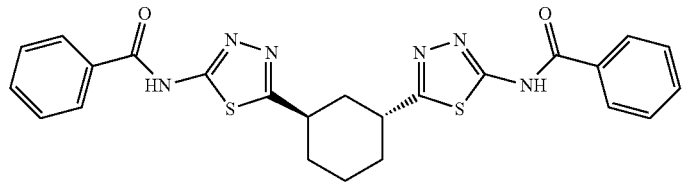 [SMILES: O=C(Nc1nnc([C@@H]2CCC[C@@H](c3nnc(NC(=O)c4ccccc4)s3)C2)s1)c1ccccc1] | N/A |
| 152 | 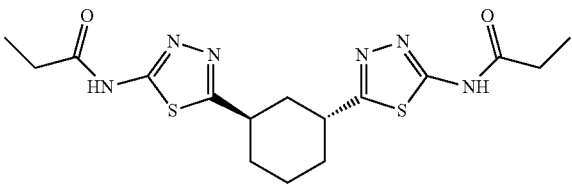 [SMILES: CCC(=O)Nc1nnc([C@@H]2CCC[C@@H](c3nnc(NC(=O)CC)s3)C2)s1] | N/A |

TABLE 1-continued

| Cmpd # | Structure | IC$_{50}$ |
|---|---|---|
| 153 | 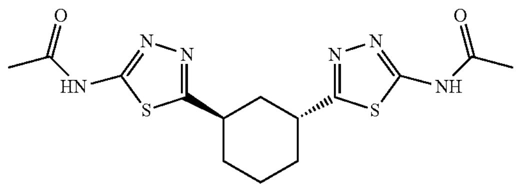 [SMILES: CC(=O)Nc1nnc([C@@H]2CCC[C@@H](c3nnc(NC(C)=O)s3)C2)s1] | N/A |
| 154 | 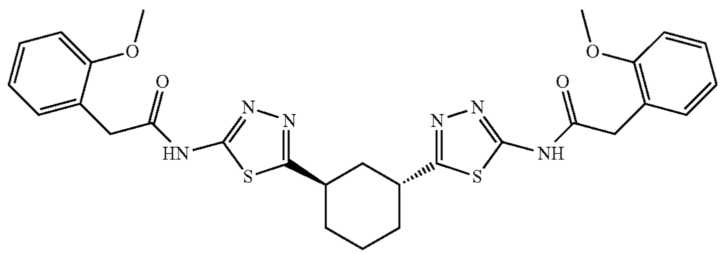 [SMILES: COc1ccccc1CC(=O)Nc1nnc([C@@H]2CCC[C@@H](c3nnc(NC(=O)Cc4ccccc4OC)s3)C2)s1] | N/A |
| 155 | 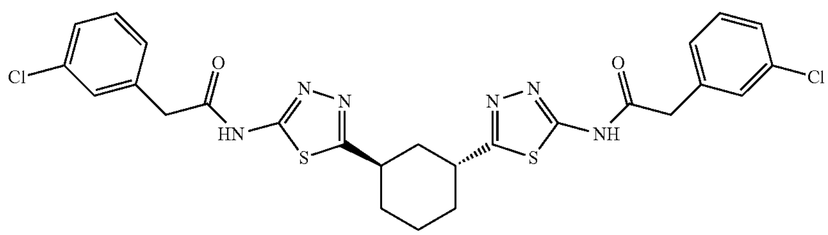 [SMILES: O=C(Cc1cccc(Cl)c1)Nc1nnc([C@@H]2CCC[C@@H](c3nnc(NC(=O)Cc4cccc(Cl)c4)s3)C2)s1] | N/A |
| 156 | 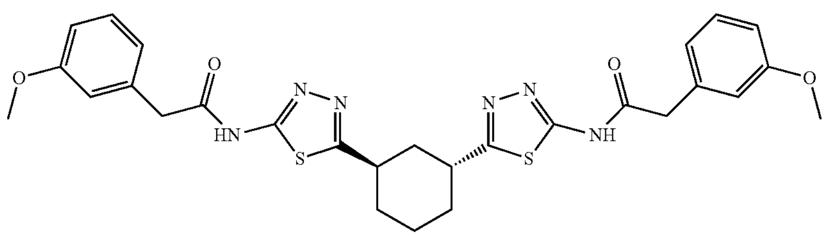 | N/A |
| 157 | 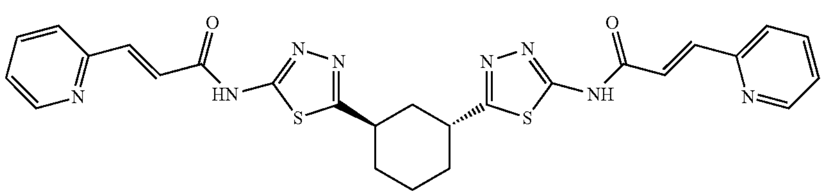 [SMILES: O=C(/C=C/c1ccccn1)Nc1nnc([C@@H]2CCC[C@@H](c3nnc(NC(=O)/C=C/c4ccccn4)s3)C2)s1] | N/A |
| 158 | 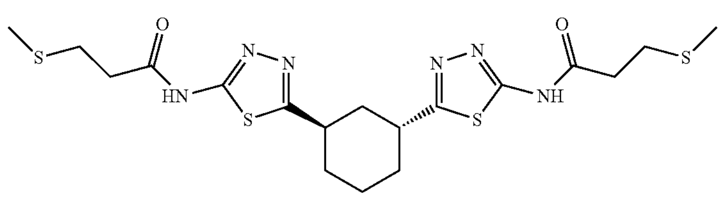 | N/A |
| 159 | 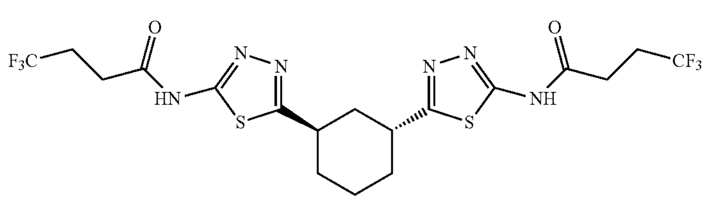 [SMILES: O=C(CCC(F)(F)F)Nc1nnc([C@@H]2CCC[C@@H](c3nnc(NC(=O)CCC(F)(F)F)s3)C2)s1] | N/A |

//
TABLE 1-continued
| Cmpd # | Structure | IC$_{50}$ |
|---|---|---|
| 160 | 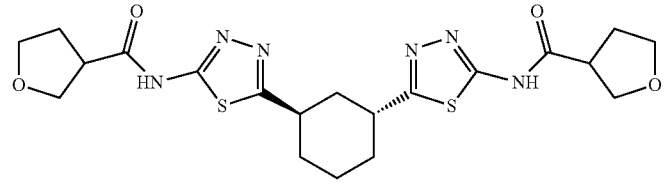 [SMILES: O=C(Nc1nnc([C@@H]2CCC[C@@H](c3nnc(NC(=O)C4CCOC4)s3)C2)s1)C1CCOC1] | N/A |
| 161 | 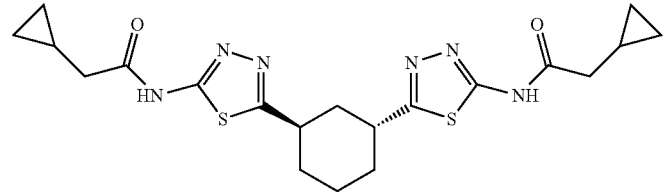 [SMILES: O=C(CC1CC1)Nc1nnc([C@@H]2CCC[C@@H](c3nnc(NC(=O)CC4CC4)s3)C2)s1] | N/A |
| 162 | 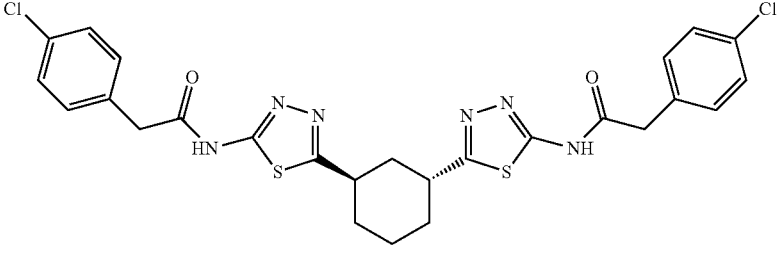 [SMILES: O=C(Cc1ccc(Cl)cc1)Nc1nnc([C@@H]2CCC[C@@H](c3nnc(NC(=O)Cc4ccc(Cl)cc4)s3)C2)s1] | N/A |
| 163 | 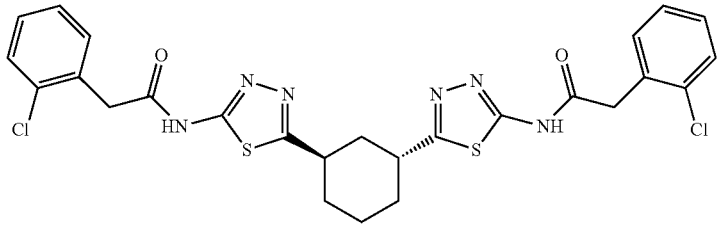 | N/A |
| 164 | 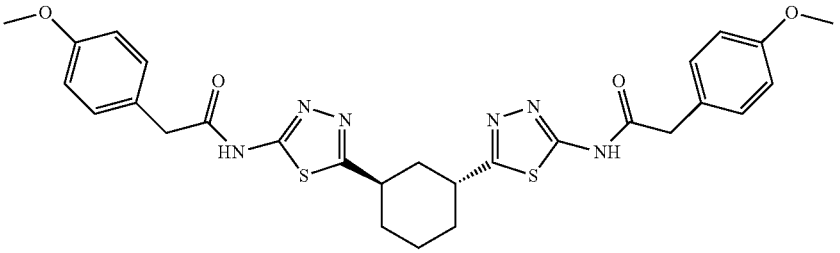 | N/A |
| 165 | 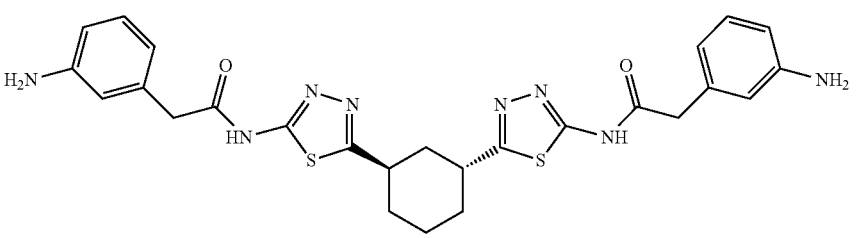 | N/A |

US 10,087,172 B2
73                                                                                                    74
TABLE 1-continued
| Cmpd # | Structure | IC$_{50}$ |
|---|---|---|
| 166 | 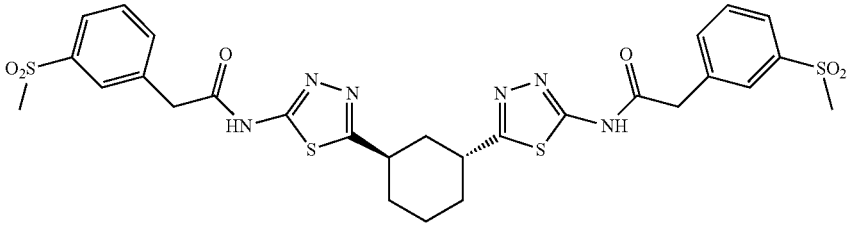 | N/A |
| 167 | 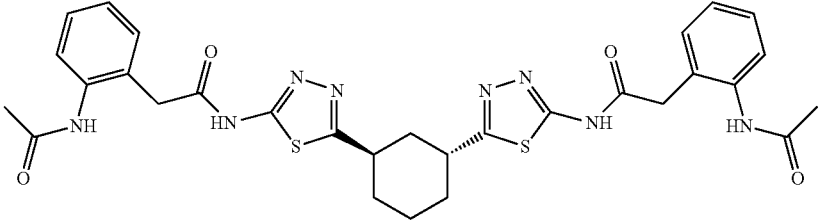 [SMILES: CC(=O)Nc1ccccc1CC(=O)Nc1nnc([C@@H]2CCC[C@@H](c3nnc(NC(=O)Cc4ccccc4NC(C)=O)s3)C2)s1] | N/A |
| 168 | 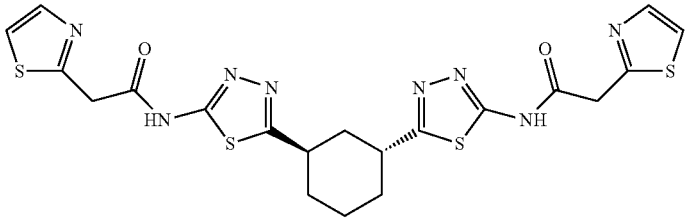 [SMILES: O=C(Cc1nccs1)Nc1nnc([C@@H]2CCC[C@@H](c3nnc(NC(=O)Cc4nccs4)s3)C2)s1] | N/A |
| 169 | 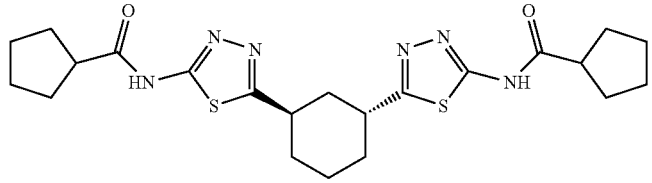 [SMILES: O=C(Nc1nnc([C@@H]2CCC[C@@H](c3nnc(NC(=O)C4CCCC4)s3)C2)s1)C1CCCC1] | N/A |
| 170 | 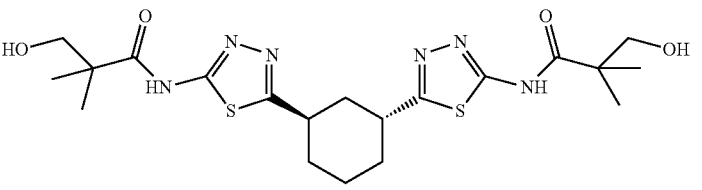 [SMILES: CC(C)(CO)C(=O)Nc1nnc([C@@H]2CCC[C@@H](c3nnc(NC(=O)C(C)(C)CO)s3)C2)s1] | N/A |
| 171 | 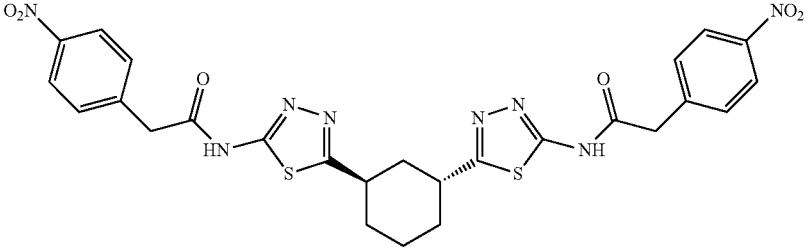 [SMILES: O=C(Cc1ccc([N+](=O)[O-])cc1)Nc1nnc([C@@H]2CCC[C@@H](c3nnc(NC(=O)Cc4ccc([N+](=O)[O-])cc4)s3)C2)s1] | N/A |

TABLE 1-continued

| Cmpd # | Structure | IC$_{50}$ |
|---|---|---|
| 172 | 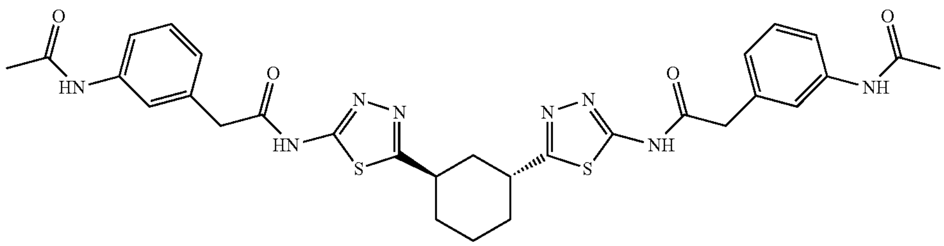 [SMILES: CC(=O)Nc1cccc(CC(=O)Nc2nnc([C@@H]3CCC[C@@H](c4nnc(NC(=O)Cc5cccc(NC(C)=O)c5)s4)C3)s2)c1] | N/A |
| 173 | 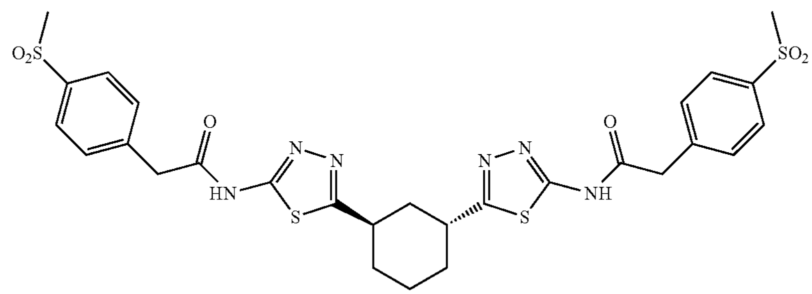 [SMILES: CS(=O)(=O)c1ccc(CC(=O)Nc2nnc([C@@H]3CCC[C@@H](c4nnc(NC(=O)Cc5ccc(S(C)(=O)=O)cc5)s4)C3)s2)cc1] | N/A |
| 174 | 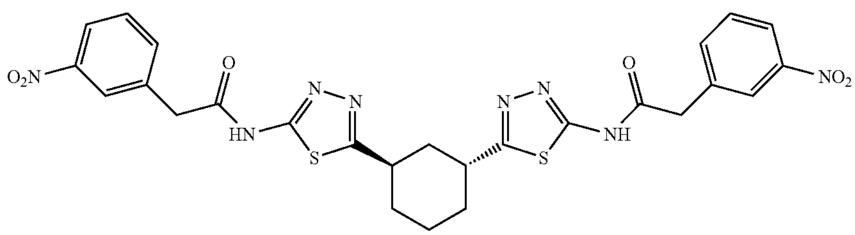 [SMILES: O=C(Cc1cccc([N+](=O)[O-])c1)Nc1nnc([C@@H]2CCC[C@@H](c3nnc(NC(=O)Cc4cccc([N+](=O)[O-])c4)s3)C2)s1] | N/A |
| 175 | 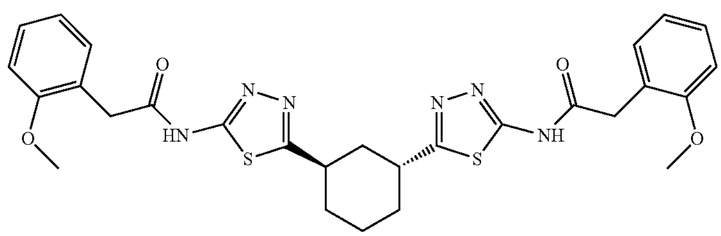 [SMILES: COc1ccccc1CC(=O)Nc1nnc([C@@H]2CCC[C@@H](c3nnc(NC(=O)Cc4ccccc4OC)s3)C2)s1] | N/A |
| 176 | 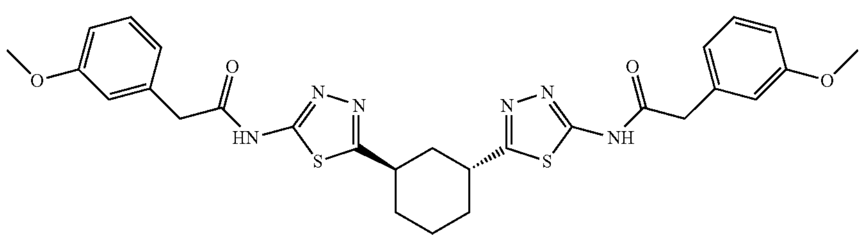 | N/A |
| 177 | 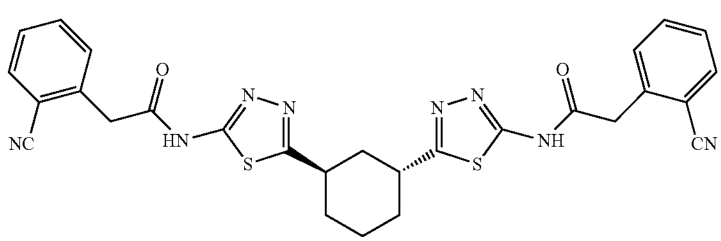 [SMILES: N#Cc1ccccc1CC(=O)Nc1nnc([C@@H]2CCC[C@@H](c3nnc(NC(=O)Cc4ccccc4C#N)s3)C2)s1] | N/A |

TABLE 1-continued

| Cmpd # | Structure | IC$_{50}$ |
|---|---|---|
| 178 | 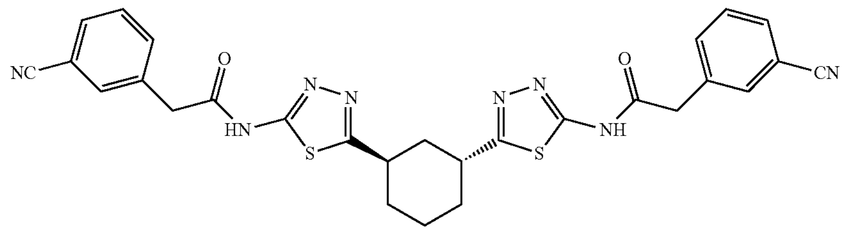 [SMILES: N#Cc1cccc(CC(=O)Nc2nnc([C@@H]3CCC[C@@H](c4nnc(NC(=O)Cc5cccc(C#N)c5)s4)C3)s2)c1] | N/A |
| 179 | 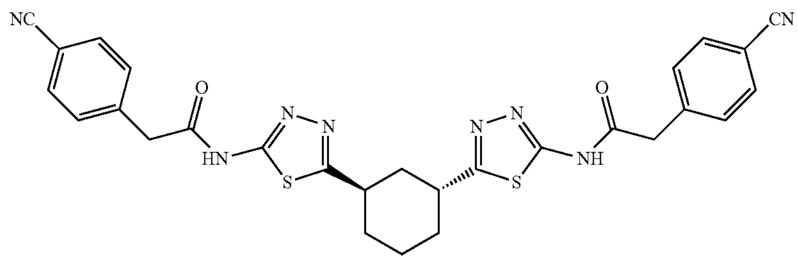 [SMILES: N#Cc1ccc(CC(=O)Nc2nnc([C@@H]3CCC[C@@H](c4nnc(NC(=O)Cc5ccc(C#N)cc5)s4)C3)s2)cc1] | N/A |
| 180 | 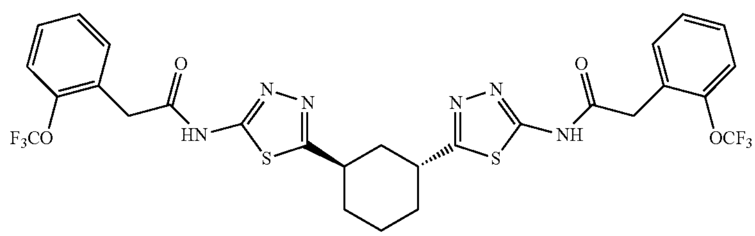 [SMILES: O=C(Cc1ccccc1OC(F)(F)F)Nc1nnc([C@@H]2CCC[C@@H](c3nnc(NC(=O)Cc4ccccc4OC(F)(F)F)s3)C2)s1] | N/A |
| 181 | 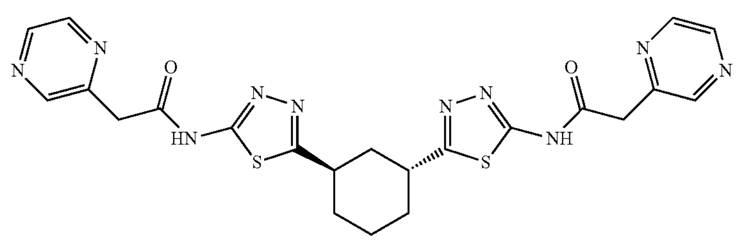 | N/A |
| 182 | 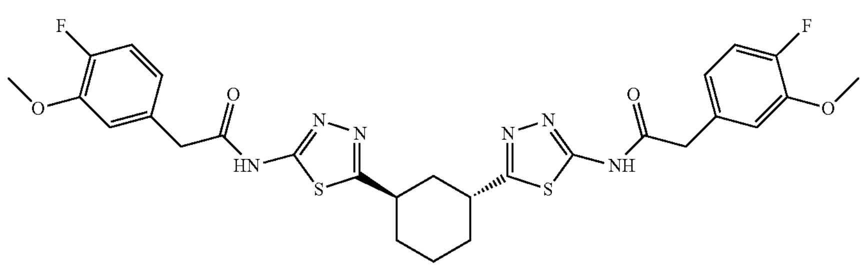 | N/A |
| 183 | 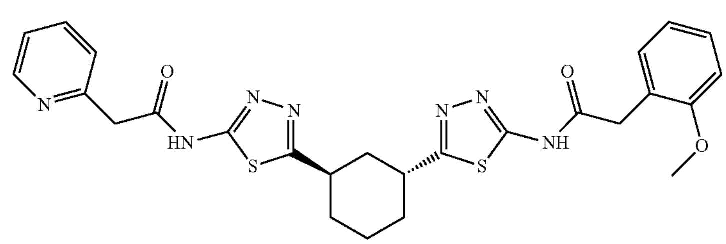 [SMILES: COc1ccccc1CC(=O)Nc1nnc([C@@H]2CCC[C@@H](c3nnc(NC(=O)Cc4ccccn4)s3)C2)s1] | N/A |

TABLE 1-continued
| Cmpd # | Structure | IC$_{50}$ |
|---|---|---|
| 184 | 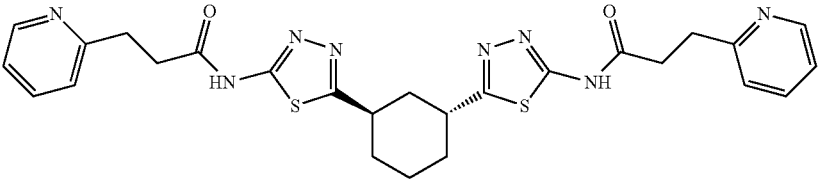 [SMILES: O=C(CCc1ccccn1)Nc1nnc([C@@H]2CCC[C@@H](c3nnc(NC(=O)CCc4ccccn4)s3)C2)s1] | N/A |
| 185 | 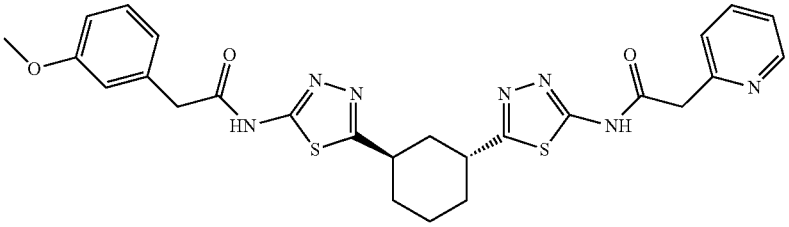 [SMILES: COc1cccc(CC(=O)Nc2nnc([C@@H]3CCC[C@@H](c4nnc(NC(=O)Cc5ccccn5)s4)C3)s2)c1] | N/A |
| 186 | 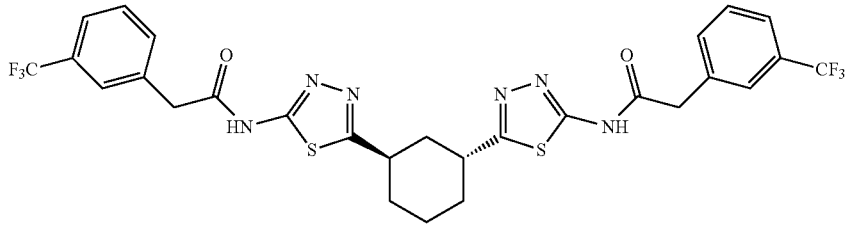 [SMILES: O=C(Cc1cccc(C(F)(F)F)c1)Nc1nnc([C@@H]2CCC[C@@H](c3nnc(NC(=O)Cc4cccc(C(F)(F)F)c4)s3)C2)s1] | N/A |
| 187 | 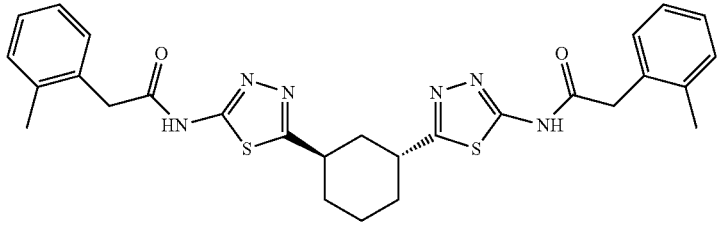 | N/A |
| 188 | 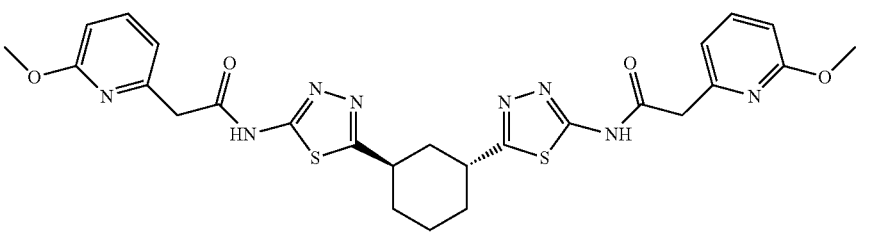 | N/A |
| 189 | 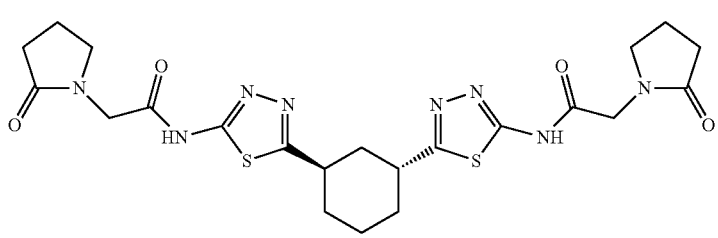 [SMILES: O=C(CN1CCCC1=O)Nc1nnc([C@@H]2CCC[C@@H](c3nnc(NC(=O)CN4CCCC4=O)s3)C2)s1] | N/A |

TABLE 1-continued
| Cmpd # | Structure | IC$_{50}$ |
|---|---|---|
| 190 | 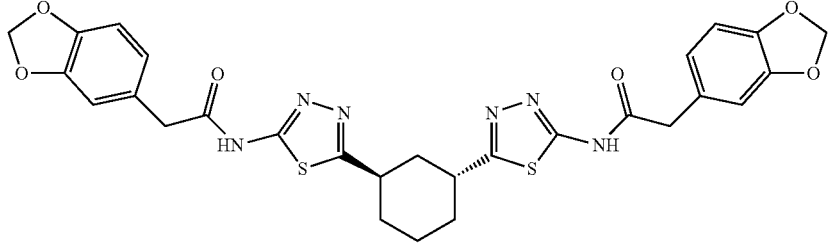 [SMILES: O=C(Cc1ccc2c(c1)OCO2)Nc1nnc([C@@H]2CCC[C@@H](c3nnc(NC(=O)Cc4ccc5c(c4)OCO5)s3)C2)s1] | N/A |
| 191 | 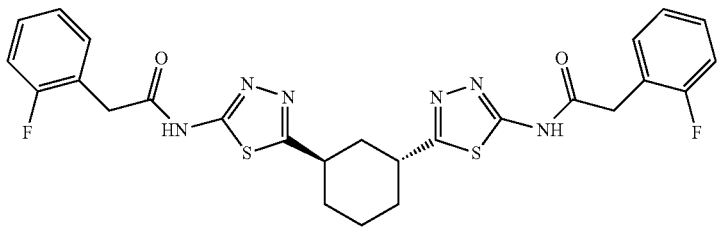 [SMILES: O=C(Cc1ccccc1F)Nc1nnc([C@@H]2CCC[C@@H](c3nnc(NC(=O)Cc4ccccc4F)s3)C2)s1] | N/A |
| 192 | 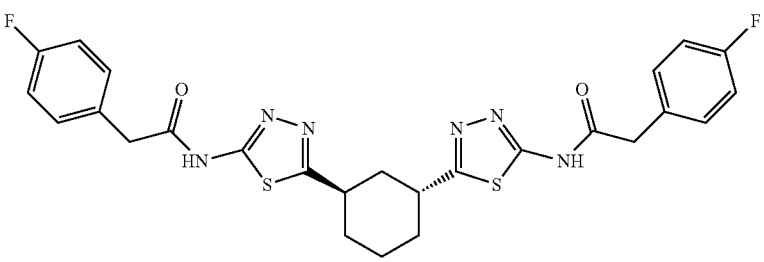 [SMILES: O=C(Cc1ccc(F)cc1)Nc1nnc([C@@H]2CCC[C@@H](c3nnc(NC(=O)Cc4ccc(F)cc4)s3)C2)s1] | N/A |
| 193 | 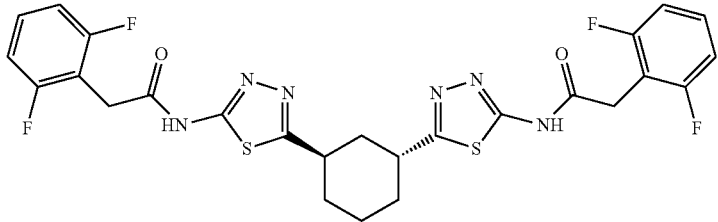 [SMILES: O=C(Cc1c(F)cccc1F)Nc1nnc([C@@H]2CCC[C@@H](c3nnc(NC(=O)Cc4c(F)cccc4F)s3)C2)s1] | N/A |
| 194 | 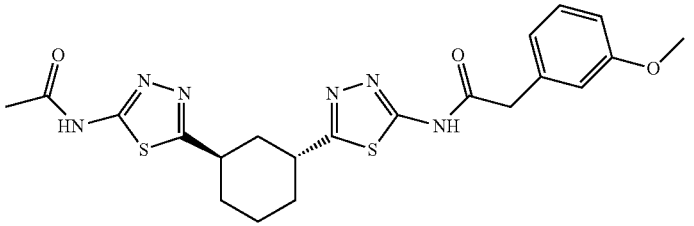 [SMILES: COc1cccc(CC(=O)Nc2nnc([C@@H]3CCC[C@@H](c4nnc(NC(C)=O)s4)C3)s2)c1] | N/A |
| 195 | 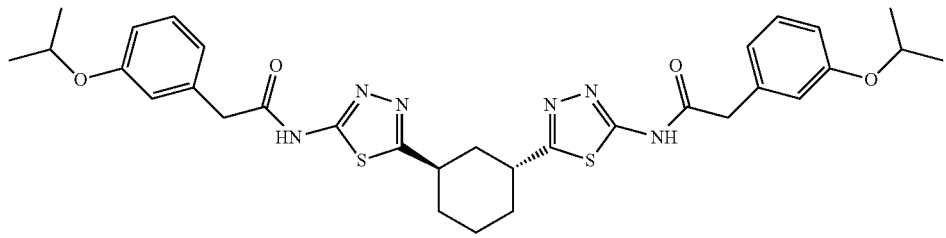 [SMILES: CC(C)Oc1cccc(CC(=O)Nc2nnc([C@@H]3CCC[C@@H](c4nnc(NC(=O)Cc5cccc(OC(C)C)c5)s4)C3)s2)c1] | N/A |

TABLE 1-continued
| Cmpd # | Structure | IC$_{50}$ |
|---|---|---|
| 196 | 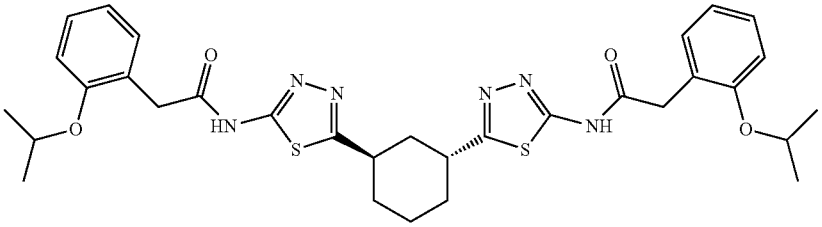 [SMILES: CC(C)Oc1ccccc1CC(=O)Nc1nnc([C@@H]2CCC[C@@H](c3nnc(NC(=O)Cc4ccccc4OC(C)C)s3)C2)s1] | N/A |
| 197 | 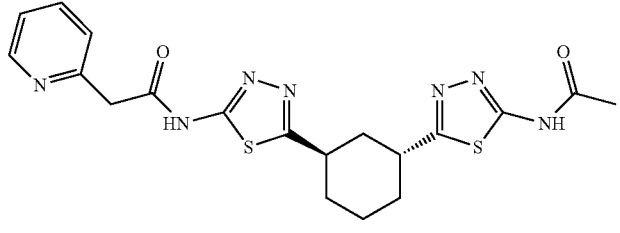 [SMILES: CC(=O)Nc1nnc([C@@H]2CCC[C@@H](c3nnc(NC(=O)Cc4ccccn4)s3)C2)s1] | N/A |
| 198 | 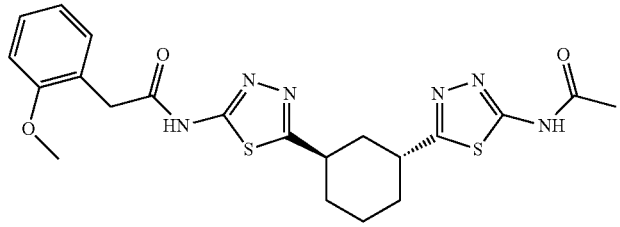 [SMILES: COc1ccccc1CC(=O)Nc1nnc([C@@H]2CCC[C@@H](c3nnc(NC(C)=O)s3)C2)s1] | N/A |
| 199 | 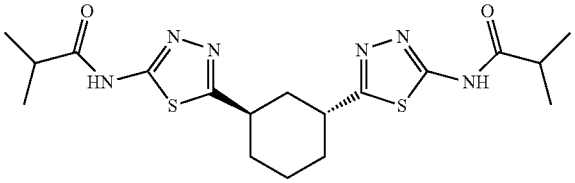 [SMILES: CC(C)C(=O)Nc1nnc([C@@H]2CCC[C@@H](c3nnc(NC(=O)C(C)C)s3)C2)s1] | N/A |
| 200 | 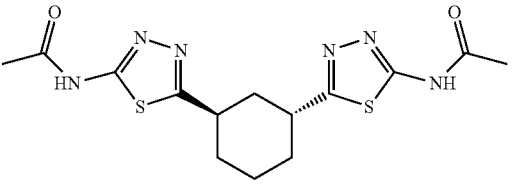 [SMILES: CC(=O)Nc1nnc([C@@H]2CCC[C@@H](c3nnc(NC(C)=O)s3)C2)s1] | N/A |
| 201 | 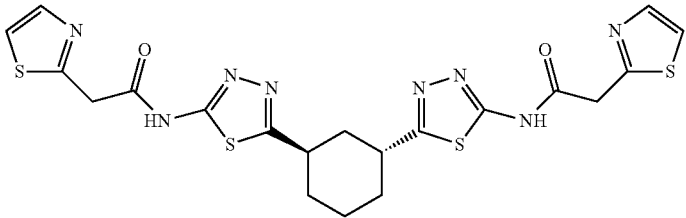 [SMILES: O=C(Cc1nccs1)Nc1nnc([C@@H]2CCC[C@@H](c3nnc(NC(=O)Cc4nccs4)s3)C2)s1] | N/A |
| 202 | 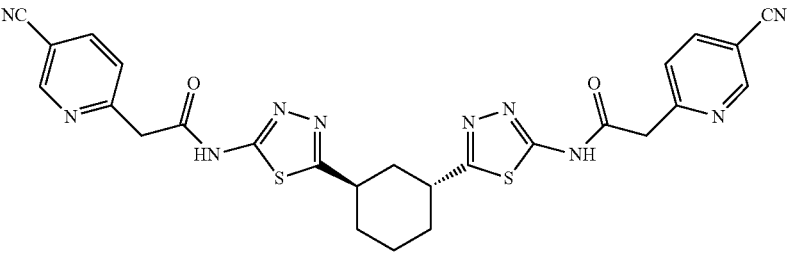 [SMILES: N#Cc1ccc(CC(=O)Nc2nnc([C@@H]3CCC[C@@H](c4nnc(NC(=O)Cc5ccc(C#N)cn5)s4)C3)s2)nc1] | N/A |

TABLE 1-continued
| Cmpd # | Structure | IC$_{50}$ |
|---|---|---|
| 203 | 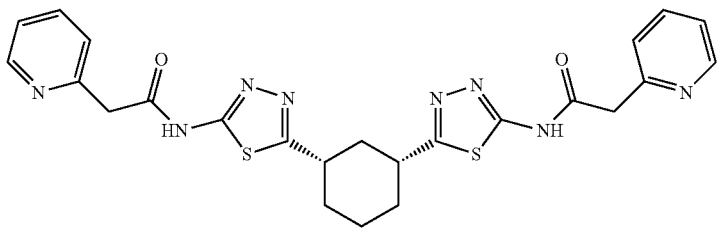 [SMILES: O=C(Cc1ccccn1)Nc1nnc([C@@H]2CCC[C@H](c3nnc(NC(=O)Cc4ccccn4)s3)C2)s1] | N/A |
| 204 | 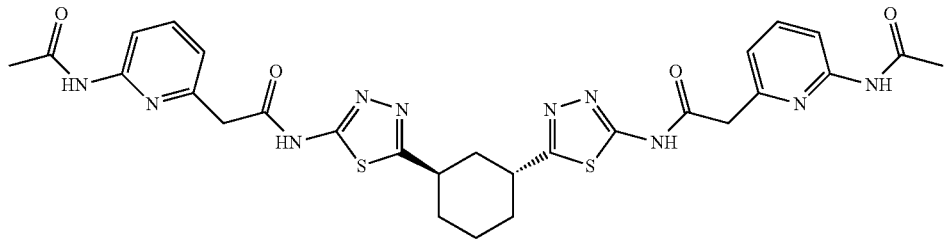 [SMILES: CC(=O)Nc1cccc(CC(=O)Nc2nnc([C@@H]3CCC[C@@H](c4nnc(NC(=O)Cc5cccc(NC(C)=O)n5)s4)C3)s2)n1] | N/A |
| 205 | 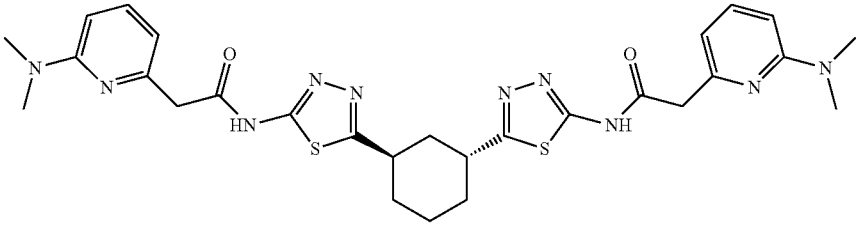 | N/A |
| 206 | 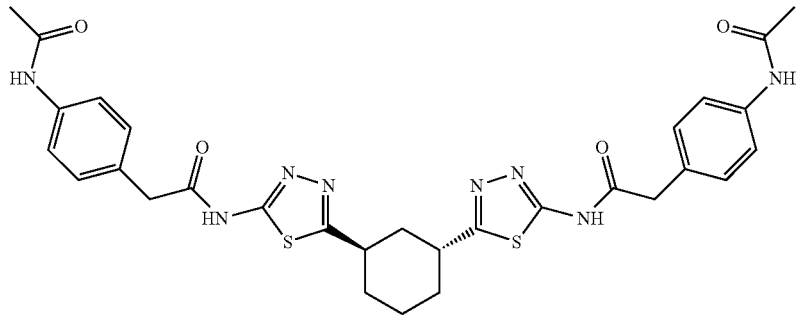 [SMILES: CC(=O)Nc1ccc(CC(=O)Nc2nnc([C@@H]3CCC[C@@H](c4nnc(NC(=O)Cc5ccc(NC(C)=O)cc5)s4)C3)s2)cc1] | N/A |
| 207 | 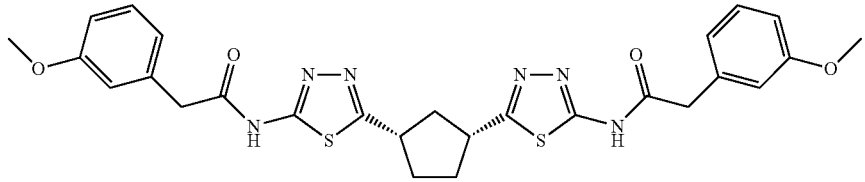 | N/A |
| 208 | 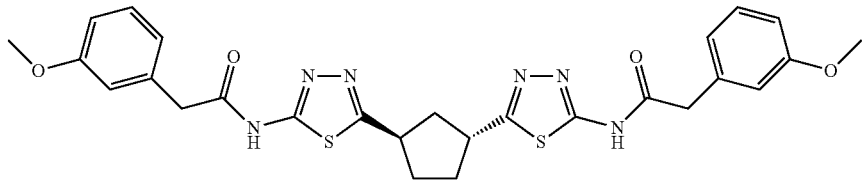 | N/A |

US 10,087,172 B2
87                                                                88
TABLE 1-continued
| Cmpd # | Structure | IC$_{50}$ |
|---|---|---|
| 209 | 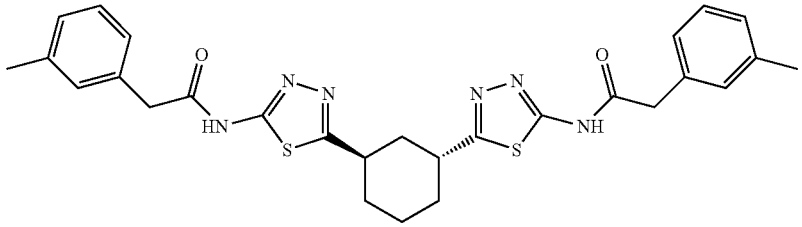 | N/A |
| 210 | 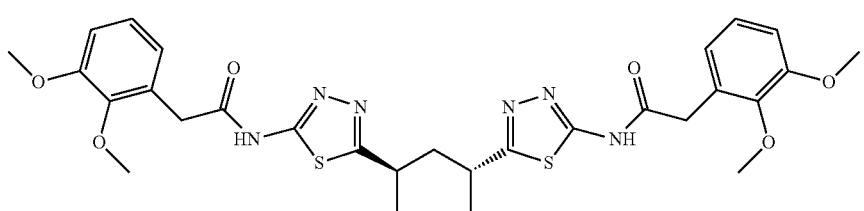 | N/A |
| 211 | 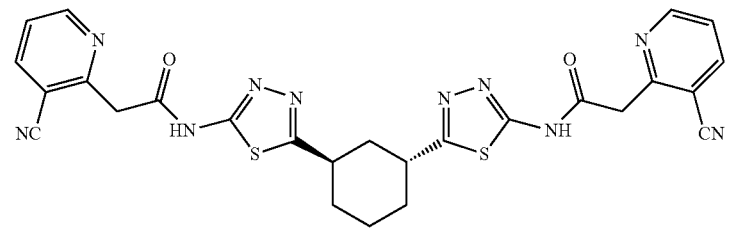 | N/A |
| 212 | 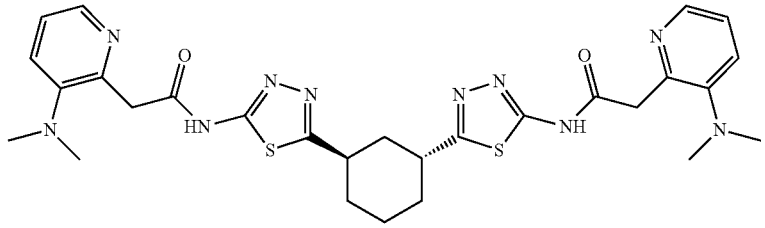 | N/A |
| 213 | 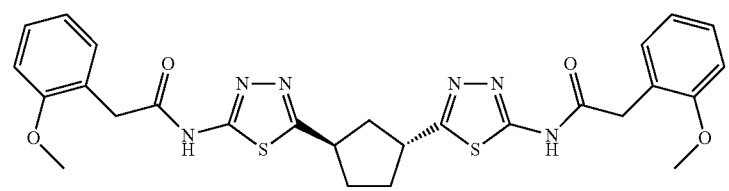 [SMILES: COc1ccccc1CC(=O)Nc1nnc([C@@H]2CC[C@@H](c3nnc(NC(=O)Cc4ccccc4OC)s3)C2)s1] | N/A |
| 214 | 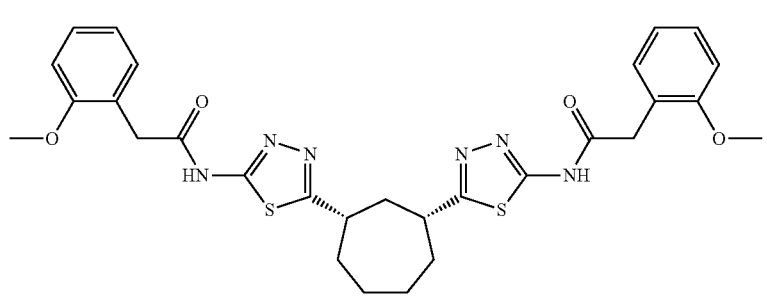 | N/A |

TABLE 1-continued

| Cmpd # | Structure | IC$_{50}$ |
|---|---|---|
| 215 | 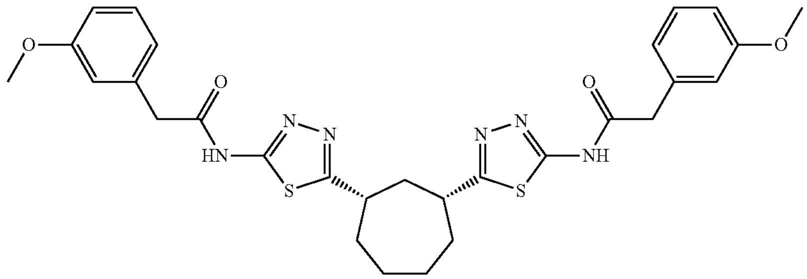 | N/A |
| 216 | 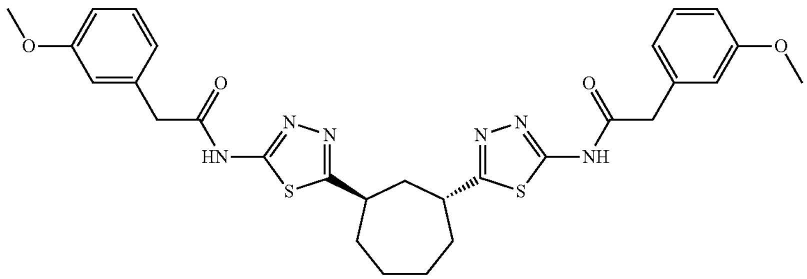 | N/A |
| 217 | 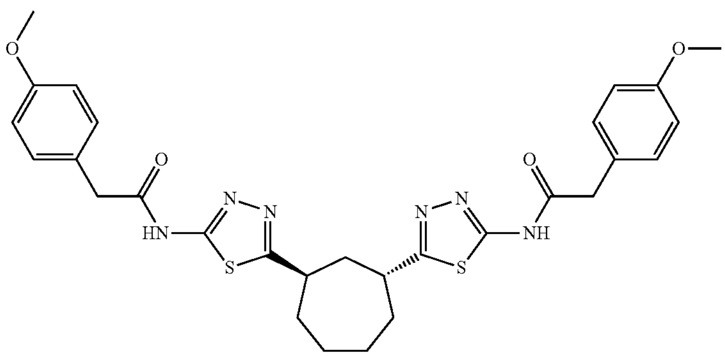 [SMILES: COc1ccc(CC(=O)Nc2nnc([C@@H]3CCCC[C@@H](c4nnc(NC(=O)Cc5ccc(OC)cc5)s4)C3)s2)cc1] | N/A |
| 218 | 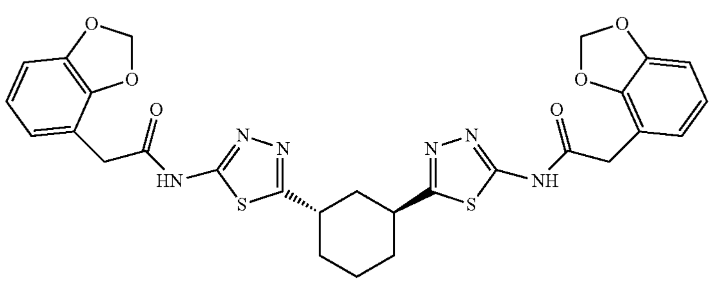 [SMILES: O=C(Cc1cccc2c1OCO2)Nc1nnc([C@H]2CCC[C@H](c3nnc(NC(=O)Cc4cccc5c4OCO5)s3)C2)s1] | A |
| 219 | 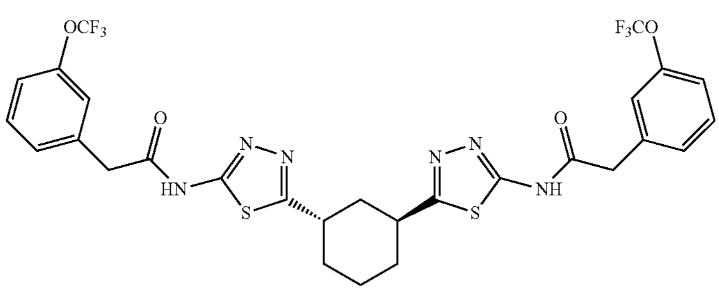 [SMILES: O=C(Cc1cccc(OC(F)(F)F)c1)Nc1nnc([C@H]2CCC[C@H](c3nnc(NC(=O)Cc4cccc(OC(F)(F)F)c4)s3)C2)s1] | D |

TABLE 1-continued

| Cmpd # | Structure | IC$_{50}$ |
|---|---|---|
| 220 | 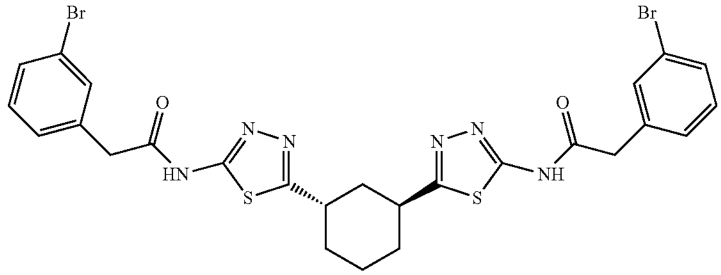 [SMILES: O=C(Cc1cccc(Br)c1)Nc1nnc([C@H]2CCC[C@H](c3nnc(NC(=O)Cc4cccc(Br)c4)s3)C2)s1] | B |
| 221 | 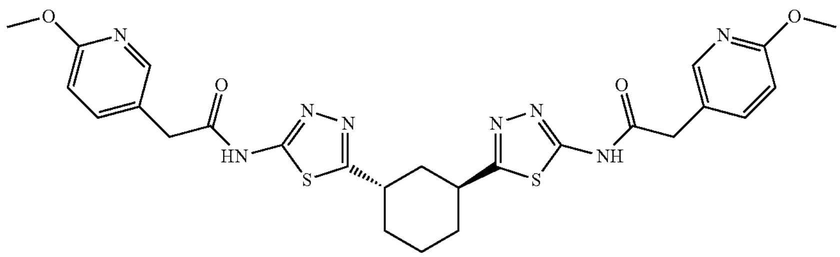 | A |
| 222 | 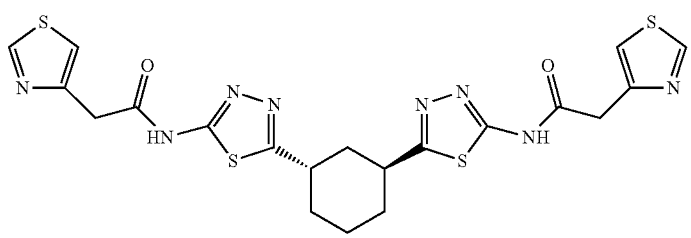 [SMILES: O=C(Cc1cscn1)Nc1nnc([C@H]2CCC[C@H](c3nnc(NC(=O)Cc4cscn4)s3)C2)s1] | A |
| 223 | 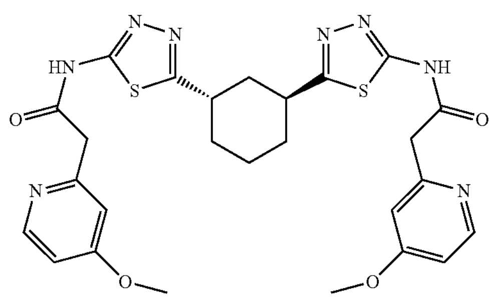 [SMILES: COc1ccnc(CC(=O)Nc2nnc([C@H]3CCC[C@H](c4nnc(NC(=O)Cc5cc(OC)ccn5)s4)C3)s2)c1] | A |
| 224 | 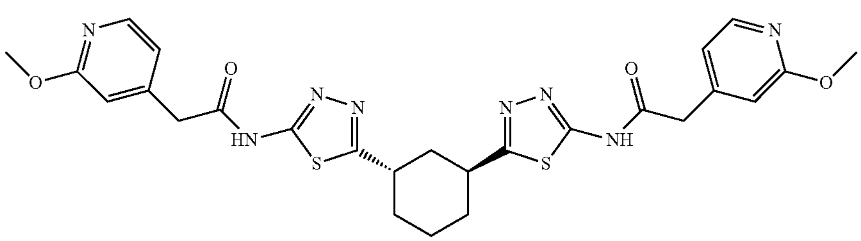 | A |

TABLE 1-continued

| Cmpd # | Structure | IC$_{50}$ |
|---|---|---|
| 225 | 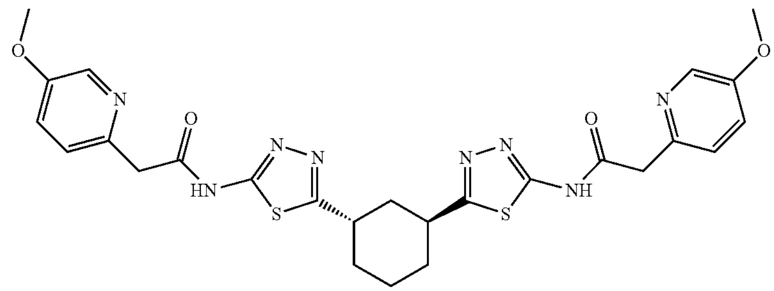 [SMILES: COc1ccc(CC(=O)Nc2nnc([C@H]3CCC[C@H](c4nnc(NC(=O)Cc5ccc(OC)cn5)s4)C3)s2)nc1] | A |
| 226 | 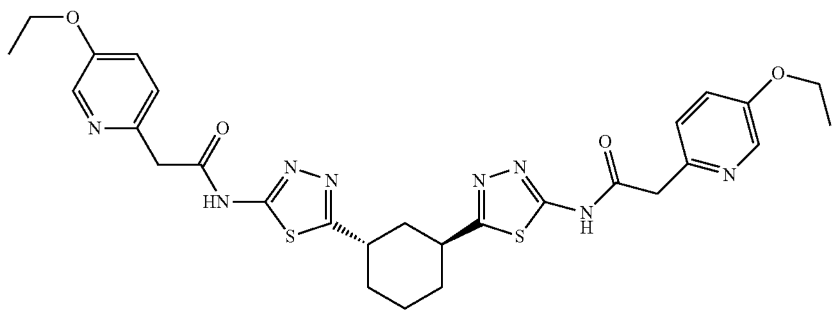 [SMILES: CCOc1ccc(CC(=O)Nc2nnc([C@H]3CCC[C@H](c4nnc(NC(=O)Cc5ccc(OCC)cn5)s4)C3)s2)nc1] | A |
| 227 | 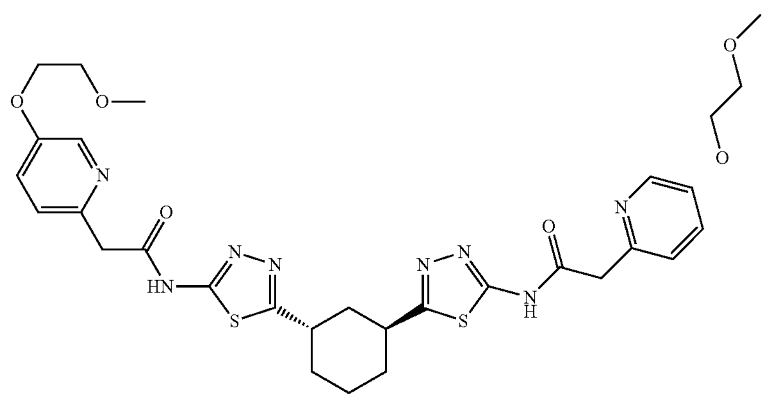 | A |
| 228 | 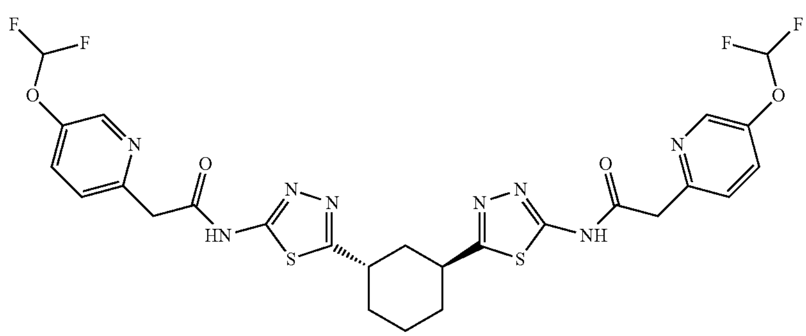 [SMILES: O=C(Cc1ccc(OC(F)F)cn1)Nc1nnc([C@H]2CCC[C@H](c3nnc(NC(=O)Cc4ccc(OC(F)F)cn4)s3)C2)s1] | A |
| 229 | 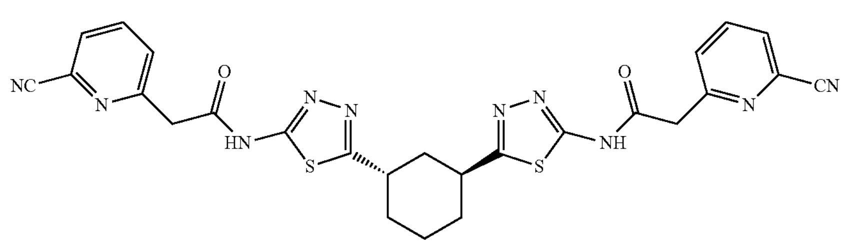 [SMILES: N#Cc1cccc(CC(=O)Nc2nnc([C@H]3CCC[C@H](c4nnc(NC(=O)Cc5cccc(C#N)n5)s4)C3)s2)n1] | A |

TABLE 1-continued

| Cmpd # | Structure | IC$_{50}$ |
|---|---|---|
| 230 | pyrimidin-4-yl-CH$_2$-C(O)NH-[1,3,4-thiadiazol-2-yl]-(1,3-cyclohexyl)-[1,3,4-thiadiazol-2-yl]-NHC(O)-CH$_2$-pyrimidin-4-yl | D |
| 231 | pyridazin-3-yl-CH$_2$-C(O)NH-[1,3,4-thiadiazol-2-yl]-(1,3-cyclohexyl)-[1,3,4-thiadiazol-2-yl]-NHC(O)-CH$_2$-pyridazin-3-yl | B |
| 232 | (6-amino-pyridin-2-yl)-CH$_2$-C(O)NH-[1,3,4-thiadiazol-2-yl]-(1,3-cyclohexyl)-[1,3,4-thiadiazol-2-yl]-NHC(O)-CH$_2$-(6-amino-pyridin-2-yl) | A |
| 233 | (5-amino-pyridin-2-yl)-CH$_2$-C(O)NH-[1,3,4-thiadiazol-2-yl]-(1,3-cyclohexyl)-[1,3,4-thiadiazol-2-yl]-NHC(O)-CH$_2$-(5-amino-pyridin-2-yl) | A |
| 234 | (5-(N,N-dimethylcarbamoyl)-pyridin-2-yl)-CH$_2$-C(O)NH-[1,3,4-thiadiazol-2-yl]-(1,3-cyclohexyl)-[1,3,4-thiadiazol-2-yl]-NHC(O)-CH$_2$-(5-(N,N-dimethylcarbamoyl)-pyridin-2-yl) | B |
| 235 | (3-(diethylamino)phenyl)-CH$_2$-C(O)NH-[1,3,4-thiadiazol-2-yl]-(1,3-cyclohexyl)-[1,3,4-thiadiazol-2-yl]-NHC(O)-CH$_2$-(3-(diethylamino)phenyl) | C |

TABLE 1-continued

| Cmpd # | Structure | IC$_{50}$ |
|---|---|---|
| 236 | 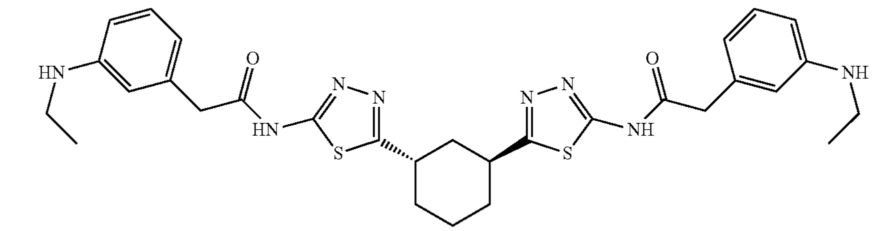 [SMILES: CCNc1cccc(CC(=O)Nc2nnc([C@H]3CCC[C@H](c4nnc(NC(=O)Cc5cccc(NCC)c5)s4)C3)s2)c1] | A |
| 237 | 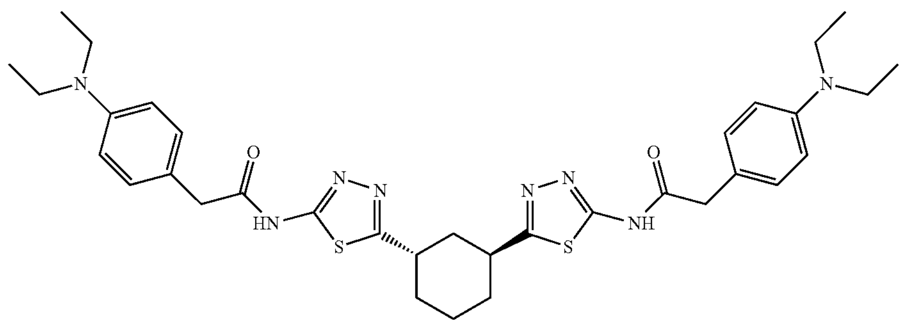 [SMILES: CCN(CC)c1ccc(CC(=O)Nc2nnc([C@H]3CCC[C@H](c4nnc(NC(=O)Cc5ccc(N(CC)CC)cc5)s4)C3)s2)cc1] | C |
| 238 | 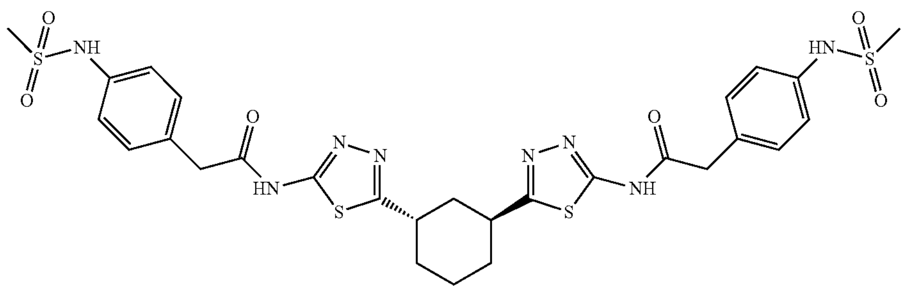 | A |
| 239 | 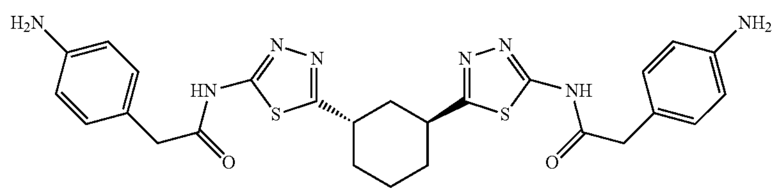 [SMILES: Nc1ccc(CC(=O)Nc2nnc([C@H]3CCC[C@H](c4nnc(NC(=O)Cc5ccc(N)cc5)s4)C3)s2)cc1] | A |
| 240 | 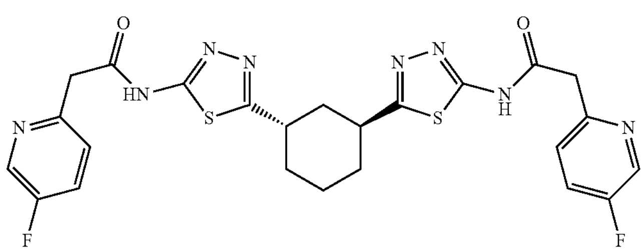 [SMILES: O=C(Cc1ccc(F)cn1)Nc1nnc([C@H]2CCC[C@H](c3nnc(NC(=O)Cc4ccc(F)cn4)s3)C2)s1] | A |
| 241 | 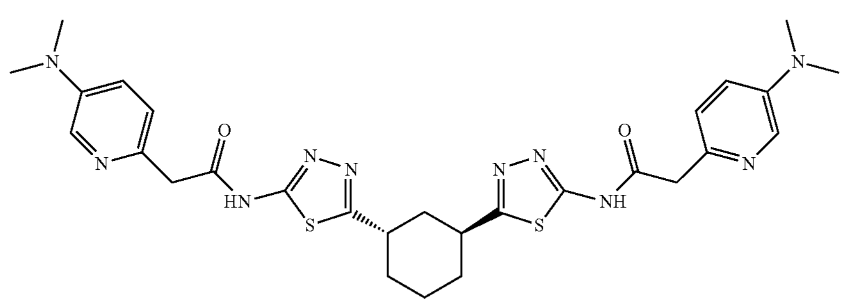 | A |

TABLE 1-continued

| Cmpd # | Structure | IC$_{50}$ |
|---|---|---|
| 242 | 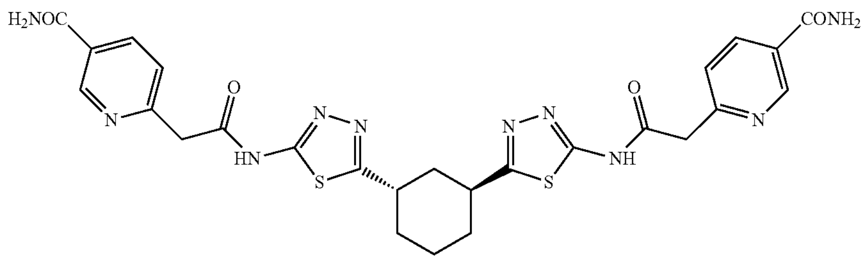 [SMILES: NC(=O)c1ccc(CC(=O)Nc2nnc([C@H]3CCC[C@H](c4nnc(NC(=O)Cc5ccc(C(N)=O)cn5)s4)C3)s2)nc1] | A |
| 243 | 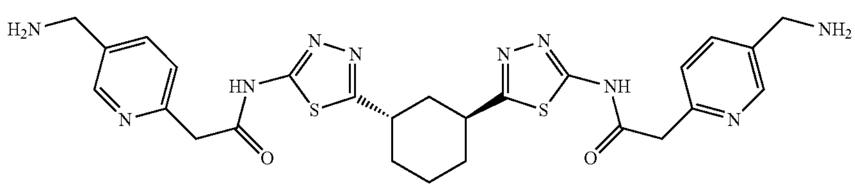 [SMILES: NCc1ccc(CC(=O)Nc2nnc([C@H]3CCC[C@H](c4nnc(NC(=O)Cc5ccc(CN)cn5)s4)C3)s2)nc1] | B |
| 244 | 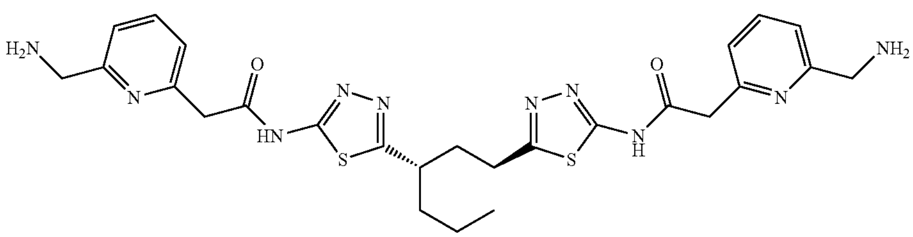 | B |
| 245 | 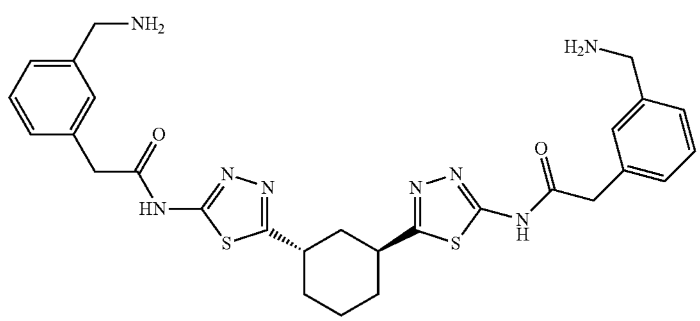 [SMILES: NCc1cccc(CC(=O)Nc2nnc([C@H]3CCC[C@H](c4nnc(NC(=O)Cc5cccc(CN)c5)s4)C3)s2)c1] | A |
| 246 | 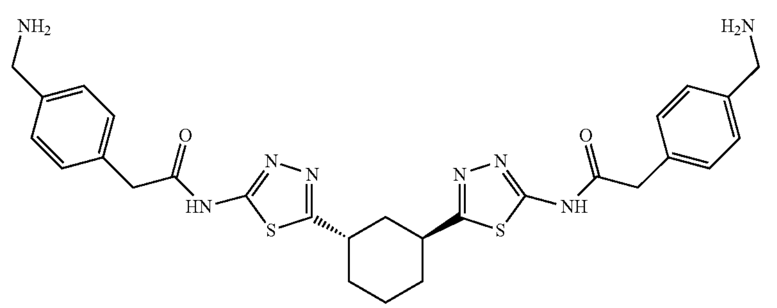 [SMILES: NCc1ccc(CC(=O)Nc2nnc([C@H]3CCC[C@H](c4nnc(NC(=O)Cc5ccc(CN)cc5)s4)C3)s2)cc1] | A |

TABLE 1-continued

| Cmpd # | Structure | IC$_{50}$ |
|---|---|---|
| 247 | 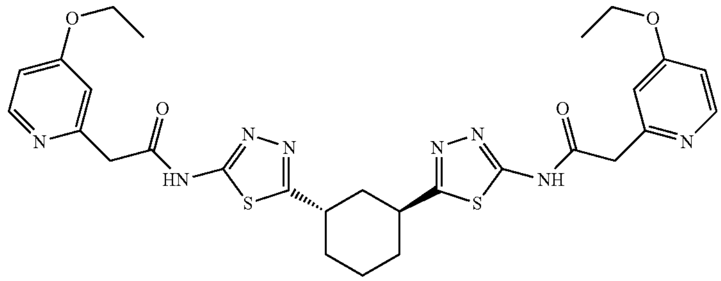 [SMILES: CCOc1ccnc(CC(=O)Nc2nnc([C@H]3CCC[C@H](c4nnc(NC(=O)Cc5cc(OCC)ccn5)s4)C3)s2)c1] | A |
| 248 | 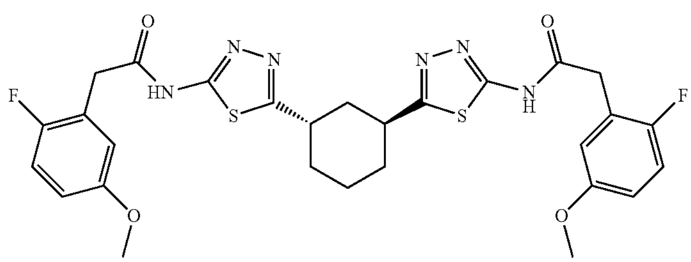 [SMILES: COc1ccc(F)c(CC(=O)Nc2nnc([C@H]3CCC[C@H](c4nnc(NC(=O)Cc5cc(OC)ccc5F)s4)C3)s2)c1] | A |
| 249 | 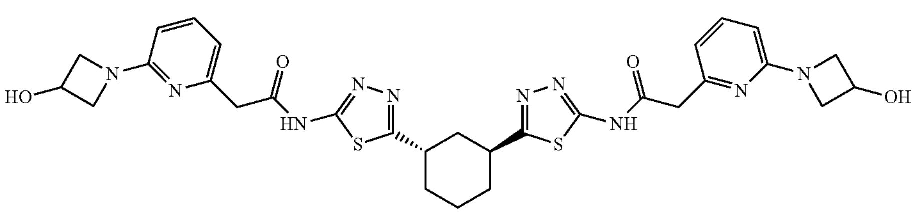 [SMILES: O=C(Cc1cccc(N2CC(O)C2)n1)Nc1nnc([C@H]2CCC[C@H](c3nnc(NC(=O)Cc4cccc(N5CC(O)C5)n4)s3)C2)s1] | A |
| 250 | 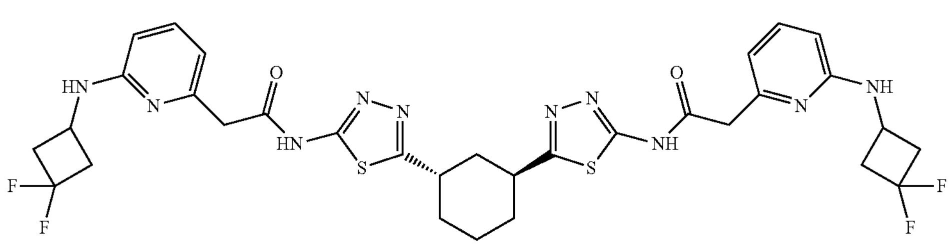 [SMILES: O=C(Cc1cccc(NC2CC(F)(F)C2)n1)Nc1nnc([C@H]2CCC[C@H](c3nnc(NC(=O)Cc4cccc(NC5CC(F)(F)C5)n4)s3)C2)s1] | B |
| 251 | 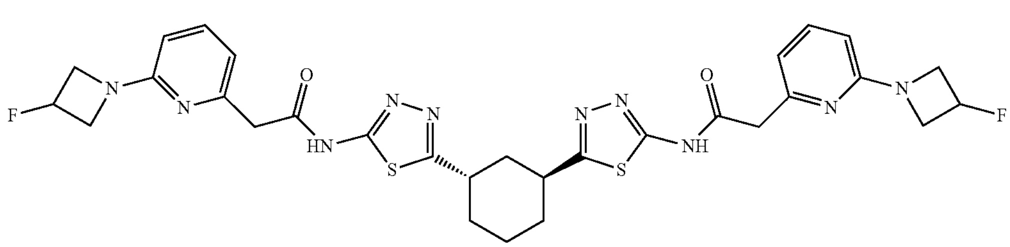 [SMILES: O=C(Cc1cccc(N2CC(F)C2)n1)Nc1nnc([C@H]2CCC[C@H](c3nnc(NC(=O)Cc4cccc(N5CC(F)C5)n4)s3)C2)s1] | A |

TABLE 1-continued

| Cmpd # | Structure | IC$_{50}$ |
|---|---|---|
| 252 | 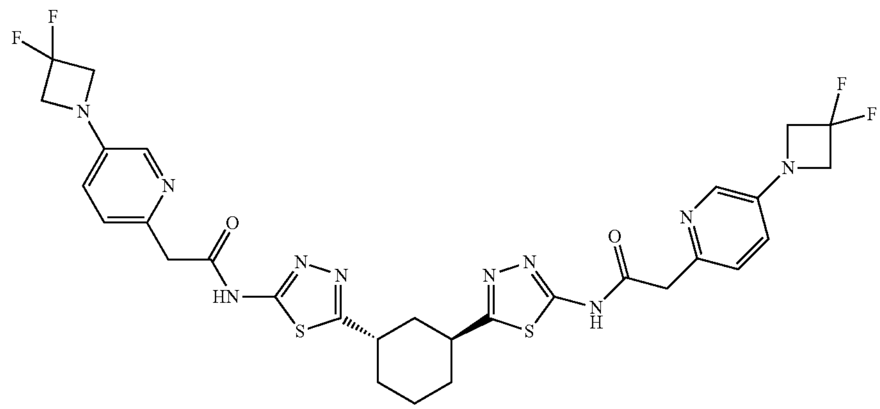 [SMILES: O=C(Cc1ccc(N2CC(F)(F)C2)cn1)Nc1nnc([C@H]2CCC[C@H](c3nnc(NC(=O)Cc4ccc(N5CC(F)(F)C5)cn4)s3)C2)s1] | A |
| 253 | 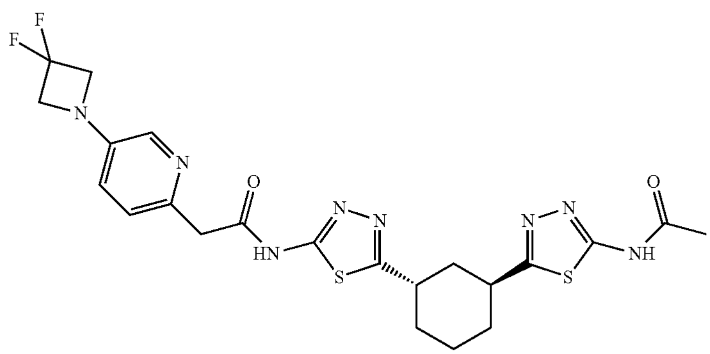 [SMILES: CC(=O)Nc1nnc([C@H]2CCC[C@H](c3nnc(NC(=O)Cc4ccc(N5CC(F)(F)C5)cn4)s3)C2)s1] | B |
| 254 | 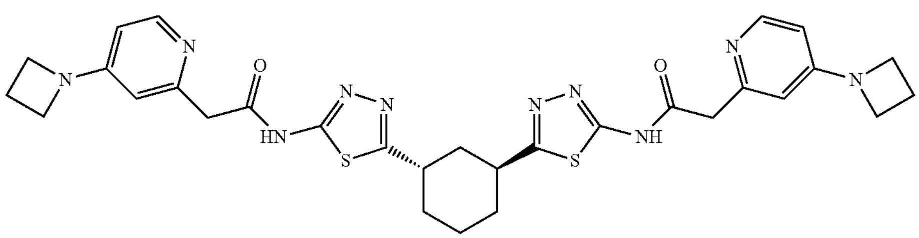 [SMILES: O=C(Cc1cc(N2CCC2)ccn1)Nc1nnc([C@H]2CCC[C@H](c3nnc(NC(=O)Cc4cc(N5CCC5)ccn4)s3)C2)s1] | B |
| 255 | 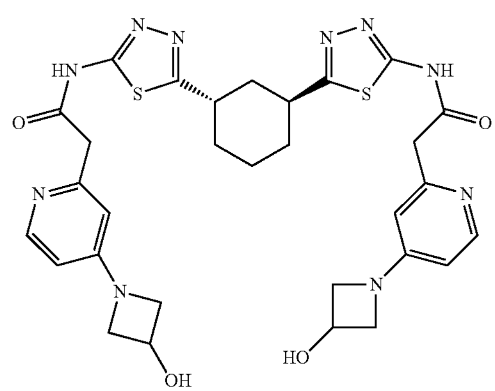 [SMILES: O=C(Cc1cc(N2CC(O)C2)ccn1)Nc1nnc([C@H]2CCC[C@H](c3nnc(NC(=O)Cc4cc(N5CC(O)C5)ccn4)s3)C2)s1] | B |

TABLE 1-continued

| Cmpd # | Structure | IC$_{50}$ |
|---|---|---|
| 256 | 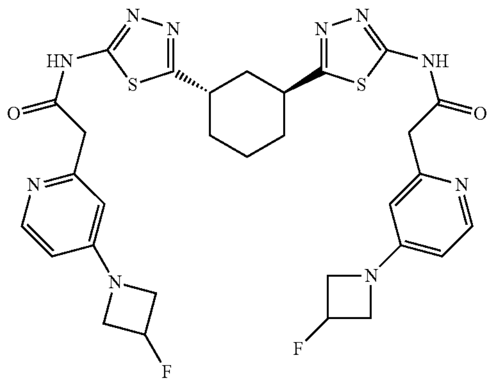 [SMILES: O=C(Cc1cc(N2CC(F)C2)ccn1)Nc1nnc([C@H]2CCC[C@H](c3nnc(NC(=O)Cc4cc(N5CC(F)C5)ccn4)s3)C2)s1] | A |
| 257 | 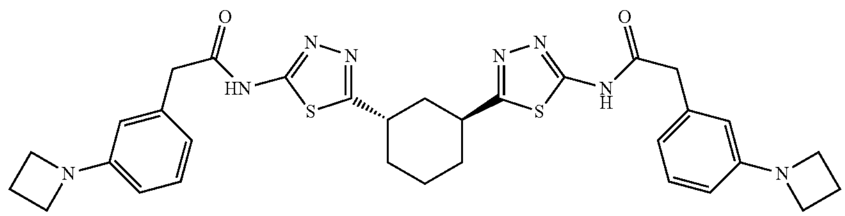 [SMILES: O=C(Cc1cccc(N2CCC2)c1)Nc1nnc([C@H]2CCC[C@H](c3nnc(NC(=O)Cc4cccc(N5CCC5)c4)s3)C2)s1] | A |
| 258 | 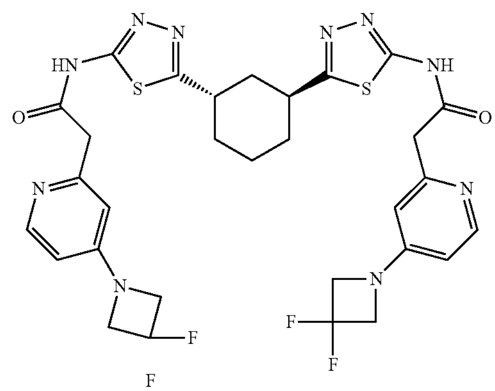 | B |
| 259 | 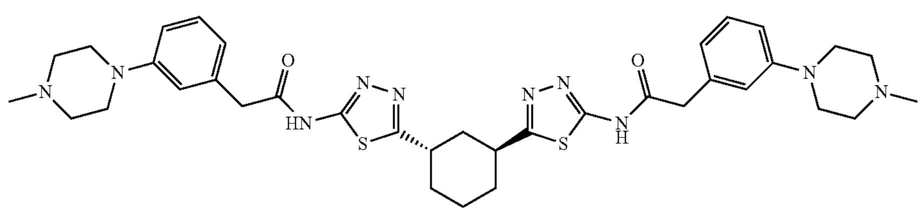 | B |
| 260 | 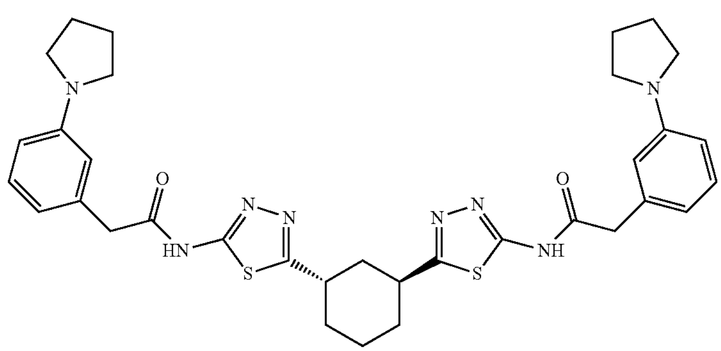 [SMILES: O=C(Cc1cccc(N2CCCC2)c1)Nc1nnc([C@H]2CCC[C@H](c3nnc(NC(=O)Cc4cccc(N5CCCC5)c4)s3)C2)s1] | B |

TABLE 1-continued

| Cmpd # | Structure | IC$_{50}$ |
|---|---|---|
| 261 | 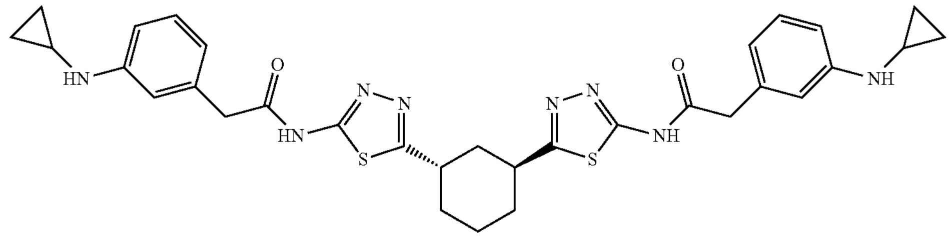 [SMILES: O=C(Cc1cccc(NC2CC2)c1)Nc1nnc([C@H]2CCC[C@H](c3nnc(NC(=O)Cc4cccc(NC5CC5)c4)s3)C2)s1] | A |
| 262 | 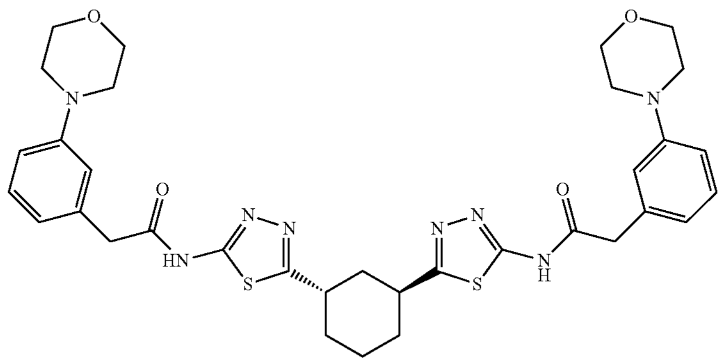 [SMILES: O=C(Cc1cccc(N2CCOCC2)c1)Nc1nnc([C@H]2CCC[C@H](c3nnc(NC(=O)Cc4cccc(N5CCOCC5)c4)s3)C2)s1] | A |
| 263 | 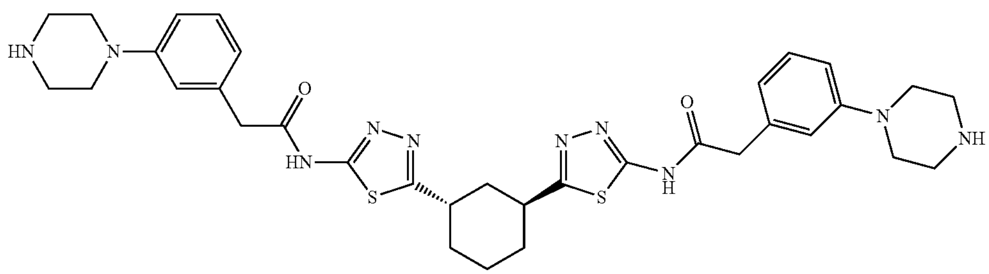 [SMILES: O=C(Cc1cccc(N2CCNCC2)c1)Nc1nnc([C@H]2CCC[C@H](c3nnc(NC(=O)Cc4cccc(N5CCNCC5)c4)s3)C2)s1] | A |
| 264 | 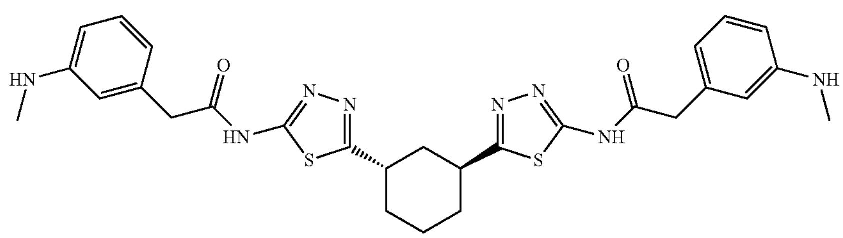 | A |
| 265 | 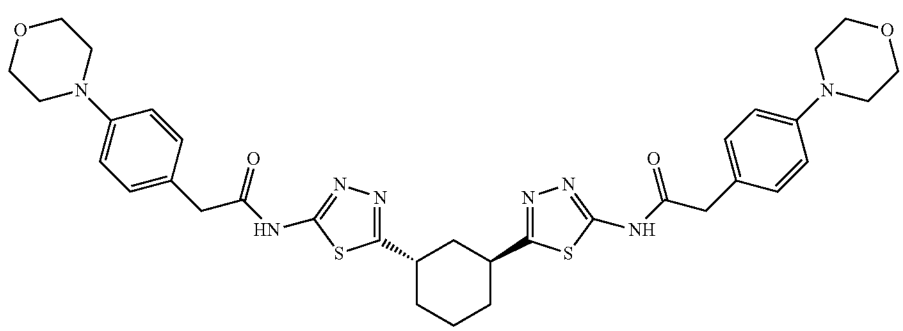 [SMILES: O=C(Cc1ccc(N2CCOCC2)cc1)Nc1nnc([C@H]2CCC[C@H](c3nnc(NC(=O)Cc4ccc(N5CCOCC5)cc4)s3)C2)s1] | B |

TABLE 1-continued

| Cmpd # | Structure | IC$_{50}$ |
|---|---|---|
| 266 | 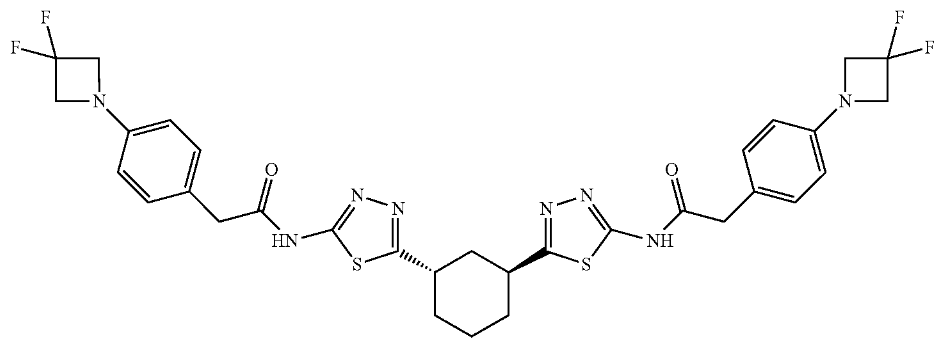 [SMILES: O=C(Cc1ccc(N2CC(F)(F)C2)cc1)Nc1nnc([C@H]2CCC[C@H](c3nnc(NC(=O)Cc4ccc(N5CC(F)(F)C5)cc4)s3)C2)s1] | A |
| 267 | 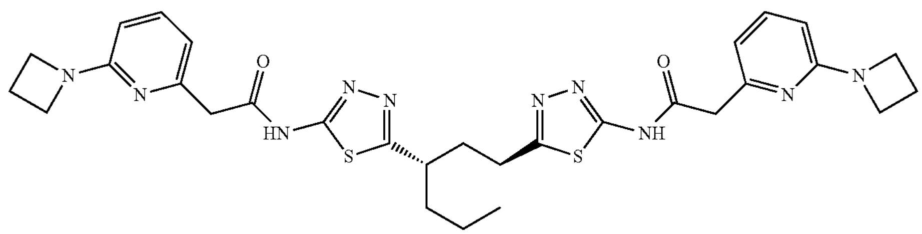 | B |
| 268 | 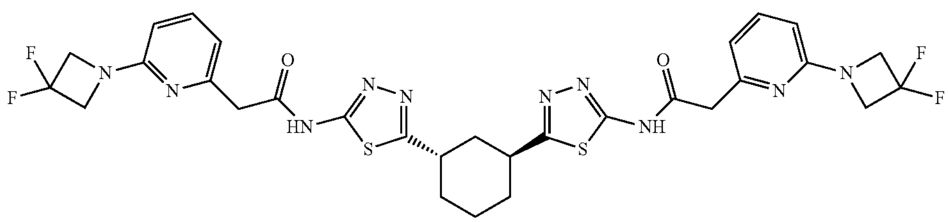 [SMILES: O=C(Cc1cccc(N2CC(F)(F)C2)n1)Nc1nnc([C@H]2CCC[C@H](c3nnc(NC(=O)Cc4cccc(N5CC(F)(F)C5)n4)s3)C2)s1] | A |
| 269 | 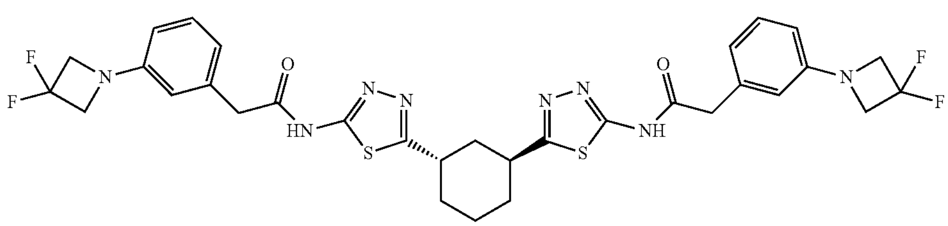 [SMILES: O=C(Cc1cccc(N2CC(F)(F)C2)c1)Nc1nnc([C@H]2CCC[C@H](c3nnc(NC(=O)Cc4cccc(N5CC(F)(F)C5)c4)s3)C2)s1] | B |
| 270 | 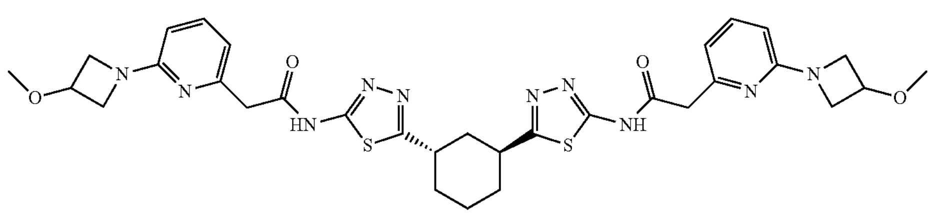 | A |

TABLE 1-continued

| Cmpd # | Structure | IC$_{50}$ |
|---|---|---|
| 271 | 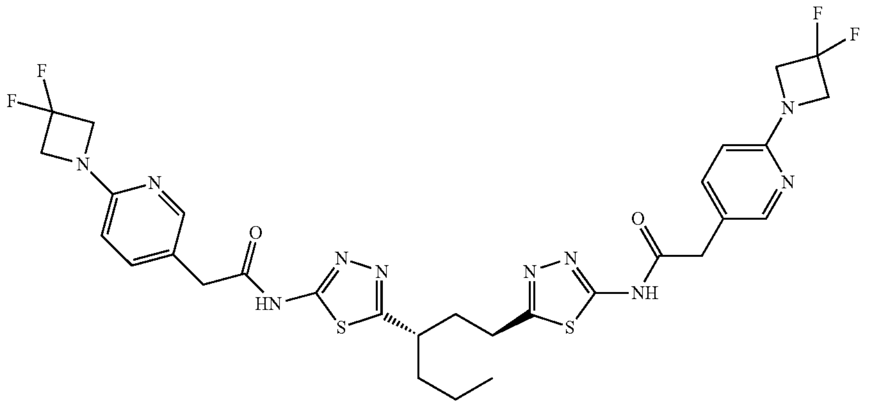 | A |
| 272 | 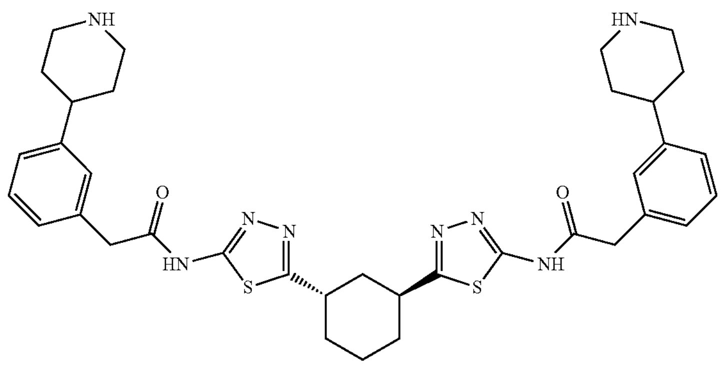 [SMILES: O=C(Cc1cccc(C2CCNCC2)c1)Nc1nnc([C@H]2CCC[C@H](c3nnc(NC(=O)Cc4cccc(C5CCNCC5)c4)s3)C2)s1] | A |
| 273 | 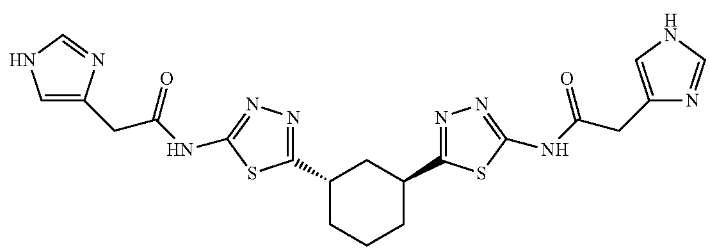 [SMILES: O=C(Cc1c[nH]cn1)Nc1nnc([C@H]2CCC[C@H](c3nnc(NC(=O)Cc4c[nH]cn4)s3)C2)s1] | A |
| 274 | 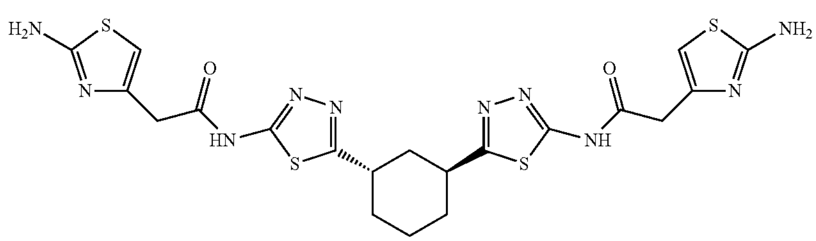 [SMILES: Nc1nc(CC(=O)Nc2nnc([C@H]3CCC[C@H](c4nnc(NC(=O)Cc5csc(N)n5)s4)C3)s2)cs1] | A |
| 275 | 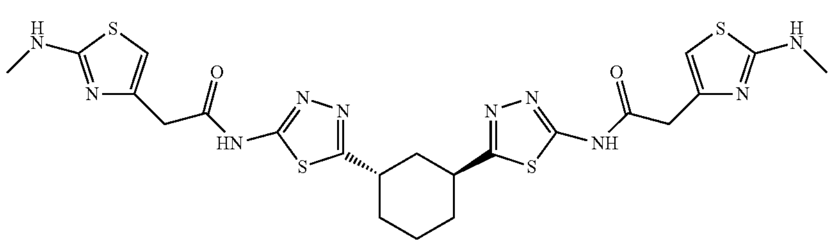 | A |

TABLE 1-continued

| Cmpd # | Structure | IC$_{50}$ |
|---|---|---|
| 276 | 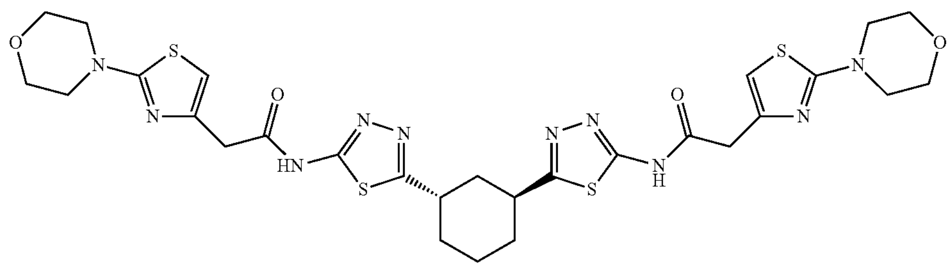 [SMILES: O=C(Cc1csc(N2CCOCC2)n1)Nc1nnc([C@H]2CCC[C@H](c3nnc(NC(=O)Cc4csc(N5CCOCC5)n4)s3)C2)s1] | B |
| 277 | 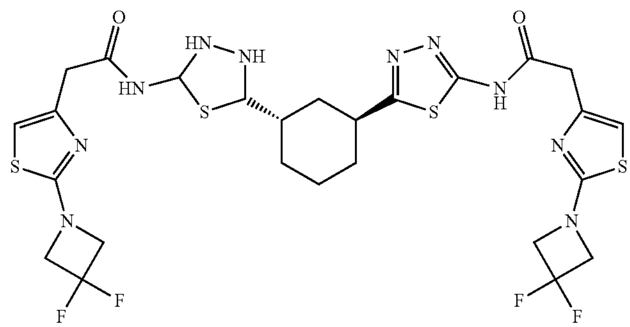 [SMILES: O=C(Cc1csc(N2CC(F)(F)C2)n1)Nc1nnc([C@H]2CCC[C@H](C3NNC(NC(=O)Cc4csc(N5CC(F)(F)C5)n4)S3)C2)s1] | A |
| 278 | 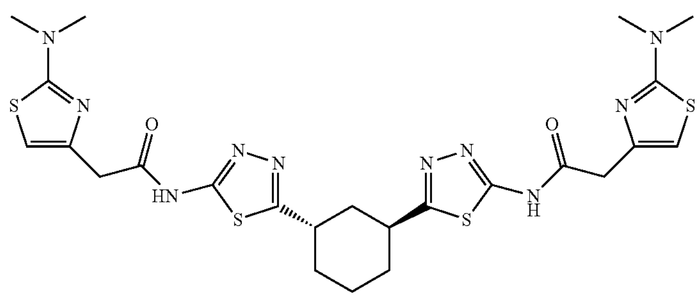 | B |
| 279 | 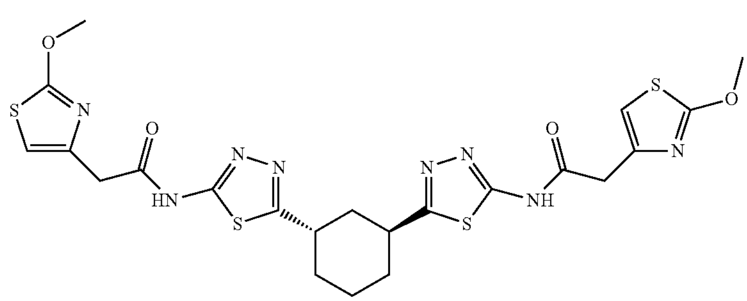 [SMILES: COc1nc(CC(=O)Nc2nnc([C@H]3CCC[C@H](c4nnc(NC(=O)Cc5csc(OC)n5)s4)C3)s2)cs1] | A |
| 280 | 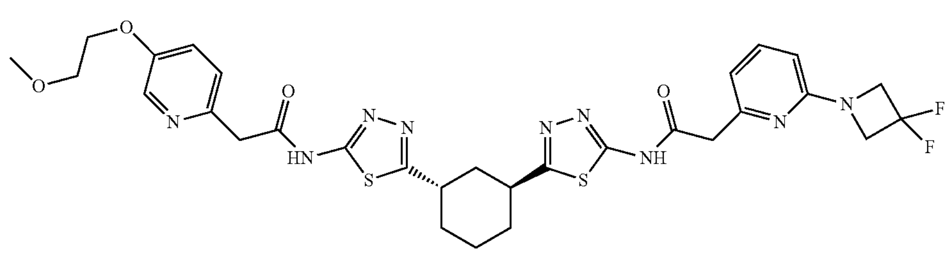 [SMILES: COCCOc1ccc(CC(=O)Nc2nnc([C@H]3CCC[C@H](c4nnc(NC(=O)Cc5cccc(N6CC(F)(F)C6)n5)s4)C3)s2)nc1] | A |

TABLE 1-continued

| Cmpd # | Structure | IC$_{50}$ |
|---|---|---|
| 281 | 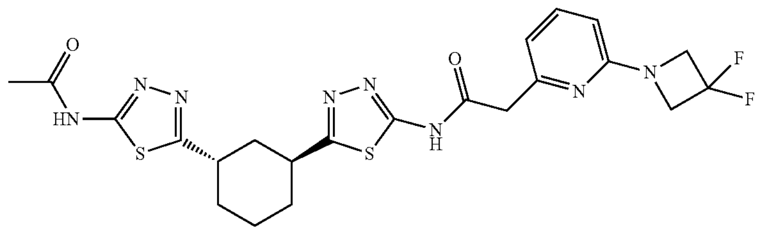 [SMILES: CC(=O)Nc1nnc([C@H]2CCC[C@H](c3nnc(NC(=O)Cc4cccc(N5CC(F)(F)C5)n4)s3)C2)s1] | A |
| 282 | 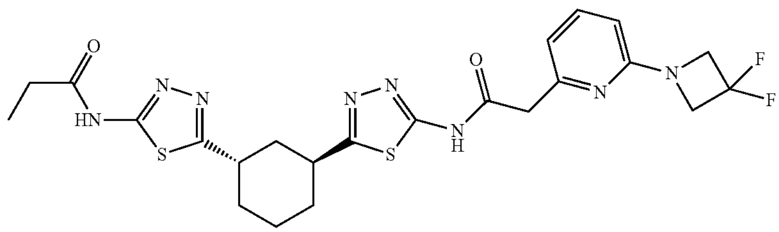 [SMILES: CCC(=O)Nc1nnc([C@H]2CCC[C@H](c3nnc(NC(=O)Cc4cccc(N5CC(F)(F)C5)n4)s3)C2)s1] | A |
| 283 | 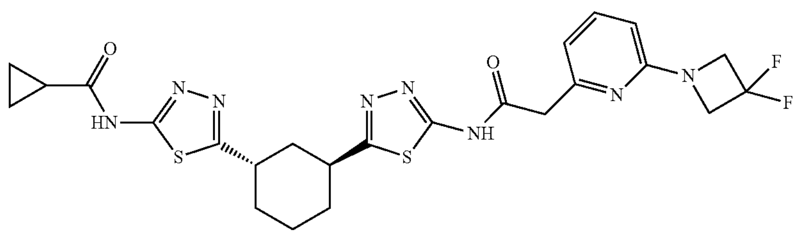 [SMILES: O=C(Cc1cccc(N2CC(F)(F)C2)n1)Nc1nnc([C@H]2CCC[C@H](c3nnc(NC(=O)C4CC4)s3)C2)s1] | B |
| 284 | 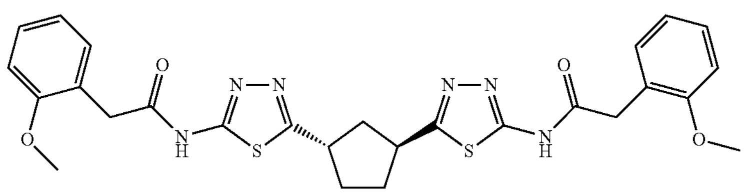 [SMILES: COc1ccccc1CC(=O)Nc1nnc([C@H]2CC[C@H](c3nnc(NC(=O)Cc4ccccc4OC)s3)C2)s1] | A |
| 285 | 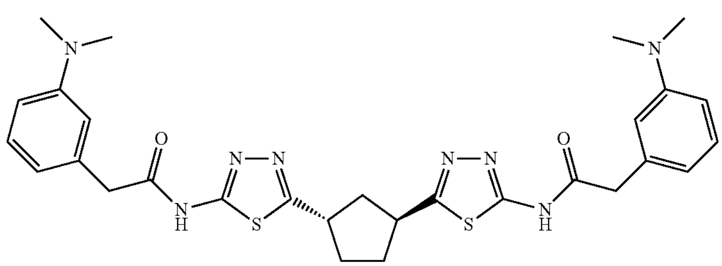 [SMILES: CN(C)c1cccc(CC(=O)Nc2nnc([C@H]3CC[C@H](c4nnc(NC(=O)Cc5cccc(N(C)C)c5)s4)C3)s2)c1] | A |
| 286 | 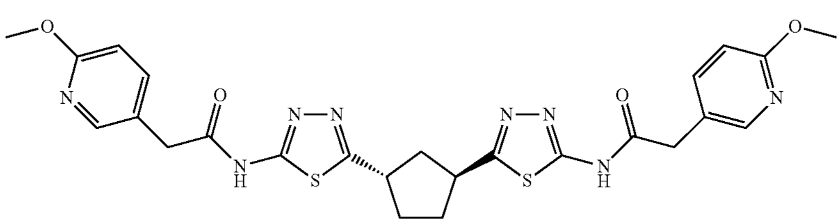 | A |

TABLE 1-continued
| Cmpd # | Structure | IC$_{50}$ |
|---|---|---|
| 287 | 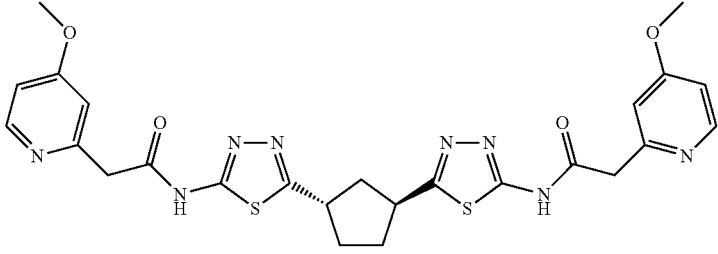 [SMILES: COc1ccnc(CC(=O)Nc2nnc([C@H]3CC[C@H](c4nnc(NC(=O)Cc5cc(OC)ccn5)s4)C3)s2)c1] | A |
| 288 | 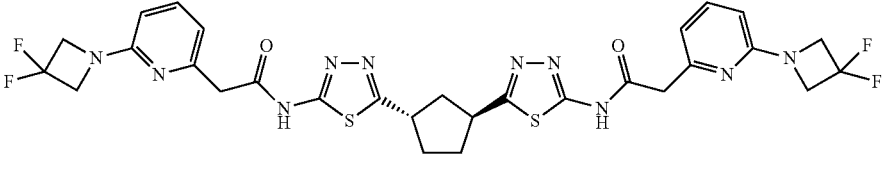 [SMILES: O=C(Cc1cccc(N2CC(F)(F)C2)n1)Nc1nnc([C@H]2CC[C@H](c3nnc(NC(=O)Cc4cccc(N5CC(F)(F)C5)n4)s3)C2)s1] | A |
| 289 | 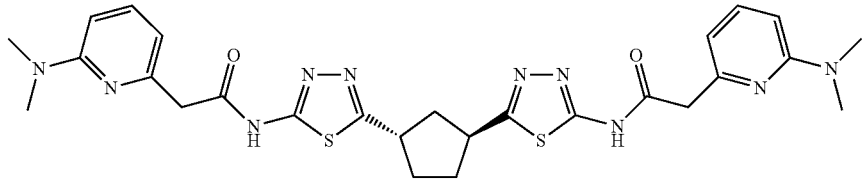 | B |
| 290 | 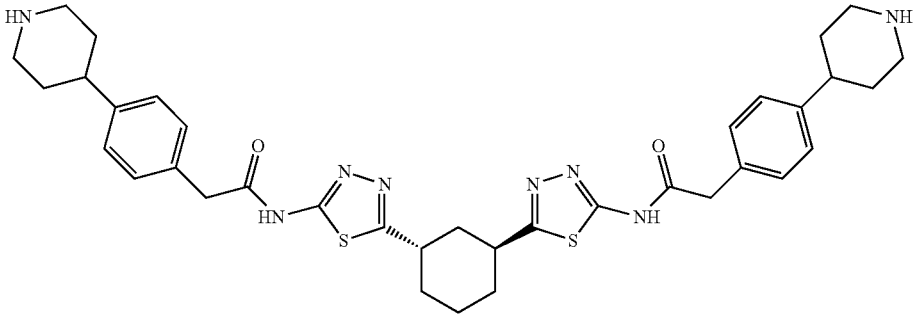 [SMILES: O=C(Cc1ccc(C2CCNCC2)cc1)Nc1nnc([C@H]2CCC[C@H](c3nnc(NC(=O)Cc4ccc(C5CCNCC5)cc4)s3)C2)s1] | A |
| 291 | 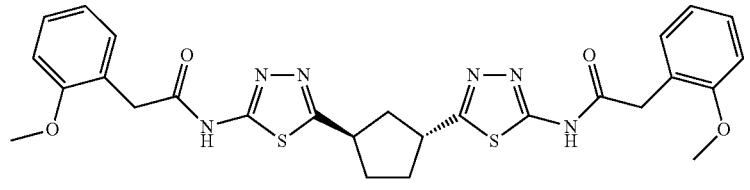 [SMILES: COc1ccccc1CC(=O)Nc1nnc([C@@H]2CC[C@@H](c3nnc(NC(=O)Cc4ccccc4OC)s3)C2)s1] | A |
| 292 | 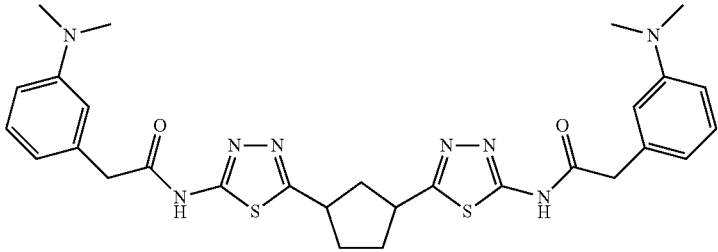 [SMILES: CN(C)c1cccc(CC(=O)Nc2nnc(C3CCC(c4nnc(NC(=O)Cc5cccc(N(C)C)c5)s4)C3)s2)c1] | A |

US 10,087,172 B2
119                                                                                                                 120
TABLE 1-continued
| Cmpd # | Structure | IC$_{50}$ |
|---|---|---|
| 293 | 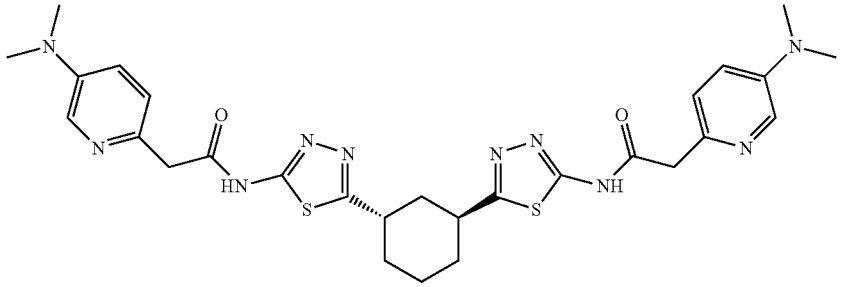 | A |
| 294 | 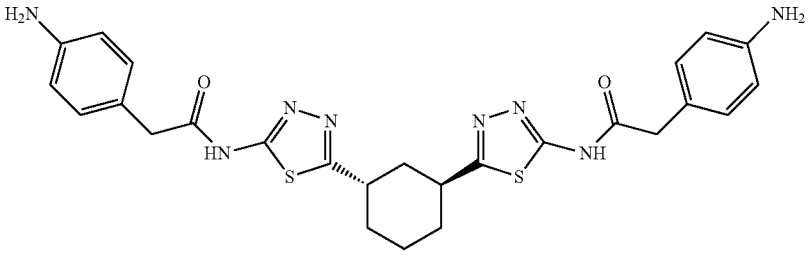 | A |
| 295 | 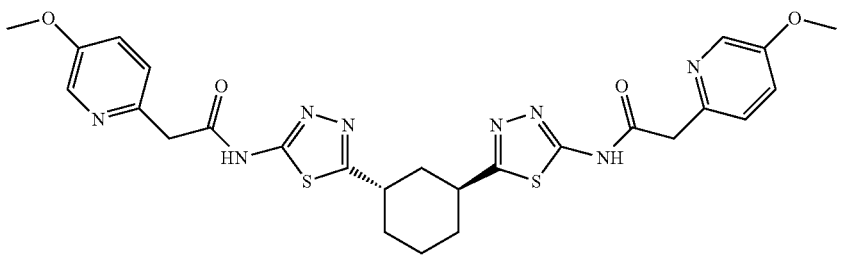 | A |
| 296 | 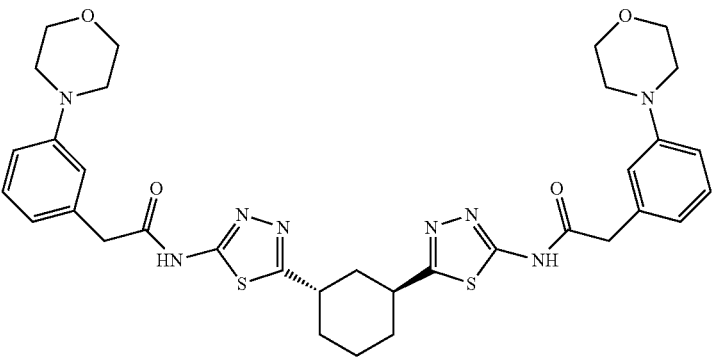 [SMILES: O=C(Cc1cccc(N2CCOCC2)c1)Nc1nnc([C@H]2CCC[C@H](c3nnc(NC(=O)Cc4cccc(N5CCOCC5)c4)s3)C2)s1] | A |
| 297 | 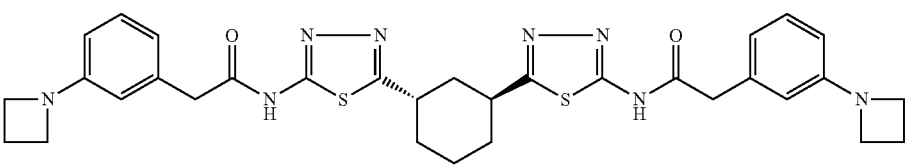 [SMILES: O=C(Cc1cccc(N2CCC2)c1)Nc1nnc([C@H]2CCC[C@H](c3nnc(NC(=O)Cc4cccc(N5CCC5)c4)s3)C2)s1] | A |
| 298 | 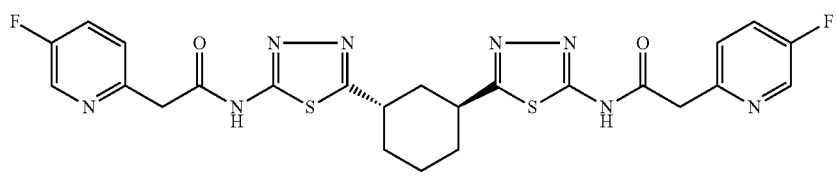 [SMILES: O=C(Cc1ccc(F)cn1)Nc1nnc([C@H]2CCC[C@H](c3nnc(NC(=O)Cc4ccc(F)cn4)s3)C2)s1] | A |

TABLE 1-continued

| Cmpd # | Structure | IC$_{50}$ |
|---|---|---|
| 299 | 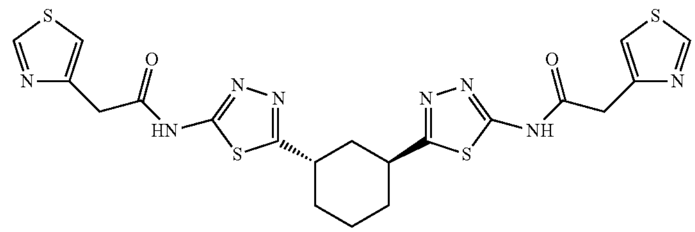 [SMILES: O=C(Cc1cscn1)Nc1nnc([C@H]2CCC[C@H](c3nnc(NC(=O)Cc4cscn4)s3)C2)s1] | A |
| 300 | 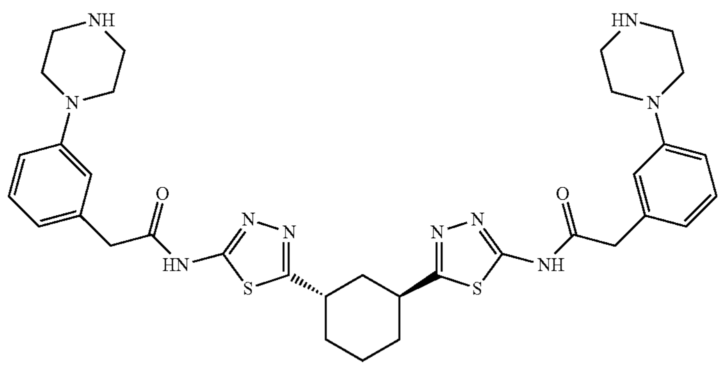 [SMILES: O=C(Cc1cccc(N2CCNCC2)c1)Nc1nnc([C@H]2CCC[C@H](c3nnc(NC(=O)Cc4cccc(N5CCNCC5)c4)s3)C2)s1] | A |
| 301 | 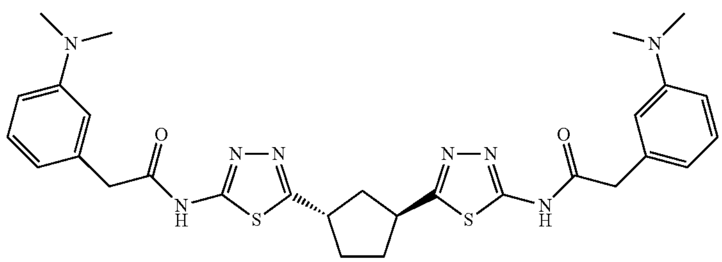 [SMILES: CN(C)c1cccc(CC(=O)Nc2nnc([C@H]3CC[C@H](c4nnc(NC(=O)Cc5cccc(N(C)C)c5)s4)C3)s2)c1] | A |
| 302 | 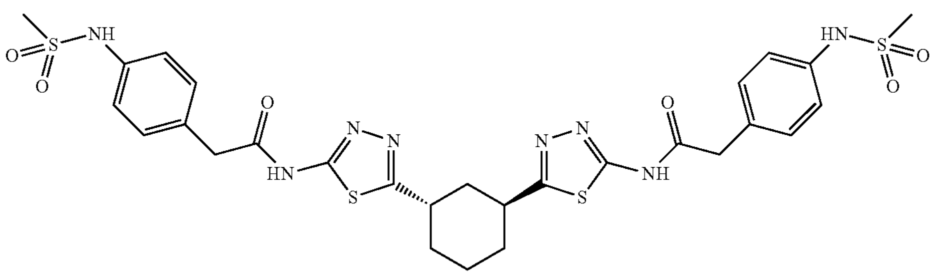 [SMILES: CS(=O)(=O)Nc1ccc(CC(=O)Nc2nnc([C@H]3CCC[C@H](c4nnc(NC(=O)Cc5ccc(NS(C)(=O)=O)cc5)s4)C3)s2)cc1] | A |
| 303 | 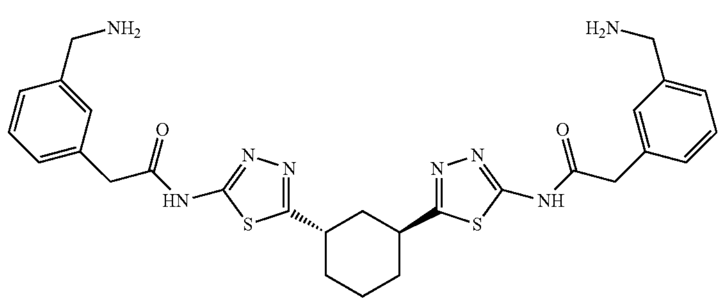 | A |

TABLE 1-continued

| Cmpd # | Structure | IC$_{50}$ |
|---|---|---|
| 304 | 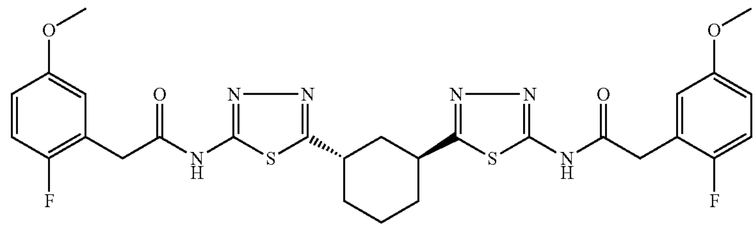 [SMILES: COc1ccc(F)c(CC(=O)Nc2nnc([C@H]3CCC[C@H](c4nnc(NC(=O)Cc5cc(OC)ccc5F)s4)C3)s2)c1] | A |
| 305 | 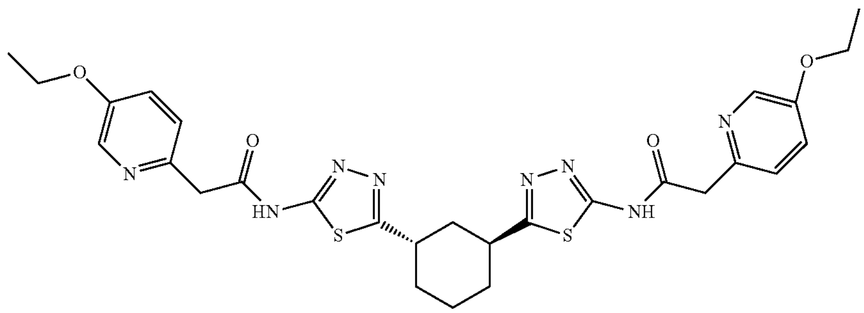 [SMILES: CCOc1ccc(CC(=O)Nc2nnc([C@H]3CCC[C@H](c4nnc(NC(=O)Cc5ccc(OCC)cn5)s4)C3)s2)nc1] | A |
| 306 | 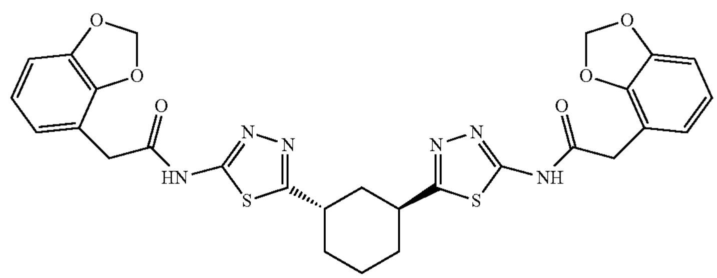 [SMILES: O=C(Cc1cccc2c1OCO2)Nc1nnc([C@H]2CCC[C@H](c3nnc(NC(=O)Cc4cccc5c4OCO5)s3)C2)s1] | A |
| 307 | 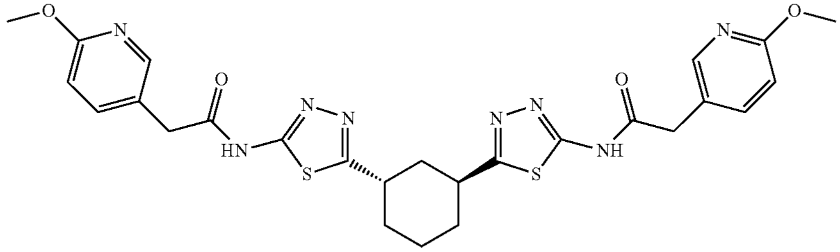 | A |
| 308 | 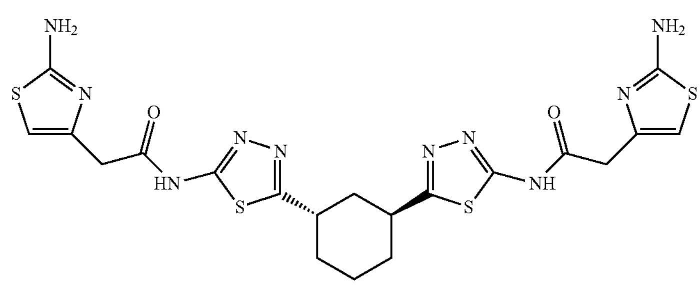 [SMILES: Nc1nc(CC(=O)Nc2nnc([C@H]3CCC[C@H](c4nnc(NC(=O)Cc5csc(N)n5)s4)C3)s2)cs1] | A |
| 309 | 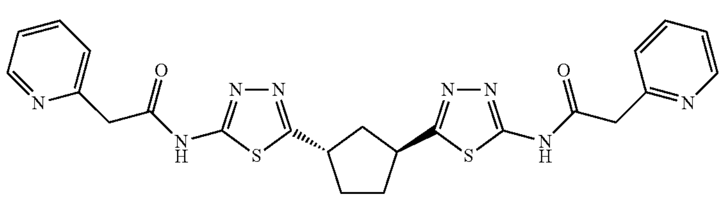 [SMILES: O=C(Cc1ccccn1)Nc1nnc([C@H]2CC[C@H](c3nnc(NC(=O)Cc4ccccn4)s3)C2)s1] | A |

TABLE 1-continued

| Cmpd # | Structure | IC$_{50}$ |
|---|---|---|
| 310 | 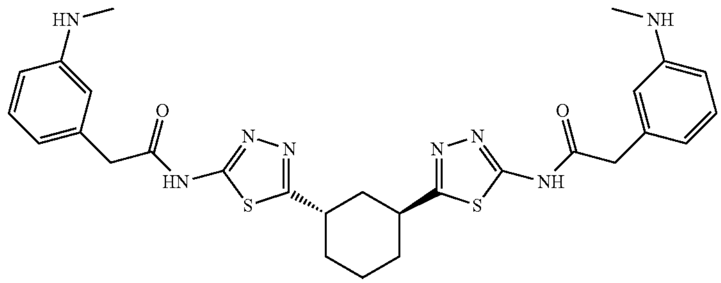 [SMILES: CNc1cccc(CC(=O)Nc2nnc([C@H]3CCC[C@H](c4nnc(NC(=O)Cc5cccc(NC)c5)s4)C3)s2)c1] | A |
| 311 | 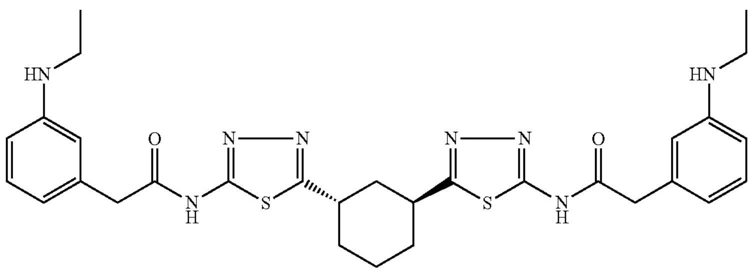 [SMILES: CCNc1cccc(CC(=O)Nc2nnc([C@H]3CCC[C@H](c4nnc(NC(=O)Cc5cccc(NCC)c5)s4)C3)s2)c1] | A |
| 312 | 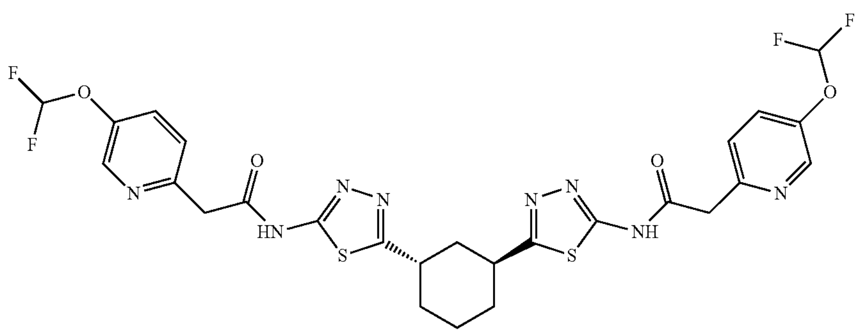 [SMILES: O=C(Cc1ccc(OC(F)F)cn1)Nc1nnc([C@H]2CCC[C@H](c3nnc(NC(=O)Cc4ccc(OC(F)F)cn4)s3)C2)s1] | A |
| 313 | 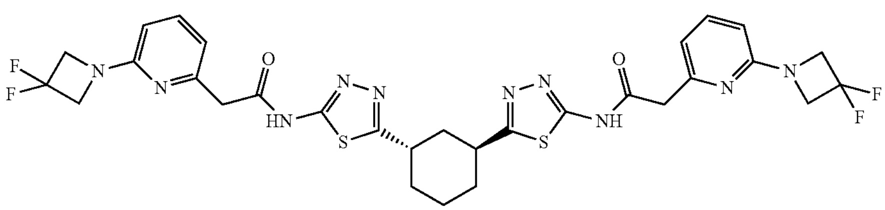 [SMILES: O=C(Cc1cccc(N2CC(F)(F)C2)n1)Nc1nnc([C@H]2CCC[C@H](c3nnc(NC(=O)Cc4cccc(N5CC(F)(F)C5)n4)s3)C2)s1] | A |
| 314 | 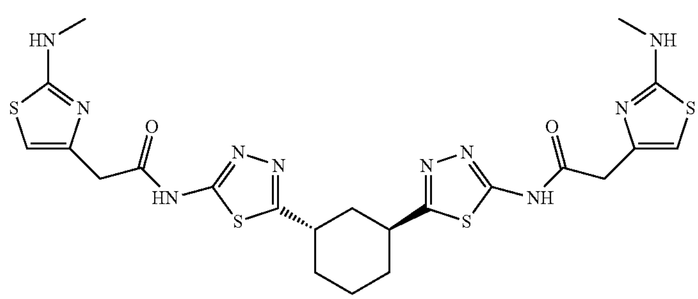 [SMILES: CNc1nc(CC(=O)Nc2nnc([C@H]3CCC[C@H](c4nnc(NC(=O)Cc5csc(NC)n5)s4)C3)s2)cs1] | A |

TABLE 1-continued

| Cmpd # | Structure | IC$_{50}$ |
|---|---|---|
| 315 | 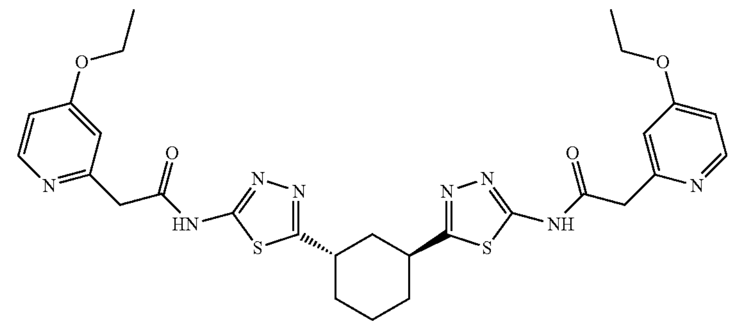 [SMILES: CCOc1ccnc(CC(=O)Nc2nnc([C@H]3CCC[C@H](c4nnc(NC(=O)Cc5cc(OCC)ccn5)s4)C3)s2)c1] | A |
| 316 | 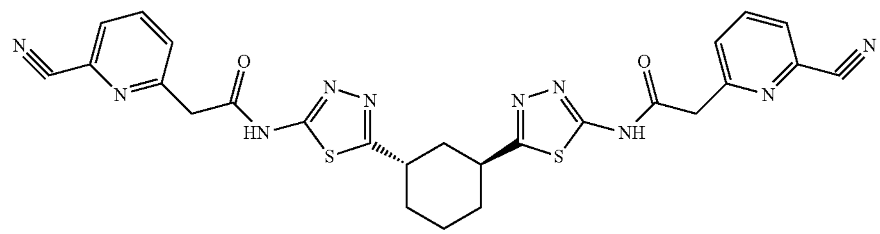 [SMILES: N#Cc1cccc(CC(=O)Nc2nnc([C@H]3CCC[C@H](c4nnc(NC(=O)Cc5cccc(C#N)n5)s4)C3)s2)n1] | A |
| 317 | 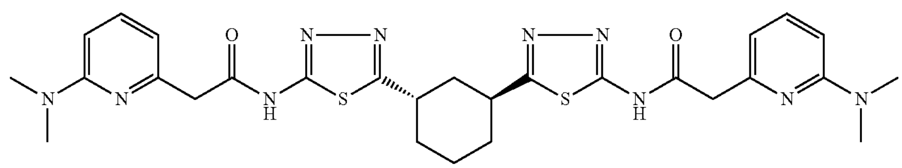 | A |
| 318 | 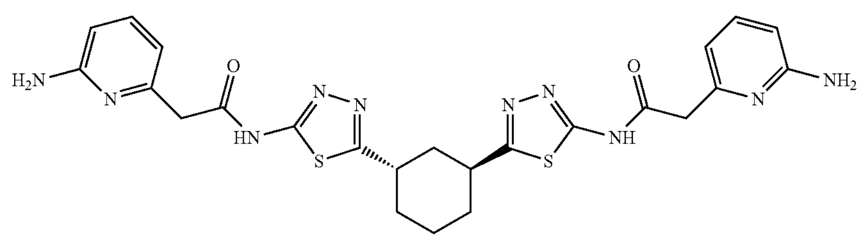 [SMILES: Nc1cccc(CC(=O)Nc2nnc([C@H]3CCC[C@H](c4nnc(NC(=O)Cc5cccc(N)n5)s4)C3)s2)n1] | A |
| 319 | 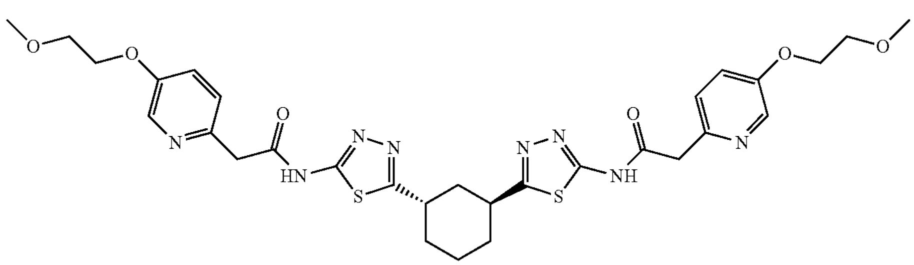 | A |
| 320 | 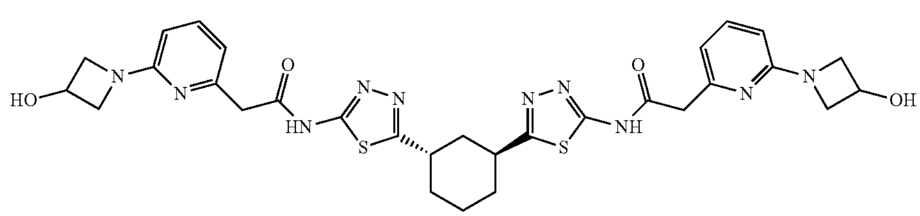 [SMILES: O=C(Cc1cccc(N2CC(O)C2)n1)Nc1nnc([C@H]2CCC[C@H](c3nnc(NC(=O)Cc4cccc(N5CC(O)C5)n4)s3)C2)s1] | A |

TABLE 1-continued

| Cmpd # | Structure | IC$_{50}$ |
|---|---|---|
| 321 | 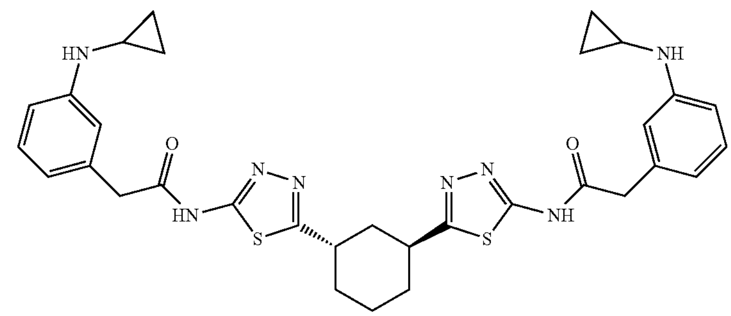 [SMILES: O=C(Cc1cccc(NC2CC2)c1)Nc1nnc([C@H]2CCC[C@H](c3nnc(NC(=O)Cc4cccc(NC5CC5)c4)s3)C2)s1] | A |
| 322 | 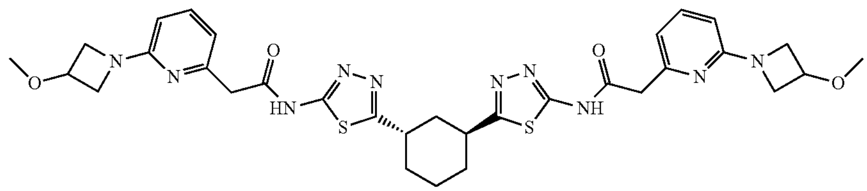 | A |
| 323 | 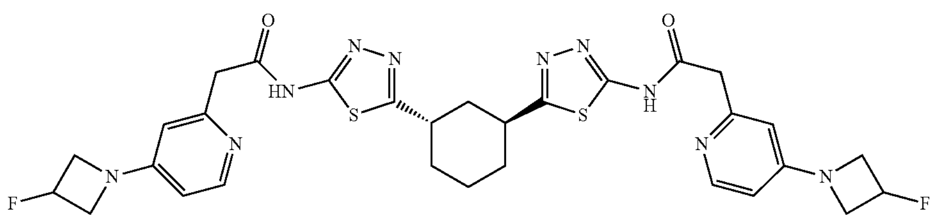 [SMILES: O=C(Cc1cc(N2CC(F)C2)ccn1)Nc1nnc([C@H]2CCC[C@H](c3nnc(NC(=O)Cc4cc(N5CC(F)C5)ccn4)s3)C2)s1] | A |
| 324 | 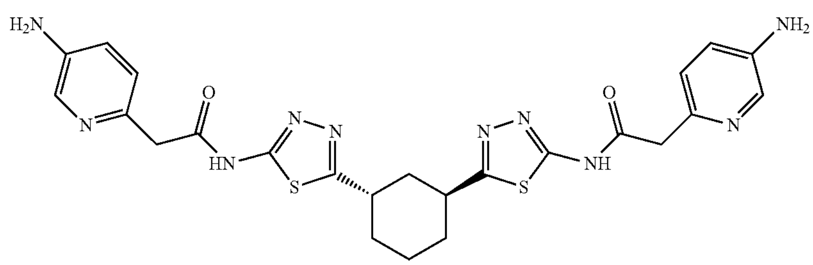 [SMILES: Nc1ccc(CC(=O)Nc2nnc([C@H]3CCC[C@H](c4nnc(NC(=O)Cc5ccc(N)cn5)s4)C3)s2)nc1] | A |
| 325 | 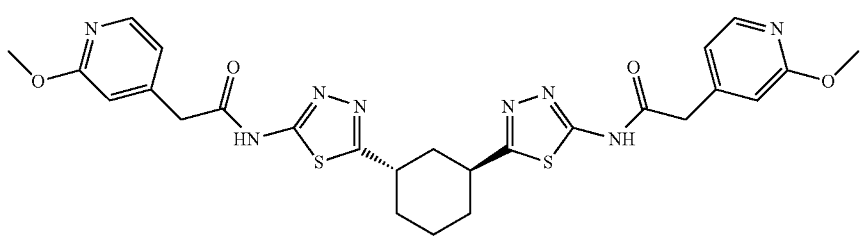 | A |
| 326 | 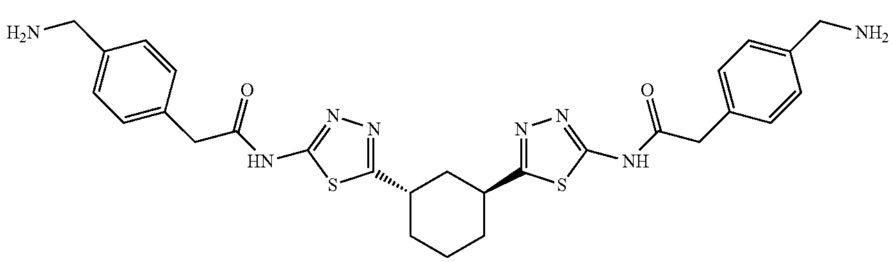 [SMILES: NCc1ccc(CC(=O)Nc2nnc([C@H]3CCC[C@H](c4nnc(NC(=O)Cc5ccc(CN)cc5)s4)C3)s2)cc1] | A |

TABLE 1-continued

| Cmpd # | Structure | IC$_{50}$ |
|---|---|---|
| 327 | 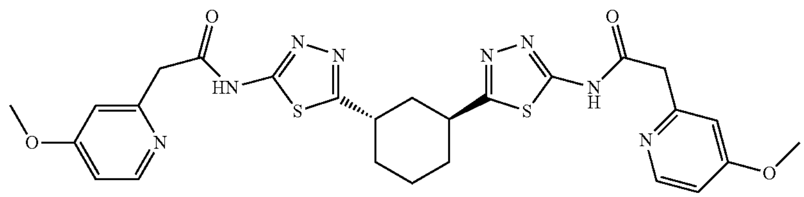 | A |
| 328 | 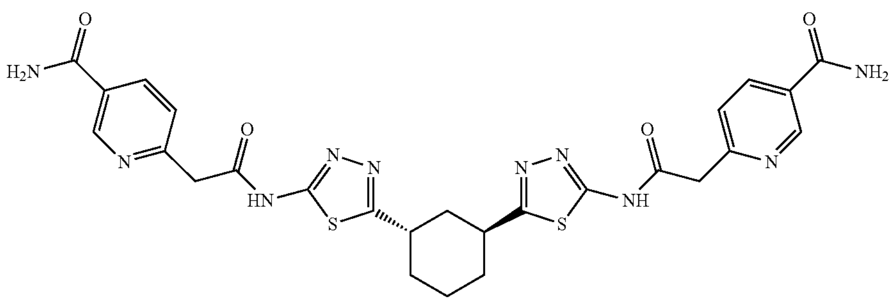 [SMILES: NC(=O)c1ccc(CC(=O)Nc2nnc([C@H]3CCC[C@H](c4nnc(NC(=O)Cc5ccc(C(N)=O)cn5)s4)C3)s2)nc1] | A |
| 329 | 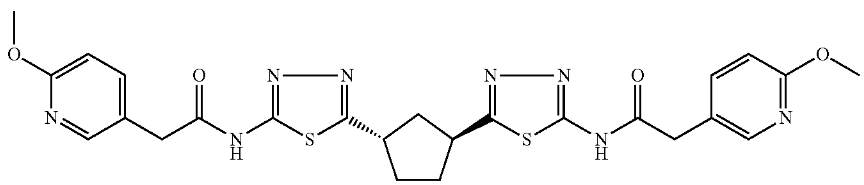 [SMILES: COc1ccc(CC(=O)Nc2nnc([C@H]3CC[C@H](c4nnc(NC(=O)Cc5ccc(OC)nc5)s4)C3)s2)cn1] | A |
| 330 | 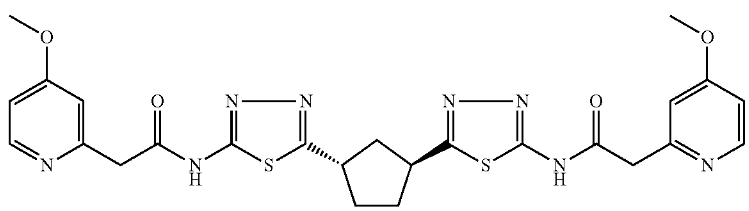 [SMILES: COc1ccnc(CC(=O)Nc2nnc([C@H]3CC[C@H](c4nnc(NC(=O)Cc5cc(OC)ccn5)s4)C3)s2)c1] | A |
| 331 | 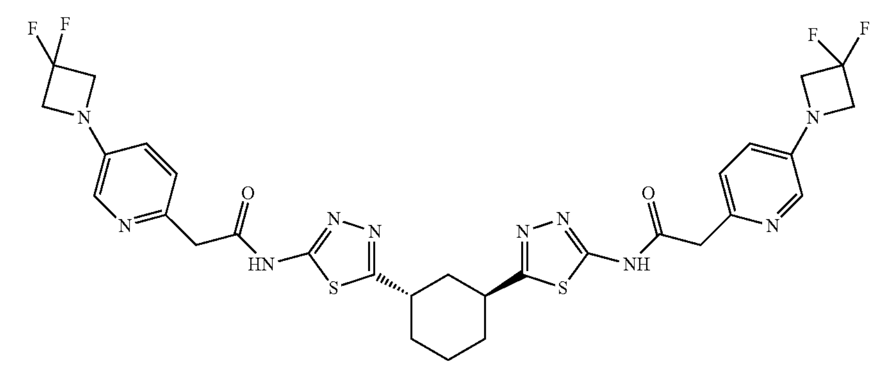 [SMILES: O=C(Cc1ccc(N2CC(F)(F)C2)cn1)Nc1nnc([C@H]2CCC[C@H](c3nnc(NC(=O)Cc4ccc(N5CC(F)(F)C5)cn4)s3)C2)s1] | A |
| 332 | 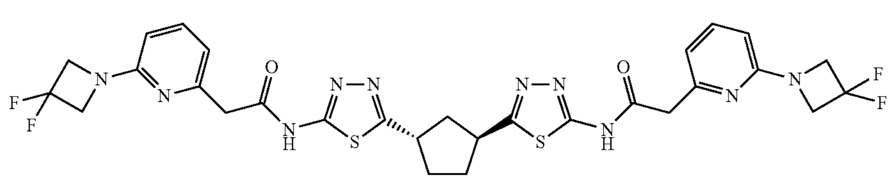 [SMILES: O=C(Cc1cccc(N2CC(F)(F)C2)n1)Nc1nnc([C@H]2CC[C@H](c3nnc(NC(=O)Cc4cccc(N5CC(F)(F)C5)n4)s3)C2)s1] | A |

TABLE 1-continued

| Cmpd # | Structure | IC$_{50}$ |
|---|---|---|
| 333 | 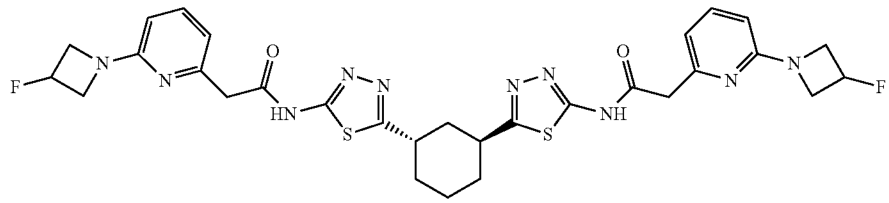 [SMILES: O=C(Cc1cccc(N2CC(F)C2)n1)Nc1nnc([C@H]2CCC[C@H](c3nnc(NC(=O)Cc4cccc(N5CC(F)C5)n4)s3)C2)s1] | A |
| 334 | 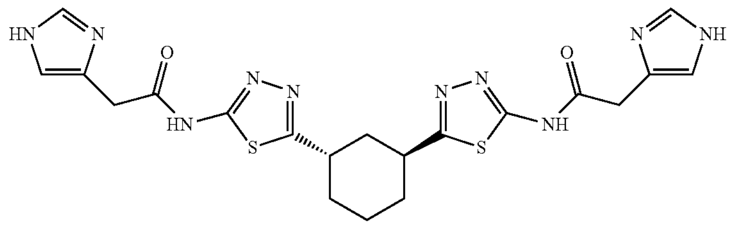 [SMILES: O=C(Cc1c[nH]cn1)Nc1nnc([C@H]2CCC[C@H](c3nnc(NC(=O)Cc4c[nH]cn4)s3)C2)s1] | A |
| 335 | 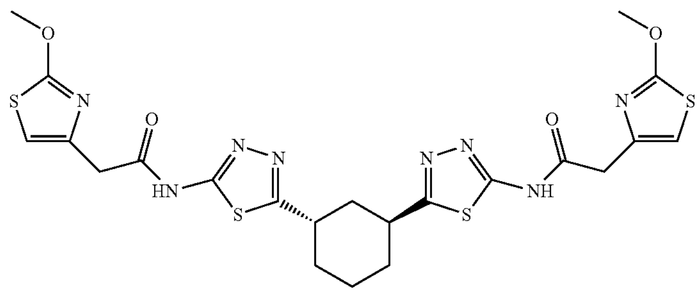 [SMILES: COc1nc(CC(=O)Nc2nnc([C@H]3CCC[C@H](c4nnc(NC(=O)Cc5csc(OC)n5)s4)C3)s2)cs1] | A |
| 336 | 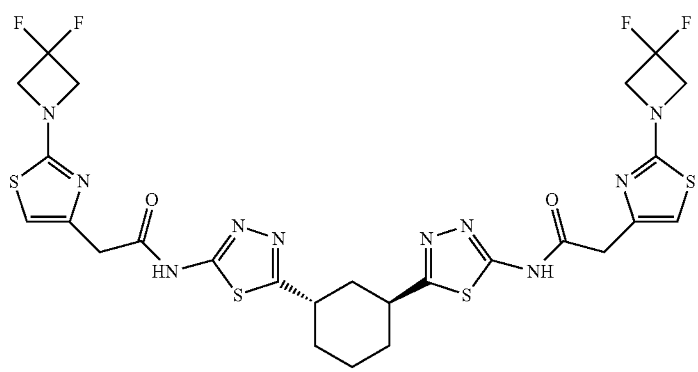 [SMILES: O=C(Cc1csc(N2CC(F)(F)C2)n1)Nc1nnc([C@H]2CCC[C@H](c3nnc(NC(=O)Cc4csc(N5CC(F)(F)C5)n4)s3)C2)s1] | A |
| 337 | 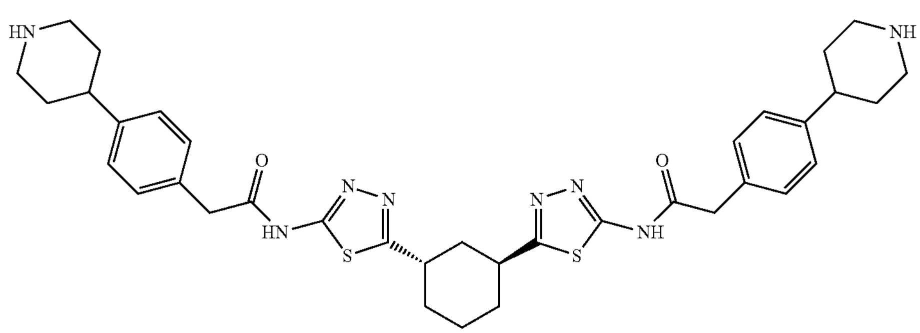 [SMILES: O=C(Cc1ccc(C2CCNCC2)cc1)Nc1nnc([C@H]2CCC[C@H](c3nnc(NC(=O)Cc4ccc(C5CCNCC5)cc4)s3)C2)s1] | A |

TABLE 1-continued
| Cmpd # | Structure | IC$_{50}$ |
|---|---|---|
| 338 | 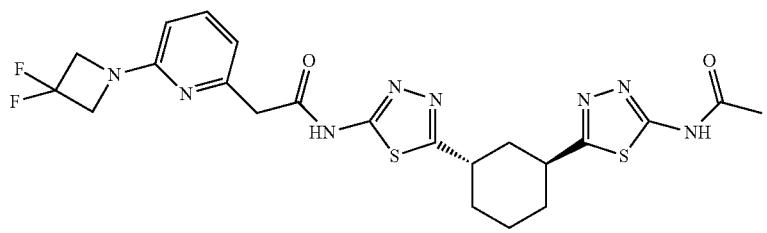 [SMILES: CC(=O)Nc1nnc([C@H]2CCC[C@H](c3nnc(NC(=O)Cc4cccc(N5CC(F)(F)C5)n4)s3)C2)s1] | A |
| 339 | 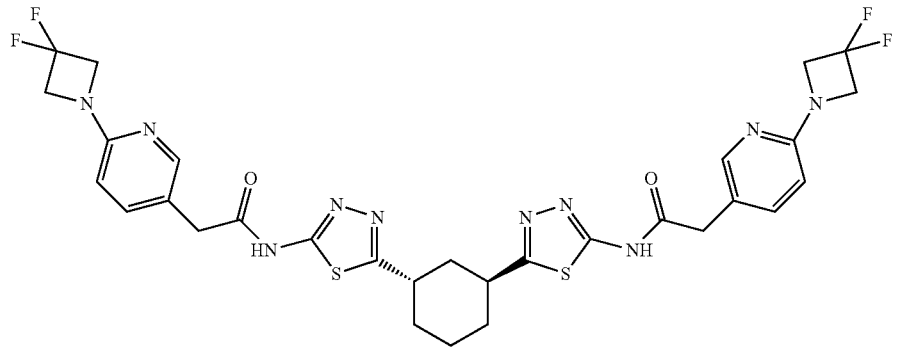 [SMILES: O=C(Cc1ccc(N2CC(F)(F)C2)nc1)Nc1nnc([C@H]2CCC[C@H](c3nnc(NC(=O)Cc4ccc(N5CC(F)(F)C5)nc4)s3)C2)s1] | A |
| 340 | 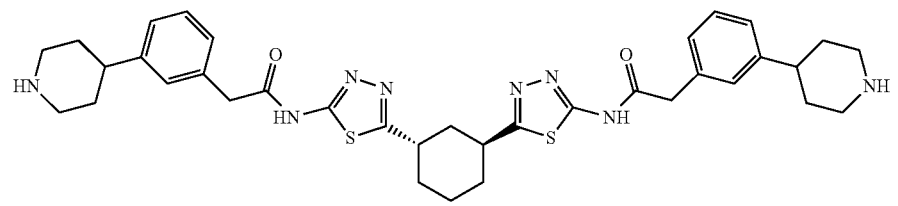 [SMILES: O=C(Cc1cccc(C2CCNCC2)c1)Nc1nnc([C@H]2CCC[C@H](c3nnc(NC(=O)Cc4cccc(C5CCNCC5)c4)s3)C2)s1] | A |
| 341 | 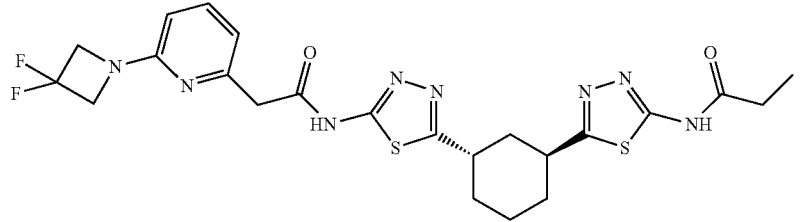 [SMILES: CCC(=O)Nc1nnc([C@H]2CCC[C@H](c3nnc(NC(=O)Cc4cccc(N5CC(F)(F)C5)n4)s3)C2)s1] | A |
| 342 | 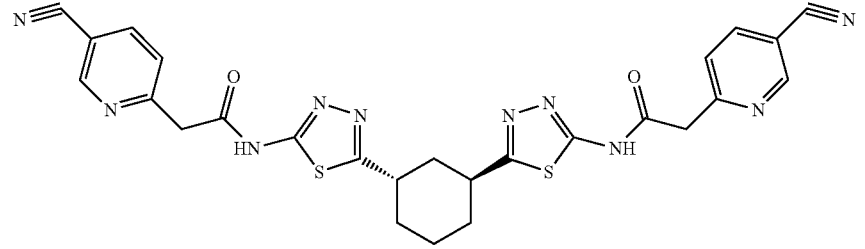 [SMILES: N#Cc1ccc(CC(=O)Nc2nnc([C@H]3CCC[C@H](c4nnc(NC(=O)Cc5ccc(C#N)cn5)s4)C3)s2)nc1] | A |
| 343 | 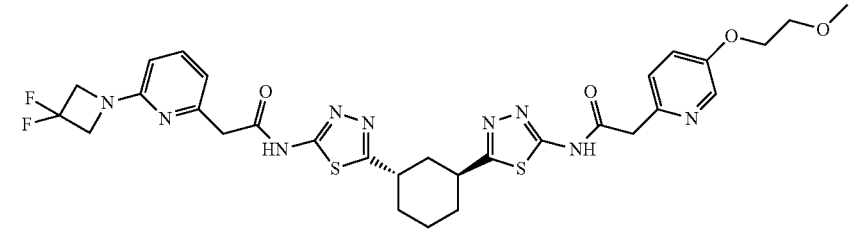 [SMILES: COCCOc1ccc(CC(=O)Nc2nnc([C@H]3CCC[C@H](c4nnc(NC(=O)Cc5cccc(N6CC(F)(F)C6)n5)s4)C3)s2)nc1] | A |

TABLE 1-continued
| Cmpd # | Structure | IC$_{50}$ |
|---|---|---|
| 344 | 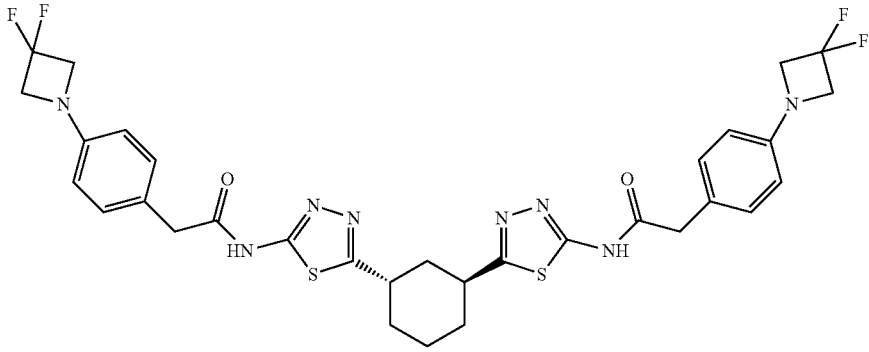 [SMILES: O=C(Cc1ccc(N2CC(F)(F)C2)cc1)Nc1nnc([C@H]2CCC[C@H](c3nnc(NC(=O)Cc4ccc(N5CC(F)(F)C5)cc4)s3)C2)s1] | A |
| 345 | 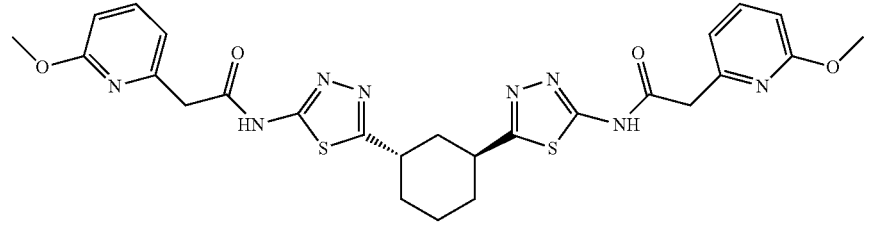 | A |
| 346 | 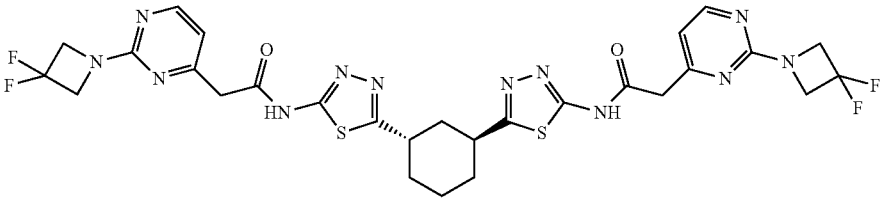 [SMILES: O=C(Cc1ccnc(N2CC(F)(F)C2)n1)Nc1nnc([C@H]2CCC[C@H](c3nnc(NC(=O)Cc4ccnc(N5CC(F)(F)C5)n4)s3)C2)s1] | A |
| 347 | 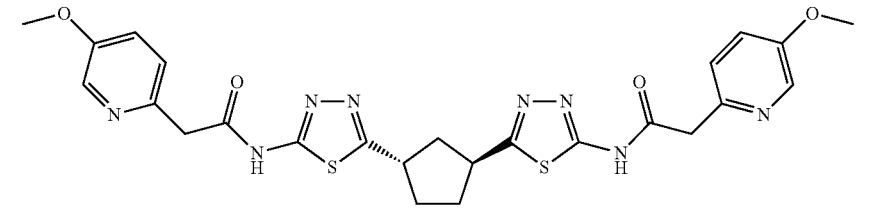 | A |
| 348 | 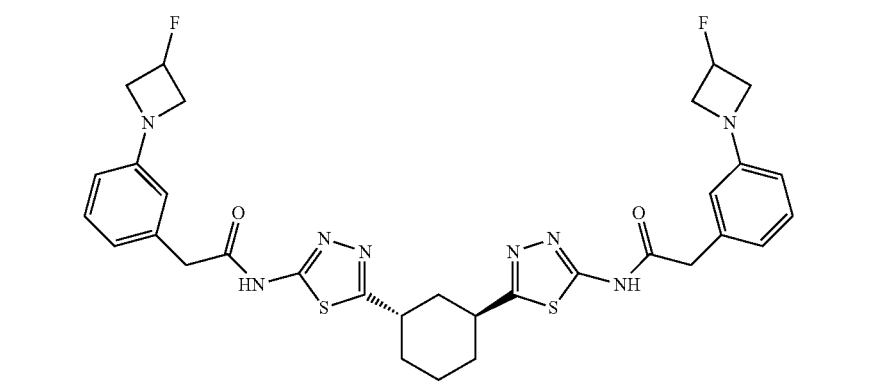 [SMILES: O=C(Cc1cccc(N2CC(F)C2)c1)Nc1nnc([C@H]2CCC[C@H](c3nnc(NC(=O)Cc4cccc(N5CC(F)C5)c4)s3)C2)s1] | A |

TABLE 1-continued

| Cmpd # | Structure | IC$_{50}$ |
|---|---|---|
| 349 | 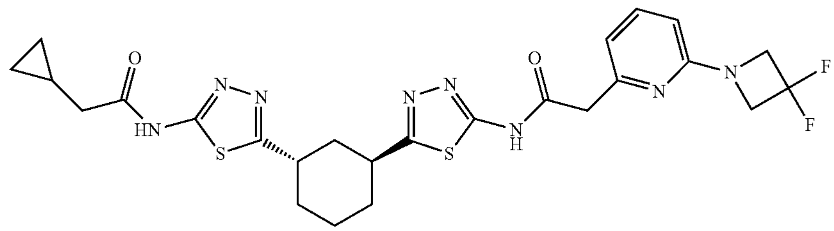 [SMILES: O=C(Cc1cccc(N2CC(F)(F)C2)n1)Nc1nnc([C@H]2CCC[C@H](c3nnc(NC(=O)CC4CC4)s3)C2)s1] | A |
| 350 | | A |
| 350 | | A |
| 351 | 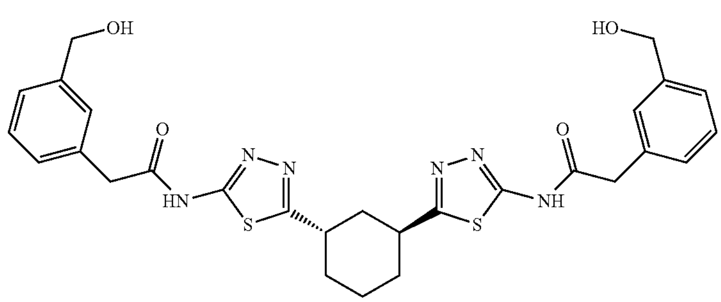 [SMILES: O=C(Cc1cccc(CO)c1)Nc1nnc([C@H]2CCC[C@H](c3nnc(NC(=O)Cc4cccc(CO)c4)s3)C2)s1] | A |
| 352 | 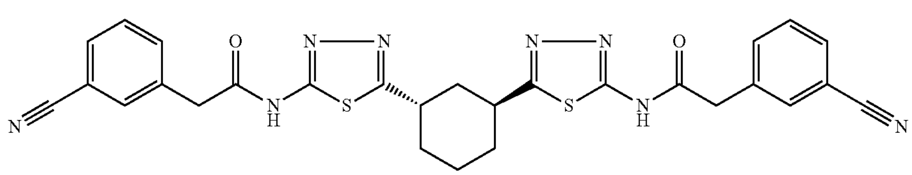 [SMILES: N#Cc1cccc(CC(=O)Nc2nnc([C@H]3CCC[C@H](c4nnc(NC(=O)Cc5cccc(C#N)c5)s4)C3)s2)c1] | A |

TABLE 1-continued
| Cmpd # | Structure | IC$_{50}$ |
|---|---|---|
| 353 | 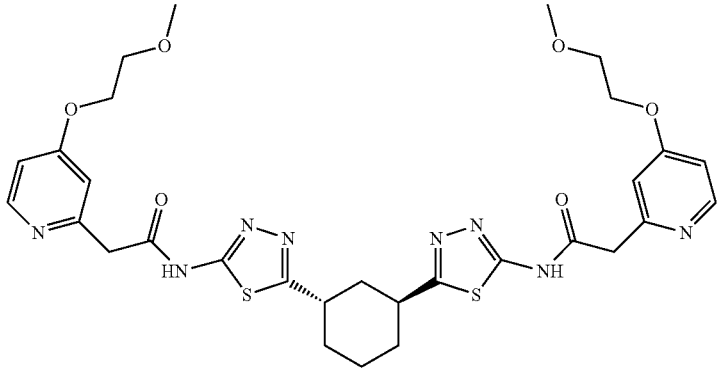 [SMILES: COCCOc1ccnc(CC(=O)Nc2nnc([C@H]3CCC[C@H](c4nnc(NC(=O)Cc5cc(OCCOC)ccn5)s4)C3)s2)c1] | A |
| 354 | 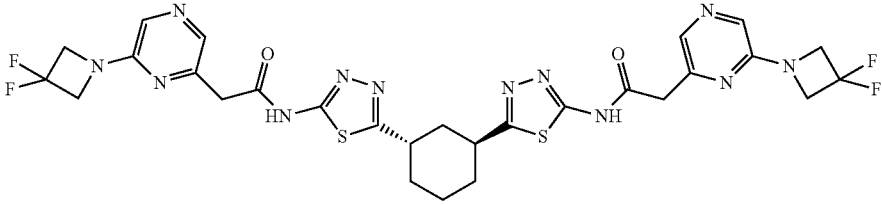 [SMILES: O=C(Cc1cncc(N2CC(F)(F)C2)n1)Nc1nnc([C@H]2CCC[C@H](c3nnc(NC(=O)Cc4cncc(N5CC(F)(F)C5)n4)s3)C2)s1] | A |
| 355 | 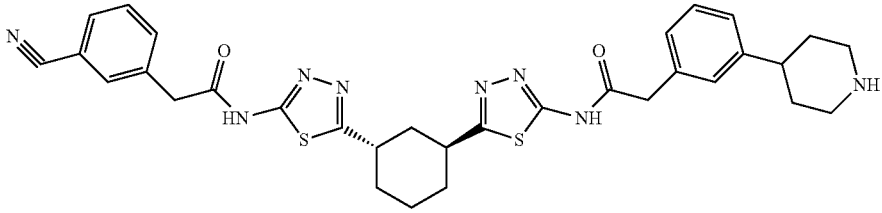 [SMILES: N#Cc1cccc(CC(=O)Nc2nnc([C@H]3CCC[C@H](c4nnc(NC(=O)Cc5cccc(C6CCNCC6)c5)s4)C3)s2)c1] | A |
| 356 | 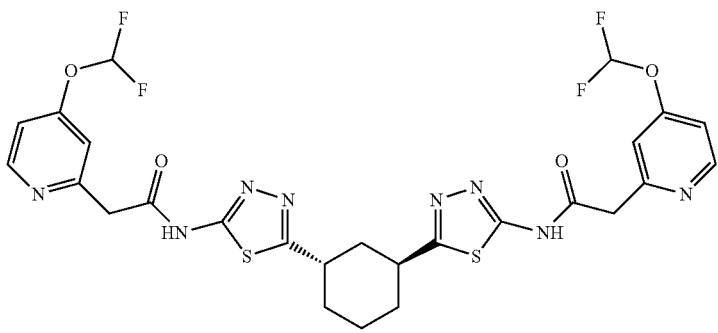 [SMILES: O=C(Cc1cc(OC(F)F)ccn1)Nc1nnc([C@H]2CCC[C@H](c3nnc(NC(=O)Cc4cc(OC(F)F)ccn4)s3)C2)s1] | A |
| 357 | 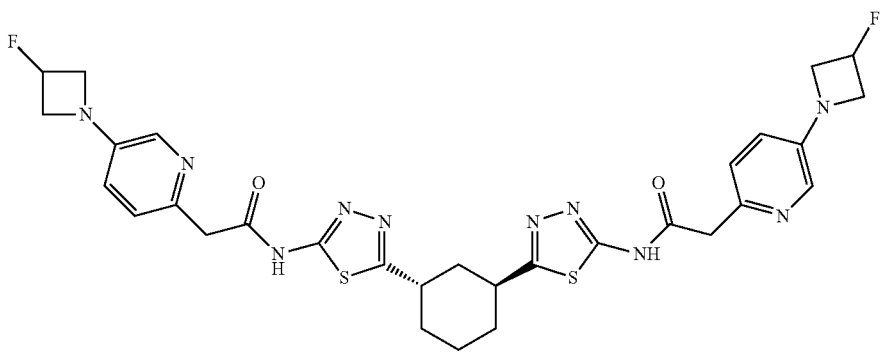 [SMILES: O=C(Cc1ccc(N2CC(F)C2)cn1)Nc1nnc([C@H]2CCC[C@H](c3nnc(NC(=O)Cc4ccc(N5CC(F)C5)cn4)s3)C2)s1] | A |

TABLE 1-continued

| Cmpd # | Structure | IC$_{50}$ |
|---|---|---|
| 358 | 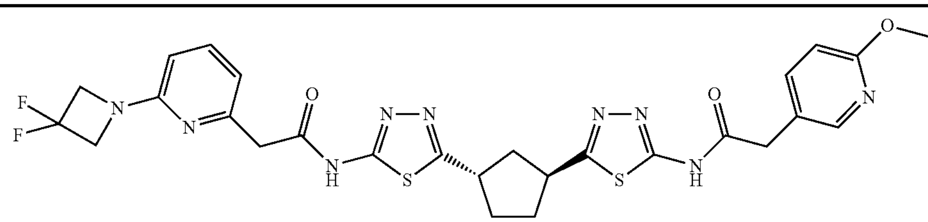 | A |
| 359 | 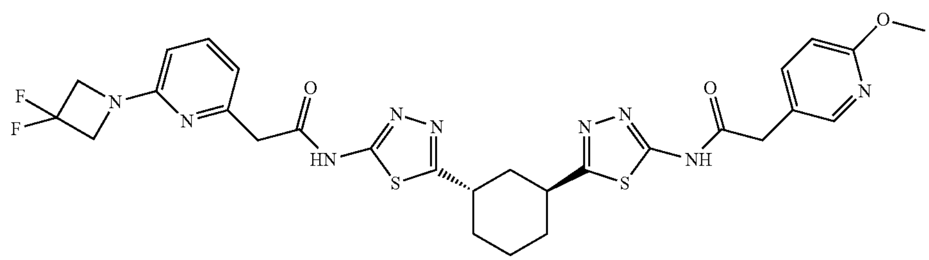 [SMILES: COc1ccc(CC(=O)Nc2nnc([C@H]3CCC[C@H](c4nnc(NC(=O)Cc5cccc(N6CC(F)(F)C6)n5)s4)C3)s2)cn1] | A |
| 360 | 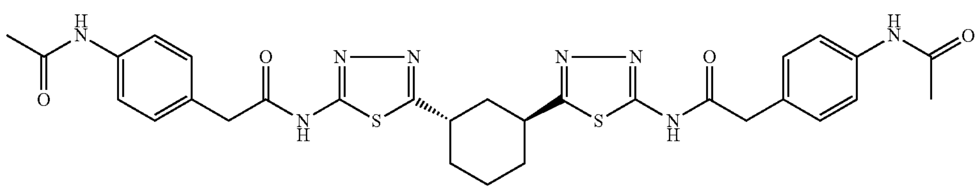 [SMILES: CC(=O)Nc1ccc(CC(=O)Nc2nnc([C@H]3CCC[C@H](c4nnc(NC(=O)Cc5ccc(NC(C)=O)cc5)s4)C3)s2)cc1] | A |
| 361 | 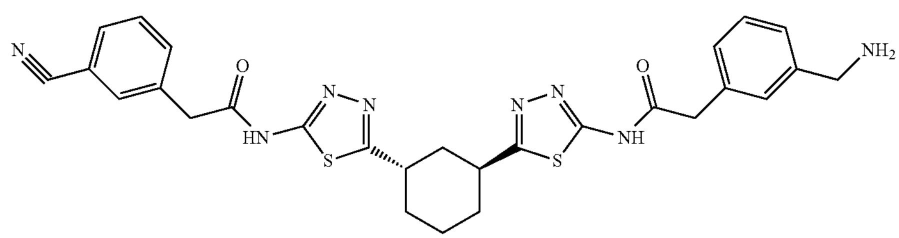 [SMILES: N#Cc1cccc(CC(=O)Nc2nnc([C@H]3CCC[C@H](c4nnc(NC(=O)Cc5cccc(CN)c5)s4)C3)s2)c1] | A |
| 362 | 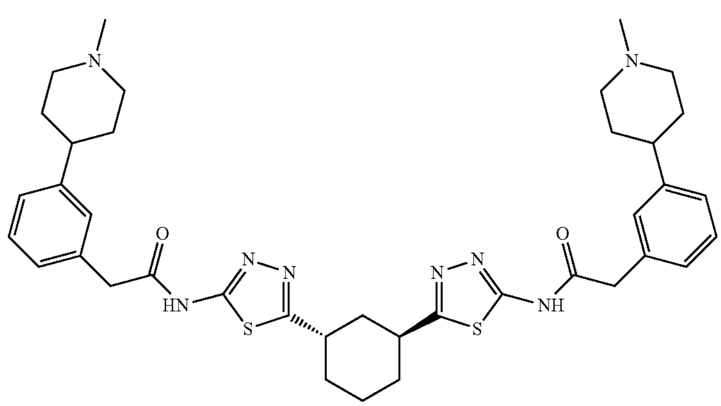 [SMILES: CN1CCC(c2cccc(CC(=O)Nc3nnc([C@H]4CCC[C@H](c5nnc(NC(=O)Cc6cccc(C7CCN(C)CC7)c6)s5)C4)s3)c2)CC1] | A |
| 363 | 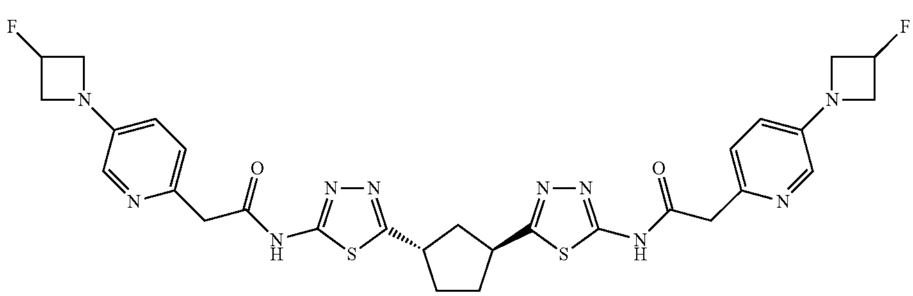 [SMILES: O=C(Cc1ccc(N2CC(F)C2)cn1)Nc1nnc([C@H]2CC[C@H](c3nnc(NC(=O)Cc4ccc(N5CC(F)C5)cn4)s3)C2)s1] | A |

TABLE 1-continued

| Cmpd # | Structure | IC$_{50}$ |
|---|---|---|
| 364 | 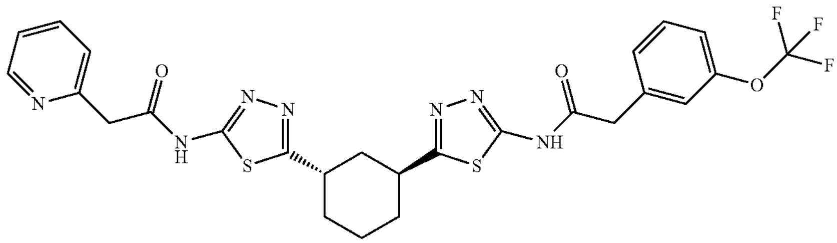 [SMILES: O=C(Cc1cccc(OC(F)(F)F)c1)Nc1nnc([C@H]2CCC[C@H](c3nnc(NC(=O)Cc4ccccn4)s3)C2)s1] | A |
| 365 | 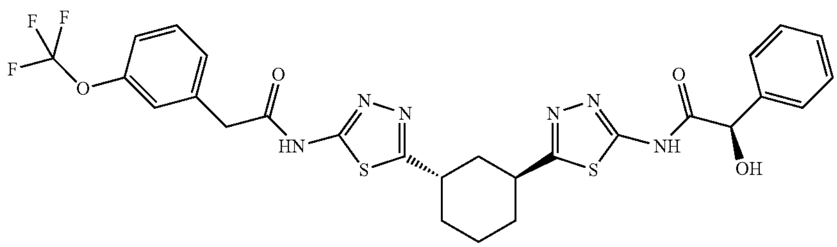 [SMILES: O=C(Cc1cccc(OC(F)(F)F)c1)Nc1nnc([C@H]2CCC[C@H](c3nnc(NC(=O)[C@H](O)c4ccccc4)s3)C2)s1] | A |
| 366 | 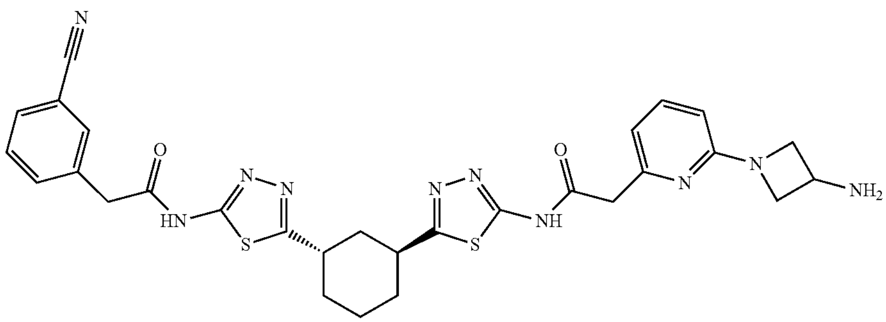 [SMILES: N#Cc1cccc(CC(=O)Nc2nnc([C@H]3CCC[C@H](c4nnc(NC(=O)Cc5cccc(N6CC(N)C6)n5)s4)C3)s2)c1] | A |
| 367 | 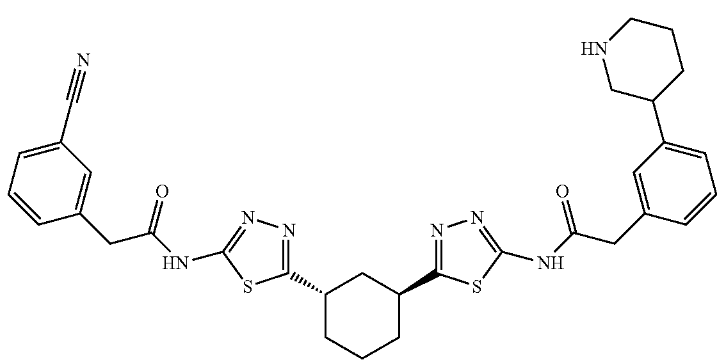 [SMILES: N#Cc1cccc(CC(=O)Nc2nnc([C@H]3CCC[C@H](c4nnc(NC(=O)Cc5cccc(C6CCCNC6)c5)s4)C3)s2)c1] | A |
| 368 | 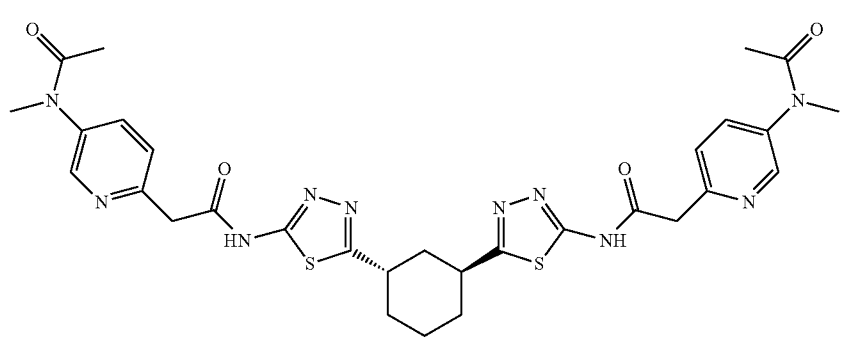 | A |

TABLE 1-continued
| Cmpd # | Structure | IC$_{50}$ |
|---|---|---|
| 369 | 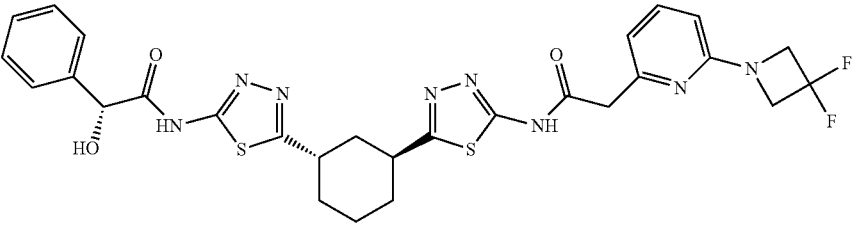 [SMILES: O=C(Cc1cccc(N2CC(F)(F)C2)n1)Nc1nnc([C@H]2CCC[C@H](c3nnc(NC(=O)[C@H](O)c4ccccc4)s3)C2)s1] | A |
| 370 | 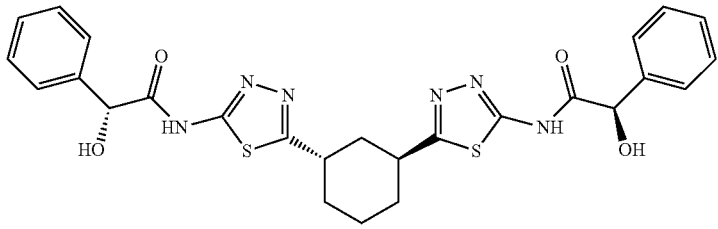 [SMILES: O=C(Nc1nnc([C@H]2CCC[C@H](c3nnc(NC(=O)[C@H](O)c4ccccc4)s3)C2)s1)[C@H](O)c1ccccc1] | A |
| 371 | 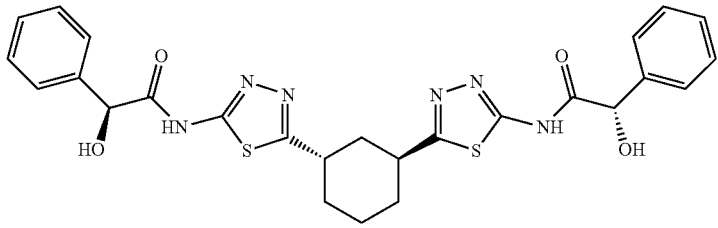 [SMILES: O=C(Nc1nnc([C@H]2CCC[C@H](c3nnc(NC(=O)[C@@H](O)c4ccccc4)s3)C2)s1)[C@@H](O)c1ccccc1] | A |
| 372 | 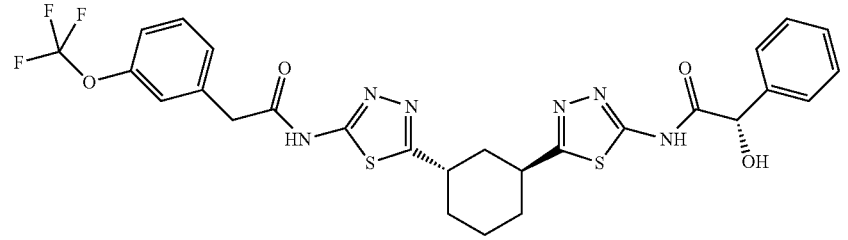 [SMILES: O=C(Cc1cccc(OC(F)(F)F)c1)Nc1nnc([C@H]2CCC[C@H](c3nnc(NC(=O)[C@@H](O)c4ccccc4)s3)C2)s1] | A |
| 373 | 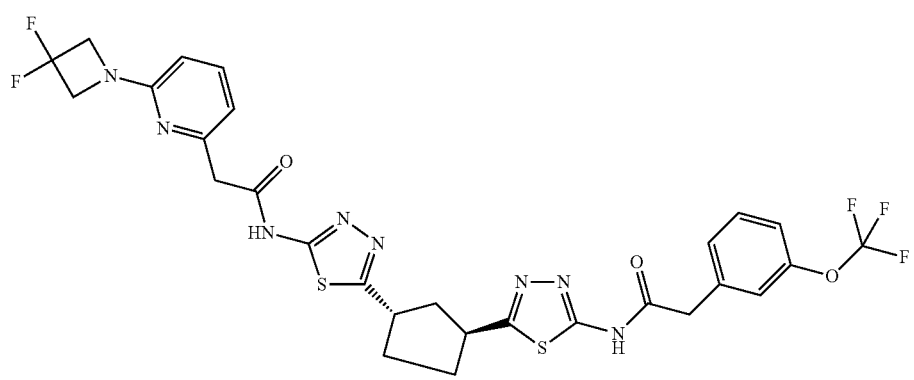 [SMILES: O=C(Cc1cccc(OC(F)(F)F)c1)Nc1nnc([C@H]2CC[C@H](c3nnc(NC(=O)Cc4cccc(N5CC(F)(F)C5)n4)s3)C2)s1] | A |
| 374 | 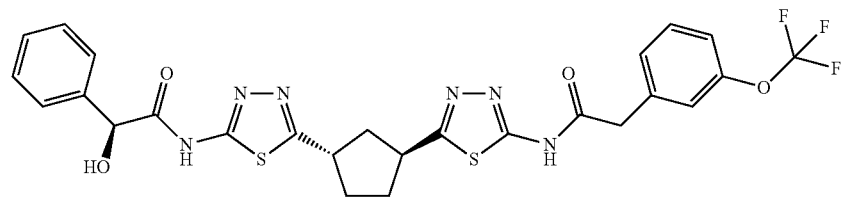 [SMILES: O=C(Cc1cccc(OC(F)(F)F)c1)Nc1nnc([C@H]2CC[C@H](c3nnc(NC(=O)[C@@H](O)c4ccccc4)s3)C2)s1] | A |

TABLE 1-continued

| Cmpd # | Structure | IC$_{50}$ |
|---|---|---|
| 375 | 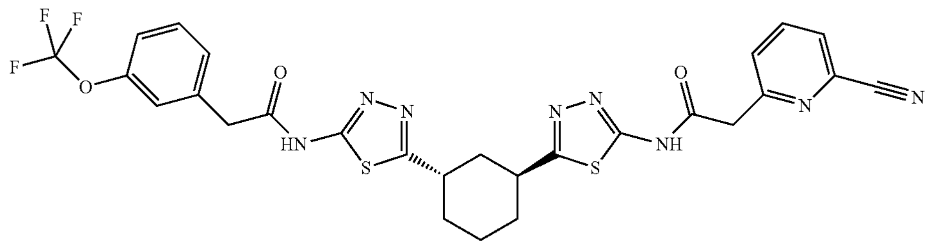 [SMILES: N#Cc1cccc(CC(=O)Nc2nnc([C@H]3CCC[C@H](c4nnc(NC(=O)Cc5cccc(OC(F)(F)F)c5)s4)C3)s2)n1] | A |
| 376 | 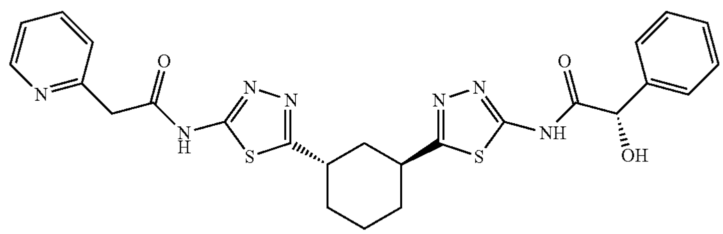 [SMILES: O=C(Cc1ccccn1)Nc1nnc([C@H]2CCC[C@H](c3nnc(NC(=O)[C@@H](O)c4ccccc4)s3)C2)s1] | A |
| 377 | 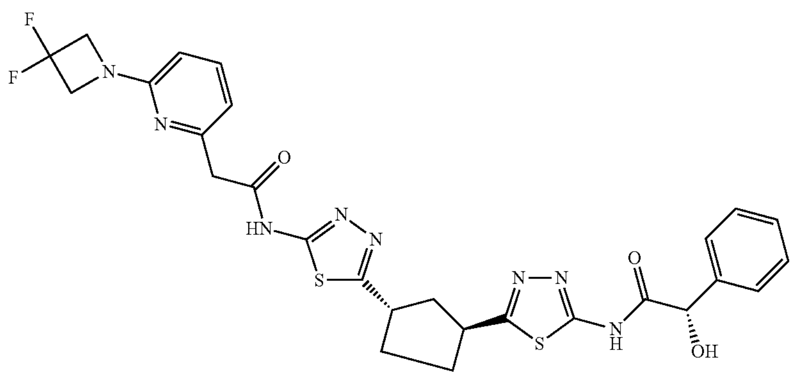 [SMILES: O=C(Cc1cccc(N2CC(F)(F)C2)n1)Nc1nnc([C@H]2CC[C@H](c3nnc(NC(=O)[C@@H](O)c4ccccc4)s3)C2)s1] | A |
| 378 | 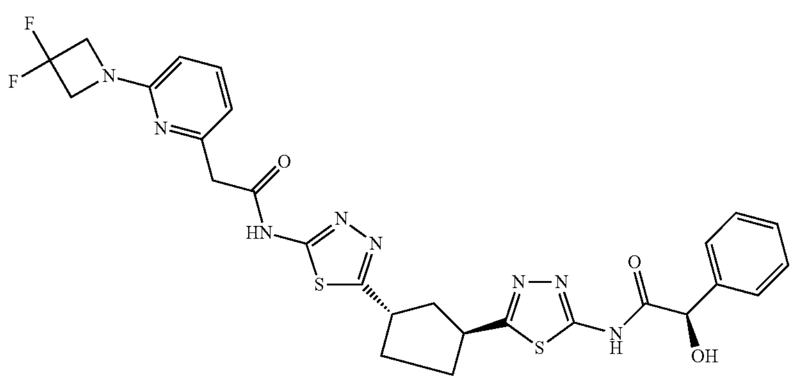 [SMILES: O=C(Cc1cccc(N2CC(F)(F)C2)n1)Nc1nnc([C@H]2CC[C@H](c3nnc(NC(=O)[C@H](O)c4ccccc4)s3)C2)s1] | A |
| 379 | 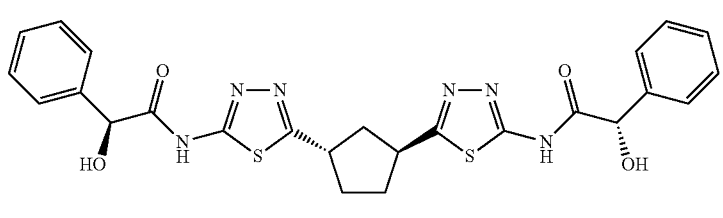 [SMILES: O=C(Nc1nnc([C@H]2CC[C@H](c3nnc(NC(=O)[C@@H](O)c4ccccc4)s3)C2)s1)[C@@H](O)c1ccccc1] | A |

TABLE 1-continued
| Cmpd # | Structure | IC$_{50}$ |
|---|---|---|
| 380 | 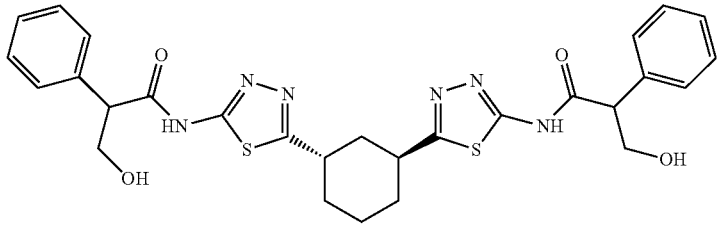 [SMILES: O=C(Nc1nnc([C@H]2CCC[C@H](c3nnc(NC(=O)C(CO)c4ccccc4)s3)C2)s1)C(CO)c1ccccc1] | A |
| 381 | 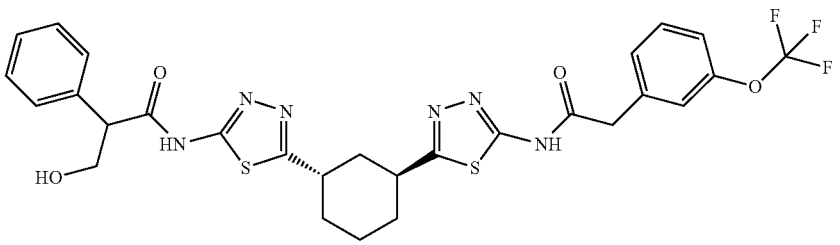 [SMILES: O=C(Cc1cccc(OC(F)(F)F)c1)Nc1nnc([C@H]2CCC[C@H](c3nnc(NC(=O)C(CO)c4ccccc4)s3)C2)s1] | A |
| 382 | 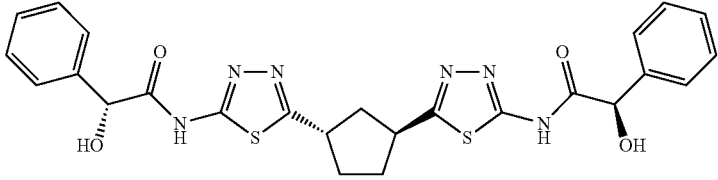 [SMILES: O=C(Nc1nnc([C@H]2CC[C@H](c3nnc(NC(=O)[C@H](O)c4ccccc4)s3)C2)s1)[C@H](O)c1ccccc1] | A |
| 383 | 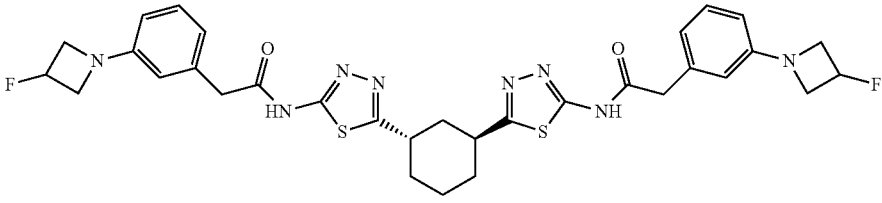 [SMILES: O=C(Cc1cccc(N2CC(F)C2)c1)Nc1nnc([C@H]2CCC[C@H](c3nnc(NC(=O)Cc4cccc(N5CC(F)C5)c4)s3)C2)s1] | A |
| 384 | 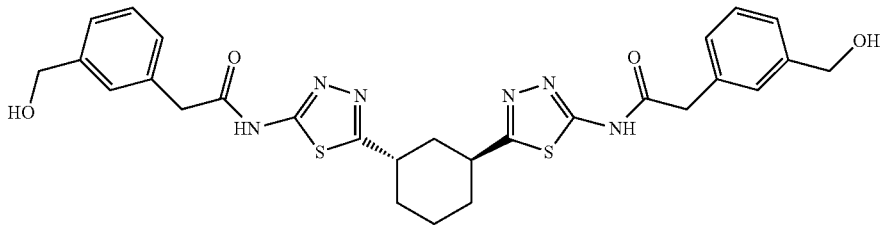 [SMILES: O=C(Cc1cccc(CO)c1)Nc1nnc([C@H]2CCC[C@H](c3nnc(NC(=O)Cc4cccc(CO)c4)s3)C2)s1] | A |
| 385 | 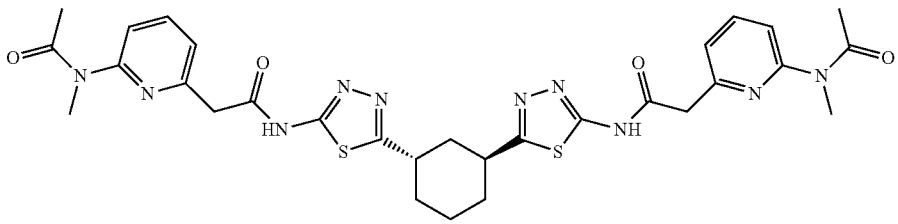 [SMILES: CC(=O)N(C)c1cccc(CC(=O)Nc2nnc([C@H]3CCC[C@H](c4nnc(NC(=O)Cc5cccc(N(C)C(C)=O)n5)s4)C3)s2)n1] | A |

TABLE 1-continued

| Cmpd # | Structure | IC$_{50}$ |
|---|---|---|
| 386 | 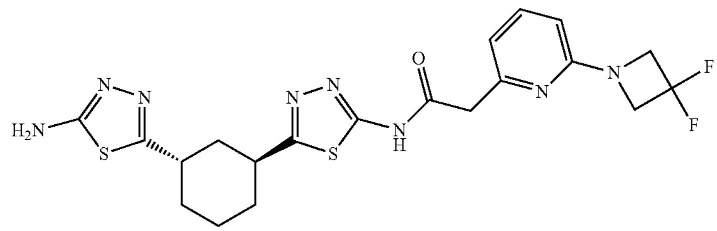 [SMILES: Nc1nnc([C@H]2CCC[C@H](c3nnc(NC(=O)Cc4cccc(N5CC(F)(F)C5)n4)s3)C2)s1] | A |
| 387 | 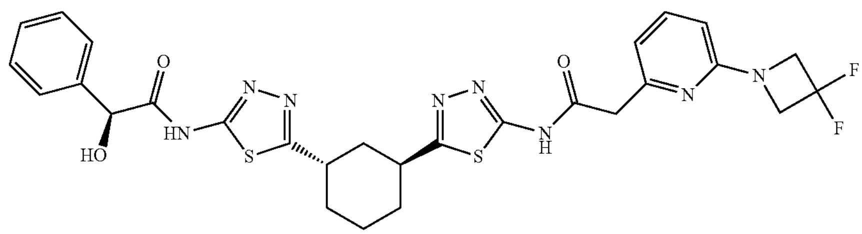 [SMILES: O=C(Cc1cccc(N2CC(F)(F)C2)n1)Nc1nnc([C@H]2CCC[C@H](c3nnc(NC(=O)[C@@H](O)c4ccccc4)s3)C2)s1] | A |
| 388 | 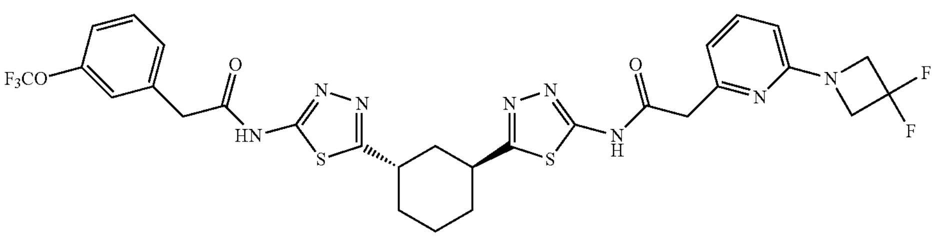 [SMILES: O=C(Cc1cccc(OC(F)(F)F)c1)Nc1nnc([C@H]2CCC[C@H](c3nnc(NC(=O)Cc4cccc(N5CC(F)(F)C5)n4)s3)C2)s1] | A |
| 389 | 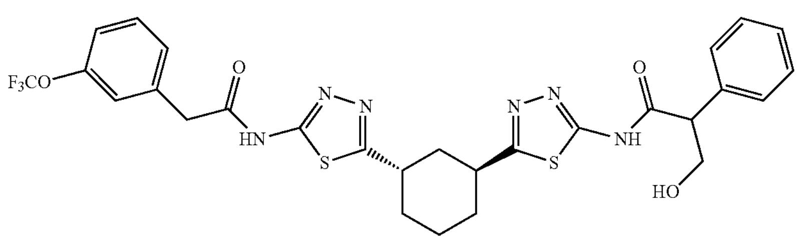 [SMILES: O=C(Cc1cccc(OC(F)(F)F)c1)Nc1nnc([C@H]2CCC[C@H](c3nnc(NC(=O)C(CO)c4ccccc4)s3)C2)s1] | A |
| 390 | 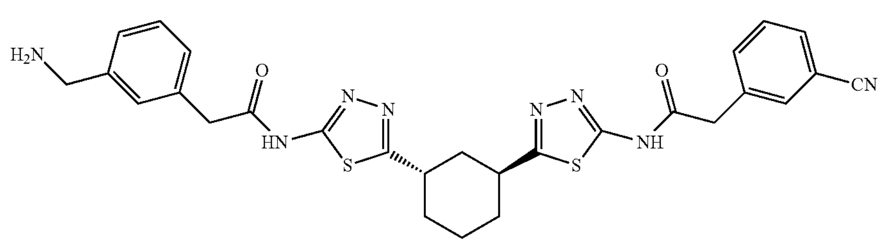 [SMILES: N#Cc1cccc(CC(=O)Nc2nnc([C@H]3CCC[C@H](c4nnc(NC(=O)Cc5cccc(CN)c5)s4)C3)s2)c1] | A |

The compounds described herein can be made using a variety of synthetic techniques such as those described in the examples provided herein. As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g. restriction resulting from the presence of a ring or double bond. Accordingly, all cis/trans and E/Z isomers are expressly included.

The compounds provided herein (e.g. of Formula I) may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Definitions

The term "halo" or "halogen" refers to any radical of fluorine, chlorine, bromine or iodine.

The term "alkyl" refers to a saturated or unsaturated hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "alkyl" includes alkenyl moieties. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" or "cycloalkylene" refers to a divalent alkyl or cycloalkyl, e.g., —CH$_2$—, —CH$_2$CH$_2$—, and —CH$_2$CH$_2$CH$_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

The term "aryl" refers to a monocyclic, bicyclic, or tricyclic aromatic hydrocarbon ring system, wherein any ring atom capable of substitution can be substituted (e.g., by one or more substituents). Examples of aryl moieties include, but are not limited to, phenyl, naphthyl, and anthracenyl. Unless otherwise specified, any ring atom in an aryl can be substituted by one or more substituents.

The term "cycloalkyl" as employed herein includes cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclohexyl, methylcyclohexyl, adamantyl, and norbornyl.

The term "cycloalkylalkyl" as employed herein refers to an alkyl group substituted with a cycloalkyl group.

The terms "heterocyclyl" or "heterocyclic group" refer to 3- to 14-membered non-aromatic ring structures (e.g., 3- to 14-membered rings, more preferably 3- to 7-membered rings), whose ring structures include one to four heteroatoms independently selected from O, N and S. The heterocyclyl or heterocyclic groups can contain fused or spiro rings. Heterocycles can also be polycycles, with each group having, e.g., 5-7 ring members. The term "heterocyclyl" or "heterocyclic group" includes saturated and partially saturated heterocyclyl structures. The heteroatom may optionally be the point of attachment of the heterocyclyl substituent.

The term "heteroaryl" refers to a 5-14 membered (i.e., a 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from 0, N, and S (e.g., 1-3, 1-6, or 1-9 ring heteroatoms of N, O, or S if monocyclic, bicyclic, or tricyclic, respectively). Any substitutable ring atom can be substituted (e.g., by one or more substituents).

Bicyclic and tricyclic ring systems containing one or more heteroatoms and both aromatic and non-aromatic rings wherein the point of attachment from the ring system to the rest of the molecule is through a non-aromatic ring are considered to be heterocyclyl groups. Bicyclic or tricyclic ring systems where an aryl or a heteroaryl is fused to a cycloalkyl or heterocyclyl and the point of attachment from the ring system to the rest of the molecule is through an aromatic ring are considered to be aryl or heteroaryl groups.

The term "heterocyclylalkyl", as used herein, refers to an alkyl group substituted with a heterocycle group.

The terms "hetaralkyl" and "heteroaralkyl", as used herein, refers to an alkyl group substituted with a heteroaryl group. The ring heteroatoms of the compounds provided herein include N—O, S(O), and S(O)$_2$.

Aryl, heteroaryl, cycloalkyl, and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —OR$^b$, —OR$^{b'}$, —SR$^b$, —SR$^{b'}$, —($C_1$-$C_4$ alkyl)-N(R$^b$)(R$^b$), —($C_1$-$C_4$ alkyl)-N(R$^b$)(R$^{b'}$), —N(R$^b$)(R$^{b'}$), —N(R$^b$)(R$^{b'}$), —O—($C_1$-$C_4$ alkyl)-N(R$^b$)(R$^b$), —O—($C_1$-$C_4$ alkyl)-N(R$^b$)(R$^{b'}$), —($C_1$-$C_4$ alkyl)-O—($C_1$-$C_4$ alkyl)-N(R$^b$)(R$^b$), —($C_1$-$C_4$ alkyl)-O—($C_1$-$C_4$ alkyl)-N(R$^b$)(R$^{b'}$), —(C(O)—N(R$^b$)(R$^b$), —($C_1$-$C_4$ alkyl)-C(O)—N(R$^b$)(R$^b$), —($C_1$-$C_4$ alkyl)-C(O)—N(R$^b$)(R$^{b'}$), —OR$^{b'}$, R$^{b'}$, —C(O)($C_1$-$C_4$ alkyl), —C(O)R$^{b'}$, —C(O)N(R$^{b'}$)(R$^b$), —N(R$^b$)C(O)(R$^b$), —N(R$^b$)C(O)(R$^{b'}$), —N(R$^b$)SO$_2$(R$^b$), —SO$_2$N(R$^b$)(R$^b$), —N(R$^b$)SO$_2$(R$^{b'}$), and —SO$_2$N(R$^b$)(R$^{b'}$), wherein any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$;

each R$^b$ is independently selected from hydrogen, and —$C_1$-$C_4$ alkyl; or two R$^b$s are taken together with the nitrogen atom to which they are bound to form a 4- to 8-membered heterocyclyl optionally comprising one additional heteroatom selected from N, S, and O; and each R$^{b'}$ is independently selected from $C_3$-$C_7$ carbocylyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo (=O), —$C_1$-$C_4$ alkyl, or fluoro-substituted $C_1$-$C_4$ alkyl.

The term "substituted" refers to the replacement of a hydrogen atom by another group.

The term "selective" is meant at least 2-fold, 3-fold, 4-fold, 5-fold, 6-fold, or 10-fold greater inhibition of glutaminase than other targets.

The term "inhibitor" as used herein means an agent that measurably slows, stops, decreases or inactivates the enzymatic activity of glutaminase to decrease to a level that is less than the glutaminase normal levels of activity. Inhibitors of glutaminase may be peptides or nucleic acids (e.g., glutamate). An agent can be evaluated to determine if it is an inhibitor by measuring either directly or indirectly the activity of glutaminase when subjected to the agent. The activity of the agent can be measured, for example, against a control substance. In some instances, the activity measured of the agent is for inhibition of glutaminase.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

As used herein a "low" of E-cadherin expression compared to a reference standard refers a low, decreased, or absent level of E-cadherin expression compared to the level of E-cadherin expression in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, a "high" level of vimentin compared to a reference standard refers to a high or increased level of vimentin expression compared to the level of expression of vimentin in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, a "low" or "decreased", level of pyruvate carboxylase expression compared to a reference standard refers to a low, decreased, or absent level of E-cadherin expression compared to the level of E-cadherin expression in an epithelial cell as characterized by methods known in the art, e.g., on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

As used herein, "cancer" and "tumor" are synonymous terms. The term "cancer" or "tumor" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. The cells can possess characteristics typical of a mesenchymal cell, such as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Methods of Evaluating Compounds

Glutaminase activity can be monitored by detecting production of either of the products of the reaction, glutamate or ammonia. In some embodiments, glutamate production is measured because ammonia is a product of any of a number of biological reactions.

Glutamate production can be measured by any of a number of standard methods known in the art, e.g., chemical and chromatographic detection methods and coupled enzyme assays that utilize NADH and glutamate dehydrogenase. Extracellular glutamate concentrations can also be measured in vivo, using microdialysis methods known in the art. One suitable method for measuring glutamate is a microtiter-based two-step assay in which glutamate formed in the initial step is quantitatively deaminated by glutamate dehydrogenase to yield an equivalent amount of NADH (Godfrey et al., 1977; Kvamme et al., 1985), which can then be detected spectrophotometrically.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I) or in Table 1).

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

The term "patient" and "subject" are synonymous, and as used herein, refer to an animal, typically a human (i.e., a male or female of any age group, e.g., a pediatric patient or adult patient or other mammal, such as primates (e.g., cynomolgus monkeys, rhesus monkeys); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

Cancers

The methods described herein can be used with any cancer, for example those described by the National Cancer Institute. A cancer can be evaluated to determine whether it is using a method described herein. Exemplary cancers can include but are not limited to, lung cancer, e.g., non-small cell lung cancer; breast cancer, e.g., triple negative breast cancer; or hepatocellular carcinoma, osteosarcoma, lipomas, chondrosarcoma, or mesothelioma. In some embodiments, the cancer is selected from colon cancer, renal cell carcinoma, acute myeloid leukemia (AML), melanoma, and multiple myeloma.

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

Cancer Combination Therapies

In some embodiments, a compound described herein is administered together with one or more additional cancer treatments. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with one or more chemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Exemplary additional therapeutic agents can also include epidermal growth factor receptor (EGFR) inhibitors, e.g., cetuximab, panitumumab, gefitinib, erlotinib, nimotuzamab, matuzamab, zalutumumab, or lapatinib. Resistance to EGFR inhibitors can occur as a result of the transition of a cell to a mesenchymal phenotype or a mesenchymal phenotype, and tumors with EGFR mutations and mesenchymal phenotype can be less sensitive to EGFR inhibitors (see for example, Sequist et al., (2011) Sci Transl Med. 3:75. Buck et al., (2007) Mol Cancer Ther. 6: 532; Thomson et al., (2008) Clin Exp Metastasis 25: 843).

Exemplary additional therapeutic agents can also include glutathione depleting agents, e.g., L-buthionine-(S,R)-sulfoximine (BSO).

Exemplary additional therapeutic agents can also include Phosphoinositide 3-kinase (PI3K) inhibitors, e.g., Perifosine, Idelalisib, BKM120, PX-866, IPI-145, NVP-BEZ235, GDC0941, and BAY 80-6946.

Exemplary additional therapeutic agents can also include Heat Shock Protein 90 (HSP90) inhibitors, e.g., geldanamycin, radicicol, 17-N-Allylamino-17-demethoxygeldanamycin (17AAG). ganetespib, 4-(4-(2,3-Dihydro-1,4-benzodioxin-6-yl)-5-methyl-1H-pyrazol-3-yl)-6-ethylresorcinol, AUY922 (NVP-AUY922), BIIB021, STA9090, AT13387, NVP-BEP800, and SNX-2112 (PF-04928473).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Nutrient Restricted Diets

In some embodiments, a compound described herein is administered in conjunction with one or more nutrient restricted diets. Since cancer cells rely on glucose to generate cellular energy, lowering glucose blood levels through carbohydrate and protein restriction may inhibit the growth of some cancers. In certain cancers, nutrient restricted diets such as caloric restriction, fasting, and ketogenic diets may be therapeutically beneficial. In some embodiments, such nutrient restricted diets can be used in combination with a compound described herein.

Neuronal Disorders

A compound or composition described herein can be used to treat or prevent neuronal cell death as a result of an injury to neuronal tissue, e.g., nervous tissue exposed to an ischemic or hypoxic event, to trauma or to a chronic neurodegenerative disorder. A "neuronal disorder" is a neurological disease or disorder that is associated with glutamate excitotoxicity, e.g., cerebral ischemia or hypoxia resulting from an neurological event such as a stroke or ischemic event. Treatment with the compound may be in an amount effective to provide a neuroprotective effect, e.g., to prevent neuronal cell death.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a subject, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can inhibit glutaminase. Accordingly, a patient and/or subject can be selected for treatment using a compound described herein by first evaluating the patient and/or subject to determine whether the subject is in need of inhibition of glutaminase, and if the subject is determined to be in need of glutaminase inhibition, then administering to the subject a compound described herein.

A subject can be evaluated as being in need of glutaminase inhibition using methods known in the art, e.g., by measuring the presence and/or activity of glutaminase in the patient. In some embodiments, the activity and/or level of glutaminase is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor). In some embodiments, the patient is evaluated using a radiological assay or evaluation of hemolytic parameters.

A patient and/or subject can be selected for treatment using a compound described hereby by optionally, acquiring a patient sample; evaluating the sample to determine whether the sample is characterized by i) a low level of E-cadherin expression compared to a reference standard, ii) a high level of vimentin expression compared to a reference standard, and/or iii) a low or decreased level of pyruvate carboxylase expression compared to a reference standard; and if the patient is determined to have a low level of E-cadherin expression compared to a reference standard, or a high level of vimentin expression compared to a reference standard, then the patient is administered a compound described herein.

In some embodiments, the level of E-cadherin expression is compared to a reference standard, wherein the reference standard is the level of E-cadherin expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of E-cadherin expression is low, decreased, or absent compared to the reference standard. In some embodiments, the level of E-cadherin expression is measured by the evaluation of the level of RNA that encodes E-cadherin. In some embodiments, the level of E-cadherin expression is evaluated by the level of E-cadherin protein expression. In some embodiments the level of E-cadherin expression is at least 5, 10, 15, 20, 25, 30, 40, 50, 60, 70, 80, or 90% less than the reference standard. In some embodiments the level of E-cadherin expression is at least a 1.5, 2, 5, 10, 15, 20, 25, 50, 75, 100 fold decrease in expression compared to the reference standard.

In some embodiments, the level of vimentin expression is compared to a reference standard, wherein the reference standard is the level of vimentin expression in an epithelial cell as characterized on any one of the following references: (Yauch et al., (2005) *Clin Cancer Res* 11:24; Savagner et al., (2010) Ann Oncol. 21(suppl 7): vii89; Thiery et al., (2002) Nature Reviews Cancer 2(6):442). In some embodiments, the level of vimentin expression is measured by the evaluation of the level of RNA that encodes vimentin. In some embodiments, the level of vimentin expression is evaluated by the level of vimentin protein expression. In some embodiments the level of vimentin expression is at least 5, 10, 15, 20, 25, 30, 40, 50, 60, 70, 80, or 90% greater than the reference standard. In some embodiments the level of vimentin expression is at least a 1.5, 2, 5, 10, 15, 20, 25, 50, 75, 100 fold increase in expression compared to the reference standard.

In some embodiments, the level of pyruvate carboxylase expression is low or decreased compared to a reference standard, wherein the reference standard is the level of pyruvate carboxylase expression in an epithelial cell as characterized on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442). In some embodiments, the level of pyruvate carboxylase expression is high or increased compared to the reference standard. In some embodiments, the level of pyruvate carboxylase expression is measured by the evaluation of the level of RNA that encodes pyruvate carboxylase. In some embodiments, the level of vimentin expression is evaluated by the level of pyruvate carboxylase protein expression. In some embodiments the level of pyruvate carboxylase expression is at least 5, 10, 15, 20, 25, 30, 40, 50, 60, 70, 80, or 90% greater than the reference standard. In some embodiments the level of pyruvate carboxylase expression is at least a 1.5, 2, 5, 10, 15, 20, 25, 50, 75, 100 fold increase in expression compared to the reference standard.

Patient Sample

The terms "patient sample", "subject sample", and "sample" are used interchangeably herein. The patient sample can be a tissue, or bodily fluid, or bodily product. Tissue samples can include fixed, paraffin embedded, fresh, or frozen samples. For example, the tissue sample can include a biopsy, cheek swab. Exemplary tissues include lung, breast, brain, nervous tissue, kidney, ovary, thyroid, pancreas, colon, prostate, lymph node, skin, hair follicles and nails. Exemplary samples include samples derived from solid tumors. Exemplary bodily fluids include blood, plasma, urine, lymph, tears, sweat, saliva, semen, and cerebrospinal fluid. Exemplary bodily products include exhaled breath.

The tissue, fluid or product can be removed from the patient and analyzed. The evaluation can include one or more of: performing the analysis of the tissue, fluid or product; requesting analysis of the tissue fluid or product; requesting results from analysis of the tissue, fluid or product; or receiving the results from analysis of the tissue, fluid or product.

The sample tissue, fluid, or product can be analyzed for the expression level of a gene described herein, e.g., E-cadherin, vimentin, pyruvate carboxylase. The sample tissue, fluid, or product can be analyzed for the expression level of a protein described herein, e.g., E-cadherin, vimentin, pyruvate carboxylase. The sample tissue, fluid or product can further be analyzed for the level of gene expression of a gene or plurality of genes of a preselected signaling pathway or phenotypic pathway, e.g., the epithelial to mesenchymal transition pathway, E-cadherin pathway, vimentin pathway, or the pyruvate carboxylase pathway. The sample tissue, fluid or product can further be analyzed for the level of protein expression of a protein or plurality of proteins of a preselected signaling pathway or phenotypic pathway, e.g., the epithelial to mesenchymal transition pathway, E-cadherin pathway, vimentin pathway, or the pyruvate carboxylase pathway.

Methods of Evaluating Samples

The expression level of a gene described herein, e.g., E-cadherin, vimentin, and pyruvate carboxylase, can be assessed using any of a wide variety of well known methods for detecting expression of a transcribed molecule, gene, protein, mRNA, genomic DNA, or cDNA. Gene expression can be measured or monitored by measure of a gene transcript, e.g., mRNA, by a measure of the quantity of a translated protein, or by a measure of gene product activity; any of which can be measured using standard techniques known to one of skill in the art. Non-limiting examples of such methods include nucleic acid hybridization methods, nucleic acid reverse transcription methods, nucleic acid amplification methods, immunological methods for detection of proteins, protein purification methods, protein function or activity assays.

E-Cadherin

The E-cadherin gene is located on human chromosome 16. E-cadherin is a classical cadherin of the cadherin superfamily. The encoded E-cadherin protein is a calcium dependent cell-cell adhesion glycoprotein comprised of five extracellular cadherin repeats, a transmembrane region and a highly conserved cytoplasmic tail. Mutations in this gene have been correlated with cancer, including gastric, breast, colorectal, thyroid and ovarian cancers. Loss of function of E-cadherin is contemplated to contribute to cancer progression by increasing proliferation, invasion, and/or metastasis. The ectodomain of this protein mediates bacterial adhesion to mammalian cells and the cytoplasmic domain is required for internalization. Identified E-cadherin transcript variants arise from mutation at consensus splice sites.

Vimentin

The vimentin gene is located on human chromosome 10 and encodes a member of the intermediate filament family of proteins. Intermediate filaments, along with microtubules and actin microfilaments, make up the cellular cytoskeleton, which helps maintain cell shape and integrity of the cytoplasm, as well as stabilizing cytoskeletal interactions. Vimentin also functions in mediating immune responses, control of the transport of low-density lipoprotein derived cholesterol from lysosomes to the sites of esterification, and as an organizer of a number of critical proteins involved in attachment, migration, and cell signaling.

Pyruvate Carboxylase (PC)

The PC gene is located on human chromosomes 11 and encodes the protein pyruvate carboxylase, which catalyzes the carboxylation of pyruvate to oxaloacetate. The active enzyme is a homotetramer arranged in a tetrahedron which is located exclusively in the mitochondrial matrix. Pyruvate carboxylase is involved in multiple cellular processes including gluconeogenesis, lipogenesis, insulin secretion and synthesis of the neurotransmitter glutamate. Mutations in this gene have been associated with pyruvate carboxylase deficiency. Alternatively spliced transcript variants with different 5' UTRs, but encoding the same protein, have been identified.

Nucleic Acid Molecules

The methods described herein can pertain to the evaluation of a sample for the expression of a gene described herein, e.g., E-cadherin, vimentin, pyruvate carboxylase; based on isolated nucleic acids which correspond to the gene described herein, e.g., the mRNA level of E-cadherin; the mRNA level of vimentin; the mRNA level of pyruvate carboxylase. As used herein, the term "nucleic acid" or "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

An "isolated" nucleic acid molecule is one which is separated from other nucleic acid molecules which are present in the natural source of the nucleic acid molecule. An "isolated" nucleic acid molecule can be free of sequences (such as protein-encoding sequences) which naturally flank the nucleic acid (i.e., sequences located at the 5' and 3' ends of the nucleic acid) in the genomic DNA of the organism from which the nucleic acid is derived. An "isolated" nucleic acid molecule, such mRNA, can be substantially free of other cellular material cellular material or other contaminating proteins from the cell or tissue source from which the nucleic acid is derived.

A nucleic acid molecule described herein can be isolated using standard molecular biology techniques and the sequence information available in database records known to those of skill in the art. Using all or a portion of such nucleic acid sequences, nucleic acid molecules described herein can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule described herein can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule can be prepared by standard synthetic techniques, e.g., using an automated DNA synthesizer.

An isolated nucleic acid molecule can comprise a nucleic acid molecule which has a nucleotide sequence complementary to the nucleotide sequence of a nucleic acid corresponding to gene described herein, or to the nucleotide sequence of a nucleic acid encoding a protein which corresponds to the gene described herein. A nucleic acid molecule which is complementary to a given nucleotide sequence is one which is sufficiently complementary to the given nucleotide sequence that it can hybridize to the given nucleotide sequence thereby forming a stable duplex.

A nucleic acid molecule described herein can comprise only a portion of a nucleic acid sequence. Such nucleic acid molecules can be used, for example, as a probe or primer. The probe/primer can be one or more substantially purified oligonucleotides. Probes based on the sequence of a nucleic acid molecules described herein can be used to detect transcripts or genomic sequences corresponding to the genes described herein. The probe can contain comprise a label group, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a patient, e.g., detecting mRNA levels.

Methods for Detection of Gene Expression

Methods of detecting and/or quantifying a gene transcript, e.g., mRNA or cDNA made therefrom, can include but are not limited to Southern Blot analysis, Northern Blot analysis, polymerase chain reaction (PCR) analyses and probe arrays. Methods of detecting and/or quantifying a gene transcript, e.g., mRNA or cDNA made therefrom, can include but are not limited to hybridization based methods, e.g., hybridization with a probe that is specific for the gene transcript, e.g., mRNA or cDNA made therefrom. The level of a gene transcript, e.g., mRNA or cDNA made therefrom, can be assayed by applying the sample, or the mRNA or cDNA made therefrom, or amplified from; to a nucleic acid microarray, or chip array.

The level of a gene transcript, e.g., mRNA or cDNA made therefrom, can be assayed by a polymerase chain reaction (PCR) based method, e.g., quantitative PCR, quantitative real time PCR, real time PCR, reverse transcription PCR, real time reverse transcription PCR. The level of a gene transcript, e.g., mRNA or cDNA made therefrom, can be assayed by a sequencing based method, e.g., quantitative RNA sequencing.

The level of a gene transcript, e.g., mRNA, can be determined by in situ or by in vitro methods known in the art. For in vitro methods, any RNA isolation technique that does not select against the isolation of mRNA can be utilized for the purification of RNA from a sample, e.g., from cells of a sample (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). For in situ methods, mRNA does not need to be isolated from the cells prior to detection. In such methods, a cell or tissue sample can be prepared/processed using known histological methods. The sample can then be immobilized on a support, and then contacted with a probe that can hybridize to mRNA that encodes the gene transcript of interest.

Determinations can be based on absolute expression level; normalized expression level, or relative expression level; of a gene transcript, e.g., mRNA. Expression levels can be normalized by correcting the absolute expression level of a gene transcript by comparing its expression level to the expression level of another gene which is stably expressed, e.g., a housekeeping gene that is constitutively expressed. Suitable genes for normalization include housekeeping genes such as histone H3 gene or the actin gene. This normalization allows the comparison of the expression level in one sample to another sample, e.g., a first sample taken from a patient to a second sample taken from the same patient, e.g., from another tissue or at a different time point; or between samples from different sources, e.g., a patient sample from one patient to a patient sample from another patient.

The expression level can be provided as a relative expression level. The relative expression level can be determined by comparing the absolute level of expression of the gene transcript, e.g., mRNA, to a reference standard. The reference standard can include the level of expression of the gene transcript of interest in a genotypically or phenotypically defined sample. The reference standard can be the level of expression of the gene transcript of interest, e.g., E-cadherin, vimentin, pyruvate carboxylase, in a cell genotypically or phenotypically characterized as an epithelial cell. An epithelial cell can be characterized as in any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

The expression level of a gene transcript described herein, e.g., E-cadherin, vimentin, pyruvate carboxylase, can be measured at least at two time-points to determine if a change in the level of expression has occurred. For example, the level of expression can be measured pre- and post-treatment with a compound described herein, or at one or more time-points while treatment with a compound described herein is ongoing. If the expression level is found to be decreased, e.g., decreased expression of E-cadherin compared to a reference standard and/or increased expression of vimentin compared to a reference standard; the subject may be administered treatment with a compound described herein. The reference standard can be the level of expression of the gene transcript of interest in an epithelial cell characterized. An epithelial cell can be characterized by methods known in the art, e.g., as in any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

Proteins

The methods described herein can pertain to the evaluation of a sample for the expression of a gene described herein, e.g., E-cadherin, vimentin, pyruvate carboxylase; based on isolated proteins which correspond to the gene described herein, e.g., the protein level of E-cadherin; the protein level of vimentin; the protein level of pyruvate carboxylase. This can also include the evaluation of biologically active portions, variants, isoforms, or splice variants thereof. The native polypeptide corresponding to the protein of interest can be isolated from the sample by an appropriate purification scheme using standard protein purification techniques known to those of skill in the art.

An "isolated" or "purified" protein or biologically active portion thereof is substantially free of cellular material or other contaminating proteins from the cell or tissue source from which the protein is derived. The language "substantially free of cellular material" includes preparations of protein in which the protein is separated from cellular components of the cells from which it is isolated. Biologically active portions of a polypeptide can include polypeptides comprising amino acid sequences sufficiently identical to or derived from the amino acid sequence of the protein, which include fewer amino acids than the full length protein, and exhibit at least one activity of the corresponding full-length protein. Typically, biologically active portions comprise a domain or motif with at least one activity of the corresponding protein.

Methods for Detection of Protein Expression

The level of expression of a protein or polypeptide can be detected and quantified by any of a number of means well known to those of skill in the art. Methods of detecting and/or quantifying a protein or polypeptide described herein, e.g., E-cadherin, vimentin, pyruvate carboxylase; can include but are not limited to biochemical methods such as electrophoresis, capillary electrophoresis, high performance liquid chromatography (HPLC), thin layer chromatography (TLC), hyperdiffusion chromatography, and the like, or various immunoassays such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry, in situ hybridization, fluorescence-activated cell sorting (FACS) and the like. A skilled artisan can readily adapt known protein/antibody detection methods for use in determining whether cells express the protein or polypeptide described herein.

A protein or polypeptide can be detected using an immunoassay. As used herein, immunoassays include assays that utilize an antibody to specifically bind to a protein or polypeptide. An immunoassay can be characterized by the detection of specific binding of a protein or polypeptide to an antibody as opposed to the use of other physical or chemical properties to isolate, target, and quantify the polypeptide. The polypeptide can be detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology Volume 37: Antibodies in Cell Biology*, Academic Press, Inc. New York; Stites & Ten (1991) *Basic and Clinical Immunology* 7th Edition. Immunoassays for the detection and/or quantification of a protein or polypeptide can take a wide variety of formats well known to those of skill in the art.

An antibody capable of binding to a protein or polypeptide, e.g., an antibody with a detectable label (either directly or indirectly labeled), corresponding to a protein or polypeptide described herein, e.g., E-cadherin, vimentin, pyruvate carboxylase, can be used to detect the protein or polypeptide. Antibodies can be polyclonal or monoclonal. An intact antibody, or a fragment thereof, e.g., Fab or F(ab')$_2$ can be used. The term "labeled", with regard to the probe or antibody, is intended to encompass direct labeling of the probe or antibody by coupling, i.e., physically linking a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The antibody can also be labeled, e.g., a radio-labeled, chromophore-labeled, fluorophore-labeled, or enzyme-labeled antibody. An antibody derivative, e.g., an antibody conjugated with a substrate or with the protein or ligand of a protein-ligand pair, e.g., biotin-streptavidin, or an antibody fragment, e.g., a single-chain antibody, an isolated antibody hypervariable domain, etc, which binds specifically with a protein described herein, e.g., E-cadherin, vimentin, pyruvate carboxylase, such as the protein encoded by the open reading frame corresponding to the gene transcript of a protein or polypeptide described herein, e.g., E-cadherin, vimentin, pyruvate carboxylase, or such a protein or polypeptide which has undergone all or a portion of its normal post-translational modification, is used.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

The expression level can be provided as a relative expression level. The relative expression level can be determined by comparing the absolute level of expression of the protein, to a reference standard. The reference standard can include the level of expression of the protein of interest in a genotypically or phenotypically defined sample. The reference standard can be the level of expression of the protein of interest, e.g., E-cadherin, vimentin, pyruvate carboxylase, in a cell genotypically or phenotypically characterized as an epithelial cell. An epithelial cell can be characterized by methods known in the art, e.g., as described in on any one of the following references: (Yauch et al., (2005) Clin Cancer Res 11:24; Savagner et al., (2010) Ann Oncol. 21(suppl 7): vii89; Thiery et al., (2002) Nature Reviews Cancer 2(6):442).

The expression level of a protein or polypeptide described herein, e.g., E-cadherin, vimentin, pyruvate carboxylase, can be measured at least at two time-points to determine if a change in the level of expression has occurred. For example, the level of expression can be measured pre- and post-treatment with a compound described herein, or at one or more time-points while treatment with a compound described herein is ongoing. If the expression level is found to be decreased, e.g., decreased expression of E-cadherin compared to a reference standard and/or increased expression of vimentin compared to a reference standard; the subject may be administered treatment with a compound described herein.

Kits

Also described herein are kits comprising a means to assay the level of gene expression of a gene described herein, e.g., E-cadherin, vimentin, pyruvate carboxylase. For example, the kit can include an agent capable of interacting with a gene expression product of a gene described herein, e.g., E-cadherin, vimentin, pyruvate carboxylase. The kit can include a plurality of agents capable of interacting with gene expression products of a plurality of genes described herein, e.g., E-cadherin, vimentin, pyruvate carboxylase. The agent can include, but is not limited to, an antibody, a plurality of antibodies, an oligonucleotide, or a plurality of oligonucleotides. The gene expression product can include, but is not limited to, a transcribed molecule, a RNA molecule, a polypeptide, a protein, genomic DNA, or cDNA.

The kit can further optionally include reagents for performing the assays described herein. For example, the kit can include buffers, solvents, stabilizers, preservatives, purification columns, detection reagents, and enzymes, which may be necessary for isolating nucleic acids from a patient sample, amplifying the samples, e.g., by qRT-PCR, and applying the samples to the agent described above; or for isolating proteins from a subject sample, and applying the samples to the agent described above; or reagents for directly applying the subject sample to the agent described above. A kit can also include positive and negative control samples, e.g., control nucleic acid samples (e.g., nucleic acid sample from a non-cancer subject, or a non-tumor tissue sample, or a subject who has not received treatment for cancer, or other test samples for testing at the same time as subject samples. A kit can also include instructional material, which may provide guidance for collecting and processing patient samples, applying the samples to the level of gene expression assay, and for interpreting assay results.

The components of the kit can be provided in any form, e.g., liquid, dried, semi-dried, or in lyophilized form, or in a form for storage in a frozen condition. Typically, the components of the kit are provided in a form that is sterile. When reagents are provided in a liquid solution, the liquid solution generally is an aqueous solution, e.g., a sterile aqueous solution. When reagents are provided in a dried form, reconstitution generally is accomplished by the addition of a suitable solvent. The solvent, e.g., sterile buffer, can optionally be provided in the kit.

The kit can include one or more containers for the kit components in a concentration suitable for use in the level of gene expression assays or with instructions for dilution for use in the assay. The kit can contain separate containers, dividers or compartments for the assay components, and the informational material. For example, the positive and negative control samples can be contained in a bottle or vial, the clinically compatible classifier can be sealed in a sterile plastic wrapping, and the informational material can be contained in a plastic sleeve or packet. The kit can include a plurality (e.g., a pack) of individual containers, each containing one or more unit forms (e.g., for use with one assay) of an agent. The containers of the kits can be air tight and/or waterproof. The container can be labeled for use.

The kit can include informational material for performing and interpreting the assay. The kit can also provide guidance as to where to report the results of the assay, e.g., to a treatment center or healthcare provider. The kit can include forms for reporting the results of a gene activity assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with an anti-cancer stem cell agent, depending on the results of the assay.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. The informational material of the kit can be contact information, e.g., a physical address, email address, website, or telephone number, where a user of the kit can obtain substantive information about the gene activity assay and/or its use in the methods described herein. The informational material can also be provided in any combination of formats.

A subject sample can be provided to an assay provider, e.g., a service provider (such as a third party facility) or a healthcare provider that evaluates the sample in an assay and provides a read out. For example, an assay provider can receive a sample from a subject, such as a tissue sample, or a plasma, blood or serum sample, and evaluate the sample using an assay described herein, and determines that the subject is a candidate to receive treatment with an inhibitor as described herein. The assay provider can inform a healthcare provider that the subject is a candidate for treatment with an inhibitor as described herein, and the candidate is administered the inhibitor as described herein. The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

EXAMPLES

Example A

In this example, the enzymatic activity of glutaminase is measured through a coupled endpoint assay. Glutamine and phosphate are supplied to GAC at a concentration equal to Km and $AC_{50}$, respectively, and GAC concentration is adjusted to give a linear reaction for 60 minutes. The glutamate produced is converted to 2-OG by a kinetic excess of glutamate dehydrogenase. This second step is configured for 2× Km for NAD, since excess NAD is inhibitory. However, a kinetic excess of the third coupling enzyme, diaphorase, recycles NAD from NADH to keep the NAD concentration constant during the timecourse of the assay. Diaphorase, also supplied in kinetic excess, oxidizes NADH produced by GDH back to NAD with the concomitant reduction of rezasurin to the highly fluorescent resorufin. Resorufin in measured after the assay is stopped with SDS by Ex544/Em590. A reduction in the signal indicates inhibition of some component of the coupled enzyme system. Prospective hits are counterscreened against GDH/diaphorase alone to remove hits to the coupling enzyme system in a second assay.

1. Materials

| | |
|---|---|
| BSA | Sigma #3294 (protease-free) |
| diaphorase | Worthington Enzyme LS004330. Resuspend at 10 mg/ml in ddH$_2$O and store at −80 C. |
| EDTA | Sigma E6758 or equivalent |
| glutamate dehydrogenase | Sigma G7882 |
| glutamine | Sigma G3126 or equivalent |
| HEPES (pH 8.5) | Sigma H3375 or equivalent, to pH 8.5 with NaOH |
| NaCl | Sigma S7653 or equivalent |
| NAD | Sigma N7004; note: power will decompose to inhibitor if stored outside dessicator. Purchase small lots and prepare stocks in solution and store at −80 C. |
| resazurin | Sigma 199303 |
| sodium dodecyl sulfate | Sigma L4390 or equivalent |
| sodium phosphate (pH 8.5) | Prepare from Sigma monobasic (S8282) and dibasic (S7907) solutions or equivalents; 1M stock final concentration prepared from 1M stocks of each of the dibasic and monobasic solutions. |

2. Buffers
2× Buffer (300 mM NaCl, 100 mM HEPES pH 8.5, 0.1% BSA, 0.5 mM EDTA, 100 mM sodium phosphate pH 8.5)
5× Substrate Mix (1× Buffer final concentration, with 13 mM glutamine, 100 µM resazurin, 50 µg/ml diaphorase)
1.2× Enzyme Mix (1× Buffer final concentration, with 0.875 µg/ml GAC, 1.56 mM NAD, 6.25 units/ml GDH)
Stop Mix (6% SDS in ddH$_2$O)
Reaction Procedure
1. Add 1 µl compound in 100% DMSO
2. Add 40 µl of Enzyme Mix and incubate for 60 minute at room temperature
3. Add 10 µl of Substrate Mix to start reaction
4. Stop reaction with 25 µl of 6% SDS and read Ex544 Em 590

Example B

In this example, the potential for a compound to inhibit the coupled enzyme assay system of the glutaminase HTS method, which comprises glutamate dehydrogenase and diaphorase, is tested through a coupled endpoint assay. Glutamate is supplied at Km to GDH, which then performs a reductive deamidation to produce 2OG. NAD is supplied at 2× Km to the system, and its conversion to NADH is monitored by the activity of diaphorase. Diaphorase, supplied in large kinetic excess to GDH, converts NADH back to NAD to keep NAD levels constant in the reaction while at the same time reducing rezasurin to the highly fluorescent resorufin. Resorufin in measured after the assay is stopped with SDS by Ex544/Em590. A reduction in the signal indicates inhibition of some component of the coupled enzyme system.

3. Materials

| | |
|---|---|
| BSA | Sigma #3294 (protease-free) |
| diaphorase | Worthington Enzyme LS004330. Resuspend at 10 mg/ml in ddH$_2$O and store at −80 C. |
| EDTA | Sigma E6758 or equivalent |
| glutamate dehydrogenase | Sigma G7882 |
| glutamic acid | Sigma G1251 or equivalent |
| HEPES (pH 8.5) | Sigma H3375 or equivalent, to pH 8.5 with NaOH |
| NaCl | Sigma S7653 or equivalent |
| NAD | Sigma N7004; note: powder will decompose to inhibitor if stored outside dessicator. Purchase small lots and prepare stocks in solution and store at −80 C. |
| resazurin | Sigma 199303 |
| sodium dodecyl sulfate | Sigma L4390 or equivalent |

4. Buffers
2× Buffer (300 mM NaCl, 100 mM HEPES pH 8.5, 0.1% BSA, 0.5 mM EDTA, 100 mM phosphate pH 8.5)
2× Substrate Mix (1× Buffer final concentration, 40 µM resazurin, 1.8 mM glutamate, 20 µg/ml diaphorase)
10× NAD Mix (1× Buffer final concentration, 12.5 mM NAD)
2.5× Enzyme Mix (1× Buffer final concentration, GDH enzyme as determined for appropriate linearity; for example 0.05 units/ml as described here to get 0.02 units/ml final concentration)
Reaction Procedure
1. Add 1 µl compound in 100% DMSO
2. Add 20 µl of Enzyme Mix and incubate for 60 minutes at room temperature
3. Add 5 µl of NAD Mix
4. Add 25 µl of Substrate Mix to start reaction 5. Stop reaction with 25 μl of 6% SDS and read Ex544 Em 590

Example 1

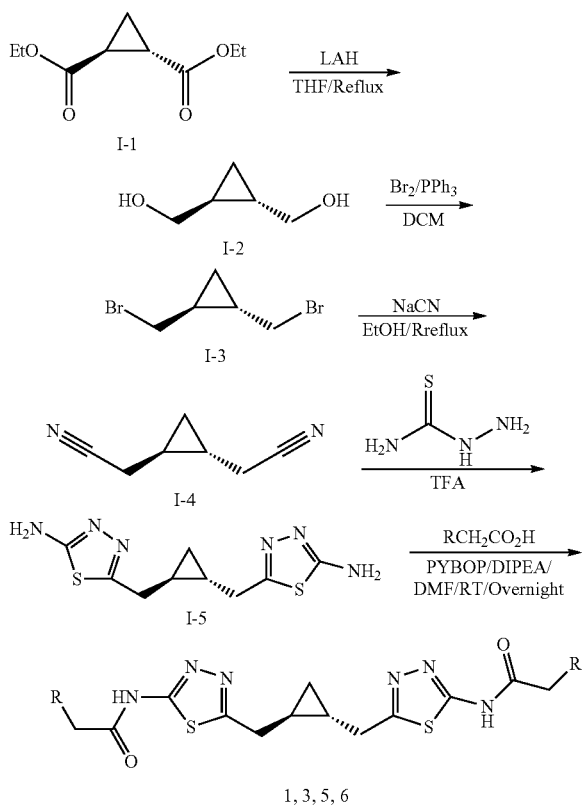

trans-cyclopropane-1,2-diyldimethanol (I-2)

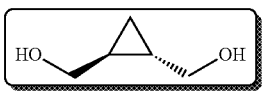

Compound I-2 was prepared by following a reported literature procedure (*Org. Synth.* 2008, 85, 15). To a suspension of LiAlH₄ (1.5 equivalents) in THF was added (1S,2S)-diethyl cyclopropane-1,2-dicarboxylate (1 equivalent) slowly at 0° C. The reaction mixture was then warmed to room temperature and refluxed for 2 h. After cooling, the heterogeneous mixture was stirred at room temperature for 18 h. The reaction was quenched by careful addition of saturated NH₄Cl solution followed by EtOAc. Stirring the reaction mass for next 5 h resulted in a precipitation of a light yellow solid which was filtered through a pad of celite. The celite layer was further washed with EtOAc. The combined organic layers were evaporated to obtain a pasty mass which was purified through column chromatography (80% EtOAC/hexane as eluent) to furnish the title compound I-2.

trans-1,2-bis(bromomethyl)cyclopropane (I-3)

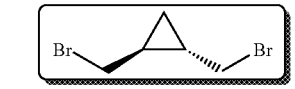

Compound I-3 was prepared by following a reported procedure (*Tetrahedron Lett.* 1997, 53, 10459). To a solution of triphenylphosphine (2.1 equivalents) in DCM was added bromine (2.1 equivalents) slowly at 0° C. The reaction mixture was stirred for 0.25 h before adding trans-cyclopropane-1,2-diyldimethanol I-2 (1 equivalent) (as a solution in THF). It was then warmed to room temperature and stirred for an hour. In workup, all the volatiles were evaporated and the crude mass was purified using column chromatography (30% EtOAc/hexane) to afford the title compound I-3.

trans-2,2'-(cyclopropane-1,2-diyl)diacetonitrile (I-4)

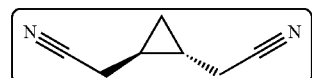

Compound I-4 was prepared by following a reported procedure (*Tetrahedron Lett.* 1997, 53, 10459). trans-1,2-bis(bromomethyl)cyclopropane I-3 (1 equivalent) was dissolved in a mixture of EtOH/water (2/1). Following the addition of NaCN (4 equivalents) the reaction mixture was refluxed overnight. All the volatile materials were evaporated to obtain a pasty mass which was dissolved in water and extracted with ether. The aqueous layer was further extracted with ether and the combined organic layers were evaporated to obtain the title compound I-4. This material was used for the next step without any purification.

trans-5,5'-(-cyclopropane-1,2-diylbis(methylene))bis (1,3,4-thiadiazol-2-amine) (I-5)

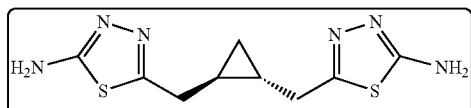

trans-2,2'-(cyclopropane-1,2-diyl)diacetonitrile I-4 (1 equivalent) was dissolved in TFA (2.0 mL) and thiosemicarbazide (2 equivalents) was added to it. The reaction mixture was refluxed for 3 h at 100° C. before quenching by careful addition of a saturated solution of NaHCO₃ at 0° C. to bring the pH around 8~9. The solid precipitated was filtered and further purified to obtain trans-5,5'-(-cyclopropane1,2-diylbis(methylene))bis(1,3,4thiadiazol2-amine) I-5.

General Procedure for the Synthesis of Compounds 1, 3, 5, and 6:

To a suspension of trans-5,5'-(-cyclopropane-1,2-diylbis(methylene))bis(1,3,4-thiadiazol-2-amine (I-5) (1 equivalent) and the appropriate acid (3 equivalents) in DMF was added PYBOP (3 equivalents) and DIPEA (6 equivalents) and stirred for overnight. Water was then added to the reaction mixture and the resulting material was filtered and purified to obtain the desired compound.

N,N'-(5,5'-(trans-cyclopropane-1,2-diylbis(methylene))bis(1,3,4-thiadiazole-5,2-diyl))bis(2-phenyl acetamide) (1)

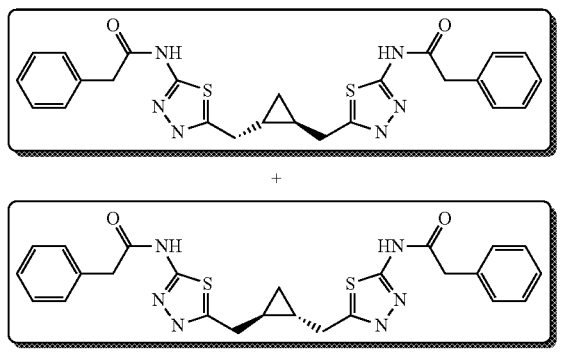

$^1$H NMR (400 MHz, DMSO-d$_6$): 0.5-0.7 (m, 2H), 1.0-1.2 (m, 2H), 2.8-3.0 (m, 4H), 3.7-3.9 (s, 4H), 7.2 (m, 10H), 12.60 (brs, 2H). Mass (M$^+$+1): 505.10.

N,N'-(5,5'-(trans-cyclopropane-1,2-diylbis(methylene))bis(1,3,4-thiadiazole-5,2-diyl))bis(2-(pyridin-2-yl)acetamide) (3)

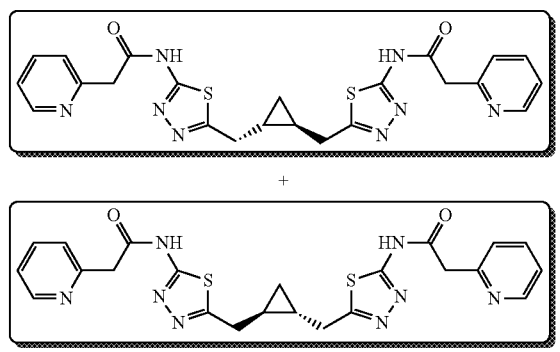

$^1$H NMR (400 MHz, DMSO-d$_6$) δ: 0.62 (m, 2H), 1.10 (m, 2H), 2.82-3.02 (m, 4H), 4.0 (s, 4H), 7.30 (t, 2H), 7.40 (d, 2H), 7.80 (t, 2H), 8.50 (d, 2H), 12.68 (brs, 2H); Mass (M$^+$+1): 507.05.

N,N'-(5,5'-(trans-cyclopropane-1,2-diylbis(methylene))bis(1,3,4-thiadiazole-5,2-diyl))bis(2-(pyridin-3-yl)acetamide) (5):

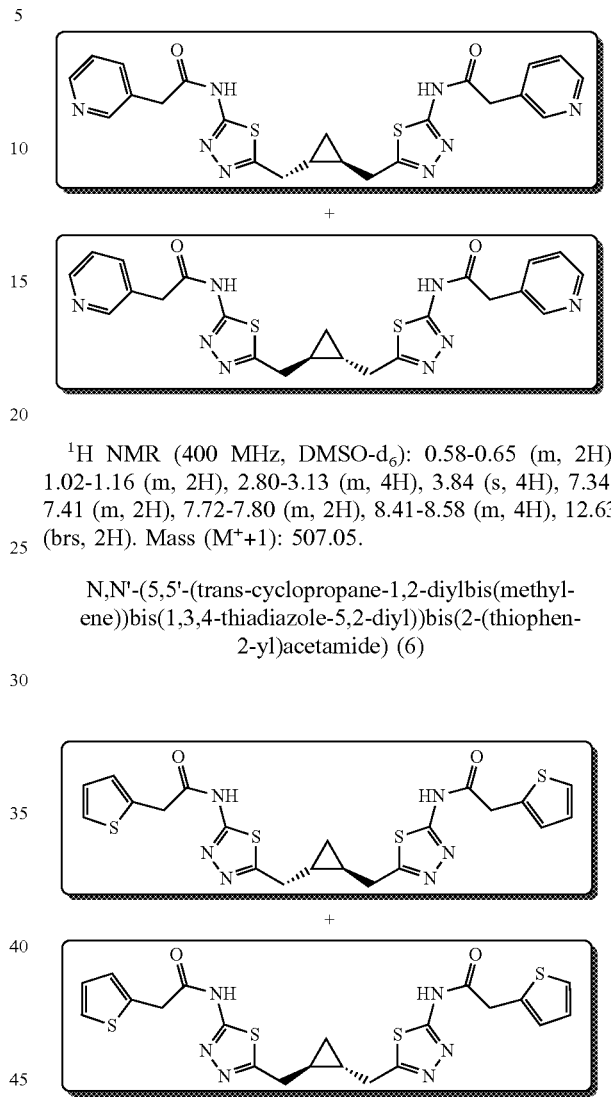

$^1$H NMR (400 MHz, DMSO-d$_6$): 0.58-0.65 (m, 2H), 1.02-1.16 (m, 2H), 2.80-3.13 (m, 4H), 3.84 (s, 4H), 7.34-7.41 (m, 2H), 7.72-7.80 (m, 2H), 8.41-8.58 (m, 4H), 12.63 (brs, 2H). Mass (M$^+$+1): 507.05.

N,N'-(5,5'-(trans-cyclopropane-1,2-diylbis(methylene))bis(1,3,4-thiadiazole-5,2-diyl))bis(2-(thiophen-2-yl)acetamide) (6)

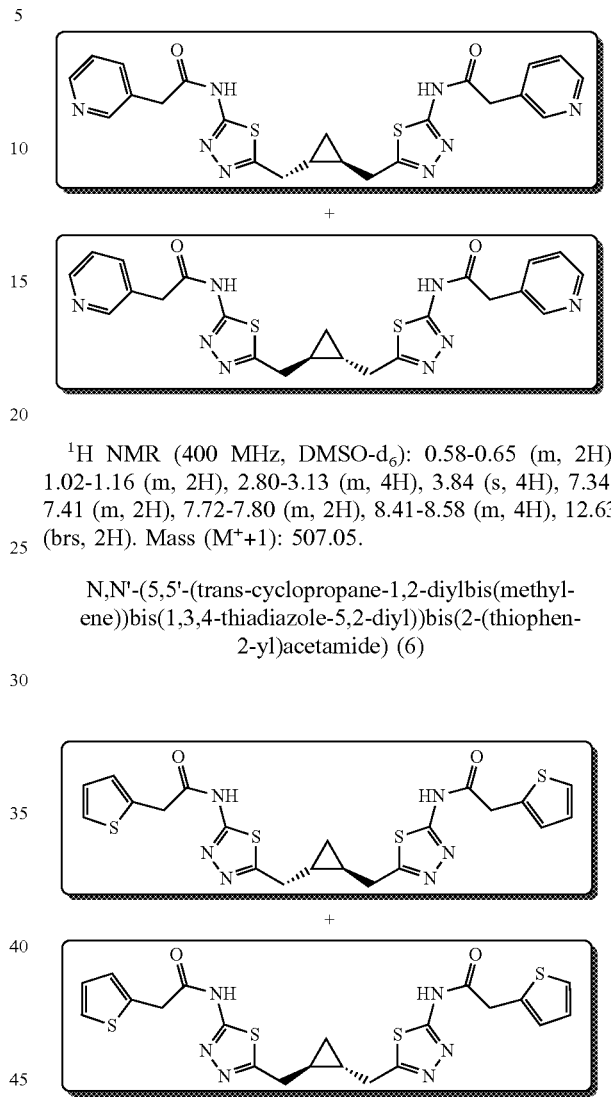

$^1$H NMR (400 MHz, DMSO-d$_6$): 0.58-0.64 (m, 2H), 1.05-1.19 (m, 2H), 2.82-3.04 (m, 4H), 4.03 (s, 4H), 6.93-7.03 (m, 4H), 7.42 (s, 2H), 12.62 (brs, 2H). Mass (M$^+$+1): 516.90.

Example 2

Scheme 12

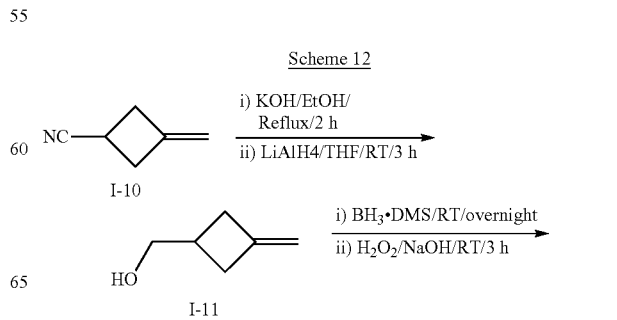

Cyclobutane-1,3-diyldimethanol (I-12)

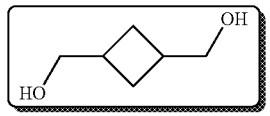

(3-Methylenecyclobutyl)methanol I-11 (1 equivalent) was dissolved in anhydrous THF and BH$_3$.DMS (1 equivalent) was added drop wise at 0° C. Following the addition, the reaction mixture was warmed to room temperature and stirred overnight. The reaction was quenched by careful addition of NaOH (3M solution in water) at 0° C. followed by the addition of H$_2$O$_2$. Stirring was continued for 3 h at room temperature before diluting with water and extracting the diol with ethyl acetate. The crude material was taken directly for the next step without any purification.

Cyclobutane-1,3-diylbis(methylene)bis(4-methylbenzenesulfonate) (I-13)

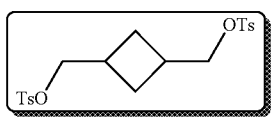

A solution of cyclobutane-1,3-diyldimethanol I-12 (1 equivalent) and TEA (3 equivalents) in dichloromethane was cooled to 0° C. and tosylchloride (2 equivalents) was added in portion. The reaction mixture was left for 12 h. During workup, the reaction mixture was diluted with dichloromethane and the organic layer was washed with water. The organic layer was concentrated to afford the desired product I-13.

2,2'-(Cyclobutane-1,3-diyl)diacetonitrile (I-14)

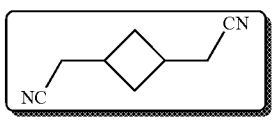

To a solution of cyclobutane-1,3-diylbis(methylene)bis(4-methylbenzenesulfonate) I-13 (1 equivalent) in DMF was added NaCN (6 equivalents) and was refluxed for 12 h. During workup, the reaction mixture was diluted with water and the desired compound was extracted with ethyl acetate. Evaporation of the organic solvent furnished I-14.

5,5'-(cyclobutane-1,3-diylbis(methylene))bis(1,3,4-thiadiazol-2-amine) (I-15)

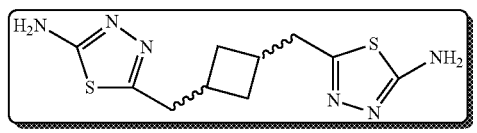

(3-methylenecyclobutyl)methanol (I-11)

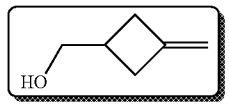

Compound I-10 was bought from a commercial source and the hydrolysis of I-10 was carried out following a literature procedure (*J. Am. Chem. Soc.* 1958, 80, 5507). To a solution of 3-methylenecyclobutanecarbonitrile I-10 (1 equivalent) in aqueous EtOH (50%) was added KOH (4 equivalents) and the homogeneous mixture was heated to reflux for 2 h. Upon cooling, all the volatile materials were evaporated and the solid was suspended in water. The pH of the solution was adjusted to 2 by the addition of 1N HCl and the desired compound was extracted with ethyl acetate. The combined organic layers were washed with brine, dried over anhydrous MgSO$_4$ and evaporated to obtain 3-methylenecyclobutanecarboxylic acid in quantitative yield. This material was carried forward directly for the next step.

To a suspension of LiAlH$_4$ (1.5 equivalents) in THF was added 3-methylenecyclobutanecarboxylic acid (in THF) (1 equivalent) slowly at 0° C. The cooling bath was removed and the reaction mixture was warmed to room temperature and stirred for 3 h. Following a Fischer workup, the desired compound I-11 was obtained. This material was used for the next step without any purification.

To a solution of 2,2'-(Cyclobutane-1,3-diyl)diacetonitrile I-14 (1 equivalent) in TFA was added thiosemicarbazide (2 equivalents) and the solution was stirred at 100° C. for 3 h. The reaction was cooled to room temperature and quenched with saturated NaHCO₃ solution. The material was filtered and washed with water, ethyl acetate and diethyl ether sequentially. The diamine I-15 was obtained.

General Procedure for the Synthesis of Compounds 7 and 8:

To a solution of the corresponding acid (2 equivalents) and DIPEA (6 equivalents) in DMF (NMP for pyridyl derivative) was added PYBOP (3 equivalents) at 0° C. and was stirred for 10 min at room temperature. Compound I-15 was added to the reaction mixture and stirring was continued overnight. Water was then added and the desired product was extracted with ethyl acetate. Organic layer was dried over anhydrous sodium sulfate and evaporated under reduced pressure. The crude product obtained was purified by standard methods to obtain the pure products.

N,N'-(5,5'-(cyclobutane-1,3-diylbis(methylene))bis(1,3,4-thiadiazole-5,2-diyl))bis(2-phenylacetamide) (8)

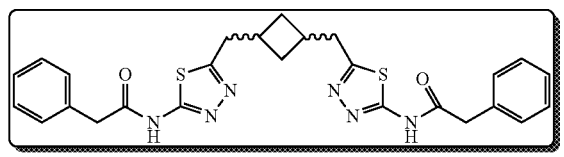

¹H NMR (400 MHz, DMSO-d₆) δ: 0.9-1.2 (m, 1H), 1.42-1.60 (m, 1H), 1.84-1.95 (m, 2H), 2.10-2.22 (m, 1H), 2.6-2.7 (m, 1H), 3.0-3.16 (m, 4H), 3.80 (s, 4H), 7.10-7.40 (m, 10H), 12.62 (brs, 2H); Mass (M⁺+1): 519.19, 541.25 (M⁺+23).

N,N'-(5,5'-(cyclobutane-1,3-diylbis(methylene))bis(1,3,4-thiadiazole-5,2-diyl))bis(2-(pyridin-2-yl) acetamide) (7)

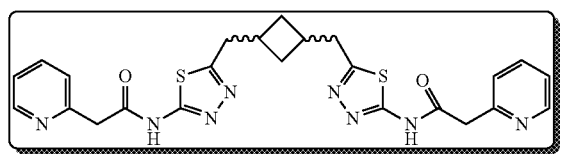

¹H NMR (400 MHz, DMSO-d₆) δ: 1.19-1.22 (m, 1H), 1.45-1.61 (m, 1H), 1.82-1.92 (m, 1H), 2.15-2.05 (m, 1H), 3.01-3.16 (m, 4H), 4.01 (s, 4H), 7.22-7.42 (m, 4H), 7.72-7.80 (m, 2H), 8.44 (s, 2H), 12.6 (brs, 2H). Mass (M⁺+23): 543.15.

Example 3

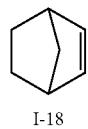

KMnO₄/CuSO₄
————————→
H₂O/t-BuOH/DCM/
RT/12 h

I-18

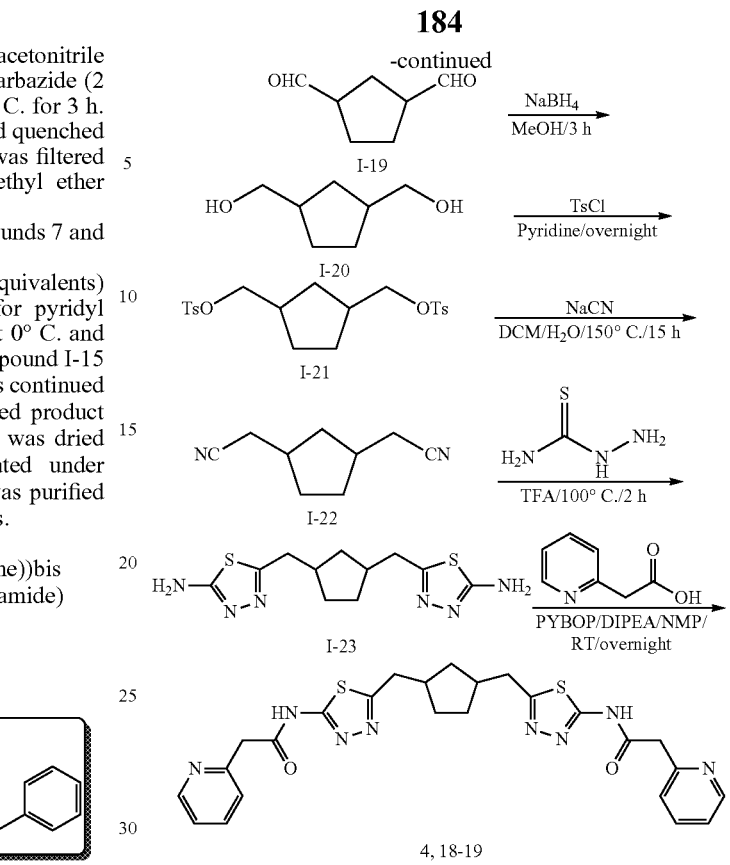

Cyclopentane-1,3-dicarbaldehyde (I-19)

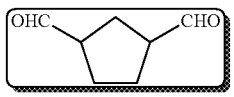

KMnO₄ (3.2 equivalents) and CuSO₄·5H₂O (2 equivalents) were taken in dichloromethane and distilled water was added to this suspension. Norbornene I-18 (1 equivalent) was dissolved in dichloromethane and added slowly to the oxidant mixture followed by t-butanol. After 3 h the reaction mixture was filtered through Celite and washed with saturated brine. The brine was then re-washed with dichloromethane. The combined organic layers were dried over sodium sulfate, and the solvent was removed by rotary evaporation under ambient temperature to afford the desired product I-19.

Cyclopentane-1,3-diyldimethanol (I-20)

To 1,3-cyclopentanedicarbaldehyde I-19 (1 equivalent) taken in a flask was added deoxygenated methanol. The reaction mixture was cooled to 0° C. and NaBH₄ (2 equivalents) was added in small aliquots in order to avoid a raise in the reaction temperature above 10° C. The reaction mixture was left to warm to room temperature and stirred for an additional 3 h under nitrogen atmosphere. Distilled water was added to the reaction mixture to quench any remaining NaBH$_4$ and then rotary evaporated to remove methanol from the solution. The remaining mixture was extracted with dichloromethane (5 times) and the combined organic fractions were dried over anhydrous sodium sulfate and evaporated to dryness to afford the title compound I-20.

Cyclopentane-1,3-diylbis(methylene)bis(4-methyl-benzenesulfonate) (I-21)

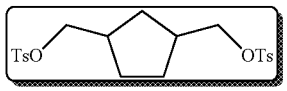

Cyclopentane-1,3-diyldimethanol I-20 (1 equivalent) taken in pyridine was cooled to 0° C. and p-toluene sulfonyl chloride (3 equivalents) was added portion wise and stirred at RT overnight. The progress of the reaction was monitored by TLC. After completion of the reaction, pyridine was distilled off. Residue was diluted with diethyl ether, washed with 1N HCl, NaHCO$_3$ solution, brine, dried over anhydrous sodium sulfate and evaporated under reduced pressure. The crude product was purified by a standard method to afford the desired product I-21.

2,2'-(cyclopentane-1,3-diyl)diacetonitrile (I-22)

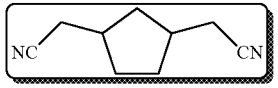

Cyclopentane-1,3-diylbis(methylene)bis(4-methylbenzenesulfonate) I-21 (1 equivalent) was taken in DMF:H$_2$O mixture (3:1) and sodium cyanide (6 equivalents) was added and stirred at 150° C. for 15 h. The progress of the reaction was monitored by TLC. After completion of the reaction, reaction mixture was quenched with water, extracted with diethyl ether. The organic layer was washed with brine, dried over anhydrous sodium sulfate and evaporated under reduced pressure. The crude product was purified to afford the desired product I-22.

5,5'-(cyclopentane-1,3-diylbis(methylene))bis(1,3,4-thiadiazol-2-amine) (I-23)

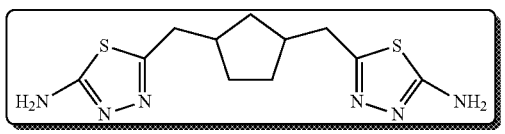

The title compound was synthesized from 2,2'-(cyclopentane-1,3-diyl)diacetonitrile I-22 by following the procedure described for compounds I-15.

N,N'-(5,5'-(cyclopentane-1,3-diylbis(methylene))bis(1,3,4-thiadiazole-5,2-diyl))bis(2-(pyridin-2-yl) acetamide) (4)

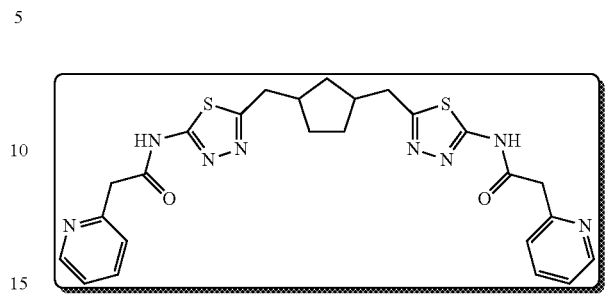

The title compound was synthesized from 5,5'-(cyclopentane-1,3-diylbis-(methylene))bis(1,3,4thiadiazol-2-amine) I-15 by following the general procedure as described for compound 7 and 8.

$^1$H NMR (400 MHz, DMSO-d$_6$) δ: 1.35-1.40 (m, 2H), 1.70-1.80 (m, 2H), 1.90-1.95 (m, 1H), 2.20-2.24 (m, 2H), 2.98 (d, 4H), 4.00 (s, 4H), 7.26 (t, 2H), 7.39 (d, 2H), 7.78 (t, 2H), 8.50 (d, 2H), 12.70 (brs, 2H); Mass (M$^+$+1): 535.10.

Example 4

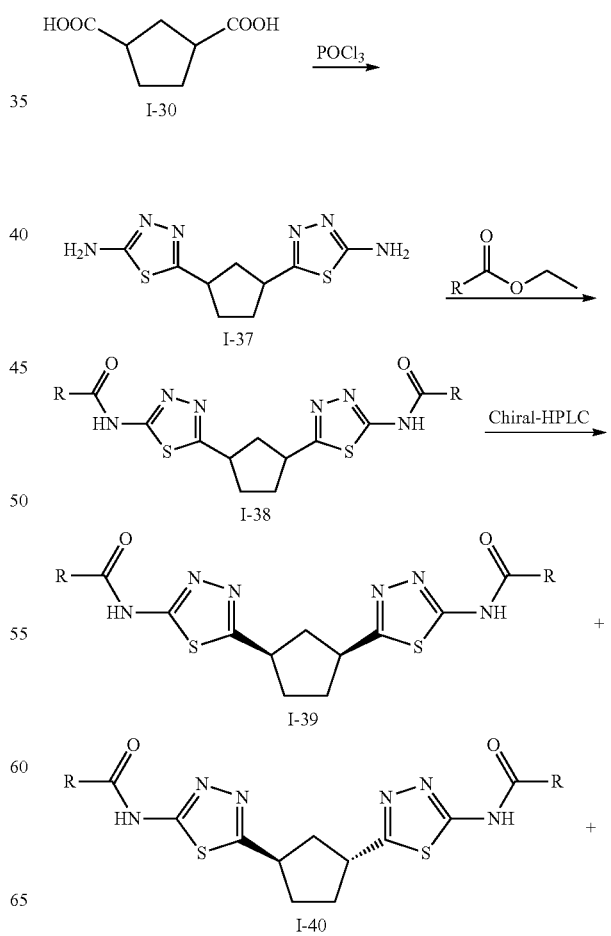

-continued

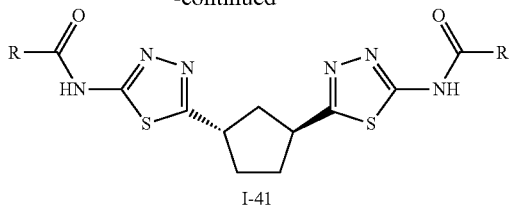

N,N'-(5,5'-((1R,3R)-cyclopentane-1,3-diyl)bis(1,3,4-thiadiazole-5,2-diyl))bis(2-phenylacetamide) (19)

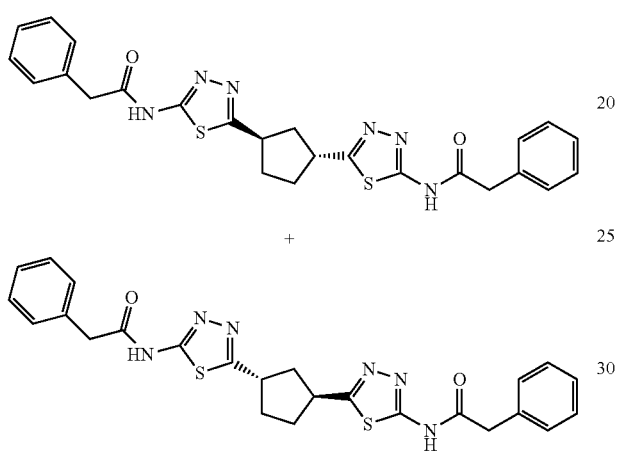

¹H NMR (500 MHz, DMSO-d₆) δ: 1.92-1.95 (m, 2H), 2.26-2.29 (m, 2H), 2.34-2.37 (t, 2H), 3.70 (s, 2H), 3.72-3.76 (m, 4H), 7.24-7.34 (m, 10H), 11.8 (s, 2H); Mass (M⁺+1): 505.7.

N,N'-(5,5'-((1R,3S)-cyclopentane-1,3-diyl)bis(1,3,4-thiadiazole-5,2-diyl))bis(2-phenylacetamide) (18)

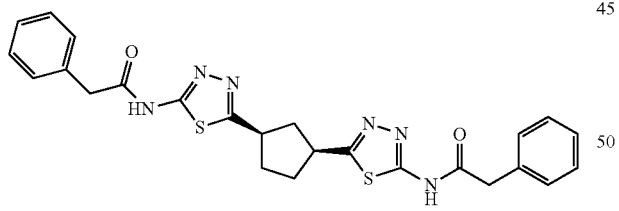

¹H NMR (500 MHz, DMSO-d₆) δ: 1.94-1.97 (m, 2H), 2.08-2.09 (t, 1H), 2.19-2.23 (m, 2H), 2.61-2.64 (t, 1H), 3.63-3.66 (m, 2H), 3.75 (s, 4H), 7.23-7.26 (m, 2H), 7.31-7.34 (t, 8H), 11.7 (s, 2H); Mass (M⁺+1): 505.7.

Example 5

N,N'-(5,5'-((1R,4R)-cyclohexane-1,4-diylbis(methylene)bis(1,3,4-thiadiazole-5,2-diyl))bis(2-(pyridin-2-yl) acetamide) (2)

The title compound was synthesized from 5,5'-((1R,4R)-cyclohexane1,4-diylbis(methylene))bis(1,3,4thiadiazol-2-amine) (trans) by following the general procedure as described for compound 7 and 8.

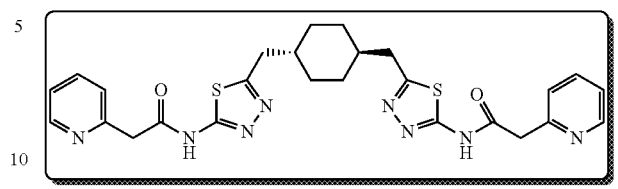

¹H NMR (400 MHz, DMSO-d₆) δ: 1.0 (t, 2H), 1.60-1.80 (m, 8H), 2.85 (d, 4H), 4.0 (s, 4H), 7.30 (t, 2H), 7.40 (d, 2H), 7.80 (t, 2H), 8.50 (d, 2H), 12.65 (brs, 2H); Mass (M⁺+1) 549.10.

Example 6

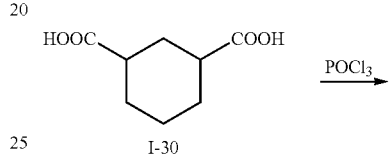

I-30

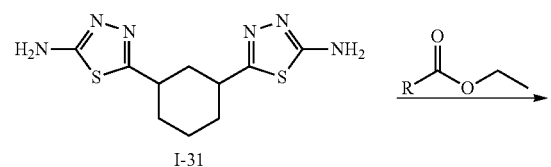

I-31

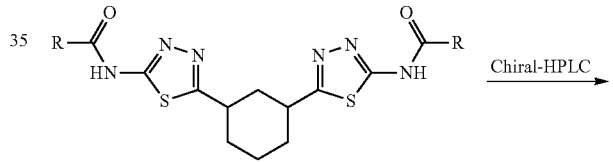

I-32

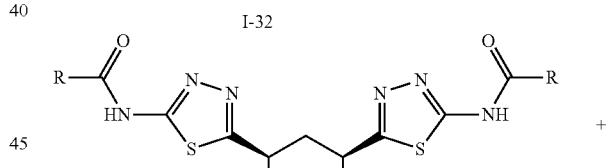

I-33

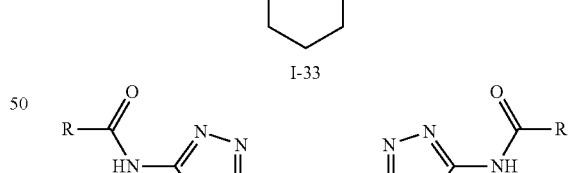

I-34

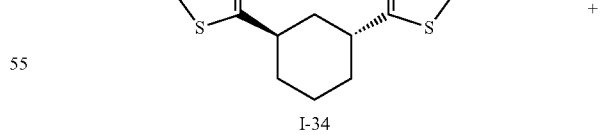

I-35

5,5'-(cyclohexane-1,3-diyl)bis(1,3,4-thiadiazol-2-amine) (I-31)

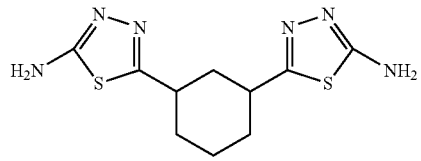 [SMILES: Nc1nnc(C2CCCC(c3nnc(N)s3)C2)s1]

A mixture of cyclohexane-1,3-dicarboxylic acid (1.0 equivalent) and thiosemicarbazide (2.0 equivalents) were taken in POCl₃ (6.0 equivalents) and stirred at 80° C. for 3 h. The reaction mixture was cooled to room temperature and poured on to ice. The resulting mixture was filtered and then brought to pH 8 using KOH. The resulting material that was formed washed with water and dried to afford the desired product (31). This material was used as such for the next step.

General Procedure for the Synthesis of Compounds (I-33 to I-35):

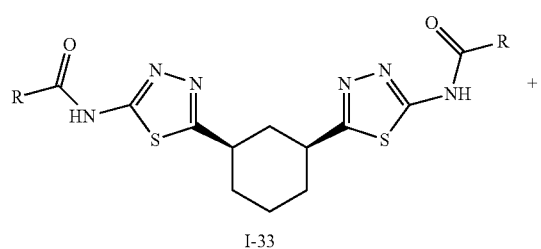

I-33

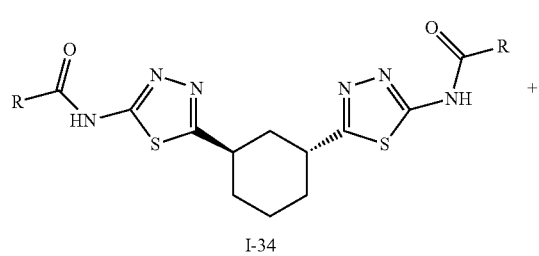

I-34

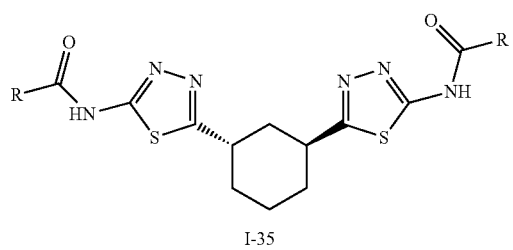

I-35

A mixture of compound (I-31) (1 equivalent), the corresponding ester (2.5 equivalents), t-BuOK (3.0 equivalents) in DMF was stirred at 120-140° C. for 30-60 min in a microwave oven. The resulting mixture was purified by standard methods to afford the desired products.

N,N'-(5,5'-((1S,3S)-cyclohexane-1,3-diyl)bis(1,3,4-thiadiazole-5,2-diyl))bis(2-(1H-indol-3-yl)acetamide (22)

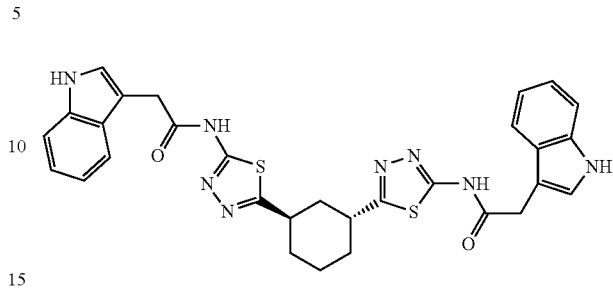

+

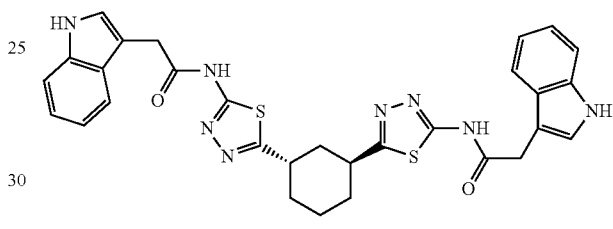

¹H NMR (500 MHz, DMSO-d₆) δ: 1.58 (s, 2H), 1.60 (m, 4H), 2.27 (s, 2H), 3.44 (s, 2H), 3.88 (s, 4H), 6.97-7.00 (t, 4H), 7.28-7.36 (m, 4H), 7.56-7.57 (d, 2H), 10.96 (s, 2H); Mass (M⁺+H): 596.7.

N,N'-(5,5'-((1S,3R)-cyclohexane-1,3-diyl)bis(1,3,4-thiadiazole-5,2-diyl))bis(2-(1H-indol-3-yl)acetamide) (23)

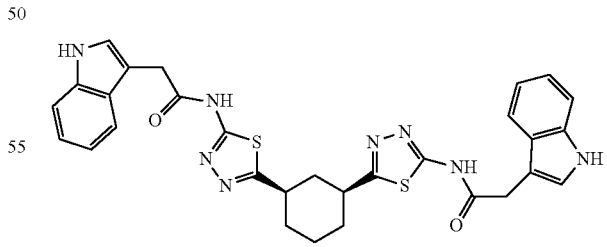

¹H NMR (500 MHz, DMSO-d₆) δ: 1.49-1.55 (s, 3H), 1.75-1.77 (m, 1H), 1.88 (m, 1H), 2.05-2.07 (m, 2H), 2.28-2.41 (d, 1H), 3.23-3.27 (t, 2H), 3.88 (s, 4H), 6.97-7.00 (t, 4H), 7.28-7.36 (m, 4H), 7.56-7.57 (d, 2H), 10.95 (s, 2H), 12.53 (s, 2H); Mass (M⁺+H): 596.7.

191

N,N'-(5,5'-((1S,3S)-cyclohexane-1,3-diyl)bis(1,3,4-thiadiazole-5,2-diyl))bis(2-(1H-indol-4-yl)acetamide) (24)

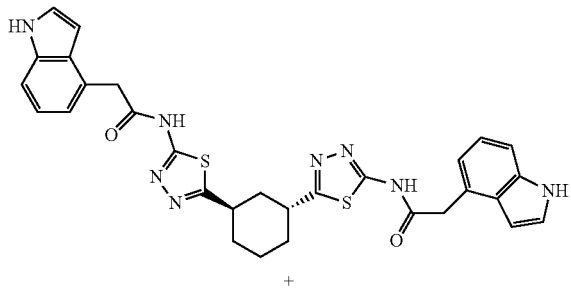

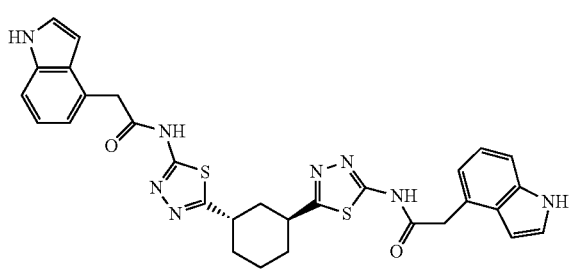

¹H NMR (500 MHz, DMSO-d₆) δ: 1.01 (s, 2H), 1.57-1.60 (s, 4H), 2.2 (S, 2H), 3.45 (S, 2H), 4.01 (s, 4H), 6.55 (s, 2H), 6.94-6.96 (d, 2H), 7.02-7.05 (d, 2H), 7.28-7.33 (m, 4H), 11.11 (s, 2H); Mass (M⁺+H): 596.7.

N,N'-(5,5'-((1S,3R)-cyclohexane-1,3-diyl)bis(1,3,4-thiadiazole-5,2-diyl))bis(2-(1H-indol-4-yl)acetamide) (25)

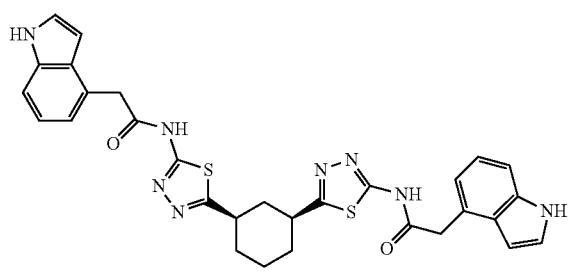 [SMILES: O=C(Cc1cccc2[nH]ccc12)Nc1nnc([C@@H]2CCC[C@H](c3nnc(NC(=O)Cc4cccc5[nH]ccc45)s3)C2)s1]

¹H NMR (500 MHz, DMSO-d₆) δ: 1.49-54 (m, 3H), 1.74-1.76 (s, 2H), 1.87-1.90 (m, 3H), 2.37-2.45 (m, 2H), 3.99 (s, 4H), 6.54 (s, 2H), 6.94-6.96 (d, 2H), 7.03-7.04 (d, 2H), 7.2-7.31 (m, 4H), 11.11 (s, 2H); Mass (M⁺+H): 597.3.

192

N,N'-(5,5'-((1S,3S)-cyclohexane-1,3-diyl)bis(1,3,4-thiadiazole-5,2-diyl))bis(2-(pyrimidin-2-yl)acetamide) (27)

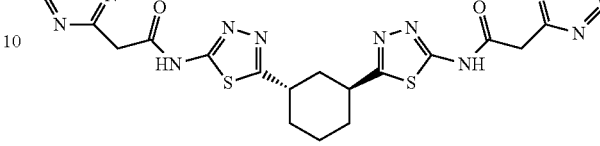

¹H NMR (500 MHz, DMSO-d₆) δ: 1.61-1.63 (m, 2H), 1.83-1.92 (d, 4H), 2.29 (s, 2H), 3.46 (s, 2H), 4.11 (s, 4H), 7.40-7.42 (t, 2H), 8.75-8.77 (d, 4H), 12.02 (s, 2H); Mass (M⁺+H): 522.8.

N,N'-(5,5'-((1S,3S)-cyclohexane-1,3-diyl)bis(1,3,4-thiadiazole-5,2-diyl))bis(2-(pyridin-3-yl)acetamide) (28)

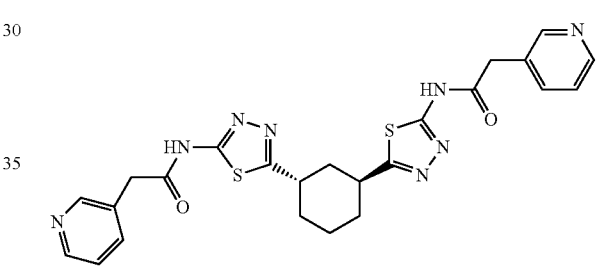

¹H NMR (500 MHz, DMSO-d₆) δ: 1.59-1.61 (m, 2H), 1.81-1.94 (d, 4H), 2.26 (s, 2H), 3.44 (s, 2H), 3.83 (s, 4H), 7.34-7.37 (m, 2H), 7.72-7.74 (d, 2H), 8.46-8.51 (d, 4H), 12.75 (s, 2H); Mass (M⁺+H): 521.3.

N,N'-(5,5'-((1S,3S)-cyclohexane-1,3-diyl)bis(1,3,4-thiadiazole-5,2-diyl))bis(2-(pyridin-4-yl)acetamide) (29)

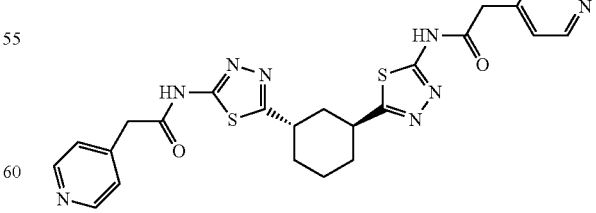

¹H NMR (500 MHz, DMSO-d₆) δ: 1.59-1.62 (m, 2H), 1.82-1.93 (d, 4H), 2.27 (s, 2H), 3.45 (s, 2H), 3.85 (s, 4H), 7.33-7.34 (d, 4H), 8.51-8.52 (d, 4H), 12.49 (s, 2H); Mass (M⁺+H): 521.2.

193

N,N'-(5,5'-((1S,3S)-cyclohexane-1,3-diyl)bis(1,3,4-thiadiazole-5,2-diyl))bis(2-(3-methylisoxazol-5-yl)acetamide) (30)

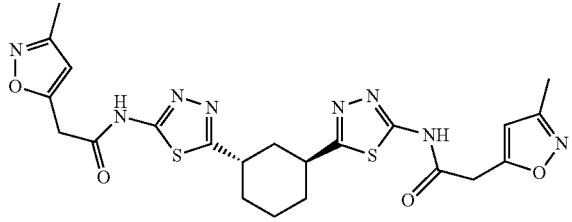 [SMILES: Cc1cc(CC(=O)Nc2nnc([C@H]3CCC[C@H](c4nnc(NC(=O)Cc5cc(C)no5)s4)C3)s2)on1]

¹H NMR (500 MHz, DMSO-d$_6$) δ: 1.61-1.64 (t, 2H), 1.83-1.97 (m, 4H), 2.21 (s, 6H), 2.30-2.32 (s, 2H), 3.49-3.51 (t, 2H), 4.07 (s, 4H), 6.30 (s, 2H), 12.82 (s, 2H); Mass (M⁺+H): 529.2.

N,N'-(5,5'-((1S,3S)-cyclohexane-1,3-diyl)bis(1,3,4-thiadiazole-5,2-diyl))bis(2-(4-(dimethylamino)phenyl)acetamide) (31)

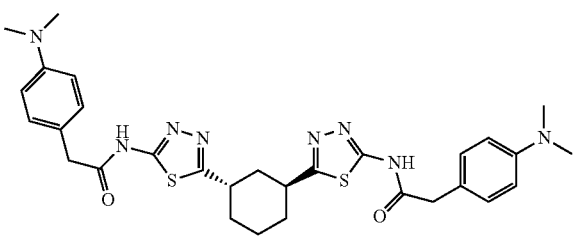

¹H NMR (500 MHz, DMSO-d$_6$) δ: 1.59 (s, 2H), 1.80-1.84 (m, 4H), 2.27-2.29 (t, 2H), 2.85 (s, 12H), 3.45-3.47 (t, 2H), 3.63 (4H), 6.67-6.69 (d, 2H), 7.13-7.14 (d, 2H), 12.55 (s, 2H); Mass (M⁺+H): 605.3.

N,N'-(5,5'-((1R,3S)-cyclohexane-1,3-diyl)bis(1,3,4-thiadiazole-5,2-diyl))bis(2-phenylacetamide) (10)

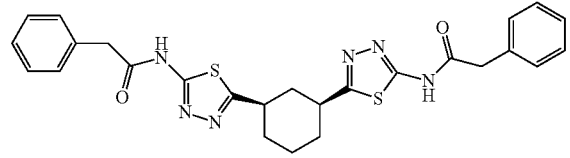 [SMILES: O=C(Cc1ccccc1)Nc1nnc([C@@H]2CCC[C@H](c3nnc(NC(=O)Cc4ccccc4)s3)C2)s1]

¹H NMR (500 MHz, DMSO-d$_6$) δ: 1.16-2.04 (m, 2H), 2.32-2.37 (d, 1H), 3.15-3.33 (d, 2H), 3.66 (s, 4H), 7.21-7.30 (m, 10H); Mass (M⁺+1): 519.7.

194

N,N'-(5,5'-((1S,3S)-cyclohexane-1,3-diyl)bis(1,3,4-thiadiazole-5,2-diyl))bis(2-phenylacetamide) (11)

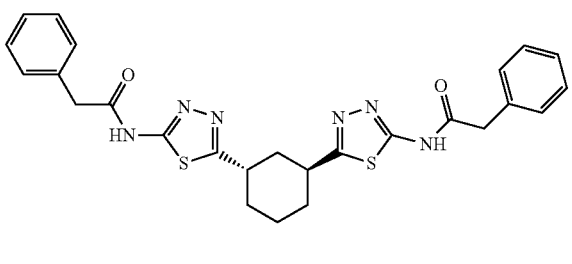 [SMILES: O=C(Cc1ccccc1)Nc1nnc([C@H]2CCC[C@H](c3nnc(NC(=O)Cc4ccccc4)s3)C2)s1]

¹H NMR (500 MHz, DMSO-d$_6$) δ: 1.5-1.61 (t, 2H), 1.91-1.93 (t, 4H), 2.29 (s, 2H), 3.46-3.47 (d, 2H), 3.80 (s, 4H), 7.25-7.35 (m, 10H), 12.7 (s, 2H); Mass (M⁺+1): 519.7.

N,N'-(5,5'-((1S,3S)-cyclohexane-1,3-diyl)bis(1,3,4-thiadiazole-5,2-diyl))diacetamide (12)

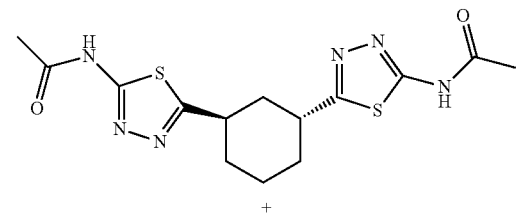

+

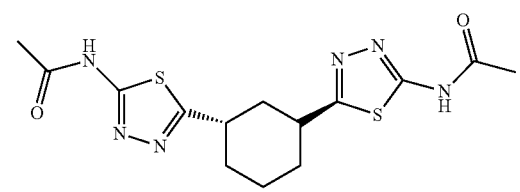

¹H NMR (500 MHz, DMSO-d$_6$) δ: 1.61-1.63 (t, 2H), 1.84-1.97 (m, 4H), 2.17 (s, 6H), 2.30-2.32 (d, 2H), 3.46-3.48 (t, 2H), 12.2 (s, 2H); Mass (M⁺+H): 367.7.

N,N'-(5,5'-((1S,3S)-cyclohexane-1,3-diyl)bis(1,3,4-thiadiazole-5,2-diyl))bis(2-(pyridin-2-yl)acetamide) (14)

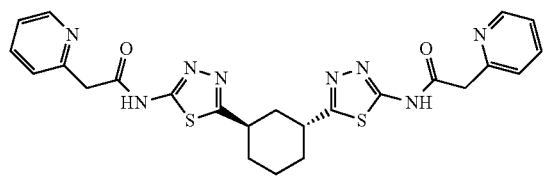

+

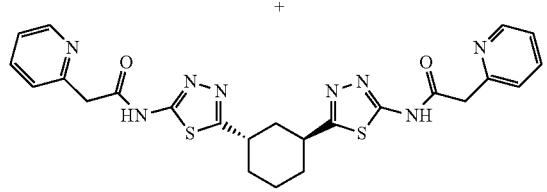

¹H NMR (500 MHz, DMSO-d$_6$) δ: 1.60-1.63 (t, 2H), 1.83-1.85 (t, 2H), 1.91-1.95 (m, 2H), 2.28-2.30 (t, 2H), 3.45-3.47 (t, 2H), 3.97 (s, 4H), 7.26-7.29 (m, 2H), 7.39-7.40 (d, 2H), 7.74-7.78 (m, 2H), 8.48-8.49 (t, 2H), 12.1 (s, 2H); Mass (M++1): 521.7.

N,N'-(5,5'-((1R,3S)-cyclohexane-1,3-diyl)bis(1,3,4-thiadiazole-5,2-diyl))bis(2-(1-methyl-1H-indol-3-yl)acetamide) (15)

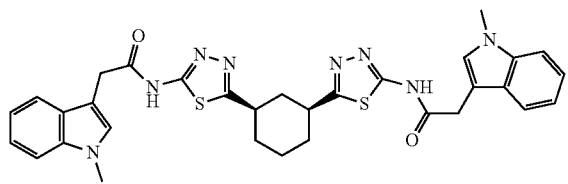 [SMILES: Cn1cc(CC(=O)Nc2nnc([C@@H]3CCC[C@H](c4nnc(NC(=O)Cc5cn(C)c6ccccc56)s4)C3)s2)c2ccccc21]

¹H NMR (500 MHz, DMSO-d₆) δ: 1.49-1.57 (m, 3H), 1.74-1.79 (t, 1H), 1.88-1.91 (d, 1H), 2.05-2.08 (t, 2H), 2.38-2.40 (d, 1H), 3.23-3.28 (t, 2H), 3.75 (s, 6H), 3.87 (s, 4H), 12.6 (s, 2H); Mass (M++1): 625.7.

N,N'-(5,5'-((1S,3S)-cyclohexane-1,3-diyl)bis(1,3,4-thiadiazole-5,2-diyl))bis(2-(1-methyl-1H-indol-3-yl)acetamide) (16)

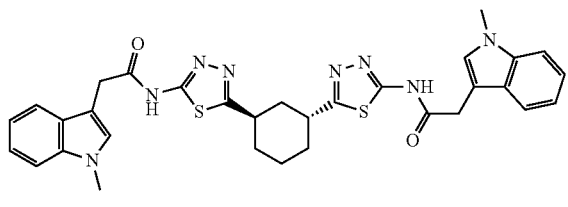

+

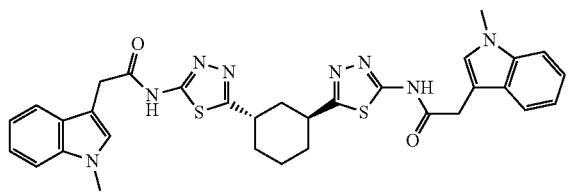

¹H NMR (500 MHz, DMSO-d₆) δ: 1.57-1.59 (t, 2H), 1.81-1.92 (m, 4H), 2.26-2.27 (d, 2H), 3.44-3.46 (t, 2H), 3.76 (s, 6H), 3.88 (s, 4H), 7.01-7.04 (t, 2H), 7.13-7.16 (t, 2H), 7.27 (s, 2H), 7.39-7.41 (d, 2H), 7.57-7.59 (d, 2H), 12.6 (s, 2H); Mass (M++1): 625.7.

N,N'-(5,5'-((1S,3S)-cyclohexane-1,3-diyl)bis(1,3,4-thiadiazole-5,2-diyl))bis(2-(pyridin-2-yl)acetamide) (21)

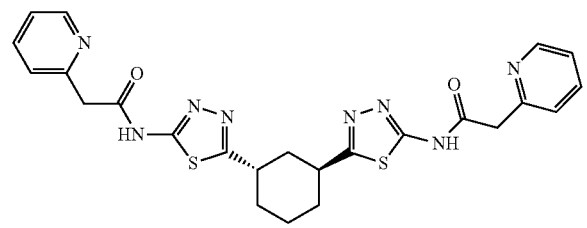

¹H NMR (500 MHz, DMSO-d₆) δ: 1.60-1.62 (t, 2H), 1.82-1.85 (m, 2H), 1.92-1.96 (m, 2H), 2.29-2.31 (t, 2H), 3.47-3.49 (t, 2H), 4.00 (s, 4H), 7.27-7.29 (m, 2H), 7.38-7.40 (d, 2H), 7.75-7.78 (m, 2H), 8.48-8.49 (d, 2H), 12.6 (t, 2H); Mass (M++1): 521.7.

N,N'-(5,5'-((1R,3S)-cyclohexane-1,3-diyl)bis(1,3,4-thiadiazole-5,2-diyl))bis(2-(pyridin-2-yl)acetamide) (20)

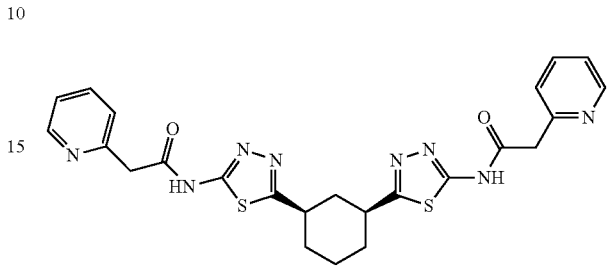

¹H NMR (500 MHz, DMSO-d₆) δ: 1.52-1.62 (m, 3H), 1.78-1.80 (d, 1H), 1.90-1.93 (d, 1H), 2.07-2.10 (d, 2H), 2.42-2.44 (d, 1H), 3.26-3.34 (m, 2H), 4.00 (s, 4H), 7.27-7.30 (m, 2H), 7.39-7.40 (d, 2H), 7.75-7.79 (m, 2H), 8.48-8.49 (d, 2H), 12.6 (s, 2H); Mass (M++1): 521.7.

N,N'-(5,5'-((1R,3R)-cyclohexane-1,3-diyl)bis(1,3,4-thiadiazole-5,2-diyl))bis(2-(pyridin-2-yl)acetamide) (17)

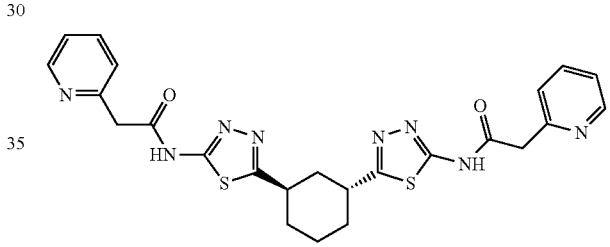

¹H NMR (500 MHz, DMSO-d₆) δ: 1.61-1.62 (d, 2H), 1.80-1.85 (m, 2H), 1.92-1.94 (t, 2H), 2.29-2.31 (t, 2H), 3.47-3.49 (t, 2H), 4.00 (s, 4H), 7.27-7.29 (m, 2H), 7.38-7.40 (d, 2H), 7.75-7.78 (m, 2H), 8.48-8.49 (d, 2H), 12.6 (t, 2H); Mass (M++1): 521.7.

N,N'-(5,5'-((1S,3S)-cyclohexane-1,3-diyl)bis(1,3,4-thiadiazole-5,2-diyl))bis(2-phenylacetamide) (9)

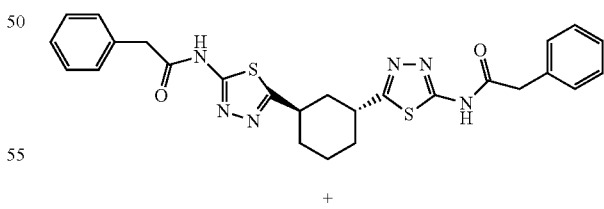

+

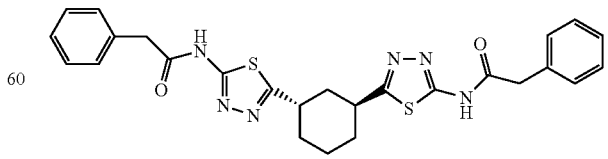

¹H NMR (500 MHz, DMSO-d₆) δ: 1.59 (s, 2H), 1.83 (s, 2H), 1.91 (s, 2H), 2.28 (s, 2H), 3.46 (s, 2H), 3.79 (s, 4H), 7.26-7.32 (t, 10H); Mass (M++1): 519.7.

Example 7
5,5'-((1S,3S)-cyclohexane-1,3-diyl)bis(1,3,4-thiadiazol-2-amine) material was collected by filtration and dried in vacuo to give trans-cyclohexyl 1,3-dicarboxylic acid. $^1$H NMR (DMSO-$d_6$) δ: 1.44 (m, 2H), 1.61 (m, 4H), 1.79 (m, 2H), 2.53 (m, 2H), 12.13 (brs, 2H). LC-MS: m/z 171.2 (M–H)$^-$
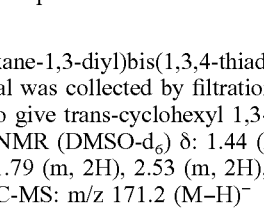
cis-, trans-cyclohexyl
1,3-dicarboxylic acid
Step A
1) NH$_4$OH
2) CaCl$_2$, separated
3) HCl
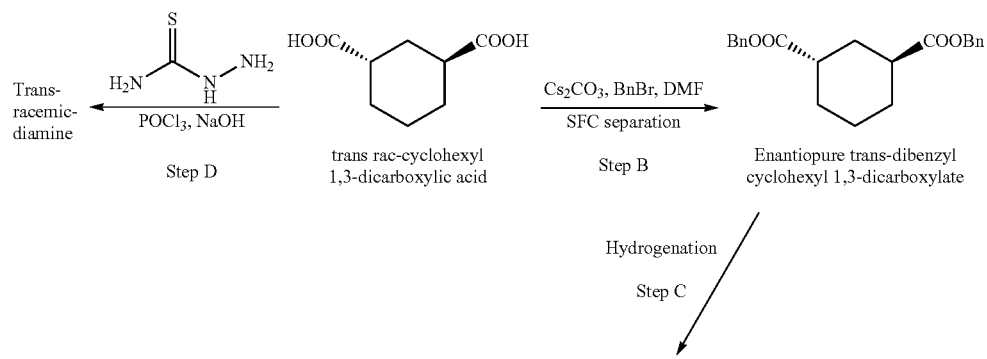
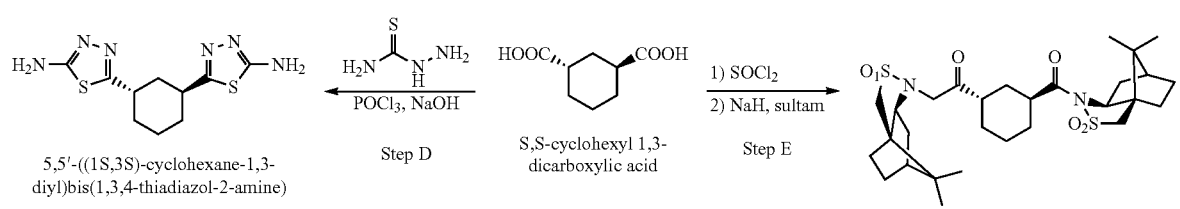
X-ray crystallography determination of chirality

Step A: trans-cyclohexyl 1,3-dicarboxylic acid

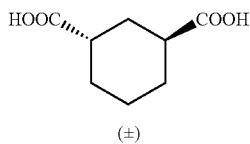

(±)

Cis, trans-cyclohexyl 1,3-dicarboxylic acid (4.00 g, 23.23 mmol) was dissolved in concentrated ammonium hydroxide at 0° C. $CaCl_2$ (3.09 g, 27.88 mmol) in water (5 mL) was added at 0° C. The resulting material was filtered off, and the filtrate was acidified with concentrated HCl. The resulting

Step B: (S,S)-dibenzyl cyclohexyl 1,3-dicarboxylate

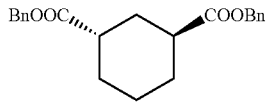

To a mixture of trans-cyclohexyl 1,3-dicarboxylic acid (1.46 g, 8.5 mmol), $Cs_2CO_3$ (8.28 g, 25.5 mmol) in DMF (20 mL) was added BnBr (4.36 g, 25.5 mmol). The mixture was stirred at rt under nitrogen for 3 h. The residue was diluted with water and extracted with ethyl acetate. The combined organic solution was washed with water, dried over $Na_2SO_4$ and concentrated in vacuo. The crude product was purified by flash chromatography to afford 3 g trans-dibenzyl cyclohexyl 1,3-dicarboxylate. $^1H$ NMR (CHLOROFORM-d) δ: 7.51-7.30 (m, 10H), 5.15 (s, 4H), 2.84-2.72 (m, 2H), 2.06 (t, J=5.9 Hz, 2H), 1.77 (m, 4H), 1.56 (p, J=6.0 Hz, 2H). LC-MS: m/z (M+H)=353.4

Chiral SFC separation: 3 g of trans-dibenzyl cyclohexyl 1,3-dicarboxylate was separated by chiral SFC to afford 1.4 g (S,S)-dibenzyl cyclohexyl 1,3-dicarboxylate (93%).

Step C: (S,S)-cyclohexyl 1,3-dicarboxylic acid

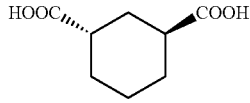

To a solution of 1 g (S,S)-dibenzyl cyclohexyl 1,3-dicarboxylate in 10 mL MeOH was added 10% Pd on carbon (0.1 g). The suspension was flushed with hydrogen and stirred for 20 min. It was then filtered and concentrated to give the desired compound.

$^1H$ NMR (DMSO-$d_6$) δ: 1.44 (m, 2H), 1.61 (m, 4H), 1.79 (m, 2H), 2.53 (m, 2H), 12.13 (brs, 2H). LC-MS: m/z (M−H)=171.2

Step D: 5,5'-((1S,3S)-cyclohexane-1,3-diyl)bis(1,3,4-thiadiazol-2-amine)

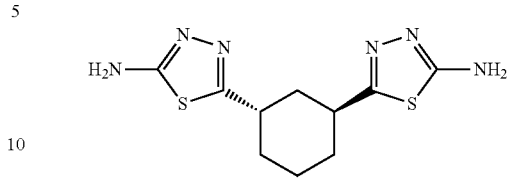

A mixture of (S,S)-cyclohexyl 1,3-dicarboxylic acid (500 mg, 0.3 mmol) and thiosemicarbazide (550 mg, 0.6 mmol) were taken up in $POCl_3$ (10 mL) and stirred at 40° C. for 30 min, 60° C. for 30 min, and 80° C. for 2 h. The reaction mixture was cooled to room temperature and poured onto ice. The resulting mixture was then basified to pH=8 using NaOH and filtrated to give crude desired compound. $^1H$ NMR (DMSO-$d_6$) δ 7.05 (s, 4H), 3.25 (m, 2H), 2.12 (t, 2H J=5.6 Hz, 2H), 1.84 (m, 2H), 1.70 (m, 2H). LC-MS: m/z (M+H)=283.3

Racemic-Trans-5,5'-(cyclohexane-1,3-diyl)bis(1,3,4-thiadiazol-2-amine) was synthesized with a similar procedure.

Step E: (S,S)-cyclohexyl 1,3-dicarboxyl bis((2S)-Bornane-10,2-sultamide)

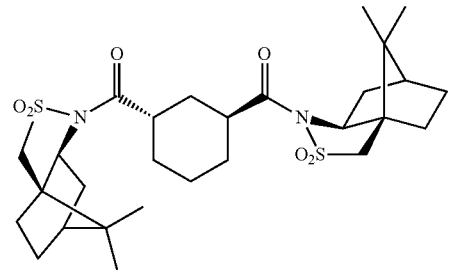

A solution of (S,S)-cyclohexyl 1,3-dicarboxylic acid (800 mg, 4.65 mmol) in $SOCl_2$ was stirred at 80° C. for 1.5 h. The extra $SOCl_2$ was removed under reduced pressure and the residue was used to next step directly. To a solution of (2S)-Bornane-10,2-sultam (2 g, 9.3 mmol) in toluene (20 mL) was added NaH (60% in oil, 465 mg, 11.63 mmol) in portions at 0° C. and the reaction mixture was stirred at this temperature for 30 min. Cyclohexane-1,3-dicarbonyl dichloride (obtained from above) in toluene (5 mL) was added dropwise and the reaction was stirred at room temperature overnight. The resulting mixture was diluted with EtOAc (50 mL) and water (10 mL), separated and the aqueous layer was extracted with EtOAc (50 mLx2). The combined organic layers were washed with brine, dried over $Na_2SO_4$, filtered and purified by flash chromatography to give the desired compound.

$^1H$ NMR (CHLOROFORM-d) δ 3.93 (dd, J=7.6, 4.8 Hz, 2H), 3.66-3.59 (m, 2H), 3.50 (d, J=13.7 Hz, 2H), 3.45 (d, J=13.8 Hz, 2H), 2.12 (dd, J=13.8, 7.7 Hz, 2H), 1.82-2.03 (m, 12H), 1.57-1.70 (m, 4H), 1.39 (dt, J=16.8, 9.5 Hz, 4H), 1.16 (s, 6H), 0.98 (s, 6H). LC-MS: m/z (M+H)=567.3.

The product was recrystallized in EtOAc to give a sample for single crystal x-ray diffraction, the result of which confirmed that the configuration of the starting material diacid was (S,S).

N,N'-(5,5'-((1S,3S)-cyclohexane-1,3-diyl)bis(1,3,4-thiadiazole-5,2-diyl))dibutyramide (37)

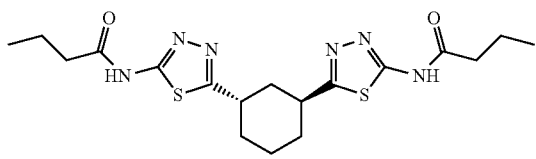 [SMILES: CCCC(=O)Nc1nnc([C@H]2CCC[C@H](c3nnc(NC(=O)CCC)s3)C2)s1]

A solution of 5,5'-((1S,3S)-cyclopentane-1,3-diyl)bis(1,3,4-thiadiazol-2-amine) (20 mg, 0.07 mmol), butyric acid (18.5 mg, 0.21 mmol), HATU (80.8 mg, 0.21 mmol), and N-ethyl-N-isopropylpropan-2-amine (29.3 mg, 0.23 mmol) in N,N-dimethylformamide (5 ml) was stirred at room temperature overnight. The mixture was poured into water (10 ml), the precipitate was filtered to give the crude product. The crude product was purified by a standard method to give the desired product.

$^1$H NMR (DMSO-$d_6$) δ: 12.41 (s, 2H), 3.43-3.55 (m, 2H), 2.44 (t, J=7.3 Hz, 4H), 2.31 (t, J=5.7 Hz, 2H), 1.91-2.02 (m, 2H), 1.82-1.91 (m, 2H), 1.57-1.68 (m, 6H), 0.90 (t, J=7.5 Hz, 6H). LC-MS: m/z (M+H)=423.6.

The following compounds were prepared in an analogous manner:

N,N'-(5,5'-((1S,3S)-cyclohexane-1,3-diyl)bis(1,3,4-thiadiazole-5,2-diyl))bis(tetrahydrofuran-3-carboxamide) (48)

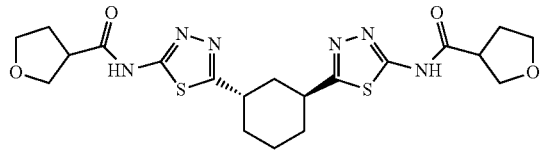 [SMILES: O=C(Nc1nnc([C@H]2CCC[C@H](c3nnc(NC(=O)C4CCOC4)s3)C2)s1)C1CCOC1]

The procedure was the same as Compound 37

$^1$H NMR (DMSO-$d_6$) δ: 12.58 (br. s., 2H), 3.87-3.98 (m, 2H), 3.65-3.83 (m, 6H), 3.47-3.55 (m, 2H), 3.27-3.34 (m, 2H), 2.31 (t, J=6.0 Hz, 2H), 2.02-2.18 (m, 4H), 1.92-2.01 (m, 2H), 1.82-1.90 (m, 2H), 1.60-1.68 (m, 2H). LC-MS: m/z (M+H)=479.6

N,N'-(5,5'-((1S,3S)-cyclohexane-1,3-diyl)bis(1,3,4-thiadiazole-5,2-diyl))bis(4,4,4-trifluorobutanamide) (47)

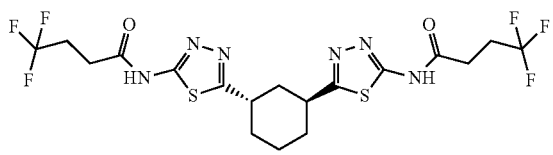 [SMILES: O=C(CCC(F)(F)F)Nc1nnc([C@H]2CCC[C@H](c3nnc(NC(=O)CCC(F)(F)F)s3)C2)s1]

The procedure was the same as Compound 37

$^1$H NMR (DMSO-$d_6$) δ: 12.61 (br. s., 2H), 3.45-3.55 (m, 2H), 2.73-2.82 (q, 4H), 2.56-2.72 (m, 4H), 2.32 (t, J=5.6 Hz, 2H), 1.92-2.01 (m, 2H), 1.81-1.90 (m, 2H), 1.57-1.70 (m, 2H). LC-MS: m/z (M+H)=531.6

N,N'-(5,5'-((1S,3S)-cyclohexane-1,3-diyl)bis(1,3,4-thiadiazole-5,2-diyl))bis(2-cyclopropylacetamide) (49)

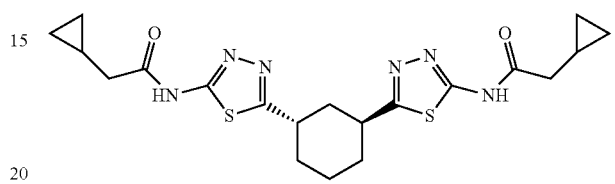

The procedure was the same as Compound 37

$^1$H NMR (DMSO-$d_6$) δ: 12.39 (s, 2H), 3.44-3.55 (m, 2H), 2.28-2.41 (m, 6H), 1.92-2.02 (m, 2H), 1.82-1.92 (m, 2H), 1.60-1.70 (m, 2H), 0.99-1.11 (m, 2H), 0.46-0.54 (m, 4H), 0.17-0.25 (m, 4H). LC-MS: m/z (M+H)=447.6

N,N'-(5,5'-((1S,3S)-cyclohexane-1,3-diyl)bis(1,3,4-thiadiazole-5,2-diyl))bis(2-(methylthio)acetamide) (60)

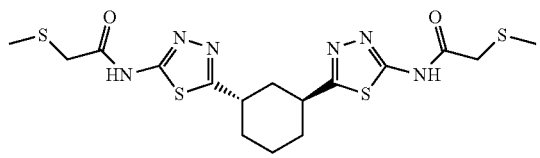

The procedure was the same as Compound 37.

$^1$H NMR (DMSO-$d_6$) δ: 12.58 (br. s., 2H), 3.47-3.54 (m, 2H), 3.41 (s, 4H), 2.33 (t, J=5.7 Hz, 2H), 2.16 (s, 6H), 1.85-1.99 (m, 4H), 1.61-1.67 (m, 2H). LC-MS: m/z (M+H)=459.5

N,N'-(5,5'-((1S,3S)-cyclohexane-1,3-diyl)bis(1,3,4-thiadiazole-5,2-diyl))bis(3-(methylthio)propanamide) (46)

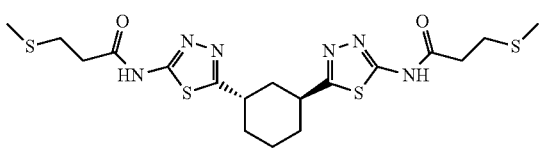

The procedure was the same as Compound 37, $^1$H NMR (DMSO-$d_6$) δ: 12.51 (br. s., 2H), 3.50 (m, 2H), 2.77 (br. s, 8H), 2.32 (m, 2H), 2.08 (s, 6H), 1.96 (m, 2H), 1.87 (m, 2H), 1.64 (m, 2H). LC-MS: m/z (M+H)=487.5

203

N,N'-(5,5'-((1S,3S)-cyclohexane-1,3-diyl)bis(1,3,4-thiadiazole-5,2-diyl))bis(2-(tetrahydrofuran-2-yl)acetamide) (77)

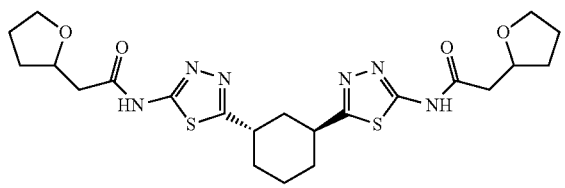 [SMILES: O=C(CC1CCCO1)Nc1nnc([C@H]2CCC[C@H](c3nnc(NC(=O)CC4CCCO4)s3)C2)s1]

The procedure was the same as Compound 37

$^1$H NMR (CHLOROFORM-d) δ: 11.96 (br. s., 2H), 4.35 (quin, J=6.6 Hz, 2H), 3.93-4.00 (m, 2H), 3.80-3.86 (m, 2H), 3.55-3.62 (m, 2H), 2.85 (d, J=6.2 Hz, 4H), 2.48 (t, J=5.5 Hz, 2H), 2.12-2.18 (m, 2H), 1.95-2.00 (m, 4H), 1.76-1.82 (m, 4H), 1.61-1.68 (m, 4H). LC-MS: m/z (M+H)=507.7.

N,N'-(5,5'-((1S,3S)-cyclohexane-1,3-diyl)bis(1,3,4-thiadiazole-5,2-diyl))bis(2-(2-oxopyrrolidin-1-yl)acetamide) (85)

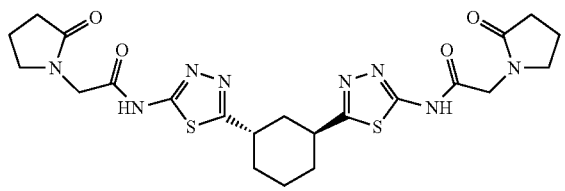 [SMILES: O=C(CN1CCCC1=O)Nc1nnc([C@H]2CCC[C@H](c3nnc(NC(=O)CN4CCCC4=O)s3)C2)s1]

The procedure was the same as Compound 37

1H NMR (CHLOROFORM-d) δ: 4.48 (s, 4H), 3.53-3.61 (m, 6H), 2.49 (t, J=7.9 Hz, 4H), 2.43 (t, J=5.4 Hz, 2H), 2.08-2.16 (m, 4H), 2.03 (m, 2H), 1.93 (m, 2H), 1.67-1.77 (m, 2H). LC-MS: m/z (M+H)=533.7

N,N'-(5,5'-((1S,3S)-cyclohexane-1,3-diyl)bis(1,3,4-thiadiazole-5,2-diyl))dibenzamide (39)

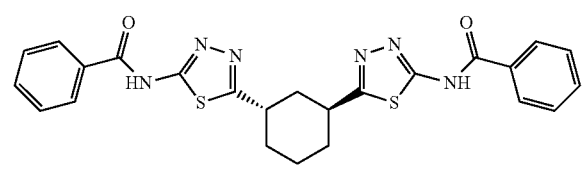 [SMILES: O=C(Nc1nnc([C@H]2CCC[C@H](c3nnc(NC(=O)c4ccccc4)s3)C2)s1)c1ccccc1]

The procedure was the same as Compound 37

$^1$H NMR (DMSO-d$_6$) δ: 12.98 (br. s., 2H), 8.12 (d, J=7.3 Hz, 4H), 7.63-7.72 (m, 2H), 7.53-7.61 (m, 4H), 3.57 (m, 2H), 2.37-2.45 (t, J=5.6 Hz, 2H), 1.98 (m, 2H), 1.89 (m, 2H), 1.70 (m, 2H). LC-MS: m/z (M+H)=491.6

204

N,N'-(5,5'-(1S,3S)-cyclohexane-1,3-diyl)bis(1,3,4-thiadiazole-5,2-diyl))diacetamide (41)

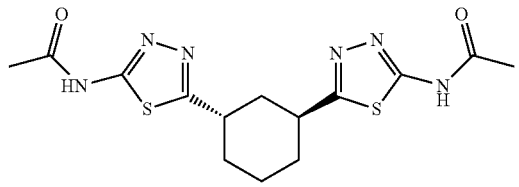 [SMILES: CC(=O)Nc1nnc([C@H]2CCC[C@H](c3nnc(NC(C)=O)s3)C2)s1]

The procedure was the same as Compound 37

$^1$H NMR (DMSO-d$_6$) δ: 12.44 (s, 2H), 3.48 (m, 2H), 2.27-2.35 (t, J=5.6 Hz, 2H), 2.18 (s, 6H), 1.95 (m, 2H), 1.87 (m, 2H), 1.59-1.67 (m, 2H). LC-MS: m/z (M+H)=367.5

N,N'-(5,5'-((1S,3S)-cyclohexane-1,3-diyl)bis(1,3,4-thiadiazole-5,2-diyl))dipropionamide (40)

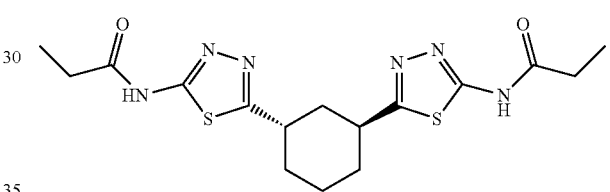

The procedure was the same as Compound 37

$^1$H NMR (DMSO-d$_6$) δ: 12.40 (s, 2H), 3.37-3.54 (m, 2H), 2.47 (q, J=7.6 Hz, 4H), 2.31 (t, J=5.6 Hz, 2H), 1.91-2.06 (m, 2H), 1.75-1.91 (m, 2H), 1.52-1.75 (m, 2H), 1.09 (t, J=7.5 Hz, 6H). LC-MS: m/z (M+H)=395.6

N,N'-(5,5'-((1S,3S)-cyclohexane-1,3-diyl)bis(1,3,4-thiadiazole-5,2-diyl))bis(2-methylpropanamide) (98)

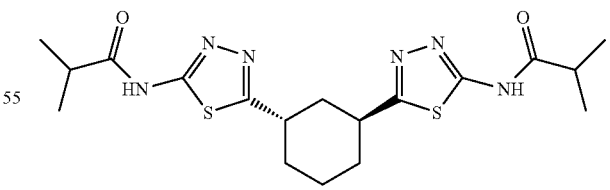

The procedure was the same as Compound 37

$^1$H NMR (DMSO-d$_6$) δ: 12.42 (s, 2H), 3.43-3.53 (m, 2H), 2.77 (septet, J=6.7 Hz, 2H), 2.31 (t, J=5.8 Hz, 2H), 1.91-2.02 (m, 2H), 1.80-1.91 (m, 2H), 1.57-1.68 (m, 2H), 1.12 (d, J=7.6 Hz, 12H). LC-MS: m/z (M+H)=423.6

N,N'-(5,5'-((1S,3S)-cyclohexane-1,3-diyl)bis(1,3,4-thiadiazole-5,2-diyl))dicyclopentanecarboxamide (62)

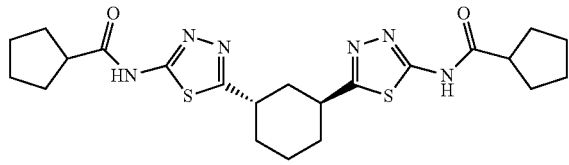 [SMILES: O=C(Nc1nnc([C@H]2CCC[C@H](c3nnc(NC(=O)C4CCCC4)s3)C2)s1)C1CCCC1]

¹H NMR (DMSO-d₆) δ 3.48 (m, 2H), 2.95 (m, 2H), 2.31 (t, J=5.8 Hz, 2H), 2.04-1.85 (m, 8H), 1.76-1.60 (m, 8H), 1.57 (m, 2H). LC-MS: m/z (M+H)=475.2

N,N'-(5,5'-((1S,3S)-cyclohexane-1,3-diyl)bis(1,3,4-thiadiazole-5,2-diyl))bis(3-hydroxy-2,2-dimethylpropanamide) (63)

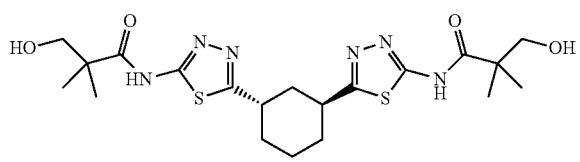 [SMILES: CC(C)(CO)C(=O)Nc1nnc([C@H]2CCC[C@H](c3nnc(NC(=O)C(C)(C)CO)s3)C2)s1]

¹H NMR (DMSO-d₆) δ 3.82 (s, 4H), 3.57 (m, 2H), 2.46 (t, J=5.8 Hz, 2H), 2.05 (m, 2H), 1.98 (m, 2H), 1.73 (m, 2H), 1.29 (s, 12H). LC-MS: m/z (M+H)=483.2.

N,N'-(5,5'-((1S,3S)-cyclohexane-1,3-diyl)bis(1,3,4-thiadiazole-5,2-diyl))bis(2-(4-fluoro-3-methoxyphenyl)acetamide) (78)

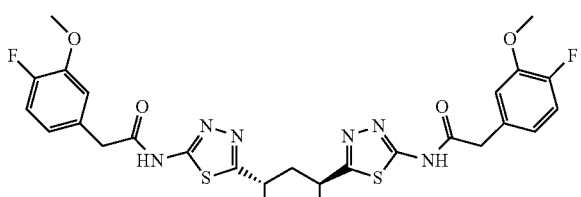

The procedure was the same as Compound 37
¹H NMR (DMSO-d₆) δ: 7.13-7.18 (m, 4H), 6.88 (d, J=2.4 Hz, 2H), 3.83 (s, 6H), 3.78 (s, 4H), 2.29 (t, J=5.4 Hz, 2H), 1.93 (m, 2H), 1.84 (m, 2H), 1.60 (m, 2H). LC-MS: m/z (M+H)=615.8

N,N'-(5,5'-((1S,3S)-cyclohexane-1,3-diyl)bis(1,3,4-thiadiazole-5,2-diyl))bis(2-(benzo[d][1,3]dioxol-5-yl)acetamide) (86)

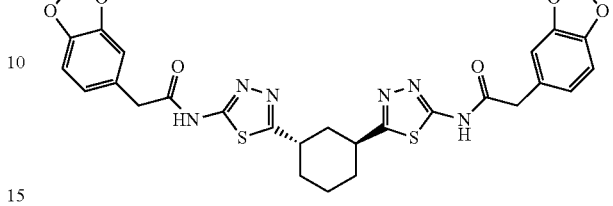

The procedure was the same as Compound 37
¹H NMR (CHLOROFORM-d) δ: 6.98 (s, 2H), 6.89-6.94 (m, J=7.8 Hz, 2H), 6.69-6.73 (m, J=8.0 Hz, 2H), 5.89 (s, 4H), 3.93 (s, 4H), 3.56-3.64 (m, 2H), 2.49 (t, J=5.4 Hz, 2H), 2.02-2.10 (m, 2H), 1.99 (m, 2H), 1.76-1.82 (m, 2H). LC-MS: m/z (M+H)=607.8

N,N'-(5,5'-((1S,3S)-cyclohexane-1,3-diyl)bis(1,3,4-thiadiazole-5,2-diyl))bis(2-(4-fluorophenyl)acetamide) (88)

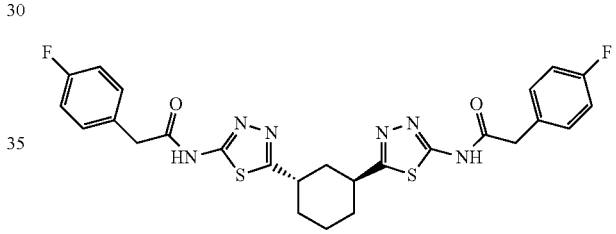

The procedure was the same as Compound 37
¹H NMR (DMSO-d₆) δ: 12.70 (s, 2H), 7.36 (dd, J=8.6, 5.6 Hz, 4H), 7.16 (t, J=8.9 Hz, 4H), 3.81 (s, 4H), 3.43-3.51 (m, 2H), 2.29 (t, J=5.6 Hz, 2H), 1.89-1.97 (m, 2H), 1.85 (m, 2H), 1.57-1.64 (m, 2H). LC-MS: m/z (M+H)=555.7

N,N'-(5,5'-((1S,3S)-cyclohexane-1,3-diyl)bis(1,3,4-thiadiazole-5,2-diyl))bis(2-(2,6-difluorophenyl)acetamide) (86)

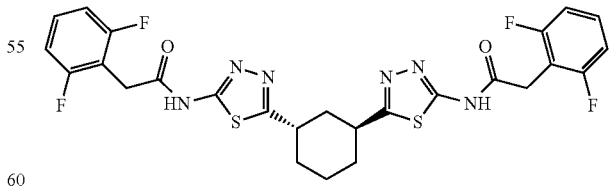

The procedure was the same as Compound 37.
¹H NMR (DMSO-d₆) δ: 12.83 (br. s., 2H), 7.42 (m, 2H), 7.12 (t, J=7.9 Hz, 4H), 3.93 (s, 4H), 3.47-3.54 (m, 2H), 2.31 (t, J=5.6 Hz, 2H), 1.89-1.99 (m, 2H), 1.80-1.89 (m, 2H), 1.58-1.67 (m, 2H). LC-MS: m/z (M+H)=591.7

N,N'-(5,5'-((1S,3S)-cyclohexane-1,3-diyl)bis(1,3,4-thiadiazole-5,2-diyl))bis(2-(2-methoxyphenyl)acetamide) (42)

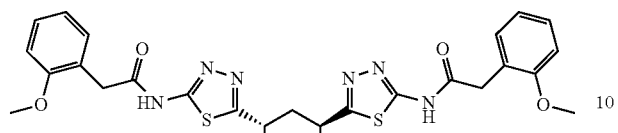

The procedure was the same as Compound 37

$^1$H NMR (DMSO-d$_6$) δ: 12.59 (s, 2H), 7.24-7.30 (m, 2H), 7.21 (dd, J=7.5, 1.6 Hz, 2H), 6.98 (d, J=7.9 Hz, 2H), 6.88-6.93 (m, 2H), 3.78 (s, 4H), 3.74 (s, 6H), 3.49 (m, 2H), 2.30 (t, J=5.7 Hz, 2H), 1.91-1.99 (m, 2H), 1.79-1.87 (m, 2H), 1.59-1.65 (m, 2H). LC-MS: m/z (M+H)=579.7.

N,N'-(5,5'-((1S,3S)-cyclohexane-1,3-diyl)bis(1,3,4-thiadiazole-5,2-diyl))bis(2-(3-chlorophenyl)acetamide) (43)

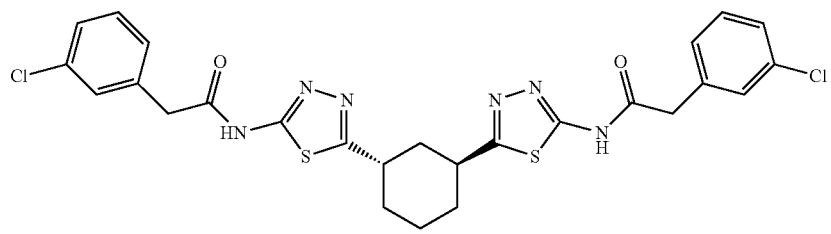 [SMILES: O=C(Cc1cccc(Cl)c1)Nc1nnc([C@H]2CCC[C@H](c3nnc(NC(=O)Cc4cccc(Cl)c4)s3)C2)s1]

The procedure was the same as Compound 37

$^1$H NMR (DMSO-d$_6$) δ: 12.73 (s, 2H), 7.42 (s, 2H), 7.34-7.38 (m, 4H), 7.27-7.31 (m, 2H), 3.84 (s, 4H), 3.43-3.52 (m, 2H), 2.30 (t, J=5.6 Hz, 2H), 1.89-1.98 (m, 2H), 1.77-1.88 (m, 2H), 1.57-1.65 (m, 2H). LC-MS: m/z (M+H)= 587.6

N,N'-(5,5'-((1S,3S)-cyclohexane-1,3-diyl)bis(1,3,4-thiadiazole-5,2-diyl))bis(2-(3-methoxyphenyl)acetamide) (44)

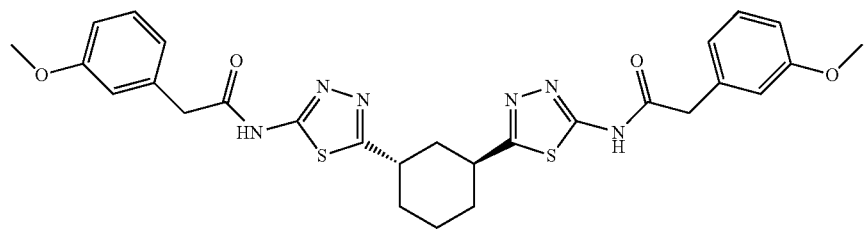

The procedure was the same as Compound 37

¹H NMR (DMSO-d₆) δ: 12.69 (s, 2H), 7.24 (t, J=7.9 Hz, 2H), 6.91 (d, J=2.1 Hz, 2H), 6.89 (d, J=7.6 Hz, 2H), 6.84 (dd, J=8.2, 2.1 Hz, 2H), 3.77 (s, 4H), 3.74 (s, 6H), 3.47 (dt, J=11.2, 5.7 Hz, 2H), 2.29 (t, J=5.7 Hz, 2H), 1.88-1.98 (m, 2H), 1.76-1.86 (m, 2H), 1.54-1.65 (m, 2H). LC-MS: m/z (M+H)=579.7

N,N'-(5,5'-((1S,3S)-cyclohexane-1,3-diyl)bis(1,3,4-thiadiazole-5,2-diyl))bis(2-(4-methoxyphenyl)acetamide) (52)

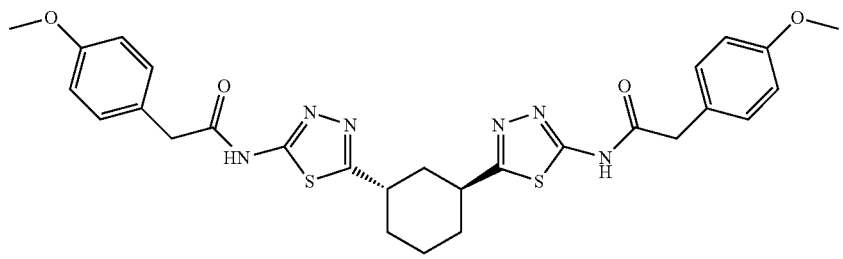

The procedure was the same as Compound 37

¹H NMR (DMSO-d₆) δ: 12.67 (s, 2H), 7.24 (d, J=8.8 Hz, 4H), 6.89 (d, J=8.5 Hz, 4H), 3.73 (s, 6H), 3.72 (s, 4H), 3.43-3.50 (m, 2H), 2.29 (t, J=5.9 Hz, 2H), 1.89-2.00 (m, 2H), 1.78-1.87 (m, 2H), 1.55-1.66 (m, 2H), LC-MS: m/z (M+H)=579.7

N,N'-(5,5'-((1S,3S)-cyclohexane-1,3-diyl)bis(1,3,4-thiadiazole-5,2-diyl))bis(2-(2-chlorophenyl)acetamide) (51)

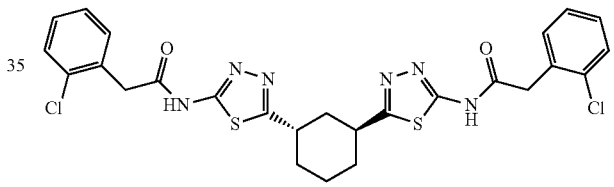

The procedure was the same as Compound 37

¹H NMR (DMSO-d₆) δ: 12.77 (s, 2H), 7.41-7.48 (m, 4H), 7.29-7.37 (m, 4H), 4.00 (s, 4H), 3.45-3.54 (m, 2H), 2.30 (t, J=5.4 Hz, 2H), 1.91-1.99 (m, 2H), 1.78-1.88 (m, 2H), 1.56-1.68 (m, 2H). LC-MS: m/z (M+H)=587.6.

N,N'-(5,5'-(1S,3S)-cyclohexane-1,3-diyl)bis(1,3,4-thiadiazole-5,2-diyl))bis(2-(4-chlorophenyl)acetamide) (50)

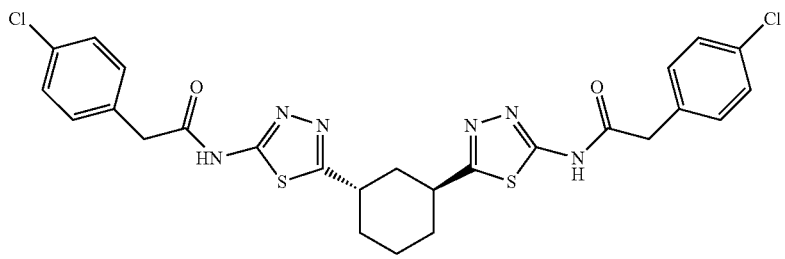 [SMILES: O=C(Cc1ccc(Cl)cc1)Nc1nnc([C@H]2CCC[C@H](c3nnc(NC(=O)Cc4ccc(Cl)cc4)s3)C2)s1]

211

The procedure was the same as Compound 37

¹H NMR (DMSO-d₆) δ: 12.73 (s, 2H), 7.40 (d, J=8.8 Hz, 4H), 7.35 (d, J=8.8 Hz, 4H), 3.82 (s, 4H), 3.42-3.51 (m, 2H), 2.29 (t, J=5.6 Hz, 2H), 1.89-1.99 (m, 2H), 1.77-1.87 (m, 2H), 1.55-1.66 (m, 2H). LC-MS: m/z (M+H)=587.6

N,N'-(5,5'-((1S,3S)-cyclohexane-1,3-diyl)bis(1,3,4-thiadiazole-5,2-diyl))bis(2-(benzo[d][1,3]dioxol-4-yl)acetamide) (218)

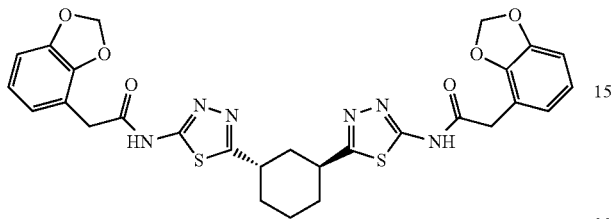

212

The procedure was the same as Compound 37

¹HNMR (CHLOROFORM-d) δ: 6.78-6.84 (m, 6H), 5.99 (s, 4H), 3.98 (s, 4H), 3.55-3.61 (m, 2H), 2.45 (t, J=5.4 Hz, 2H), 2.02 (m, 2H), 1.92 (m, 2H), 1.74 (m, 2H). LC-MS: m/z (M+H)=607.7.

N,N'-(5,5'-((1S,3S)-cyclohexane-1,3-diyl)bis(1,3,4-thiadiazole-5,2-diyl))bis(2-(3-(methylsulfonyl)phenyl)acetamide) (54)

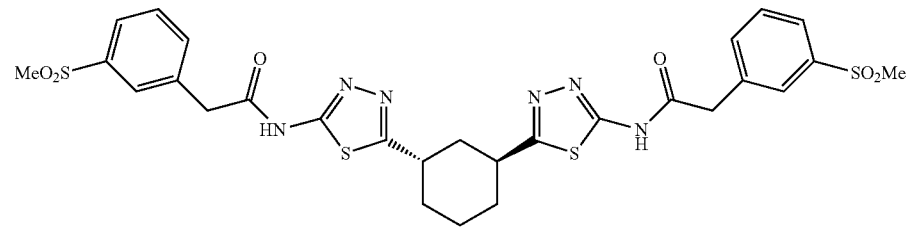 [SMILES: CS(=O)(=O)c1cccc(CC(=O)Nc2nnc([C@H]3CCC[C@H](c4nnc(NC(=O)Cc5cccc(S(C)(=O)=O)c5)s4)C3)s2)c1]

The procedure was the same as Compound 37

¹H NMR (DMSO-d₆) δ: 12.78 (s, 2H), 7.92 (s, 2H), 7.83-7.88 (d, J=7.6 Hz, 2H), 7.57-7.73 (m, 4H), 3.97 (s, 4H), 3.43-3.51 (m, 2H), 3.22 (s, 6H), 2.30 (t, J=5.5 Hz, 2H), 1.90-1.98 (m, 2H), 1.76-1.88 (m, 2H), 1.55-1.65 (m, 2H). LC-MS: m/z (M+H)=675.7

N,N'-(5,5'-((1S,3S)-cyclohexane-1,3-diyl)bis(1,3,4-thiadiazole-5,2-diyl))bis(2-(4-(methylsulfonyl)phenyl)acetamide) (66)

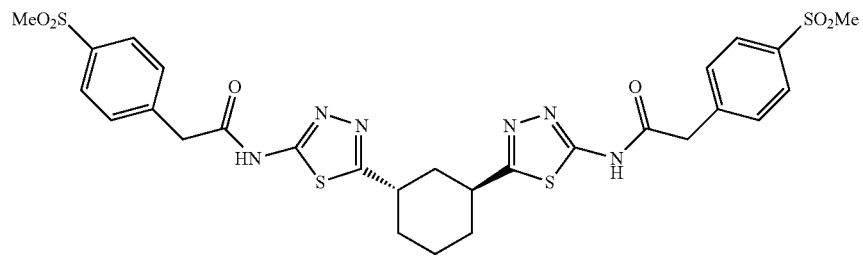 [SMILES: CS(=O)(=O)c1ccc(CC(=O)Nc2nnc([C@H]3CCC[C@H](c4nnc(NC(=O)Cc5ccc(S(C)(=O)=O)cc5)s4)C3)s2)cc1]

The procedure was the same as Compound 37

¹H NMR (DMSO-d₆) δ: 12.80 (s, 1H), 7.90 (d, J=8.3 Hz, 4H), 7.60 (d, J=8.3 Hz, 4H), 3.96 (s, 4H), 3.46 (m, 2H), 3.20 (s, 6H), 2.30 (t, J=5.5 Hz, 2H), 1.92 (m, 2H), 1.83 (m, 2H), 1.61 (m, 2H). LC-MS: m/z (M+H)=675.7.

N,N'-(5,5'-((1S,3S)-cyclohexane-1,3-diyl)bis(1,3,4-thiadiazole-5,2-diyl))bis(2-(2-methoxyphenyl)acetamide) (70)

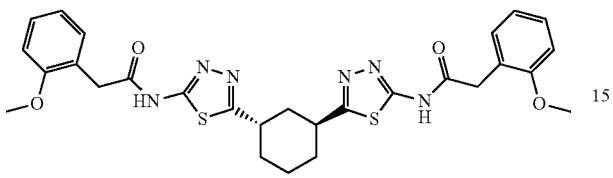

The procedure was the same as Compound 37

¹H NMR (DMSO-d₆) δ: 12.59 (s, 2H), 7.27 (t, J=7.7 Hz, 2H), 7.21 (d, J=7.5 Hz, 2H), 6.98 (d, J=8.3 Hz, 2H), 6.85-6.94 (m, 2H), 3.78 (s, 4H), 3.74 (s, 6H), 3.49 (m, 2H), 2.30 (t, J=5.5 Hz, 2H), 1.90-1.98 (m, 2H), 1.84 (m, 2H), 1.63 (m, 2H). LC-MS: m/z (M+H)=579.7

N,N'-(5,5'-((1S,3S)-cyclohexane-1,3-diyl)bis(1,3,4-thiadiazole-5,2-diyl))bis(2-(3-methoxyphenyl)acetamide) (71)

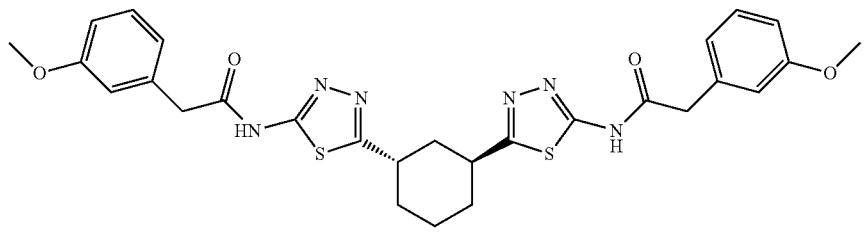

The procedure was the same as Compound 37

¹H NMR (DMSO-d₆) δ: 12.68 (s, 2H), 7.25 (t, J=7.7 Hz, 2H), 6.8-6.91 (m, 4H), 6.84 (d, 0.1=7.5 Hz, 3H), 3.77 (s, 4H), 3.75 (s, 6H), 2.29 (t, J=5.4 Hz, 2H), 1.91 (m, 2H), 1.84 (m, 2H), 1.61 (m, 2H). LC-MS: m/z (M+H)=579.7

N,N'-(5,5'-((1S,3S)-cyclohexane-1,3-diyl)bis(1,3,4-thiadiazole-5,2-diyl))bis(2-(2-cyanophenyl)acetamide) (72)

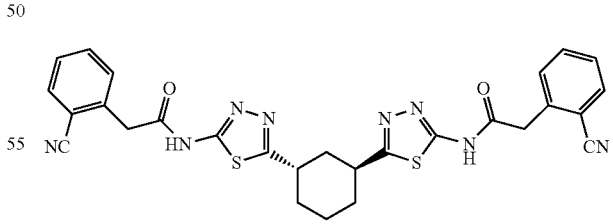

The procedure was the same as Compound 37

¹H NMR (DMSO-d₆) δ: 12.86 (s, 2H), 7.85 (d, J=7.8 Hz, 2H), 7.70 (t, J=7.7 Hz, 2H), 7.56 (d, J=7.5 Hz, 2H), 7.46-7.54 (m, 2H), 4.11 (s, 4H), 3.44-3.53 (m, 2H), 2.32 (t, J=5.1 Hz, 2H), 1.89-2.01 (m, 2H), 1.78-1.88 (m, 2H), 1.58-1.67 (m, 2H). LC-MS: m/z (M+H)=569.7.

N,N'-(5,5'-((1S,3S)-cyclohexane-1,3-diyl)bis(1,3,4-thiadiazole-5,2-diyl))bis(2-(3-cyanophenyl)acetamide) (73)

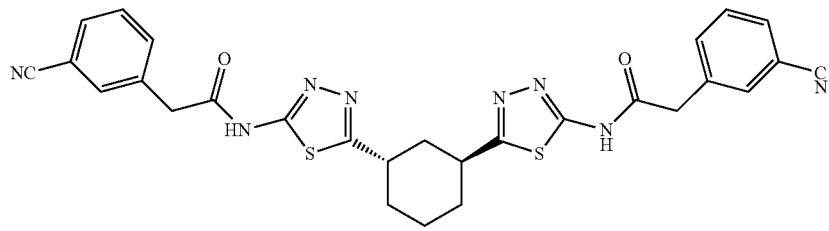 [SMILES: N#Cc1cccc(CC(=O)Nc2nnc([C@H]3CCC[C@H](c4nnc(NC(=O)Cc5cccc(C#N)c5)s4)C3)s2)c1]

The procedure was the same as Compound 37

$^1$H NMR (DMSO-$d_6$) δ: 12.75 (s, 2H), 7.79 (s, 2H), 7.76 (d, J=7.5 Hz, 2H), 7.67 (d, J=7.8 Hz, 2H), 7.56 (t, J=7.8 Hz, 2H), 3.92 (s, 4H), 3.45-3.51 (m, 2H), 2.30 (t, J=5.5 Hz, 2H), 1.90-1.99 (m, 2H), 1.80-1.88 (m, 2H), 1.62 (m, 2H). LC-MS: m/z (M+H)=569.7.

N,N'-(5,5'-((1S,3S)-cyclohexane-1,3-diyl)bis(1,3,4-thiadiazole-5,2-diyl))bis(2-(4-cyanophenyl)acetamide) (74)

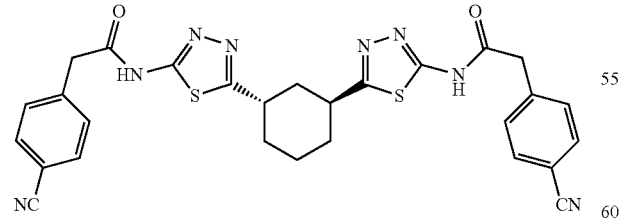

The procedure was the same as Compound 37

$^1$H NMR (DMSO-$d_6$) δ: 12.77 (s, 2H), 7.81 (d, J=8.3 Hz, 4H), 7.53 (d, J=8.3 Hz, 4H), 3.94 (s, 4H), 3.46 (m, 2H), 2.29 (t, J=5.5 Hz, 2H), 1.92 (m, 2H), 1.83 (m, 2H), 1.61 (m, 2H). LC-MS: m/z (M+H)=569.7.

N,N'-(5,5'-((1S,3S)-cyclohexane-1,3-diyl)bis(1,3,4-thiadiazole-5,2-diyl))bis(2-(2-(trifluoromethoxy)phenyl)acetamide) (75)

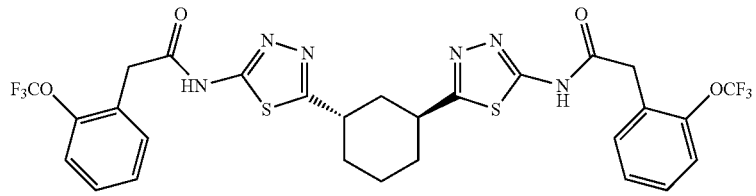 [SMILES: O=C(Cc1ccccc1OC(F)(F)F)Nc1nnc([C@H]2CCC[C@H](c3nnc(NC(=O)Cc4ccccc4OC(F)(F)F)s3)C2)s1]

The procedure was the same as Compound 37

¹H NMR (DMSO-d₆) δ: 12.77 (s, 2H), 7.50 (d, J=7.5 Hz, 2H), 7.41-7.47 (m, 2H), 7.27-7.41 (m, 4H), 3.82-4.10 (s, 4H), 3.48-3.51 (m, 2H), 2.31 (t, J=5.4 Hz, 2H), 1.89-2.01 (m, 2H), 1.76-1.88 (m, 2H), 1.62 (m 2H). LC-MS: m/z (M+H)=687.7

N,N'-(5,5'-((1S,3S)-cyclohexane-1,3-diyl)bis(1,3,4-thiadiazole-5,2-diyl))bis(2-(3-(trifluoromethoxy)phenyl)acetamide) (219)

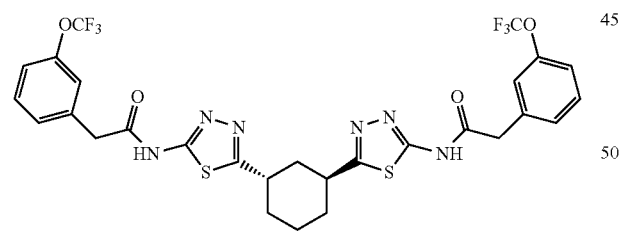

The procedure was the same as Compound 37

¹H NMR (CHLOROFORM-d) δ: 7.40-7.44 (d, J=7.8 Hz, 2H), 7.38 (s, 2H), 7.32 (t, J=7.9 Hz, 2H), 7.09-7.12 (d, J=8.3 Hz, 2H), 4.08 (s, 4H), 3.61 (m, 2H), 2.51 (t, J=5.4 Hz, 2H), 2.07 (m, 2H), 1.99 (m, 2H), 1.78 (m, 2H). LC-MS: m/z (M+H)=687.9.

N,N'-(5,5'-((1S,3S)-cyclohexane-1,3-diyl)bis(1,3,4-thiadiazole-5,2-diyl))bis(2-o-tolylacetamide) (83)

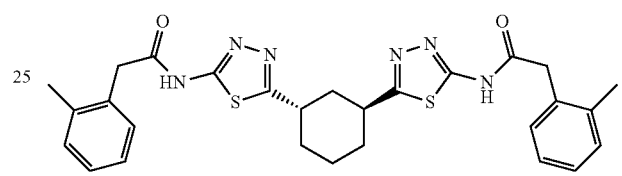

The procedure was the same as Compound 37

¹H NMR (DMSO-d₆) δ: 12.70 (s, 2H), 7.22-7.26 (m, 2H), 7.16-7.20 (m, 4H), 7.10-7.16 (m, 2H), 3.84 (s, 4H), 3.44-3.52 (m, 2H), 2.30 (t, J=5.4 Hz, 2H), 2.27 (s, 6H), 1.89-2.01 (m, 2H), 1.76-1.88 (m, 2H), 1.56-1.66 (m, 2H). LC-MS: m/z (M+H)=547.7

N,N'-(5,5'-((1S,3S)-cyclohexane-1,3-diyl)bis(1,3,4-thiadiazole-5,2-diyl))bis(2-(2-(trifluoromethyl)phenyl)acetamide) (82)

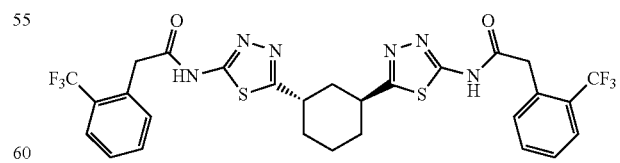

The procedure was the same as Compound 37

¹H NMR (DMSO-d₆) δ: 12.75 (s, 2H), 7.72 (b.s., 2H), 7.55-7.67 (m, 6H), 3.95 (s, 4H), 3.45-3.51 (m, 2H), 2.29 (t, J=5.6 Hz, 2H), 1.88-2.04 (m, 2H), 1.74-1.88 (m, 2H), 1.62 (m, 2H). LC-MS: m/z (M+H)=655.8.

N,N'-(5,5'-((1S,3S)-cyclohexane-1,3-diyl)bis(1,3,4-thiadiazole-5,2-diyl))bis(2-(3-(dimethylamino)phenyl)acetamide) (35)

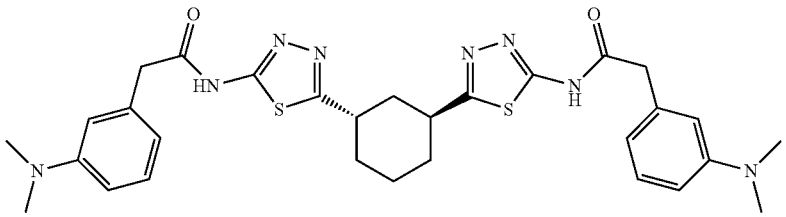

The procedure was the same as Compound 37

¹H NMR (DMSO-d₆) δ: 12.66 (s, 2H), 7.12 (t, J=7.9 Hz, 2H), 6.71 (s, 2H), 6.57-6.65 (m, 4H), 3.70 (s, 4H), 3.43-3.50 (m, 2H), 2.88 (s, 12H), 2.30 (d, J=5.1 Hz, 2H), 1.88-1.97 (m, 2H), 1.77-1.88 (m, 2H), 1.56-1.63 (m, 2H). LC-MS: m/z (M+H)=605.8.

N,N'-(5,5'-((1S,3S)-cyclohexane-1,3-diyl)bis(1,3,4-thiadiazole-5,2-diyl))bis(2-(2-fluorophenyl)acetamide) (87)

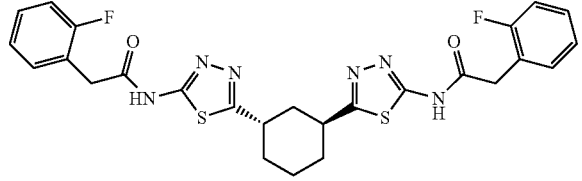 [SMILES: O=C(Cc1ccccc1F)Nc1nnc([C@H]2CCC[C@H](c3nnc(NC(=O)Cc4ccccc4F)s3)C2)s1]

The procedure was the same as Compound 37

¹H NMR (DMSO-d₆) δ: 12.75 (s, 2H), 7.32-7.42 (m, 4H), 7.15-7.22 (m, 4H), 3.90 (s, 4H), 3.44-3.54 (m, 2H), 2.30 (t, J=5.8 Hz, 2H), 1.89-1.98 (m, 2H), 1.80-1.89 (m, 2H), 1.59-1.67 (m, 2H). LC-MS: m/z (M+H)=555.7

N,N'-(5,5'-((1S,3S)-cyclohexane-1,3-diyl)bis(1,3,4-thiadiazole-5,2-diyl))bis(2-(2-isopropoxyphenyl)acetamide) (92)

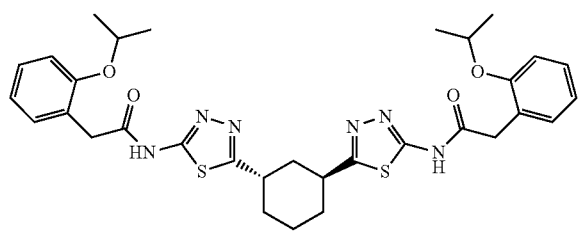 [SMILES: CC(C)Oc1ccccc1CC(=O)Nc1nnc([C@H]2CCC[C@H](c3nnc(NC(=O)Cc4ccccc4OC(C)C)s3)C2)s1]

The procedure was the same as Compound 37

¹H NMR (CHLOROFORM-d) δ: 10.35 (br. s., 2H), 7.26-7.28 (m, 4H), 7.22-7.28 (m, 4H), 6.91-6.94 (m, 4H), 4.73 (septet, J=6.0 Hz, 2H), 3.85 (s, 4H), 3.49-3.56 (m, 2H), 2.44 (t, J=4.8 Hz, 2H), 1.92-2.03 (m, 4H), 1.72-1.76 (m, 2H), 1.43 (d, J=5.9 Hz, 12H). LC-MS: m/z (M+H)=635.8

N,N'-(5,5'-((1S,3S)-cyclohexane-1,3-diyl)bis(1,3,4-thiadiazole-5,2-diyl))bis(2-(3-isopropoxyphenyl)acetamide) (91)

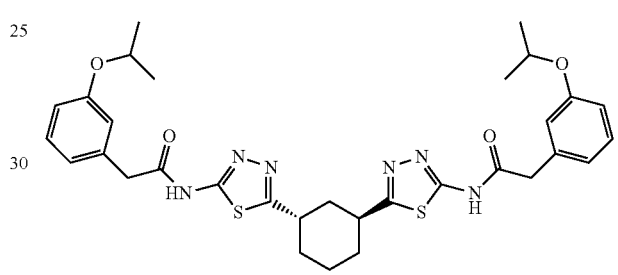

The procedure was the same as Compound 37

¹H NMR (CHLOROFORM-d) δ: 7.15-7.21 (m, 2H), 7.01-7.04 (m, 4H), 6.74-6.78 (m, 2H), 4.45-4.53 (m, 2H), 3.99 (s, 4H), 3.57-3.63 (m, 2H), 2.52 (t, J=4.8 Hz, 2H), 2.08 (m, 2H), 2.00-2.05 (m, 2H), 1.81 (m, 2H), 1.28 (d, J=6.2 Hz, 12H). LC-MS: m/z (M+H)=635.9

N,N'-(5,5'-((1S,3S)-cyclohexane-1,3-diyl)bis(1,3,4-thiadiazole-5,2-diyl))bis(2-(3-bromophenyl)acetamide) (220)

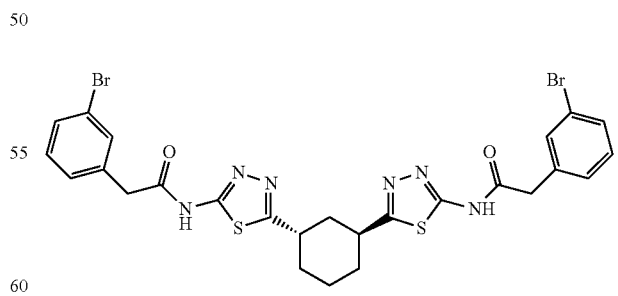

The procedure was the same as Compound 37

¹H NMR (CHLOROFORM-d) δ: 7.66 (s, 2H), 7.40 (d, J=7.8 Hz, 2H), 7.34-7.37 (m, 2H), 7.13-7.17 (m, 2H), 3.98 (s, 4H), 3.62 (m, 2H), 2.54 (t, J=5.0 Hz, 2H), 2.08 (m, 2H), 2.00-2.05 (m, 2H), 1.80 (m, 2H). LC-MS: m/z (M+H)=674.9

221

N,N'-(5,5'-((1S,3S)-cyclohexane-1,3-diyl)bis(1,3,4-thiadiazole-5,2-diyl))bis(2-m-tolylacetamide) (111)

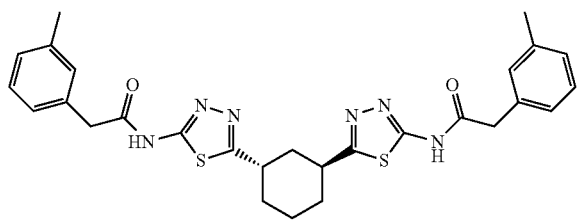 [SMILES: Cc1cccc(CC(=O)Nc2nnc([C@H]3CCC[C@H](c4nnc(NC(=O)Cc5cccc(C)c5)s4)C3)s2)c1]

The procedure was the same as Compound 37
$^1$H NMR (DMSO-d$_6$) δ: 12.72 (s, 2H), 7.23-7.25 (m, 2H), 7.14-7.17 (m, 6H), 3.84 (s, 4H), 3.45-3.50 (m, 2H), 2.30 (t, J=5.8 Hz, 2H), 2.26 (s, 6H), 1.88-1.96 (m, 2H), 1.81-1.88 (m, 2H), 1.58-1.64 (m, 2H). LC-MS: m/z (M+H)=547.7

N,N'-(5,5'-((1S,3S)-cyclohexane-1,3-diyl)bis(1,3,4-thiadiazole-5,2-diyl))bis(2-(2,3-dimethoxyphenyl)acetamide) (112)

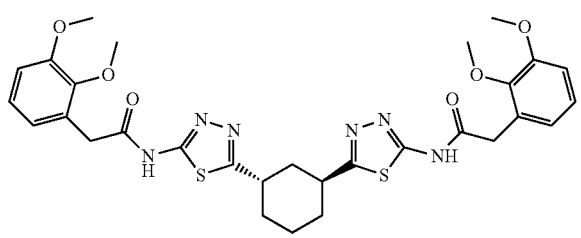 [SMILES: COc1cccc(CC(=O)Nc2nnc([C@H]3CCC[C@H](c4nnc(NC(=O)Cc5cccc(OC)c5OC)s4)C3)s2)c1OC]

The procedure was the same as Compound 37
$^1$H NMR (CHLOROFORM-d) δ: 7.00-7.05 (m, 2H), 6.88 (d, J=8.1 Hz, 2H), 6.91 (d, J=6.7 Hz, 2H), 3.99 (s, 4H), 3.86 (s, 12H), 3.48-3.55 (m, 2H), 2.41 (t, J=5.2 Hz, 2H), 1.87-2.01 (m, 4H), 1.68-1.76 (m, 2H). LC-MS: m/z (M+H)=639.8

N,N'-(5,5'-((1S,3S)-cyclohexane-1,3-diyl)bis(1,3,4-thiadiazole-5,2-diyl))bis(2-(6-methoxypyridin-3-yl)acetamide) (221)

222

The procedure was the same as Compound 37.
$^1$H NMR (DMSO-d$_6$) δ: 8.21 (s, 2H), 7.70 (dd, J=8.6, 2.1 Hz, 2H), 6.70 (d, J=8.3 Hz, 2H), 3.97 (s, 4H), 3.88 (s, 6H), 3.56-3.62 (m, 2H), 2.50 (t, J=5.4 Hz, 2H), 2.06 (m, 2H), 1.98 (m, 2H), 1.78 (m, 2H). LC-MS: m/z (M+H)=581.8

N,N'-(5,5'-((1S,3S)-cyclohexane-1,3-diyl)bis(1,3,4-thiadiazole-5,2-diyl))bis(2-(thiophen-2-yl)acetamide) (59)

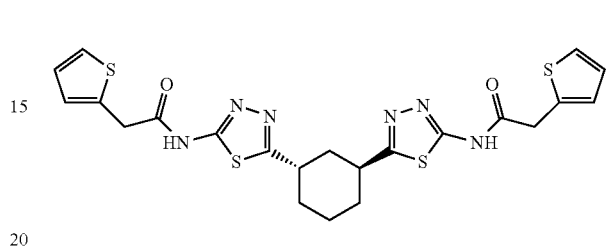

The procedure was the same as Compound 37
$^1$H NMR (DMSO-d$_6$) δ: 12.74 (br. s., 2H), 7.43 (d., 2H), 7.01 (br. s., 4H), 4.05 (s, 4H), 3.49 (m, 2H), 2.31 (br. s., 2H), 1.94 (m, 2H), 1.86 (m, 2H), 1.62 (m, 2H). LC-MS: m/z (M+H)=531.6

N,N'-(5,5'-((1S,3S)-cyclohexane-1,3-diyl)bis(1,3,4-thiadiazole-5,2-diyl))bis(2-(thiazol-4-yl)acetamide) (222)

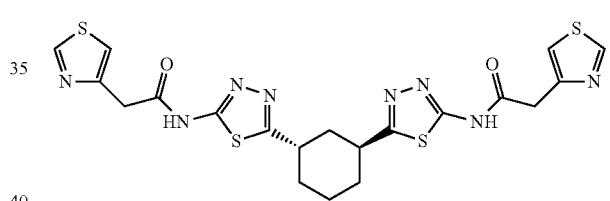

The procedure was the same as Compound 37
$^1$H NMR (CHLOROFORM-d) δ: 8.88 (d, J=1.9 Hz, 2H), 7.37-7.42 (d, J=1.9 Hz, 2H), 4.22 (s, 4H), 3.55-3.61 (m, 2H), 2.47 (t, J=5.4 Hz, 2H), 2.03 (d, J=5.4 Hz, 2H), 1.93-1.98 (m, 2H), 1.71-1.77 (m, 2H). LC-MS: m/z (M+H)=533.6

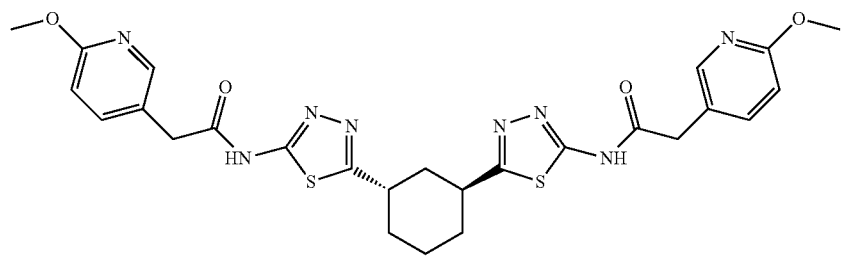

223

N,N'-(5,5'-((1S,3S)-cyclohexane-1,3-diyl)bis(1,3,4-thiadiazole-5,2-diyl))bis(2-(3-methylisoxazol-5-yl)acetamide) (30)

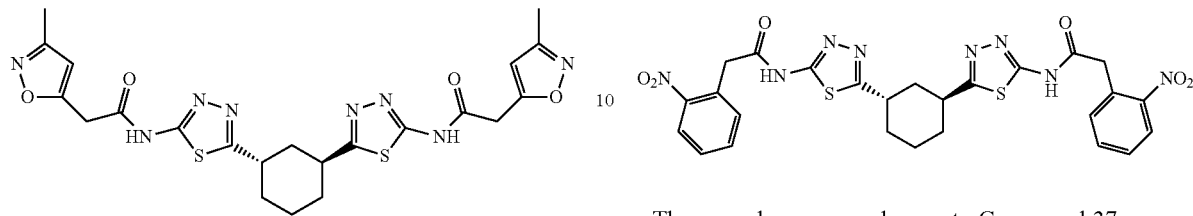

The procedure was the same as Compound 37

¹H NMR (CHLOROFORM-d) δ: 6.24 (s, 2H), 4.26 (s, 4H), 3.60 (s, 2H), 2.49 (t, J=4.8 Hz, 2H), 2.28 (s, 6H), 2.07 (m, 2H), 1.99 (m, 2H), 1.78 (m, 2H). LC-MS: m/z (M+H)= 529.7.

224

Step A: N,N'-(5,5'-((1S,3S)-cyclohexane-1,3-diyl)bis(1,3,4-thiadiazole-5,2-diyl))bis(2-(2-nitrophenyl)acetamide) (57)

The procedure was analogous to Compound 37

¹H NMR (DMSO-d₆) δ: 12.78 (s, 2H), 8.11 (d, J=7.6 Hz, 2H), 7.73-7.78 (m, 2H), 7.58-7.63 (m, 4H), 4.27 (s, 4H), 3.44-3.53 (m, 2H), 2.30 (t, J=5.7 Hz, 2H), 1.88-1.98 (m, 2H), 1.76-1.88 (m, 2H), 1.55-1.67 (m, 2H). LC-MS: m/z (M+H)=609.7

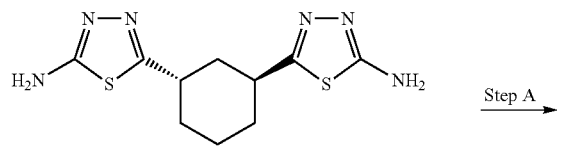

Step A →

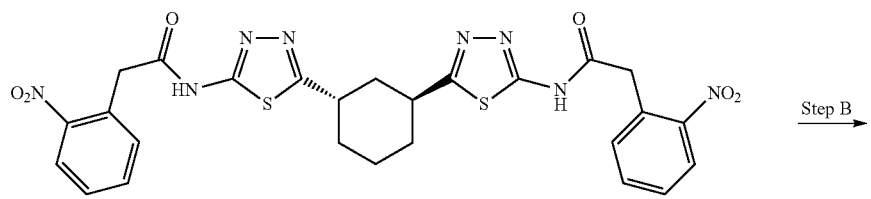

Compound 57

Step B →

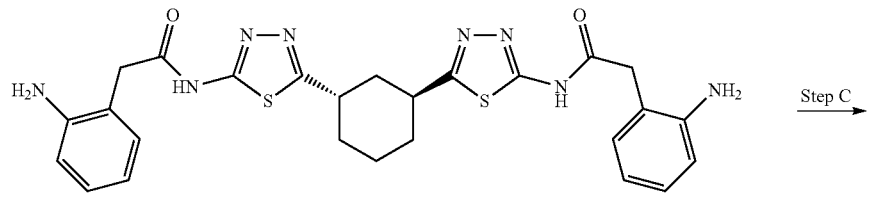

Compound 56

Step C →

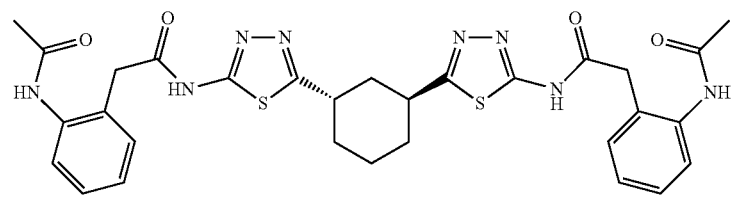

Compound 55

Step B: N,N'-(5,5'-((1S,3S)-cyclohexane-1,3-diyl)bis(1,3,4-thiadiazole-5,2-diyl))bis(2-(2-aminophenyl)acetamide) (56)

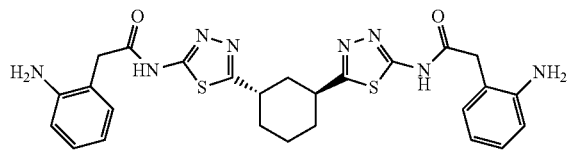 [SMILES: O=C(Cc1ccccc1[N+](=O)[O-])Nc1nnc([C@H]2CCC[C@H](c3nnc(NC(=O)Cc4ccccc4[N+](=O)[O-])s3)C2)s1]

The solution of N,N'-(5,5'-((1S,3S)-cyclohexane-1,3-diyl)bis(1,3,4-thiadiazole-5,2-diyl))bis(2-(3-nitrophenyl)acetamide) (30 mg, 0.05 mmol) and Pd/C (3 mg) in methanol was stirred at room temperature for 3 h. The mixture was filtered and evaporated in vacuum to dryness. The residue was purified by a standard method to afford desired compound.

$^1$H NMR (DMSO-$d_6$) δ: 12.58 (s, 2H), 7.01-7.07 (m, 2H), 6.94-7.00 (m, 2H), 6.66 (d, J=7.0 Hz, 2H), 6.50-6.57 (m, 2H), 5.03 (b, 4H), 3.65 (s, 4H), 3.45-3.50 (m, 2H), 2.30 (t, J=5.3 Hz, 2H), 1.90-2.00 (m, 2H), 1.79-1.88 (m, 2H), 1.57-1.64 (m, 2H). LC-MS: m/z (M+H)=549.7

Step C: N,N'-(5,5'-((1S,3S)-cyclohexane-1,3-diyl)bis(1,3,4-thiadiazole-5,2-diyl))bis(2-(2-acetamidophenyl)acetamide) (55)

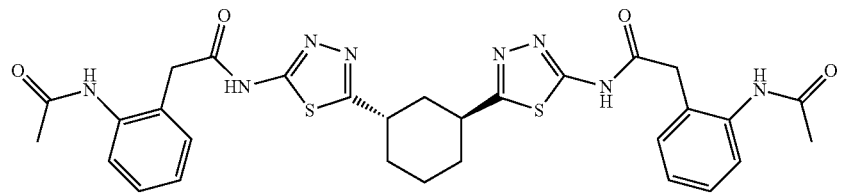 [SMILES: CC(=O)Nc1ccccc1CC(=O)Nc1nnc([C@H]2CCC[C@H](c3nnc(NC(=O)Cc4ccccc4NC(C)=O)s3)C2)s1]

A solution of acetic acid (11.5 mg, 0.19 mmol), HATU (72.6 mg, 0.19 mmol), and N-ethyl-N-isopropylpropan-2-amine (26.5 mg, 0.20 mmol) in N,N-dimethylformamide (2 ml) was stirred at room temperature for 15 min, then, N,N'-(5,5'-((1S,3S)-cyclohexane-1,3-diyl)bis(1,3,4-thiadiazole-5,2-diyl))bis(2-(2-aminophenyl)acetamide) (35 mg, 0.06 mmol) was added and continued to stir overnight. The mixture was poured into water (10 ml), the precipitate was filtered to give the crude product. The crude product was purified by a standard method to give the desired product.

$^1$H NMR (DMSO-$d_6$) δ: 12.61 (s, 2H), 9.45 (s, 2H), 7.38 (d, J=7.6 Hz, 2H), 7.23-7.32 (m, 4H), 7.11-7.20 (m, 2H), 3.83 (s, 4H), 3.47 (m, 2H), 2.30 (t, J=5.6 Hz, 2H), 2.03 (s, 6H), 1.94 (m, 2H), 1.84 (m, 2H), 1.62 (m, 2H). LC-MS: m/z (M+H)=633.7

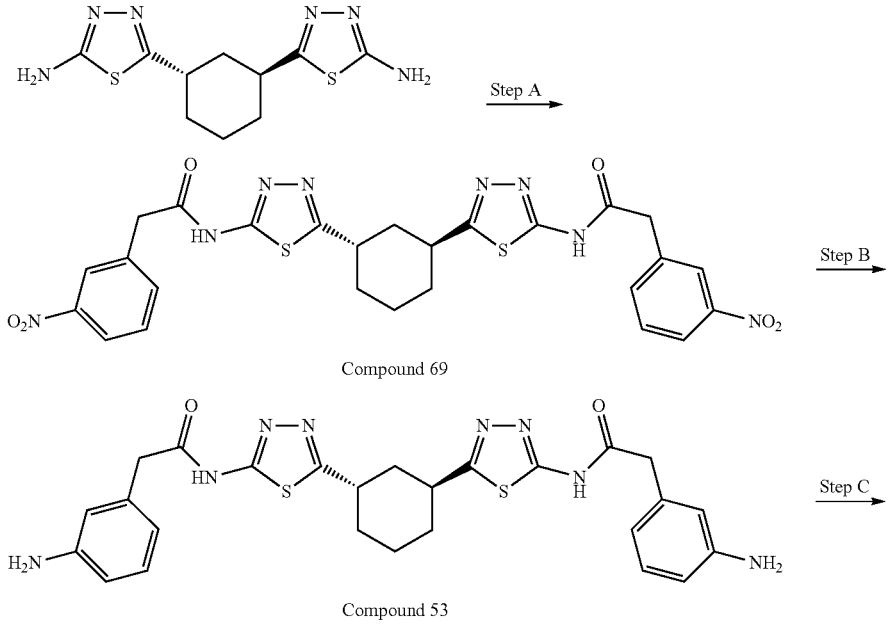

Compound 69

Compound 53

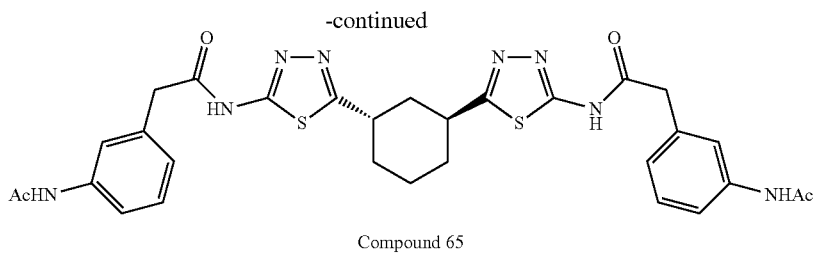

Compound 65

Step A: N,N'-(5,5'-((1S,3S)-cyclohexane-1,3-diyl) bis(1,3,4-thiadiazole-5,2-diyl))bis(2-(3-nitrophenyl) acetamide) (69)

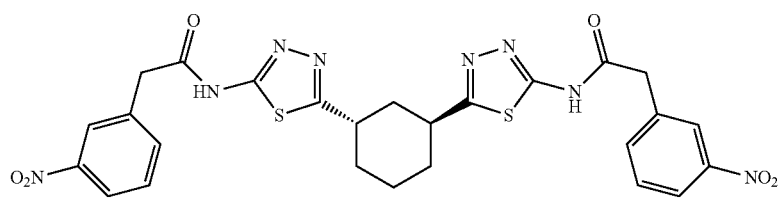 [SMILES: O=C(Cc1cccc([N+](=O)[O-])c1)Nc1nnc([C@H]2CCC[C@H](c3nnc(NC(=O)Cc4cccc([N+](=O)[O-])c4)s3)C2)s1]

The procedure was analogous to Compound 37

$^1$H NMR (DMSO-d$_6$) δ: 12.79 (s, 2H), 8.25 (s, 2H), 8.16 (d, J=8.3 Hz, 2H), 7.79 (d, J=7.5 Hz, 2H), 7.65 (t, J=7.9 Hz, 2H), 4.02 (s, 4H), 3.48 (m, 2H), 2.30 (d, J=5.4 Hz, 2H), 1.89-2.00 (m, 2H), 1.83 (m, 2H), 1.62 (m, 2H). LC-MS: m/z (M+H)=609.7

Step B: N,N'-(5,5'-((1S,3S)-cyclohexane-1,3-diyl) bis(1,3,4-thiadiazole-5,2-diyl))bis(2-(3-aminophenyl)acetamide) (53)

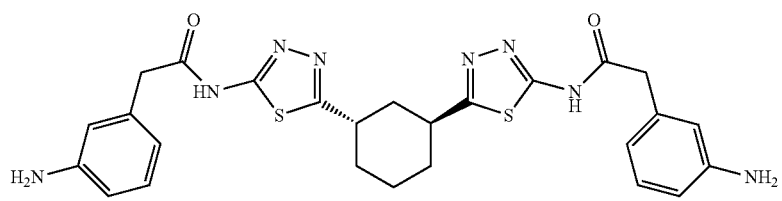

The procedure was the same as Compound 56

$^1$H NMR (DMSO-d$_6$) δ: 12.64 (s, 2H), 6.95 (t, J=7.8 Hz, 2H), 6.51 (s, 2H), 6.40-6.47 (m, 4H), 5.07 (s, 4H), 3.61 (s, 4H), 3.48 (m, 2H), 2.30 (t, J=5.6 Hz, 2H), 1.92 (m, 2H), 1.75-1.88 (m, 2H), 1.62 (m, 2H). LC-MS: m/z (M+H)=549.7

Step C: N,N'-(5,5'-((1S,3S)-cyclohexane-1,3-diyl)bis(1,3,4-thiadiazole-5,2-diyl))bis(2-(3-acetamidophenyl)acetamide) (65)

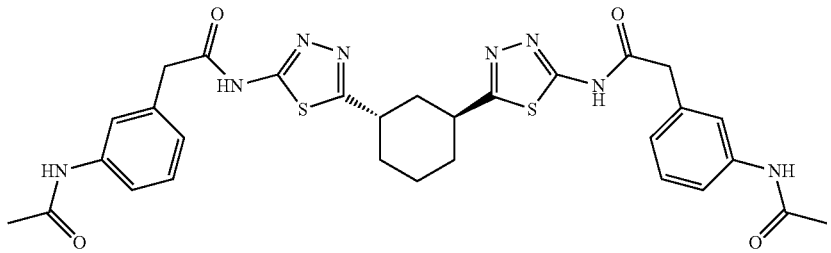 [SMILES: CC(=O)Nc1cccc(CC(=O)Nc2nnc([C@H]3CCC[C@H](c4nnc(NC(=O)Cc5cccc(NC(C)=O)c5)s4)C3)s2)c1]

The procedure was the same as Compound 55

¹H NMR (DMSO-d₆) δ: 12.73 (s, 2H), 9.94 (s, 2H), 7.54 (s, 2H), 7.50 (d, J=8.1 Hz, 2H), 7.24 (t, J=7.8 Hz, 2H), 6.94-7.03 (d, J=7.5 Hz, 2H), 3.76 (s, 4H), 3.43-3.52 (m, 2H), 2.30 (t, J=5.6 Hz, 2H), 2.03 (s, 6H), 1.90-1.98 (m, 2H), 1.77-1.89 (m, 2H), 1.57-1.65 (m, 2H). LC-MS: m/z (M+H)=633.8

N,N'-(5,5'-((1S,3S)-cyclohexane-1,3-diyl)bis(1,3,4-thiadiazole-5,2-diyl))bis(2-(4-nitrophenyl)acetamide) (64)

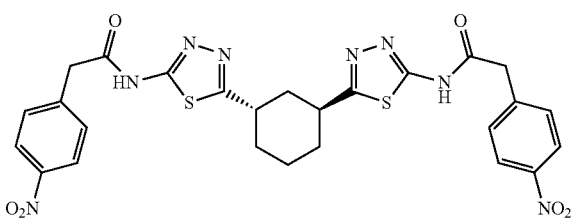 [SMILES: O=C(Cc1ccc([N+](=O)[O-])cc1)Nc1nnc([C@H]2CCC[C@H](c3nnc(NC(=O)Cc4ccc([N+](=O)[O-])cc4)s3)C2)s1]

The procedure was the same as Compound 37

¹H NMR (DMSO-d₆) δ: 12.81 (s, 2H), 8.20 (d, J=8.6 Hz, 4H), 7.61 (d, J=8.6 Hz, 4H), 4.01 (s, 4H), 3.40-3.55 (m, 2H), 2.29 (t, J=5.6 Hz, 2H), 1.89-1.99 (m, 2H), 1.77-1.88 (m, 2H), 1.55-1.66 (m, 2H). LC-MS: m/z (M+H)=609.7.

N,N'-(5,5'-((1S,3S)-cyclohexane-1,3-diyl)bis(1,3,4-thiadiazole-5,2-diyl))bis(2-(4-acetamidophenyl)acetamide) (106)

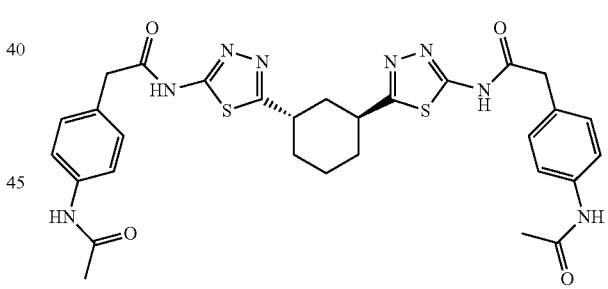

The procedure was the same as Compound 55

¹H NMR (DMSO-d₆) δ: 12.67 (s, 2H), 9.93 (s, 2H), 7.52 (d, J=8.6 Hz, 4H), 7.23 (d, J=8.3 Hz, 4H), 3.74 (s, 4H), 3.44-3.49 (m, 2H), 2.29 (t, J=5.5 Hz, 2H), 2.03 (s, 6H), 1.90-1.97 (m, 2H), 1.76-1.86 (m, 2H), 1.51-1.65 (m, 2H). LC-MS: m/z (M+H)=633.8.

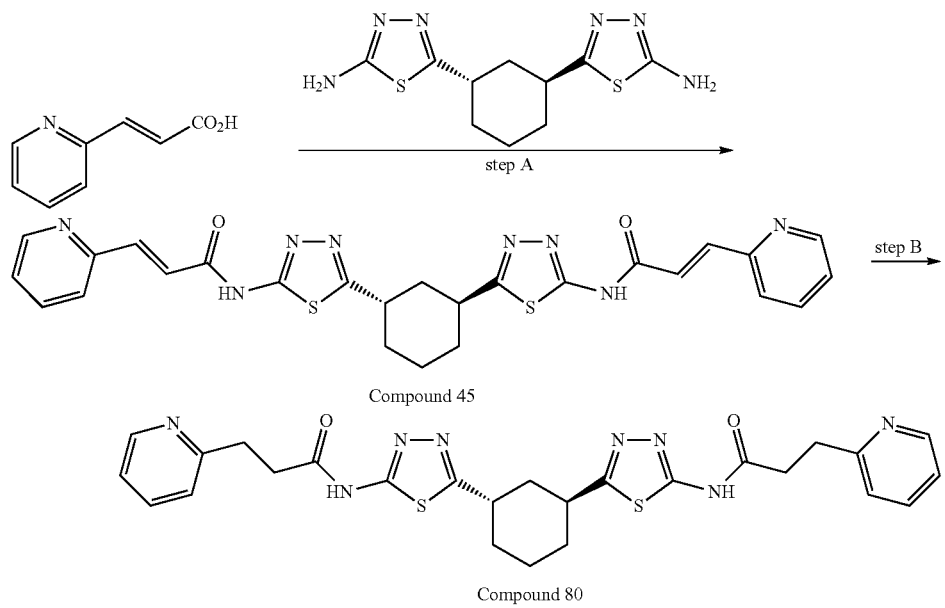
Step A: (2E,2'E)-N,N'-(5,5'-((1S,3S)-cyclohexane-1,3-diyl)bis(1,3,4-thiadiazole-5,2-diyl))bis(3-(pyridin-2-yl)acrylamide) (45)
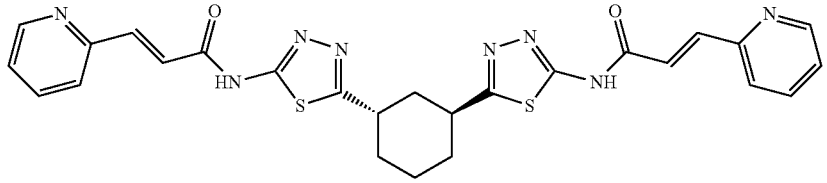 [SMILES: O=C(/C=C/c1ccccn1)Nc1nnc([C@H]2CCC[C@H](c3nnc(NC(=O)/C=C/c4ccccn4)s3)C2)s1]
The procedure was the same as Compound 37
$^1$H NMR (DMSO-$d_6$) δ: 12.88 (s, 2H), 8.69 (d, J=4.7 Hz, 2H), 7.90 (td, J=7.8, 1.8 Hz, 2H), 7.79 (d, J=15.4 Hz, 2H), 7.70 (d, J=7.8 Hz, 2H), 7.44 (dd, J=7.1, 5.2 Hz, 2H), 7.38 (d, J=15.4 Hz, 2H), 3.52-3.59 (m, 2H), 2.37 (t, J=5.4 Hz, 2H), 1.96-2.05 (m, 2H), 1.88-1.96 (m, 2H), 1.64-1.71 (m, 2H); LC-MS: m/z (M+H)=545.7.
Step B: N,N'-(5,5'-((1S,3S)-cyclohexane-1,3-diyl)bis(1,3,4-thiadiazole-5,2-diyl))bis(3-(pyridin-2-yl)propanamide) (80)
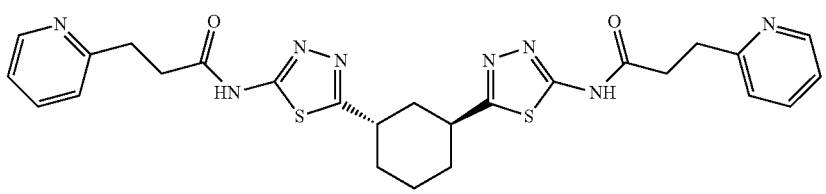 [SMILES: O=C(CCc1ccccn1)Nc1nnc([C@H]2CCC[C@H](c3nnc(NC(=O)CCc4ccccn4)s3)C2)s1]

A solution of 50 mg of Compound 45 was dissolved in 2 mL MeOH. 5 mg Pd/C was added and the suspension was degassed and hydrogenated for 30 min. It was then filtered and concentrated to get the title compound 80.

$^1$H NMR (CHLOROFORM-d) δ: 8.59 (d, J=4.6 Hz, 2H), 7.64 (td, J=7.7, 1.4 Hz, 2H), 7.27 (d, J=7.7 Hz 2H), 7.18 (dd, J=7.3, 5.1 Hz, 2H), 3.55 (d, J=5.6 Hz, 2H), 3.27-3.32 (m, 4H), 3.11-3.17 (m, 4H), 2.43 (t, J=5.4 Hz, 2H), 1.94-2.03 (m, 4H), 1.74 (m, 2H). LC-MS: m/z (M+H)=549.7.

Compounds 291, 292, 295, 370, 371, 380, and 352 were prepared in an analogous manner to Compound 37:

N,N'-(5,5'-((1S,3S)-cyclopentane-1,3-diyl)bis(1,3,4-thiadiazole-5,2-diyl))bis(2-(2-methoxyphenyl)acetamide) (291)

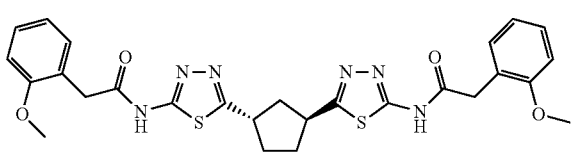 [SMILES: COc1ccccc1CC(=O)Nc1nnc([C@H]2CC[C@H](c3nnc(NC(=O)Cc4ccccc4OC)s3)C2)s1]

$^1$H NMR (DMSO-d$_6$) δ: 7.14-7.32 (m, 4H), 6.85-7.03 (m, 4H), 3.54-3.83 (m, 12H), 2.39 (t, J=7.7 Hz, 2H), 2.32 (m, 2H), 1.99 (m, 2H). LC-MS: m/z (M+H)=565.5

N,N'-(5,5'-((1S,3S)-cyclopentane-1,3-diyl)bis(1,3,4-thiadiazole-5,2-diyl))bis(2-(3-(dimethylamino)phenyl)acetamide) (292)

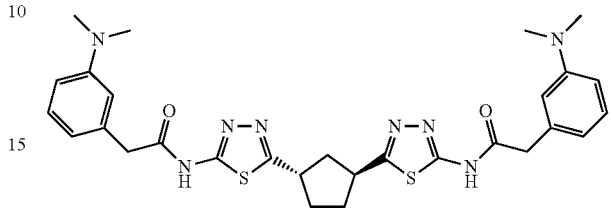

$^1$H NMR (DMSO-d$_6$) δ: 12.66 (br. s., 2H), 7.11 (t, J=7.8 Hz, 2H), 6.70 (s, 2H), 6.61 (t, J=6.0 Hz, 4H), 3.72-3.82 (m, 6H), 2.88 (s, 12H), 2.38 (t, J=7.7 Hz, 2H), 2.29 (m, 2H), 1.93 (m, 2H). LC-MS: m/z (M+H)=591.5

N,N'-(5,5'-((1S,3S)-cyclopentane-1,3-diyl)bis(1,3,4-thiadiazole-5,2-diyl))bis(2-(6-methoxypyridin-3-yl)acetamide) (295)

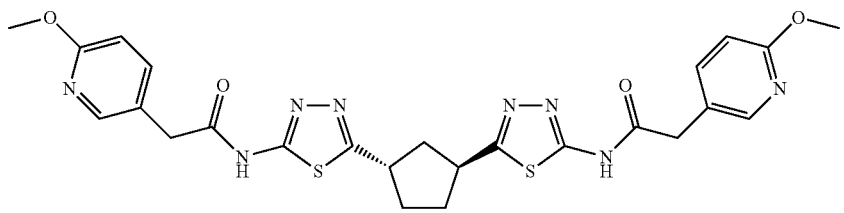

$^1$H NMR (DMSO-d$_6$) δ: 12.71 (s, 2H), 8.09 (d, J=1.9 Hz, 2H), 7.65 (dd, J=8.6, 2.4 Hz, 2H), 6.80 (d, J=8.6 Hz, 2H), 3.83 (s, 6H), 3.77 (s, 4H), 3.74 (m, 2H), 2.38 (t, J=7.8 Hz, 2H), 2.24-2.34 (m, 2H), 1.89-2.02 (m, 2H). LC-MS: m/z (M+H)=567.8

(2R,2'R)—N,N'-(5,5'-((1S,3S)-cyclohexane-1,3-diyl)bis(1,3,4-thiadiazole-5,2-diyl))bis(2-hydroxy-2-phenylacetamide) (370)

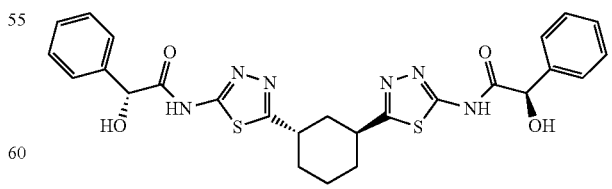

$^1$H NMR (CHLOROFORM-d) δ: 7.51 (d, J=6.2 Hz, 4H), 7.19-7.34 (m, 6H), 5.55 (s, 2H), 3.51 (s, 2H), 2.32 (t, J=5.5 Hz, 2H), 1.95 (m, 2H), 1.88 (m, 2H), 1.63 (m, 2H); LC-MS: m/z (M+H)=551.2

(2R,2'S)—N,N'-(5,5'-((1S,3S)-cyclohexane-1,3-diyl)bis(1,3,4-thiadiazole-5,2-diyl))bis(2-hydroxy-2-phenylacetamide) (371)

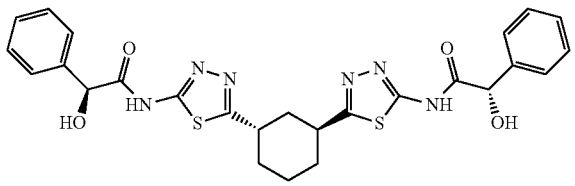 [SMILES: O=C(Nc1nnc([C@H]2CCC[C@H](c3nnc(NC(=O)[C@@H](O)c4ccccc4)s3)C2)s1)[C@@H](O)c1ccccc1]

¹H NMR (CHLOROFORM-d) δ: 7.50 (d, J=5.6 Hz, 4H), 7.24-7.33 (m, 6H), 5.55 (s, 2H), 3.53 (m, 2H), 2.36 (t, J=5.5 Hz, 2H), 1.95 (m, 2H), 1.86 (m, 2H), 1.65 (m, 2H); LC-MS: m/z (M+H)=551.5

N,N'-(5,5'-((1S,3S)-cyclohexane-1,3-diyl)bis(1,3,4-thiadiazole-5,2-diyl))bis(3-hydroxy-2-phenylpropanamide) (380)

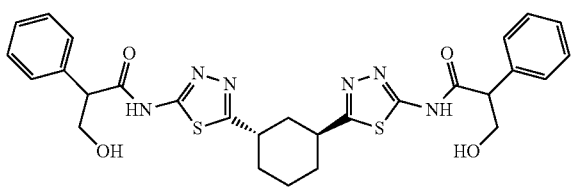 [SMILES: O=C(Nc1nnc([C@H]2CCC[C@H](c3nnc(NC(=O)C(CO)c4ccccc4)s3)C2)s1)C(CO)c1ccccc1]

¹H NMR (CHLOROFORM-d) δ: 7.39 (m, 4H), 7.20 (m, 6H), 4.39 (m, 2H), 4.31 (m, 2H), 3.91 (m, 2H), 3.72 (m, 2H), 2.50 (t, J=5.5 Hz, 2H), 2.08 (m, 2H), 1.96 (m, 2H), 1.78 (m, 2H); LC-MS: m/z (M+H)=579.2

N,N'-(5,5'-((1S,3S)-cyclohexane-1,3-diyl)bis(1,3,4-thiadiazole-5,2-diyl))bis(2-(3-cyanophenyl)acetamide) (352)

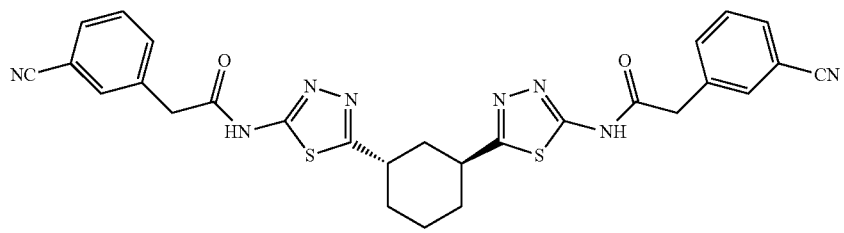 [SMILES: N#Cc1cccc(CC(=O)Nc2nnc([C@H]3CCC[C@H](c4nnc(NC(=O)Cc5cccc(C#N)c5)s4)C3)s2)c1]

¹H NMR (DMSO-d₆) δ: 12.76 (s, 2H), 7.79 (s, 2H), 7.76 (d, J=7.8 Hz, 2H), 7.65-7.69 (d, J=7.8 Hz, 2H), 7.56 (t, J=7.8 Hz, 2H), 3.92 (s, 4H), 3.40-3.55 (m, 2H), 2.29 (t, J=5.5 Hz, 2H), 1.89-2.01 (m, 2H), 1.73-1.89 (m, 2H), 1.50-1.67 (m, 2H). LC-MS: m/z (M+H)=569.5

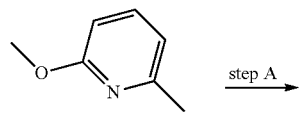 step A →

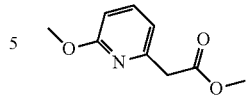 + 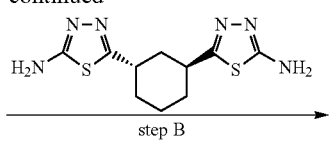 → step B

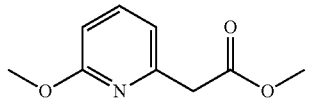

Compound 84

Step A: methyl 2-(6-methoxypyridin-2-yl)acetate

To the solution of LDA (18.3 mL, 36.5 mmol) in THF (120 mL) cooled to −78° C. was added 2-methoxy-6-methylpyridine (1.5 g, 12.2 mmol) in THF (15 mL) dropwise, and then the mixture was stirred at −78 degree for 2 h. Dimethyl carbonate (1.2 mL, 14.6 mmol) was added quickly and continued to stir at −78° C. for 15 min. The reaction was quenched by H₂O at −78° C. The solution was extracted with ethyl acetate, dried over sodium sulfate and evaporated under reduced pressure. The residue was purified with a standard method to give desired compound.

¹H NMR (CHLOROFORM-d) δ: 7.55 (dd, J=8.3, 7.3 Hz, 1H), 6.85 (d, J=7.3 Hz, 1H), 6.65 (d, J=8.3 Hz, 1H), 3.92 (s, 3H), 3.77 (s, 2H), 3.74 (s, 3H). LC-MS: m/z (M+H)=182.6.

Step B: N,N'-(5,5'-((1S,3S)-cyclohexane-1,3-diyl)bis(1,3,4-thiadiazole-5,2-diyl))bis(2-(6-methoxypyridin-2-yl)acetamide) (84)

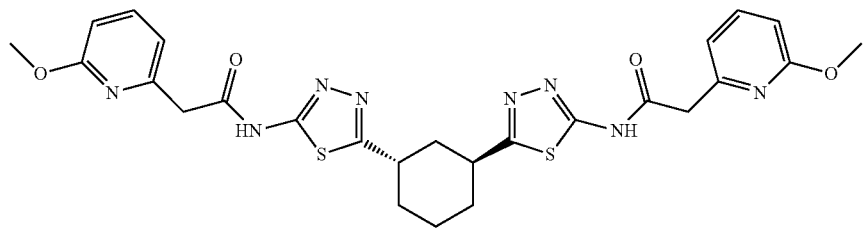

A mixture of methyl 2-(6-methoxypyridin-2-yl)acetate (128.7 mg, 0.71 mmol), 5,5'-((1S,3S)-cyclohexane-1,3-diyl)bis(1,3,4-thiadiazol-2-amine) (50 mg, 0.18 mmol), cesium carbonate (346.1 mg, 1.06 mmol) in DMF (3 mL) was heated to 130° C. under nitrogen atmosphere and microwave for 45 min. The mixture was evaporated in vacuum to dryness. The residue was purified by a standard method to afford desired compound.

$^1$H NMR (DMSO-d$_6$) δ: 12.70 (s, 2H), 7.60-7.76 (m, 2H), 6.98 (d, J=7.3 Hz, 2H), 6.72 (d, J=8.1 Hz, 2H), 3.92 (s, 4H), 3.79 (s, 6H), 3.49 (m, J=6.2 Hz, 2H), 2.32 (t, J=6.2 Hz, 2H), 1.94 (m, 2H), 1.85 (m, 2H), 1.63 (m, 2H). LC-MS: m/z (M+H)=581.7.

-continued

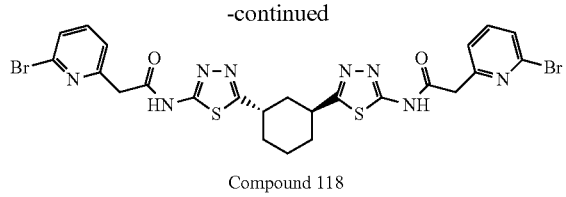

Compound 118

The procedure was the same as Compound 84

Step A: methyl 2-(6-bromopyridin-2-yl)acetate

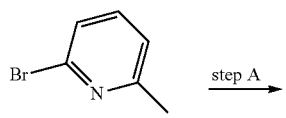 step A →

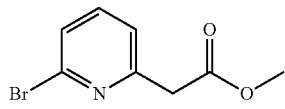

$^1$H NMR (CHLOROFORM-d) δ: 7.55 (t, J=7.7 Hz, 1H), 7.42 (d, J=7.8 Hz, 1H), 7.30 (d, J=7.5 Hz, 1H), 3.86 (s, 2H), 3.75 (s, 3H). LC-MS: m/z (M+H)=230.2

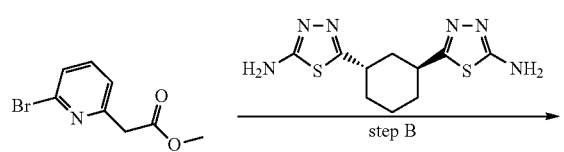

Step B: N,N'-(5,5'-((1S,3S)-cyclohexane-1,3-diyl)bis(1,3,4-thiadiazole-5,2-diyl))bis(2-(6-bromopyridin-2-yl)acetamide) (118)

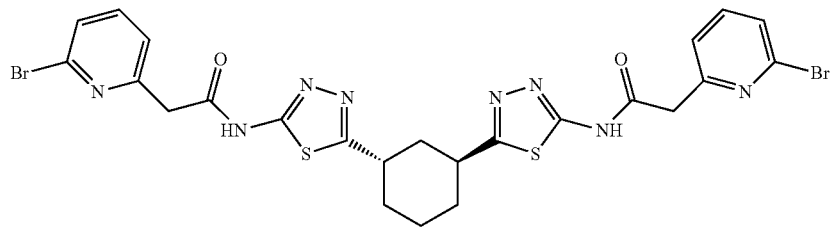 [SMILES: O=C(Cc1cccc(Br)n1)Nc1nnc([C@H]2CCC[C@H](c3nnc(NC(=O)Cc4cccc(Br)n4)s3)C2)s1]

¹H NMR (DMSO-d₆) δ: 7.71-7.82 (m, 2H), 7.58 (s, 2H), 7.47 (d, J=7.5 Hz, 2H), 4.03 (s, 4H), 3.50 (m, 2H), 2.32 (t, J=6.4 Hz, 2H), 1.84-1.99 (m, 4H), 1.63 (m, 2H). LC-MS: m/z (M+H)=677.6.

Compound 223

The procedure was the same as Compound 84

Step A: Methyl 2-(4-methoxypyridin-2-yl)acetate

¹HNMR (CHLOROFORM-d) δ 8.38 (d, J=6.0 Hz, 1H), 6.83 (d, J=2.4 Hz, 1H), 6.73 (dd, J=6.0 Hz, 2.4 Hz, 1H), 3.85 (s, 3H), 3.81 (s, 2H), 3.73 (s, 3H). LC-MS: m/z 182.3 (M+H)

Step B: N,N'-(5,5'-((1S,3S)-cyclohexane-1,3-diyl)bis(1,3,4-thiadiazole-5,2-diyl))bis(2-(4-methoxypyridin-2-yl)acetamide) (223)

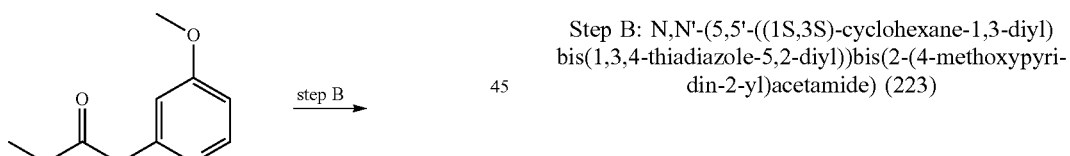

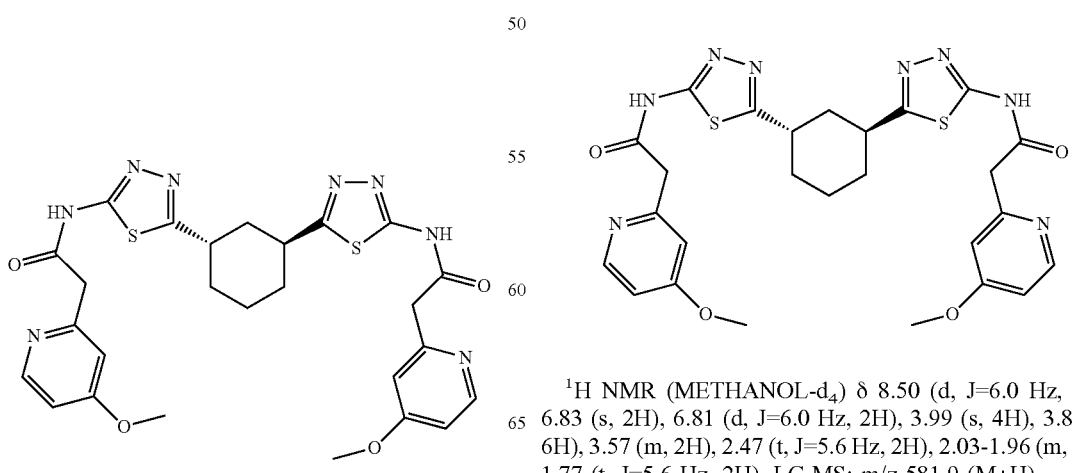

¹H NMR (METHANOL-d₄) δ 8.50 (d, J=6.0 Hz, 2H), 6.83 (s, 2H), 6.81 (d, J=6.0 Hz, 2H), 3.99 (s, 4H), 3.88 (s, 6H), 3.57 (m, 2H), 2.47 (t, J=5.6 Hz, 2H), 2.03-1.96 (m, 4H), 1.77 (t, J=5.6 Hz, 2H). LC-MS: m/z 581.9 (M+H)

Compound 224
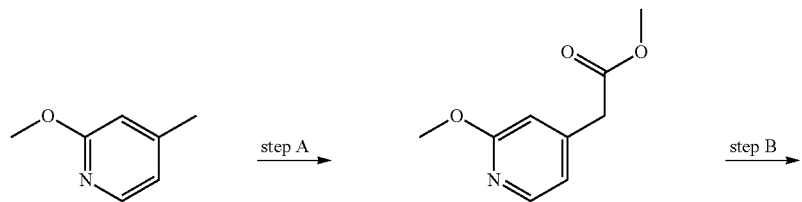
The procedure was the same as Compound 84
Step B: 2-(2-methoxypyridin-4-yl)-N-[5-[(1S,3S)-3-[5-[[2-(2-methoxypyridin-4-yl)acetyl]amino]-1,3,4-thiadiazol-2-yl]cyclohexyl]-1,3,4-thiadiazol-2-yl]acetamide (224)
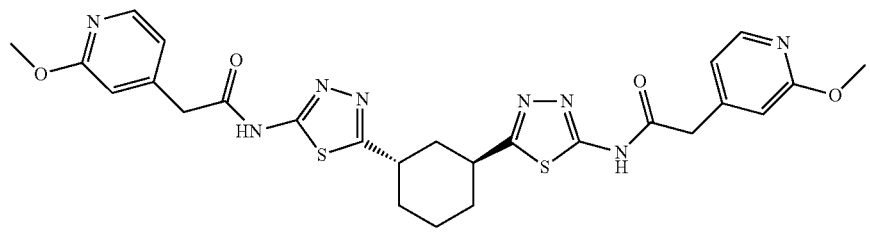
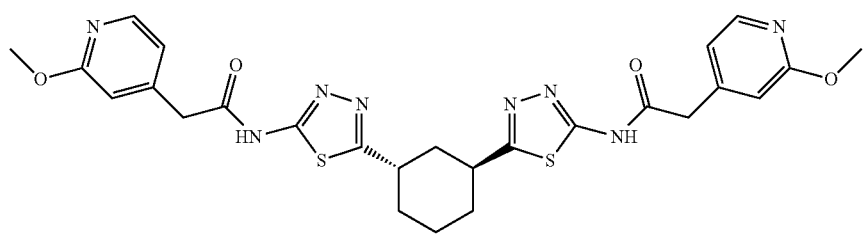

¹H NMR (CHLOROFORM-d) δ: 8.11 (d, J=5.1 Hz, 2H), 7.02 (d, J=4.6 Hz, 2H), 6.91 (s, 2H), 4.01 (s, 4H), 3.89 (s, 6H), 3.58-3.67 (m, 2H), 2.52 (t, J=6.4 Hz, 2H), 2.08 (m, 2H), 1.99-2.04 (m, 2H), 1.76-1.84 (m, 2H). LC-MS: m/z (M+H)= 581.4

N,N'-(5,5'-trans-cyclohexane-1,3-diyl)bis(1,3,4-thiadiazole-5,2-diyl))bis(2-(3-methoxypyridin-2-yl)acetamide) (116)

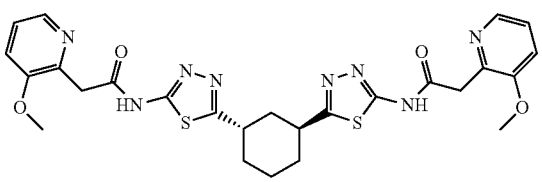 [SMILES: COc1cccnc1CC(=O)Nc1nnc([C@H]2CCC[C@H](c3nnc(NC(=O)Cc4ncccc4OC)s3)C2)s1]

The procedure was the same as Step B of Compound 84

¹H NMR (METHANOL-d4) δ: 8.08 (dd, J=4.8, 1.1 Hz, 2H), 7.46 (dd, J 8.3, 1.1 Hz, 2H), 7.36 (dd, J=8.6, 4.8 Hz, 2H), 3.94 (s, 4H), 3.49-3.60 (m, 2H), 2.43 (t, J=5.8 Hz, 2H), 2.01-2.11 (m, 2H), 1.89-1.98 (m, 2H), 1.67-1.80 (m, 2H). LC-MS: m/z (M+H)=581.7

N,N'-(5,5'-((1S,3S)-cyclohexane-1,3-diyl)bis(1,3,4-thiadiazole-5,2-diyl))bis(2-(5-methoxypyridin-2-yl)acetamide) (225)

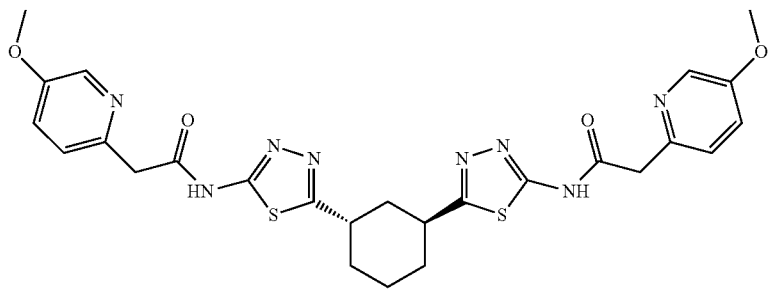 [SMILES: COc1ccc(CC(=O)Nc2nnc([C@H]3CCC[C@H](c4nnc(NC(=O)Cc5ccc(OC)cn5)s4)C3)s2)nc1]

The procedure was the same as Step B of Compound 84

¹H NMR (CHLOROFORM-d) δ: 8.27 (d, J=3.0 Hz, 2H), 7.24-7.40 (d, J=8.6 Hz, 2H), 7.17 (dd, J=8.6, 3.0 Hz, 2H), 4.09 (s, 4H), 3.83 (s, 6H), 3.55 (m, 2H), 2.48 (t, J=5.6 Hz, 2H), 1.85-2.09 (m, 4H), 1.62-1.78 (m, 2H). LC-MS: m/z (M+H)=581.7

Compound 226

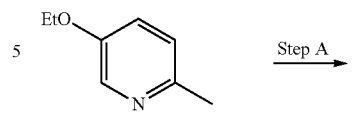

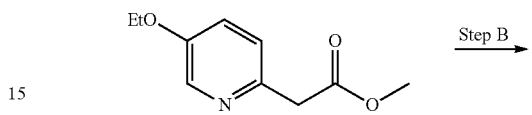

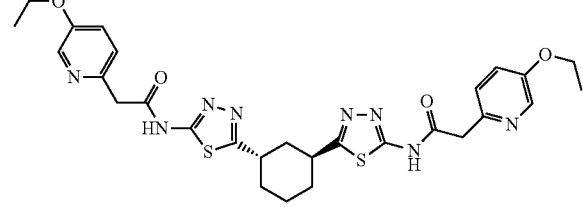

The procedure was the same as Compound 84

Step A: methyl 2-(5-ethoxypyridin-2-yl)acetate

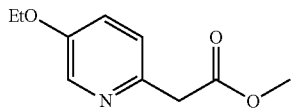

¹H NMR (CHLOROFORM-d) δ: 8.24 (m, 1H), 7.09-7.27 (m, 2H), 4.07 (q, J=7.0 Hz, 2H), 3.80 (s, 2H), 3.72 (s, 3H), 1.44 (t, J=7.0 Hz, 4H). LC-MS: m/z (M+H)=196.3

Step B: N,N'-(5,5'-((1S,3S)-cyclohexane-1,3-diyl) bis(1,3,4-thiadiazole-5,2-diyl))bis(2-(5-ethoxypyridin-2-yl)acetamide) (226)

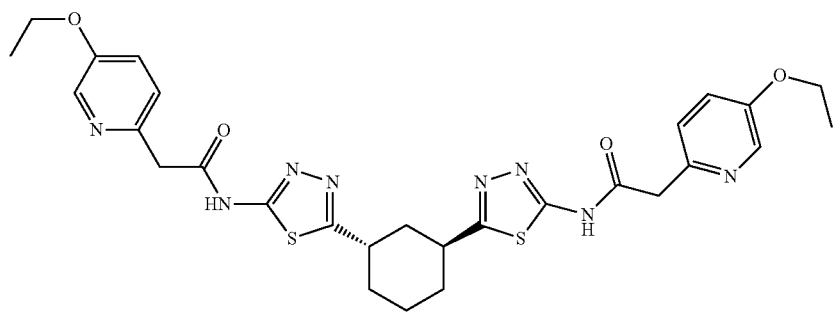 [SMILES: CCOc1ccc(CC(=O)Nc2nnc([C@H]3CCC[C@H](c4nnc(NC(=O)Cc5ccc(OCC)cn5)s4)C3)s2)nc1]

¹H NMR (CHLOROFORM-d) δ: 8.28 (d, J=2.7 Hz, 2H), 7.23-7.33 (d, J=5.1 Hz, 2H), 7.09-7.22 (dd, J=2.7 Hz, 5.1 Hz, 2H), 3.96-4.19 (m, 8H), 3.51-3.61 (m, 2H), 2.45 (t, J=5.4 Hz, 2H), 1.90-2.07 (m, 4H), 1.74 (m, 2H), 1.33-1.49 (t, J=7.0 Hz, 6H). LC-MS: m/z (M+H)=609.2

Compound 227

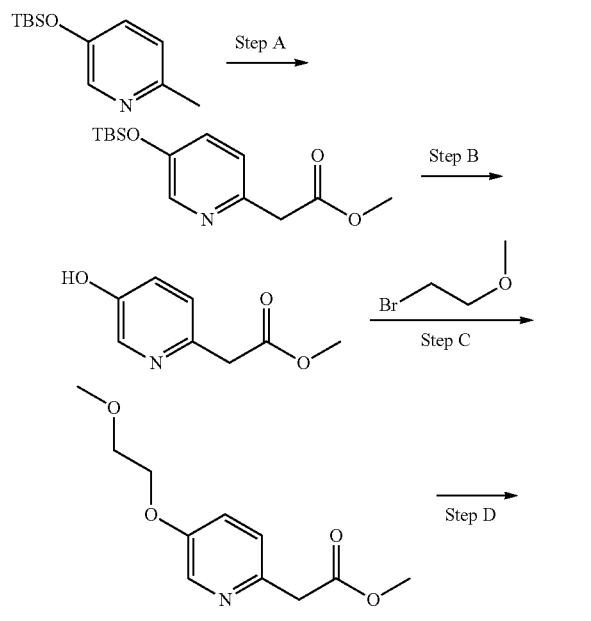

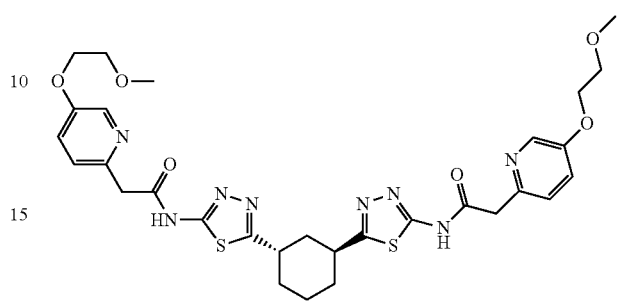

Step A: methyl 2-(5-((tert-butyldimethylsilyl)oxy)pyridin-2-yl)acetate

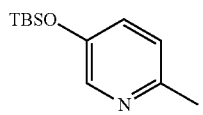

The procedure was the same as Step A of Compound 84

Step B: methyl 2-(5-hydroxypyridin-2-yl)acetate

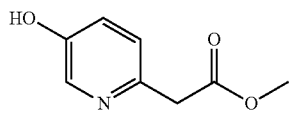

To the stirred solution of methyl 2-(5-((tert-butyldimethylsilyl)oxy)pyridin-2-yl)acetate (1 g, 3.5 mmol) in THF was added TBAF (1M, 3.5 ml) at room temperature. The whole mixture was stirred at room temperature overnight. It was evaporated and extracted with EtOAc, the organic layer was washed with water, evaporated and purified by a standard method.

¹H NMR (CHLOROFORM-d) δ: 8.18 (s, 1H), 7.23-7.32 (m, 2H), 3.84 (s, 2H), 3.70 (s, 3H). LC-MS: m/z (M+H)=168.2

247

Step C: methyl 2-(5-(2-methoxyethoxyl)pyridin-2-yl)acetate

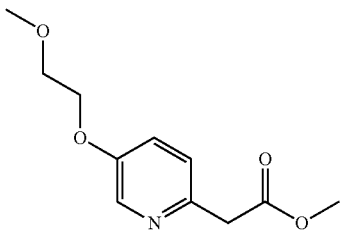

To a stirred solution of methyl 2-(5-((tert-butyldimethylsilyl)oxy)pyridin-2-yl)acetate (500 mg, 3 mmol) in MeCN was added Cs$_2$CO$_3$ (1.4 g, 4.5 mmol) followed by 1-bromo-2-methoxyethane (621 mg, 4.5 mmol) at room temperature. The whole mixture was heated to 80° overnight. LC-MS showed desired product. It was filtered, evaporated and purified by a standard method.

$^1$H NMR (CHLOROFORM-d) δ: 8.28 (s, 1H), 7.22 (d, J=1.9 Hz, 2H), 4.16 (dd, J=5.5, 3.9 Hz, 2H), 3.80 (s, 2H), 3.74-3.78 (dd, J=5.5, 3.9 Hz, 2H), 3.72 (s, 3H), 3.46 (s, 3H). LC-MS: m/z (M+H)=226.2

248

Step D: N,N'-(5,5'-((1S,3S)-cyclohexane-1,3-diyl)bis(1,3,4-thiadiazole-5,2-diyl))bis(2-(5-(2-methoxyethoxyl)pyridin-2-yl)acetamide) (227)

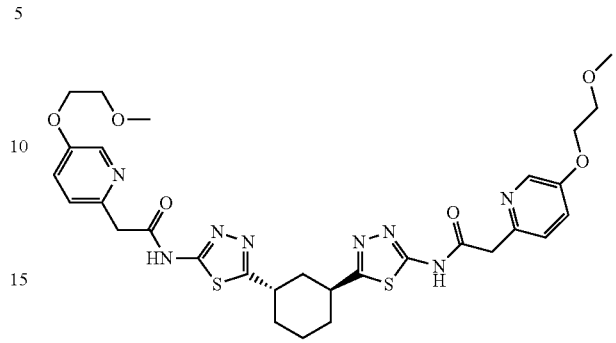

The procedure was the same as Step B of Compound 84

$^1$H NMR (CHLOROFORM-d) δ: 8.40 (d, J=2.4 Hz, 2H), 7.21-7.25 (dd, J=8.6, 2.4 Hz, 2H), 7.19 (d, J=8.9 Hz, 2H), 4.17-4.23 (t, J=4.0 Hz, 4H), 3.97 (s., 4H), 3.76-3.83 (t, J=4.0 Hz, 4H), 3.54 (m, 2H), 3.48 (s, 6H), 2.48 (t, J=5.6 Hz, 2H), 1.95-2.09 (m, 4H), 1.77 (m, 2H). LC-MS: m/z (M+H)=669.2 Compound 228

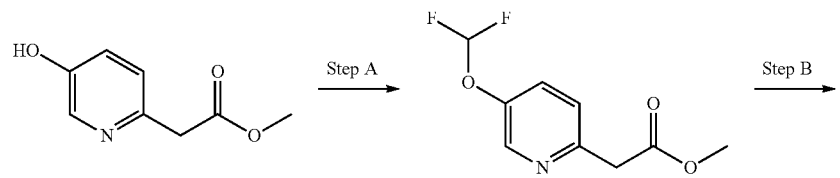

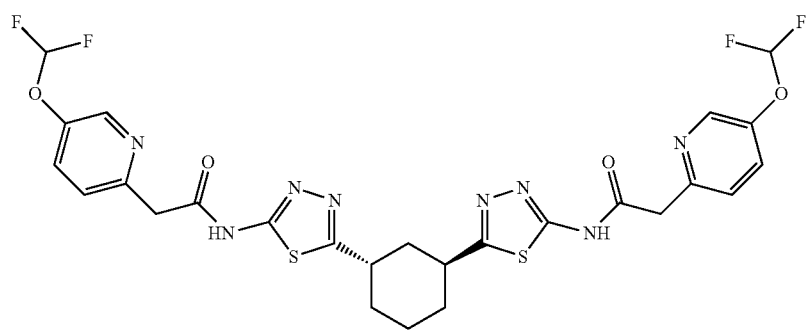

Step A: methyl 2-(5-(difluoromethoxy)pyridin-2-yl)acetate

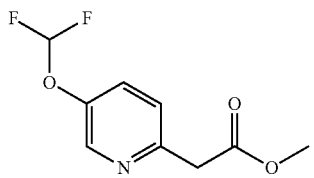

To a stirred solution of compound 7 (500 mg, 3 mmol) in MeCN was added Cs$_2$CO$_3$ (1.4 g, 4.5 mmol) followed by sodium 2-chloro-2,2-difluoroacetate (685 mg, 4.5 mmol) at room temperature. The whole mixture was heated to 80° overnight. LC-MS showed desired product. It was filtered, evaporated and purified by a standard method.

$^1$H NMR (CHLOROFORM-d) δ: 8.44 (s, 1H), 7.48 (dd, J=8.6, 2.7 Hz, 1H), 7.34 (d, J=8.6 Hz, 1H), 6.55 (t, 1H, J=76 Hz), 3.88 (s, 2H), 3.74 (s, 3H). LC-MS: m/z (M+H)=218.2

Step B: N,N'-(5,5'-((1S,3S)-cyclohexane-1,3-diyl)bis(1,3,4-thiadiazole-5,2-diyl))bis(2-(5-(difluoromethoxy)pyridin-2-yl)acetamide) (228)

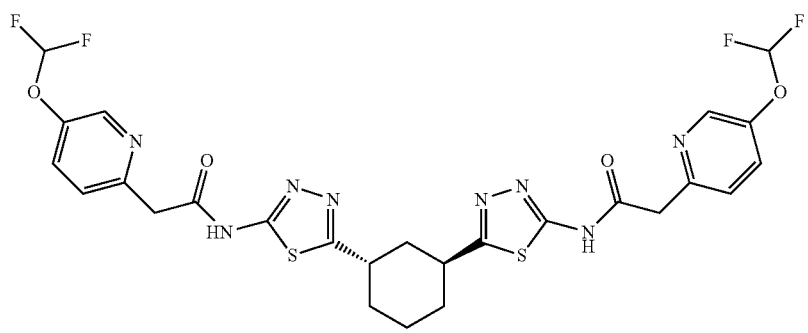 [SMILES: O=C(Cc1ccc(OC(F)F)cn1)Nc1nnc([C@H]2CCC[C@H](c3nnc(NC(=O)Cc4ccc(OC(F)F)cn4)s3)C2)s1]

The procedure was the same as Step B of Compound 84

$^1$H NMR (METHANOL-d$_4$) δ: 8.46 (d, J=2.4 Hz, 2H), 7.65 (dd, J=8.6, 2.4 Hz, 2H), 7.53 (d, J=8.9 Hz, 2H), 6.83 (t, J=72 Hz, 2H), 3.86 (s, 4H), 3.50 (m, 2H), 2.40 (t, J=5.6 Hz, 2H), 1.97 (m, 4H), 1.71 (tm, 2H). LC-MS: m/z (M+H)= 653.1

Compound 229

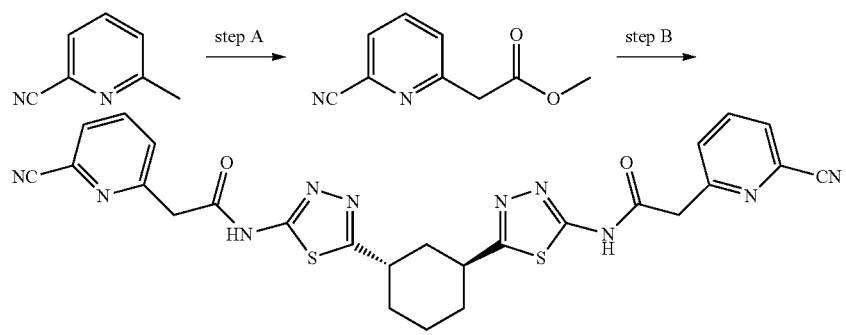

251

Step A: methyl 2-(6-cyanopyridin-2-yl) acetate

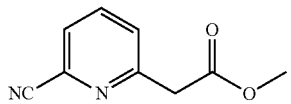

To a solution of 6-methylpicolinonitrile (2 g, 16.9 mmol) in THF (20 ml) was added slowly LiHMDS (17 ml, 1M in THF) at −78° C. under N2. Then the reaction mixture was stirred for 1 h at −78° C. and then dimethyl carbonate (1.52 g, 16.9 mmol) was added at −78° C. The mixture was stirred for 30 mins at −78° C. and allowed to 0° C. for 30 mins. Saturated ammonium chloride was added to neutralize to adjust to PH=7-8, the mixture was extracted by ethyl acetate (100 ml*3), the organic layer was dried by sodium sulfate, filtered, concentrated under vacuo to give the residue. The residue was purified by a standard method to give the desired product.

$^1$H NMR (CHLOROFORM-d): 7.84 (t, J=7.8 Hz, 1H), 7.64 (d, J=7.3 Hz, 1H), 7.58 (d, J=8.1 Hz, 1H), 3.93 (s, 2H), 3.76 (s, 3H). LC-MS: m/z (M+H)=177.3

Step B: N,N'-(5,5'-((1S,3S)-cyclohexane-1,3-diyl) bis(1,3,4-thiadiazole-5,2-diyl))bis(2-(6-cyanopyridin-2-yl)acetamide) (229)

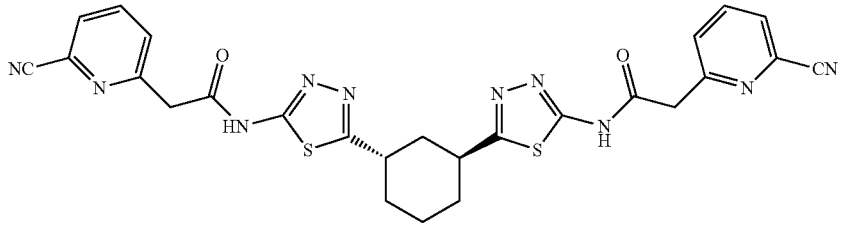 [SMILES: N#Cc1cccc(CC(=O)Nc2nnc([C@H]3CCC[C@H](c4nnc(NC(=O)Cc5cccc(C#N)n5)s4)C3)s2)n1]

The procedure was the same as Step B of Compound 84

$^1$H NMR (CHLOROFORM-d) δ: 7.84 (t, J=7.8 Hz, 2H), 7.71 (d, J=8.1 Hz, 2H), 7.62 (d, J=7.8 Hz, 2H), 4.35 (s, 4H), 3.55-3.63 (m, 2H), 2.45 (t, J=5.8 Hz, 2H), 2.06 (m, 2H), 1.93-2.01 (m, 2H), 1.74 (m, 2H). LC-MS: m/z (M+H)=571.5

N,N'-(5,5'-((1S,3S)-cyclohexane-1,3-diyl)bis(1,3,4-thiadiazole-5,2-diyl))bis(2-(pyrimidin-4-yl)acetamide) (230)

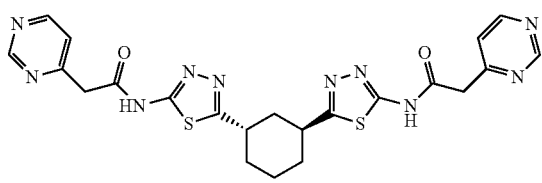 [SMILES: O=C(Cc1ccncn1)Nc1nnc([C@H]2CCC[C@H](c3nnc(NC(=O)Cc4ccncn4)s3)C2)s1]

The procedure was the same as Compound 84

$^1$H NMR (CHLOROFORM-d) δ: 9.11-9.24 (s, 2H), 8.72 (d, J=5.1 Hz, 2H), 7.42-7.59 (d, J=5.1 Hz, 2H), 4.24 (s, 4H), 3.59 (m, 2H), 2.45 (t, J=5.6 Hz 0.2H), 1.89-2.13 (m, 4H), 1.74 (m, 2H). LC-MS: m/z (M+H)=523.7

252

N,N'-(5,5'-((1S,3S)-cyclohexane-1,3-diyl)bis(1,3,4-thiadiazole-5,2-diyl))bis(2-(pyridazin-3-yl)acetamide) (231)

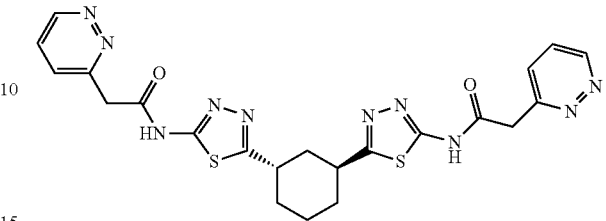

The procedure was the same as Step B of Compound 84

$^1$H NMR (DMSO-d$_6$) δ: 9.16 (dd, J=4.8, 1.9 Hz, 2H), 7.72-7.75 (dd, J=4.8, 1.9 Hz, 2H), 7.67-7.71 (dd, J=4.8, 1.9 Hz, 2H), 4.25 (s, 4H), 3.43-3.61 (m, 2H), 2.31 (t, J=5.5 Hz, 2H), 1.93 (m, 2H), 1.84 (m, 2H), 1.49-1.70 (m, 2H). LC-MS: m/z (M+H)=523.7

N,N'-(5,5'-(trans)-cyclohexane-1,3-diyl)bis(1,3,4-thiadiazole-5,2-diyl))bis(2-(pyrazin-2-yl) acetamide) (76)

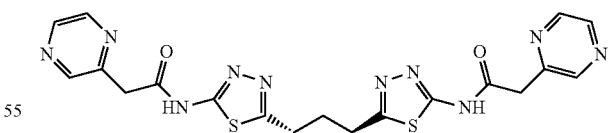

The procedure was the same as Step B of Compound 84

$^1$H NMR (CDCl$_3$, 400 MHz) δ 8.73 (s, 2H), 8.57 (d, J=17.2 Hz, 4H), 4.26 (s, 4H), 3.60-3.57 (m, 2H), 2.46 (t, J=5, 6 Hz, 2H), 2.04 (m, 2H), 1.96 (m, 2H), 1.75-1.73 (m, 2H). LC-MS: m/z (M+H)=523.6

253

N,N'-(5,5')-((1S,3S)-cyclohexane-1,3-diyl)bis(1,3,4-thiadiazole-5,2-diyl))bis(2-(thiazol-2-yl)acetamide) (100)

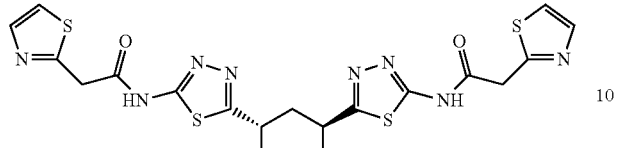

254

¹H NMR (CDCl₃, 400 MHz) δ: 7.76 (d, J=2.3 Hz, 2H), 7.37 (d, J=2.3 Hz, 2H), 3.53 (s, 4H), 3.40 (m, 2H), 2.42 (t, J=5.0 Hz, 2H), 1.99 (m, 2H), 1.93 (m, 2H), 1.72 (m, 2H). LC-MS: m/z (M+H)=533.6

N,N'-(5,5'-((1S,3S)-cyclohexane-1,3-diyl)bis(1,3,4-thiadiazole-5,2-diyl))bis(2-(6-aminopyridin-2-yl)acetamide) (232)

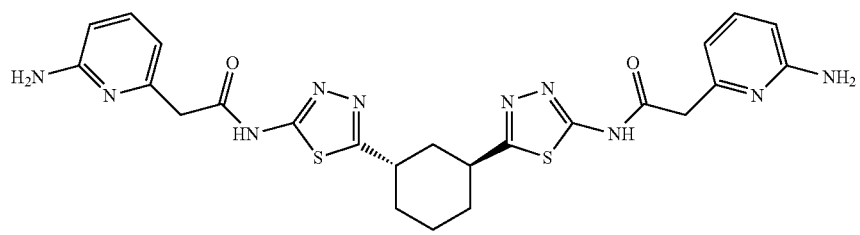 [SMILES: Nc1cccc(CC(=O)Nc2nnc([C@H]3CCC[C@H](c4nnc(NC(=O)Cc5cccc(N)n5)s4)C3)s2)n1]

The procedure was the same as Step B of Compound 84
¹H NMR (DMSO-d₆) δ: 12.70 (s, 2H), 7.25-7.38 (dd, J=7.3, 8.3 Hz 2H), 6.47 (d, J=7.3 Hz, 2H), 6.33 (d, J=8.3 Hz, 2H), 5.88 (s, 4H), 3.72 (s, 4H), 3.45-3.52 (m, 2H), 2.25-2.34 (t, J=5.4 Hz, 2H), 1.89-2.00 (m, 2H), 1.83 (m, 2H), 1.62 (m, 2H). LC-MS: m/z (M+H)=551.7

N,N'-(5,5'-((1S,3S)-cyclohexane-1,3-diyl)bis(1,3,4-thiadiazole-5,2-diyl))bis(2-(5-aminopyridin-2-yl)acetamide) (233)

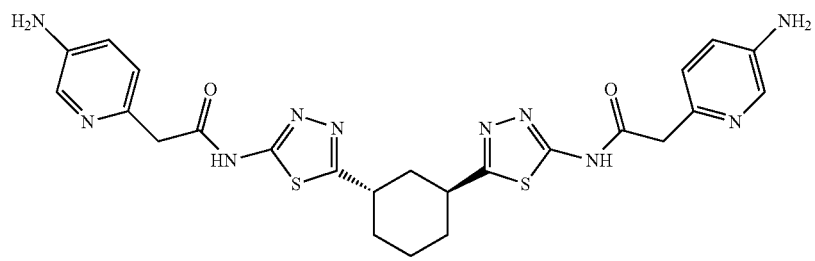 [SMILES: Nc1ccc(CC(=O)Nc2nnc([C@H]3CCC[C@H](c4nnc(NC(=O)Cc5ccc(N)cn5)s4)C3)s2)nc1]

The procedure was the same as Step B of Compound 84
¹H NMR (DMSO-d₆) δ: 12.61 (s, 2H), 7.84 (d, J=2.4 Hz, 2H), 7.02 (d, J=8.1 Hz, 2H), 6.89 (dd, J=8.3, 2.7 Hz, 2H), 5.23 (s, 4H), 3.78 (s, 4H), 3.48 (m, 2H), 2.29 (t, J=5.4 Hz, 2H), 1.93 (m, 2H), 1.85 (m, 2H), 1.62 (m, 2H). LC-MS: m/z (M+H)=551.8

N,N'-(5,5'-(trans-cyclohexane-1,3-diyl)bis(1,3,4-thiadiazole-5,2-diyl))bis(2-(3-cyanopyridin-2-yl)acetamide) (113)

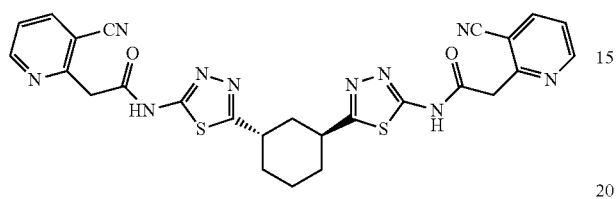

The procedure was the same as Step B of Compound 84
¹H NMR (DMSO-d6) δ: 12.90 (br. s., 2H), 8.78 (dd, J=5.0, 1.7 Hz, 2H), 8.35 (dd, J=7.9, 1.7 Hz, 2H), 7.56 (dd, J=7.9, 5.0 Hz, 2H), 4.19 (s, 4H), 3.50 (dt, J=11.1, 5.6 Hz, 2H), 2.31 (t, J=5.5 Hz, 2H), 1.89-2.03 (m, 2H), 1.77-1.89 (m, 2H), 1.54-1.66 (m, 2H). LC-MS: m/z (M+H)=571.7
Compound 234

Step A: 6-(2-methoxy-2-oxoethyl)nicotinic acid

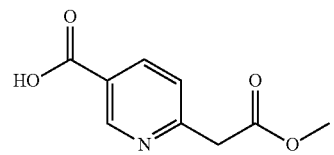

The procedure is the same as step A of Compound 84
LC-MS: m/z (M–H)=194.1

Step B: methyl 2-(5-(dimethylcarbamoyl)pyridin-2-yl)acetate

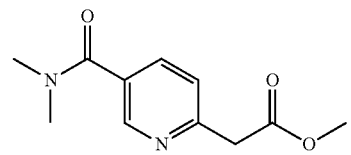

A solution of 6-(2-methoxy-2-oxoethyl)nicotinic acid (37 mg, 0.19 mmol), HATU (72.6 mg, 0.19 mmol), and N-ethyl-

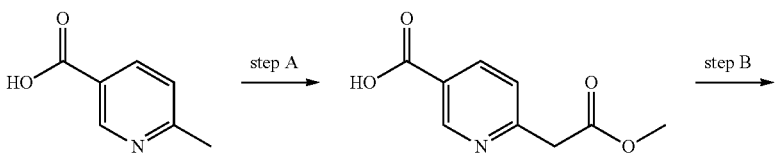

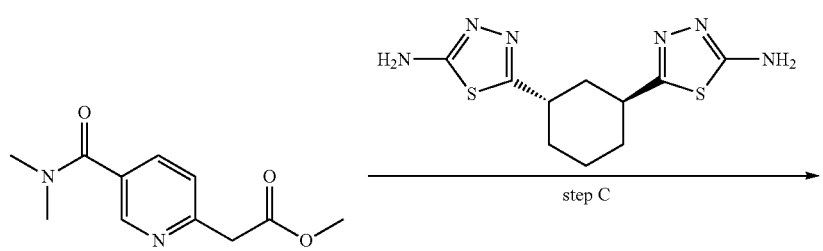

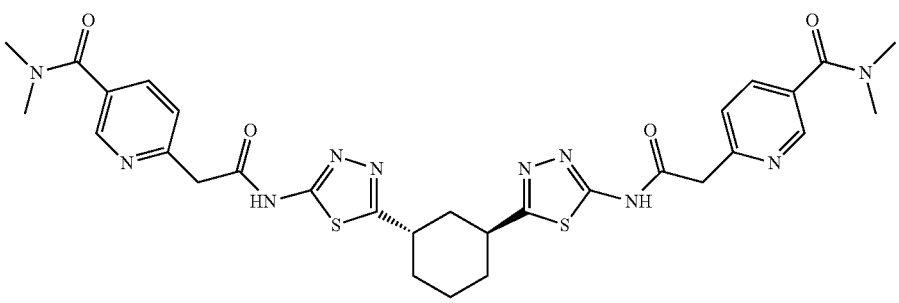

N-isopropylpropan-2-amine (26.5 mg, 0.20 mmol) in N,N-dimethylformamide (2 ml) was stirred at room temperature for 15 min, then, dimethyl amine (0.05 mL, 1 mol solution in THF) was added and continued to stir overnight. The reaction is quenched with water, extracted with EtOAc and purified by a standard method to give the desired compound.

$^1$H NMR (CHLOROFORM-d) δ: 8.65 (d, J=1.9 Hz, 1H), 7.79 (dd, J=7.9, 2.3 Hz, 1H), 7.40 (d, J=8.1 Hz, 1H), 3.92 (s, 2H), 3.75 (s, 3H), 3.15 (s, 3H), 3.04 (s, 3H). LC-MS: m/z (M+H)=223.1.

Step C: 6-[[5-[3-[5-[[2-[5-(dimethylcarbamoyl)pyridin-2-yl]acetyl]amino]-1,3,4-thiadiazol-2-yl]cyclohexyl]-1,3,4-thiadiazol-2-yl]carbamoylmethyl]-N,N-dimethyl-pyridine-3-carboxamide (234)

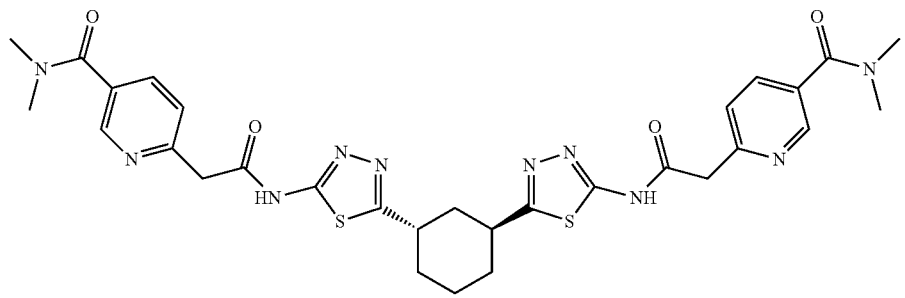

The procedure was the same as Step B of Compound 84

$^1$H NMR (CHLOROFORM-d) δ: 8.75 (s, 2H), 7.88 (d, J=6.2 Hz, 2H), 7.48 (d, J=7.8 Hz, 2H), 4.20 (s, 4H), 3.55-3.62 (m, 2H), 3.16 (s, 6H), 3.06 (s, 6H), 2.47 (t, J=5.4 Hz, 2H), 2.01-2.07 (m, 2H), 1.92-1.99 (m, 2H), 1.72-1.79 (m, 2H). LC-MS: m/z (M+H)=663.3.

Compound 105

Step A: ethyl 2-(6-(dimethylamino)pyridin-2-yl)acetate

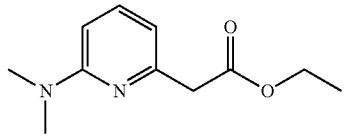

To the solution of ethyl 2-(6-aminopyridin-2-yl)acetate (150 mg, 0.83 mmol) and paraformaldehyde (54.8 mg, 1.83 mmol) in methanol (6 mL) was added NaBH$_3$CN (130.3 mg, 2.08 mmol) and AcOH (1 drop, cat.). The mixture was stirred at room temperature for 12 h. Then, the reaction was quenched with aqueous ammonium chloride and extracted with DCM. The organic layer was with brine, dried over sodium sulfate and evaporated under reduced pressure. The residue was purified by a standard method to get desired product (100 mg).

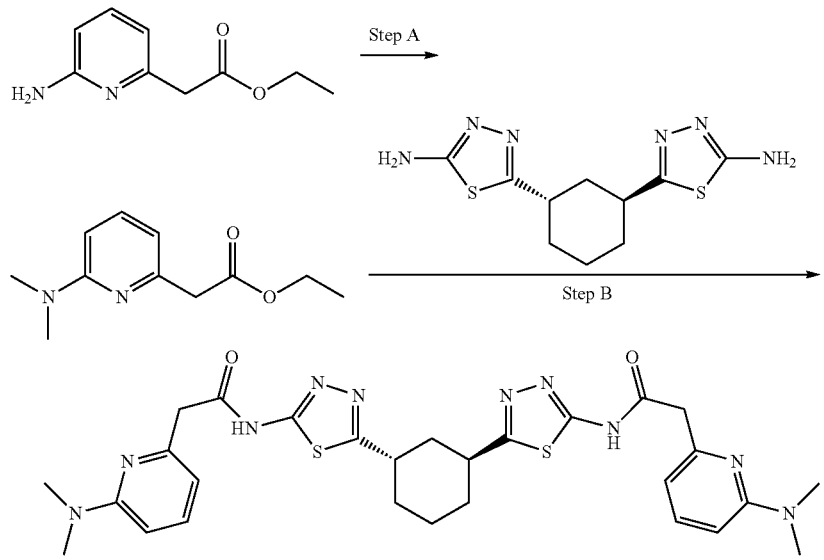

¹H NMR (CHLOROFORM-d) δ: 7.41 (t, J=7.8 Hz, 1H), 6.52 (d, J=7.3 Hz, 1H), 6.40 (d, J=8.6 Hz, 1H), 4.20 (q, J=7.3 Hz, 2H), 3.70 (s, 2H), 3.08 (s, 6H), 1.24-1.32 (t, J=7.3 Hz, 3H). LC-MS: m/z (M+H)=208.6

Step B: N,N'-(5,5'-((1S,3S)-cyclohexane-1,3-diyl)bis(1,3,4-thiadiazole-5,2-diyl))bis(2-(6-(dimethylamino)pyridin-2-yl)acetamide)

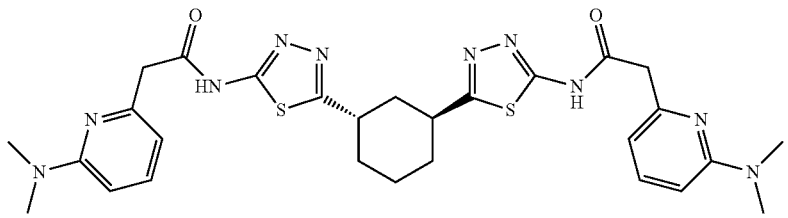

The procedure was the same as Step B of Compound 84
¹H NMR (DMSO-d₆) δ: 12.67 (s, 2H), 7.46 (t, J=7.9 Hz, 2H), 6.52 (d, J=8.6 Hz, 2H), 6.55 (d, J=7.3 Hz, 2H), 3.81 (s, 4H), 3.49 (m, 2H), 2.98 (s, 12H), 2.32 (d, J=5.4 Hz, 2H), 1.94 (m, 2H), 1.78-1.89 (m, 2H), 1.63 (m, 2H). LC-MS: m/z (M+H)=607.8
Compound 115

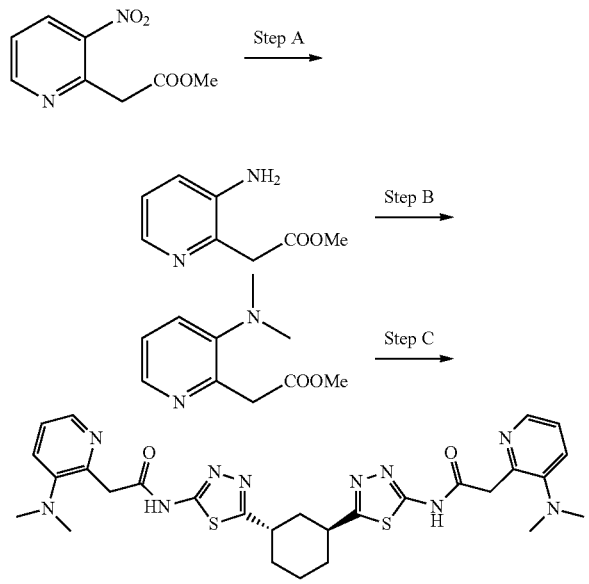

Step A: methyl 2-(3-aminopyridin-2-yl)acetate

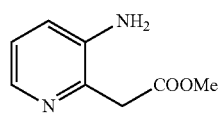

Methyl 2-(3-nitropyridin-2-yl)acetate (1 g, 5 mmol) was dissolved in MeOH and stirred under the atmosphere of H2 at room temperature overnight. LC-MS find the desired product. It was filtered through a pad of Celite and evaporated to get the desired product. It was directly used for the next step. LC-MS: m/z (M+H)=167.1

Step B: methyl 2-(3-(dimethylamino)pyridin-2-yl)acetate

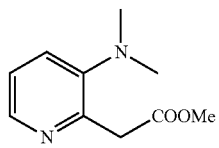

To the solution of methyl 2-(5-aminopyridin-2-yl)acetate (600 mg, 3.6 mmol) and paraformaldehyde (578.3 mg, 19.3 mmol) in methanol (20 mL) was added NaBH3CN (1.2 g, 19.3 mmol) and AcOH (1 drop, cat.). The mixture was stirred at room temperature for 12 h. Then, the reaction was quenched with aqueous ammonium chloride and extracted with DCM. The organic layer was with brine, dried over sodium sulfate and evaporated under reduced pressure. The residue was purified by a standard method to get desired product. LC-MS: m/z (M+H)=195.1

Step C: N,N'-(5,5'-(trans-cyclohexane-1,3-diyl)bis(1,3,4-thiadiazole-5,2-diyl))bis(2-(3-(dimethylamino)pyridin-2-yl)acetamide) (115)

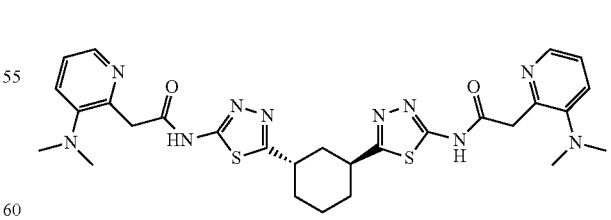

The procedure was the same as Step B of Compound 84
¹H NMR (METHANOL-d4) δ: 8.24 (d, J=3.8 Hz, 2H), 7.72 (d, J=8.3 Hz, 2H), 7.37 (dd, J=8.1, 4.8 Hz, 2H), 4.61 (s, 4H), 3.57 (m, 2H), 2.71 (s, 12H), 2.45-2.52 (t, J=5.4 Hz, 2H), 1.93-2.15 (m, 4H), 1.69-1.83 (m, 2H). LC-MS: m/z (M+H)=607.8

Compound 235 and Compound 236

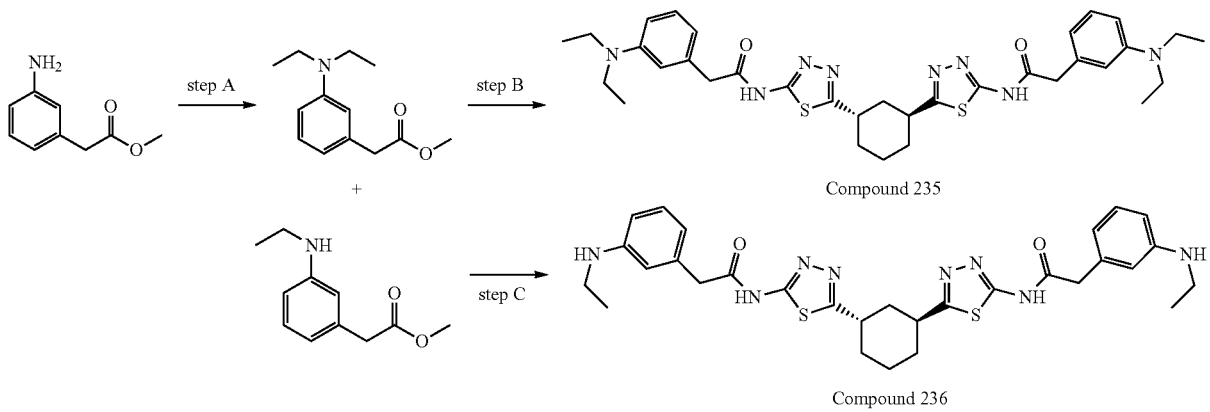

Compound 235

Compound 236

The procedure was the same as Compound 105

Step A

To the solution of methyl 2-(3-aminophenyl)acetate (150 mg, 0.83 mmol) and acetaldehyde (80.5 mg, 1.83 mmol) in methanol (6 mL) was added NaBH3CN (130.3 mg, 2.08 mmol) and AcOH (1 drop, cat.). The mixture was stirred at room temperature for 12 h. Then, the reaction was quenched with aqueous ammonium chloride and extracted with DCM. The organic layer was with brine, dried over sodium sulfate and evaporated under reduced pressure. The residue was purified by a standard method to get methyl 2-(3-(diethylamino)phenyl)acetate and methyl 2-(3-(ethylamino)phenyl)acetate.

methyl 2-(3-(diethylamino)phenyl)acetate

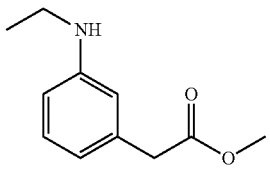

LC-MS: m/z (M+H)=222.4 methyl 2-(3-(ethylamino)phenyl)acetate

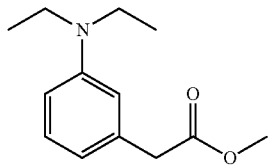 [SMILES: CCN(CC)c1cccc(CC(=O)OC)c1]

LC-MS: m/z (M+H)=194.4

Step B: N,N'-(5,5'-((1S,3S)-cyclohexane-1,3-diyl)bis(1,3,4-thiadiazole-5,2-diyl))bis(2-(3-(diethylamino)phenyl)acetamide) (235)

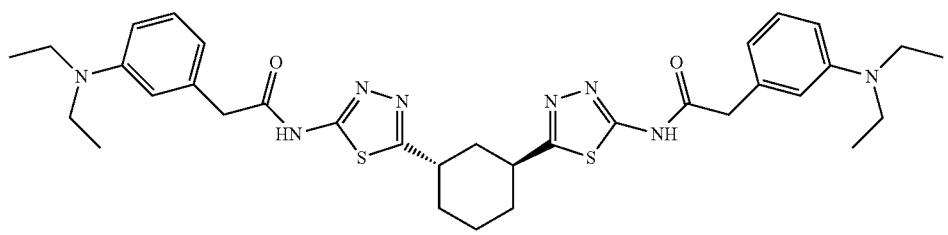 [SMILES: CCN(CC)c1cccc(CC(=O)Nc2nnc([C@H]3CCC[C@H](c4nnc(NC(=O)Cc5cccc(N(CC)CC)c5)s4)C3)s2)c1]

The procedure was the same as Step B of Compound 105.
¹H NMR (DMSO-d₆) δ: 12.60 (s, 2H), 7.07 (t, J=7.9 Hz, 2H), 6.65 (s, 2H), 6.46-6.57 (m, 4H), 3.65 (s, 4H), 3.47 (m, 2H), 3.31 (q, J=7.0 Hz, 8H), 2.28 (t, J=5.5 Hz, 2H), 1.87-1.99 (m, 2H), 1.71-1.87 (m, 2H), 1.52-1.66 (m, 2H), 1.07 (t, J=7.0 Hz, 12H). LC-MS: m/z (M+H)=661.9
Step C: N,N'-(5,5'-((1S,3S)-cyclohexane-1,3-diyl)bis(1,3,4-thiadiazole-5,2-diyl))bis(2-(3-(ethylamino)phenyl)acetamide) (236)
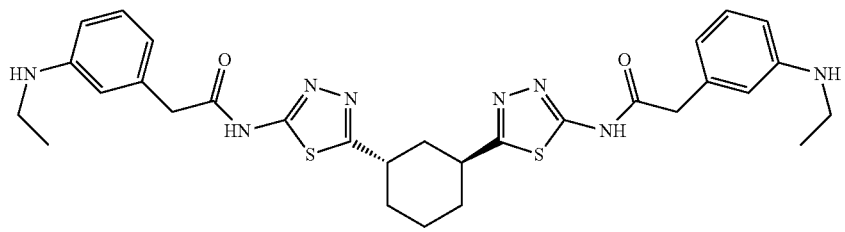 [SMILES: CCNc1cccc(CC(=O)Nc2nnc([C@H]3CCC[C@H](c4nnc(NC(=O)Cc5cccc(NCC)c5)s4)C3)s2)c1]
¹H NMR (DMSO-d₆) δ: 12.65 (s, 2H), 7.01 (t, J=7.8 Hz, 2H), 6.51 (s, 2H), 6.43 (d, J=8.1 Hz, 2H), 6.47 (dd, J=7.5, 8.1 Hz, 2H), 5.55 (t, J=5.5 Hz, 2H), 3.64 (s, 4H), 3.41-3.52 (m, 2H), 2.94-3.07 (m, 4H), 2.29 (t, J=5.6 Hz, 2H), 1.92 (d, J=4.8 Hz, 2H), 1.80-1.89 (m, 2H), 1.61 (d, J=5.6 Hz, 2H), 1.14 (t, J=7.1 Hz, 6H). LC-MS: m/z (M+H)=605.9
Compound 237
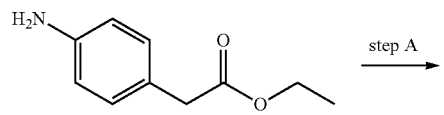
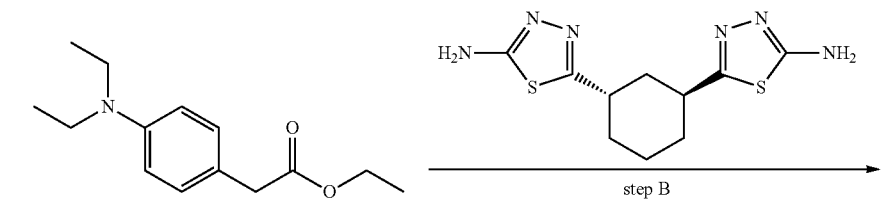
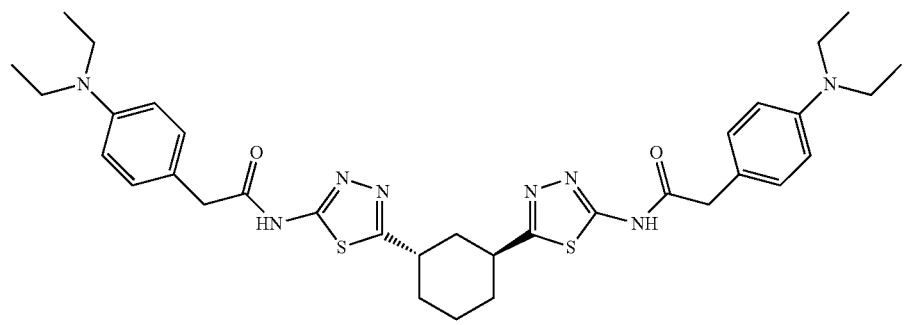

265

The procedure was the same as Compound 105

Step A: ethyl 2-(4-(diethylamino)phenyl)acetate

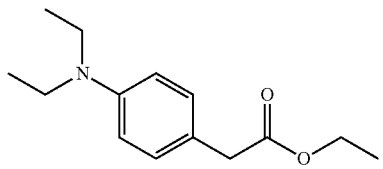 [SMILES: CCOC(=O)Cc1ccc(N(CC)CC)cc1]

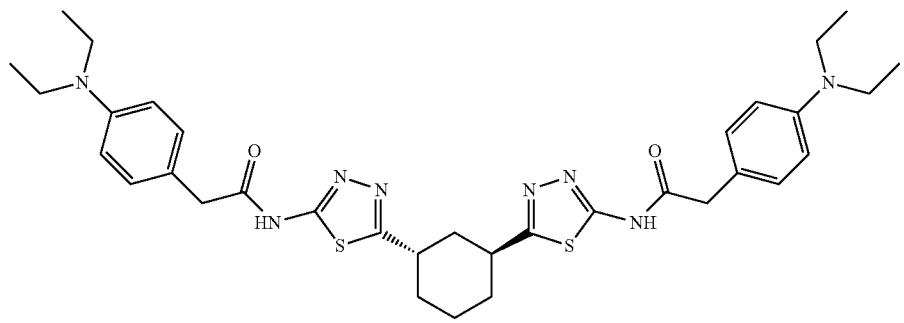 [SMILES: CCN(CC)c1ccc(CC(=O)Nc2nnc([C@H]3CCC[C@H](c4nnc(NC(=O)Cc5ccc(N(CC)CC)cc5)s4)C3)s2)cc1]

266

The procedure was the same as Step B of Compound 105.

¹H NMR (CHLOROFORM-d) δ: 7.15 (d, J=8.3 Hz, 2H), 6.66 (d, J=7.3 Hz, 2H), 4.16 (q, J=7.0 Hz, 2H), 3.52 (s, 2H), 3.36 (q, J=7.1 Hz, 4H), 1.24-1.31 (t, J=7.0 Hz, 3H), 1.17 (t, J=7.1 Hz, 6H). LC-MS: m/z (M+H)=236.5

Step B: N,N'-(5,5'-((1S,3S)-cyclohexane-1,3-diyl) bis(1,3,4-thiadiazole-5,2-diyl))bis(2-(4-(diethyl-amino)phenyl)acetamide) (237)

¹H NMR (DMSO-d₆) δ: 12.60 (s, 2H), 7.10 (d, J=8.6 Hz, 4H), 6.54-6.65 (d, J=8.5 Hz, 4H), 3.60 (s, 4H), 3.46 (m, 2H), 3.29 (q, J=6.9 Hz, 8H), 2.28 (t, J=5.5 Hz, 2H), 1.87-1.98 (m, 2H), 1.77-1.87 (m, 2H), 1.55-1.64 (m, 2H), 1.02-1.08 (t, J=7.0 Hz, 12H). LC-MS: m/z (M+H)=661.9

Compound 104

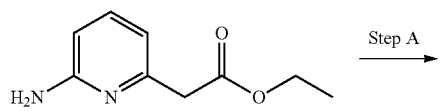

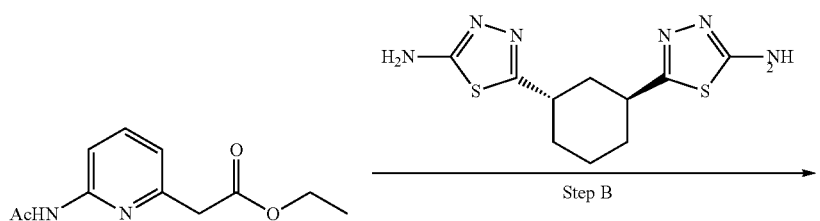

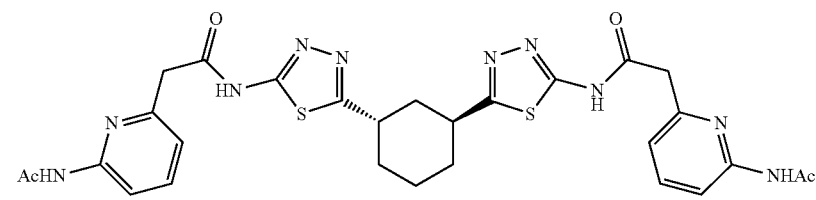

267

Step A: ethyl 2-(6-acetamidopyridin-2-yl)acetate

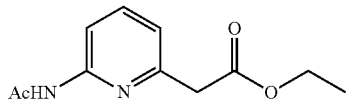 [SMILES: CCOC(=O)Cc1cccc(NC(C)=O)n1]

To the solution of ethyl 2-(6-aminopyridin-2-yl)acetate (50 mg, 0.28 mmol) and N-ethyl-N-isopropylpropan-2-amine (71.0 mg, 0.55 mmol) in DCM was added acetyl chloride (43.2 mg, 0.55 mmol) dropwise at room temperature. The mixture was continued to stir for 1 h, washed with brine and evaporated in vacuum to dryness. The residue was purified by a standard method to afford desired compound. LC-MS: m/z (M+H)=222.4

Step B: N,N'-(5,5'-((1S,3S)-cyclohexane-1,3-diyl)bis(1,3,4-thiadiazole-5,2-diyl))bis(2-(6-acetamidopyridin-2-yl)acetamide) (104)

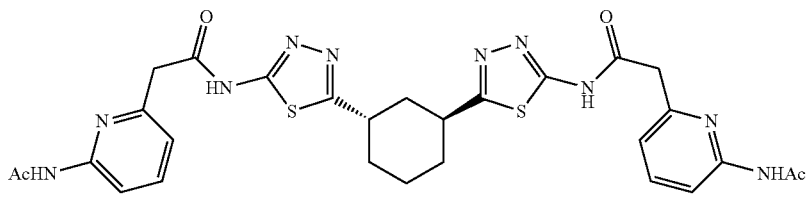 [SMILES: CC(=O)Nc1cccc(CC(=O)Nc2nnc([C@H]3CCC[C@H](c4nnc(NC(=O)Cc5cccc(NC(C)=O)n5)s4)C3)s2)n1]

The procedure was the same as Step B of Compound 84
$^1$H NMR (DMSO-$d_6$) δ: 12.71 (s, 2H), 10.42 (s, 2H), 7.97 (d, J=8.6 Hz, 2H), 7.74 (t, J=7.8 Hz, 2H), 7.09 (d, J=7.3 Hz, 2H), 3.94 (s, 4H), 3.49 (m, 2H), 2.31 (d, J=5.4 Hz, 2H), 2.07 (s, 6H), 1.94 (m, 2H), 1.85 (m, 2H), 1.62 (m, 2H). LC-MS: m/z (M+H)=635.8
Compound 384

268

Step A: methyl 2-(3-vinylphenyl)acetate

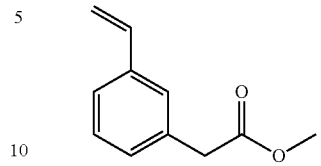

To a solution of methyl 2-(3-bromophenyl)acetate (3 g, 13 mmol) in dioxane (40 ml) were added tributyl(vinyl)stannane (4.5 g, 14.3 mmol) and tetrakis(triphenylphosphine)palladium(0) (300 mg, 0.02 eq), CsF (2 g, 2.0 eq) under nitrogen atmosphere, and the mixture was heated for 2 hours at 100° C. After cooling to ambient temperature, the organic layer was evaporated under reduced pressure. The residue was taken up into ethyl acetate, washed in turn with a 10 percent aqueous potassium carbonate solution and brine, and dried over sodium sulfate. After concentration, the residue was purified by a standard method to afford desired compound.

$^1$H NMR (CHLOROFORM-d) δ: 7.30-7.38 (m, 3H), 7.20 (d, J=7.0 Hz, 1H), 6.66-6.78 (m, 1H), 5.74-5.82 (m, 1H), 5.23-5.32 (m, 1H), 3.73 (s, 3H), 3.65 (s, 2H).

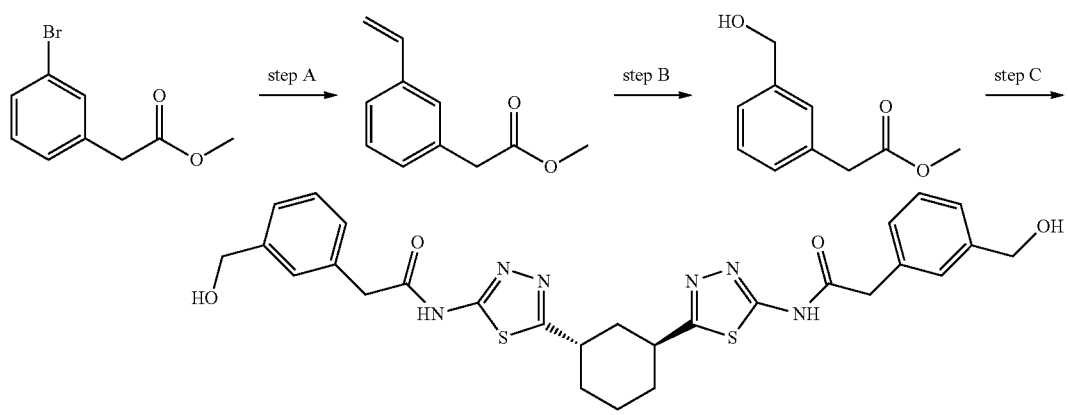

Step B: methyl 2-(3-(hydroxymethyl)phenyl)acetate

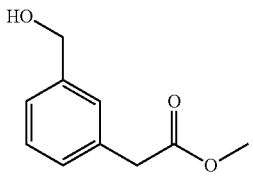

To a solution of methyl 2-(3-vinylphenyl)acetate (1.8 g, 10 m mol) in CH$_2$Cl$_2$ was bubbling O$_3$ for 20 min at −78 C. Me$_2$S was added into the flask, the mixture was warmed to r.t. slowly. Removed the solvent in reduced pressure and the residue was used for the next step without further purification.

To a solution of methyl 2-(3-formylphenyl)acetate in MeOH was added sodium tetrahydroborate in portion, and the mixture was stirred for 1 h at r.t. The mixture was poured into aqueous NH4Cl, and extracted with ethyl acetate, the combined organic phase was dried on anhydrous Na$_2$SO$_4$. After evaporation, the residue was purified by a standard method to afford desired compound.

$^1$H NMR (CHLOROFORM-d) δ: 7.30-7.37 (m, 3H), 7.23 (d, J=7, 3 Hz, 1H), 4.71 (s, 2H), 3.71 (s, 3H), 3.66 (s, 2H)

Step C: N,N'-(5,5'-((1S,3S)-cyclohexane-1,3-diyl) bis(1,3,4-thiadiazole-5,2-diyl))bis(2-(3-(hydroxymethyl)phenyl)acetamide)

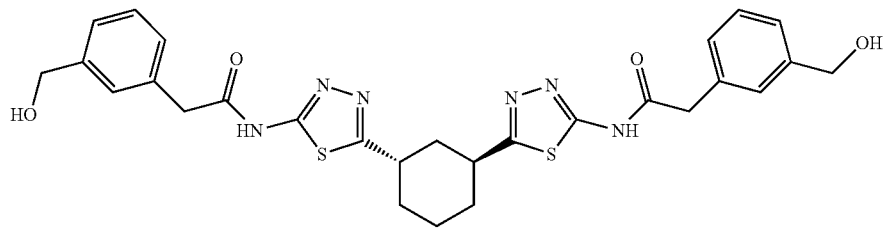 [SMILES: O=C(Cc1cccc(CO)c1)Nc1nnc([C@H]2CCC[C@H](c3nnc(NC(=O)Cc4cccc(CO)c4)s3)C2)s1]

A solution of 5,5'-((1S,3S)-cyclohexane-1,3-diyl)bis(1,3,4-thiadiazol-2-amine) (73 mg, 0.26 mmol), methyl 2-(3-(3-fluoroazetidin-1-yl)phenyl)acetate (140 mg, 0.78 mmol), and t-BuOK (87 mg, 0.78 mmol) in DMSO (5 ml) was heated to 100° C. for 40 min under microwave. Then the reaction mixture was cooled to room temperature and was poured into to water. The mixture was extracted by ethyl acetate (3×10 ml), the combined organic layer was washed by brine, dried by sodium sulfate, filtered, concentrated to give the residue, which was purified by a standard method to afford desired compound.

$^1$H NMR (DMSO-d$_6$) □: 12.73 (s, 2H), 7.24-7.35 (m, 4H), 7.14-7.24 (m, 4H), 5.21 (t, J=5.6 Hz, 2H), 4.48 (d, J=5.6 Hz, 4H), 3.79 (s, 4H), 3.43-3.51 (m, 2H), 2.29 (t, J=5.5 Hz, 2H), 1.88-1.97 (m, 2H), 1.79-1.88 (m, 2H), 1.54-1.66 (m, 2H). LC-MS: m/z (M+H)=579.5.

Compound 385
N,N'-(5,5'-((1S,3S)-cyclohexane-1,3-diyl)bis(1,3,4-thiadiazole-5,2-diyl))bis(2-(6-(N-methylacetamido)pyridin-2-yl)acetamide)
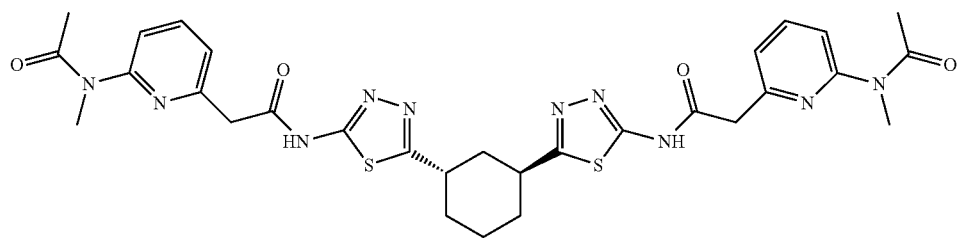 [SMILES: CC(=O)N(C)c1cccc(CC(=O)Nc2nnc([C@H]3CCC[C@H](c4nnc(NC(=O)Cc5cccc(N(C)C(C)=O)n5)s4)C3)s2)n1]
The procedure is the same as that of Compound 104
$^1$H NMR (CHLOROFORM-d) δ: 8.52 (m, 2H), 7.58 (m, 2H), 7.53 (m, 2H), 4.62 (s, 2H), 4.22 (s, 4H), 3.53-3.63 (m, 2H), 3.28 (s, 6H), 2.46 (t, J=4.3 Hz, 2H), 2.04 (m, 2H), 1.82-2.00 (m, 8H), 1.65-1.78 (m, 2H). LC-MS: m/z (M+H)= 663.4
Compound 238
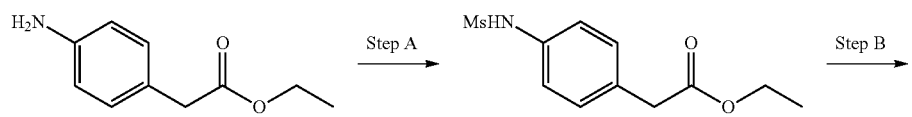
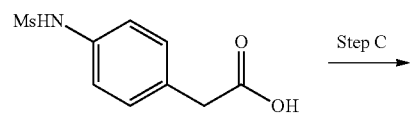
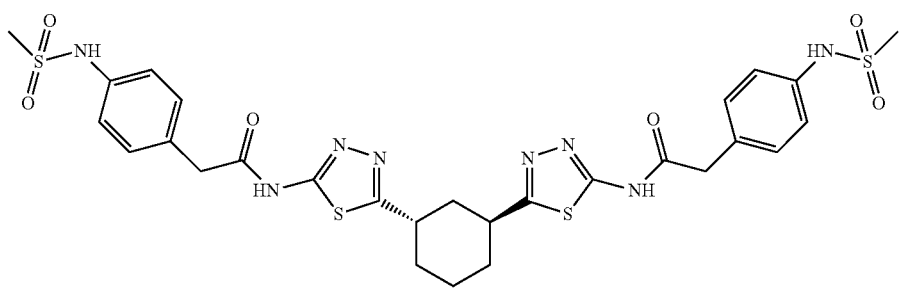

Step A: ethyl 2-(4-(methylsulfonamido)phenyl)acetate

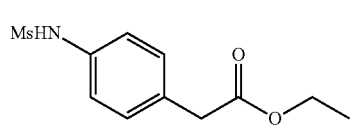

The solution of ethyl 2-(4-aminophenyl)acetate (500 mg, 2.79 mmol) and triethylamine (0.58 mL, 4.18 mmol) in dichloromethane (30 mL) was added methanesulfonyl chloride (0.24 mL, 3.07 mmol) dropwise at room temperature and stirred overnight. The mixture was washed with brine, dried over sodium sulfate and evaporated under reduced pressure. The residue was purified by a standard method to give desired compound. LC-MS: m/z (M+H)=258.3

Step B: 2-(4-(methylsulfonamido)phenyl)acetic acid

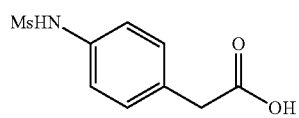

The solution of ethyl 2-(4-(methylsulfonamido)phenyl) acetate (200 mg, 0.77 mmol) and lithium hydroxide hydrate (130.4 mg, 3.11 mmol) in MeOH/H$_2$O (10 mL, 1:1) was stirred at room temperature for 12 h. The reaction mixture was evaporated under reduced pressure. The residue was used for the next step without purification. LC-MS: m/z (M+H)=230.4

Step C: N,N'-(5,5'-((1S,3S)-cyclohexane-1,3-diyl)bis(1,3,4-thiadiazole-5,2-diyl))bis(2-(4-(methylsulfonamido)phenyl)acetamide) (238)

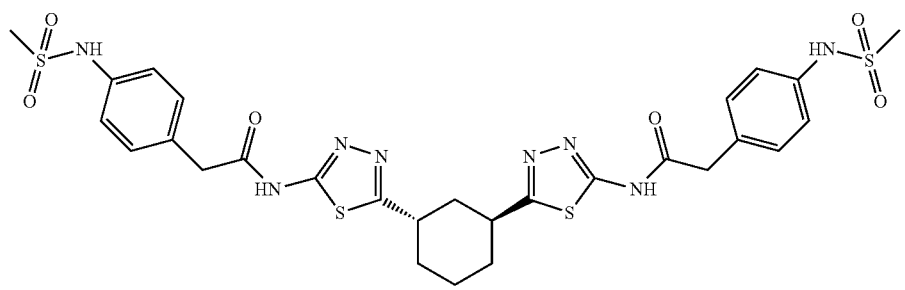

The procedure was the same as Compound 37

$^1$H NMR (DMSO-d$_6$) δ: 12.70 (br. s., 2H), 9.71 (br. s., 2H), 7.29 (d, J=8.6 Hz, 4H), 7.17 (d, J=8.6 Hz, 4H), 3.76 (s, 4H), 3.43-3.52 (m, 2H), 2.94-3.00 (m, 6H), 2.29 (t, J=5.6 Hz, 2H), 1.78-1.98 (m, 4H), 1.56-1.67 (m, 2H). LC-MS: m/z (M+H)=705.7

Compound 239

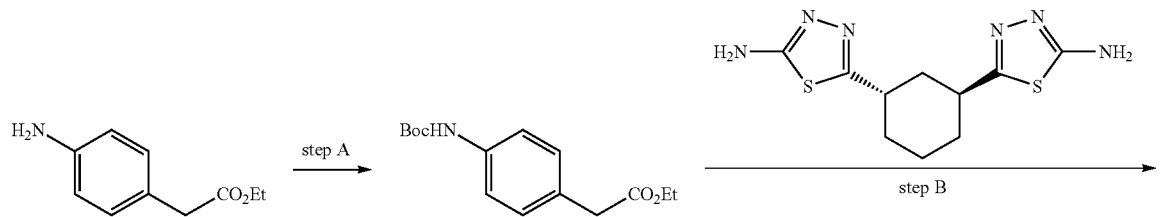

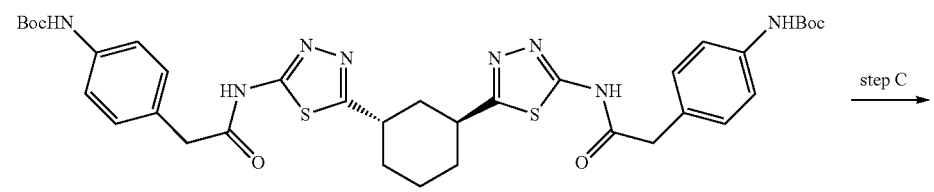

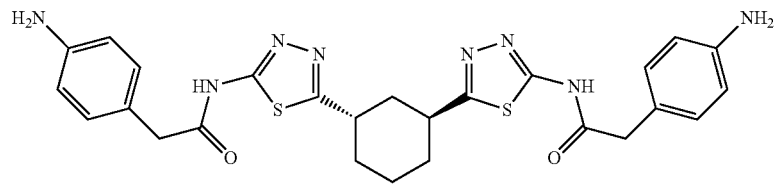

Step A: ethyl 2-(4-((tert-butoxycarbonyl)amino)phenyl)acetate

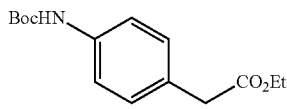 [SMILES: CCOC(=O)Cc1ccc(NC(=O)OC(C)(C)C)cc1]

A solution of di-tert-butyl dicarbonate (387 mg, 1.77 mmol) in toluene (5 ml) was added a vessel containing ethyl 2-(4-aminophenyl)acetate (288 mg, 1.61 mmol), the reaction mixture was heated at 85° C. for 4 h. LCMS showed that the desired product was detected, the mixture was concentrated to give the residue, which was purified by a standard method to give the desired product. LC-MS: m/z (M+H)=280.3

Step B: di-tert-butyl (((((5,5'-((1S,3S)-cyclohexane-1,3-diyl)bis(1,3,4-thiadiazole-5,2-diyl))bis(azanediyl))bis(2-oxoethane-2,1-diyl))bis(4,1-phenylene))dicarbamate

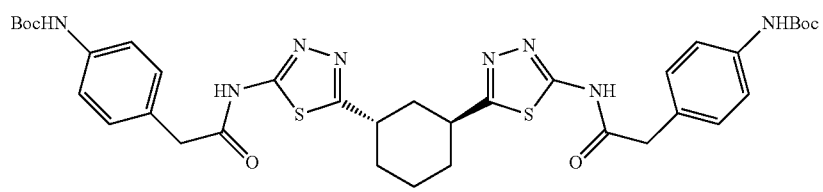 [SMILES: CC(C)(C)OC(=O)Nc1ccc(CC(=O)Nc2nnc([C@H]3CCC[C@H](c4nnc(NC(=O)Cc5ccc(NC(=O)OC(C)(C)C)cc5)s4)C3)s2)cc1]

A solution of 5,5'-((1S,3S)-cyclohexane-1,3-diyl)bis(1,3,4-thiadiazol-2-amine) (68 mg, 0.241 mmol), ethyl 2-(4-(tert-butoxycarbonylamino)phenyl)acetate (201 mg, 0.72 mmol), and cesium carbonate (251 mg, 0.771 mmol) in N,N-dimethylformamide (2 ml) was heated to 130° C. for 45 mins under microwave. Then the reaction mixture was cooled to room temperature and was poured into to water. The mixture was extracted by ethyl acetate (50 ml*3), the organic layer was washed by brine, dried by sodium sulfate, filtered, concentrated to give the residue; the residue was purified by a standard method to give the desired product.

$^1$H NMR (CHLOROFORM-d) δ: 7.36 (br, 8H), 3.96 (s, 4H), 3.53-3.57 (m, 2H), 2.40 (t, J=5.6 Hz, 2H), 1.97-2.06 (m, 4H), 1.77 (m, 2H), 1.52 (s, 18H). LC-MS: m/z (M+H)= 750.0.

Step C: N,N'-(5,5'-((1S,3S)-cyclohexane-1,3-diyl) bis(1,3,4-thiadiazole-5,2-diyl))bis(2-(4-aminophenyl)acetamide) (239)

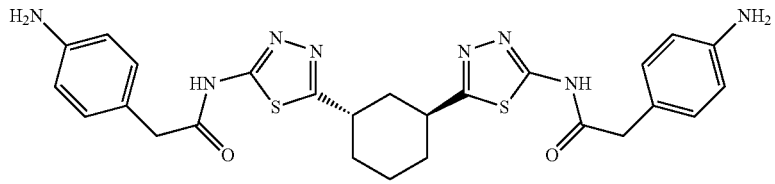 [SMILES: Nc1ccc(CC(=O)Nc2nnc([C@H]3CCC[C@H](c4nnc(NC(=O)Cc5ccc(N)cc5)s4)C3)s2)cc1]

To a solution of tert-butyl 4,4'-(2,2'-(5,5'-((1S,3S)-cyclohexane-1,3-diyl)bis(1,3,4-thiadiazole-5,2-diyl))bis(azanediyl)bis(2-oxoethane-2,1-diyl))bis(4,1-phenylene)dicarbamate (20 mg) in DCM (2 ml) was added TFA (0.5 mL). The reaction mixture was concentrated after 0.5 h to give the desired product.

$^1$H NMR (METHANOL-d$_4$) δ: 7.09 (d, J=8.3 Hz, 4H), 6.70-6.74 (d, J=8.3 Hz, 4H), 3.68 (s, 4H), 3.53-3.57 (m, 2H), 2.43 (t, J=5.6 Hz, 2H), 1.97-2.06 (m, 4H), 1.72-1.77 (m, 2H). LC-MS: m/z (M+H)=549.7.

Compound 240

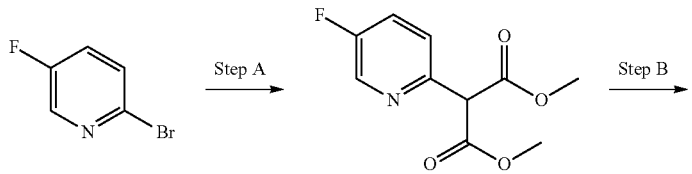

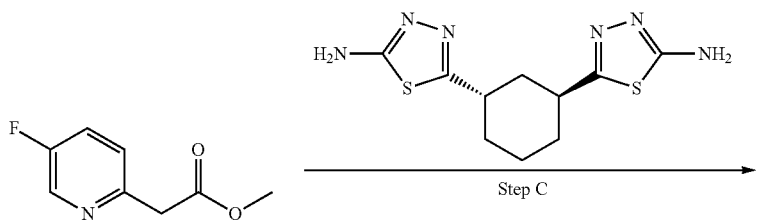

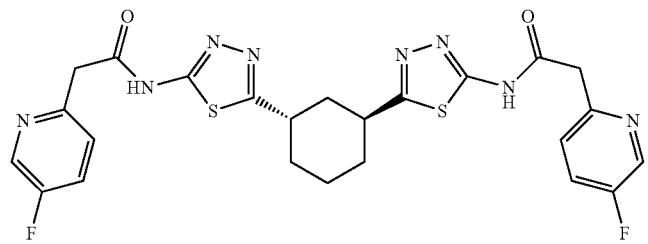

The procedure was the same as Compound 241

Step A: dimethyl 2-(5-fluoropyridin-2-yl)malonate

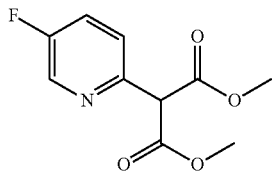

The solution of 2-bromo-5-fluoropyridine (1.0 g, 5.68 mmol), dimethyl malonate (3.0 g, 22.7 mmol) picolinic acid (559.6 mg, 4.54 mmol), CuI (431.8 mg, 2.27 mmol) and $Cs_2CO_3$ (5.6 g, 17.05 mmol) in DMF (30 mL) was stirred at 100 degree for 12 h. After cooling to room temperature, the reaction mixture was filtered, diluted with $H_2O$ and extracted with ethyl acetate. The organic layer was washed with brine, dried over sodium sulfate and evaporated under reduced pressure. The residue was purified by a standard method to give desired compound. LC-MS: m/z (M+H)= 228.2

Step B: methyl 2-(5-fluoropyridin-2-yl)acetate

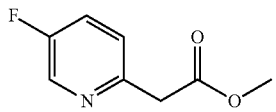

The solution of dimethyl 2-(5-fluoropyridin-2-yl)malonate (400 mg 1.76 mmol), NaCl (109.2 mg, 1.87 mmol) and $H_2O$ (56.3 g, 3.13 mmol) in DMSO (3 mL) was stirred at 130 degree for 6 h. After cooling to room temperature, the reaction mixture was diluted with $H_2O$ and extracted with ethyl acetate. The organic layer was dried over sodium sulfate and evaporated under reduced pressure. The residue was purified by a standard method to get desired product. LC-MS: m/z (M+H)=170.1

Step C: N,N'-(5,5'-((1S,3S)-cyclohexane-1,3-diyl)bis(1,3,4-thiadiazole-5,2-diyl))bis(2-(5-fluoropyridin-2-yl)acetamide) (240)

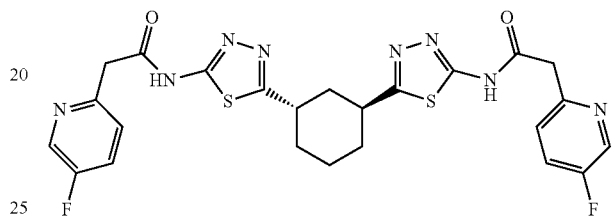

The procedure was the same as Step B of Compound 84

$^1$H NMR (DMSO-$d_6$) δ: 12.74 (br. s., 2H), 8.50 (d, J=3.0 Hz, 2H), 7.72 (td, J=8.7, 3.0 Hz, 2H), 7.49 (dd, J=8.7, 4.4 Hz, 2H), 4.03 (s, 4H), 3.43-3.55 (m, 2H), 2.31 (t, J=5.4 Hz, 2H), 1.90-2.00 (m, 2H), 1.79-1.89 (m, 2H), 1.56-1.67 (m, 2H). LC-MS: m/z (M+H)=557.6

Compound 101 and Compound 242

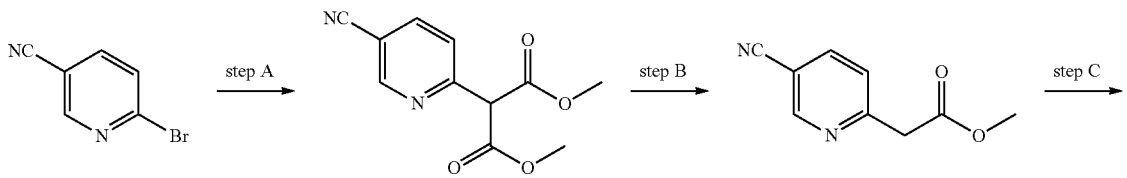

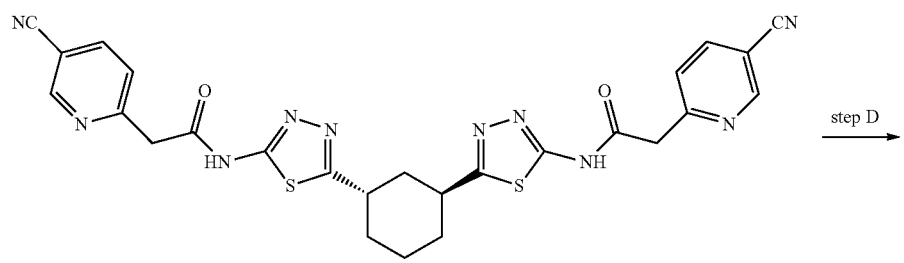

-continued
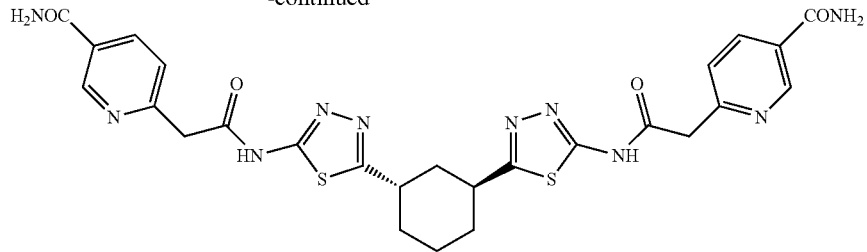
The procedure was the same as Compound 240 for steps A-C
Step A: dimethyl 2-(5-cyanopyridin-2-yl)malonate
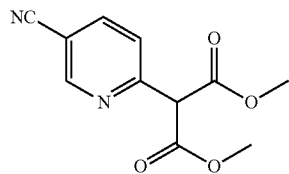 [SMILES: COC(=O)C(C(=O)OC)c1ccc(C#N)cn1]
LC-MS: m/z (M+H)=235.4
Step B: methyl 2-(5-cyanopyridin-2-yl)acetate
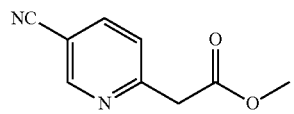
LC-MS: m/z (M+H)=177.3
Step C: N,N'-(5,5'-((1S,3S)-cyclohexane-1,3-diyl)bis(1,3,4-thiadiazole-5,2-diyl))bis(2-(5-cyanopyridin-2-yl)acetamide) (101)
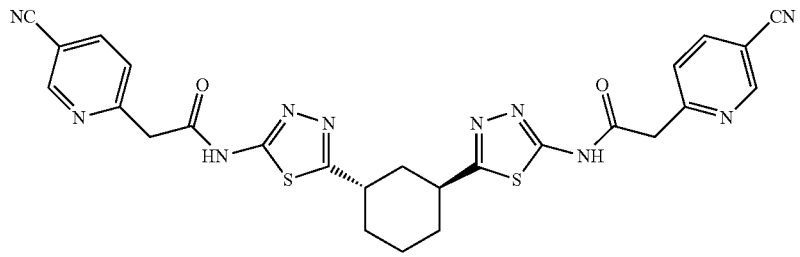 [SMILES: N#Cc1ccc(CC(=O)Nc2nnc([C@H]3CCC[C@H](c4nnc(NC(=O)Cc5ccc(C#N)cn5)s4)C3)s2)nc1]

¹H NMR (DMSO-d₆) δ: 12.80 (br. s., 2H), 8.97 (s, 2H), 8.24-8.37 (d, J=8.1 Hz, 2H), 7.59-7.73 (d, J=8.3 Hz, 2H), 4.15 (s, 4H), 3.49 (m, 2H), 2.32 (t, J=5.8 Hz, 2H), 1.94 (m, 2H), 1.85 (m., 2H), 1.62 (m, 2H). LC-MS: m/z (M+H)= 571.7

Step D: 6,6'-(((5,5'-((1S,3S)-cyclohexane-1,3-diyl) bis(1,3,4-thiadiazole-5,2-diyl))bis(azanediyl))bis(2-oxoethane-2,1-diyl))dinicotinamide (242)

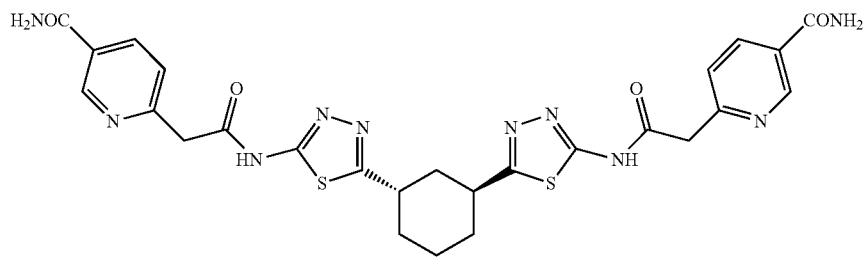 [SMILES: NC(=O)c1ccc(CC(=O)Nc2nnc([C@H]3CCC[C@H](c4nnc(NC(=O)Cc5ccc(C(N)=O)cn5)s4)C3)s2)nc1]

To a solution of N,N'-(5,5'-((1S,3S)-cyclohexane-1,3-diyl)bis(1,3,4-thiadiazole-5,2-diyl))bis(2-(5-cyanopyridin-2-yl)acetamide) (30 mg, 0.053 mmol) in DMSO (1 ml) was added sodium hydroxide solution (4 M, 0.1 mL) at 0° C. Then the reaction mixture was stirred for 2 mins and then hydrogen peroxide (30% in water, 1 ml) was added. The mixture was stirred for 10 mins. TLC indicated that the starting material was consumed. The mixture was purified by a standard method to give the desired product.

¹H NMR (METHANOL-d₄) δ: 9.00 (d, J=1.9 Hz, 2H), 8.27 (dd, J=8.2, 2.3 Hz, 2H), 7.58 (d, J=8.3 Hz, 2H), 4.06-4.20 (s, 4H), 3.50-3.63 (m, 2H), 2.45 (t, J=5.8 Hz, 2H), 1.95-2.11 (m, 4H), 1.70-1.82 (m, 2H); LC-MS: m/z (M+H)= 607.5

Compound 243

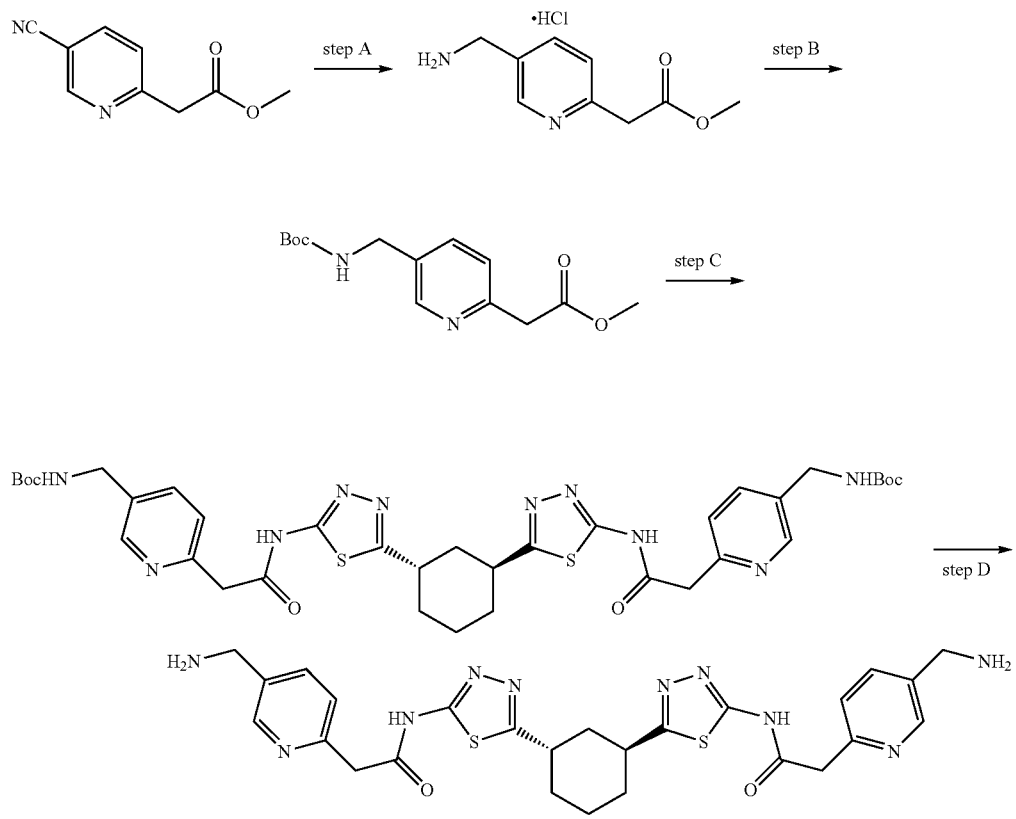

Step A: (6-(2-methoxy-2-oxoethyl)pyridin-3-yl) methanaminium chloride

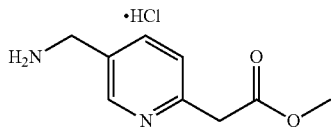

To a solution of methyl 2-(5-cyanopyridin-2-yl)acetate (1.2 g, 6.8 mmol) in methanol (20 ml) was added hydrogen chloride in methanol (4 M, 20 ml), and then Pd/C (200 mg). Then the reaction mixture was hydrogenated under hydrogen atmosphere overnight. The reaction mixture was filtered and, the filtrate was concentrated to give the crude product and was washed by ethyl acetate to give the desired product. LC-MS: m/z (M+H)=181.5

Step B: methyl 2-(5-((tert-butoxycarbonylamino) methyl)pyridin-2-yl)acetate

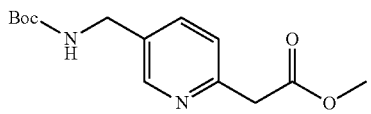 [SMILES: COC(=O)Cc1ccc(CNC(=O)OC(C)(C)C)cn1]

To a solution of (6-(2-methoxy-2-oxoethyl)pyridin-3-yl) methanaminium chloride (400 mg, 2.22 mmol) in $CH_2Cl_2$ (50 ml) was added triethylamine (561 mg, 5.55 mmol), and then was added $(Boc)_2O$ (726 g, 3.33 mmol). The reaction mixture was stirred overnight. LCMS showed that the desired product was detected, the mixture was concentrated to give the residue, the residue was purified by a standard method to give the desired product.

$^1$H NMR (CHLOROFORM-d) δ: 8.49 (d, J=1.9 Hz, 1H), 7.63 (d, J=6.4 Hz, 1H), 7.28 (t, J=4.0 Hz, 1H), 4.33 (d, J=5.6 Hz, 2H), 3.86 (s, 2H), 3.74 (s, 3H). LC-MS: m/z (M+H)= 281.5

Step C: tert-butyl (6,6'-(2,2'-(5,5'-((1S,3S)-cyclohexane-1,3-diyl)bis(1,3,4-thiadiazole-5,2-diyl))bis (azanediyl)bis(2-oxoethane-2,1-diyl))bis(pyridine-6,3-diyl))bis(methylene)dicarbamate

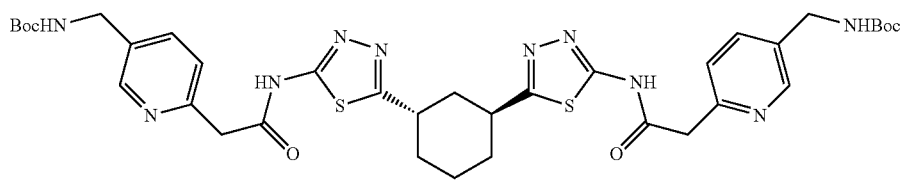 [SMILES: CC(C)(C)OC(=O)NCc1ccc(CC(=O)Nc2nnc([C@H]3CCC[C@H](c4nnc(NC(=O)Cc5ccc(CNC(=O)OC(C)(C)C)cn5)s4)C3)s2)nc1]

The procedure is the same as Step B of Compound 84
LC-MS: m/z (M+H)=779.5

Step D: N,N'-(5,5'-((1S,3S)-cyclohexane-1,3-diyl)
bis(1,3,4-thiadiazole-5,2-diyl))bis(2-(5-(aminomethyl)pyridin-2-yl)acetamide) (243)

To a solution of tert-butyl (6,6'-(2,2'-(5,5'-((1S,3S)-cyclohexane-1,3-diyl)bis(1,3,4-thiadiazole-5,2-diyl))bis(azanediyl)bis(2-oxoethane-2,1-diyl))bis(pyridine-6,3-diyl))bis(methylene)dicarbamate (20 mg, 0.026 mmol) was added hydrogen chloride solution in methanol (4M, 10 ml) and the resulting solution was stirred for 1 h. LCMS showed the starting material was consumed and the desired product was detected. The mixture was concentrated to give the desired product.

$^1$H NMR (METHANOL-d$_4$) δ: 9.10 (s, 2H), 8.68-8.82 (d, J=8.3 Hz, 2H), 8.12-8.28 (d, J=8.3 Hz, 2H), 4.48 (s, 4H), 3.60-3.64 (m, 6H), 2.45 (t, J=5.4 Hz, 2H), 2.05-2.12 (m, 2H), 1.99 (m, 2H), 1.75 (m, 2H). LC-MS: m/z (M+H)=579.5
Compound 244

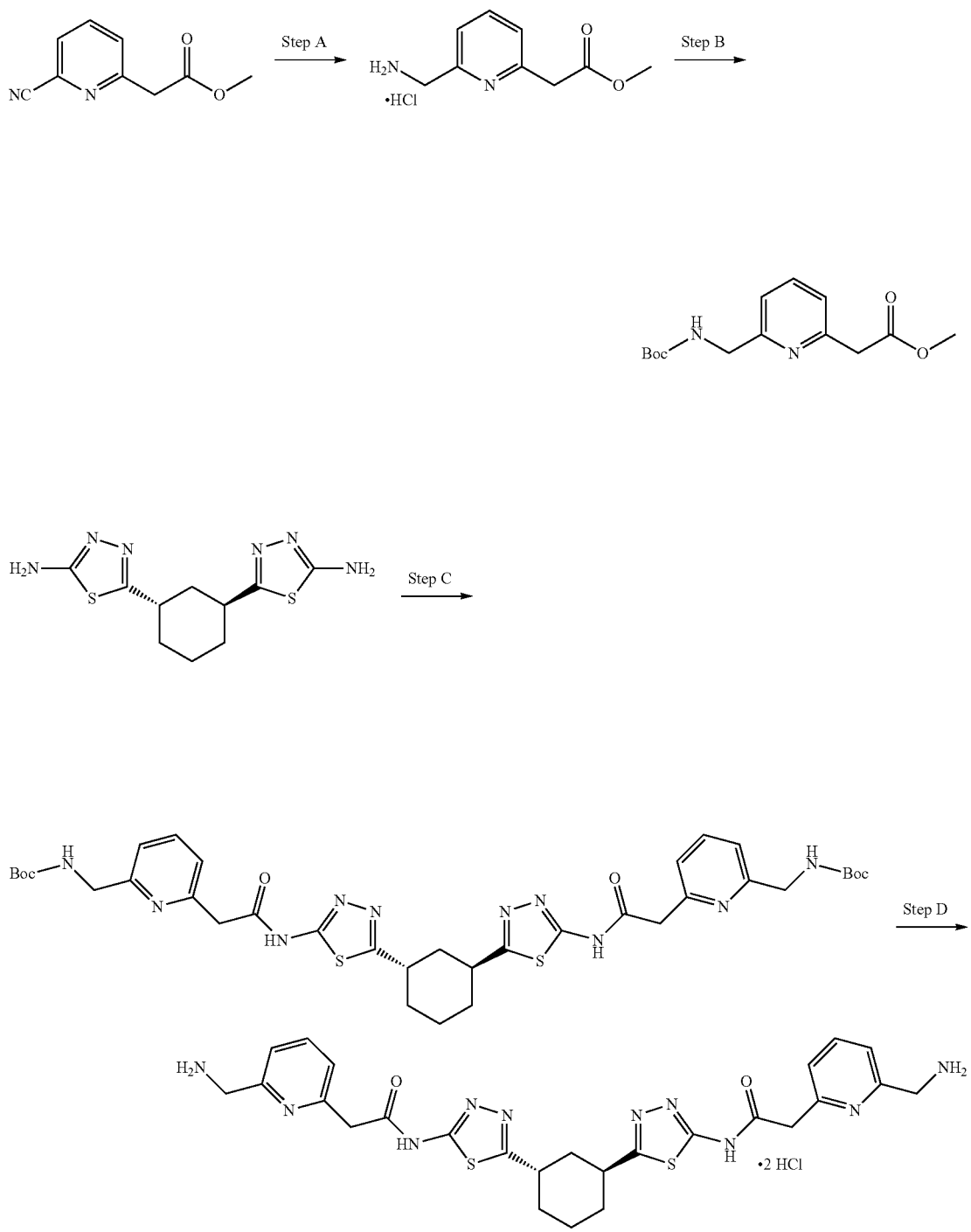

The procedure was the same as Compound 243

Step A to Step B: methyl 2-(6-((tert-butoxycarbonylamino)methyl)pyridin-2-yl)acetate

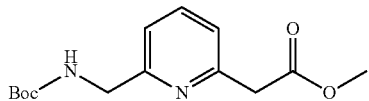 [SMILES: COC(=O)Cc1cccc(CNC(=O)OC(C)(C)C)n1]

¹H NMR (CHLOROFORM-d) δ: 7.65 (t, J=7.7 Hz, 1H), 7.14-7.23 (m, 2H), 5.59 (br. s., 1H), 4.44 (d, J=5.1 Hz, 2H), 3.86 (s, 2H), 3.74 (s, 3H), 1.48 (s, 9H); LC-MS: m/z (M+H)=281.5.

Step C to Step D: N,N'-(5,5'-((1S,3S)-cyclohexane-1,3-diyl)bis(1,3,4-thiadiazole-5,2-diyl))bis(2-(6-(aminomethyl)pyridin-2-yl)acetamide) (244)

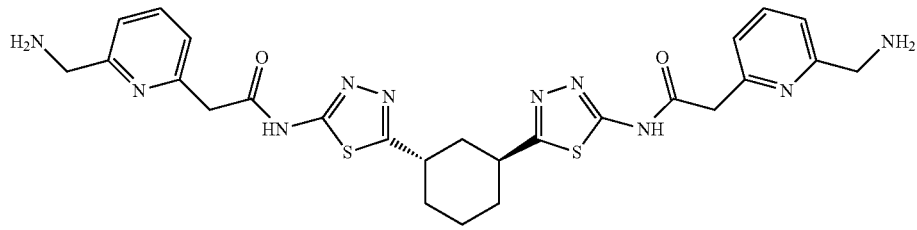 [SMILES: NCc1cccc(CC(=O)Nc2nnc([C@H]3CCC[C@H](c4nnc(NC(=O)Cc5cccc(CN)n5)s4)C3)s2)n1]

¹H NMR (METHANOL-d₄) δ: 7.92 (t, J=7.8 Hz, 2H), 7.50 (d, J=7.8 Hz, 2H), 7.44 (d, J=7.8 Hz, 2H), 4.28-4.36 (m, 4H), 3.56-3.67 (m, 6H), 2.46 (t, J=5.8 Hz, 2H), 2.07 (d, J=5.9 Hz, 2H), 1.94-2.01 (m, 2H), 1.73-1.79 (m, 2H); LC-MS: m/z (M+H)=579.5

Compound 245

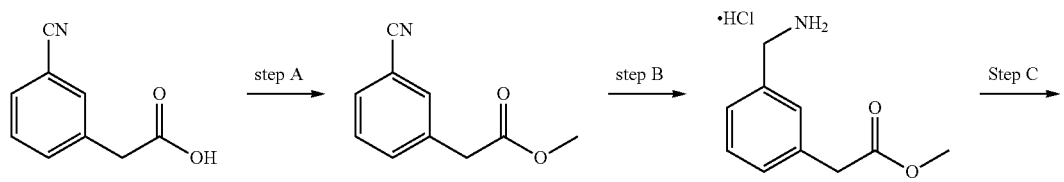

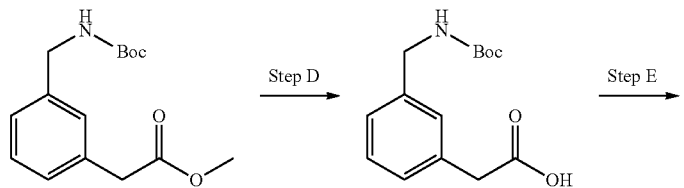

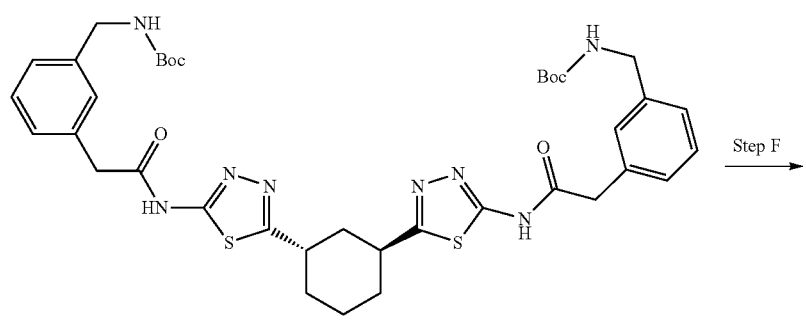

-continued

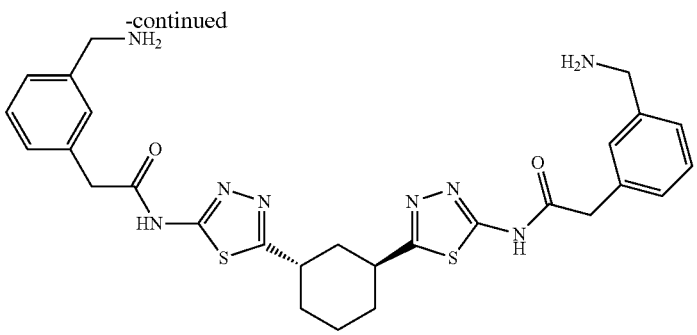

Step A: methyl 2-(3-cyanophenyl)acetate

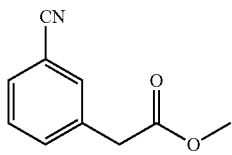

To a solution of 2-(3-cyanophenyl) acetic acid (1, 6.2 mmol) in methanol (20 ml) was added sulfurous dichloride (5 ml) and 0.1 ml N,N-dimethylformamide. Then the reaction mixture was heated to 80° C. for 2 h. When TLC indicated that the starting material was consumed, the mixture was concentrated to give the residue. The residue was poured into water (20 ml) and was extracted by ethyl acetate (50 ml*2). The organic layer was dried by anhydrous sodium sulfate, filtered, concentrated to give the desired product. LC-MS: m/z (M+H)=176.5

Step B: (3-(2-methoxy-2-oxoethyl)phenyl)methanaminium chloride

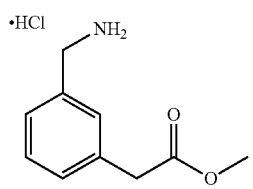

The procedure is the same as Step A of Compound 243
$^1$H NMR (METHANOL-d$_4$) δ: 7.33-7.47 (m, 4H), 3.73 (s, 2H), 3.70 (s, 3H), 3.37 (s, 2H). LC-MS: m/z (M+H)=180.5

Step C: methyl 2-(3-((tert-butoxycarbonylamino)methyl)phenyl)acetate

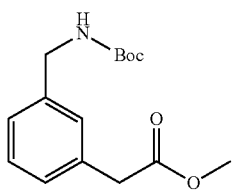 [SMILES: COC(=O)Cc1cccc(CNC(=O)OC(C)(C)C)c1]

The procedure is the same as Step B of Compound 243
$^1$H NMR (CHLOROFORM-d) δ: 7.14-7.26 (m, 4H), 4.87 (br. s., 1H), 4.33 (d, J=5.4 Hz, 2H), 3.72 (s, 3H), 3.64 (s, 2H), 1.48 (s, 9H). LC-MS: m/z (M+H)=280.5

Step D to Step E: tert-butyl (3,3'-(2,2'-(5,5'-((1S,3S)-cyclohexane-1,3-diyl)bis(1,3,4-thiadiazole-5,2-diyl))bis(azanediyl))bis(2-oxoethane-2,1-diyl))bis(3,1-phenylene))bis(methylene)dicarbamate

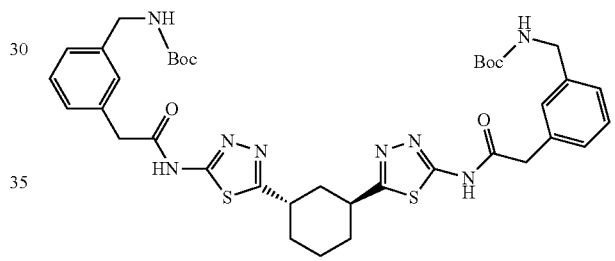

The procedure is the same as Step B to Step C of Compound 238
LC-MS: m/z (M+H)=777.5

Step F: N,N'-(5,5'-((1S,3S)-cyclohexane-1,3-diyl)bis(1,3,4-thiadiazole-5,2-diyl))bis(2-(3-(aminomethyl)phenyl)acetamide) (245)

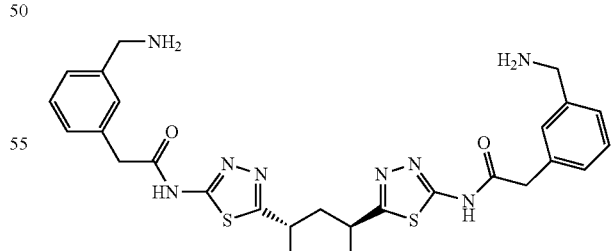

The procedure is the same as Step D of Compound 243
$^1$H NMR (METHANOL-d$_4$) δ: 7.34-7.52 (m, 8H), 4.09-4.18 (m, 4H), 3.93 (s, 4H), 3.62 (m, 2H), 2.45 (t, J=5.5 Hz, 2H), 2.04-2.13 (m, 4H), 1.70-1.81 (m, 2H). LC-MS: m/z (M+H)=577.5

Compound 27
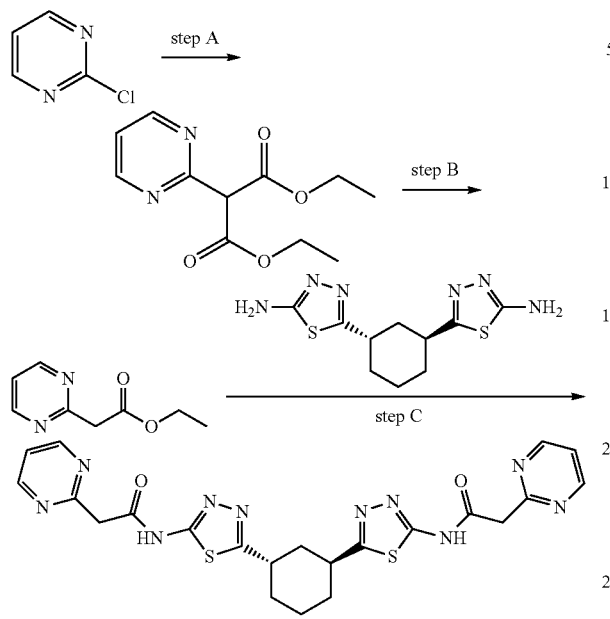
The procedure was the same as Compound 245
Step A: diethyl 2-(pyrimidin-2-yl)malonate
LC-MS: m/z (M+H)=239.5
Step B: methyl 2-(pyrimidin-2-yl)acetate
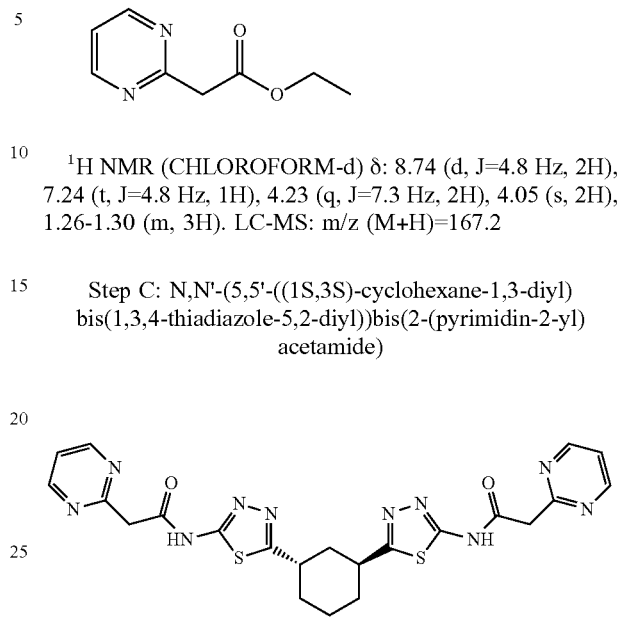
$^1$H NMR (CHLOROFORM-d) δ: 8.74 (d, J=4.8 Hz, 2H), 7.24 (t, J=4.8 Hz, 1H), 4.23 (q, J=7.3 Hz, 2H), 4.05 (s, 2H), 1.26-1.30 (m, 3H). LC-MS: m/z (M+H)=167.2
Step C: N,N'-(5,5'-((1S,3S)-cyclohexane-1,3-diyl)bis(1,3,4-thiadiazole-5,2-diyl))bis(2-(pyrimidin-2-yl)acetamide)
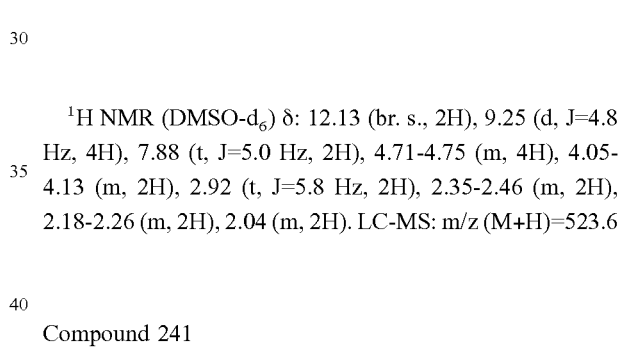
$^1$H NMR (DMSO-d$_6$) δ: 12.13 (br. s., 2H), 9.25 (d, J=4.8 Hz, 4H), 7.88 (t, J=5.0 Hz, 2H), 4.71-4.75 (m, 4H), 4.05-4.13 (m, 2H), 2.92 (t, J=5.8 Hz, 2H), 2.35-2.46 (m, 2H), 2.18-2.26 (m, 2H), 2.04 (m, 2H). LC-MS: m/z (M+H)=523.6
Compound 241
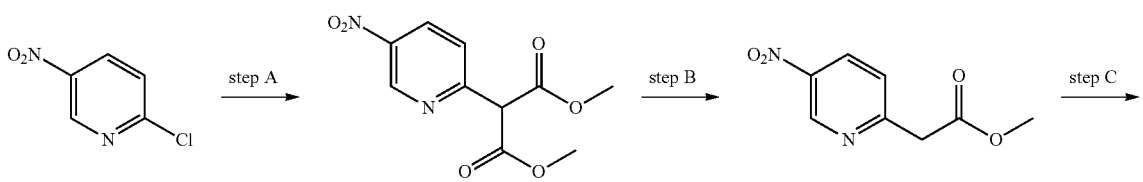
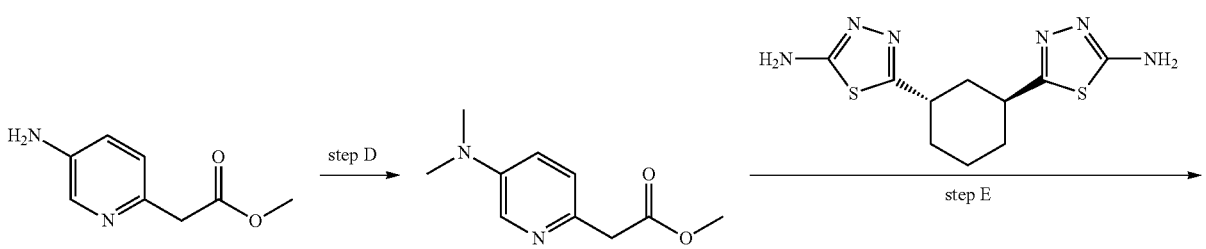

-continued

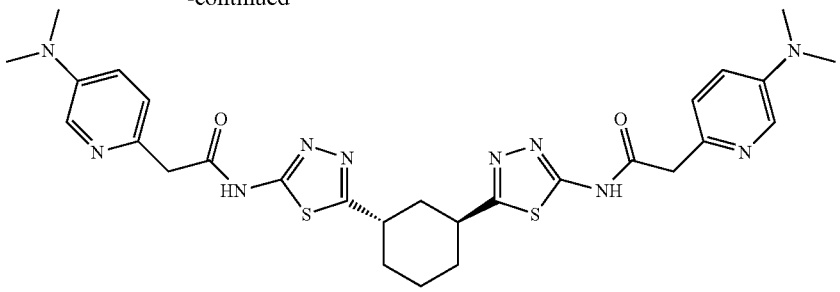

Step A: dimethyl 2-(5-nitropyridin-2-yl)malonate

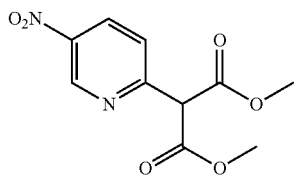 [SMILES: COC(=O)C(C(=O)OC)c1ccc([N+](=O)[O-])cn1]

The solution of dimethyl 2-(5-nitropyridin-2-yl)malonate (6.0 g, 37.8 mmol), dimethyl malonate (10.0 g, 75.7 mmol) and $Cs_2CO_3$ (24.7 g, 75.7 mmol) in DMF (50 mL) was stirred at 100 degree for 12 h. After cooling to room temperature, the reaction mixture was filtered, diluted with $H_2O$ and extracted with ethyl acetate. The organic layer was washed with brine, dried over sodium sulfate and evaporated under reduced pressure to get crude product. LC-MS: m/z (M+H)=255.3

Step B: methyl 2-(5-nitropyridin-2-yl)acetate

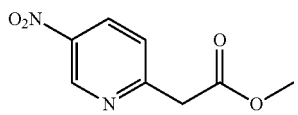

The solution of dimethyl 2-(5-nitropyridin-2-yl)malonate (10.0 g 41.7 mmol), NaCl (2.58 g, 44.20 mmol) and $H_2O$ (1.3 g, 74.23 mmol) in DMSO (50 mL) was stirred at 130 degree for 6 h. After cooling to room temperature, the reaction mixture was diluted with $H_2O$ and extracted with ethyl acetate. The organic layer was dried over sodium sulfate and evaporated under reduced pressure. The residue was purified by a standard method to get desired product.

$^1$H NMR (CHLOROFORM-d) δ: 9.40 (d, J=2.4 Hz, 1H), 8.48 (dd, J=8.6, 2.7 Hz, 1H), 7.56 (d, J=8.6 Hz, 1H), 4.02 (s, 2H), 3.77 (s, 3H). LC-MS: m/z (M+H)=197.1

Step C: methyl 2-(5-aminopyridin-2-yl)acetate

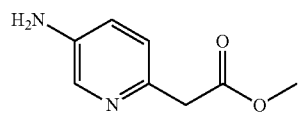

The solution of methyl 2-(5-nitropyridin-2-yl)acetate (500 mg, 2.5 mmol) and Pd/C (50 mg) in methanol (20 mL) was stirred under $H_2$ at room temperature for 3 h. Then, the reaction mixture was filtered and evaporated under reduced pressure to get desired product for the next step without further purification.

$^1$H NMR (CHLOROFORM-d) δ: 8.05 (d, J=2.7 Hz, 1H), 7.08 (d, J=8.3 Hz, 1H), 6.98 (dd, J=8.2, 2.8 Hz, 1H), 3.75 (s, 2H), 3.72 (s, 3H). LC-MS: m/z (M+H)=167.3

Step D: methyl 2-(5-(dimethylamino)pyridin-2-yl)acetate

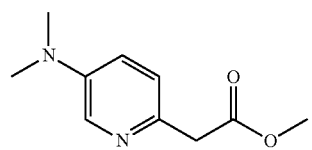

To the solution of methyl 2-(5-aminopyridin-2-yl)acetate (800 mg, 4.8 mmol) and paraformaldehyde (578.3 mg, 19.3 mmol) in methanol (20 mL) was added $NaBH_3CN$ (1.2 g, 19.26 mmol) and AcOH (1 drop, cat.). The mixture was stirred at room temperature for 12 h. Then, the reaction was quenched with aqueous ammonium chloride and extracted with DCM. The organic layer was with brine, dried over sodium sulfate and evaporated under reduced pressure. The residue was purified by a standard method to get desired product.

$^1$H H NMR (CHLOROFORM-d) δ: 8.09 (d, J=3.2 Hz, 1H), 7.14 (d, J=8.6 Hz, 1H), 6.99 (dd, J=8.6, 3.2 Hz, 1H), 3.77 (s, 2H), 3.72 (s, 3H), 2.98 (s, 6H). LC-MS: m/z (M+H)=195.2

Step E: N,N'-(5,5'-((1S,3S)-cyclohexane-1,3-diyl)bis(1,3,4-thiadiazole-5,2-diyl))bis(2-(5-(dimethylamino)pyridin-2-yl)acetamide) (241)
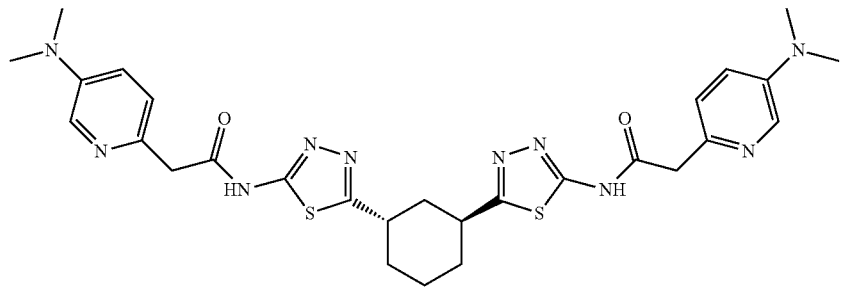
The procedure was the same as Step B of Compound 84
$^1$H NMR (CHLOROFORM-d) δ: 8.02 (d, J=3.0 Hz, 2H), 7.16 (d, J=8.6 Hz, 2H), 6.98 (dd, J=8.6, 3.2 Hz, 2H), 3.49 (dt, J=11.4, 5.7 Hz, 2H), 3.04-3.34 (m, 4H), 2.95 (s, 12H), 2.39 (t, J=5.6 Hz, 2H), 1.87-2.05 (m, 4H), 1.65-1.77 (m, 2H). LC-MS: m/z (M+H)=607.7
Compound 246
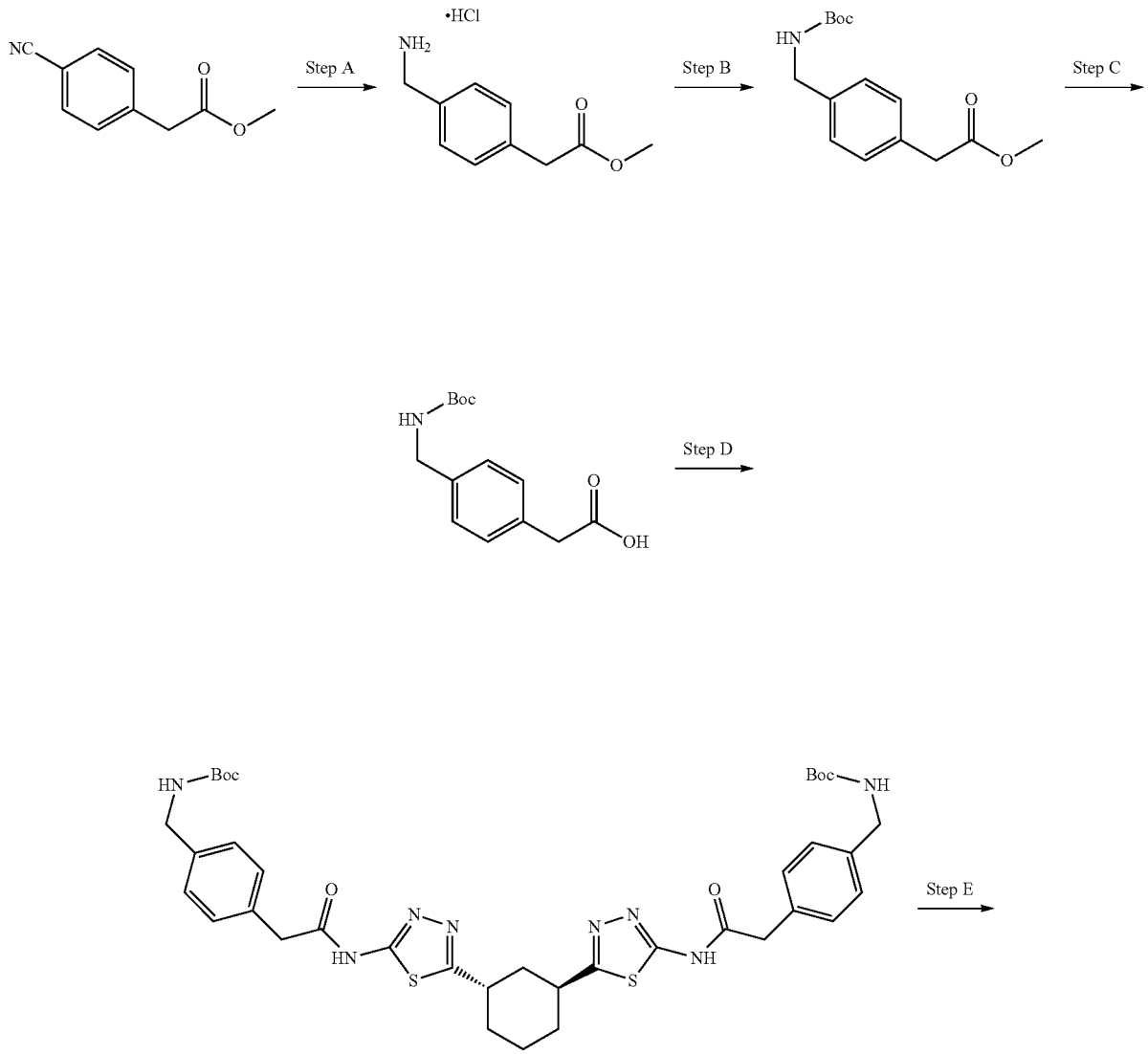

-continued

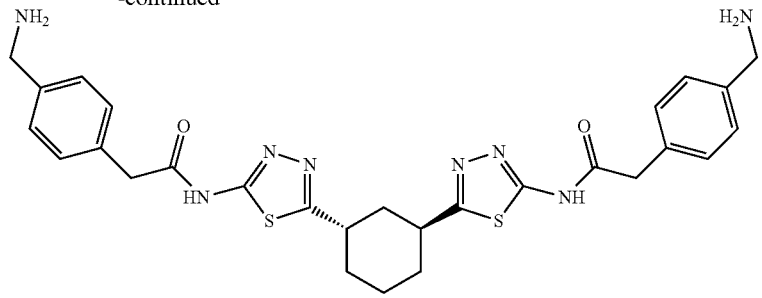

The procedure is the same as Step B to Step F of Compound 245

Step A: (4-(2-methoxy-2-oxoethyl)phenyl)methanaminium chloride

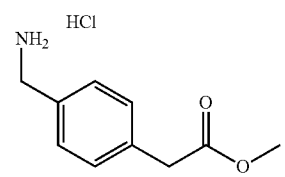

¹H NMR (DMSO-d₆) δ: 8.47 (br. s., 2H), 7.45 (d, J=7.8 Hz, 2H), 7.30 (d, J=7.5 Hz, 2H), 3.98 (br. s., 2H), 3.71 (s, 2H), 3.71 (s, 3H).

Step B to Step C: 2-(4-(((tert-butoxycarbonylamino)methyl)phenyl)acetic acid

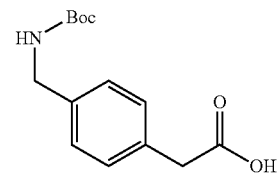 [SMILES: CC(C)(C)OC(=O)NCc1ccc(CC(=O)O)cc1]

¹H NMR (DMSO-d₆) δ: 7.34 (t, J=6.0 Hz, 1H), 7.11-7.20 (m, J=7.8 Hz, 2H), 7.00-7.10 (m, J=7.8 Hz, 2H), 4.05 (d, J=6.2 Hz, 2H), 3.20 (s, 2H), 1.38 (s, 9H)

Step D to Step F: N,N'-(5,5'-(((1S,3S)-cyclohexane-1,3-diyl)bis(1,3,4-thiadiazole-5,2-diyl))bis(2-(4-(aminomethyl)phenyl)acetamide) (246)

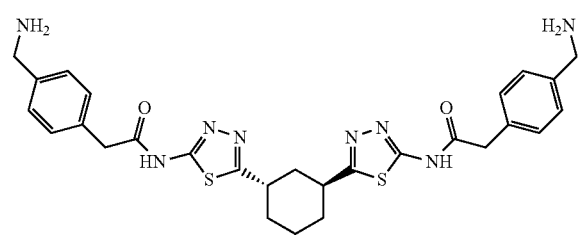 [SMILES: NCc1ccc(CC(=O)Nc2nnc([C@H]3CCC[C@H](c4nnc(NC(=O)Cc5ccc(CN)cc5)s4)C3)s2)cc1]

¹H NMR (METHANOL-d₄) δ: 7.42-7.50 (m, 8H), 4.09-4.15 (m, 4H), 3.90 (s, 4H), 3.57-3.65 (m, 2H), 2.45 (t, J=5.6 Hz, 2H), 2.05-2.13 (m, 2H), 1.92-2.02 (m, 2H), 1.70-1.80 (m, 2H); LC-MS: m/z (M+H)=577.5

Compound 247

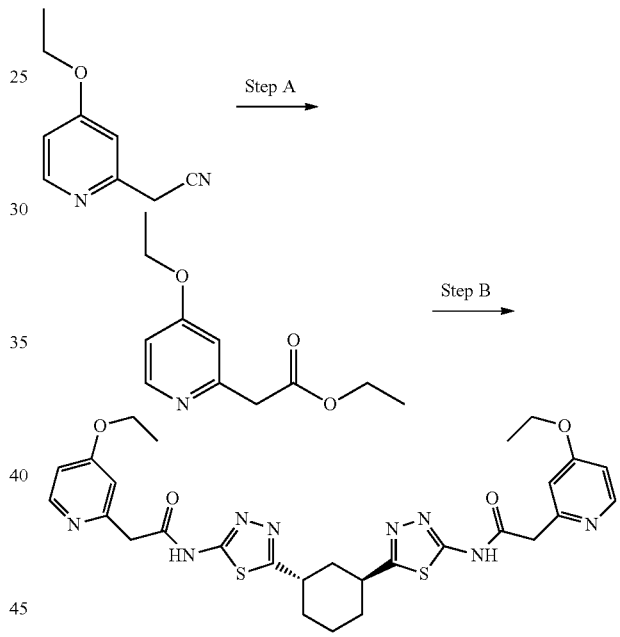

Step A: ethyl 2-(4-ethoxypyridin-2-yl)acetate

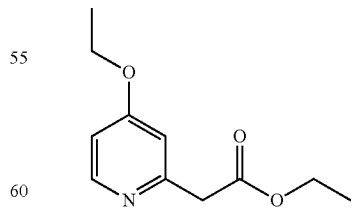

The solution of 2-(4-ethoxypyridin-2-yl)acetonitrile (150 mg, 0.92 mmol) in EtOH/HCl (6 mL/2 mL) was stirred at 70 degree for 2 h. The mixture was evaporated in vacuum. The residue was used for the next step without further purification. LC-MS: m/z (M+H)=210.2

Step B: N,N'-(5,5'-((1S,3S)-cyclohexane-1,3-diyl)bis(1,3,4-thiadiazole-5,2-diyl))bis(2-(4-ethoxypyridin-2-yl)acetamide) (247)

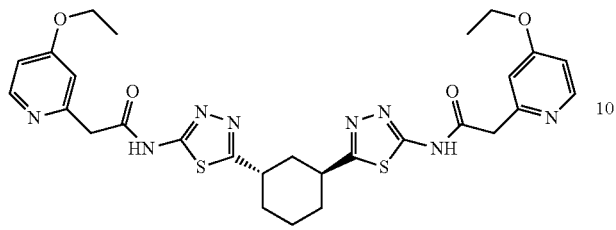

The procedure was the same as Step B of Compound 84
$^1$H NMR (CHLOROFORM-d) δ: 8.31 (d, J=5.6 Hz, 2H), 6.92 (d, J=2.1 Hz, 2H), 6.80 (dd, J=5.8, 2.0 Hz, 2H), 4.32 (br. s., 4H), 4.11 (q, J=6.9 Hz, 4H), 3.46-3.56 (m, 2H), 2.35-2.45 (m, 2H), 1.85-2.03 (m, 4H), 1.67-1.76 (m, 2H), 1.42 (t, J=7.0 Hz, 6H). LC-MS: m/z (M+H)=609.8

Compounds 356, 350, and 353 were prepared in an analogous manner to Compound 84:

N,N'-(5,5'-((1S,3S)-cyclohexane-1,3-diyl)bis(1,3,4-thiadiazole-5,2-diyl))bis(2-(4-(difluoromethoxy)pyridin-2-yl)acetamide) (356)

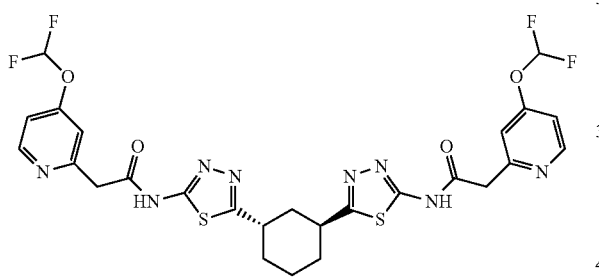

$^1$H NMR (CHLOROFORM-d) δ: 8.63 (d, J=5.6 Hz, 2H), 7.08-7.14 (m, 2H), 7.03 (dd, J=5.6, 2.1 Hz, 2H), 6.69 (t, J=72 Hz, 1H), 4.09 (s, 4H), 3.54-3.66 (m, 2H), 2.47 (t, J=5.5 Hz, 2H), 1.96-2.10 (m, 4H), 1.71-1.80 (m, 2H); LC-MS: m/z (M+H)=653.5

N,N'-(5,5'-((1S,3S)-cyclohexane-1,3-diyl)bis(1,3,4-thiadiazole-5,2-diyl))bis(2-(4-(difluoromethoxy)pyridin-2-yl)acetamide) (350)

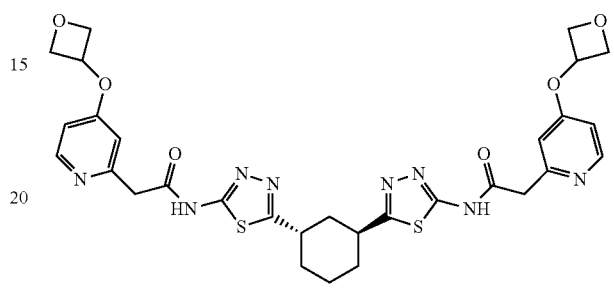

$^1$H NMR (CHLOROFORM-d) δ: 8.51 (d, J=5.7 Hz, 1H), 6.65 (d, J=2.3 Hz, 1H), 6.60 (dd, J=5.8, 2.4 Hz, 1H), 5.29 (m, 2H), 5.02 (t, J=7.0 Hz, 2H), 4.77 (dd, J=8.0, 5.1 Hz, 2H), 3.57 (m, 2H), 2.48 (t, J=6.0 Hz, 2H), 2.05-1.96 (m, 4H), 1.80-1.74 (m, 2H). LC-MS: m/z (M+H)=665.5

N,N'-(5,5'-((1S,3S)-cyclohexane-1,3-diyl)bis(1,3,4-thiadiazole-5,2-diyl))bis(2-(4-(difluoromethoxy)pyridin-2-yl)acetamide) (353)

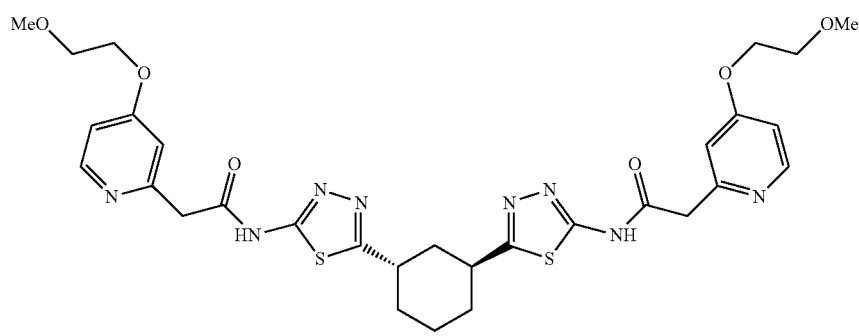 [SMILES: COCCOc1ccnc(CC(=O)Nc2nnc([C@H]3CCC[C@H](c4nnc(NC(=O)Cc5cc(OCCOC)ccn5)s4)C3)s2)c1]

¹H NMR (CHLOROFORM-d) δ: 8.40 (d, J=2.7 Hz, 2H), 7.33-7.29 (m, 2H), 7.23 (d, J=8.5 Hz, 2H), 4.24-4.19 (m, 4H), 3.98 (s, 4H), 3.82-3.78 (m, 4H), 3.57 (m, 2H), 2.47 (t, J=5.5 Hz, 2H), 2.06-1.94 (m, 4H), 1.80-1.74 (m, 2H). LC-MS: m/z (M+H)=669.5

N,N'-(5,5'-((1S,3S)-cyclopentane-1,3-diyl)bis(1,3,4-thiadiazole-5,2-diyl))bis(2-(5-methoxypyridin-2-yl)acetamide) (347)

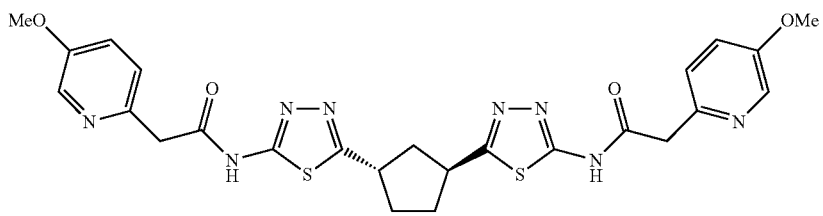 [SMILES: COc1ccc(CC(=O)Nc2nnc([C@H]3CC[C@H](c4nnc(NC(=O)Cc5ccc(OC)cn5)s4)C3)s2)nc1]

¹H NMR (CHLOROFORM-d) d: 8.36 (t, J=1.7 Hz, 2H), 7.25 (d, J=1.6 Hz, 4H), 4.00 (s, 4H), 3.90 (s, 6H), 3.83 (quint, J=7.4 Hz, 2H), 2.56 (t, J=7.7 Hz, 2H), 2.39-2.50 (m, 2H), 2.10 (m, 2H). LC-MS: m/z (M+H)=567.7
Compound 248

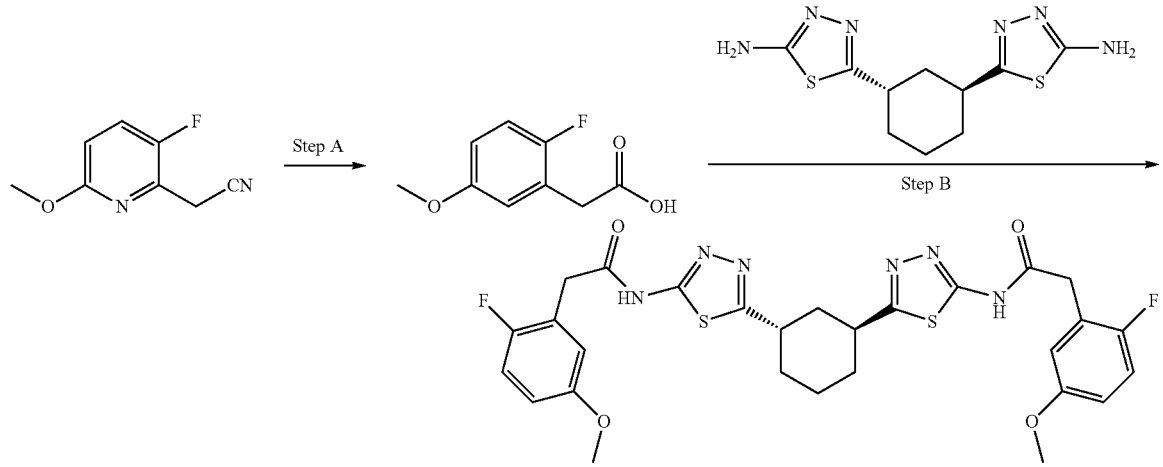

Step A: 2-(2-fluoro-5-methoxyphenyl)acetic acid

Step B: N,N'-(5,5'-((1S,3S)-cyclohexane-1,3-diyl)bis(1,3,4-thiadiazole-5,2-diyl))bis(2-(2-fluoro-5-methoxyphenyl)acetamide) (248)

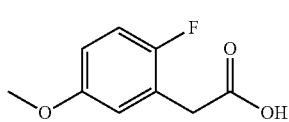

The solution of 2-(2-fluoro-5-methoxyphenyl)acetonitrile (200 mg, 1.0 mmol) and sodium hydroxide (81.5 mg, 2.0 mmol) in water was stirred at 100 degree for 8 h. The reaction mixture was evaporated under reduced pressure to get the crude product for the next step without further purification. LC-MS: m/z (M−H)=183.2

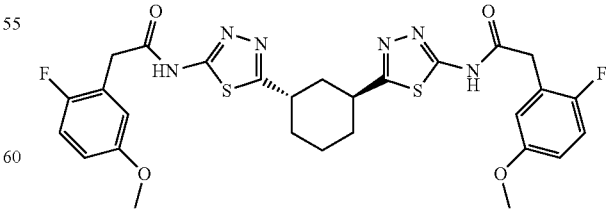

The procedure was the same as Compound 37
¹H NMR (DMSO-d₆) δ: 12.74 (s, 2H), 7.07-7.16 (m, 2H), 6.97 (dd, J=5.9, 3.2 Hz, 2H), 6.87 (dt, J=8.9, 3.6 Hz, 2H), 3.86 (s, 4H), 3.68-3.77 (s, 8H), 3.44-3.53 (m, 2H), 2.30 (t, J=5.4 Hz, 2H), 1.89-2.02 (m, 2H), 1.76-1.89 (m, 2H), 1.62 (m, 2H). LC-MS: m/z (M+H)=615.7

Compound 249

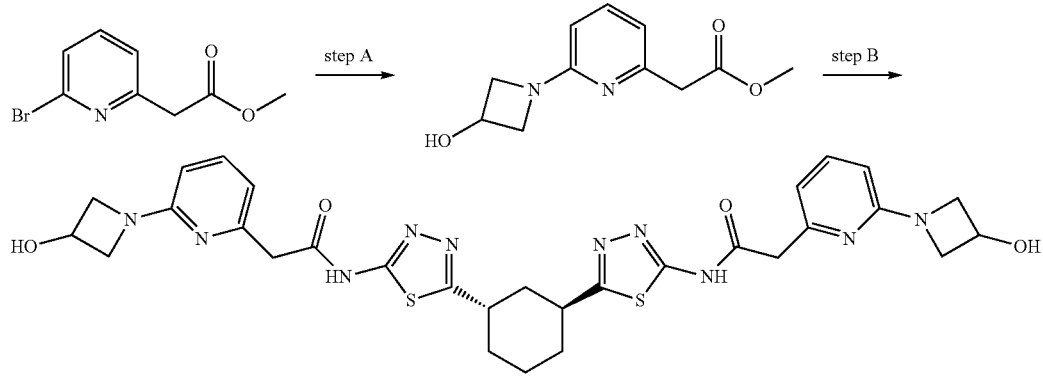

Step A: methyl 2-(6-(3-hydroxyazetidin-1-yl)pyridin-2-yl)acetate

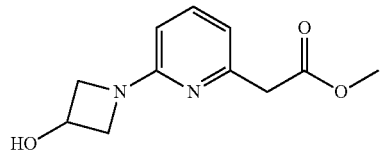 [SMILES: COC(=O)Cc1cccc(N2CC(O)C2)n1]

The solution of methyl 2-(6-bromopyridin-2-yl)acetate (500.0 mg, 2.17 mmol), azetidin-3-ol hydrochloride (285.9 mg, 2.61 mmol), CuI (248.3 mg, 1.30 mmol), L-proline (149.7 mg, 1.30 mmol) and Cs$_2$CO$_3$ (24.7 g, 75.7 mmol) in DMSO (6 mL) was stirred at 90 degree for 12 h under N$_2$. After cooling to room temperature, the reaction mixture was filtered, diluted with H$_2$O and extracted with ethyl acetate. The organic layer was washed with brine, dried over sodium sulfate and evaporated under reduced pressure. The residue was purified by a standard method to give desired compound.

$^1$H NMR (CHLOROFORM-d) δ: 7.43 (dd, J=8.1, 7.5 Hz, 1H), 6.59 (d, J=7.3 Hz, 1H), 6.21 (d, J=8.3 Hz, 1H), 4.75 (tt, J=6.4, 4.6 Hz, 1H), 4.29 (dd, J=9.4, 6.4 Hz, 2H), 3.86 (dd, J=9.5, 4.4 Hz, 2H), 3.69-3.77 (m, 5H). LC-MS: m/z (M+H)=223.4

Step B: N,N'-(5,5'-((1S,3S)-cyclohexane-1,3-diyl)bis(1,3,4-thiadiazole-5,2-diyl))bis(2-(6-(3-hydroxyazetidin-1-yl)pyridin-2-yl)acetamide) (249)

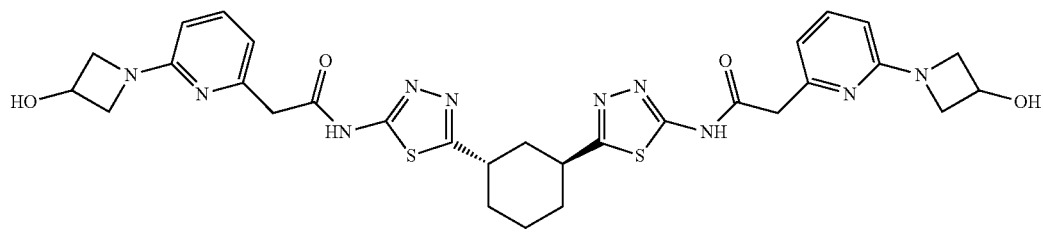 [SMILES: O=C(Cc1cccc(N2CC(O)C2)n1)Nc1nnc([C@H]2CCC[C@H](c3nnc(NC(=O)Cc4cccc(N5CC(O)C5)n4)s3)C2)s1]

The procedure was the same as Step B of Compound 84

$^1$H NMR (CHLOROFORM-d) δ: 7.32 (t, J=7.8 Hz, 2H), 6.43 (d, J=7.3 Hz, 2H), 6.14 (d, J=8.3 Hz, 2H), 4.56-4.70 (m, 2H), 4.23 (t, J=7.5 Hz, 4H), 3.77-3.88 (m, 4H), 3.64-3.74 (m, 2H), 3.36-3.47 (m, 2H), 2.31 (d, J=5.1 Hz, 2H), 1.75-1.98 (m, 4H), 1.55-1.68 (m, 2H). LC-MS: m/z (M+H)=663.9

Compound 383
The procedure was the same as Compound 249
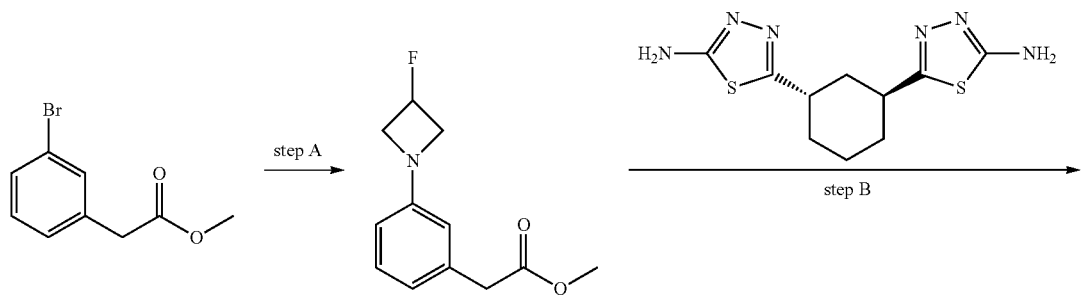
Step A: methyl 2-(3-(3-fluoroazetidin-1-yl)phenyl)acetate
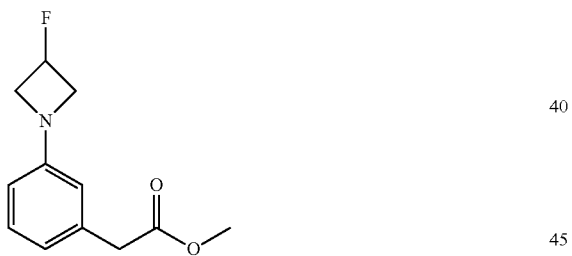
¹H NMR (CHLOROFORM-d) δ: 7.18-7.24 (m, 1H), 6.74 (d, J=7.5 Hz, 1H), 6.48-6.38 (m, 2H), 5.44 (m, 1H), 4.27-4.16 (m, 2H), 3.71 (s, 3H), 3.60 (s, 2H). LC-MS: m/z (M+H)=224.2
Step B: N,N'-(5,5'-((1S,3S)-cyclohexane-1,3-diyl)bis(1,3,4-thiadiazole-5,2-diyl))bis(2-(3-(3-fluoroazetidin-1-yl)phenyl)acetamide)
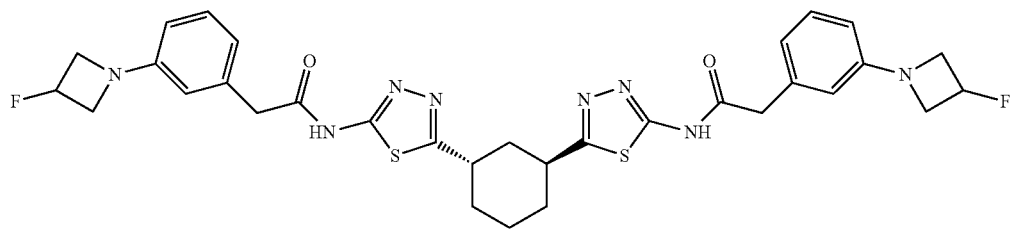 [SMILES: O=C(Cc1cccc(N2CC(F)C2)c1)Nc1nnc([C@H]2CCC[C@H](c3nnc(NC(=O)Cc4cccc(N5CC(F)C5)c4)s3)C2)s1]

| 309 | 310 |
|---|---|
| ¹H NMR (DMSO-d₆) δ: 12.67 (s, 2H), 7.14 (t, J=7.8 Hz, 2H), 6.68 (d, J=7.5 Hz, 2H), 6.46 (s, 2H), 6.38 (dd, J=7.9, 1.7 Hz, 2H), 5.55 (dtt, J=56, 5.8, 2.8 Hz, 2H), 4.20-4.07 (m, 4H), 3.78-3.93 (m, 4H), 3.70 (s, 4H), 3.48 (m, 2H), 2.29 (t, | J=5.4 Hz, 2H), 1.88-1.97 (m, 2H), 1.77-1.88 (m, 2H), 1.61 (m, 2H). LC-MS: m/z (M+H)=665.6

Compound 250 |

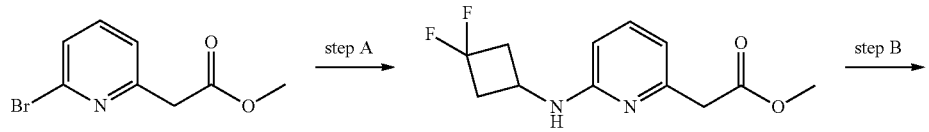

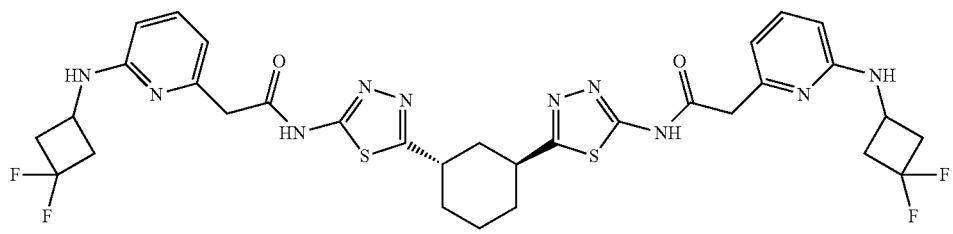 [SMILES: O=C(Cc1cccc(NC2CC(F)(F)C2)n1)Nc1nnc([C@H]2CCC[C@H](c3nnc(NC(=O)Cc4cccc(NC5CC(F)(F)C5)n4)s3)C2)s1]

The procedure was the same as Compound 249.

Step A: methyl 2-(6-(3,3-difluorocyclobutylamino)pyridin-2-yl)acetate

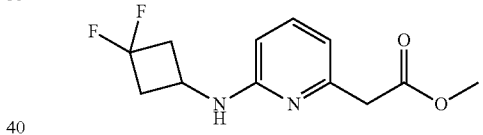

¹H NMR (CHLOROFORM-d) δ: 7.40-7.50 (m, 1H), 6.65 (d, J=7.3 Hz, 1H), 6.26 (d, J=8.3 Hz, 1H), 4.94 (br. s., 1H), 4.02-4.17 (m, 1H), 3.71-3.77 (m, 3H), 3.66-3.71 (m, 2H), 3.00-3.15 (m, 2H), 2.39-2.60 (m, 2H). LC-MS: m/z (M+H)= 257.6

Step B: N,N'-(5,5'-((1S,3S)-cyclohexane-1,3-diyl)bis(1,3,4-thiadiazole-5,2-diyl))bis(2-(6-(3,3-difluorocyclobutylamino)pyridin-2-yl)acetamide) (250)

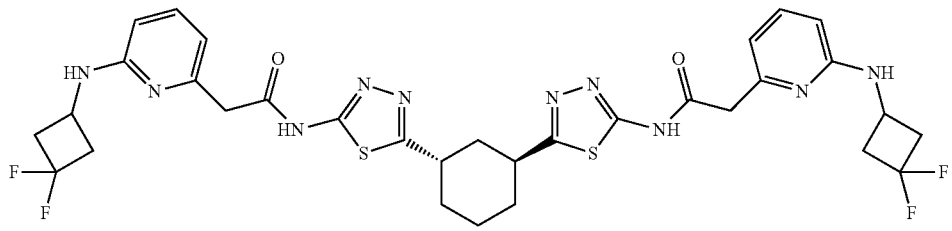

311

$^1$H NMR (CHLOROFORM-d) δ: 7.41-7.49 (m, 2H), 6.57 (d, J=7.3 Hz, 2H), 6.29 (d, J=8.3 Hz, 2H), 5.86 (d, J=5.4 Hz, 2H), 4.07-4.23 (m, 2H), 3.84 (s, 4H), 3.52-3.58 (m, 2H),

312

3.08-3.25 (m, 4H), 2.51-2.63 (m, 4H), 2.46 (t, J=5.6 Hz, 2H), 1.88-2.11 (m, 4H), 1.70-1.82 (m, 2H). LC-MS: m/z (M+H)=731.5

Compound 251

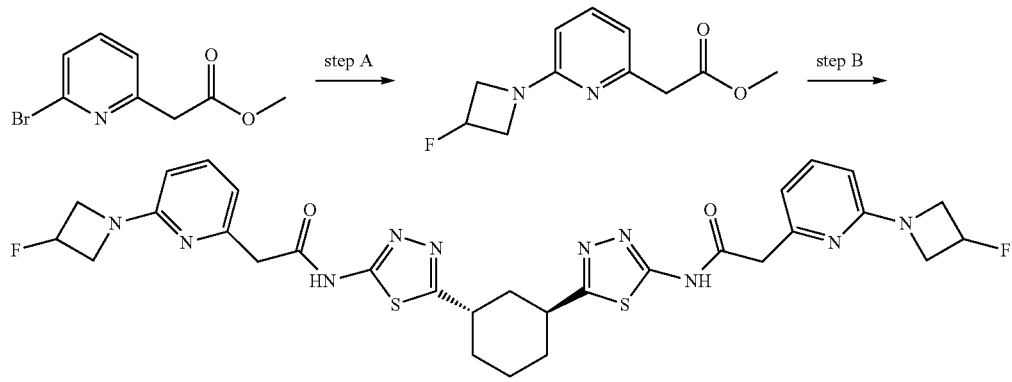

The procedure was the same as Compound 249

Step A: methyl 2-(6-(3-fluoroazetidin-1-yl)pyridin-2-yl)acetate

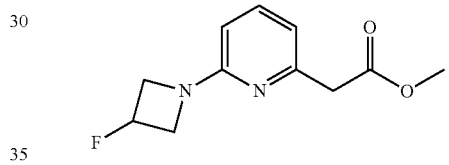

$^1$H NMR (CHLOROFORM-d) δ: 7.46 (t, J=7.8 Hz, 1H), 6.65 (d, J=7.3 Hz, 1H), 6.24 (d, J=8.3 Hz, 1H), 5.46-5.55 (m, 0.5H), 5.33-5.40 (m, 0.5H), 4.26-4.39 (m, 2H), 4.05-4.20 (m, 2H), 3.71-3.77 (m, 5H). LC-MS: m/z (M+H)=211.6

Step B: N,N'-(5,5'-((1S,3S)-cyclohexane-1,3-diyl)bis(1,3,4-thiadiazole-5,2-diyl))bis(2-(6-(3-fluoroazetidin-1-yl)pyridin-2-yl)acetamide) (251)

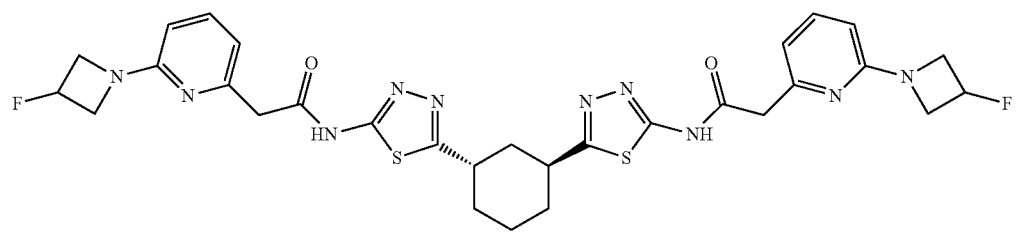 [SMILES: O=C(Cc1cccc(N2CC(F)C2)n1)Nc1nnc([C@H]2CCC[C@H](c3nnc(NC(=O)Cc4cccc(N5CC(F)C5)n4)s3)C2)s1]

$^1$H NMR (DMSO-d$_6$) δ: 12.70 (br. s., 2H), 7.55 (t, J=7.0 Hz, 2H), 6.70 (d, J=7.3 Hz, 2H), 6.38 (d, J=7.5 Hz, 2H), 5.52-5.63 (m, 1H), 5.35-5.47 (m, 1H), 4.18-4.42 (m, 4H), 3.91-4.09 (m, 4H), 3.86 (br. s., 4H), 3.45-3.54 (m, 2H), 2.31 (br. s., 2H), 1.90-2.05 (m, 2H), 1.78-1.90 (m, 2H), 1.62 (d, J=5.6 Hz, 2H). LC-MS: m/z (M+H)=667.8

Compound 252 and Compound 253

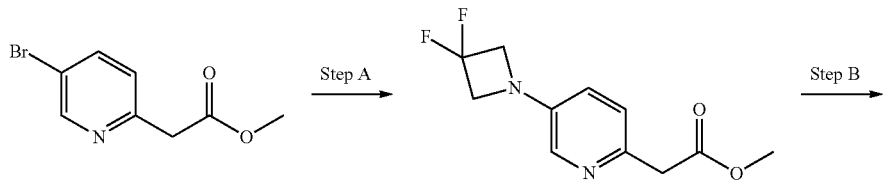

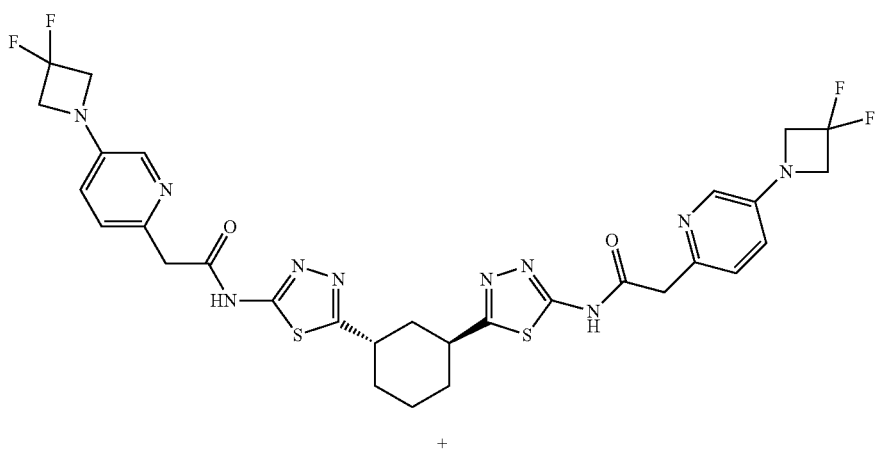

+

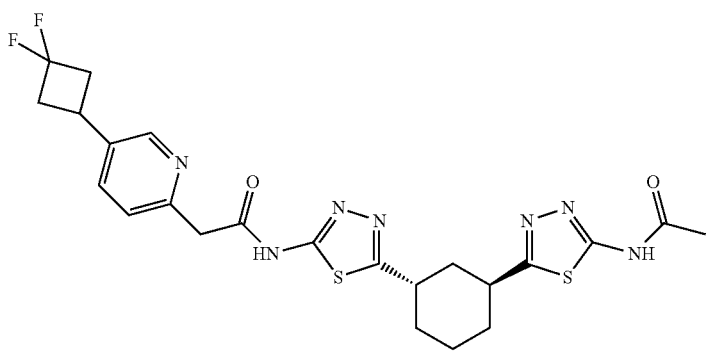

Step A: methyl 2-(5-(3,3-difluoroazetidin-1-yl)pyridin-2-yl)acetate

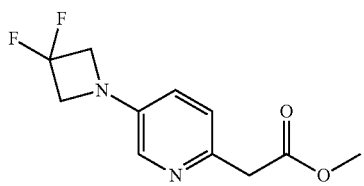 [SMILES: COC(=O)Cc1ccc(N2CC(F)(F)C2)cn1]

Step B: N,N'-(5,5'-((1S,3S)-cyclohexane-1,3-diyl)bis(1,3,4-thiadiazole-5,2-diyl))bis(2-(5-(3,3-difluoroazetidin-1-yl)pyridin-2-yl)acetamide) (252) and N-(5-((1S,3S)-3-(5-acetamido-1,3,4-thiadiazol-2-yl)cyclohexyl)-1,3,4-thiadiazol-2-yl)-2-(5-(3,3-difluoroazetidin-1-yl)pyridin-2-yl)acetamide (253)

A mixture of methyl 2-(5-(3,3-difluoroazetidin-1-yl)pyridin-2-yl)acetate (100 mg), 5,5'-((1S,3S)-cyclohexane-1,3-diyl)bis(1,3,4-thiadiazol-2-amine) (50 mg, 0.18 mmol), cesium carbonate (346.1 mg, 1.06 mmol) in DMA (3 mL) was heated to 130° C. under nitrogen atmosphere and The procedure is the same as Step B of Compound 254
$^1$H NMR (CHLOROFORM-d) δ: 7.88 (d, J=2.7 Hz, 1H), 7.23 (d, J=8.3 Hz, 1H), 6.87 (dd, J=8.5, 2.8 Hz, 1H), 4.31 (t, J=11.6 Hz, 4H), 3.84 (s, 2H), 3.74 (s, 3H). LC-MS: m/z (M+H)=243.2 microwave for 45 min. The mixture was evaporated in vacuum to dryness. The residue was purified by a standard method to give Compound 252 and Compound 253.
Compound 252
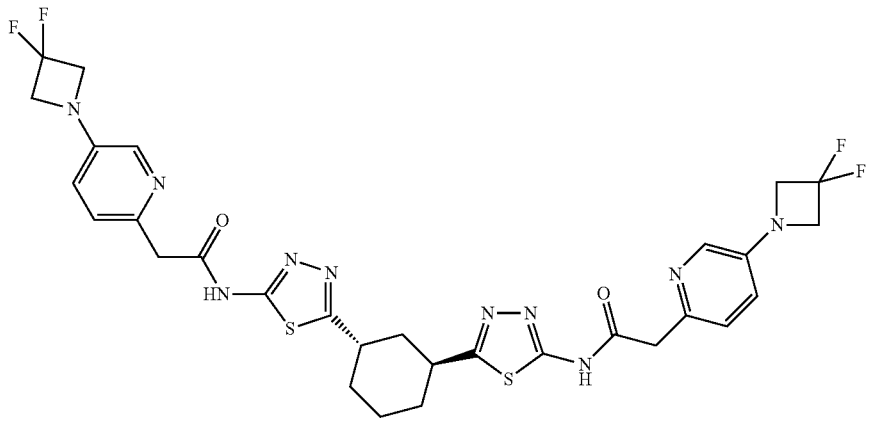 [SMILES: O=C(Cc1ccc(N2CC(F)(F)C2)cn1)Nc1nnc([C@H]2CCC[C@H](c3nnc(NC(=O)Cc4ccc(N5CC(F)(F)C5)cn4)s3)C2)s1]
$^1$H NMR (CHLOROFORM-d) δ: 7.81 (d, J=2.7 Hz, 2H), 7.25 (d, J=8.3 Hz, 2H), 6.87 (dd, J=8.5, 2.8 Hz, 2H), 4.27 (t, J=11.7 Hz, 9H), 3.44-3.54 (m, 2H), 2.29-2.49 (t, J=5.6 Hz, 2H), 1.97 (m, 2H), 1.91 (m, 2H), 1.72 (m, 2H). LC-MS: m/z (M+H)=703.2
Compound 253
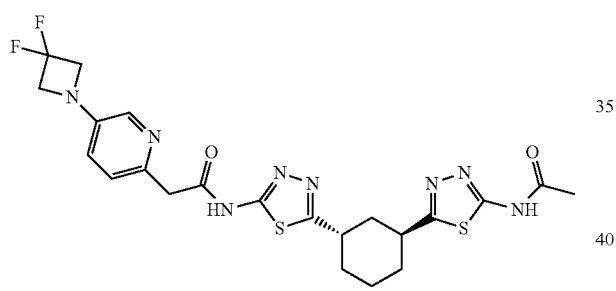
$^1$H NMR (CHLOROFORM-d) δ: 8.01 (s, 1H), 7.25 (d, J=8.3 Hz, 1H), 6.89 (d, J=6.7 Hz, 1H), 4.33 (t, J=11.6 Hz, 4H), 4.04 (s, 2H), 3.59 (m, 2H), 2.20 (m, 5H), 2.05 (m, 2H), 1.98 (m, 2H), 1.77 (m, 2H). LC-MS: m/z (M+H)=535.7
Compound 254
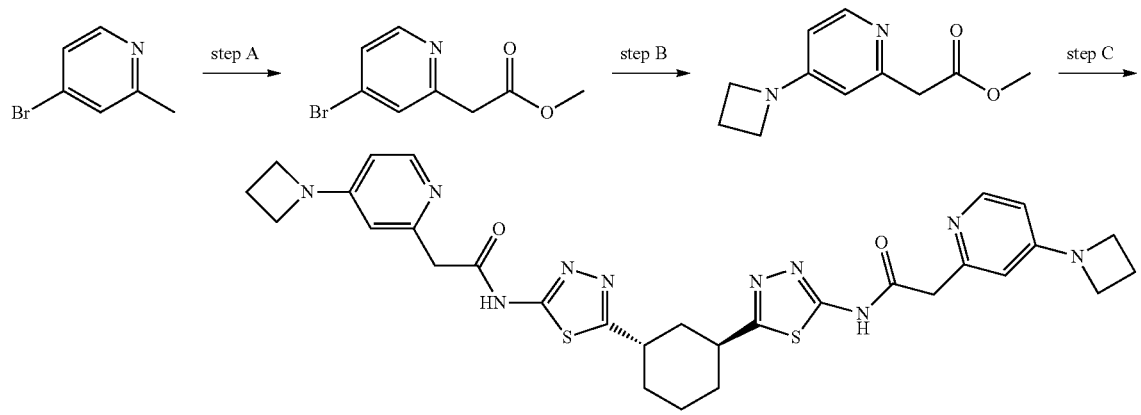

Step A: methyl 2-(4-bromopyridin-2-yl)acetate

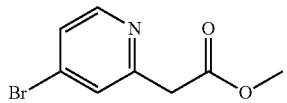

To a mixture of 4-bromo-2-methylpyridine (1 g, 5.8 mmol) in 15 mL of anhydrous THF was added LDA (9.2 mL, 2M) dropwise at −70, stirred for 30 min. dimethyl carbonate (630 mg, 7.0 mmol) was added dropwise to the above solution. After stirring for another 1 h, LC-MS found the reaction finished. It was quenched by Sat. NH4Cl solution and extracted with EtOAc. The organic layer was separated and evaporated under reduced pressure. The crude product was purified by a standard method to give desired product. LC-MS: m/z (M+H) 231.1.

Step B: methyl 2-(4-(azetidin-1-yl)pyridin-2-yl)acetate

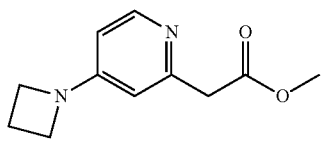

To a solution of (500 g, 2.2 mmol) in a mixture of dioxane (10 ml) and were added Pd2(dba)3 (200 mg, 0.22 mmol) and Xantphos (185 mg, 0.22 mmol), Cs2CO3 (1.4 g, 4.3 mmol) followed by azetidine (135 mg, 2.4 mmol) under nitrogen atmosphere, and the mixture was heated overnight at 90 .deg. C. After cooling to ambient temperature, the separated organic layer was evaporated under reduced pressure. The residue was taken up into ethyl acetate, washed with aqueous potassium carbonate solution and brine, and dried over sodium sulfate. After evaporation, the residue was purified by a standard method to give methyl 2-(4-(azetidin-1-yl)pyridin-2-yl)acetate.

$^1$H NMR (CHLOROFORM-d) δ: 8.02 (d, J=7.0 Hz, 1H), 6.36 (d, J=2.4 Hz, 1H), 6.27 (dd, J=6.7, 2.4 Hz, 1H), 4.81 (s, 2H), 4.25 (t, J=7.7 Hz, 4H), 3.38 (s, 3H), 2.60 (m, 2H). LC-MS: m/z (M+H) 207.3

Step C: N,N'-(5,5'-((1S,3S)-cyclohexane-1,3-diyl)bis(1,3,4-thiadiazole-5,2-diyl))bis(2-(4-(azetidin-1-yl)pyridin-2-yl)acetamide) (254)

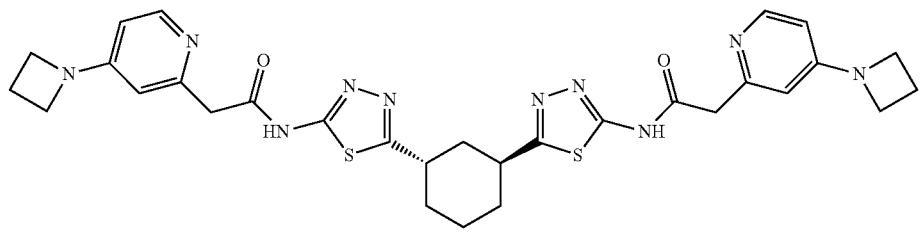 [SMILES: O=C(Cc1cc(N2CCC2)ccn1)Nc1nnc([C@H]2CCC[C@H](c3nnc(NC(=O)Cc4cc(N5CCC5)ccn4)s3)C2)s1]

319

The procedure was the same as Step B of Compound 249

¹H NMR (DMSO-d₆) δ: 8.06 (d, J=5.9 Hz, 2H), 6.41 (d, J=1.9 Hz, 2H), 6.30 (dd, J=5.9, 2.1 Hz, 2H), 3.91-4.02 (t, 8H, J=7.2 Hz), 3.87 (s, 4H), 3.48-3.52 (m, 2H), 2.36-2.41 (m, 4H), 2.31 (t, 2H, J=4 Hz), 1.94 (m, 2H), 1.85 (m, 2H), 1.63 (m, 2H). LC-MS: m/z (M+H) 631.2

Compound 255

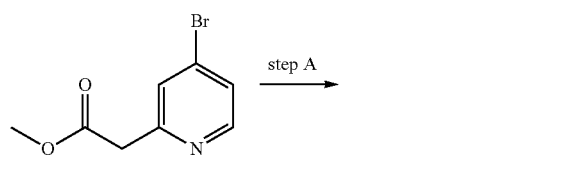

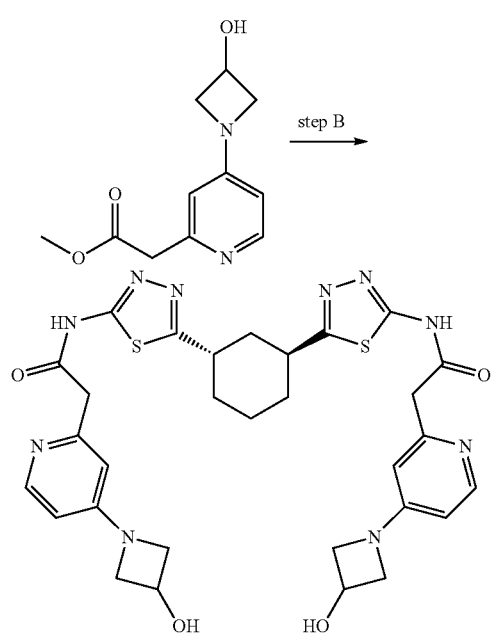

The procedure was the same as Compound 254

Step A: methyl 2-(4-(3-hydroxyazetidin-1-yl)pyridin-2-yl)acetate

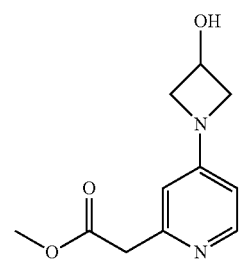 [SMILES: COC(=O)Cc1cc(N2CC(O)C2)ccn1]

¹H NMR (methanol-d4, 400 MHz) δ 8.03 (d, J=6.8 Hz, 1H), 6.54 (d, J=2.4 Hz, 1H), 6.50 (dd, J=6.8 Hz, 2.4 Hz, 1H), 4.89 (s, 2H), 4.80-4.77 (m, 1H), 4.22-4.38 (m, 2H), 3.96-3.92 (m, 2H), 3.75 (s, 3H). LC-MS: m/z (M+H) 223.4

320

Step B: N,N'-(5,5'-((1S,3S)-cyclohexane-1,3-diyl)bis(1,3,4-thiadiazole-5,2-diyl))bis(2-(4-(3-hydroxyazetidin-1-yl)pyridin-2-yl)acetamide) (255)

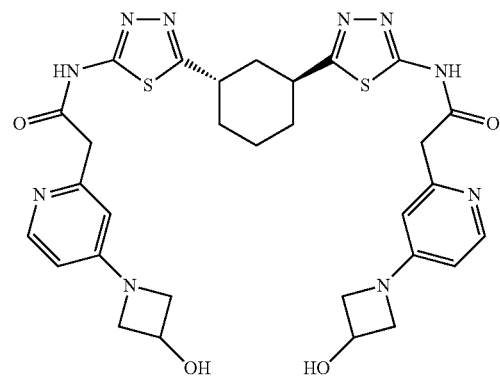 [SMILES: O=C(Cc1cc(N2CC(O)C2)ccn1)Nc1nnc([C@H]2CCC[C@H](c3nnc(NC(=O)Cc4cc(N5CC(O)C5)ccn4)s3)C2)s1]

¹H NMR (methanol-d4, 400 MHz) δ 8.04 (d, J=6.80 Hz, 2H), 6.28 (d, J=2.0 Hz, 2H), 6.18 (dd, J=6.0 Hz, 2.0 Hz, 2H), 4.72-4.69 (m, 2H), 4.20-4.17 (m, 4H), 4.06 (s, 4H), 3.81-3.75 (m, 4H), 3.50-3.47 (m, 2H), 2.39 (t, J=5.6 Hz, 2H), 1.99-1.90 (m, 4H), 1.71 (t, J=5.6 Hz, 2H). LC-MS: m/z (M+H) 664.1

Compound 256

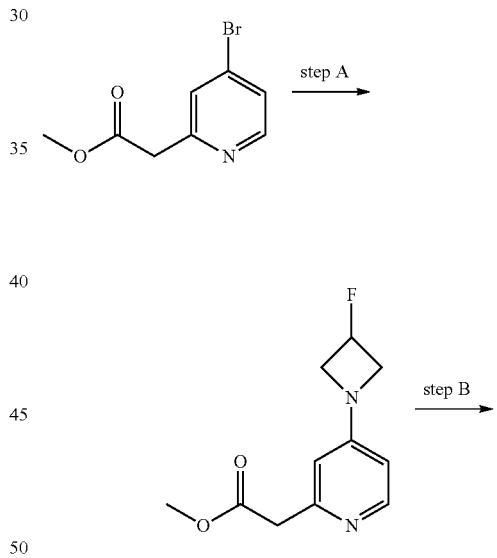

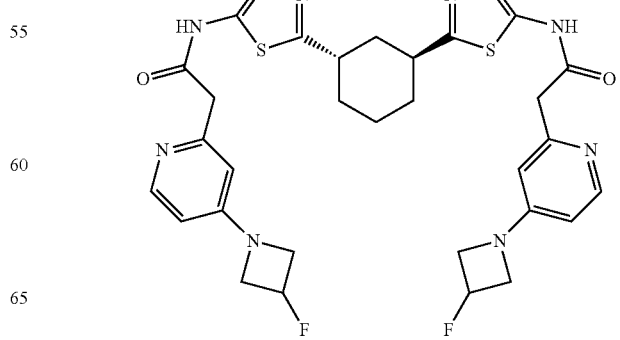

321
The procedure was the same as Compound 254
Step A: Methyl 2-(4-(3-fluoroazetidin-1-yl)pyridin-2-yl)acetate
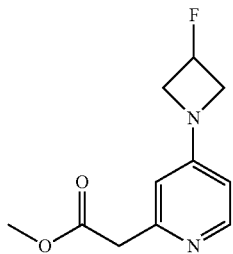 [SMILES: COC(=O)Cc1cc(N2CC(F)C2)ccn1]
¹H NMR (CDCl₃, 400 MHz) δ 8.21 (d, J=5.6 Hz, 1H), 6.33 (d, J=2.0 Hz, 1H), 6.26 (dd, J=6.0 Hz, 2.0 Hz, 1H), 5.58-5.40 (m, 1H), 4.36-4.27 (m, 2H), 4.19-4.09 (m, 2H), 3.83 (s, 2H), 3.75 (s, 3H). LC-MS: m/z (M+H) 225.4.
322
Step B: N,N'-(5,5'-((1S,3S)-cyclohexane-1,3-diyl)bis(1,3,4-thiadiazole-5,2-diyl))bis(2-(4-(3-fluoroazetidin-1-yl)pyridin-2-yl)acetamide) (256)
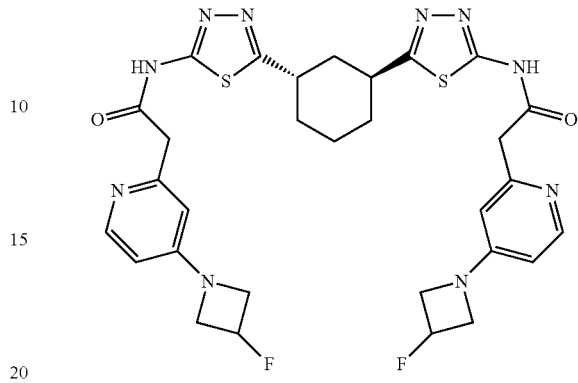
¹H NMR (METHANOL-d₄) δ 8.07 (s, 2H), 6.32-6.23 (m, 4H), 5.37 (d, J=60 Hz, 2H), 4.26 (m, 4H), 4.10 (m, 4H), 3.87 (s, 4H), 3.40 (m, 2H), 2.28 (t, J=5.6 Hz, 2H), 1.87 (m, 4H), 1.60 (m, 2H). LC-MS: m/z (M+H) 668.0.
Compound 257
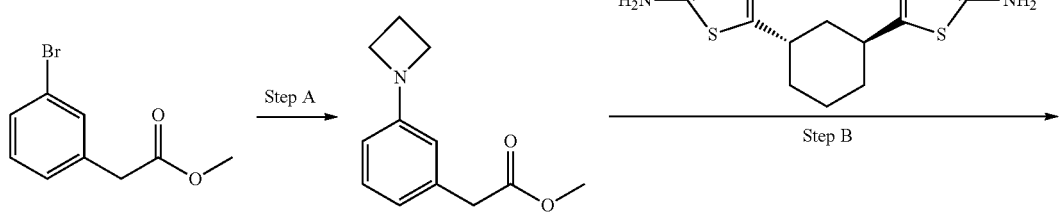
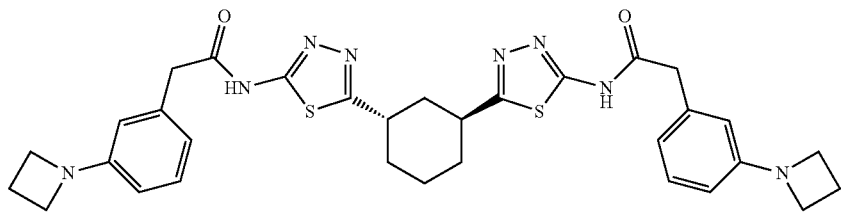

The procedure was the same as Compound 249

Step A: methyl 2-(3-(azetidin-1-yl)phenyl)acetate

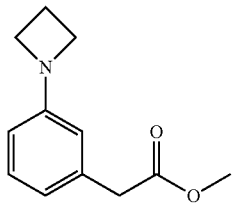

$^1$H NMR (CHLOROFORM-d) δ: 7.12-7.22 (s, 1H), 6.66 (d, J=7.5 Hz, 1H), 6.31-6.42 (m, 2H), 3.90 (t, J=7.3 Hz, 4H), 3.71 (s, 3H), 3.58 (s, 2H), 2.38 (quin, J=7.2 Hz, 2H). LC-MS: m/z (M+H)=206.5

Step B: N,N'-(5,5'-((1S,3S)-cyclohexane-1,3-diyl) bis(1,3,4-thiadiazole-5,2-diyl))bis(2-(3-(azetidin-1-yl)phenyl)acetamide) (257)

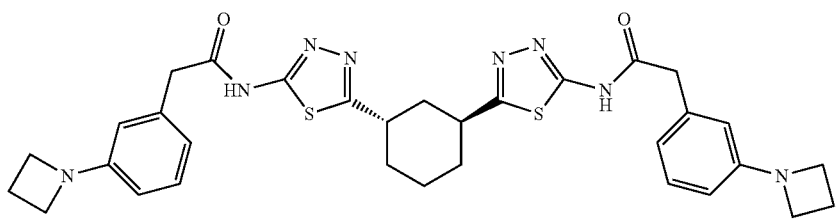 [SMILES: O=C(Cc1cccc(N2CCC2)c1)Nc1nnc([C@H]2CCC[C@H](c3nnc(NC(=O)Cc4cccc(N5CCC5)c4)s3)C2)s1]

$^1$H NMR (DMSO-d$_6$) δ: 12.66 (s, 2H), 7.10 (t, J=7.8 Hz, 2H), 6.62 (d, J=7.5 Hz, 2H), 6.38 (s, 2H), 6.30 (dd, J=7.9, 1.7 Hz, 2H), 3.78 (t, J=7.3 Hz, 8H), 3.68 (s, 4H), 3.44-3.49 (m, 2H), 2.25-2.34 (m, 6H), 1.89-1.98 (m, 2H), 1.76-1.87 (m, 2H), 1.53-1.66 (m, 2H). LC-MS: m/z (M+H)=629.8

Compound 258

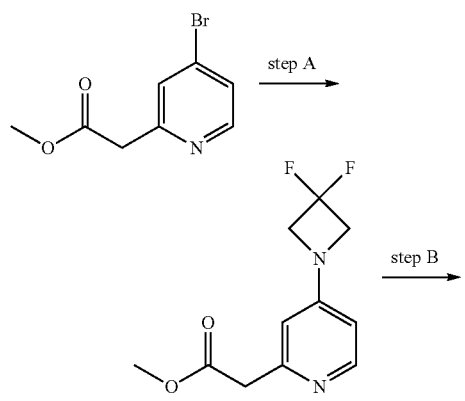

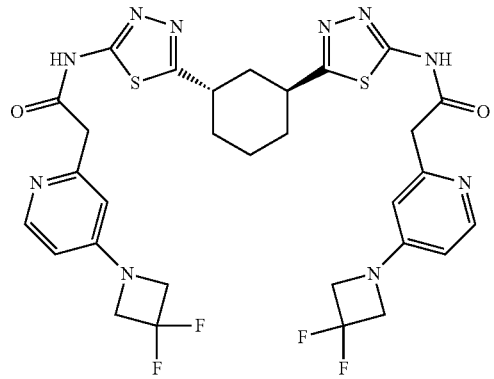

The procedure was the same as Compound 254

Step A: Methyl 2-(4-(3,3-difluoroazetidin-1-yl)pyridin-2-yl)acetate

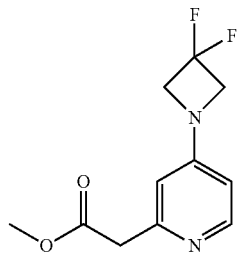 [SMILES: COC(=O)Cc1cc(N2CC(F)(F)C2)ccn1]

$^1$H NMR (METHANOL-d$_4$) δ 8.29 (d, J=6.4 Hz, 2H), 6.73 (d, J=2.4 Hz, 2H), 6.66 (dd, J=6.4 Hz, 2.4 Hz, 2H), 4.82-4.79 (m, 2H), 4.72-4.70 (m, 2H), 3.81 (s, 2H), 3.74 (s, 3H). LC-MS: m/z (M+H)=243.4.

325
Step B: N,N'-(5,5'-((1S,3S)-cyclohexane-1,3-diyl)bis(1,3,4-thiadiazole-5,2-diyl))bis(2-(4-(3,3-difluoro-azetidin-1-yl)pyridin-2-yl)acetamide) (258)
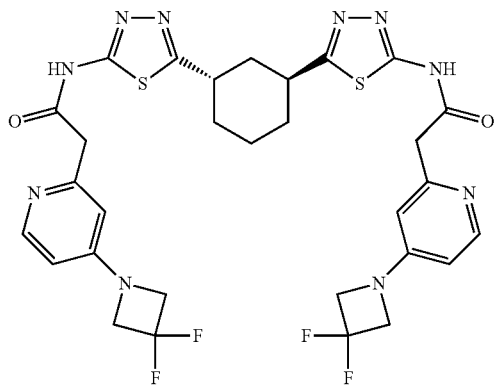 [SMILES: O=C(Cc1cc(N2CC(F)(F)C2)ccn1)Nc1nnc([C@H]2CCC[C@H](c3nnc(NC(=O)Cc4cc(N5CC(F)(F)C5)ccn4)s3)C2)s1]
¹H NMR (METHANOL-d₄) δ 8.20 (d, J=6.4 Hz, 2H), 6.74 (d, J=2.4 Hz, 2H), 6.68 (dd, J=6.4 Hz, 2.4 Hz, 2H), 4.62-4.56 (m, 8H), 3.57 (t, J=5.6 Hz, 2H), 2.44 (t, J=5.6 Hz, 2H), 2.09-2.04 (m, 2H), 1.99-1.96 (m, 2H), 1.76-1.74 (m, 2H). LC-MS: m/z (M+H)=703.2.
Compound 259
326
Step A: methyl 2-(3-(4-methylpiperazin-1-yl)phenyl)acetate
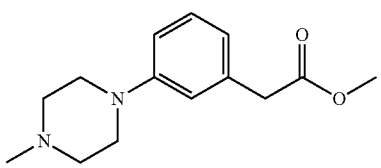
¹H NMR (CHLOROFORM-d) δ: 7.21 (t, J=7.9 Hz, 1H), 6.81-6.86 (m, 2H), 6.77 (d, J=7.3 Hz, 1H), 3.68 (s, 3H), 3.58 (s, 2H), 3.19-3.27 (m, 4H), 2.55-2.61 (m, 4H), 2.37 (s, 3H). LC-MS: m/z (M+H)=249.2
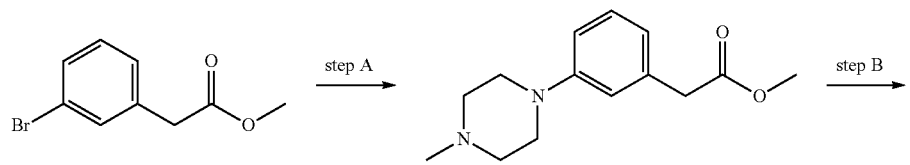
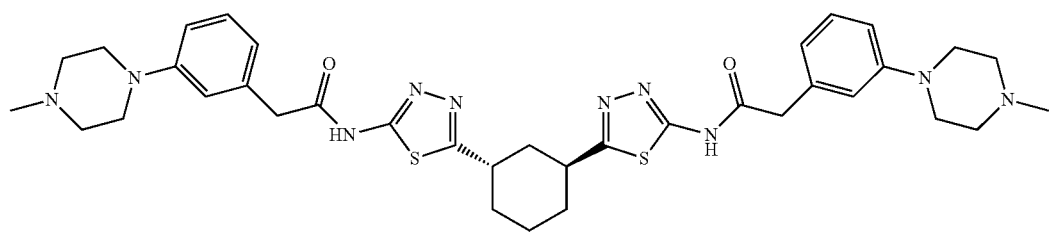

Step B: N,N'-(5,5'-((1S,3S)-cyclohexane-1,3-diyl) bis(1,3,4-thiadiazole-5,2-diyl))bis(2-(3-4-methylpiperazin-1-yl)phenyl)acetamide) (259)

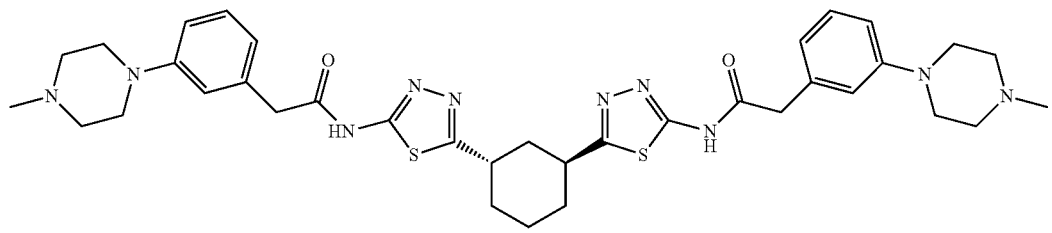

To a solution of 5,5'-((1S,3S)-cyclohexane-1,3-diyl)bis(1,3,4-thiadiazol-2-amine) (50 mg, 0.19 mmol) in 3 mL of DMSO were added methyl 2-(3-(4-methylpiperazin-1-yl)phenyl)acetate (140 mg, 0.57 mmol) and potassium 2-methylpropan-2-olate (63 mg, 0.57 mmol) under nitrogen atmosphere, and the mixture was stirred for 40 min at 100 .deg. C. under microwave irradiation. The reaction mixture was poured into water and extracted with ethyl acetate. The organic layer was washed with saturated aqueous sodium bicarbonate and brine and dried over sodium sulfate. The solvent was evaporated under reduced pressure. The residue was purified by a standard method to give the desired compound.

$^1$H NMR (METHANOL-$d_4$) δ: 7.18-7.25 (m, 2H), 6.98 (br. s., 2H), 6.91 (d, J=8.3 Hz, 2H), 6.84 (d, J=7.0 Hz, 2H), 3.77 (d, J=2.4 Hz, 4H), 3.42-3.52 (m, 2H), 3.18-3.26 (m, 8H), 2.61-2.69 (m, 8H), 2.37 (s, 6H), 2.30 (t, 2H, J=4.0 Hz), 1.88-1.97 (m, 2H), 1.78-1.88 (m, 2H), 1.53 (m, 2H). LC-MS: m/z (M+H) 715.3

Compound 260

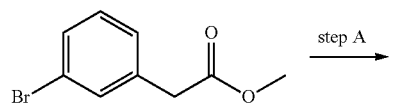

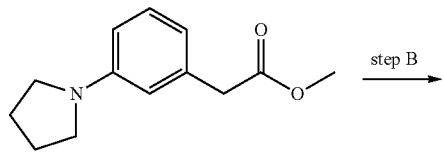

-continued

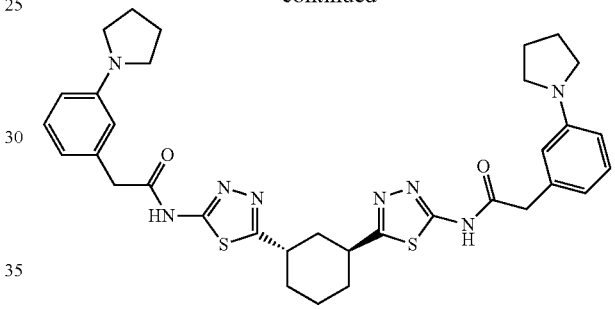

The procedure was the same as Compound 259

Step A: methyl 2-(3-(pyrrolidin-1-yl)phenyl)acetate

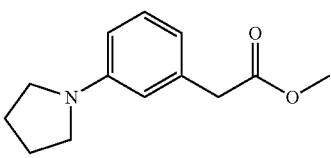 [SMILES: COC(=O)Cc1cccc(N2CCCC2)c1]

$^1$H NMR (CHLOROFORM-d) δ: 7.20 (dd, J=8.7, 7.4 Hz, 1H), 6.61 (d, J=7.0 Hz, 1H), 6.51 (br. s., 2H), 3.71 (s, 3H), 3.60 (s, 2H), 3.3 (m, 4H), 1.98-2.06 (m, 4H). LC-MS: (M+H) m/z 220.3

Step B: N,N'-(5,5'-((1S,3S)-cyclohexane-1,3-diyl)bis(1,3,4-thiadiazole-5,2-diyl))bis(2-(3-(pyrrolidin-1-yl)phenyl)acetamide) (260)
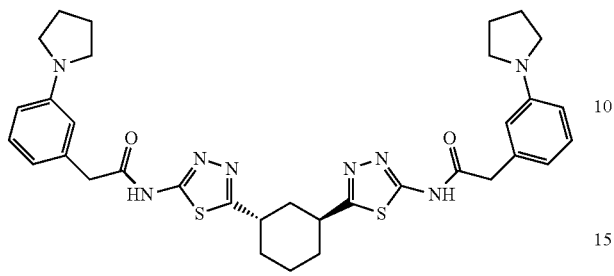
$^1$H NMR (DMSO-d$_6$) δ: 12.65 (s, 2H), 7.09 (t, J=7.8 Hz, 2H), 6.49-6.57 (m, 4H), 6.42 (d, J=8.3 Hz, 2H), 3.68 (s, 4H), 3.47 (m, 2H), 3.15-3.23 (t, 8H, J=8 Hz), 2.29 (t, 2H, J=4 Hz), 1.94 (m, 10H), 1.84 (m, 2H), 1.61 (m, 2H). LC-MS: (M+H) m/z 657.3
Compound 261
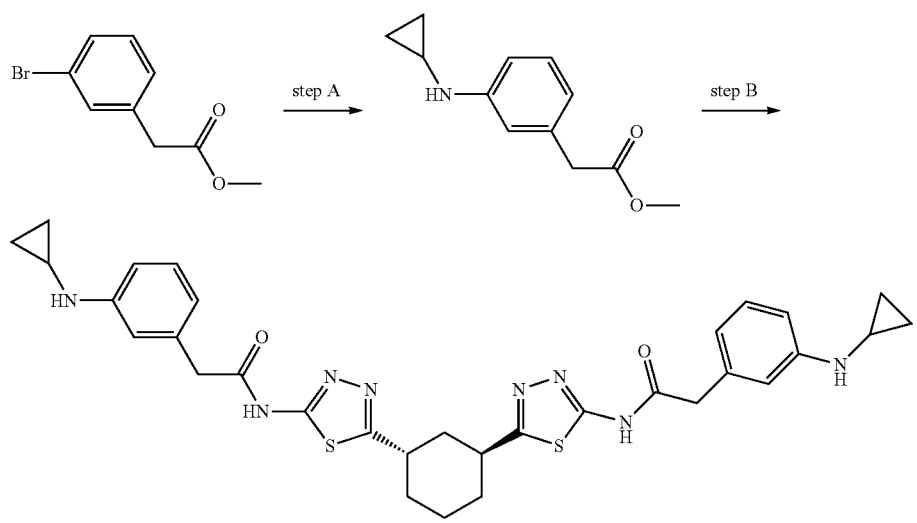
The procedure was the same as Compound 259.
Step A: methyl 2-(3-(cyclopropylamino)phenyl)acetate
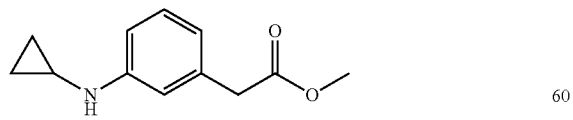
$^1$H NMR (CHLOROFORM-d): 7.17 (t, J=7.7 Hz, 1H), 6.74-6.79 (m, 2H), 6.69 (d, J=7.5 Hz, 1H), 3.71 (s, 3H), 3.58 (s, 2H), 2.46 (dt, J=6.6, 3.3 Hz, 1H), 0.72-0.78 (m, 2H), 0.51-0.59 (m, 2H). LC-MS: m/z (M+H) 206.3

Step B: N,N'-(5,5'-((1S,3S)-cyclohexane-1,3-diyl)bis(1,3,4-thiadiazole-5,2-diyl))bis(2-(3-(cyclopropylamino)phenyl)acetamide) (261)

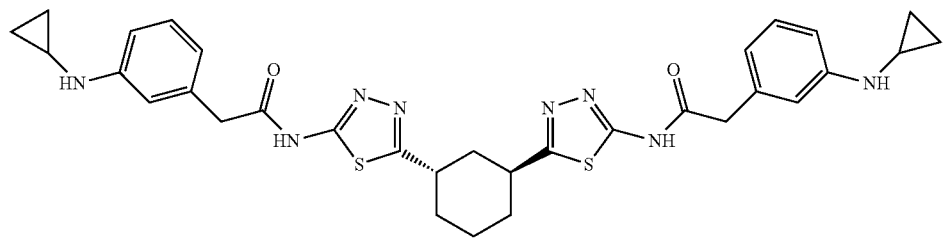 [SMILES: O=C(Cc1cccc(NC2CC2)c1)Nc1nnc([C@H]2CCC[C@H](c3nnc(NC(=O)Cc4cccc(NC5CC5)c4)s3)C2)s1]

¹H NMR (DMSO-d₆) δ: 12.73 (br. s., 2H), 7.04 (t., J=4.0 Hz, 2H), 6.61-6.53 (m, 6H), 6.10 (s, 2H), 3.65 (s, 4H), 3.48 (m, 2H), 2.29 (m, 4H), 1.92 (m, 2H), 1.84 (m, 2H), 1.60 (m, 2H), 0.67 (m, 4H), 0.34 (m, 4H). LC-MS: m/z (M+H) 628.3

Compound 262

The procedure was the same as Compound 259

Step A: methyl 2-(3-morpholinophenyl)acetate

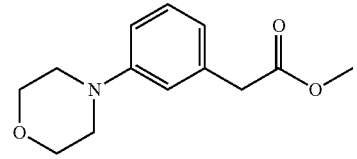 [SMILES: COC(=O)Cc1cccc(N2CCOCC2)c1]

¹H NMR (CHLOROFORM-d) δ: 7.21 (t, J=7.9 Hz, 1H), 6.82-6.86 (m, 2H), 6.77 (d, J=7.3 Hz, 1H), 3.68 (s, 3H), 3.74 (t, J=8 Hz, 4H), 3.58 (s, 2H), 3.10 (t, J=8 Hz, 4H). LC-MS: m/z (M+H) 235.3

Step B: N,N'-(5,5'-((1S,3S)-cyclohexane-1,3-diyl)bis(1,3,4-thiadiazole-5,2-diyl))bis(2-(3-morpholinophenyl)acetamide) (262)

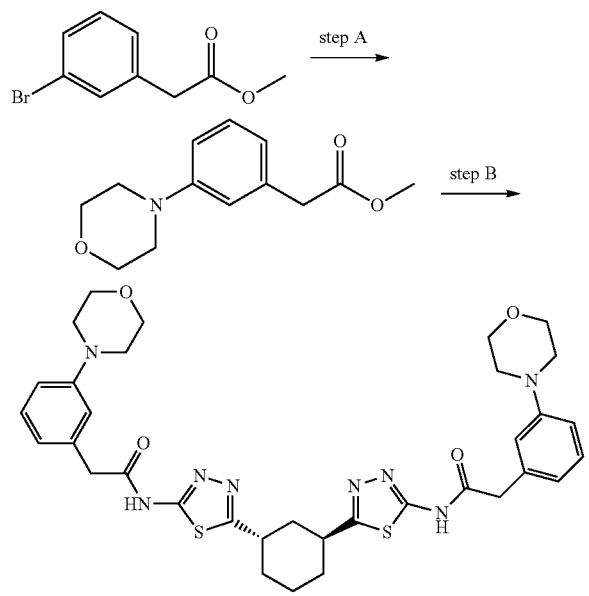

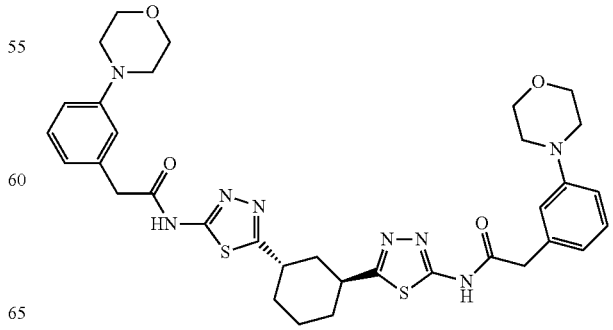

333
¹H NMR (DMSO-d₆) δ: 12.67 (br. s, 2H), 7.17 (t, J=7.9 Hz, 2H), 6.92 (s, 2H), 6.84 (dd, J=8.2, 2.0 Hz, 2H), 6.76 (d, J=7.5 Hz, 2H), 3.67-3.80 (m, 12H), 3.43-3.50 (m, 2H),
334
3.05-3.14 (m, 8H), 2.29 (t. 2H, J=4 Hz), 1.87-1.98 (m, 2H), 1.83 (m, 2H), 1.61 (m, 2H). LC-MS: m/z 689.3 (M+H). Compound 263
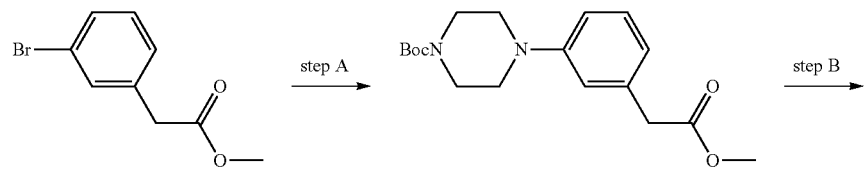
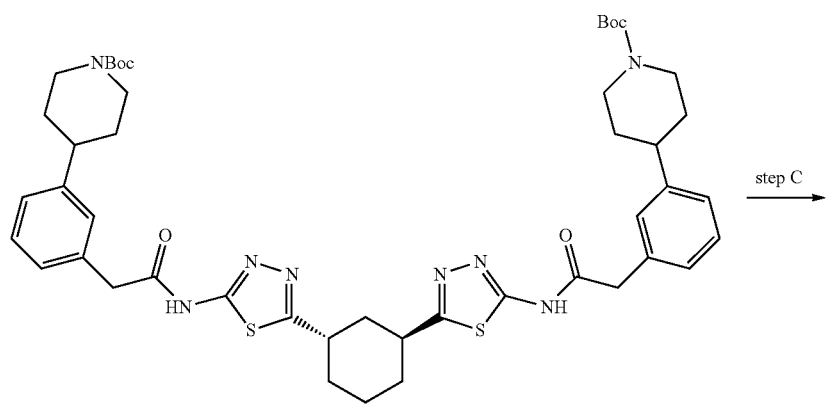
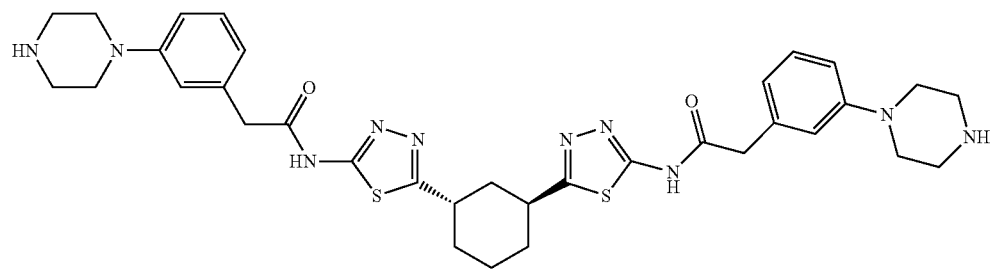

335

Step A to Step B: ditert-butyl 4,4'-(3,3'-(2,2'-(5,5'-((1S,3S)-cyclohexane-1,3-diyl)bis(1,3,4-thiadiazole-5,2-diyl))bis(azanediyl)bis(2-oxoethane-2,1-diyl))bis(3,1-phenylene))dipiperazine-1-carboxylate

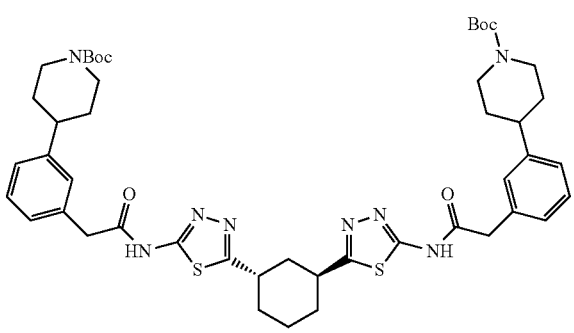 [SMILES: CC(C)(C)OC(=O)N1CCC(c2cccc(CC(=O)Nc3nnc([C@H]4CCC[C@H](c5nnc(NC(=O)Cc6cccc(C7CCN(C(=O)OC(C)(C)C)CC7)c6)s5)C4)s3)c2)CC1]

The procedure was the same as Compound 259

¹H NMR (DMSO-d₆) δ: 12.67 (s, 2H), 7.17 (t, J=7.9 Hz, 2H), 6.94 (s, 2H), 6.82-6.90 (m, 2H), 6.77 (d, J=7.5 Hz, 2H), 3.72 (s, 4H), 3.41-3.51 (m, 10H), 3.00-3.14 (t, 8H, J=5.2 Hz), 2.30 (t, J=5.6 Hz, 2H), 1.89-1.99 (m, 4H), 1.80-1.88 (m, 2H), 1.42 (s, 18H). LC-MS: m/z (M+H) 888.1

336

Step C: N,N'-(5,5'-((1S,3S)-cyclohexane-1,3-diyl)bis(1,3,4-thiadiazole-5,2-diyl))bis(2-(3-(piperazin-1-yl)phenyl)acetamide) (263)

The procedure was the same as Step C of Compound 239.

¹H NMR (DMSO-d6) δ: 7.15 (t, J=7.8 Hz, 2H), 6.91 (s, 2H), 6.79-6.85 (m, 2H), 6.73 (d, J=7.5 Hz, 2H), 4.15 (br, 2H), 3.68 (s, 4H), 3.47 (m, 2H), 3.01-3.11 (t, 8H, J=4.8 Hz), 2.80-2.93 (t, 8H, J=4.8 Hz), 2.29 (t, 2H, J=9.6 Hz), 1.92 (m, 2H), 1.95 (m, 2H), 1.61 (m, 2H). LC-MS: 687.3 (M+H) m/z

N,N'-(5,5'-((1S,3S)-cyclohexane-1,3-diyl)bis(1,3,4-thiadiazole-5,2-diyl))bis(2-(3-(1-methylpiperidin-4-yl)phenyl)acetamide) (362)

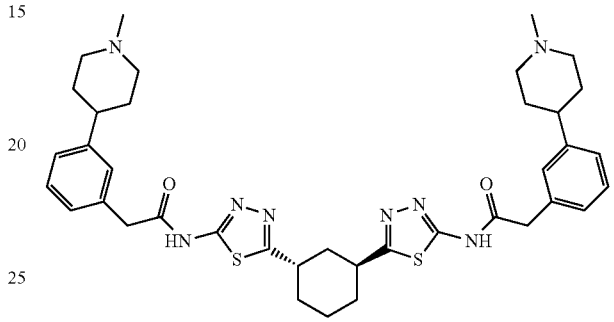

The procedure was the same as Compound 259

¹H NMR (METHANOL-d₄) δ: 7.18-7.31 (m, 6H), 7.15 (d, J=7.3 Hz, 2H), 3.81 (s, 4H), 3.47-3.57 (m, 2H), 3.23-3.36 (m, 4H), 2.56-2.73 (m, 12H), 2.40 (t, J=5.4 Hz, 2H), 1.85-2.08 (m, 12H), 1.68-1.77 (m, 2H); LC-MS: m/z (M+H)= 713.3
Compound 264

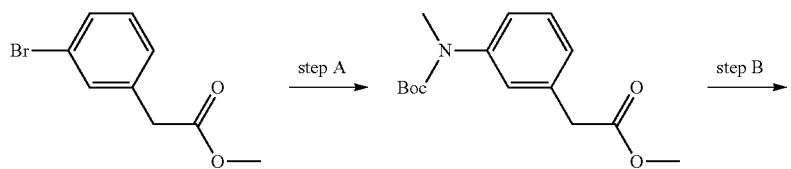

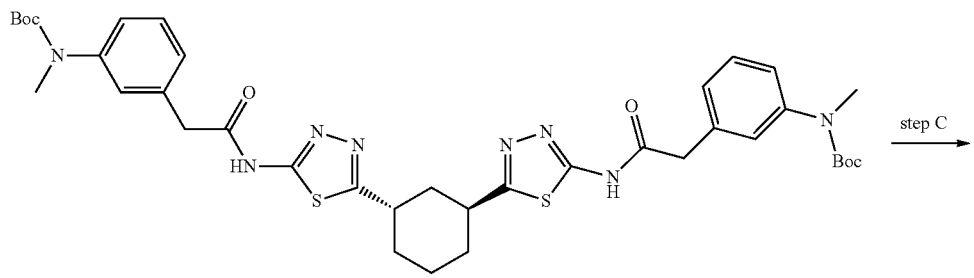

-continued

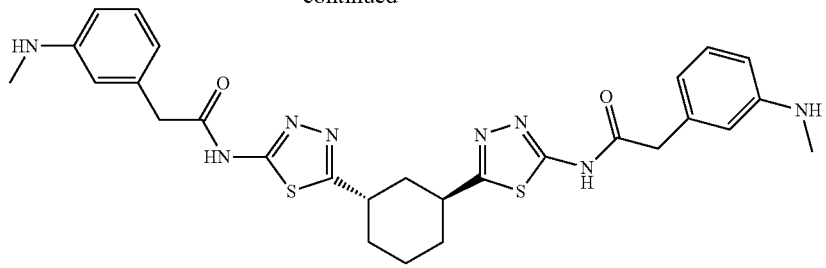

The procedure is same to the reaction to make Compound 263.

Step B: di-tert-butyl (((((5,5'-((1S,3S)-cyclohexane-1,3-diyl)bis(1,3,4-thiadiazole-5,2-diyl)bis(azanediyl))bis(2-oxoethane-2,1-diyl))bis(3,1-phenylene))bis(methylcarbamate)

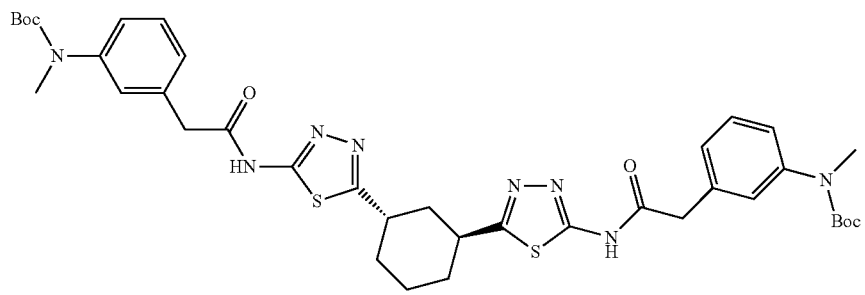

$^1$H NMR (DMSO-$d_6$) δ: 12.73 (br. s., 1H), 7.27-7.33 (m, 2H), 7.24 (s, 2H), 7.18 (d, J=8.1 Hz, 2H), 7.13 (d, J=7.5 Hz, 2H), 3.79 (s, 4H), 3.47 (m, 2H), 3.17 (s, 6H), 2.28 (t, 2H, J=8 Hz), 1.93-1.83 (m, 4H), 1.61 (m, 2H), 1.36 (s, 18H). LC-MS: m/z 778.2 (M+H)

Step C: N,N'-(5,5'-((1S,3S)-cyclohexane-1,3-diyl)bis(1,3,4-thiadiazole-5,2-diyl))bis(2-(3-(methylamino)phenyl)acetamide) (264)

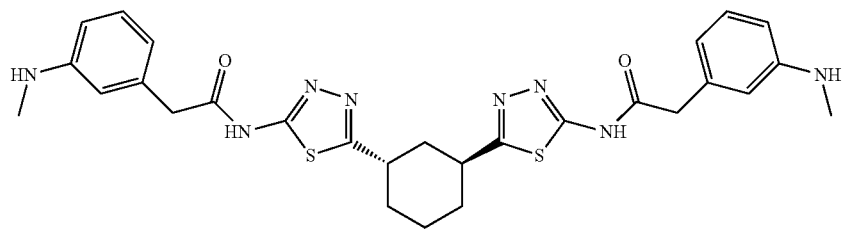

$^1$H NMR (DMSO-d6) δ: 12.65 (s, 2H), 7.02 (t, J=7.9 Hz, 2H), 6.47-6.54 (m, 4H), 6.42 (d, J=7.3 Hz, 2H), 4.16 (br, 2H), 3.64 (s, 4H), 3.46 (m, 2H), 2.65 (s, 6H), 2.29 (t, 2H, J=4 Hz), 1.88-1.98 (m, 2H), 1.78-1.88 (m, 2H), 1.61 (m, 2H). LC-MS: m/z (M+H) 577.9

Compound 265
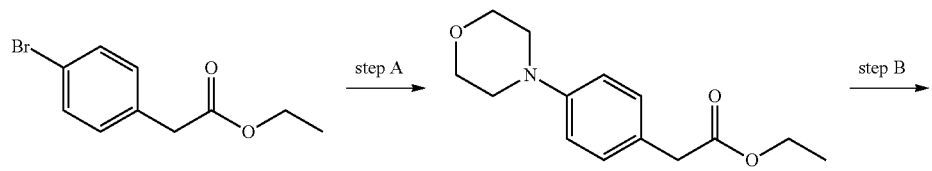
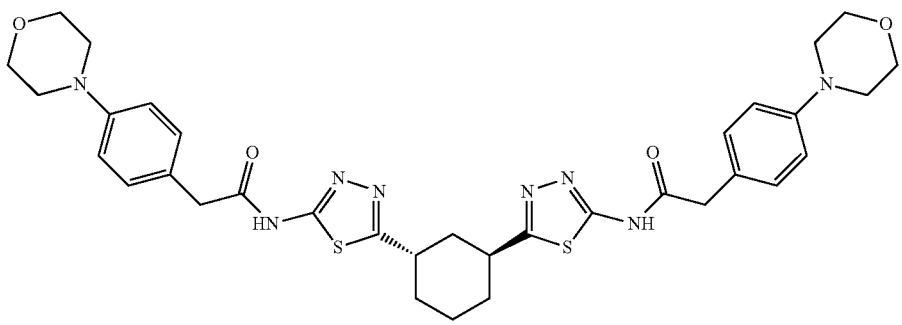 [SMILES: O=C(Cc1ccc(N2CCOCC2)cc1)Nc1nnc([C@H]2CCC[C@H](c3nnc(NC(=O)Cc4ccc(N5CCOCC5)cc4)s3)C2)s1]
The procedure was the same as Compound 249
Step A: ethyl 2-(4-morpholinophenyl)acetate
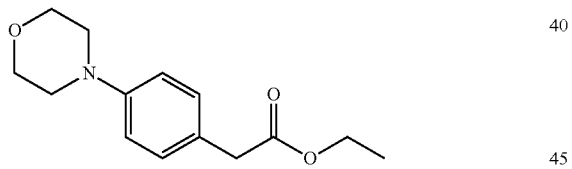
$^1$H NMR (CHLOROFORM-d) δ: 7.193 (d, 2H); 6.872 (d, 2H); 4.272 (q, J=7.14 Hz, 2H); 3.853 (m, 2H); 3.533 (s, 2H); 3.140 (m, 2H); 1.247 (t, J=7.14, 3H). LC-MS m/z 250.1 (M+H).
Step B: N,N'-(5,5'-((1S,3S)-cyclohexane-1,3-diyl)bis(1,3,4-thiadiazole-5,2-diyl))bis(2-(4-morpholinophenyl)acetamide) (265)
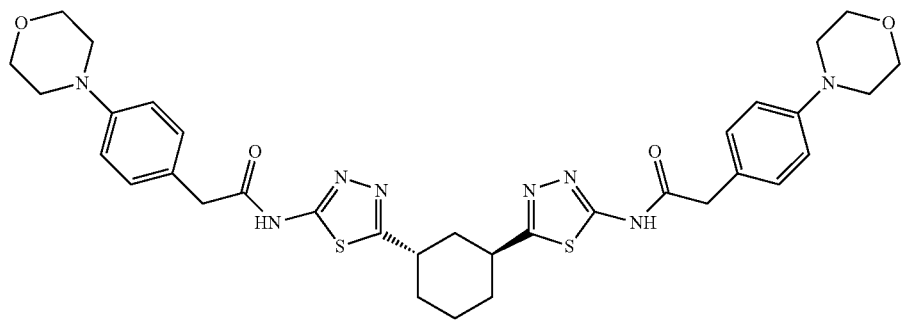

¹H NMR (CHLOROFORM-d) δ: 7.45 (d, J=6.4 Hz, 4H), 7.20 (m, 4H), 4.03 (m, 8H), 3.98 (m, 4H), 3.54-3.60 (m, 2H), 3.30 (m, 8H), 2.49 (t, J=5.4 Hz, 2H), 2.05 (m, 2H), 1.96 (m, 2H), 1.76 (m, 2H). LC-MS: m/z (M+H)=689.9
Compound 266
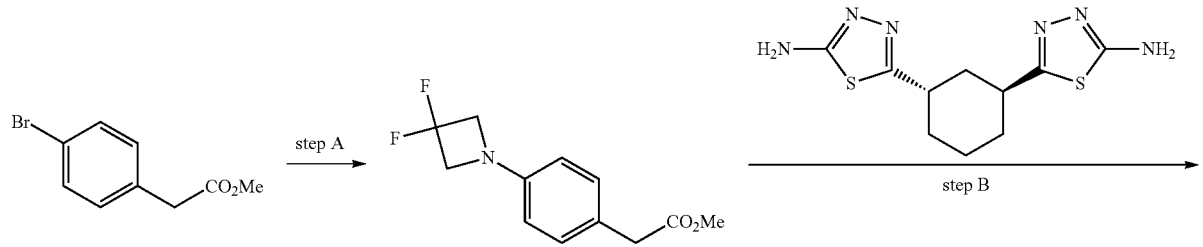
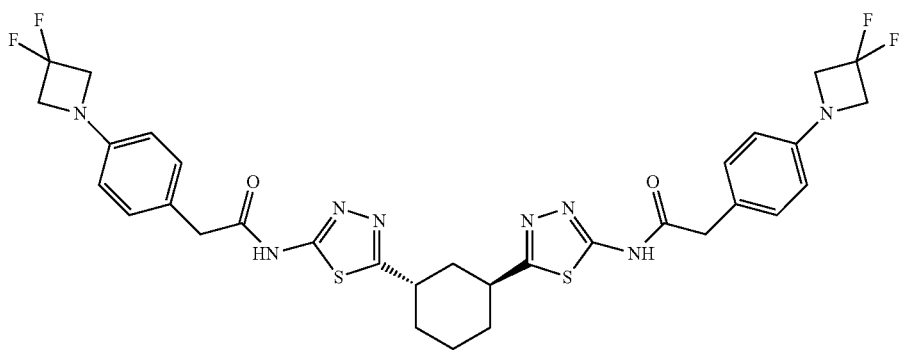 [SMILES: O=C(Cc1ccc(N2CC(F)(F)C2)cc1)Nc1nnc([C@H]2CCC[C@H](c3nnc(NC(=O)Cc4ccc(N5CC(F)(F)C5)cc4)s3)C2)s1]
The procedure was the same as Compound 249
Step B: N,N'-(5,5'-((1S,3S)-cyclohexane-1,3-diyl)bis(1,3,4-thiadiazole-5,2-diyl))bis(2-(4-(3,3-difluoro-azetidin-1-yl)phenyl)acetamide) (266)
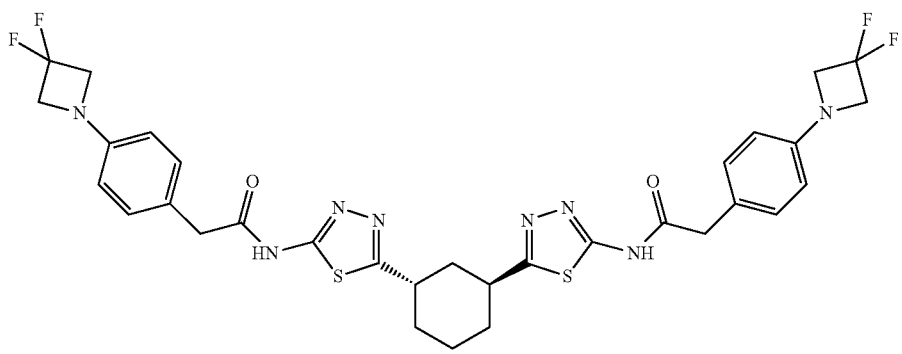
¹H NMR (DMSO-d$_6$) δ: 12.63 (s, 2H), 7.20 (d, J=8.3 Hz, 4H), 6.54 (d, J=8.3 Hz, 4H), 4.23 (t, J=12.2 Hz, 8H), 3.68 (s, 4H), 3.46 (m, 2H), 2.28 (t, J=5.6 Hz, 2H), 1.92 (m, 2H), 1.83 (m, 2H), 1.60 (m, 2H). LC-MS: m/z (M+H)=701.9

Compound 267
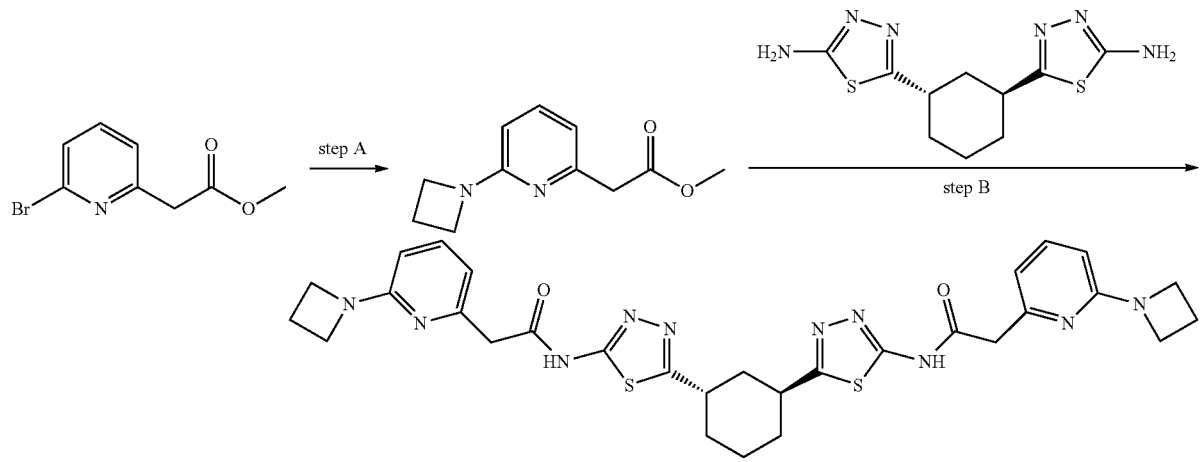
The procedure was the same as Compound 249
Step A: methyl 2-(6-(azetidin-1-yl)pyridin-2-yl)acetate
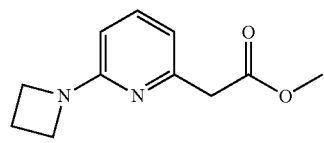
LC-MS: m/z (M+H)=207.2
Step B: N,N'-(5,5'-((1S,3S)-cyclohexane-1,3-diyl)bis(1,3,4-thiadiazole-5,2-diyl))bis(2-(6-(azetidin-1-yl)pyridin-2-yl)acetamide) (267)
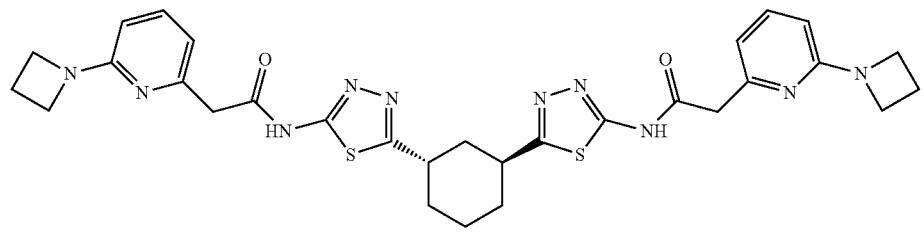 [SMILES: O=C(Cc1cccc(N2CCC2)n1)Nc1nnc([C@H]2CCC[C@H](c3nnc(NC(=O)Cc4cccc(N5CCC5)n4)s3)C2)s1]
$^1$H NMR (DMSO-$d_6$) δ: 12.70 (s, 2H), 7.47 (dd, J=8.2, 7.4 Hz, 2H), 6.61 (d, J=7.3 Hz, 2H), 6.24 (d, J=8.1 Hz, 2H), 3.90 (t, J=7.4 Hz, 8H), 3.81 (s, 4H), 3.44-3.55 (m, 2H), 2.24-2.37 (m, 6H), 1.90-2.02 (m, 2H), 1.77-1.90 (m, 2H), 1.55-1.69 (m, 2H). LC-MS: m/z (M+H)=631.8.
Compound 268
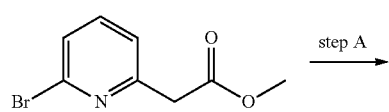

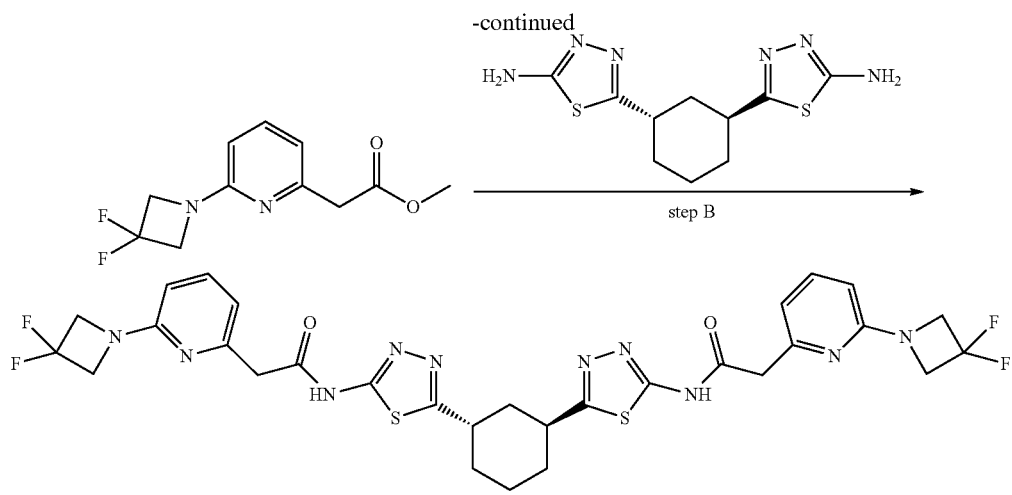
The procedure was the same as Compound 249
Step A: methyl 2-(6-(3,3-difluoroazetidin-1-yl)pyridin-2-yl)acetate
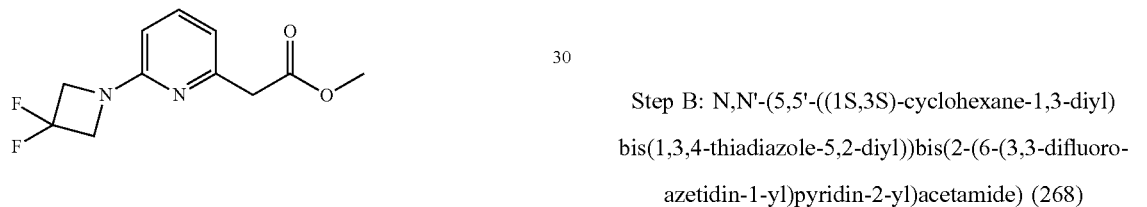
¹H NMR (CHLOROFORM-d) δ: 7.50 (t, J=7.8 Hz, 1H), 6.72 (d, J=7.3 Hz, 1H), 6.30 (d, J=8.1 Hz, 1H), 4.35 (t, J=12.1 Hz, 4H), 3.73 (s, 2H), 3.75 (s, 3H). LC-MS: m/z (M+H)=243.4
Step B: N,N'-(5,5'-((1S,3S)-cyclohexane-1,3-diyl)bis(1,3,4-thiadiazole-5,2-diyl))bis(2-(6-(3,3-difluoroazetidin-1-yl)pyridin-2-yl)acetamide) (268)
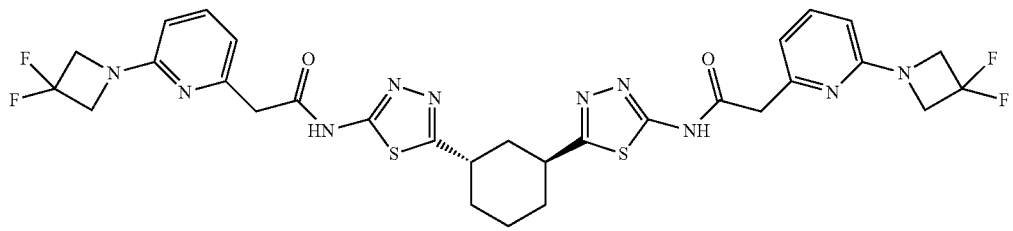 [SMILES: O=C(Cc1cccc(N2CC(F)(F)C2)n1)Nc1nnc([C@H]2CCC[C@H](c3nnc(NC(=O)Cc4cccc(N5CC(F)(F)C5)n4)s3)C2)s1]
¹H NMR (DMSO-d₆) δ: 12.70 (s, 2H), 7.59 (dd, J=7.3, 8.3 Hz, 2H), 6.79 (d, J=7.3 Hz, 2H), 6.48 (d, J=8.3 Hz, 2H), 4.34 (t, J=12.5 Hz, 8H), 3.87 (s, 4H), 3.45-3.52 (m, 2H), 2.32 (t, J=5.9 Hz, 2H), 1.95 (m, 2H), 1.78-1.89 (m, 2H), 1.62 (m, 2H). LC-MS: m/z (M+H)=703.9
Compound 269
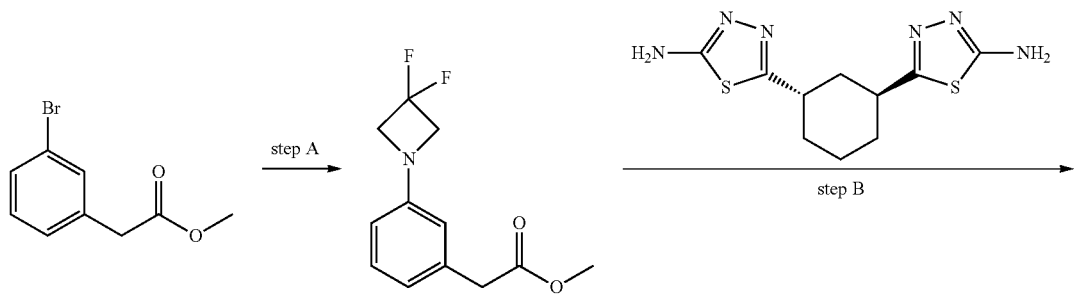

-continued

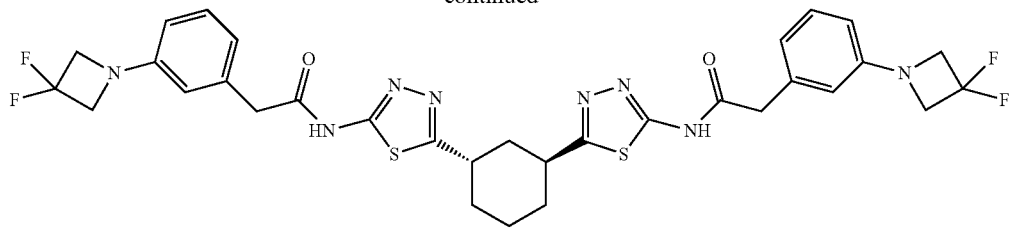

The procedure was the same as Compound 249

Step A: methyl 2-(3-(3,3-difluoroazetidin-1-yl)phenyl)acetate

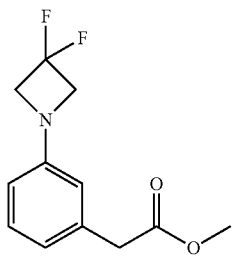 [SMILES: COC(=O)Cc1cccc(N2CC(F)(F)C2)c1]

$^1$H NMR (CHLOROFORM-d) δ: 7.19-7.28 (m, 1H), 6.80 (d, J=7.5 Hz, 1H), 6.48 (m, 2H), 4.26 (t, J=11.8 Hz, 4H), 3.72 (s, 3H), 3.61 (s, 2H). LC-MS: m/z (M+H)=242.4

Step B: N,N'-(5,5'-((1S,3S)-cyclohexane-1,3-diyl)bis(1,3,4-thiadiazole-5,2-diyl))bis(2-(3-(3,3-difluorocyclobutyl)phenyl)acetamide) (269)

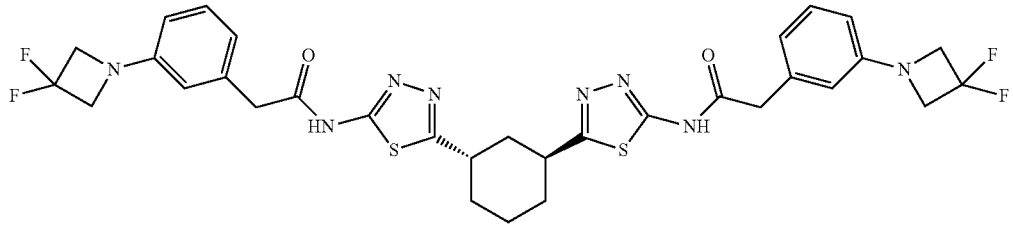 [SMILES: O=C(Cc1cccc(N2CC(F)(F)C2)c1)Nc1nnc([C@H]2CCC[C@H](c3nnc(NC(=O)Cc4cccc(N5CC(F)(F)C5)c4)s3)C2)s1]

$^1$H NMR (DMSO-d$_6$) δ: 12.68 (s, 2H), 7.18 (t, J=7.8 Hz, 2H), 6.76 (d, J=7.5 Hz, 2H), 6.54 (s, 2H), 6.48 (d, J=7.5 Hz, 2H), 4.25 (t, J=12.2 Hz, 8H), 3.73 (s, 4H), 3.48 (m, 2H), 2.29 (t, J=5.4 Hz, 2H), 1.88-1.99 (m, 2H), 1.77-1.87 (m, 2H), 1.61 (m, 2H). LC-MS: m/z (M+H)=701.9

Compound 270

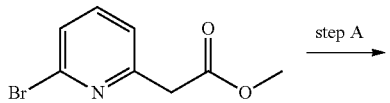 step A →

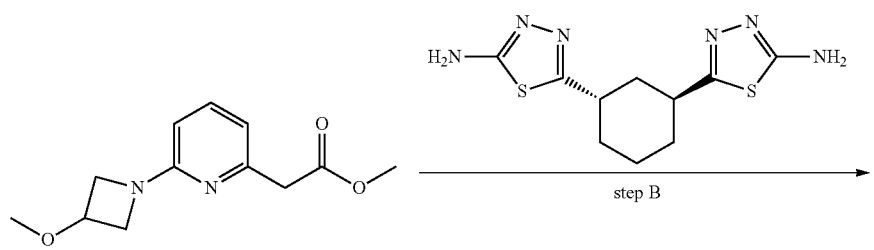 step B →

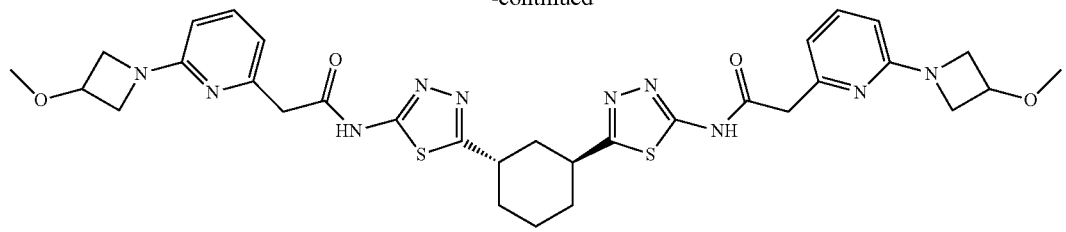
The procedure was the same as Compound 249
Step A: methyl 2-(6-(3-methoxyazetidin-1-yl)pyridin-2-yl)acetate
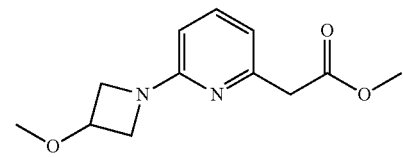
LC-MS: m/z (M+H)=237.2
Step B: N,N'-(5,5'-((1S,3S)-cyclohexane-1,3-diyl)bis(1,3,4-thiadiazole-5,2-diyl))bis(2-(6-(3-methoxyazetidin-1-yl)pyridin-2-yl)acetamide) (270)
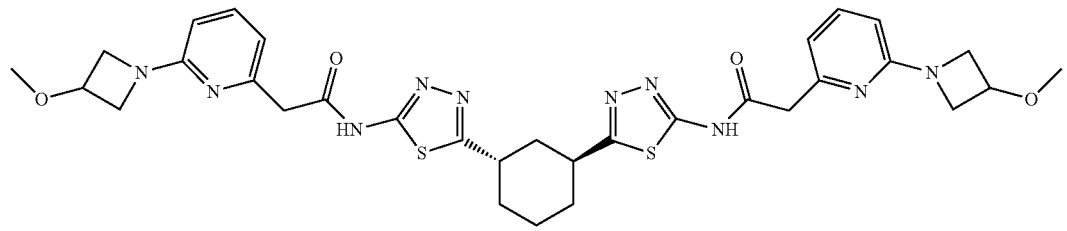
$^1$H NMR (DMSO-d$_6$) δ: 12.69 (s, 2H), 7.49 (dd, J=7.3, 8.3 Hz 2H), 6.64 (d, J=7, 3 Hz, 2H), 6.30 (d, J=8.3 Hz, 2H), 4.26-4.33 (m, 2H), 4.04-4.16 (m, 4H), 3.81 (s, 4H), 3.71 (dd, J=8.9, 4.0 Hz, 4H), 3.44-3.54 (m, 2H), 3.34 (s, 6H), 2.32 (d, J=5.4 Hz, 2H), 1.91-2.00 (m, 2H), 1.78-1.90 (m, 2H), 1.63 (d, J=5.4 Hz, 2H). LC-MS: m/z (M+H)=691.8
Compound 271
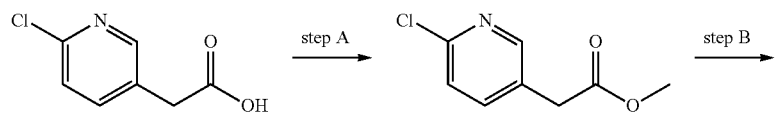
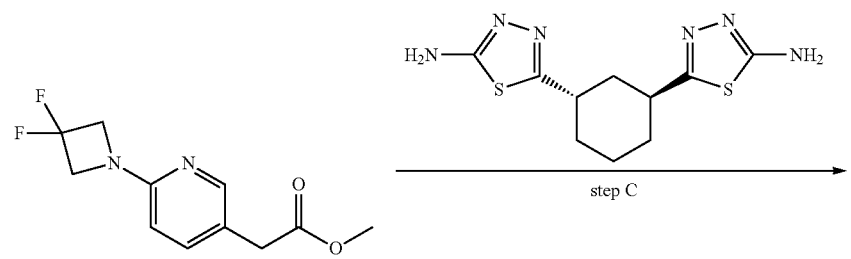

-continued

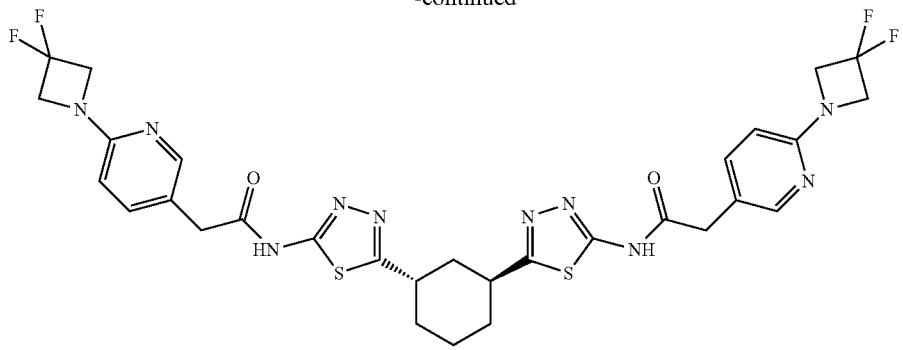

Step A: methyl 2-(6-chloropyridin-3-yl)acetate

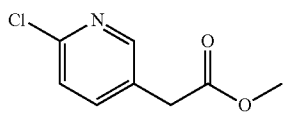

To a solution of 2-(6-chloropyridin-3-yl)acetic acid (2 g, 117 mmol) in methanol (40 ml) was added SOCl$_2$ (1.38 g, 117 mmol). The reaction mixture was concentrated after two hours to give the desired product. LC-MS: m/z (M+H)= 186.6

Step B: methyl 2-(6-(3,3-difluoroazetidin-1-yl)pyridin-3-yl)acetate

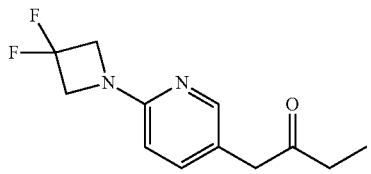 [SMILES: CCC(=O)Cc1ccc(N2CC(F)(F)C2)nc1]

To a sealed microwave reaction vessel containing methyl 2-(6-chloropyridin-3-yl)acetate (200 m g, 1.08 mmol), 3,3-difluoroazetidine hydrochloride (154 mg, 1.19 mmol), Xantphos (93 mg, 0.162 mmol), Cs2CO3 (1.054 g, 3.23 mmol), and Pd2(dba)3 (99.0 mg, 0.11 mmol) was added 3.0 ml of dioxane. The reaction mixture was microwave radiated at 90 C for 60.0 min. It was cooled to room temperature and diluted with CH2Cl2 (20.0 ml). The suspension was filtered, washed with CH2Cl2 (3×10.0 ml), and the filtrate was washed with water and brine. The organic layer was dried over anhydrous Na2SO4, filtered. The filtrate was concentrated. The residue was purified by a standard method to give the title compound.

$^1$H NMR (CHLOROFORM-d) δ: 8.09 (d, J=1.9 Hz, 1H), 7.54 (dd, J=8.3, 2.1 Hz, 1H), 6.42 (d, J=8.3 Hz, 1H), 4.41 (t, J=12.0 Hz, 4H), 3.72 (s, 3H), 3.55 (s, 2H). LC-MS: m/z (M+H)=243.3

Step C: N,N'-(5,5'-((1S,3S)-cyclohexane-1,3-diyl) bis(1,3,4-thiadiazole-5,2-diyl))bis(2-(6-(3,3-difluoroazetidin-1-yl)pyridin-3-yl)acetamide) (271)

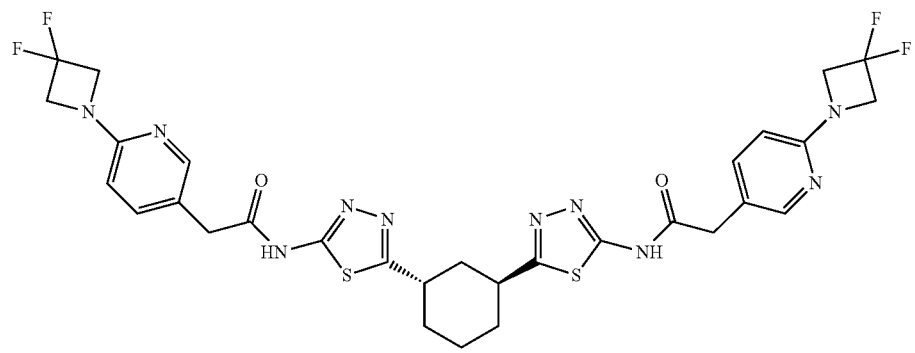 [SMILES: O=C(Cc1ccc(N2CC(F)(F)C2)nc1)Nc1nnc([C@H]2CCC[C@H](c3nnc(NC(=O)Cc4ccc(N5CC(F)(F)C5)nc4)s3)C2)s1]

The procedure was the same as Step B of Compound 84
$^1$H NMR (CHLOROFORM-d) δ: 13.72 (br. s., 2H), 8.24 (d, J=1.9 Hz, 2H), 7.65 (dd, J=8.6, 2.1 Hz, 2H), 6.34 (d, J=8.3 Hz, 2H), 4.30 (t, J=12.1 Hz, 8H), 3.94 (s, 4H), 3.55-3.63 (m, 2H), 2.50 (t, J=5.4 Hz, 2H), 2.07 (m, 2H), 1.96-2.01 (m, 2H), 1.73-1.82 (m, 2H). LC-MS: m/z (M+H)= 703.8
Compound 272
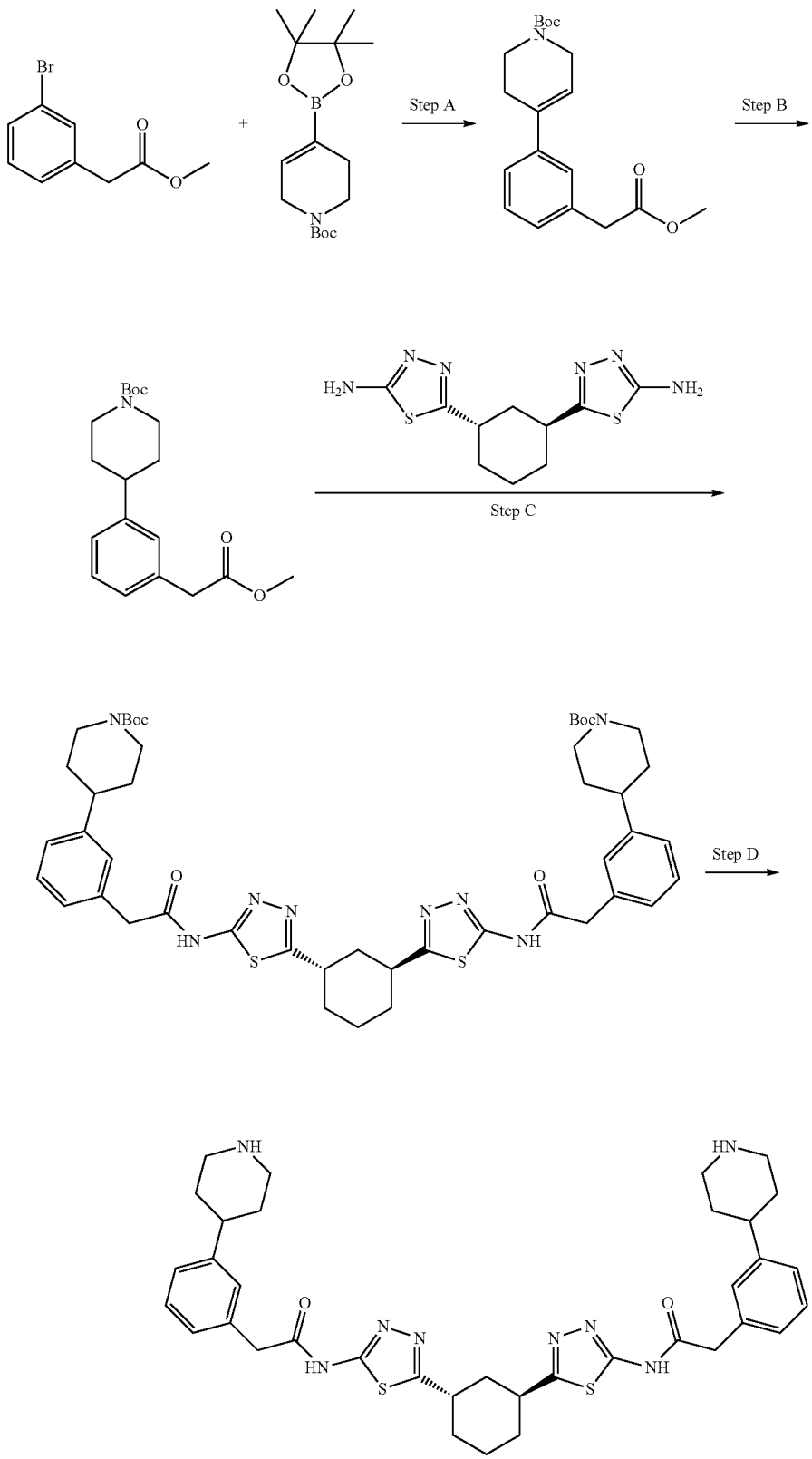

Step A: tert-butyl 4-(3-(2-methoxy-2-oxoethyl)phenyl)-5,6-dihydropyridine-1(2H)-carboxylate

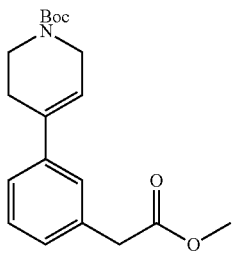 [SMILES: COC(=O)Cc1cccc(C2=CCN(C(=O)OC(C)(C)C)CC2)c1]

The solution of methyl 2-(3-bromophenyl)acetate (288.9 mg, 1.26 mmol), tert-butyl 4-(4,4,5,5-tetramethyl-1,3,2-dioxaborolan-2-yl)-5,6-dihydropyridine-1(2H)-carboxylate (300 mg, 0.97 mmol), $PdCl_2(dppf)$ (35.5 mg, 4.8% mmol) and $K_2CO_3$ (268.1 mg, 1.94 mmol) in DMF (20 mL) was stirred at 90 degree under $N_2$ overnight. After cooling to room temperature, the mixture was filtered with celite, diluted with EtOAc, washed with water, dried over $Na_2SO_4$ and evaporated under reduced pressure. The residue was purified by a standard method to get desired product. LC-MS: m/z (M+H)=332.4

Step B: tert-butyl 4-(3-(2-methoxy-2-oxoethyl)phenyl)piperidine-1-carboxylate

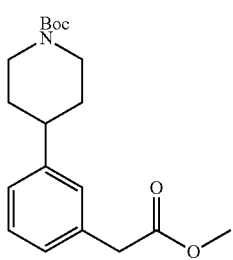 [SMILES: COC(=O)Cc1cccc(C2CCN(C(=O)OC(C)(C)C)CC2)c1]

The solution of tert-butyl 4-(3-(2-methoxy-2-oxoethyl) phenyl)-5,6-dihydropyridine-1(2H)-carboxylate (330 mg, 1.0 mmol) and Pd/C (30 mg) in methanol (10 mL) was stirred under $H_2$ at room temperature for 12 h. Then, the reaction mixture was filtered and evaporated under reduced pressure to get desired product for the next step without further purification. LC-MS: m/z (M+H)=334.4

Step C: tert-butyl 4,4'-(3,3'-(2,2'-(5,5'-((1S,3S)-cyclohexane-1,3-diyl)bis(1,3,4-thiadiazole-5,2-diyl))bis(azanediyl)bis(2-oxoethane-2,1-diyl))bis(3,1-phenylene))dipiperidine-1-carboxylate

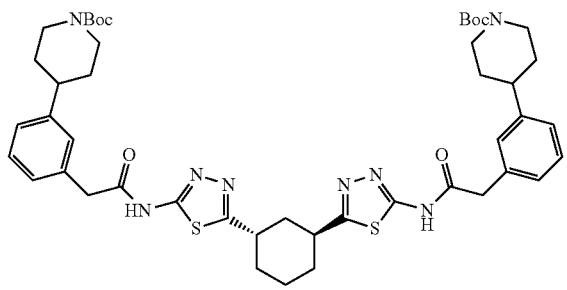 [SMILES: CC(C)(C)OC(=O)N1CCC(c2cccc(CC(=O)Nc3nnc([C@H]4CCC[C@H](c5nnc(NC(=O)Cc6cccc(C7CCN(C(=O)OC(C)(C)C)CC7)c6)s5)C4)s3)c2)CC1]

The procedure was the same as Step B of Compound 84
LC-MS: m/z (M+H)=886.1

Step D: N,N'-(5,5'-((1S,3S)-cyclohexane-1,3-diyl) bis(1,3,4-thiadiazole-5,2-diyl))bis(2-(3-(piperidin-4-yl)phenyl)acetamide) (272)

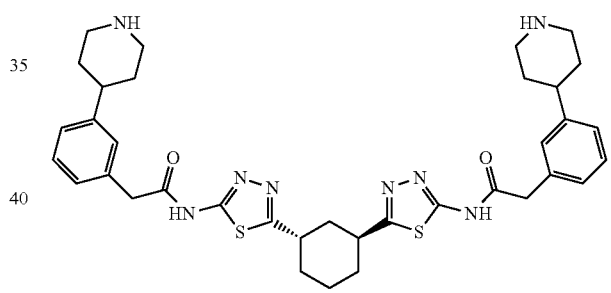

The solution of tert-butyl 4,4'-(3,3'-(2,2'-(5,5'-((1S,3S)-cyclohexane-1,3-diyl)bis(1,3,4-thiadiazole-5,2-diyl))bis (azanediyl)bis(2-oxoethane-2,1-diyl))bis(3,1-phenylene)) dipiperidine-1-carboxylate (15 mg, 0.01 mmol) in HCl/MeOH (6 mL, 3 N) was stirred at room temperature for 6 h. The mixture was evaporated under reduced pressure to purify by a standard method.

$^1$H NMR (METHANOL-$d_4$) δ: 12.66 (s, 2H), 8.46 (br. s., 2H), 7.27 (t, J=7.8 Hz, 2H), 7.19 (s, 2H), 7.13 (d, J=8.1 Hz, 2H), 3.72 (s, 4H), 3.41-3.45 (m, 2H), 3.39 (d, J=12.6 Hz, 4H), 3.02 (td, J=13.0, 2.6 Hz, 4H), 2.75-2.84 (m, 2H), 2.19-2.35 (t, J=5.4 Hz, 2H), 1.90-2.00 (m, 6H), 1.73-1.85 (m, 6H), 1.54-1.67 (m, 2H). LC-MS: m/z (M+H)=686.0

N,N'-(5,5'-((1S,3S)-cyclohexane-1,3-diyl)bis(1,3,4-thiadiazole-5,2-diyl))bis(2-(4-(piperidin-4-yl)phenyl)acetamide) (290)

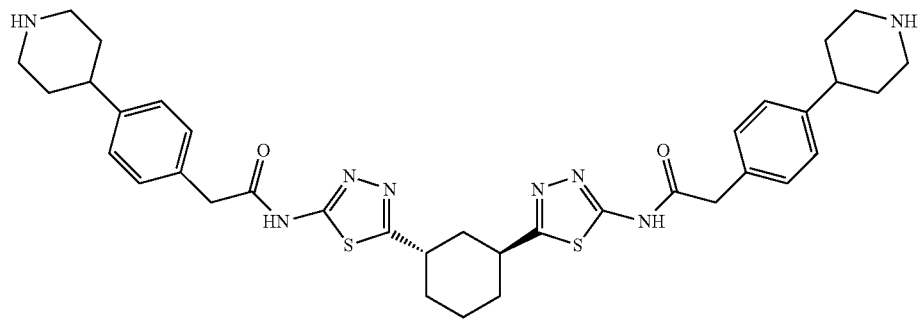 [SMILES: O=C(Cc1ccc(C2CCNCC2)cc1)Nc1nnc([C@H]2CCC[C@H](c3nnc(NC(=O)Cc4ccc(C5CCNCC5)cc4)s3)C2)s1]

The procedure was the same as Compound 272

$^1$H NMR (METHANOL-d$_4$) δ: 12.68 (s, 2H), 8.44 (br. s., 2H), 7.22 (d, J=8.6 Hz, 4H), 7.15 (d, J=8.5 Hz, 4H), 3.70 (s, 4H), 3.41-3.46 (m, 2H), 3.39 (d, J=12.6 Hz, 4H), 3.02 (td, J=13.0, 2.6 Hz, 4H), 2.75-2.84 (m, 2H), 2.19-2.36 (t, J=5.4 Hz, 2H), 1.90-2.00 (m, 6H), 1.73-1.85 (m, 6H), 1.55-1.68 (m, 2H). LC-MS: m/z (M+H)=686.0

Compound 273

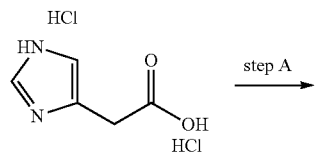

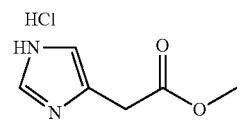

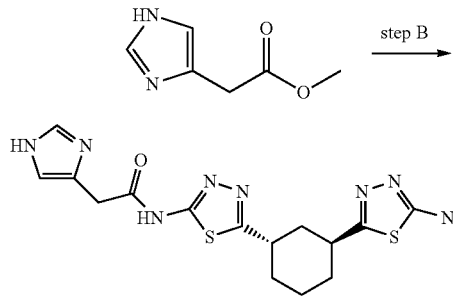

Step A: methyl 2-(1H-imidazol-4-yl)acetate hydrochloride

To a solution of 2-(1H-imidazol-4-yl)acetic acid hydrochloride (200 mg, 1.23 mmol) in methanol (5 ml) was added SOCl$_2$ (145 mg, 1.23 mmol). The reaction mixture was concentrated after two hours to give the desired product. LC-MS: m/z (M+H)=141.1

Step B: N,N'-(5,5'-((1S,3S)-cyclohexane-1,3-diyl)bis(1,3,4-thiadiazole-5,2-diyl))bis(2-(1H-imidazol-4-yl)acetamide) (273)

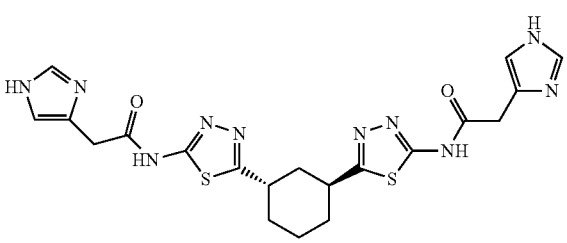 [SMILES: O=C(Cc1c[nH]cn1)Nc1nnc([C@H]2CCC[C@H](c3nnc(NC(=O)Cc4c[nH]cn4)s3)C2)s1]

A solution of 5,5'-((1S,3S)-cyclohexane-1,3-diyl)bis(1,3,4-thiadiazol-2-amine) (33 mg, 0.119 mmol), methyl 2-(1H- imidazol-4-yl)acetate hydrochloride (50 mg, 0.357 mmol), and cesium carbonate (300 mg, 1.19 mmol) in N,N-dimethylformamide (1 ml) was heated to 130° C. for 45 mins under microwave. Then the reaction mixture was cooled to room temperature and was poured into to water. The mixture was extracted by ethyl acetate (50 ml*3), the organic layer was washed by brine, dried by sodium sulfate, filtered, concentrated to give the residue; the residue was purified by a standard method to give the desired product.

$^1$H NMR (METHANOL-d$_4$) δ: 8.20 (br. s., 2H), 7.27 (br. s., 2H), 3.97 (s, 4H), 3.56-3.60 (m, 2H), 2.45 (t, J=5.6 Hz, 2H), 2.05 (m, 2H), 2.00 (m, 2H), 1.74-1.78 (m, 2H). LC-MS: m/z (M+H)=499.5

Compound 274

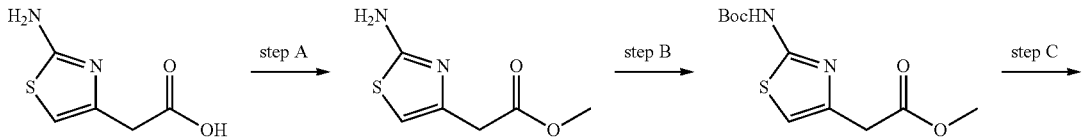

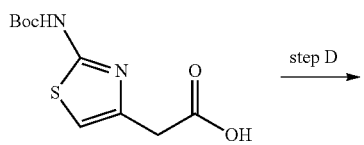

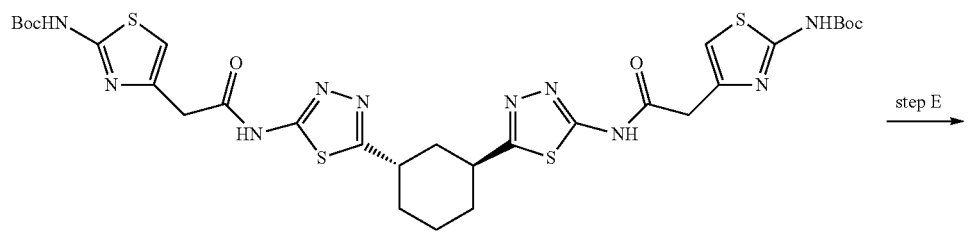

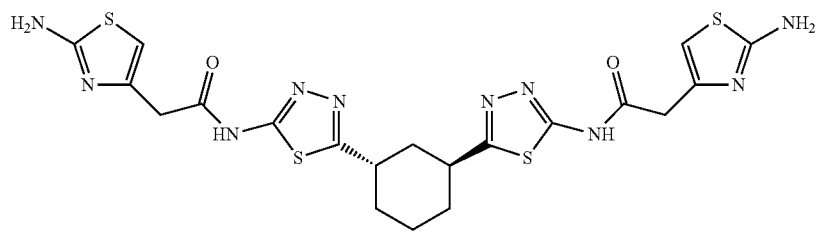

Step A: methyl 2-(2-aminothiazol-4-yl)acetate

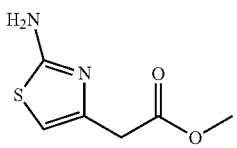

The procedure is the same as Step A of Compound 273. LC-MS: m/z (M+H)=173.2.

Step B: methyl 2-(2-(tert-butoxycarbonylamino)thiazol-4-yl)acetate

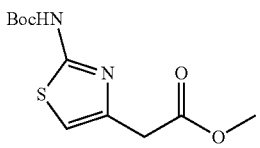 [SMILES: COC(=O)Cc1csc(NC(=O)OC(C)(C)C)n1]

A solution of di-tert-butyl dicarbonate (279 mg, 1.28 mmol) in toluene (3 ml) was added a vessel containing methyl 2-(2-aminothiazol-4-yl)acetate (200 mg, 1.16 mmol), the reaction mixture was heated at 85° C. for 24 h. LCMS showed that the desired product was detected, the mixture was concentrated to give the residue, the residue was purified by a standard method to give the desired product. LC-MS: m/z (M+H)=273.3

Step C: 2-(2-(tert-butoxycarbonyl(methyl)amino)thiazol-4-yl)acetic acid

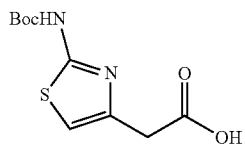

A solution of methyl 2-(2-(tert-butoxycarbonyl(methyl)amino)thiazol-4-yl)acetate (360 mg, 1.258 mmol), and LiOH.H$_2$O (106 mg, 2.52 mmol) in THF:H$_2$O=6 ml:3 ml was stirred at rt overnight. Then the reaction mixture was concentrated to give the desired product. LC-MS: m/z (M+H)=259.3

Step D: tert-butyl 4,4'-(2,2'-(5,5'-((1S,3S)-cyclohexane-1,3-diyl)bis(1,3,4-thiadiazole-5,2-diyl))bis(azanediyl)bis(2-oxoethane-2,1-diyl))bis(thiazole-4,2-diyl)bis(methylcarbamate)

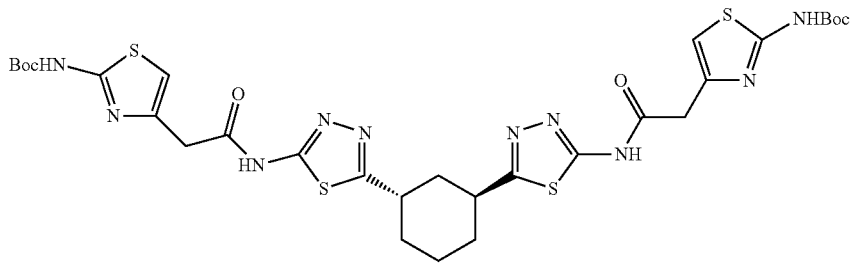 [SMILES: CC(C)(C)OC(=O)Nc1nc(CC(=O)Nc2nnc([C@H]3CCC[C@H](c4nnc(NC(=O)Cc5csc(NC(=O)OC(C)(C)C)n5)s4)C3)s2)cs1]

363
The procedure was the same as Compound 37
¹H NMR (CHLOROFORM-d) δ: 6.78 (s, 2H), 3.92 (s, 4H), 3.54 (m, 2H), 2.41 (t, J=5.5 Hz, 2H), 2.01 (m, 2H), 1.93 (m, 2H), 1.73-1.75 (m, 2H), 1.55 (s, 18H). LC-MS: m/z (M+H)=591.8. LC-MS: m/z (M+H)=791.0
364
Step E: N,N'-(5,5'-((1S,3S)-cyclohexane-1,3-diyl)bis(1,3,4-thiadiazole-5,2-diyl))bis(2-(2-aminothiazol-4-yl)acetamide) (274)
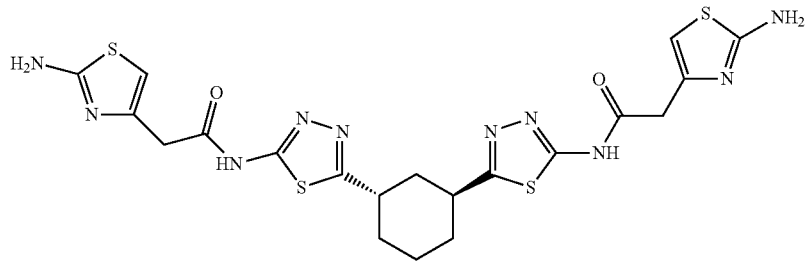 [SMILES: Nc1nc(CC(=O)Nc2nnc([C@H]3CCC[C@H](c4nnc(NC(=O)Cc5csc(N)n5)s4)C3)s2)cs1]
The procedure was the same as Step C of Compound 239
¹H NMR (METHANOL-d₄) δ: 6.42 (s, 2H), 3.73 (s, 4H), 3.54-3.60 (m, 2H), 2.44 (t, J=5.6 Hz, 2H), 2.03-2.07 (m, 2H), 1.96-2.01 (m, 2H), 1.74-1.78 (m, 2H). LC-MS: m/z (M+H)=563.8
Compound 275
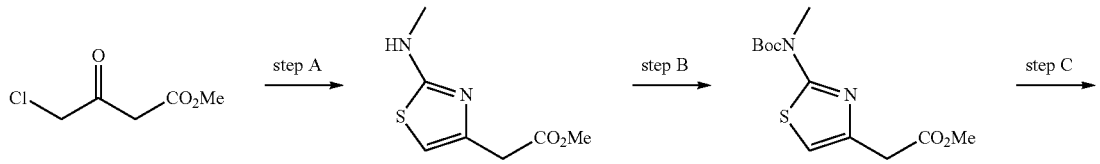
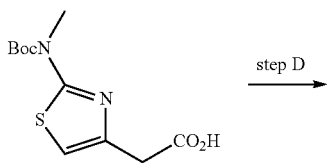
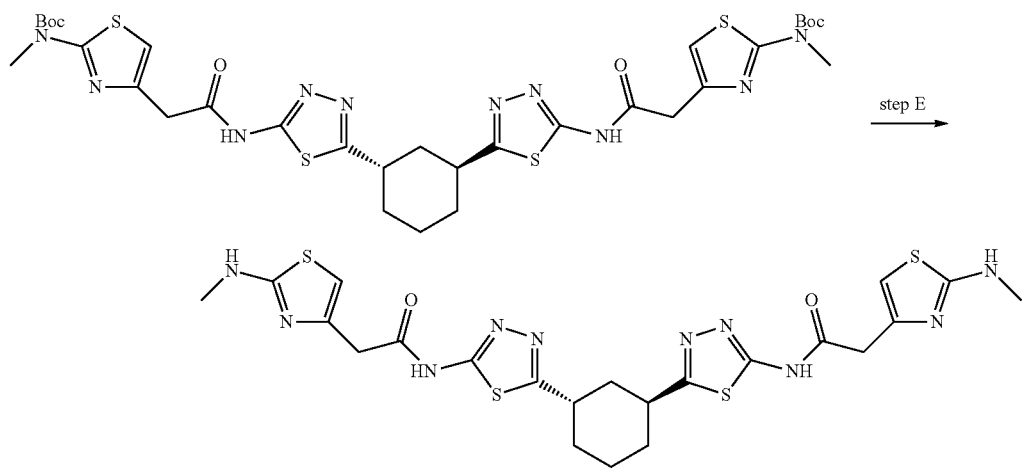

Step A: methyl 2-(2-(methylamino)thiazol-4-yl)acetate

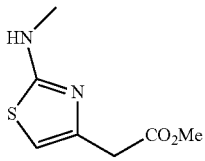

A mixture of methyl 4-chloro-3-oxobutanoate (1 g, 11.1 mmol) and 1-methylthiourea (1.72 g, 11.43 mmol) in MeOH (5 mL) was heated to 80° C. for 3 hours. The mixture was cooled, ethanol evaporated, and diluted with saturated sodium bicarbonate, and extracted with ethyl acetate. The organic layers were dried over magnesium sulfate and the reaction mixture purified by a standard method to provide methyl 2-(2-(methylamino)thiazol-4-yl)acetate. LC-MS: m/z (M+H)=187.2

Step B to Step D: tert-butyl 4,4'-(2,2'-(5,5'-((1S, 3S)-cyclohexane-1,3-diyl)bis(1,3,4-thiadiazole-5,2-diyl))bis(azanediyl))bis(2-oxoethane-2,1-diyl))bis(thiazole-4,2-diyl))bis(methylcarbamate)

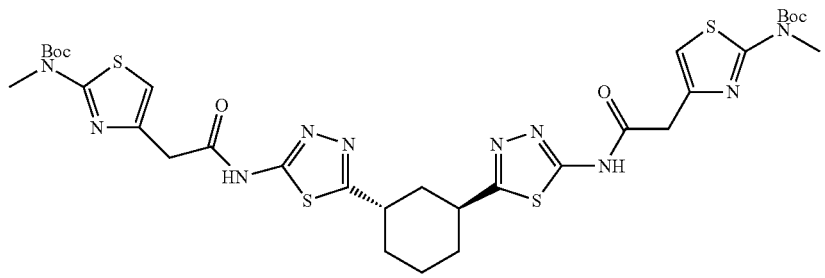

The procedure was the same as Step B to Step D of Compound 274

$^1$H NMR (CHLOROFORM-d) δ: 6.75 (s, 2H), 3.85 (s, 4H), 3.65 (s, 6H), 3.53-3.55 (m, 2H), 2.45 (t, J=5.5 Hz, 2H), 2.01 (m, 2H), 1.97 (m, 2H), 1.73 (m, 2H), 1.58 (s, 18H). LC-MS: m/z (M+H)=791.0

Step E: N,N'-(5,5'-((1S,3S)-cyclohexane-1,3-diyl)bis(1,3,4-thiadiazole-5,2-diyl))bis(2-(2-(methylamino)thiazol-4-yl)acetamide) (275)

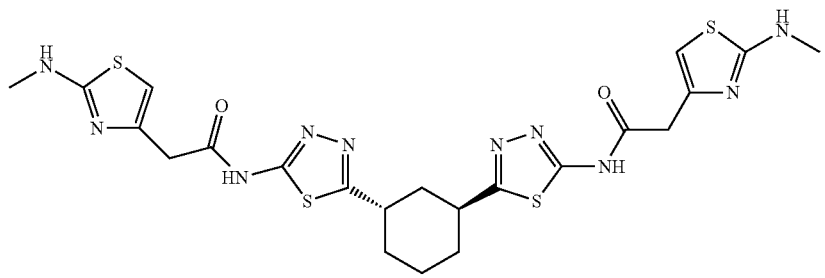

367
The procedure was the same as Step E of Compound 274
$^1$H NMR (METHANOL-d$_4$) δ: 6.46 (s, 2H), 3.78 (s, 4H), 3.54-3.60 (m, 2H), 2.94 (s, 6H), 2.44 (t, J=5.5 Hz, 2H), 2.05
368
(m, 2H), 1.99 (m, 2H), 1.73-1.78 (m, 2H). LC-MS: m/z (M+H)=591.8
Compound 276
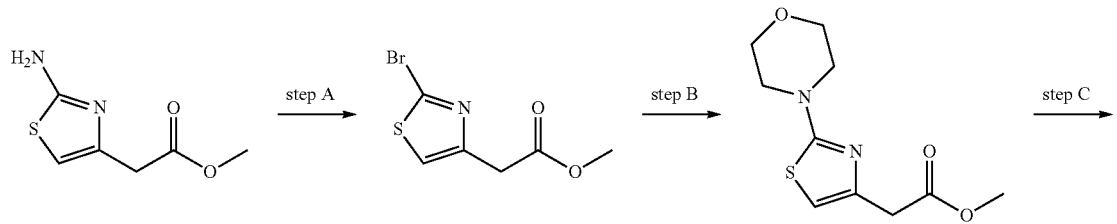
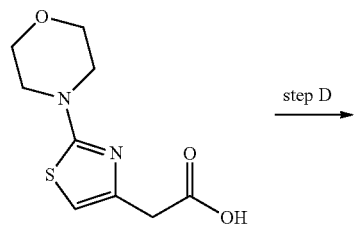
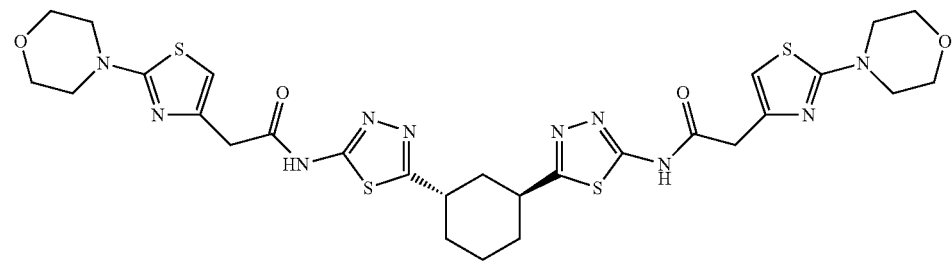

369

Step A: methyl 2-(2-bromothiazol-4-yl)acetate

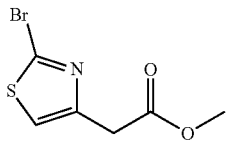

Methyl 2-(2-aminothiazol-4-yl)acetate (5 g, 26.8 mmol) was added under nitrogen to a solution of copper(II) bromide (6.77 g, 30 mmol) and f-butyl nitrite (4.79 ml, 40 mmol) in acetonitrile (20 ml) at −20° C. The reaction mixture was slowly warmed to room temperature and stirred for two hours. The solution was then diluted with diethyl ether and washed with 25 ml of 10 percent hydrochloric acid solution; the aqueous phase was extracted with 20 ml of diethyl ether. The combined organic phases were dried and evaporated to dryness. The residue was purified by a standard method to yield the title compound. LC-MS: m/z (M+H)==235.9

Step B: methyl 2-(2-morpholinothiazol-4-yl)acetate

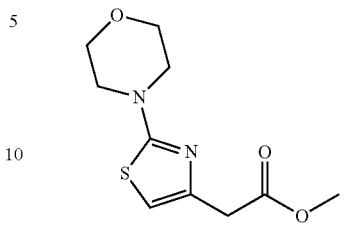

The procedure was the same as Step A of Compound 249

$^1$H NMR (CHLOROFORM-d) δ: 6.47 (s, 1H), 3.80-3.85 (m, 4H), 3.75 (s, 3H), 3.67 (s, 2H). LC-MS: m/z (M+H)= 243.3.

Step C to Step D: N,N'-(5,5'-((1S,3S)-cyclohexane-1,3-diyl)bis(1,3,4-thiadiazole-5,2-diyl))bis(2-(2-morpholinothiazol-4-yl)acetamide)

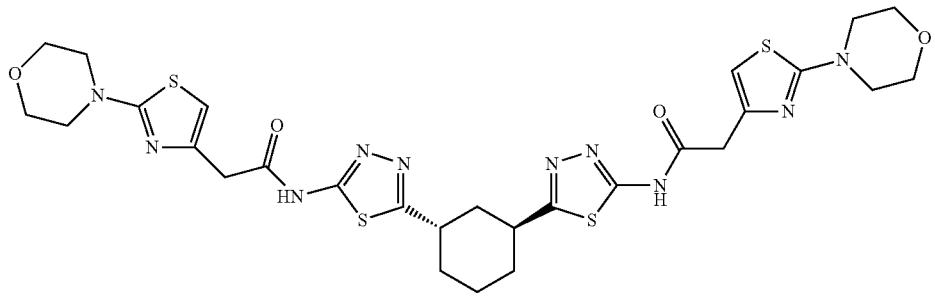 [SMILES: O=C(Cc1csc(N2CCOCC2)n1)Nc1nnc([C@H]2CCC[C@H](c3nnc(NC(=O)Cc4csc(N5CCOCC5)n4)s3)C2)s1]

The procedure was the same as Step C to Step D of Compound 274

$^1$H NMR (CHLOROFORM-d) δ: 6.50 (s, 2H), 3.85-3.93 (m, 12H), 3.64 (m, 8H), 3.53-3.59 (m, 2H), 2.47 (t, J=5.4 Hz, 2H), 1.97-2.06 (m, 4H), 1.73-1.80 (m, 2H). LC-MS: m/z (M+H)=703.9

N,N'-(5,5'-((1R,3R)-cyclohexane-1,3-diyl)bis(1,3,4-thiadiazole-5,2-diyl))bis(2-(2-(3,3-difluoroazetidin-1-yl)pyrimidin-4-yl)acetamide) (346)

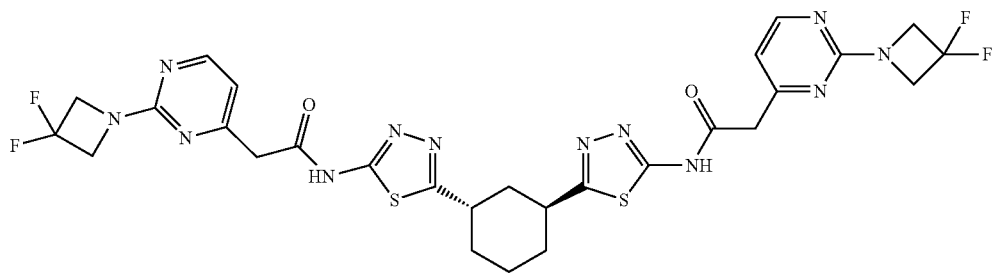 [SMILES: O=C(Cc1ccnc(N2CC(F)(F)C2)n1)Nc1nnc([C@H]2CCC[C@H](c3nnc(NC(=O)Cc4ccnc(N5CC(F)(F)C5)n4)s3)C2)s1]

371

The procedure was the same as Compound 249

¹H NMR (CHLOROFORM-d) d: 8.38 (d, J=4.8 Hz, 2H), 6.73 (d, J=4.8 Hz, 2H), 4.61 (t, J=12.0 Hz, 8H), 3.96 (s, 4H), 3.58 (m, 2H), 2.49 (t, J=5.5 Hz, 2H), 1.94-2.11 (m, 4H), 1.72-1.82 (m, 2H). LC-MS: m/z (M+H)=705.7

Compound 277

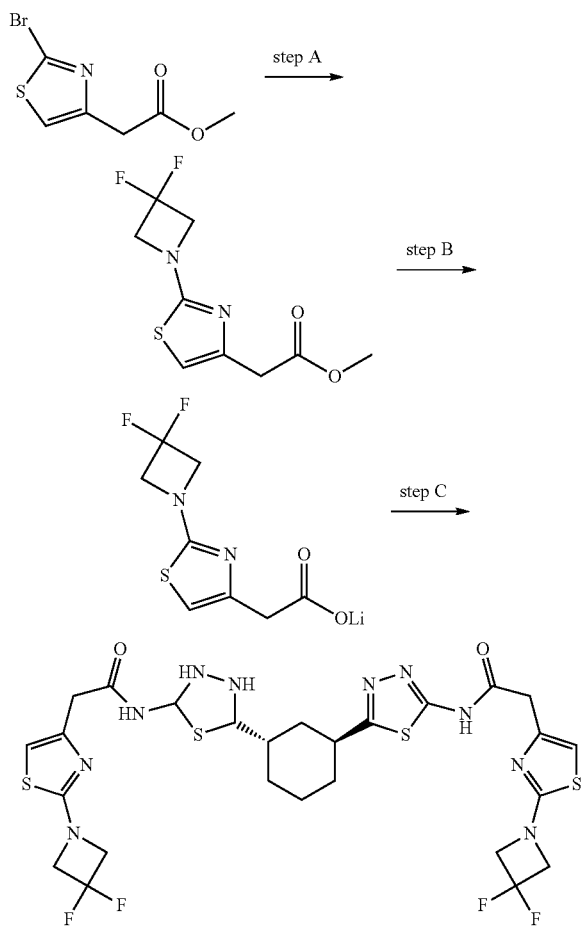

The procedure was the same as Compound 276

Step A: methyl 2-(2-(3,3-difluoroazetidin-1-yl)thiazol-4-yl)acetate

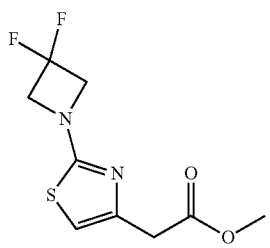 [SMILES: COC(=O)Cc1csc(N2CC(F)(F)C2)n1]

¹H NMR (CHLOROFORM-d) δ: 6.53 (s, 1H), 4.42 (t, J=11.8 Hz, 4H), 3.73 (s, 3H), 3.65 (s, 2H). LC-MS: m/z (M+H)=249.3

372

Step B to Step C: N,N'-(5,5'-((1S,3S)-cyclohexane-1,3-diyl)bis(1,3,4-thiadiazole-5,2-diyl))bis(2-(2-(3,3-difluoroazetidin-1-yl)thiazol-4-yl)acetamide) (277)

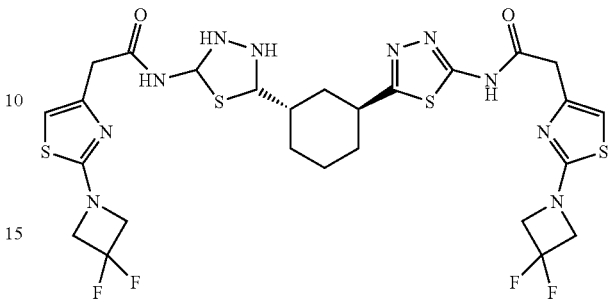

¹H NMR (CHLOROFORM-d) δ: 6.57 (s, 2H), 4.50 (t, J=11.7 Hz, 8H), 3.84 (s, 4H), 3.54-3.61 (m, 2H), 2.47 (t, J=5.6 Hz, 2H), 2.01-2.05 (m, 2H), 1.98 (m, 2H), 1.74-1.80 (m, 2H). LC-MS: m/z (M+H)=715.5.

Compound 278

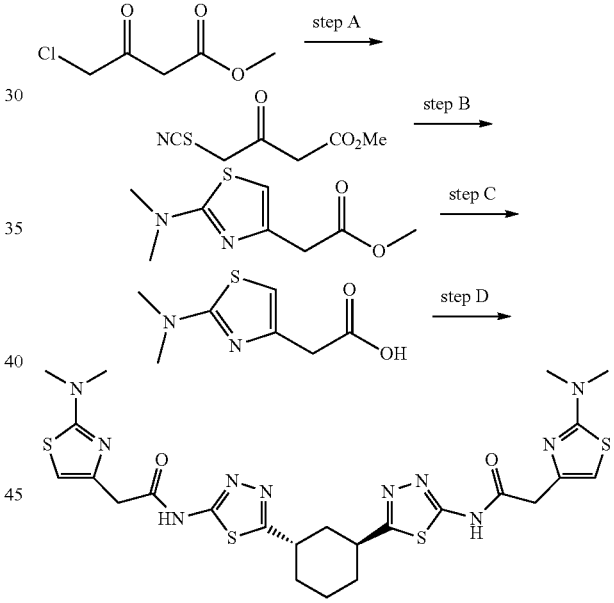

Step A: methyl 3-oxo-4-thiocyanatobutanoate

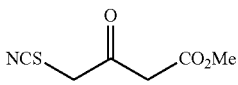

A solution of methyl 4-chloro-3-oxobutanoate (10 g, 66 mmol) in toluene (100 ml) was added a vessel containing KSCN (9.6 g, 99 mmol), the reaction mixture was stirred at rt for 24 h. LCMS showed that the desired product was detected, the mixture was concentrated to give the residue, the residue was purified by a standard method to give the desired product. LC-MS: m/z (M+H)=174.3

Step B: methyl 2-(2-(dimethylamino)thiazol-4-yl)acetate

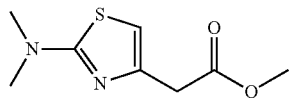

A solution of methyl 3-oxo-4-thiocyanatobutanoate (350 mg, 2.02 mmol) in THF (4 ml) was added a vessel containing dimethylamine in THF (2M; 1.01 ml, 2.02 mmol), the reaction mixture was stirred at rt for 3 h. LCMS showed that the desired product was detected, the mixture was concentrated to give the residue, the residue was purified by a standard method to give the desired product.

$^1$H NMR (CHLOROFORM-d) δ: 6.36 (s, 1H), 3.74 (s, 3H), 3.68 (s, 2H), 3.13 (s, 6H). LC-MS: m/z (M+H)=201.3

Step C to Step D: N,N'-(5,5'-((1S,3S)-cyclohexane-1,3-diyl)bis(1,3,4-thiadiazole-5,2-diyl))bis(2-(2-(dimethylamino)thiazol-4-yl)acetamide) (278)

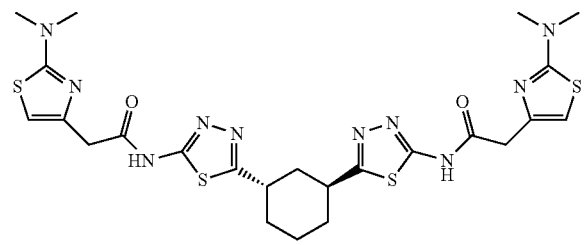

The procedure was the same as Step C to Step D of Compound 268

$^1$H NMR (METHANOL-d$_4$) δ: 6.51 (s, 2H), 3.79 (s, 4H), 3.54-3.61 (m, 2H), 3.11 (s, 12H), 2.44 (t, J=5.8 Hz, 2H), 2.04-2.07 (m, 2H), 2.00 (m, 2H), 1.74-1.79 (m, 2H). LC-MS: m/z (M+H)=619.9

Compound 279

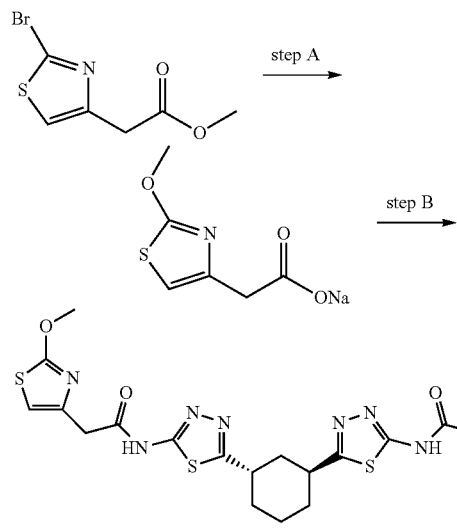

Step A: sodium 2-(2-methoxythiazol-4-yl)acetate

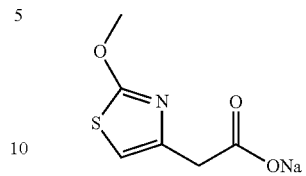

A solution of methyl 2-(2-bromothiazol-4-yl)acetate (80 mg, 0.34 mmol), and sodium methanolate (300 mg) in MeOH was stirred at 85° C. overnight. Then the reaction mixture was concentrated to give the desired product. $^1$H NMR (METHANOL-d4) δ: 4.04 (s, 3H), 3.47 (d, J=1.1 Hz, 2H), 3.37 (s, 1H). LC-MS: m/z (M+H)=174.2

Step B: N,N'-(5,5'-((1S,3S)-cyclohexane-1,3-diyl)bis(1,3,4-thiadiazole-5,2-diyl))bis(2-(2-methoxythiazol-4-yl)acetamide) (279)

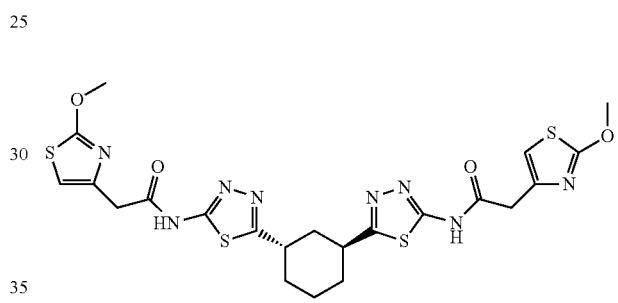

A solution of 5,5'-((1S,3S)-cyclohexane-1,3-diyl)bis(1,3,4-thiadiazol-2-amine) (10 mg, 0.04 mmol), sodium 2-(2-methoxythiazol-4-yl)acetate (28 mg, 0.14 mmol), HATU (83 mg, 0.22 mmol), and DIPEA (30 mg, 0.234 mmol) in N,N-dimethylformamide (2 ml) was heated to 50° C. overnight. The mixture was poured into water (20 ml), the precipitate was filtered to give the desired product.

$^1$H NMR (CHLOROFORM-d) δ: 6.95-7.19 (s, 2H), 6.59 (s, 2H), 4.16-4.20 (m, 6H), 3.84 (s, 4H), 3.55-3.62 (m, 2H), 2.48 (t, J=5.4 Hz, 2H), 2.04 (d, J=5.1 Hz, 2H), 1.96-2.00 (m, 2H), 1.74-1.80 (m, 2H). LC-MS: m/z (M+H)=593.6

Compound 79

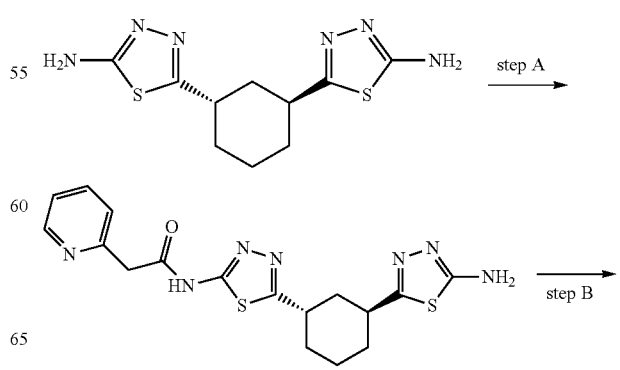

375

-continued

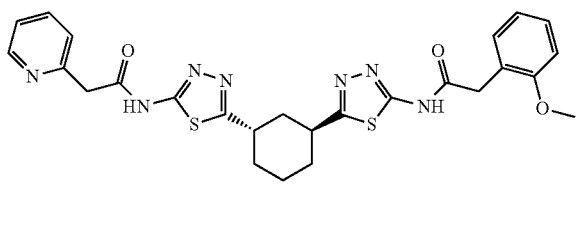

Step A: N-(5-((1S,3S)-3-(5-amino-1,3,4-thiadiazol-2-yl)cyclohexyl)-1,3,4-thiadiazol-2-yl)-2-(pyridin-2-yl)acetamide

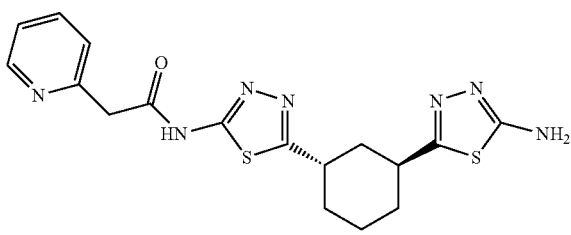 [SMILES: Nc1nnc([C@H]2CCC[C@H](c3nnc(NC(=O)Cc4ccccn4)s3)C2)s1]

A mixture of methyl 2-(pyridin-2-yl)acetate (107.0 mg, 0.71 mmol), 5,5'-((1S,3S)-cyclohexane-1,3-diyl)bis(1,3,4-thiadiazol-2-amine) (200 mg, 0.71 mmol), cesium carbonate (762.7 mg, 1.42 mmol) in DMF (6 mL) was heated to 130° C. under nitrogen atmosphere and microwave for 45 min. The mixture was evaporated in vacuum to dryness. The residue was purified by a standard method to afford desired compound.

¹H NMR (DMSO-d6) δ: 12.72 (s, 1H), 8.52 (d, J=4.0 Hz, 1H), 7.85 (td, J=7.7, 1.7 Hz, 1H), 7.48 (d, J=7.8 Hz, 1H), 7.37 (ddd, J=6.9, 5.7, 1.1 Hz, 1H), 7.06 (s, 2H), 4.01 (s, 2H), 3.64 (m, 2H), 2.22 (t, J=5.8 Hz, 2H), 1.76-1.91 (m, 4H), 1.60 (m, 2H). LC-MS: m/z (M+H)=402.2

376

Step B: 2-(2-methoxyphenyl)-N-(5-((1S,3S)-3-(5-(2-(pyridin-2-yl)acetamido)-1,3,4-thiadiazol-2-yl)cyclohexyl)-1,3,4-thiadiazol-2-yl)acetamide (79)

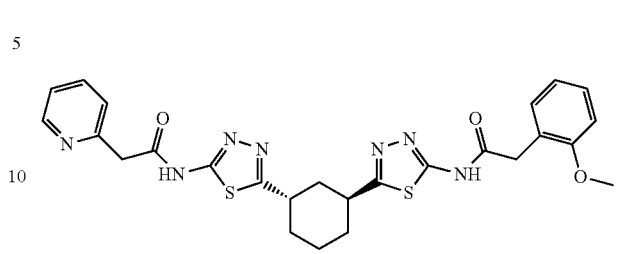

A solution of N-(5-((1S,3S)-3-(5-amino-1,3,4-thiadiazol-2-yl)cyclohexyl)-1,3,4-thiadiazol-2-yl)-2-(pyridin-2-yl)acetamide (50 mg, 0.12 mmol), 2-(2-methoxyphenyl)acetic acid (31.0 mg, 0.19 mmol), HATU (71.0 mg, 0.19 mmol), and N-ethyl-N-isopropylpropan-2-amine (29.0 mg, 0.22 mmol) in N,N-dimethylformamide (5 ml) was stirred at 50 degree overnight. The mixture was poured into water (10 ml), the precipitate was filtered to give the crude product. The crude product was purified by a standard method to give the desired product.

¹H NMR (METHANOL-d₄) δ: 8.52 (d, J=4.0 Hz, 1H), 7.85 (td, J=7.7, 1.7 Hz, 1H), 7.48 (d, J=7.8 Hz, 1H), 7.37 (ddd, J=6.9, 5.7, 1.1 Hz, 1H), 7.27-7.33 (m, 1H), 7.25 (d, J=7.3 Hz, 1H), 6.86-7.05 (m, 2H), 4.62 (s, 4H), 3.83 (s, 3H), 3.53-3.64 (m, 2H), 2.44 (t, J=5.8 Hz, 2H), 1.91-2.11 (m, 4H), 1.72-1.81 (m, 2H). LC-MS: m/z (M+H)=550.7

2-(3-methoxyphenyl)-N-(5-((1S,3S)-3-(5-(2-(pyridin-2-yl)acetamido)-1,3,4-thiadiazol-2-yl)cyclohexyl)-1,3,4-thiadiazol-2-yl)acetamide (81)

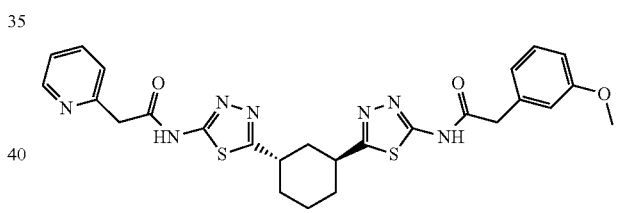

The procedure was the same as Compound 279

¹H NMR (DMSO-d₆) δ: 12.74 (s, 1H), 12.70 (s, 1H), 8.50 (d, J=4.8 Hz, 1H), 7.67-7.87 (m, 1H), 7.40 (d, J=8.1 Hz, 1H), 7.27-7.32 (m, 1H), 7.24 (t, J=7.9 Hz, 1H), 6.87-6.93 (m, 2H), 6.84 (d, J=8.3 Hz, 1H), 4.01 (s, 2H), 3.77 (s, 2H), 3.74 (s, 3H), 3.48 (m, 2H), 2.31 (t, J=5.6 Hz, 2H), 1.93 (m, 2H), 1.85 (m, 2H), 1.61 (m, 2H). LC-MS: m/z (M+H)=550.7
Compound 280

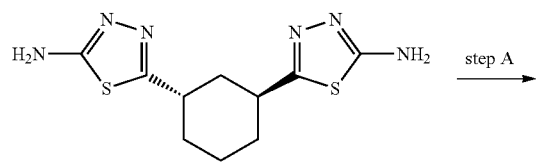 step A →

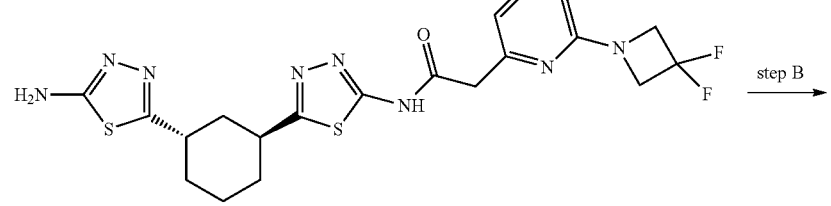 step B →

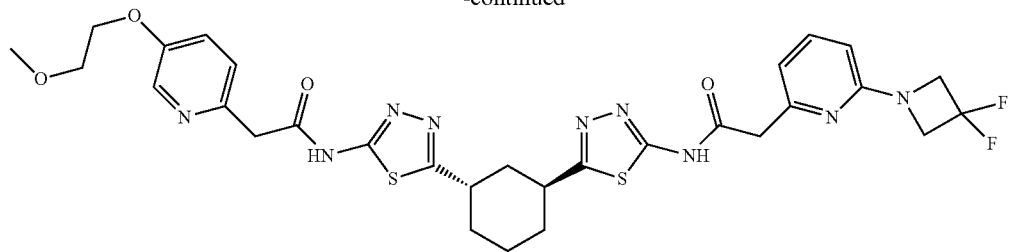

The procedure was the same as Compound 79

Step B: 2-(6-(3,3-difluoroazetidin-1-yl)pyridin-2-yl)-N-(5-((1S,3S)-3-(5-(2-(5-(2-methoxyethoxy)pyridin-2-yl)acetamido)-1,3,4-thiadiazol-2-yl)cyclohexyl)-1,3,4-thiadiazol-2-yl)acetamide (280)

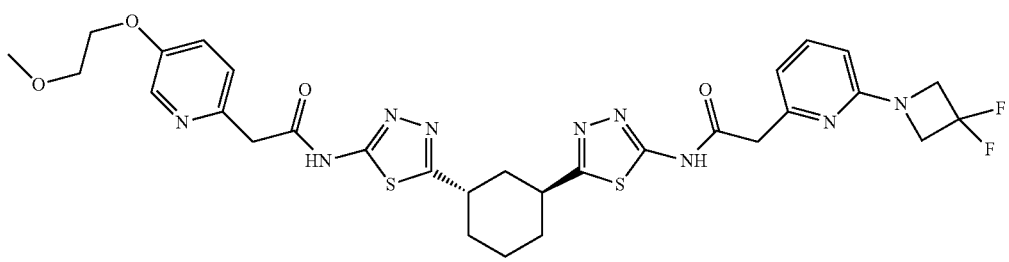 [SMILES: COCCOc1ccc(CC(=O)Nc2nnc([C@H]3CCC[C@H](c4nnc(NC(=O)Cc5cccc(N6CC(F)(F)C6)n5)s4)C3)s2)nc1]

$^1$H NMR (METHANOL-$d_4$) δ: 8.23 (d, J=2.7 Hz, 1H), 7.54-7.70 (m, 1H), 7.30-7.54 (m, 2H), 6.81 (d, J=7.3 Hz, 1H), 6.49 (d, J=8.3 Hz, 1H), 4.38 (t, J=12.2 Hz, 4H), 4.20-4.25 (m, 2H), 3.94 (s, 2H), 3.90 (s, 2H), 3.73-3.82 (m, 2H), 3.52-3.61 (m, 2H), 3.44 (s, 3H), 2.45 (t, J=5.8 Hz, 2H), 2.03-2.13 (m, 2H), 1.91-2.03 (m, 2H), 1.70-1.82 (m, 2H). LC-MS: m/z (M+H)=687.0

Compounds 364, 376, 366, 367, 365, 372, and 374 were prepared in an analogous manner to Compound 81:

2-(pyridin-2-yl)-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)acetamide (364)

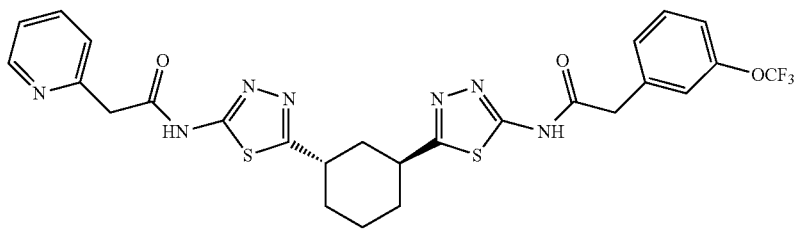 [SMILES: O=C(Cc1cccc(OC(F)(F)F)c1)Nc1nnc([C@H]2CCC[C@H](c3nnc(NC(=O)Cc4ccccn4)s3)C2)s1]

$^1$H NMR (CHLOROFORM-d) δ: 13.74 (br. s., 1H), 8.62 (d, J=4.3 Hz, 1H), 7.69 (m, 1H), 7.20-7.48 (m, 5H), 7.10 (d, J=8.1 Hz, 1H), 4.13 (s, 2H), 4.08 (s, 2H), 3.52-3.68 (m, 2H), 2.40-2.57 (m, 2H), 1.93-2.15 (m, 4H), 1.72-1.84 (m, 2H); LC-MS: m/z (M+H)=604.5

379

(S)-2-hydroxy-2-phenyl-N-(5-((1S,3S)-3-(5-(2-(pyridin-2-yl)acetamido)-1,3,4-thiadiazol-2-yl)cyclohexyl)-1,3,4-thiadiazol-2-yl)acetamide (376)

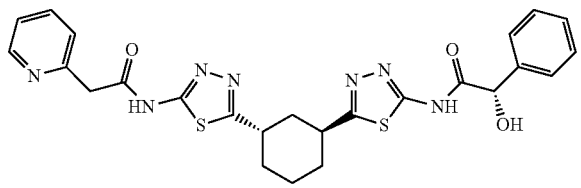 [SMILES: O=C(Cc1ccccn1)Nc1nnc([C@H]2CCC[C@H](c3nnc(NC(=O)[C@@H](O)c4ccccc4)s3)C2)s1]

380

$^1$H NMR (CHLOROFORM-d) δ: 8.63 (d, J=4.0 Hz, 1H), 7.72 (t, J=7.7 Hz, 1H), 7.56 (d, J=6.4 Hz, 2H), 7.21-7.39 (m, 5H), 5.56 (s, 1H), 4.08 (s, 2H), 3.51-3.65 (m, 2H), 2.40 (m, 2H), 1.95-2.11 (m, 2H), 1.92 (m, 2H), 1.65-1.76 (m, 2H); LC-MS: m/z (M+H)=536.3

2-(6-(3-aminoazetidin-1-yl)pyridin-2-yl)-N-(5-((1S,3S)-3-(5-(2-(3-cyanophenyl)acetamido)-1,3,4-thiadiazol-2-yl)cyclohexyl)-1,3,4-thiadiazol-2-yl)acetamide (366)

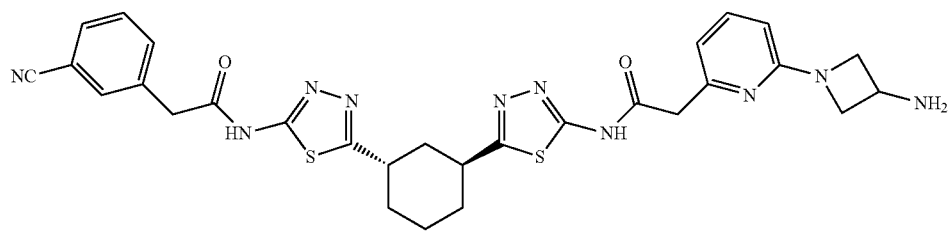 [SMILES: N#Cc1cccc(CC(=O)Nc2nnc([C@H]3CCC[C@H](c4nnc(NC(=O)Cc5cccc(N6CC(N)C6)n5)s4)C3)s2)c1]

$^1$H NMR (CHCl$_3$-d) δ: 7.68 (s, 1H), 7.60 (m, 2H), 7.48 (m, 2H), 6.63 (d, J=7.2 Hz, 1H), 6.31 (d, J=8.3 Hz, 1H), 4.40 (m, 2H), 4.15-4.09 (m, 5H), 3.86 (s, 2H), 3.50 (m, 2H), 2.40 (s, 2H), 2.00-1.95 (m, 4H), 1.74 (m, 2H). LC-MS: m/z (M+H)=615.7

2-(3-cyanophenyl)-N-(5-((1S,3S)-3-(5-(2-(3-(piperidin-3-yl)phenyl)acetamido)-1,3,4-thiadiazol-2-yl)cyclohexyl)-1,3,4-thiadiazol-2-yl)acetamide (367)

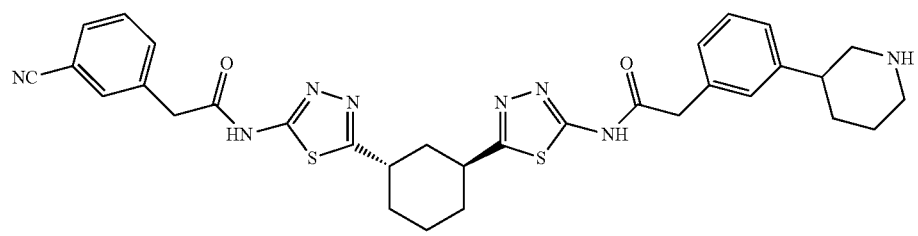 [SMILES: N#Cc1cccc(CC(=O)Nc2nnc([C@H]3CCC[C@H](c4nnc(NC(=O)Cc5cccc(C6CCCNC6)c5)s4)C3)s2)c1]

¹H NMR (METHANOL-d₄) δ: 7.68 (s, 1H), 7.62 (d, J=7.5 Hz, 1H), 7.55 (d, J=7.8 Hz, 1H), 7.43 (t, J=7.7 Hz, 1H), 7.32 (s, 1H), 7.21-7.30 (m, 2H), 7.10 (s, 1H), 3.88 (s, 2H), 3.83 (s, 2H), 3.52 (m, 2H), 3.26 (m, 2H), 2.67-2.93 (m, 3H), 2.28-2.51 (m, 2H), 2.02-1.98 (m, 6H), 1.86 (m, 2H), 1.69 (m, 2H). LC-MS: m/z (M+H)=627.2

(R)-2-hydroxy-2-phenyl-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)acetamide (365)

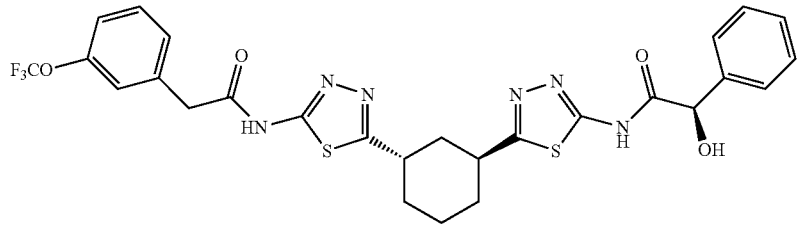 [SMILES: O=C(Cc1cccc(OC(F)(F)F)c1)Nc1nnc([C@H]2CCC[C@H](c3nnc(NC(=O)[C@H](O)c4ccccc4)s3)C2)s1]

¹H NMR (400 MHz, DMSO-d₆) δ: 12.62 (b, 2H), 7.55-7.45 (m, 3H), 7.36 (t, J=7.1 Hz, 4H), 7.33-7.24 (m, 2H), 5.32 (s, 1H), 3.90 (s, 2H), 3.47 (m, 2H), 2.29 (t, J=5.6 Hz, 2H), 1.93 (m, 2H), 1.88-1.75 (m, 2H), 1.66-1.53 (m, 2H). LC-MS: m/z (M+H)=619.2

(S)-2-hydroxy-2-phenyl-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)acetamide (372)

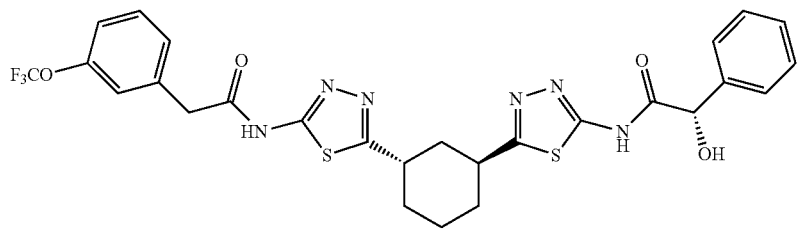 [SMILES: O=C(Cc1cccc(OC(F)(F)F)c1)Nc1nnc([C@H]2CCC[C@H](c3nnc(NC(=O)[C@@H](O)c4ccccc4)s3)C2)s1]

¹H NMR (400 MHz, DMSO-d₆) δ: 12.62 (b, 2H), 7.54-7.46 (m, 3H), 7.36-7.24 (m, 6H), 5.32 (s, 1H), 3.90 (s, 2H), 3.47 (m, 2H), 2.29 (t, J=5.6 Hz, 2H), 1.93 (m, 2H), 1.88-1.75 (m, 2H), 1.66-1.53 (m, 2H). LC-MS: m/z (M+H)=619.2

(S)-2-hydroxy-2-phenyl-N-(5-((1S,3S)-3-(5-(2-(3-(trifluoromethoxy)phenyl)acetamido)-1,3,4-thiadiazol-2-yl)cyclopentyl)-1,3,4-thiadiazol-2-yl)acetamide (374)

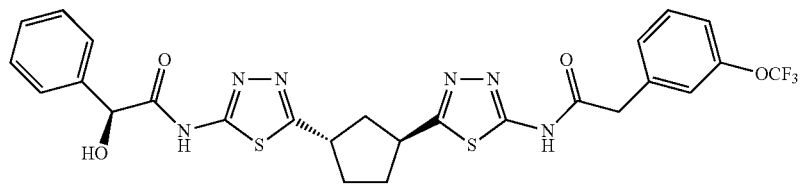 [SMILES: O=C(Cc1cccc(OC(F)(F)F)c1)Nc1nnc([C@H]2CC[C@H](c3nnc(NC(=O)[C@@H](O)c4ccccc4)s3)C2)s1]

¹H NMR (400 MHz, CDCl₃) δ: 7.53 (d, J=7.8 Hz, 2H), 7.44-7.39 (m, 2H), 7.37-7.32 (m, 4H), 7.14 (d, J=7.8 Hz, 1H), 5.52 (s, 1H), 4.05 (s, 2H), 3.78 (m, 2H), 2.55 (t, J=7.5 Hz, 2H), 2.42 (m, 2H), 2.03-2.10 (m, 2H). LC-MS: m/z (M+H)=605.2
Compound 281

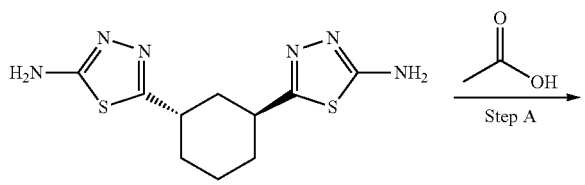

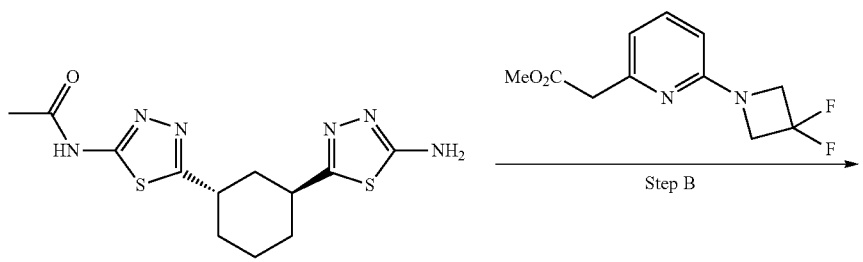

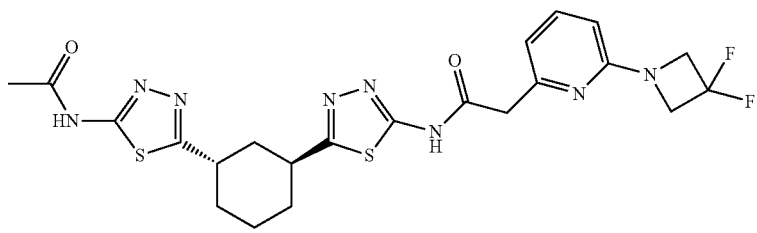

Step A: N-(5-((1S,3S)-3-(5-amino-1,3,4-thiadiazol-2-yl)cyclohexyl)-1,3,4-thiadiazol-2-yl)acetamide

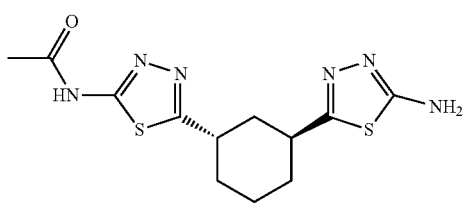 [SMILES: CC(=O)Nc1nnc([C@H]2CCC[C@H](c3nnc(N)s3)C2)s1]

A solution of 5,5'-((1S,3S)-cyclopentane-1,3-diyl)bis(1,3,4-thiadiazol-2-amine) (200 mg, 0.71 mmol), acetic acid (42.5 mg, 0.71 mmol), HATU (260.0 mg, 0.71 mmol), and N-ethyl-N-isopropylpropan-2-amine (110.0 mg, 0.85 mmol) in N,N-dimethylformamide (10 ml) was stirred at room temperature overnight. The mixture evaporated in vacuum to dryness. The residue was purified by a standard method to afford desired compound. LC-MS: m/z (M+H)=325.4

Step B: N-(5-((1S,3S)-3-(5-acetamido-1,3,4-thiadiazol-2-yl)cyclohexyl)-1,3,4-thiadiazol-2-yl)-2-(6-(3,3-difluoroazetidin-1-yl)pyridin-2-yl)acetamide (281)

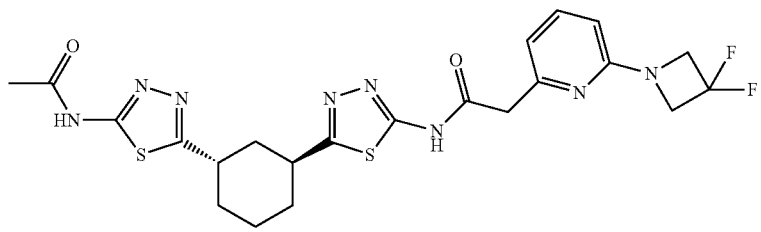 [SMILES: CC(=O)Nc1nnc([C@H]2CCC[C@H](c3nnc(NC(=O)Cc4cccc(N5CC(F)(F)C5)n4)s3)C2)s1]

The procedure was the same as Step B of Compound 84

¹H NMR (CHLOROFORM-d) δ: 12.61 (br. s., 1H), 7.59 (t, J=7.8 Hz, 1H), 6.73 (d, J=7.3 Hz, 1H), 6.39 (d, J=8.3 Hz, 1H), 4.59 (t, J=11.6 Hz, 4H), 3.98 (s, 2H), 3.60 (m, 2H), 2.47 (s, 3H), 2.17-2.36 (m, 2H), 1.96 (m, 2H), 1.66 (m, 2H), 1.34 (m, 2H. LC-MS: m/z (M+H)=535.7

Compound 282

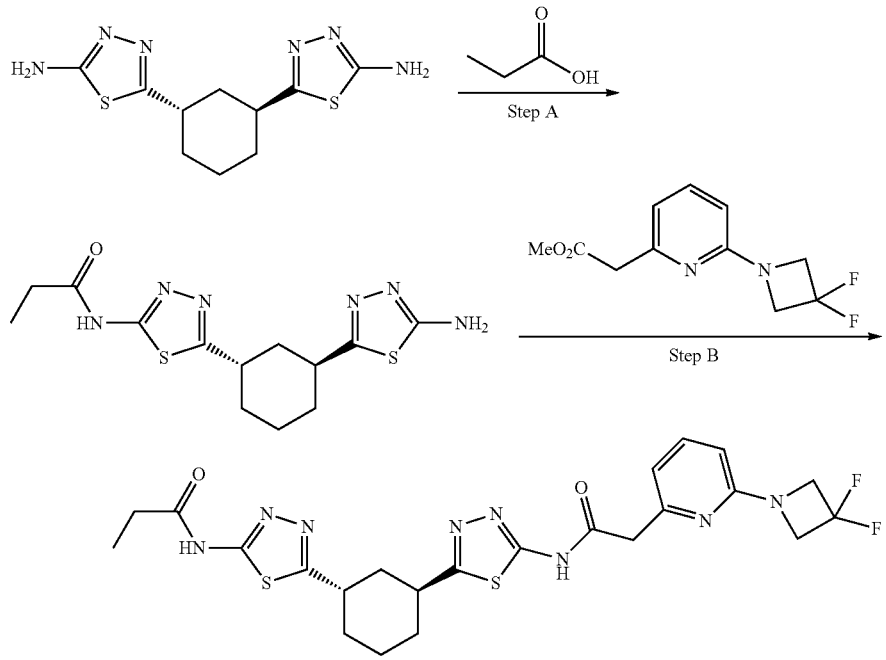

The procedure was the same as Compound 281

Step A: N-(5-((1S,3S)-3-(5-amino-1,3,4-thiadiazol-2-yl)cyclohexyl)-1,3,4-thiadiazol-2-yl)propionamide LC-MS: m/z (M+H)=339.5

Step B: N-(5-((1S,3S)-3-(5-(2-(6-(3,3-difluoroazetidin-1-yl)pyridin-2-yl)acetamido)-1,3,4-thiadiazol-2-yl)cyclohexyl)-1,3,4-thiadiazol-2-yl)propionamide (282)

¹H NMR (DMSO-d₆) δ: 12.69 (s, 1H), 12.40 (s, 1H), 7.59 (dd, J=7.3, 8.1 Hz, 1H), 6.80 (d, J=7.3 Hz, 1H), 6.48 (d, J=8.1 Hz, 1H), 4.34 (t, J=12.5 Hz, 4H), 3.86 (s, 2H), 3.49 (m, 2H), 2.44-2.49 (q, J=7.5 Hz, 2H), 2.31 (t, J=5.6 Hz, 2H), 1.90-2.01 (m, 2H), 1.86 (m, 2H), 1.57-1.66 (m, 2H), 1.05-1.14 (t, 3H). LC-MS: m/z (M+H)=549.7
Compound 283
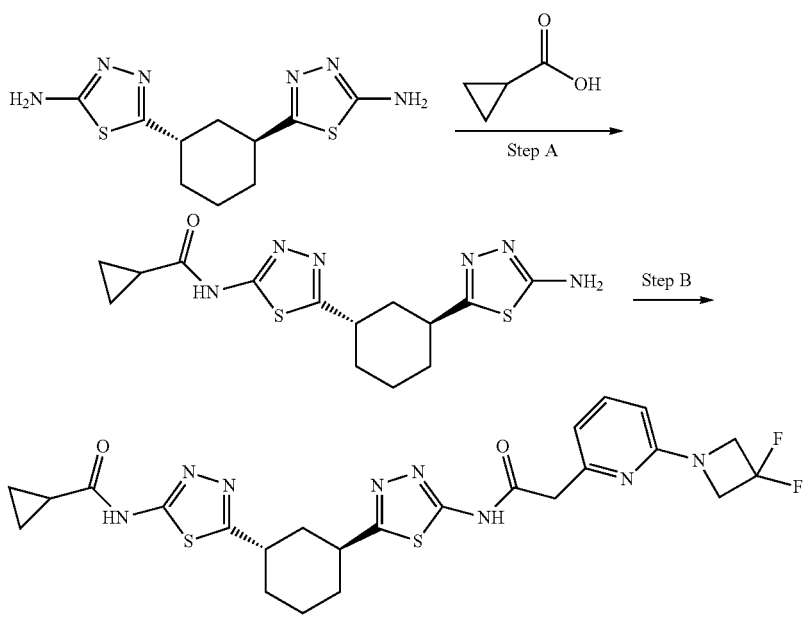
The procedure was the same as Compound 281
Step A: N-(5-((1S,3S)-3-(5-amino-1,3,4-thiadiazol-2-yl)cyclohexyl)-1,3,4-thiadiazol-2-yl)cyclopropanecarboxamide
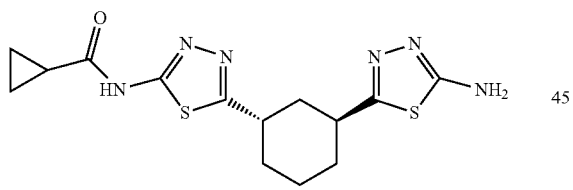
LC-MS: m/z (M+H)=351.4
Step B: N-(5-((1S,3S)-3-(5-acetamido-1,3,4-thiadiazol-2-yl)cyclohexyl)-1,3,4-thiadiazol-2-yl)-2-(6-(3,3-difluoroazetidin-1-yl)pyridin-2-yl)acetamide (283)
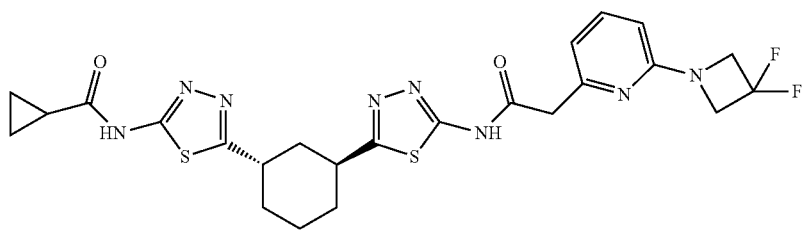 [SMILES: O=C(Cc1cccc(N2CC(F)(F)C2)n1)Nc1nnc([C@H]2CCC[C@H](c3nnc(NC(=O)C4CC4)s3)C2)s1]

¹H NMR (CHLOROFORM-d) δ: 7.58 (t, J=7.8 Hz, 1H), 6.73 (d, J=7.3 Hz, 1H), 6.38 (d, J=8.3 Hz, 1H), 4.57 (t, J=11.7 Hz, 4H), 3.99 (br. s., 2H), 3.49-3.69 (m, 2H), 2.38-2.55 (m, 2H), 2.29-2.38 (m, 1H), 1.90-2.12 (m, 4H), 1.64-1.84 (m, 2H), 1.17-1.23 (m, 2H), 1.05-1.13 (m, 2H). LC-MS: m/z (M+H)=561.6

N-(5-((1S,3S)-3-(5-acetamido-1,3,4-thiadiazol-2-yl)cyclohexyl)-1,3,4-thiadiazol-2-yl)-2-(3-methoxyphenyl)acetamide (90)

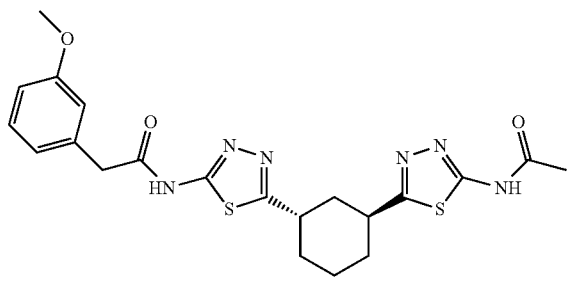 [SMILES: COc1cccc(CC(=O)Nc2nnc([C@H]3CCC[C@H](c4nnc(NC(C)=O)s4)C3)s2)c1]

A solution of 5,5'-((1S,3S)-cyclohexane-1,3-diyl)bis(1,3,4-thiadiazol-2-amine) (50 mg, 0.18 mmol), acetic acid (1 eq), HATU (202 mg, 0.53 mmol), and DIPEA (73 mg, 0.57 mmol) in N,N-dimethylformamide (2 ml) was heated to 50° C. for 2 h, then 3-methoxy-2-phenylacetic acid was added. The mixture was heated at 50° C. overnight and then poured into water (20 ml), the precipitate was filtered to give the crude product. The crude product was purified by a standard method to give the desired product.

¹H NMR (CHLOROFORM-d) δ: 7.22 (s, 1H), 7.00-7.06 (m, 2H), 6.78-6.82 (m, 1H), 4.01 (s, 2H), 3.76 (s, 3H), 3.60 (m, 2H), 2.47-2.50 (m, 5H), 2.02-2.09 (m, 2H), 1.99 (m, 2H), 1.79 (m, 2H). LC-MS: m/z (M+H)=473.6

N-(5-((1S,3S)-3-(5-acetamido-1,3,4-thiadiazol-2-yl)cyclohexyl)-1,3,4-thiadiazol-2-yl)-2-(2-methoxyphenyl)acetamide (94)

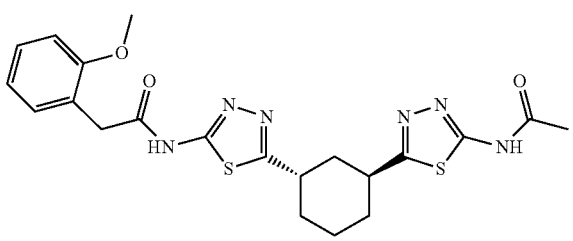 [SMILES: COc1ccccc1CC(=O)Nc1nnc([C@H]2CCC[C@H](c3nnc(NC(C)=O)s3)C2)s1]

The procedure was the same as Compound 90
¹H NMR (CHLOROFORM-d) δ: 7.29-7.37 (m, 2H), 6.95-7.03 (m, 2H), 3.93 (s, 3H), 3.90 (s, 2H), 3.53-3.61 (m, 2H), 2.46 (m, 5H), 1.95-2.06 (m, 4H), 1.74-1.79 (m, 2H). LC-MS: m/z (M+H)=473.6

N-(5-((1S,3S)-3-(5-acetamido-1,3,4-thiadiazol-2-yl)cyclohexyl)-1,3,4-thiadiazol-2-yl)-2-(pyridin-2-yl)acetamide (93)

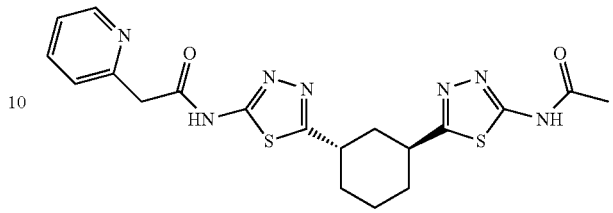

The procedure was the same as Compound 90
¹H NMR (CHLOROFORM-d) δ: 8.67 (d, J=4.3 Hz, 1H), 7.71-7.78 (m, 1H), 7.35 (d, J=7.8 Hz, 1H), 7.31 (m, 1H), 4.10 (s, 2H), 3.55-3.64 (m, 2H), 2.47 (m, 5H), 1.95-2.08 (m, 4H), 1.78 (m, 2H). LC-MS: m/z (M+H)=444.6

5,5'-((1S,3S)-cyclopentane-1,3-diyl)bis(1,3,4-thiadiazol-2-amine)

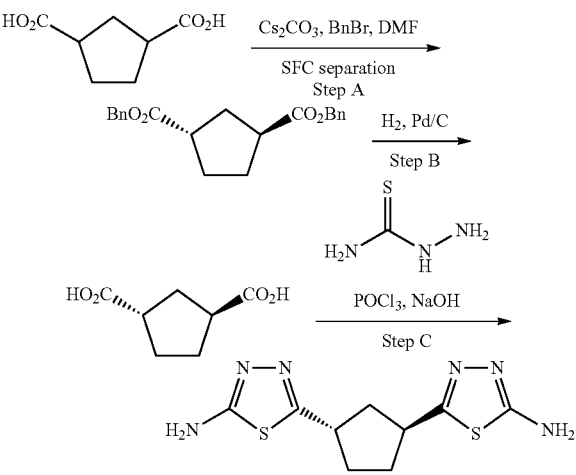

Step A: (S,S)-dibenzyl cyclopentyl 1,3-dicarboxylate

To a mixture of cis and trans-cyclopentyl 1,3-dicarboxylic acid (1.58 g, 10.0 mmol), Cs₂CO₃ (8.28 g, 25.5 mmol) in DMF (20 mL) was added BnBr (4.36 g, 25.5 mmol). The mixture was stirred at rt under nitrogen for 3 h. The residue was diluted with water and extracted with ethyl acetate. The combined organic solution was washed with water, dried over Na₂SO₄ and concentrated in vacuo. The crude product was purified by a standard method to afford trans-dibenzyl cyclopentyl 1,3-dicarboxylate.

Chiral SFC separation: cis- and trans-dibenzyl cyclopentyl 1,3-dicarboxylate was separated by chiral SFC to afford (S,S)-dibenzyl cyclohexyl 1,3-dicarboxylate.

¹H NMR (400 MHz, CHLOROFORM-d) δ 7.43-7.34 (m, 10H), 5.15 (s, 4H), 2.99-3.06 (m, 2H), 2.22 (t, J=7.8 Hz, 2H), 2.11 (m, 2H), 1.90 (m, 2H). LC-MS: m/z 171.2 (M−H)⁻. LC-MS: m/z (M+H)=423.6

Step B: (S,S)-cyclopentyl 1,3-dicarboxylic acid

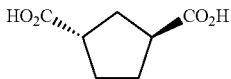

To a solution of 0.5 g (S,S)-dibenzyl cyclopentyl 1,3-dicarboxylate in 10 mL MeOH was added 10% Pd on carbon (0.05 g). The suspension was flushed with hydrogen and stirred for 20 min. It was then filtered and concentrated to give the desired compound. The configuration was confirmed by comparing the optical rotation of the product with standard value.

¹H NMR (DMSO-d₆) δ: 12.12 (br. s., 2H), 2.71-2.82 (m, 2H), 1.97 (t, J=7.8 Hz, 2H), 1.87-1.94 (m, 2H), 1.64-1.76 (m, 2H). LC-MS: m/z 157.2 (M−H)⁻. [a]$_D^{20}$=+32.8, c=5.0, H₂O [reported: [a]$_D^{20}$=+32.5, reported in *Aust. J. Chem.;* 1979, 32, 2517].

Step C: 5,5'-((1S,3S)-cyclopentane-1,3-diyl)bis(1,3,4-thiadiazol-2-amine)

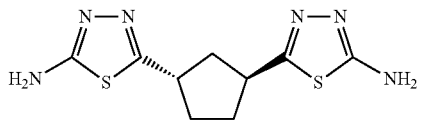 [SMILES: Nc1nnc([C@H]2CC[C@H](c3nnc(N)s3)C2)s1]

The compound was synthesized with a method similar to 5,5'-((1S,3S)-cyclohexane-1,3-diyl)bis(1,3,4-thiadiazol-2-amine).

¹H NMR (DMSO-d₆) δ: 7.06 (s, 4H), 3.49-3.55 (m, 2H), 2.22 (t, J=7.7 Hz, 2H), 2.14-2.20 (m, 2H), 1.78-1.89 (m, 2H). LC-MS: m/z 269.3 (M+H)

N,N'-(5,5'-((1S,3S)-cyclopentane-1,3-diyl)bis(1,3,4-thiadiazole-5,2-diyl))bis(2-(2-methoxyphenyl)acetamide) (284)

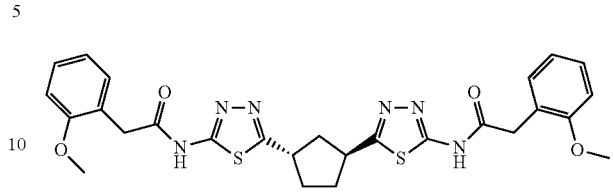

The procedure was the same as Compound 37

¹H NMR (DMSO-d₆) δ: 7.14-7.32 (m, 4H), 6.85-7.03 (m, 4H), 3.54-3.83 (m, 12H), 2.39 (t, J=7.7 Hz, 2H), 2.32 (m, 2H), 1.99 (m, 2H). LC-MS: m/z (M+H)=565.5

N,N'-(5,5'-((1S,3S)-cyclopentane-1,3-diyl)bis(1,3,4-thiadiazole-5,2-diyl))bis(2-(3-(dimethylamino)phenyl)acetamide) (285)

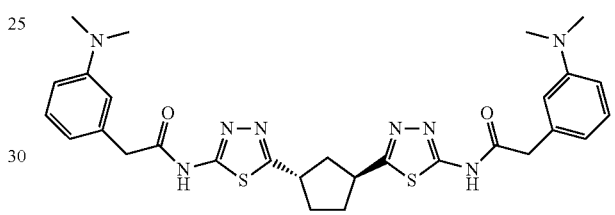

The procedure was the same as Compound 37

¹H NMR (DMSO-d₆): 12.66 (br. s., 2H), 7.11 (t, J=7.8 Hz, 2H), 6.70 (s, 2H), 6.61 (t, J=6.0 Hz, 4H), 3.72-3.82 (m, 6H), 2.88 (s, 12H), 2.38 (t, J=7.7 Hz, 2H), 2.29 (m, 2H), 1.93 (m, 2H). LC-MS: m/z (M+H)=591.5

N,N'-(5,5'-((1S,3S)-cyclopentane-1,3-diyl)bis(1,3,4-thiadiazole-5,2-diyl))bis(2-(6-methoxypyridin-3-yl)acetamide) (286)

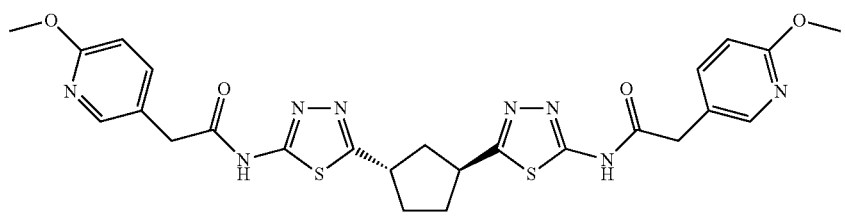

The procedure was the same as Compound 37
¹H NMR (DMSO-d₆) δ: 12.71 (s, 2H), 8.09 (d, J=1.9 Hz, 2H), 7.65 (dd, J=8.6, 2.4 Hz, 2H), 6.80 (d, J=8.6 Hz, 2H), 3.83 (s, 6H), 3.77 (s, 4H), 3.74 (m, 2H), 2.38 (t, J=7.8 Hz, 2H), 2.24-2.34 (m, 2H), 1.89-2.02 (m, 2H). LC-MS: m/z (M+H)=567.8

N,N'-(5,5'-((1S,3S)-cyclohexane-1,3-diyl)bis(1,3,4-thiadiazole-5,2-diyl))bis(2-(5-methoxypyridin-2-yl)acetamide) (287)

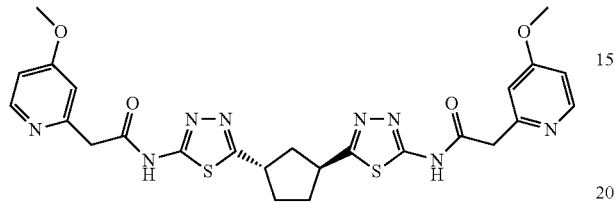

The procedure was the same as Step B of Compound 84
¹H NMR (DMSO-d₆) δ: 12.61 (s, 2H), 8.27 (d, J=5.6 Hz, 2H), 6.96 (d, J=2.4 Hz, 2H), 6.84 (dd, J=5.6, 2.4 Hz, 2H), 3.81 (s, 6H), 3.78 (s, 4H), 3.61-3.69 (m, 2H), 2.31 (t, J=7.7 Hz, 2H), 2.21-2.28 (m, 2H), 1.88-1.96 (m, 2H). LC-MS: m/z (M+H)=567.9

N,N'-(5,5'-((1S,3S)-cyclopentane-1,3-diyl)bis(1,3,4-thiadiazole-5,2-diyl))bis(2-(6-(3,3-difluoroazetidin-1-yl)pyridin-2-yl)acetamide) (288)

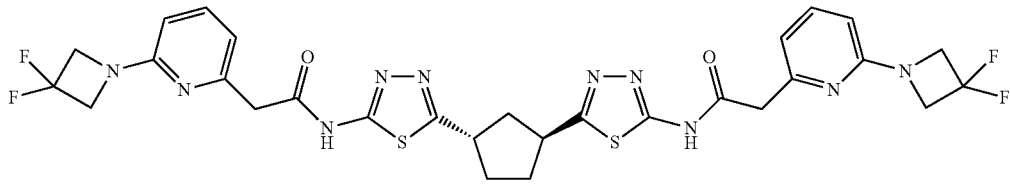 [SMILES: O=C(Cc1cccc(N2CC(F)(F)C2)n1)Nc1nnc([C@H]2CC[C@H](c3nnc(NC(=O)Cc4cccc(N5CC(F)(F)C5)n4)s3)C2)s1]

The procedure was the same as Step B of Compound 84
¹H NMR (DMSO-d₆) δ: 12.67 (s, 2H), 7.59 (t, J=7.8 Hz, 2H), 6.79 (d, J=7.3 Hz, 2H), 6.48 (d, J=8.1 Hz, 2H), 4.34 (t, J=12.5 Hz, 8H), 3.86 (s, 4H), 3.74-3.79 (m, 2H), 2.40 (t, J=7.7 Hz, 2H), 2.27-2.36 (m, 2H), 1.89-2.02 (m, 2H). LC-MS: m/z (M+H)=689.8

N,N'-(5,5'-((1S,3S)-cyclopentane-1,3-diyl)bis(1,3,4-thiadiazole-5,2-diyl))bis(2-(6-(dimethylamino)pyridin-2-yl)acetamide) (289)

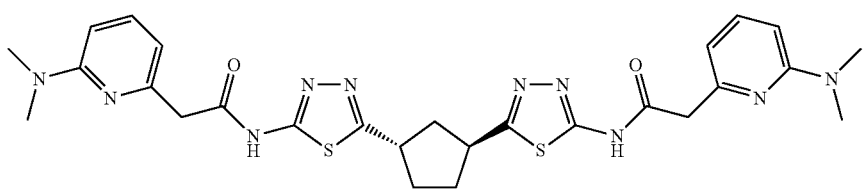

The procedure was the same as Step B of Compound 84

¹H NMR (DMSO-d₆) δ: 12.67 (s, 2H), 7.46 (t, J=7.9 Hz, 2H), 6.52 (d, J=8.6 Hz, 2H), 6.55 (d, J=7.3 Hz, 2H), 3.81 (s, 4H), 3.49 (m, 2H), 2.98 (s, 12H), 2.38 (t, J=7.7 Hz, 2H), 2.22-2.33 (m, 2H), 1.85-2.01 (m, 2H). LC-MS: m/z (M+H)= 593.9

Compound 386

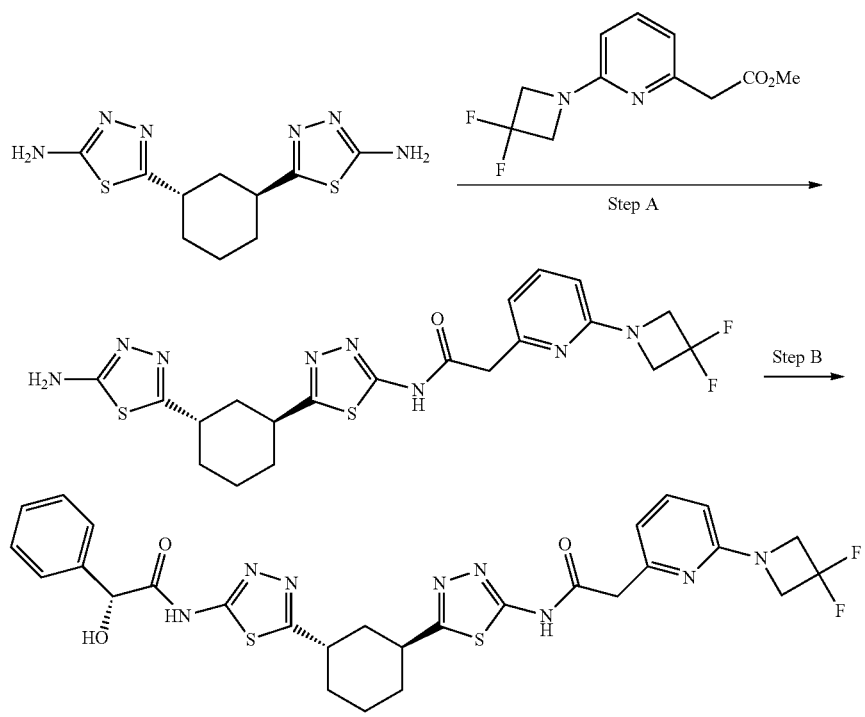

Step A: N-(5-((1S,3S)-3-(5-amino-1,3,4-thiadiazol-2-yl)cyclohexyl)-1,3,4-thiadiazol-2-yl)-2-(6-(3,3-difluoroazetidin-1-yl)pyridin-2-yl)acetamide

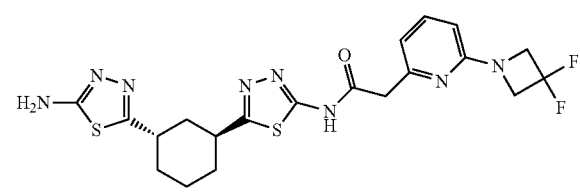 [SMILES: Nc1nnc([C@H]2CCC[C@H](c3nnc(NC(=O)Cc4cccc(N5CC(F)(F)C5)n4)s3)C2)s1]

To a solution of 5,5'-((1S,3S)-cyclohexane-1,3-diyl)bis(1,3,4-thiadiazol-2-amine) (1 g, 3.5 mmol) and tBuOK (392 mg, 3.5 mmol) in 15 mL DMF was added methyl 2-(6-(3,3-difluoroazetidin-1-yl)pyridin-2-yl)acetate (0.6 g, 2.5 mmol) in 5 mL DMF dropwise. The solution was stirred at room temperature for 12 h and quenched by saturated NaHCO3 solution. The resulting product was purified under standard conditions to give the title compound.

LC-MS: m/z (M+H)=493.2

Step B: (R)—N-(5-((1S,3S)-3-(5-(2-(6-(3,3-difluoroazetidin-1-yl)pyridin-2-yl)acetamido)-1,3,4-thiadiazol-2-yl)cyclohexyl)-1,3,4-thiadiazol-2-yl)-2-hydroxy-2-phenylacetamide

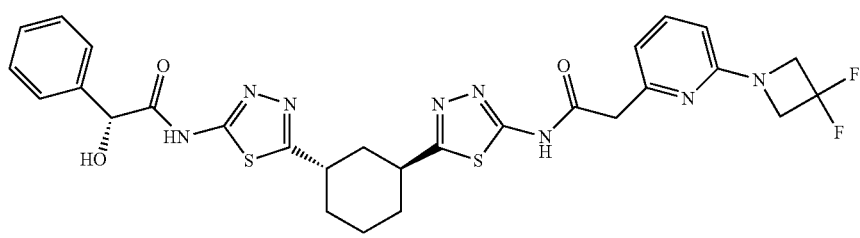 [SMILES: O=C(Cc1cccc(N2CC(F)(F)C2)n1)Nc1nnc([C@H]2CCC[C@H](c3nnc(NC(=O)[C@H](O)c4ccccc4)s3)C2)s1]

A solution of R-mendelic acid (155 mg, 1 mmol), HBTU (380 mg, 1 mmol), N-(5-((1S,3S)-3-(5-amino-1,3,4-thiadiazol-2-yl)cyclohexyl)-1,3,4-thiadiazol-2-yl)-2-(6-(3,3-difluoroazetidin-1-yl)pyridin-2-yl)acetamide (50 mg, 0.1 mmol) and DMAP (12 mg, 0.1 mmol) in 2 mL CH$_2$Cl$_2$ was stirred for 2 h at room temperature. The mixture was quenched with H$_2$O, extracted with CH$_2$Cl$_2$, and concentrated and purified by a standard method to give the desired product.

$^1$H NMR (400 MHz, MeOH-d$_4$) δ: 7.61 (dd, J=8.2, 7.3 Hz, 1H), 7.54 (m, 2H), 7.37 (m, 3H), 6.81 (d, J=7.3 Hz, 1H), 6.49 (d, J=8.2 Hz, 1H), 4.61 (b.s., 1H), 4.38 (t, J=12.2 Hz, 3H), 3.57 (m, 2H), 3.33 (s, 2H), 2.44 (t, J=5.7 Hz, 2H), 2.11-1.93 (m, 4H), 1.81-1.74 (m, 2H). LC-MS: m/z (M+H)=627.2

Compounds 387, 388, 349, 389, 375, 390, 377, and 378, were prepared in an analogous manner as Compound 386:

(S)—N-(5-((1S,3S)-3-(5-(2-(6-(3,3-difluoroazetidin-1-yl)pyridin-2-yl)acetamido)-1,3,4-thiadiazol-2-yl)cyclohexyl)-1,3,4-thiadiazol-2-yl)-2-hydroxy-2-phenylacetamide (387)

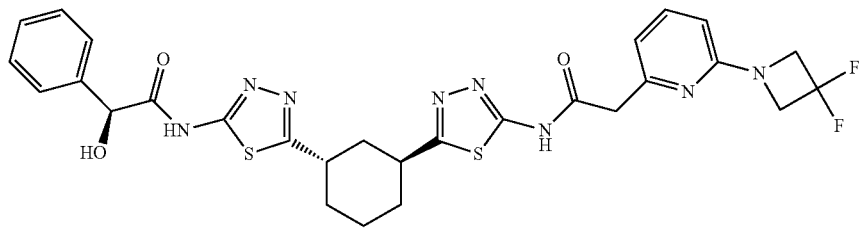 [SMILES: O=C(Cc1cccc(N2CC(F)(F)C2)n1)Nc1nnc([C@H]2CCC[C@H](c3nnc(NC(=O)[C@@H](O)c4ccccc4)s3)C2)s1]

$^1$H NMR (400 MHz, MeOH-d$_4$) δ: 7.62-7.58 (dd, J=8.3, 7.3 Hz, 1H), 7.54 (m, 2H), 7.43-7.32 (m, 3H), 6.81 (d, J=7.3 Hz, 1H), 6.50 (d, J=8.3 Hz, 1H), 4.61 (b.s., 1H), 4.38 (t, J=12.2 Hz, 3H), 3.57 (m, 2H), 3.33 (s, 2H), 2.44 (t, J=5.7 Hz, 2H), 2.08-1.96 (m, 4H), 1.82-1.71 (m, 2H). LC-MS: m/z (M+H)=627.2

2-(6-(3,3-difluoroazetidin-1-yl)pyridin-2-yl)-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)acetamide (388)

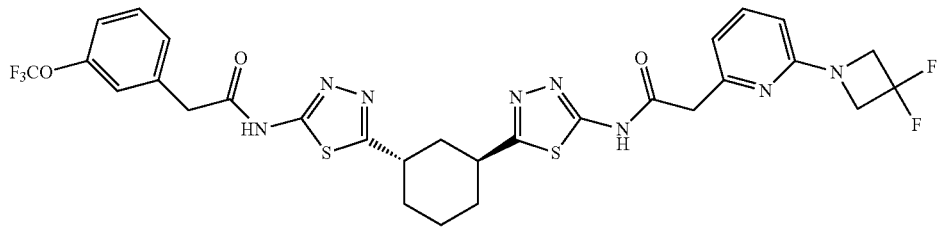 [SMILES: O=C(Cc1cccc(OC(F)(F)F)c1)Nc1nnc([C@H]2CCC[C@H](c3nnc(NC(=O)Cc4cccc(N5CC(F)(F)C5)n4)s3)C2)s1]

¹H NMR (400 MHz, CDCl₃) δ: 7.54 (dd, J=8.3, 7.3 Hz, 1H), 7.44 (d, J=7.3 Hz, 1H), 7.41 (s, 1H), 7.34 (t, J=7.9 Hz, 1H), 7.11 (d, J=8.0 Hz, 1H), 6.69 (d, J=7.3 Hz, 1H), 6.34 (d, J=8.3 Hz, 1H), 4.50 (t, J=11.8 Hz, 4H), 4.09 (s, 2H), 3.90 (s, 2H), 3.60 (m, 2H), 2.59-2.41 (m, 2H), 2.11-1.91 (m, 4H), 1.79 (s, 2H). LC-MS: m/z (M+H)=695.2

2-cyclopropyl-N-(5-((1S,3S)-3-(5-(2-(6-(3,3-difluoroazetidin-1-yl)pyridin-2-yl)acetamido)-1,3,4-thiadiazol-2-yl)cyclohexyl)-1,3,4-thiadiazol-2-yl)acetamide (349)

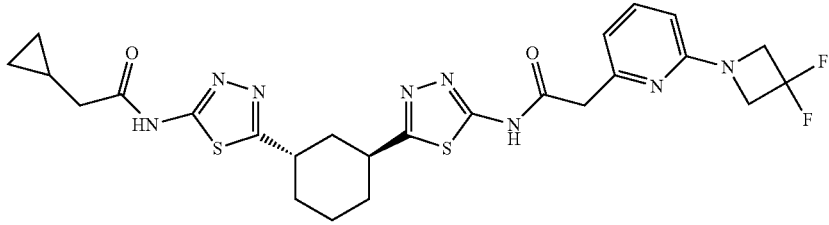 [SMILES: O=C(Cc1cccc(N2CC(F)(F)C2)n1)Nc1nnc([C@H]2CCC[C@H](c3nnc(NC(=O)CC4CC4)s3)C2)s1]

¹H NMR (400 MHz, CHLOROFORM-d) d: 7.74 (dd, J=8.3, 7.3 Hz, 1H), 6.86 (d, J=7.3 Hz, 1H), 6.51 (d, J=8.3 Hz, 1H), 4.77 (t, J=11.8 Hz, 4H, 4H), 4.28 (s, 2H), 3.58 (m, 2H), 2.60 (d, J=7.4 Hz, 2H), 2.47 (m, 2H), 1.97-2.07 (m, 5H), 1.77 (m, 2H), 0.59-0.70 (m, 2H), 0.34 (q, J=4.9 Hz, 2H); LC-MS: m/z (M+H)=575.4

3-hydroxy-2-phenyl-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)propanamide (389)

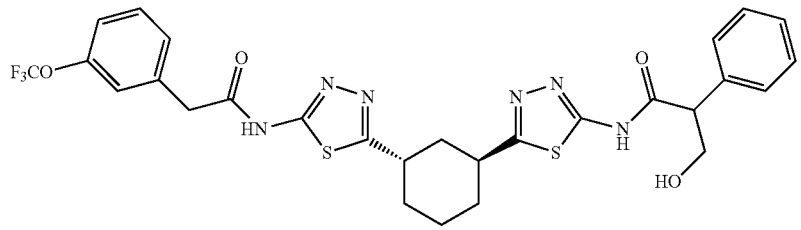 [SMILES: O=C(Cc1cccc(OC(F)(F)F)c1)Nc1nnc([C@H]2CCC[C@H](c3nnc(NC(=O)C(CO)c4ccccc4)s3)C2)s1]

¹H NMR (400 MHz, DMSO-d6) δ: 7.44-7.51 (t, J=8.8 Hz, 1H), 7.32-7.38 (m, 6H), 7.25-7.32 (m, 2H), 5.10 (m, 1H), 3.99-4.15 (m, 2H), 3.90 (s, 2H), 3.47 (m, 2H), 2.30 (t, J=5.9 Hz, 2H), 1.93 (m, 2H), 1.85 (m, 2H), 1.61 (m, 2H). LC-MS: m/z (M+H)=633.5

2-(6-cyanopyridin-2-yl)-N-(5-((1S,3S)-3-(5-(2-(3-(trifluoromethoxy)phenyl)acetamido)-1,3,4-thiadiazol-2-yl)cyclohexyl)-1,3,4-thiadiazol-2-yl)acetamide (375)

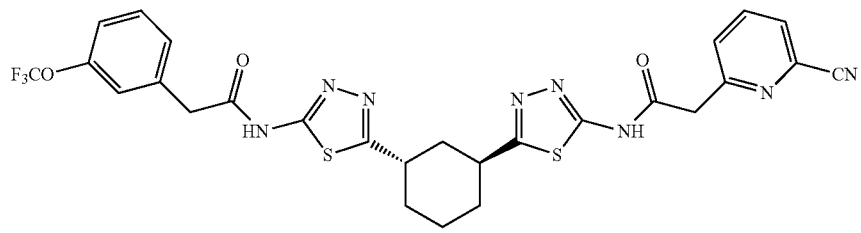 [SMILES: N#Cc1cccc(CC(=O)Nc2nnc([C@H]3CCC[C@H](c4nnc(NC(=O)Cc5cccc(OC(F)(F)F)c5)s4)C3)s2)n1]

¹H NMR (400 MHz, CDCl₃) δ: 7.81 (t, J=7.8 Hz, 1H), 7.68 (d, J=8.0 Hz, 1H), 7.60 (d, J=7.8 Hz, 1H), 7.46-7.38 (m, 2H), 7.34 (t, J=8.0 Hz, 1H), 7.12 (d, J=7.7 Hz, 1H), 4.33 (s, 2H), 4.07 (s, 2H), 3.60 (m, 2H), 2.49 (t, J=5.9 Hz, 2H), 2.07-2.10 (m, 2H), 2.00-2.05 (m, 2H), 1.71-1.95 (m, 2H). LC-MS: m/z (M+H)=629.2

2-(3-(aminomethyl)phenyl)-N-(5-((1S,3S)-3-(5-(2-(3-cyanophenyl)acetamido)-1,3,4-thiadiazol-2-yl)cyclohexyl)-1,3,4-thiadiazol-2-yl)acetamide (390)

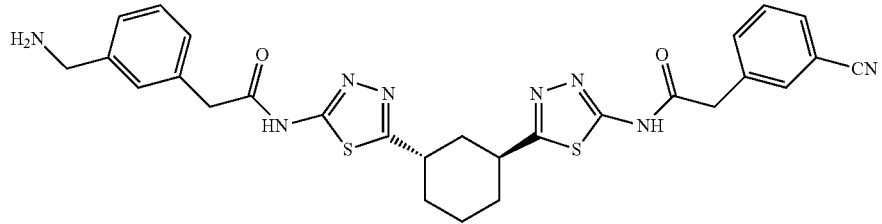 [SMILES: N#Cc1cccc(CC(=O)Nc2nnc([C@H]3CCC[C@H](c4nnc(NC(=O)Cc5cccc(CN)c5)s4)C3)s2)c1]

¹H NMR (CHLOROFORM-d) d: 7.84 (s, 1H), 7.73 (d, J=8.1 Hz, 1H), 7.54 (d, J=7.5 Hz, 1H), 7.48 (s, 1H), 7.38-7.45 (t, J=7.8 Hz, 1H), 7.32 (m, 1H), 7.23 (m, 2H), 4.08 (s, 2H), 4.02 (s, 2H), 3.92 (s, 2H), 3.61 (m, 2H), 2.22 (t, J=7.6 Hz, 1H), 2.02 (m, 2H), 1.94 (m, 2H), 1.77 (m, 2H). LC-MS: m/z (M+H)=573.3

(S)—N-(5-((1S,3S)-3-(5-(2-(6-(3,3-difluoroazetidin-1-yl)pyridin-2-yl)acetamido)-1,3,4-thiadiazol-2-yl)cyclopentyl)-1,3,4-thiadiazol-2-yl)-2-hydroxy-2-phenylacetamide (377)

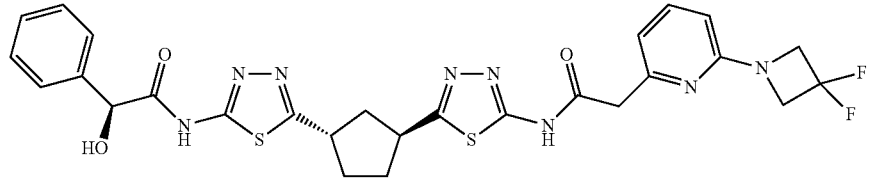 [SMILES: O=C(Cc1cccc(N2CC(F)(F)C2)n1)Nc1nnc([C@H]2CC[C@H](c3nnc(NC(=O)[C@@H](O)c4ccccc4)s3)C2)s1]

¹H NMR (400 MHz, CDCl₃) δ: 7.60-7.50 (m, 3H), 7.37 (m, 3H), 6.68 (d, J=7.3 Hz, 1H), 6.35 (d, J=8.3 Hz, 1H), 5.51 (s, 1H), 5.37 (s, 1H), 4.53 (t, J=11.8 Hz, 1H), 3.88 (s, 2H), 3.84-3.71 (m, 2H), 2.62-2.46 (m, 2H), 2.40 (m, 2H), 2.10-1.98 (m, 2H). LC-MS: m/z (M+H)=613.2

(R)—N-(5-((1S,3S)-3-(5-(2-(6-(3,3-difluoroazetidin-1-yl)pyridin-2-yl)acetamido)-1,3,4-thiadiazol-2-yl)cyclopentyl)-1,3,4-thiadiazol-2-yl)-2-hydroxy-2-phenylacetamide (378)

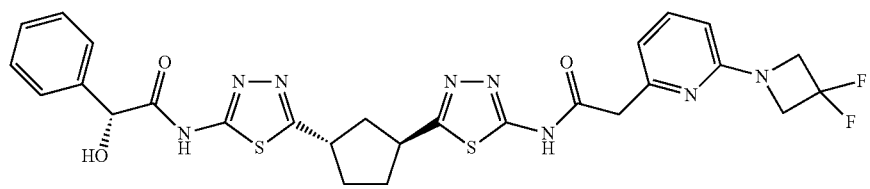 [SMILES: O=C(Cc1cccc(N2CC(F)(F)C2)n1)Nc1nnc([C@H]2CC[C@H](c3nnc(NC(=O)[C@H](O)c4ccccc4)s3)C2)s1]

¹H NMR (400 MHz, CDCl₃) δ: 7.55 (m, 3H), 7.39 (m, 3H), 6.68 (d, J=7.2 Hz, 1H), 6.35 (d, J=8.4 Hz, 1H), 5.52 (s, 1H), 5.37 (s, 1H), 4.54 (t, J=11.8 Hz, 1H), 3.88 (s, 2H), 3.84-3.72 (m, 2H), 2.57 (m, 1H), 2.50-2.37 (m, 3H), 2.08 (m, 2H). LC-MS: m/z (M+H)=613.2

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

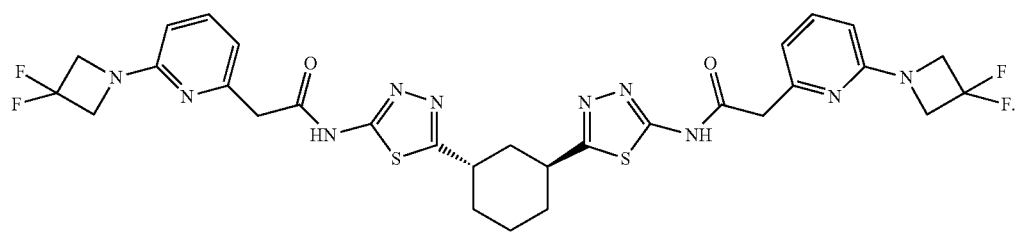

What is claimed is:

1. A compound or a pharmaceutically acceptable salt thereof, which is

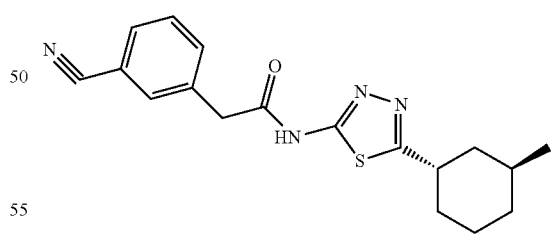

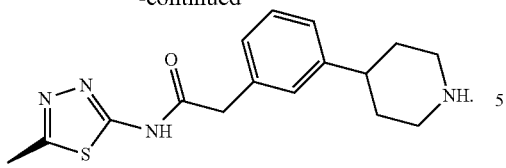
2. A compound or a pharmaceutically acceptable salt thereof, which is
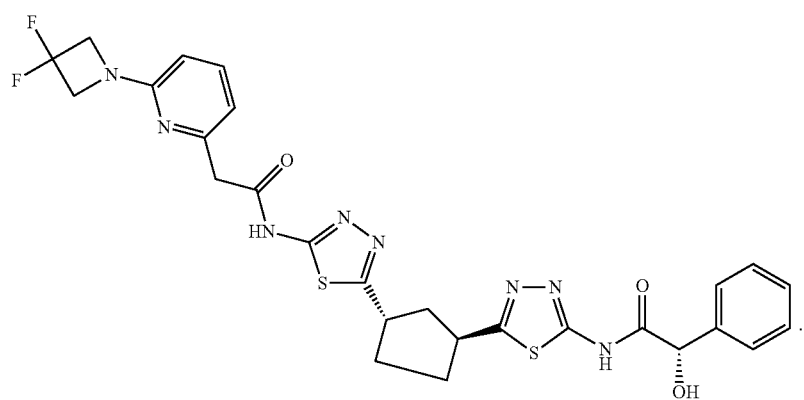 [SMILES: O=C(Cc1cccc(N2CC(F)(F)C2)n1)Nc1nnc([C@H]2CC[C@H](c3nnc(NC(=O)[C@@H](O)c4ccccc4)s3)C2)s1]
3. A compound or a pharmaceutically acceptable salt thereof, which is
4. A compound or a pharmaceutically acceptable salt thereof, which is
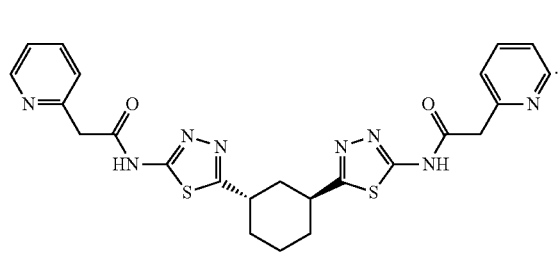 [SMILES: O=C(Cc1ccccn1)Nc1nnc([C@H]2CCC[C@H](c3nnc(NC(=O)Cc4ccccn4)s3)C2)s1]
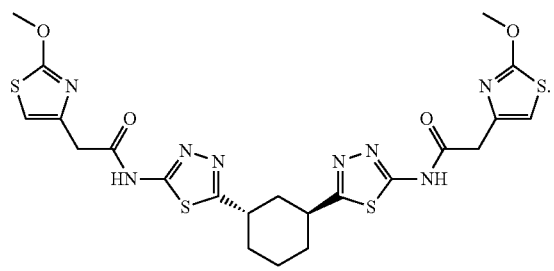 [SMILES: COc1nc(CC(=O)Nc2nnc([C@H]3CCC[C@H](c4nnc(NC(=O)Cc5csc(OC)n5)s4)C3)s2)cs1]

5. A compound or a pharmaceutically acceptable salt thereof, which is

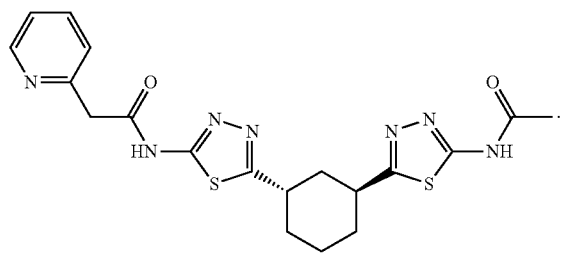 [SMILES: CC(=O)Nc1nnc([C@H]2CCC[C@H](c3nnc(NC(=O)Cc4ccccn4)s3)C2)s1]

6. A compound or a pharmaceutically acceptable salt thereof, which is

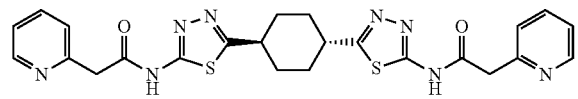

7. A compound or a pharmaceutically acceptable salt thereof, which is

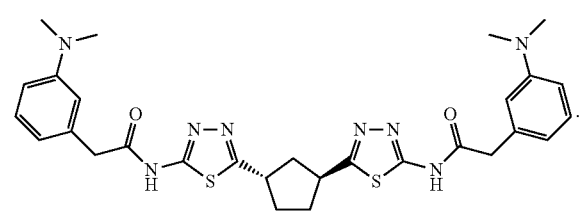 [SMILES: CN(C)c1cccc(CC(=O)Nc2nnc([C@H]3CC[C@H](c4nnc(NC(=O)Cc5cccc(N(C)C)c5)s4)C3)s2)c1]

8. A compound or a pharmaceutically acceptable salt thereof, which is

9. A compound or a pharmaceutically acceptable salt thereof, which is

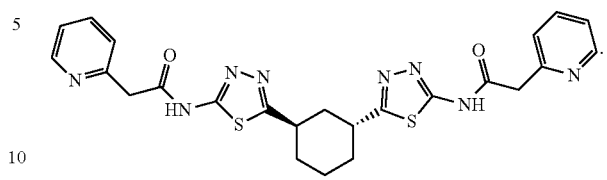

10. A compound or a pharmaceutically acceptable salt thereof, which is

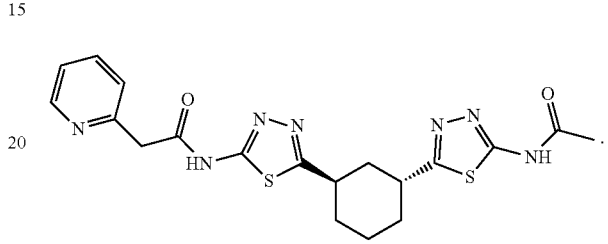

11. A compound or a pharmaceutically acceptable salt thereof, which is

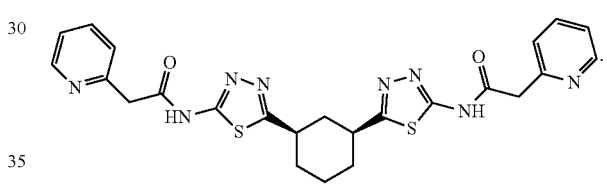

\* \* \* \* \*